US010414763B2

(12) United States Patent
Dorsey et al.

(10) Patent No.: US 10,414,763 B2
(45) Date of Patent: *Sep. 17, 2019

(54) AZAQUINAZOLINE INHIBITORS OF ATYPICAL PROTEIN KINASE C

(71) Applicant: CANCER RESEARCH TECHNOLOGY LIMITED

(72) Inventors: Bruce D. Dorsey, Ambler, PA (US); Benjamin J. Dugan, Glen Mills, PA (US); Katherine M. Fowler, Berkshire (GB); Robert L. Hudkins, Chester Springs, PA (US); Eugen F. Mesaros, Wallingford, PA (US); Nathaniel J T Monck, Berks (GB); Emma L. Morris, Bedfordshire (GB); Ikeoluwa Olowoye, Hertfordshire (GB); Gregory R. Ott, Media, PA (US); Gregoire A. Pave, London (GB); Jonathan R. A. Roffey, Berkshire (GB); Christelle N. Soudy, London (GB); Craig A. Zificsak, Downingtown, PA (US); Allison L. Zulli, Wayne, PA (US)

(73) Assignee: Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/668,022

(22) Filed: Mar. 25, 2015

(65) Prior Publication Data

US 2015/0274720 A1    Oct. 1, 2015

Related U.S. Application Data

(60) Provisional application No. 61/970,006, filed on Mar. 25, 2014.

(51) Int. Cl.
| | | |
|---|---|---|
| *C07D 471/04* | (2006.01) | |
| *C07D 519/00* | (2006.01) | |
| *A61P 35/00* | (2006.01) | |
| *A61P 35/02* | (2006.01) | |
| *A61P 35/04* | (2006.01) | |
| *A61K 31/437* | (2006.01) | |

(52) U.S. Cl.
CPC ............ *C07D 471/04* (2013.01); *A61P 35/00* (2018.01); *A61P 35/02* (2018.01); *A61P 35/04* (2018.01); *C07D 519/00* (2013.01)

(58) Field of Classification Search
CPC ... C07D 471/04; C07D 519/00; A61K 31/437
See application file for complete search history.

(56) References Cited

FOREIGN PATENT DOCUMENTS

| WO | WO-0222602 A2 | 3/2002 |
|---|---|---|
| WO | WO-2005/070934 | 8/2005 |
| WO | WO-2013/078126 | 5/2013 |
| WO | WO-2014/052699 | 4/2014 |

OTHER PUBLICATIONS

ISR&WO PCT/US2015/022368 dated Jun. 25, 2015.
Van Eis, et al. "2, 6-Naphthyridines as Potent and Selective Inhibitors of the Novel Protein Kinase C Isozymes", Bioorganic & Medicinal Chemistry Letters, Pergamon, Amsterdam, NL, vol. 21, No. 24, Oct. 7, 2011 (Oct. 7, 2011), pp. 7367-7372, XP028113889, ISSN: 0960-894X, DOI: 10.1016/J.BMCL.2011.10.025.
Adams, Nicholas D., et al., "Discovery of GSK1070916, a potent and selective inhibitor of Aurora B/C kinase." *Journal of medicinal chemistry* 53.10 (2010): 3973-4001.
Berge, Stephen M., et al., "Pharmaceutical salts." *Journal of pharmaceutical sciences* 66.1 (1977): 1-19.
Eder, Astrid M., et al., "Atypical PKC$_I$ contributes to poor prognosis through loss of apical-basal polarity and cyclin E overexpression in ovarian cancer." *Proceedings of the National Academy of Sciences of the United States of America* 102.35 (2005): 12519-12524.
Farese, Robert V., et al., "Muscle-specific knockout of PKC-λ impairs glucose transport and induces metabolic and diabetic syndromes." *The Journal of clinical investigation* 117.8 (2007): 2289-2301.
Fields, Alan P., et al., "Protein kinase C$_I$ human oncogene, prognostic marker and therapeutic target." *Pharmacological research* 55.6 (2007): 487-497.
Filomenko, Rodolphe, et al., "Atypical protein kinase C ζ as a target for chemosensitization of tumor cells." *Cancer research* 62.6 (2002): 1815-1821.

(Continued)

*Primary Examiner* — Susanna Moore
(74) *Attorney, Agent, or Firm* — Mintz Levin Cohn Ferris Glovsky and Popeo PC

(57) ABSTRACT

The present application provides a compound of formula (I)

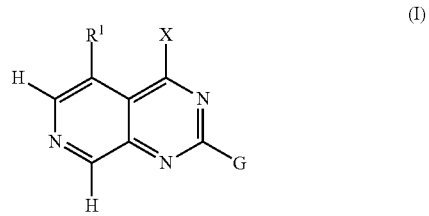

and/or a salt thereof, wherein $R^1$, G, and X are as defined herein. A compound of formula (I) and/or its salts have aPKC inhibitory activity, and may be used to treat proliferative disorders. Compositions comprising a compound of Formula (I) and/or a salt thereof are also provided.

29 Claims, No Drawings

(56) References Cited

OTHER PUBLICATIONS

Garcia-Cao, Isabel, et al., "Tumour-suppression activity of the proapoptotic regulator Par4." *EMBO reports* 6.6 (2005): 577-583.

Herdemann, Matthias, et al., "From a Biogenetic Scenario to a Synthesis of the ABC Ring of Manzamine A." *The Journal of organic chemistry* 67.6 (2002): 1890-1897.

Inoue, Takahiro, et al., "Requirement of androgen-dependent activation of protein kinase C$\zeta$ for androgen-dependent cell proliferation in LNCaP cells and its roles in transition to androgen-independent cells." *Molecular Endocrinology* 20.12 (2006): 3053-3069.

Iorns, Elizabeth, et al., "Parallel RNAi and compound screens identify the PDK1 pathway as a target for tamoxifen sensitization." *Biochemical Journal* 417.1 (2009): 361-371.

Joshi, Jayashree, et al., "Par-4 inhibits Akt and suppresses Ras-induced lung tumorigenesis." *The EMBO journal* 27.16 (2008): 2181-2193.

Kojima, Yasuyuki, et al., "The overexpression and altered localization of the atypical protein kinase C $\lambda/\iota$ in breast cancer correlates with the pathologic type of these tumors." *Human pathology* 39.6 (2008): 824-831.

Leitges, Michael, et al., "Targeted disruption of the $\zeta$PKC gene results in the impairment of the NF-$\kappa$B pathway." *Molecular cell* 8.4 (2001): 771-780.

Leseux, Ludivine, et al., "PKC $\zeta$-mTOR pathway: a new target for rituximab therapy in follicular lymphoma." *Blood* 111.1 (2008): 285-291.

Moumne, Roba, et al., "Fluorinated diaminocyclopentanes as chiral sensitive NMR probes of RNA structure." *Journal of the American Chemical Society* 132.38 (2010): 13111-13113.

Murray, Nicole R., et al., "Protein kinase $C_I$ is required for Ras transformation and colon carcinogenesis in vivo." *J cell Biol* 164.6 (2004): 797-802.

Ono, Yoshitaka, et al., "Protein kinase C zeta subspecies from rat brain: its structure, expression, and properties." *Proceedings of the National Academy of Sciences* 86.9 (1989): 3099-3103.

Osborne, C. Kent, et al., "Role of the estrogen receptor coactivator AIB1 (SRC-3) and HER-2/neu in tamoxifen resistance in breast cancer." *Journal of the National Cancer Institute* 95.5 (2003): 353-361.

Plo, Isabelle, et al., "Overexpression of the atypical protein kinase C $\zeta$ reduces topoisomerase II catalytic activity, cleavable complexes formation, and drug-induced cytotoxicity in monocytic U937 leukemia cells." *Journal of Biological Chemistry* 277.35 (2002): 31407-31415.

Regala, Roderick P., et al. "Atypical protein kinase $C_I$ plays a critical role in human lung cancer cell growth and tumorigenicity." *Journal of Biological Chemistry* 280.35 (2005): 31109-31115.

Regala, Roderick P., et al., "Atypical protein kinase $C_I$ expression and aurothiomalate sensitivity in human lung cancer cells." *Cancer Research* 68.14 (2008): 5888-5895.

Regala, Roderick P., et al., "Atypical protein kinase $C_I$ is an oncogene in human non-small cell lung cancer." *Cancer research* 65.19 (2005): 8905-8911.

Suzuki, Atsushi, et al.,"The PAR-aPKC system: lessons in polarity." *Journal of cell science* 119.6 (2006): 979-987.

Xin, Meiguo, et al., "Protein kinase C$\zeta$ abrogates the proapoptotic function of Bax through phosphorylation." *Journal of Biological Chemistry* 282.29 (2007): 21268-21277.

Yang, Yi-Ling, et al., "Amplification of PRKCI, located in 3q26, is associated with lymph node metastasis in esophageal squamous cell carcinoma." *Genes, Chromosomes and Cancer* 47.2 (2008): 127-136.

Yi, Ping, et al., "Atypical protein kinase C regulates dual pathways for degradation of the oncogenic coactivator SRC-3/AIB1." *Molecular cell* 29.4 (2008): 465-476.

Zhang, Lin, et al., "Integrative genomic analysis of protein kinase C (PKC) family identifies $PKC_I$ as a biomarker and potential oncogene in ovarian carcinoma." *Cancer research* 66.9 (2006): 4627-4635.

AZAQUINAZOLINE INHIBITORS OF ATYPICAL PROTEIN KINASE C

CROSS REFERENCE TO RELATED APPLICATIONS

This application claims the benefit of U.S. Provisional Application No. 61/970,006, filed Mar. 25, 2014, the entirety of which is incorporated by reference herein.

BACKGROUND

PKCι and PKCζ (accession numbers NM_002740 and NM_002744 respectively) together define the atypical sub-class of the protein kinase C (PKC) family. The aPKCs are structurally and functionally distinct from the other PKCζ sub-classes, classic/conventional and novel, as their catalytic activity is not dependent on diacylglycerol and calcium (Ono, Y., Fujii, T., Ogita, K., Kikkawa, U., Igarashi, K., and Nishizuka, Y. (1989). Protein kinase C zeta subspecies from rat brain: its structure, expression, and properties. Proc Natl Acad Sci USA 86, 3099-3103). Structurally, PKCι and PKCζ contain a C-terminal serine/threonine kinase domain (AGC class) and an N-terminal regulatory region containing a Phox Bem 1 (PB1) domain involved in mediating protein: protein interactions critical for aPKC function. At the amino acid level the aPKCs share 72% overall homology, however, the kinase domains share 84% identity and differ in the active site by just a single amino acid. This striking homology suggests an ATP-competitive ligand would not be expected to exhibit significant aPKC isoform selectivity.

The aPKCs have been implicated in a diverse number of signalling pathways, demonstrating both redundant and distinct signalling functions. Both isoforms have emerged as central players in the mechanisms that regulate the establishment and maintenance of cellular polarity in multiple cell types (reviewed in Suzuki, A., and Ohno, S. (2006). The PAR-aPKC system: lessons in polarity. J Cell Sci 119, 979-987). Genetic dissection of their functions using knockout mice have also revealed preferential roles for PKCζ in the regulation of NF-kB signalling (Leitges, M., Sanz, L., Martin, P., Duran, A., Braun, U., Garcia, J. F., Camacho, F., Diaz-Meco, M. T., Rennert, P. D., and Moscat, J. (2001). Targeted disruption of the zetaPKC gene results in the impairment of the NF-kappaB pathway. Mol Cell 8, 771-780), and PKCι in insulin secretion and action (Farese, R. V., Sajan, M. P., Yang, H., Li, P., Mastorides, S., Gower, W. R., Jr., Nimal, S., Choi, C. S., Kim, S., Shulman, G. I., et al. (2007). Muscle-specific knockout of PKC-lambda impairs glucose transport and induces metabolic and diabetic syndromes. J Clin Invest 117, 2289-2301). In addition, both isoforms have been implicated in the pathogenesis of cancer making a strong case for the inhibition of the aPKCs as a novel therapeutic avenue.

PKCι is a known oncogene in non-small cell lung cancer (NSCLC). In one study it was shown to be overexpressed in 69% of NSCLC cases at the protein level. Consistent with this, the PKCι gene (PRKCI residing on chromosome 3q26) was shown to be amplified in 36.5% of NSCLC tumours examined, including 96% of the squamous cell carcinoma sub-type (Regala, R. P., Weems, C., Jamieson, L., Khoor, A., Edell, E. S., Lohse, C. M., and Fields, A. P. (2005b). Atypical protein kinase C iota is an oncogene in human non-small cell lung cancer. Cancer Res 65, 8905-8911). Amplification of 3q26 has also been reported in 44% of ovarian cancers, including >70% of serous epithelial ovarian cancers where 3q26 amplification is translated into increased PKCι protein expression. Moreover, increased PKCι expression is associated with poor prognosis in NSCLC and ovarian cancer where it may serve as a diagnostic biomarker of aggressive disease (Eder, A. M., Sui, X., Rosen, D. G., Nolden, L. K., Cheng, K. W., Lahad, J. P., Kango-Singh, M., Lu, K. H., Warneke, C. L., Atkinson, E. N., et al. (2005). Atypical PKCiota contributes to poor prognosis through loss of apical-basal polarity and cyclin E overexpression in ovarian cancer. Proc Natl Acad Sci USA 102, 12519-12524; Zhang, L., Huang, J., Yang, N., Liang, S., Barchetti, A., Giannakakis, A., Cadungog, M. G., O'Brien-Jenkins, A., Massobrio, M., Roby, K. F., et al. (2006). Integrative genomic analysis of protein kinase C (PKC) family identifies PKCiota as a biomarker and potential oncogene in ovarian carcinoma. Cancer Res 66, 4627-4635). 3q26 amplifications have been observed in many other cancers including oesophageal squamous cell carcinoma (Yang, Y. L., Chu, J. Y., Luo, M. L., Wu, Y. P., Zhang, Y., Feng, Y. B., Shi, Z. Z., Xu, X., Han, Y. L., Cai, Y., et al. (2008). Amplification of PRKCI, located in 3q26, is associated with lymph node metastasis in esophageal squamous cell carcinoma. Genes Chromosomes Cancer 47, 127-136) and breast cancer (Kojima, Y., Akimoto, K., Nagashima, Y., Ishiguro, H., Shirai, S., Chishima, T., Ichikawa, Y., Ishikawa, T., Sasaki, T., Kubota, Y., et al. (2008). The overexpression and altered localization of the atypical protein kinase C lambda/iota in breast cancer correlates with the pathologic type of these tumors. Hum Pathol 39, 824-831) suggesting that PKCι may also participate in the pathogenesis of these diseases.

In NSCLC the primary function of PKCι is to drive transformed growth via a Rac1/PAK/MEK/ERK signalling axis. However, PKCι also functions in NSCLC survival, resistance to chemotherapy, and invasion via distinct pathways (reviewed in Fields, A. P., and Regala, R. P. (2007). Protein kinase C iota: human oncogene, prognostic marker and therapeutic target. Pharmacol Res 55, 487-497). In ovarian cancer transformed growth is correlated with deregulated epithelial cell polarity and increased cycle E expression (Eder et al., 2005) suggesting that PKCι can influence the cancer phenotype through multiple mechanisms. Compelling evidence has emerged to suggest that inhibition of PKCι may be a useful therapeutic approach to combat tumours characterised by increased PKCι expression. In transgenic models, mice with elevated PKCι activity in the colon are more susceptible to carcinogen-induced colon carcinogenesis, and expression of a kinase-dead mutant of PKCι blocks the transformation of intestinal cells by oncogenic Ras (Murray, N. R., Jamieson, L., Yu, W., Zhang, J., Gokmen-Polar, Y., Sier, D., Anastasiadis, P., Gatalica, Z., Thompson, E. A., and Fields, A. P. (2004). Protein kinase Ciota is required for Ras transformation and colon carcinogenesis in vivo. J Cell Biol 164, 797-802). Finally, genetic or pharmacological inhibition of PKCι by a gold derivative—aurothiomalate (ATM)—blocks the growth of NSCLC cells in soft agar and significantly decreases tumour volume in xenograft models of NSCLC (Regala, R. P., Thompson, E. A., and Fields, A. P. (2008). Atypical protein kinase C iota expression and aurothiomalate sensitivity in human lung cancer cells. Cancer Res 68, 5888-5895; Regala, R. P., Weems, C., Jamieson, L., Copland, J. A., Thompson, E. A., and Fields, A. P. (2005a). Atypical protein kinase Ciota plays a critical role in human lung cancer cell growth and tumorigenicity. J Biol Chem 280, 31109-31115).

Despite the high degree of similarity between aPKC isoforms, the role of PKCζ in cancer is distinct from that of PKCι. PKCζ plays a role in NSCLC cell survival by phosphorylating and antagonising the pro-apoptotic effects of Bax in response to nicotine (Xin, M., Gao, F., May, W. S., Flagg, T., and Deng, X. (2007). Protein kinase Czeta abrogates the proapoptotic function of Bax through phosphorylation. J Biol Chem 282, 21268-21277). PKCζ activity has also been linked to resistance against a wide range of cytotoxic and genotoxic agents. For instance, in human leukaemia cells, overexpression of PKCζ confers resistance against 1-β-D-arabinofuranosylcytosine (ara-C), daunorubicin, etoposide, and mitoxantrone-induced apoptosis (Filomenko, R., Poirson-Bichat, F., Billerey, C., Belon, J. P., Garrido, C., Solary, E., and Bettaieb, A. (2002). Atypical protein kinase C zeta as a target for chemosensitization of tumor cells. Cancer Res 62, 1815-1821; Plo, I., Hernandez, H., Kohlhagen, G., Lautier, D., Pommier, Y., and Laurent, G. (2002). Overexpression of the atypical protein kinase C zeta reduces topoisomerase II catalytic activity, cleavable complexes formation, and drug-induced cytotoxicity in monocytic U937 leukemia cells. J Biol Chem 277, 31407-31415). Furthermore, inhibition of PKC activity through expression of a kinase-dead mutant sensitises leukaemia cells to the cytotoxic effects of etoposide both in vitro and in vivo (Filomenko et al., 2002). Atypical protein kinase C regulates dual pathways for degradation of the oncogenic coactivator SRC-3/AIB1. Mol Cell 29, 465-476), and both of these proteins have been postulated to play a role in tamoxifen resistance in breast cancer (Iorns, E., Lord, C. J., and Ashworth, A. (2009). Parallel RNAi and compound screens identify the PDK1 pathway as a target for tamoxifen sensitization. Biochem J 417, 361-370; Osborne, C. K., Bardou, V., Hopp, T. A., Chamness, G. C., Hilsenbeck, S. G., Fuqua, S. A., Wong, J., Allred, D. C., Clark, G. M., and Schiff, R. (2003). Role of the estrogen receptor coactivator AIB1 (SRC-3) and HER-2/neu in tamoxifen resistance in breast cancer. J Natl Cancer Inst 95, 353-361). Together these studies suggest that inhibition of PKCζ activity may have beneficial therapeutic effects by acting as a chemosensitiser to a wide array of commonly used chemotoxic agents in the clinic.

Further evidence that small molecule inhibition of PKCζ could have important therapeutic benefits has recently emerged from tumour models that link PKCζ signalling to the mTOR pathway. PKCζ is constitutively activated in follicular lymphoma and has been identified as a novel target for the anti-CD20 therapeutic antibody rituximab (Leseux, L., Laurent, G., Laurent, C., Rigo, M., Blanc, A., Olive, D., and Bezombes, C. (2008). PKC zeta mTOR pathway: a new target for rituximab therapy in follicular lymphoma. Blood 111, 285-291). Rituximab inhibits follicular lymphoma proliferation by targeting a PKCζ-MAPK-mTOR pathway, suggesting that PKCζ is both a target of Rituximab, and a key regulator of its' anti-leukaemic effect. Regulation of the mTOR/p70S6K pathway by PKCζ has also been implicated in the transition of prostate cancer cells to an androgen-independent state (Inoue, T., Yoshida, T., Shimizu, Y., Kobayashi, T., Yamasaki, T., Toda, Y., Segawa, T., Kamoto, T., Nakamura, E., and Ogawa, O. (2006). Requirement of androgen-dependent activation of protein kinase Czeta for androgen-dependent cell proliferation in LNCaP Cells and its roles in transition to androgen-independent cells. Mol Endocrinol 20, 3053-3069). Finally, mice containing a homozygous deletion of Par4, a negative regulator of PKCζ, exhibit greatly enhanced PKCζ activity. These mice spontaneously develop tumours of the prostate and endometrium, and potentiate Ras-induced lung carcinogenesis consistent with a role for PKCζ in lung cancer (Garcia-Cao, I., Duran, A., Collado, M., Carrascosa, M. J., Martin-Caballero, J., Flores, J. M., Diaz-Meco, M. T., Moscat, J., and Serrano, M. (2005). Tumour-suppression activity of the proapoptotic regulator Par4. EMBO Rep 6, 577-583; Joshi, J., Fernandez-Marcos, P. J., Galvez, A., Amanchy, R., Linares, J. F., Duran, A., Pathrose, P., Leitges, M., Canamero, M., Collado, M., et al. (2008). Par-4 inhibits Akt and suppresses Ras-induced lung tumorigenesis. EMBO J 27, 2181-2193).

A need exists for aPKC inhibitors for use as pharmaceutical agents.

SUMMARY

This application provides a compound of formula (I)

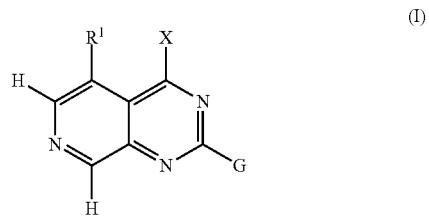

and/or a salt thereof, wherein $R^1$, G, and X are as defined herein.

A compound of formula (I) and/or its salts have aPKC inhibitory activity, and may be used to treat aPKC-dependent disorders or conditions.

The present application further provides a pharmaceutical composition comprising a compound of formula (I) and/or a salt thereof together with at least one pharmaceutically acceptable carrier, diluent, or excipient therefor.

In another aspect, the present application provides a method of treating a subject suffering from an aPKC-dependent disorder or condition comprising: administering to the subject a compound of formula (I) and/or a pharmaceutically acceptable salt thereof.

The present application further provides a method of treating a proliferative disorder in a subject, comprising administering to the subject a therapeutically effective amount of a compound of formula (I) and/or a pharmaceutically acceptable salt thereof.

DETAILED DESCRIPTION

I. Definitions

"About" as used herein when referring to a measurable value such as an amount, a temporal duration, and the like, is meant to encompass reasonable variations of the value, such as, for example, ±10% from the specified value. For example, the phrase "about 50" encompasses reasonable variations of 50, such as ±10% of the numerical value 50, or from 45 to 55.

"Alkyl" or "alkyl group" refers to a monoradical of a branched or unbranched saturated hydrocarbon chain. Examples include, but are not limited to, methyl, ethyl, n-propyl, n-butyl, n-pentyl, n-hexyl, n-heptyl, n-octyl, n-nonyl, n-decyl, isopropyl, tert-butyl, isobutyl, etc. Alkyl groups typically contain 1-10 carbon atoms, such as 1-6 carbon atoms or 1-4 carbon atoms, and can be substituted or unsubstituted.

"Alkylene" or "alkylene group" refers to a diradical of a branched or unbranched saturated hydrocarbon chain. Examples include, but are not limited to, methylene (—CH$_2$—), the ethylene isomers (—CH(CH$_3$)— and —CH$_2$CH$_2$—), the propylene isomers (—CH(CH$_3$)CH$_2$—, —CH(CH$_2$CH$_3$)—, —C(CH$_3$)$_2$—, and —CH$_2$CH$_2$CH$_2$—), etc. Alkylene groups typically contain 1-10 carbon atoms, such as 1-6 carbon atoms, and can be substituted or unsubstituted.

"Alkenyl" or "alkenyl group" refers to a monoradical of a branched or unbranched hydrocarbon chain containing at least one double bond. Examples include, but are not limited to, ethenyl, 3-buten-1-yl, 2-ethenylbutyl, and 3-hexen-1-yl. Alkenyl groups typically contain 2-10 carbon atoms, such as 2-6 carbon atoms or 2-4 carbon atoms, and can be substituted or unsubstituted.

"Alkynyl" or "alkynyl group" refers to a monoradical of a branched or unbranched hydrocarbon chain containing at least one triple bond. Examples include, but are not limited to, ethynyl, 3-butyn-1-yl, propynyl, 2-butyn-1-yl, and 3-pentyn-1-yl. Alkynyl groups typically contain 2-10 carbon atoms, such as 2-6 carbon atoms or 2-4 carbon atoms, and can be substituted or unsubstituted.

"Aryl" or "aryl group" refers to phenyl and 7-15 membered monoradical bicyclic or tricyclic hydrocarbon ring systems, including bridged, spiro, and/or fused ring systems, in which at least one of the rings is aromatic. Aryl groups can be substituted or unsubstituted. Examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. An aryl group may contain 6 (i.e., phenyl) or 9 to 15 ring atoms, such as 6 (i.e., phenyl) or 9-11 ring atoms, e.g., 6 (i.e., phenyl), 9 or 10 ring atoms.

"Arylene" or "arylene group" refers to a phenylene (—C$_6$H$_4$—) or a 7-15 membered diradical bicyclic or tricyclic hydrocarbon ring systems, including bridged, spiro, and/or fused ring systems, in which at least one of the rings is aromatic. Arylene groups can be substituted or unsubstituted. For example, an arylene group may contain 6 (i.e., phenylene) or 9 to 15 ring atoms; such as 6 (i.e., phenylene) or 9-11 ring atoms; e.g., 6 (i.e., phenylene), 9 or 10 ring atoms. An arylene group can also include ring systems substituted on ring carbons with one or more —OH functional groups (which may further tautomerize to give a ring C=O group).

"Arylalkyl" or "arylalkyl group" refers to an alkyl group in which a hydrogen atom is replaced by an aryl group, wherein alkyl group and aryl group are as previously defined (i.e., arylalkyl-). Arylalkyl groups can be substituted or unsubstituted. Examples include, but are not limited to, benzyl (C$_6$H$_5$CH$_2$—).

"Cycloalkyl" or "cycloalkyl group" refers to a monoradical non-aromatic carbocyclic ring system, which may be saturated or unsaturated, substituted or unsubstituted, and may be monocyclic, bicyclic, or tricyclic, and may be bridged, spiro, and/or fused. Examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane. The cycloalkyl group may contain from 3 to 10 ring atoms, such as 3 to 7 ring atoms (e.g., 3 ring atoms, 5 ring atoms, 6 ring atoms, or 7 ring atoms).

"Cycloalkylalkyl" or "cycloalkylalkyl group" refers to an alkyl group in which a hydrogen atom is replaced by a cycloalkyl group, wherein alkyl group and cycloalkyl group are as previously defined (i.e., cycloalkylalkyl-). Cycloalkylalkyl groups can be substituted or unsubstituted. Examples include, but are not limited to, cyclohexylmethyl (C$_6$H$_{11}$CH$_2$—).

"Haloalkyl" or "haloalkyl group" refers to alkyl groups in which one or more hydrogen atoms are replaced by halogen atoms. Haloalkyl includes both saturated alkyl groups and unsaturated alkenyl and alkynyl groups, such as for example —CF$_3$, —CHF$_2$, —CH$_2$F, —CF$_2$CF$_3$, —CHFCF$_3$, —CH$_2$CF$_3$, —CF$_2$CH$_3$, —CHFCH$_3$, —CF$_2$CF$_2$CF$_3$, —CF$_2$CH$_2$CH$_3$, —CF=CF$_2$, —CCl=CH$_2$, —CBr=CH$_2$, —CI=CH$_2$, —C≡C—CF$_3$, —CHFCH$_2$CH$_3$ and —CHFCH$_2$CF$_3$.

"Halogen" includes fluorine, chlorine, bromine and iodine atoms.

"Heteroaryl" or "heteroaryl group" refers to (a) 5 and 6 membered monocyclic aromatic rings, which contain, in addition to carbon atom(s), at least one heteroatom, such as nitrogen, oxygen or sulfur, and (b) 7-15 membered bicyclic and tricyclic rings, which contain, in addition to carbon atom(s), at least one heteroatom, such as nitrogen, oxygen or sulfur, and in which at least one of the rings is aromatic. Heteroaryl groups can be substituted or unsubstituted, and may be bridged, spiro, and/or fused. Examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0$^{2,7}$]dodeca-2(7),3,5-trienyl, 12-oxa-10-aza-tricyclo[6.3.1.0$^{2,7}$]dodeca-2(7),3,5-trienyl, 12-aza-tricyclo[7.2.1.0$^{2,7}$]dodeca-2(7),3,5-trienyl, 10-aza-tricyclo[6.3.2.0$^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. For example, a heteroaryl group may contain 5, 6, or 8-15 ring atoms. As another example, a heteroaryl group may contain 5 to 10 ring atoms, such as 5, 6, 9, or 10 ring atoms.

"Heteroarylalkyl" or "heteroarylalkyl group" refers to an alkyl group in which a hydrogen atom is replaced by a heteroaryl group, wherein alkyl group and heteroaryl group are as previously defined (i.e., heteroarylalkyl-).

Heteroarylalkyl groups can be substituted or unsubstituted. Examples include, but are not limited to, the pyridinylmethyl isomers

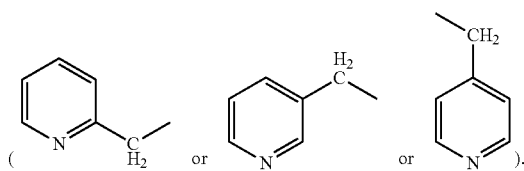

"Heterocycloalkyl" or "heterocycloalkyl group" refers to 3-15 membered monocyclic, bicyclic, and tricyclic non-aromatic rings, which may be saturated or unsaturated, can be substituted or unsubstituted, may be bridged, spiro, and/or fused, and which contain, in addition to carbon atom(s), at least one heteroatom, such as nitrogen, oxygen, sulfur or phosphorus. Examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-azabicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2]nonanyl, [1,4]oxaphosphinanyl-4-oxide, [1,4]azaphosphinanyl-4-oxide, [1,2]oxaphospholanyl-2-oxide, phosphinanyl-1-oxide, [1,3]azaphospholidinynl-3-oxide, [1,3]oxaphospholanyl-3-oxide and 7-oxabicyclo[2.2.1]heptanyl. A heterocycloalkyl group may contain, in addition to carbon atom(s), at least one nitrogen, oxygen, or sulfur. For example, a heterocycloalkyl group may contain, in addition to carbon atom(s), at least one nitrogen or oxygen. A heterocycloalkyl group may contain, in addition to carbon atom(s), at least one nitrogen. A heterocycloalkyl group may contain carbon atoms and 1 or 2 nitrogen atoms. A heterocycloalkyl group may contain carbon atoms and an oxygen atom. A heterocycloalkyl group may contain carbon atoms, a nitrogen atom, and an oxygen atom. A heterocycloalkyl group may contain carbon atoms, a nitrogen atom, and a sulfur atom. A heterocycloalkyl group may contain carbon atoms and a sulfur atom. A heterocycloalkyl group may contain from 3 to 10 ring atoms. A heterocycloalkyl group may contain from 3 to 7 ring atoms. A heterocycloalkyl group may contain from 5 to 7 ring atoms, such as 5 ring atoms, 6 ring atoms, or 7 ring atoms. Unless otherwise indicated, the foregoing heterocycloalkyl groups can be C-attached or N-attached where such is possible and results in the creation of a stable structure. For example, piperidinyl can be piperidin-1-yl (N-attached) or piperidin-4-yl (C-attached).

"Heterocycloalkylene" or "heterocycloalkylene group" refers to diradical, 3-15 membered monocyclic, bicyclic, or tricyclic non-aromatic ring systems, which may be saturated or unsaturated, can be substituted or unsubstituted, may be bridged, spiro, and/or fused, and which contain, in addition to carbon atom(s), at least one heteroatom, such as nitrogen, oxygen, sulfur or phosphorus. Examples include, but are not limited to, the azridinylene isomers

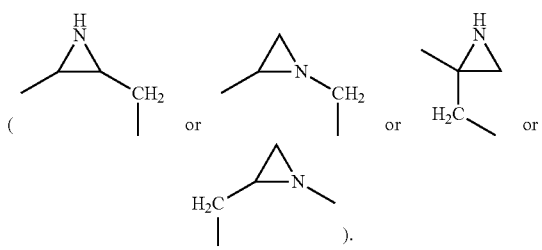

The heterocycloalkylene group may contain, in addition to carbon atom(s), at least one nitrogen, oxygen, or sulfur. The heterocycloalkylene group may contain, in addition to carbon atom(s), at least one nitrogen or oxygen. The heterocycloalkylene group may contain, in addition to carbon atom(s), at least one nitrogen. For example, a heterocycloalkylene group may contain from 3 to 10 ring atoms; such as from 3 to 7 ring atoms. A heterocycloalkylene group may contain from 5 to 7 ring atoms, such as 5 ring atoms, 6 ring atoms, or 7 ring atoms. Unless otherwise indicated, the foregoing heterocycloalkylene groups can be C-attached and/or N-attached where such is possible and results in the creation of a stable structure. A heterocycloalkylene group can also include ring systems substituted on ring carbons with one or more —OH functional groups (which may further tautomerize to give a ring C=O group) and/or substituted on a ring sulfur atom by one (1) or two (2) oxygen atoms to give S=O or $SO_2$ groups, respectively, and/or substituted on a ring phosphorus by an oxygen atom to give P=O.

"Heterocycloalkylalkyl" or "heterocycloalkylalkyl group" refers to an alkyl group in which a hydrogen atom is replaced by a heterocycloalkyl group, wherein alkyl group and heterocycloalkyl group are as previously defined (i.e., heterocycloalkylalkyl-). Heteroycloalkylalkyl groups can be substituted or unsubstituted. Examples include, but are not limited to, pyrrolidinylmethyl ($C_4H_8NCH_2$—).

"Pharmaceutically acceptable" refers to physiologically tolerable materials, which do not typically produce an allergic or other untoward reaction, such as gastric upset, dizziness and the like, when administered to a human.

"Pharmaceutical composition" refers to a composition that can be used to treat a disease, condition, or disorder in a human.

"Pseudohalogen" refers to —OCN, —SCN, —$CF_3$, and —CN.

"Stable" or "chemically stable" refers to a compound that is sufficiently robust to be isolated to a useful degree of purity from a reaction mixture. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, $R^1$ can be $C_{1-6}$alkyl optionally substituted by 1-13 $R^{19}$; when $R^1$ is methyl, the methyl group is optionally substituted by 1-3 $R^{19}$.

"Therapeutically effective amount" refers to an amount of a compound sufficient to inhibit, halt, or cause an improvement in a disorder or condition being treated in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated. It should be appreciated that determination of proper dosage forms, dosage amounts, and routes of administration is within the level of ordinary skill in the pharmaceutical and medical arts.

"Treatment" refers to the acute or prophylactic diminishment or alleviation of at least one symptom or characteristic associated or caused by a disorder being treated. For example, treatment can include diminishment of several symptoms of a disorder or complete eradication of a disorder.

II. Compounds

The compounds of the present application are described by but not limited to the following numbered Embodiments. When a higher numbered Embodiment refers back to multiple previous lower numbered Embodiments in the alternative and contains a new limitation not present in the lower numbered Embodiments, the higher numbered Embodiment is intended to be an express description of each and every one of the alternatives. For example, if Embodiment 2 refers back to Embodiment 1 and contains a limitation not present in Embodiment 1, and Embodiment 3 refers back Embodiments 1 or 2 and contains a limitation(s) not present in Embodiments 1 or 2, and Embodiment 4 refers back to any of Embodiments 1-3 and contains a limitation(s) not present in Embodiments 1, 2, or 3, then Embodiment 4 is intended to be an explicit description of a genus having the limitations of Embodiments 1 and 4, an explicit description of a genus having the limitations of Embodiments 2 and 4 (i.e., 1, 2, and 4), and an explicit description of a genus having the limitations of Embodiments 3 and 4 (i.e., 1, 3, and 4, and 1, 2, 3 and 4). By way of example, if Embodiment 1 is a compound of formula (I) having $R^2$, $R^3$ and $R^4$ independently as alkyl or aryl, and Embodiment 2 is a compound of Embodiment 1 defining $R^2$ as alkyl, and Embodiment 3 is a compound of Embodiments 1 or 2 defining $R^3$ as alkyl, and Embodiment 4 is a compound of any of Embodiments 1-3 defining $R^4$ as alkyl, then Embodiment 4 is an explicit description of a genus having the limitations of Embodiments 1 and 4 (i.e., a compound of formula (I) in which $R^2$ and $R^3$ are alkyl or aryl, and $R^4$ is alkyl), an explicit description of a genus having the limitations of Embodiments 2 and 4 (i.e., a compound of formula (I) in which $R^3$ is alkyl or aryl, and $R^2$ and $R^4$ are alkyl), an explicit description of a genus having the limitations of Embodiments 3 and 4 (i.e., a compound of formula (I) in which $R^2$ is alkyl or aryl, and $R^3$ and $R^4$ are alkyl; and a compound of formula (I) in which $R^2$, $R^3$ and $R^4$ are all alkyl).

It should be noted in this regard that when a higher numbered Embodiment refers to a lower numbered Embodiment and contains limitations for a group(s) not present in the lower numbered Embodiment, the higher numbered Embodiment should be interpreted in context to ignore the missing group(s). For example, if Embodiment 1 recites a compound of formula (I) in which X is H, $C_{1-10}$alkyl, or —C(=O)$R^{28}$, Embodiment 2 recites a compound of Embodiment 1 in which X is H or $C_{1-10}$alkyl, and Embodiment 3 recites a compound of Embodiments 1 or 2 in which $R^{28}$ is alkyl, then Embodiment 3 defines a genus having the limitations of Embodiments 1 and 3 and a genus having the limitation of Embodiments 2 and 3 (i.e., 1, 2, and 3). In the genus defined by the limitations of Embodiments 2 and 3, X cannot be —C(=O)$R^{28}$; therefore this genus should be interpreted to ignore the Embodiment 3 definition of $R^{28}$=alkyl (i.e., the genus of Embodiments 2 and 3 has the same scope as the genus of Embodiment 2).

The compounds of the present application are defined herein using structural formulas that do not specifically recite the mass numbers or the isotope ratios of the constituent atoms. It is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^1H$, $^2H$, and $^3H$; etc. Preferably, the constituent atoms in the compounds of the present application are present in their naturally occurring ratios of isotope forms.

Embodiment 1

A compound of formula (I)

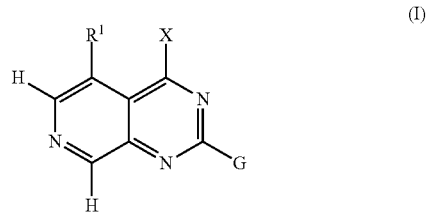

and/or a salt thereof, wherein:
G is chosen from the group consisting of

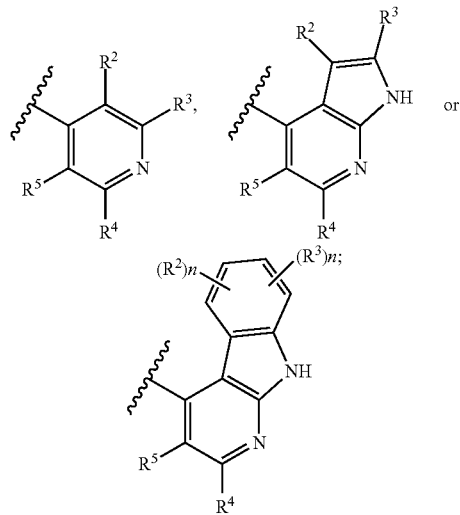

X is chosen from the group consisting of halogen, —CN, —C(=O)$R^{28}$, —C(=O)O$R^{28}$, —C(=O)N$R^{24}R^{28}$, —C(=O)C(=O)$R^{28}$, —N$R^{24}R^{28}$, —N$R^{24}$N$R^{24}R^{28}$, —N=N$R^{28}$, —N$R^{24}$O$R^{28}$, —N$R^{24}$C(=O)$R^{28}$, —N$R^{24}$C(=O)C(=O)$R^{28}$, —N$R^{24}$C(=O)O$R^{28}$, —N$R^{24}$C(=O)C(=O)O$R^{28}$, —N$R^{24}$C(=O)N$R^{24}R^{28}$, —N$R^{24}$C(=O)

—NR$^{24}$C(=O)R$^{28}$, —NR$^{24}$C(=O)NR$^{24}$C(=O)OR$^{28}$, —NR$^{24}$C(=O)C(=O)NR$^{24}$R$^{28}$, —NR$^{24}$S(=O)$_2$R$^{28}$, —NR$^{24}$S(O)$_2$NR$^{24}$R$^{28}$, —OR$^{28}$, —OC(=O)R$^{28}$, —OC(=O)NR$^{24}$R$^{28}$, —OC(=O)OR$^{28}$, —OS(=O)R$^{28}$, —OS(=O)$_2$R$^{28}$, —OS(=O)$_2$OR$^{28}$, —OS(=O)$_2$NR$^{24}$R$^{28}$, —S(=O)$_n$R$^{28}$, —S(=O)$_2$NR$^{24}$R$^{28}$, and —S(=O)NR$^{24}$R$^{28}$;

or X is chosen from the group consisting of C$_{1-10}$alkyl, C$_{2-6}$alkenyl, C$_{2-6}$alkynyl, C$_{6-11}$aryl, C$_{7-16}$arylalkyl, C$_{3-11}$cycloalkyl, C$_{4-12}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing are optionally substituted by 1-10 R$^{19}$, R$^1$ is chosen from the group consisting of C$_{3-11}$cycloalkyl optionally substituted with 1-10 R$^{19}$, C$_{1-6}$-haloalkyl, and —OC$_{1-6}$alkyl;

R$^2$, R$^3$, R$^4$, R$^5$, are each independently chosen from the group consisting of H, halogen, —CN, —C(=O)R$^{20}$, —C(=O)OR$^{20}$, —C(=O)NR$^{22}$R$^{23}$, —C(=O)C(=O)R$^{20}$, —C(=NR$^{25}$)R$^{20}$, —C(=NR$^{25}$)NR$^{22}$R$^{23}$, —C(=NOH)NR$^{22}$R$^{23}$, —C(=NOR$^{26}$)R$^{20}$, —C(=NNR$^{22}$R$^{23}$)R$^{20}$, —C(=NNR$^{24}$C(=O)R$^{21}$)R$^{20}$, —C(=NNR$^{24}$C(=O)OR$^{21}$)R$^{20}$, —C(=S)NR$^{22}$R$^{23}$, —NC, —NO$_2$, —NR$^{22}$R$^{23}$, —NR$^{24}$NR$^{22}$R$^{23}$, —N=NR$^{24}$, —NR$^{24}$OR$^{26}$, —NR$^{24}$C(=O)R$^{20}$, —NR$^{24}$C(=O)C(=O)R$^{20}$, —NR$^{24}$C(=O)OR$^{21}$, —NR$^{24}$C(=O)C(=O)OR$^{21}$, —NR$^{24}$C(=O)NR$^{22}$R$^{23}$, —NR$^{24}$C(=O)NR$^{24}$C(=O)R$^{20}$, —NR$^{24}$C(=O)NR$^{24}$C(=O)OR$^{20}$, —NR$^{24}$C(=NR$^{25}$)NR$^{22}$R$^{23}$, —NR$^{24}$C(=O)C(=O)NR$^{22}$R$^{23}$, —NR$^{24}$C(=S)R$^{20}$, —NR$^{24}$C(=S)OR$^{20}$, —NR$^{24}$C(=S)NR$^{22}$R$^{23}$, —NR$^{24}$S(=O)$_2$R$^{21}$, —NR$^{24}$S(=O)$_2$NR$^{22}$R$^{23}$, —NR$^{24}$P(=O)R$^{38}$R$^{38}$, —NR$^{24}$P(=O)(NR$^{22}$R$^{23}$)(NR$^{22}$R$^{23}$), —NR$^{24}$P(=O)(OR$^{20}$)(OR$^{20}$), —NR$^{24}$P(=O)(SR$^{20}$)(SR$^{20}$), —OR$^{20}$, —OCN, —OC(=O)R$^{20}$, —OC(=O)NR$^{22}$R$^{23}$, —OC(=O)OR$^{20}$, —OC(=NR$^{25}$)NR$^{22}$R$^{23}$, —OS(=O)R$^{20}$, —OS(=O)$_2$R$^{20}$, —OS(=O)$_2$OR$^{20}$, —OS(=O)$_2$NR$^{22}$R$^{23}$, —OP(=O)R$^{38}$R$^{38}$, —OP(=O)(NR$^{22}$R$^{23}$)(NR$^{22}$R$^{23}$), —OP(=O)(OR$^{20}$)(OR$^{20}$), —OP(=O)(SR$^{20}$)(SR$^{20}$), —Si(R$^{24}$)$_3$, —SCN, —S(=O)$_n$R$^{20}$, —S(=O)$_2$OR$^{20}$, —SO$_3$R$^{27}$, —S(=O)$_2$NR$^{22}$R$^{23}$, —S(=O)NR$^{22}$R$^{23}$, —SP(=O)R$^{38}$R$^{38}$, —SP(=O)(NR$^{22}$R$^{23}$)(NR$^{22}$R$^{23}$), —SP(=O)(OR$^{20}$)(OR$^{20}$), —SP(=O)(SR$^{20}$)(SR$^{20}$), —P(=O)R$^{38}$R$^{38}$, —P(=O)(NR$^{22}$R$^{23}$)(NR$^{22}$R$^{23}$), —P(=O)(OR$^{20}$)(OR$^{20}$), and —P(=O)(SR$^{20}$)(SR$^{20}$);

or R$^2$, R$^3$, R$^4$, R$^5$, are each independently chosen from the group consisting of C$_{1-6}$alkyl, C$_{2-6}$alkenyl, C$_{2-6}$alkynyl, C$_{6-11}$aryl, C$_{7-16}$arylalkyl, C$_{3-11}$cycloalkyl, C$_{4-12}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted with 1-10 R$^{19}$;

or any of R$^2$ and R$^3$ or R$^4$ and R$^5$ can, together with the atoms to which they are attached, form a C$_{6-11}$aryl, C$_{3-11}$cycloalkyl, 3-15 membered heterocycloalkyl or a 5-15 membered heteroaryl wherein each of the foregoing groups may be optionally substituted by 1-10 R$^{19}$;

R$^{19}$ at each occurrence is independently chosen from the group consisting of C$_{1-6}$alkyl optionally substituted by 1-13 R$^{39}$, C$_{2-6}$alkenyl optionally substituted by 1-11 R$^{39}$, C$_{2-6}$alkynyl optionally substituted by 1-9 R$^{39}$, C$_{6-11}$aryl optionally substituted by 1-11 R$^{39}$, C$_{7-16}$arylalkyl optionally substituted by 1-19 R$^{39}$, C$_{3-11}$cycloalkyl optionally substituted by 1-21 R$^{39}$, C$_{4-12}$cycloalkylalkyl optionally substituted by 1-32 R$^{39}$, 3-15 membered heterocycloalkyl optionally substituted by 1-28 R$^{39}$, 4-21 membered heterocycloalkylalkyl optionally substituted by 1-40 R$^{39}$, 5-15 membered heteroaryl optionally substituted by 1-15 R$^{39}$, 6-21 membered heteroarylalkyl optionally substituted by 1-27 R$^{39}$, halogen, —CN, —C(=O)R$^{30}$, —C(=O)OR$^{30}$, —C(=O)NR$^{32}$R$^{33}$, —C(=O)C(=O)R$^{30}$, —C(=NR$^{35}$)R$^{30}$, —C(=NR$^{35}$)NR$^{32}$R$^{33}$, —C(=NOH)NR$^{32}$R$^{33}$, —C(=NOR$^{36}$)R$^{30}$, —C(=NNR$^{32}$R$^{33}$)R$^{30}$, —C(=NNR$^{34}$C(=O)R$^{31}$)R$^{30}$, —C(=NNR$^{34}$C(=O)OR$^{31}$)R$^{30}$, —C(=S)NR$^{32}$R$^{33}$, —NC, —NO$_2$, —NR$^{32}$R$^{33}$, —NR$^{34}$NR$^{32}$R$^{33}$, —N=NR$^{34}$, =NR$^{30}$, =NOR$^{30}$, —NR$^{34}$OR$^{36}$, —NR$^{34}$C(=O)R$^{30}$, —NR$^{34}$C(=O)C(=O)R$^{30}$, —NR$^{34}$C(=O)OR$^{31}$, —NR$^{34}$C(=O)C(=O)OR$^{31}$, —NR$^{34}$C(=O)NR$^{32}$R$^{33}$, —NR$^{34}$C(=O)NR$^{34}$C(=O)R$^{30}$, —NR$^{34}$C(=O)NR$^{34}$C(=O)OR$^{30}$, —NR$^{34}$C(=NR$^{35}$)NR$^{32}$R$^{33}$, —NR$^{34}$C(=O)C(=O)NR$^{32}$R$^{33}$, —NR$^{34}$C(=S)R$^{30}$, —NR$^{34}$C(=S)OR$^{30}$, —NR$^{34}$C(=S)NR$^{32}$R$^{33}$, —NR$^{34}$S(=O)$_2$R$^{31}$, —NR$^{34}$S(=O)$_2$NR$^{32}$R$^{33}$, —NR$^{34}$P(=O)R$^{38}$R$^{38}$, —NR$^{34}$P(=O)(NR$^{32}$R$^{33}$)(NR$^{32}$R$^{33}$), —NR$^{34}$P(=O)(OR$^{30}$)(OR$^{30}$), —NR$^{34}$P(=O)(SR$^{30}$)(SR$^{30}$), —OR$^{30}$, =O, —OCN, —OC(=O)R$^{30}$, —OC(=O)NR$^{32}$R$^{33}$, —OC(=O)OR$^{30}$, —OC(=NR$^{35}$)NR$^{32}$R$^{33}$, —OS(=O)R$^{30}$, —OS(=O)$_2$R$^{30}$, —OS(=O)$_2$OR$^{30}$, —OS(=O)$_2$NR$^{32}$R$^{33}$, —OP(=O)R$^{38}$R$^{38}$, —OP(=O)(NR$^{32}$R$^{33}$)(NR$^{32}$R$^{33}$), —OP(=O)(OR$^{30}$)(OR$^{30}$), —OP(=O)(SR$^{30}$)(SR$^{30}$), —Si(R$^{34}$)$_3$, —SCN, =S, —S(=O)$_n$R$^{30}$, —S(=O)$_2$OR$^{30}$, —SO$_3$R$^{37}$, —S(=O)$_2$NR$^{32}$R$^{33}$, —S(=O)NR$^{32}$R$^{33}$, —SP(=O)R$^{38}$R$^{38}$, —SP(=O)(NR$^{32}$R$^{33}$)(NR$^{32}$R$^{33}$), —SP(=O)(OR$^{30}$)(OR$^{30}$), —SP(=O)(SR$^{30}$)(SR$^{30}$), —P(=O)R$^{38}$R$^{38}$, —P(=O)(NR$^{32}$R$^{33}$)(NR$^{32}$R$^{33}$), —P(=O)(OR$^{30}$)(OR$^{30}$), and —P(=O)(SR$^{30}$)(SR$^{30}$);

R$^{20}$, R$^{21}$, R$^{24}$, R$^{25}$, R$^{26}$, R$^{27}$, R$^{30}$, R$^{31}$, R$^{34}$, R$^{35}$, R$^{36}$ and R$^{37}$ at each occurrence is independently chosen from the group consisting of H, C$_{1-6}$alkyl, C$_{2-6}$alkenyl, C$_{2-6}$alkynyl, C$_{6-11}$aryl, C$_{2-16}$arylalkyl, C$_{3-11}$cycloalkyl, C$_{4-12}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups (except for Hydrogen) may be optionally substituted by 1-10 R$^{19}$;

R$^{28}$ at each occurrence is independently chosen from the group consisting of C$_{1-10}$alkyl, C$_{2-10}$alkenyl, C$_{2-6}$alkynyl, C$_{6-11}$aryl, C$_{2-16}$arylalkyl, C$_{3-11}$cycloalkyl, C$_{4-12}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted by 1-10 R$^{19}$;

R$^{22}$, R$^{23}$, R$^{32}$ and R$^{33}$ at each occurrence is independently chosen from the group consisting of H, C$_{1-6}$alkyl, C$_{2-6}$alkenyl, C$_{2-6}$alkynyl, C$_{6-11}$aryl, C$_{2-16}$arylalkyl, C$_{3-11}$cycloalkyl, C$_{4-17}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups (except for Hydrogen) may be optionally substituted by 1-10 R$^{19}$;

or any R$^{22}$ and R$^{23}$ and/or R$^{32}$ and R$^{33}$ may form, together with the nitrogen atom to which they are attached, a 3-15 membered heterocycloalkyl optionally substituted by 1-10 R$^{19}$ or a 5-15 membered heteroaryl optionally substituted by 1-10 R$^{19}$;

R$^{38}$ at each occurrence is independently chosen from the group consisting of C$_{1-6}$alkyl, C$_{2-6}$alkenyl, C$_{2-6}$alkynyl, C$_{6-11}$aryl, C$_{7-16}$arylalkyl, C$_{3-11}$cycloalkyl, C$_{4-12}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted by 1-10 R$^{19}$;

or any two R³⁸ attached to the same phosphorus atom can, together with the phosphorus atom linking them, form a 3-10 membered heterocycloalkyl optionally substituted by 1-6 R¹⁹;

R³⁹ at each occurrence is independently chosen from the group consisting of $C_{1-6}$alkyl optionally substituted by 1-13 halogen, $C_{2-6}$alkenyl, $C_{2-6}$alkynyl, $C_{6-11}$aryl, $C_{7-16}$arylalkyl, $C_{3-11}$cycloalkyl, $C_{4-12}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R⁴⁰, —C(=O)OR⁴⁰, —C(=O)NR⁴⁰R⁴⁰, —C(=O)C(=O)R⁴⁰, —C(=NR⁴⁰)R⁴⁰, —C(=NR⁴⁰)NR⁴⁰R⁴⁰, —C(=NOH)NR⁴⁰R⁴⁰, —C(=NOR⁴⁰R⁴⁰)R⁴⁰, —C(=NNR⁴⁰R⁴⁰R⁴⁰, —C(=NNR⁴⁰C(=O)R⁴⁰)R⁴⁰, —C(=NNR⁴⁰C(=O)OR⁴⁰)R⁴⁰, —C(=S)NR⁴⁰R⁴⁰, —NC, —NO₂, —NR⁴⁰R⁴⁰, —NR⁴⁰NR⁴⁰R⁴⁰, —N=NR⁴⁰, =NR⁴⁰, =NOR⁴⁰, —NR⁴⁰OR⁴⁰, —NR⁴⁰C(=O)R⁴⁰, —NR⁴⁰C(=O)C(=O)R⁴⁰, —NR⁴⁰C(=O)OR⁴⁰, —NR⁴⁰C(=O)C(=O)OR⁴⁰, —NR⁴⁰C(=O)NR⁴⁰R⁴⁰, —NR⁴⁰C(=O)NR⁴⁰C(=O)R⁴⁰, —NR⁴⁰C(=O)NR⁴⁰C(=O)OR⁴⁰, —NR⁴⁰C(=NR⁴⁰)NR⁴⁰R⁴⁰, —NR⁴⁰C(=O)C(=O)NR⁴⁰R⁴⁰, —NR⁴⁰C(=S)R⁴⁰, —NR⁴⁰C(=S)OR⁴⁰, —NR⁴⁰C(=S)NR⁴⁰R⁴⁰, —NR⁴⁰S(=O)₂R⁴⁰, —NR⁴⁰S(=O)₂NR⁴⁰R⁴⁰, —NR⁴⁰P(=O)R⁴¹R⁴¹, —NR⁴⁰P(=O)(NR⁴⁰R⁴⁰)(NR⁴⁰R⁴⁰), —NR⁴⁰P(=O)(OR⁴⁰)(OR⁴⁰), —NR⁴⁰P(=O)(SR⁴⁰)(SR⁴⁰), —OR⁴⁰, =O, —OCN, —OC(=O)R⁴⁰, —OC(=O)NR⁴⁰R⁴⁰, —OC(=O)OR⁴⁰, —OC(=NR⁴⁰)NR⁴⁰R⁴⁰, —OS(=O)R⁴⁰, —OS(=O)₂R⁴⁰, —OS(=O)₂OR⁴⁰, —OS(=O)₂NR⁴⁰R⁴⁰, —OP(=O)R⁴¹R⁴¹, —OP(=O)(NR⁴⁰R⁴⁰)(NR⁴⁰R⁴⁰), —OP(=O)(OR⁴⁰)(OR⁴⁰), —OP(=O)(SR⁴⁰)(SR⁴⁰), —Si(R⁴⁰)₃, —SCN, =S, —S(=O)—R⁴⁰, —S(=O)₂OR⁴⁰, —SO₃R⁴⁰, —S(=O)₂NR⁴⁰R⁴⁰, —S(=O)NR⁴⁰R⁴⁰, —SP(=O)R⁴¹R⁴¹, —SP(=O)(NR⁴⁰R⁴⁰)(NR⁴⁰R⁴⁰), —SP(=O)(OR⁴⁰)(OR⁴⁰), —SP(=O)(SR⁴⁰)(SR⁴⁰), —P(=O)R⁴¹R⁴¹, —P(=O)(NR⁴⁰R⁴⁰)(NR⁴⁰R⁴⁰), —P(=O)(OR⁴⁰)(OR⁴⁰), and —P(=O)(SR⁴⁰)(SR⁴⁰);

R⁴⁰ at each occurrence is independently chosen from the group consisting of H, $C_{1-6}$alkyl and $C_{1-6}$-haloalkyl;

R⁴¹ at each occurrence is independently chosen from the group consisting of $C_{1-6}$alkyl and $C_{1-6}$-haloalkyl; and n at each occurrence is independently chosen from the group consisting of 0, 1, and 2.

Embodiment 2

A compound according to embodiment 1 wherein R¹ is optionally substituted cyclopropyl.

Embodiment 3

A compound according to embodiment 1 wherein R¹ is optionally substituted cyclobutyl.

Embodiment 4A

A compound according to embodiment 1 wherein R¹ is $C_{1-6}$-haloalkyl.

Embodiment 4B

A compound according to embodiment 1 wherein R¹ is —O$C_{1-6}$alkyl.

Embodiment 5

A compound according to any of embodiments 1 through 4 wherein G is

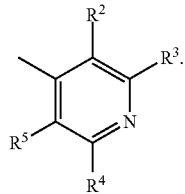

Embodiment 6

A compound according to any of embodiments 1 through 4 wherein G is

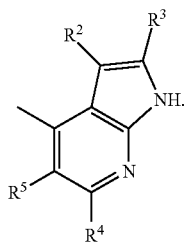

Embodiment 7

A compound according to any of embodiments 1 through 4 wherein
G is

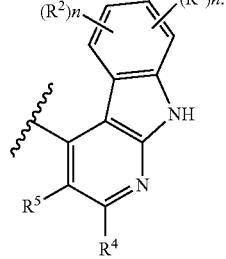

Embodiment 8

A compound according to any of embodiments 1 through 7, wherein X is chosen from the group consisting of 3-10 membered heterocycloalkyl optionally substituted by 1-6 R¹⁹, 5-10 membered heteroaryl optionally substituted by 1-6 R¹⁹, —C(=O)R²⁸, —C(=O)NR²⁴R²⁸, —NR²⁴R²⁸, —NR²⁴C(=O)R²⁸, —NR²⁴S(=O)₂R²⁸, —OC(=O)OR²⁸, —OS(=O)R²⁸, —OS(=O)₂R²⁸, and —OR²⁸.

Embodiment 9

A compound according to embodiment 8, wherein X is chosen from the group consisting of 3-10 membered heterocycloalkyl optionally substituted by 1-6 R¹⁹, 5-10 membered heteroaryl optionally substituted by 1-6 R¹⁹, and —OR²⁸.

Embodiment 10

A compound according to any of embodiments 1 through 9, wherein $R^2$ and $R^3$ are each independently chosen from the group consisting of H, halogen, —CN, —C(=O)$R^{20}$, —C(=O)O$R^{20}$, —C(=O)N$R^{22}R^{23}$, —C(=O)C(=O)$R^{20}$, —C(=N$R^{25}$)$R^{20}$, —C(=N$R^{25}$)N$R^{22}R^{23}$, —C(=NOH)N$R^{22}R^{23}$, —C(=NO$R^{26}$)$R^{20}$, —C(=NN$R^{22}R^{23}$)$R^{20}$, —C(=NN$R^{24}$C(=O)$R^{21}$)$R^{20}$, —C(=NN$R^{24}$C(=O)O$R^{21}$)$R^{20}$, —C(=S)N$R^{22}R^{23}$, —NC, —NO$_2$, —N$R^{22}R^{23}$, —N$R^{24}$N$R^{22}R^{23}$, —N=N$R^{24}$, —N$R^{24}$O$R^{26}$, —N$R^{24}$C(=O)$R^{20}$, —N$R^{24}$C(=O)C(=O)$R^{20}$, —N$R^{24}$C(=O)O$R^{21}$, —N$R^{24}$C(=O)C(=O)O$R^{21}$, —N$R^{24}$C(=O)N$R^{22}R^{23}$, —N$R^{24}$C(=O)N$R^{24}$C(=O)$R^{20}$, —N$R^{24}$C(=O)N$R^{24}$C(=O)O$R^{20}$, —N$R^{24}$C(=N$R^{25}$)N$R^{22}R^{23}$, —N$R^{24}$C(=O)C(=O)N$R^{22}R^{23}$, —N$R^{24}$C(=S)$R^{20}$, —N$R^{24}$C(=S)O$R^{20}$, —N$R^{24}$C(=S)N$R^{22}R^{23}$, —N$R^{24}$S(=O)$_2R^{21}$, —N$R^{24}$S(=O)$_2$N$R^{22}R^{23}$, —N$R^{24}$P(=O)$R^{38}R^{38}$, —N$R^{24}$P(=O)(N$R^{22}R^{23}$)(N$R^{22}R^{23}$), —O$R^{20}$, —OCN, —OC(=O)$R^{20}$, —OC(=O)N$R^{22}R^{23}$, —OC(=O)O$R^{20}$, —OC(=N$R^{25}$)N$R^{22}R^{23}$, —OS(=O)$R^{20}$, —OS(=O)$_2R^{20}$, —OS(=O)$_2$O$R^{20}$, —OS(=O)$_2$N$R^{22}R^{23}$, —S(=O)$_nR^{20}$, —S(=O)$_2$O$R^{20}$, —SO$_3R^{27}$, —S(=O)$_2$N$R^{22}R^{23}$, and —S(=O)N$R^{22}R^{23}$; or $R^2$ and $R^3$ are each independently chosen from the group consisting of $C_{1-6}$alkyl, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted with 1-10 $R^{19}$.

Embodiment 11

A compound according to embodiment 10 wherein $R^2$ and $R^3$ are each independently chosen from the group consisting of H, halogen, —S(=O)—$R^{20}$, —C(=O)N$R^{22}R^{23}$, N$R^{24}$S(=O)$_2R^{21}$, and —N$R^{22}R^{23}$; or $R^2$ and $R^3$ are each independently chosen from the group consisting of $C_{1-6}$alkyl, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted with 1-10 $R^{19}$.

Embodiment 12

A compound according to any of embodiments 1 through 9, wherein $R^2$ and $R^3$ are taken together with the atoms to which they are attached to form a $C_{6-11}$aryl, $C_{3-11}$cycloalkyl, 3-15 membered heterocycloalkyl or a 5-15 membered heteroaryl wherein each of the foregoing groups may be optionally substituted by 1-10 $R^{19}$.

Embodiment 13

A compound according to embodiment 1 wherein $R^1$ is optionally substituted cyclopropyl and G is

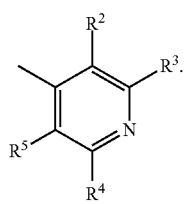

Embodiment 14

A compound according to embodiment 1 wherein $R^1$ is optionally substituted cyclobutyl and G is

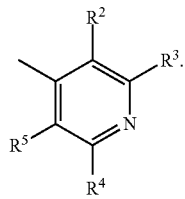

Embodiment 15

A compound according to embodiment 1 wherein $R^1$ is optionally substituted cyclopropyl and G is

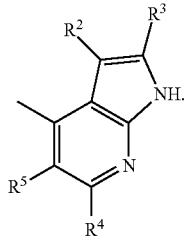

Embodiment 16

A compound according to embodiment 1 wherein $R^1$ is optionally substituted cyclobutyl and G is

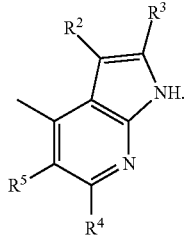

Embodiment 17

A compound according to embodiment 1 wherein $R^1$ is optionally substituted cyclopropyl and G is

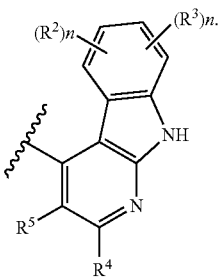

Embodiment 18

A compound according to embodiment 1 wherein $R^1$ is optionally substituted cyclobutyl and G is

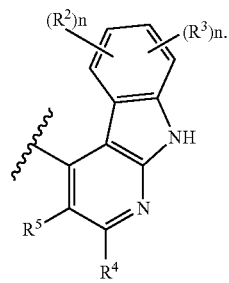

Embodiment 19

A compound according to embodiment 1 wherein $R^1$ is $C_{1-6}$-haloalkyl and G is

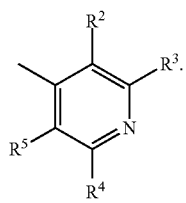

Embodiment 20

A compound according to embodiment 1 wherein $R^1$ is $C_{1-6}$-haloalkyl and G is

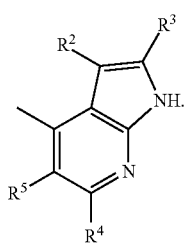

Embodiment 21

A compound according to embodiment 1 wherein $R^1$ is $C_{1-6}$-haloalkyl and G is

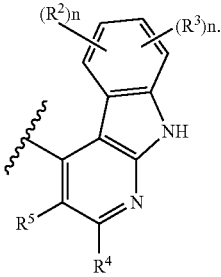

Embodiment 22

A compound according to any of embodiments 19 through 21 wherein $R^1$ is trifluoromethyl.

Embodiment 23

A compound according to any of embodiments 13 through 22 wherein X is chosen from the group consisting of 3-10 membered heterocycloalkyl optionally substituted by 1-6 $R^{19}$, 5-10 membered heteroaryl optionally substituted by 1-6 $R^{19}$, —C(=O)$R^{28}$, —C(=O)$NR^{24}R^{28}$, —$NR^{24}R^{28}$, —$NR^{24}$C(=O)$R^{28}$, —$NR^{24}$S(=O)$_2R^{28}$, —OC(=O)$OR^{28}$, —OS(=O)$R^{28}$, —OS(=O)$_2R^{28}$, and —$OR^{28}$.

Embodiment 24

A compound according to any of embodiments 1, 17, 18 and 21 wherein $R^2$, $R^3$, $R^4$ and $R^5$ are all H.

Embodiment 25

A compound according to any of embodiments 1 though 23 wherein $R^4$ and $R^5$ are H.

Embodiment 26

A compound according to any of embodiments 13 through 23 wherein $R^2$ and $R^3$ are each independently chosen from the group consisting of H, halogen, —S(=O)—$R^{20}$, —C(O)$NR^{22}R^{23}$, $NR^{24}$S(=O)$_2R^{21}$, and —$NR^{22}R^{23}$; or $R^2$ and $R^3$ are each independently chosen from the group consisting of $C_{1-6}$alkyl, $C_{2-6}$alkenyl, $C_{2-6}$alkynyl, $C_{6-11}$aryl, $C_{2-16}$arylalkyl, $C_{3-11}$cycloalkyl, $C_{4-12}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted with 1-10 $R^{19}$.

Embodiment 27

A compound according to embodiment 26 wherein $R^4$ and $R^5$ are H.

Embodiment 28

A compound according to any of the preceeding embodiments 1 through 27, wherein X is chosen from the group consisting of:

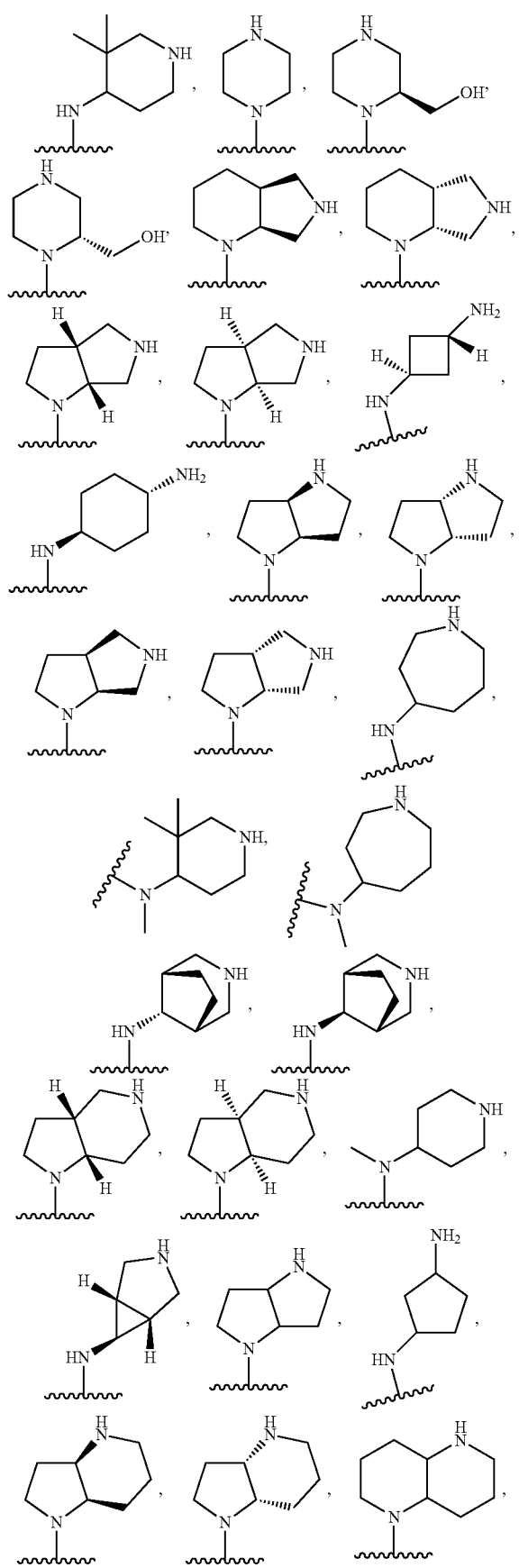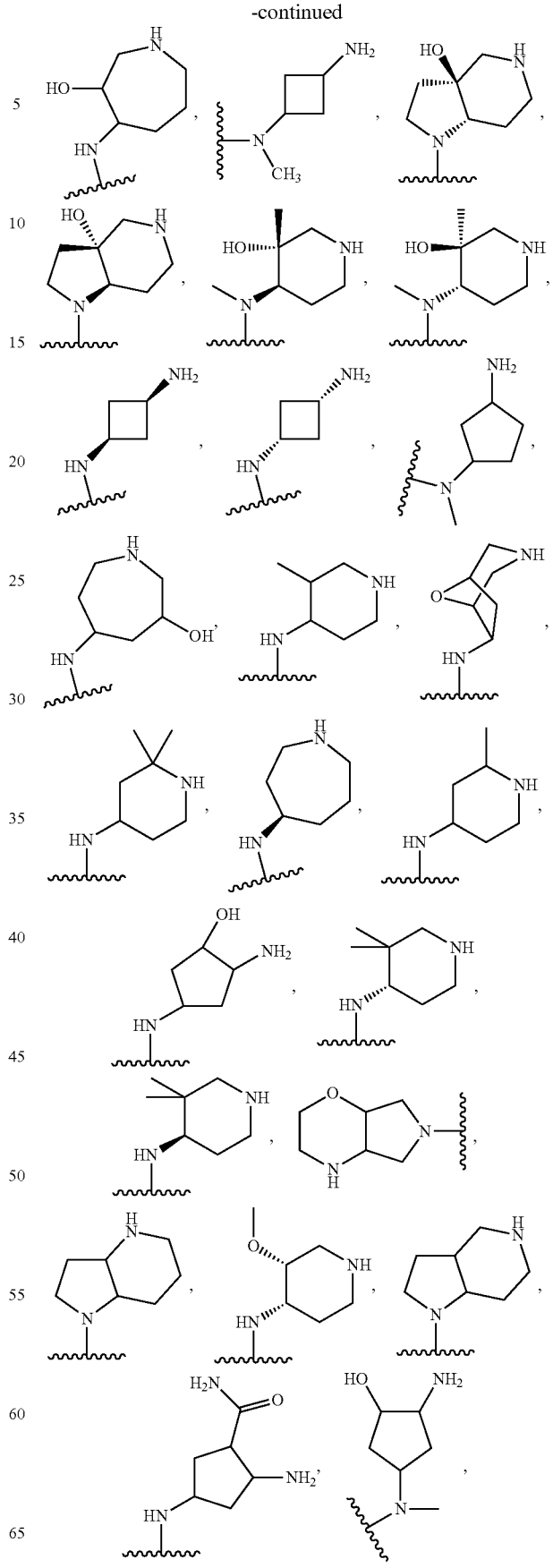

-continued
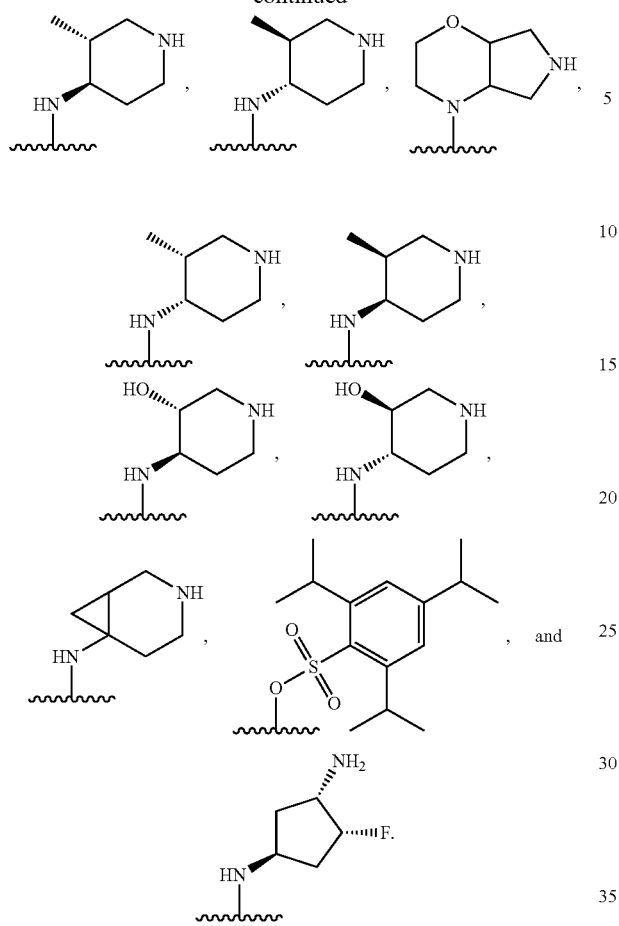
Embodiment 29
A compound according to any of the preceeding embodiments 1 through 28 wherein $R^2$ and $R^3$ are each independently chosen from the group consisting of:
-continued
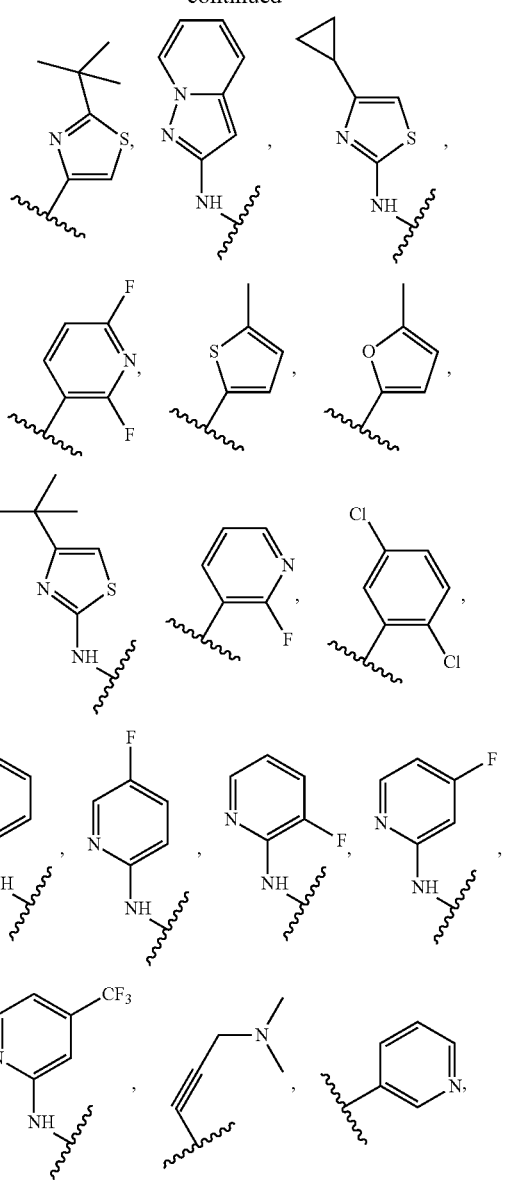
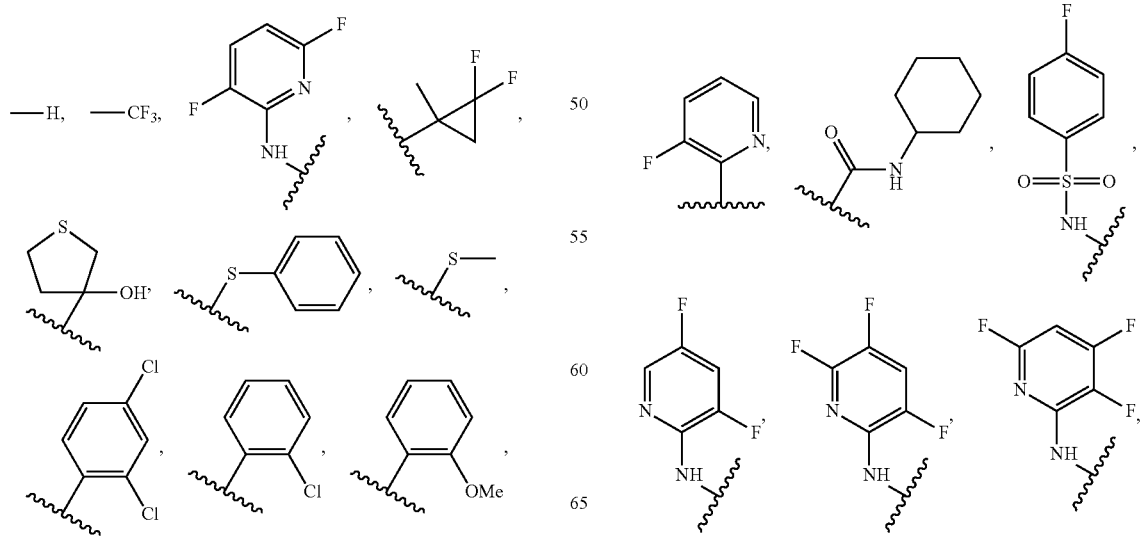

-continued

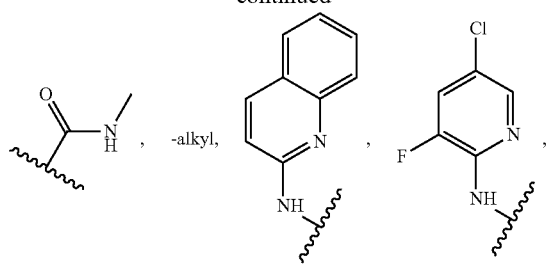

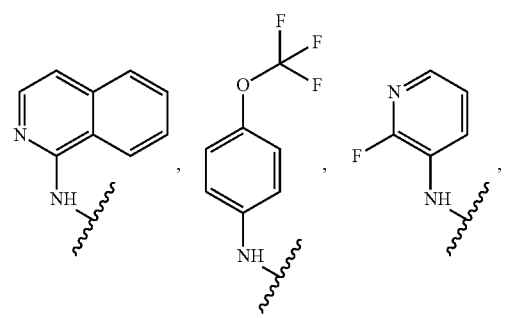

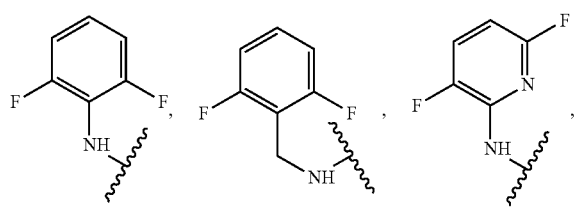

—SO₂alkyl, -halogen,

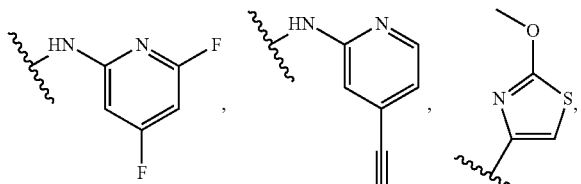

—S(alkyl),

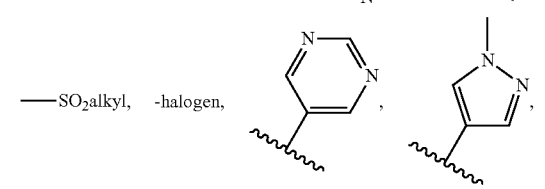

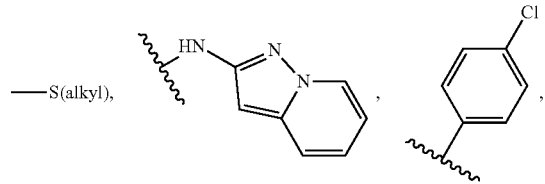

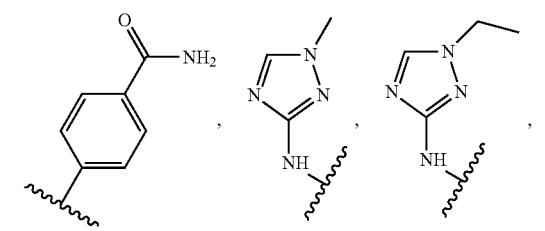

-continued

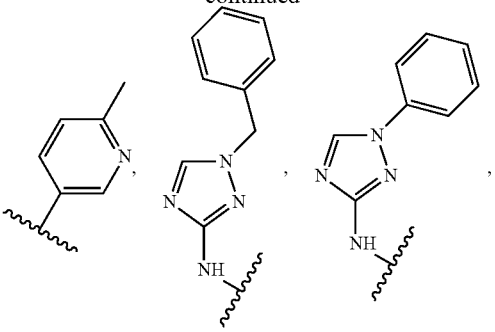

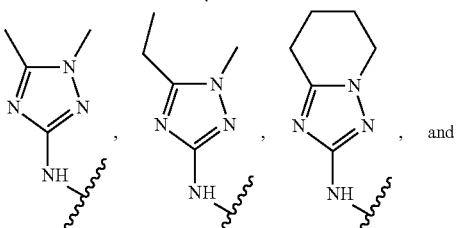

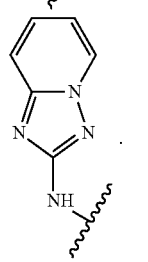

Embodiment 30

A compound according to any of the preceding embodiments 1 through 29 wherein the compound is chosen from the group consisting of those compounds listed in Table A.

The above Embodiments include salts of acidic and basic compounds of formula (I). Preferably, the salts are pharmaceutically acceptable. Pharmaceutically acceptable acid addition salts of basic compounds of formula (I) include, but are not limited to, salts derived from inorganic acids such as hydrochloric, nitric, phosphoric, sulfuric, hydrobromic, hydriodic, and phosphorus, as well as the salts derived from organic acids, such as aliphatic mono- and dicarboxylic acids, phenyl-substituted alkanoic acids, hydroxy alkanoic acids, alkanedioic acids, aromatic acids, and aliphatic and aromatic sulfonic acids. Such salts thus include, but are not limited to, sulfate, pyrosulfate, bisulfate, sulfite, bisulfate, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, and methanesulfonate. See, for example, Berge et al., "Pharmaceutical Salts," J. of Pharmaceutical Science, 1977; 66:1-19.

Acid addition salts may be prepared by contacting a compound of formula (I) with a sufficient amount of the desired acid to produce the salt in the conventional manner. The free base form of the compound of formula (I) may be regenerated by contacting the salt form with a base and isolating the free base in the conventional manner.

Pharmaceutically acceptable base salts of acidic compounds of formula (I) are formed with metals or amines, such as alkali and alkaline earth metal hydroxides, or of organic amines. Examples of metals used as cations include, but are not limited to, sodium, potassium, magnesium, and calcium. Examples of suitable amines include, but are not limited to, N,N'-dibenzylethylenediamine, chloroprocaine, choline, diethanolamine, ethylenediamine (ethane-1,2-diamine), N-methylglucamine, and procaine. See, for example, Berge et al., "Pharmaceutical Salts," J. of Pharmaceutical Science, 1977; 66:1-19.

Base salts may be prepared by contacting a compound of formula (I) with a sufficient amount of the desired base to produce the salt in the conventional manner. The acid form of the compound of formula (I) may be regenerated by contacting the salt form with an acid and isolating the acid in a conventional manner.

Some compounds of the present application may exist as stereoisomers, including enantiomers, diastereomers, and geometric isomers. Geometric isomers include compounds of the present application that have alkenyl groups, which may exist as entgegen or zusammen conformations, in which case all geometric forms thereof, both entgegen and zusammen, cis and trans, and mixtures thereof, are within the scope of the present application. Some compounds of the present application have cycloalkyl groups, which may be substituted at more than one carbon atom, in which case all geometric forms thereof, both cis and trans, and mixtures thereof, are within the scope of the present application. All of these forms, including (R), (S), epimers, diastereomers, cis, trans, syn, anti, (E), (Z), tautomers, and mixtures thereof, are included in the compounds of the present application.

III. Pharmaceutical Compositions

The present application further provides compositions comprising a compound of any of the above Embodiments (e.g., a compound of formula (I) and/or a pharmaceutically acceptable salt thereof), together with a pharmaceutically acceptable excipient. In some embodiments such compositions are suitable for pharmaceutical use. Such compositions may be referred to as pharmaceutical compositions. In preparing a pharmaceutical composition from a compound of the present application, pharmaceutically acceptable excipients can be either solid or liquid. An excipient can be one or more substances which may act as, e.g., a carrier, diluent, flavoring agent, binder, preservative, tablet disintegrating agent, or an encapsulating material. It should be understood that when the term "excipient" is used in this application, that the term can denote any of a carrier, diluent, flavoring agent, binder, preservative, tablet disintegrating agent, or an encapsulating material. When the term excipient used in conjunction with the phrase "at least one" it should be understood that one or more excipients may be present in the composition and that if there is more than one excipient present that the excipients may be of the same general type (i.e., two or more binders) or different types (i.e., a diluent and a preservative). The pharmaceutical composition may contain two or more compounds of the present application (e.g., two different salt forms of a compound of formula (I), may be used together in the same pharmaceutical composition or a single composition may contain a mixture of a non-salt and a salt form of the same compound). Preferably, the pharmaceutical composition contains a therapeutically effective amount of a compound of formula (I) and/or a pharmaceutically acceptable salt thereof. In one embodiment, the composition contains an amount of a compound of formula (I) and/or a pharmaceutically acceptable salt thereof effective to treat an atypical protein kinase C (aPKC)-dependent disorder or condition. Preferably, a compound of the present application will cause a decrease in symptoms or disease indicia associated with an aPKC-dependent disorder as measured quantitatively or qualitatively. The composition may also contain, in addition to a compound of formula (I) or a pharmaceutically acceptable salt thereof and a pharmaceutically acceptable excipient, another therapeutic compound, such as a compound useful in the treatment of cancer.

A compound of the present application can be formulated as a pharmaceutical composition in any delivery form, such as a syrup, an elixir, a suspension, a powder, a granule, a tablet, a capsule, a lozenge, a troche, an aqueous solution, a cream, an ointment, a lotion, a gel, an emulsion, etc. Solid form preparations include powders, tablets, pills, capsules, cachets, suppositories, and dispersible granules. Preferably, the pharmaceutical composition is a tablet or capsule. In one embodiment, the pharmaceutical composition is a tablet. In another embodiment, the pharmaceutical composition is a capsule.

In powders, the excipient may be a finely divided solid in a mixture with a finely divided active component (i.e., compound of the present application). In tablets, the active component may be mixed with an excipient having the necessary binding properties in suitable proportions and compacted in the shape and size desired. Suitable excipients include magnesium carbonate, magnesium stearate, talc, sugar, lactose, pectin, dextrin, starch, gelatin, tragacanth, methylcellulose, sodium carboxymethylcellulose, low melting wax, cocoa butter, and the like.

The pharmaceutical composition preferably contains from 1% to 95% (w/w) of the active compound (i.e., compound of the present application). More preferably, the pharmaceutical composition contains from 5% to 70% (w/w) of the active compound.

For preparing suppositories, a low melting wax, such as a mixture of fatty acid glycerides or cocoa butter, may be melted and the active component dispersed homogeneously therein, as by stirring. The molten homogeneous mixture may then be poured into convenient sized molds, allowed to cool, and thereby to solidify.

Liquid form preparations include solutions, suspensions, and emulsions. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of the subject matter of this application, compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

A compound of the present application, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Pharmaceutically acceptable excipients are determined in part by the particular composition being administered, as well as by the particular method used to administer the composition. Accordingly, there is a wide variety of suitable formulations of pharmaceutical compositions of the present application (see, e.g., *Remington: The Science and Practice of Pharmacy,* 20th ed., Gennaro et al. Eds., Lippincott Williams and Wilkins, 2000).

The quantity of active component in a pharmaceutical composition may be varied or adjusted from, e.g., 1 mg to 1,000 mg, 5 mg to 500 mg, 10 mg to 300 mg, or 25 mg to 250 mg, according to the particular application and the desired size of the dosage form.

The dose administered to a subject is preferably sufficient to induce a beneficial therapeutic response in the subject over time. The beneficial dose can vary from subject to subject depending upon, e.g., the subject's condition, body weight, surface area, and side effect susceptibility. Administration can be accomplished via single or divided doses.

IV. Method of Treatment

In another aspect, the present application provides a method of treating an aPKC-dependent disorder or condition in a subject comprising: administering to the subject a compound of formula (I) as defined in any of the above Embodiments and/or a pharmaceutically acceptable salt thereof. In another aspect, the present application provides a compound of formula (I) as defined in any of the above Embodiments and/or a pharmaceutically acceptable salt thereof for use in treating an aPKC-dependent disorder or condition in a subject. In another aspect, the present application provides a compound of formula (I) as defined in any of the above Embodiments and/or a pharmaceutically acceptable salt thereof for use in the preparation of a medicament for treating an aPKC-dependent disorder or condition in a subject. Preferably, the compound is administered to the subject as a pharmaceutical composition comprising a pharmaceutically acceptable excipient. Preferably, the compound is administered to the subject in a pharmaceutically acceptable amount. In one embodiment, the aPKC-dependent condition or disorder is cancer. In another embodiment, the aPKC-dependent condition is selected from non-small cell lung cancer (NSCLC), squamous cell carcinoma (e.g., oesophageal squamous cell carcinoma), leukaemia, prostate cancer, non-Hodgkin's lymphoma (e.g., follicular lymphoma), endometrial cancer, lung cancer and breast cancer.

The aPKC-dependent disorder or condition can be treated prophylactically, acutely, or chronically using compounds of the present application, depending on the nature of the disorder or condition. Typically, the subject in each of these methods is human, although other mammals can also benefit from the administration of a compound of the present application. It should be understood that the subject to be treated by any of the methods described herein is in recognized need of such treatment.

In another embodiment, the present application provides a method of treating a proliferative disorder in a subject, comprising administering to the subject a compound of formula (I) as defined in any of the above Embodiments and/or a pharmaceutically acceptable salt thereof. In another aspect, the present application provides a compound of formula (I) as defined in any of the above Embodiments and/or a pharmaceutically acceptable salt thereof for use in treating a proliferative disorder in a subject. In another aspect, the present application provides a compound of formula (I) as defined in any of the above Embodiments and/or a pharmaceutically acceptable salt thereof for use in the preparation of a medicament for treating a proliferative disorder in a subject. Preferably, the compound and/or salt thereof is administered to the subject in a pharmaceutical composition comprising a pharmaceutically acceptable excipient. Preferably, the compound and/or salt thereof is administered to the subject in a pharmaceutically acceptable amount. In certain embodiments, the proliferative disorder is aPKC-dependent. In certain embodiments, the proliferative disorder is cancer. In certain embodiments, the proliferative disorder is selected from non-small cell lung cancer (NSCLC), squamous cell carcinoma (e.g., oesophageal squamous cell carcinoma), leukaemia, prostate cancer, non-Hodgkin's lymphoma (e.g., follicular lymphoma), endometrial cancer, lung cancer and breast cancer.

The proliferative disorder can be treated prophylactically, acutely, or chronically using a compound of the present application, depending on the nature of the disorder or condition. Typically, the subject in each of these methods is human, although other mammals can also benefit from the administration of a compound of the present application.

In therapeutic applications, the compounds of the present application can be prepared and administered in a wide variety of oral and parenteral dosage forms. Thus, the compounds of the present application can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present application can be administered transdermally. In another embodiment, the compounds of the present application are delivered orally. The compounds can also be delivered rectally, bucally or by insufflation.

Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired. A typical dose is about 1 mg to about 1,000 mg per day, such as about 5 mg to about 500 mg per day. In certain embodiments, the dose is about 10 mg to about 300 mg per day, such as about 25 mg to about 250 mg per day.

V. Chemistry

Abbreviations

For convenience, the following common abbreviations are used herein:
LCMS for Liquid Chromatography-Mass Spectrometry.
HPLC for High Pressure Liquid Chromatography.
NMR for Nuclear Magnetic Resonance.
RT for Retention Time.
MI for Molecular Ion
h for hours
min for minutes
$AlCl_3$ for aluminium chloride
$BBr_3$ for boron tribromide
Boc for tert-butoxycarbonyl cataCXium C for trans-Bis(acetato)bis[o-(di-o-tolylphosphino)benzyl]dipalladium(II).
Cs$_2$CO$_3$ for cesium carbonate
CuI for copper(I)iodide
DAST for diethylaminosulfur trifluoride
DBU for 1,8-diazabicyclo(5.4.0)undec-7-ene
DMAP for 4-(dimethylamino) pyridine
DCE for 1,1-dichloroethane or ethylidene chloride
DCM for dichloromethane or methylene chloride
DEA for diethanolamine
DIPEA for N,N,-di-isopropyethylamine, Hunig's base
DMA for N,N-dimethylacetamide
DMF for N,N-dimethylformamide
DMSO for dimethylsulfoxide.
Et$_3$N for triethylamine
EtOH for ethyl alcohol, ethanol
Ex for example
HCl for hydrochloric acid
H$_2$SO$_4$ for sulfuric acid
Int for intermediate
KOH for potassium hydroxide
MW for microwave
mCPBA for meta-Chloroperoxybenzoic acid
MeOH for methyl alcohol, methanol
Mo(CO)$_6$ for Molybdenum hexacarbonyl
MP-BH$_4$ for macroporous triethylammonium methyl polystyrene borohydride
NaOH for sodium hydroxide
Na$_2$CO$_3$ for sodium carbonate
Na$_2$SO$_4$ for sodium sulphate
NaOAc for sodium acetate
NaOtBu for sodium t-butoxide
NMP for 1-methyl-2-pyrrolidinone
NMM for N-methylmorpholine
Pd(dba)$_2$ for Bis(dibenzylideneacetone)palladium
Pd(OAc)$_2$ for Palladium diacetate
Pd(Ph$_3$)$_4$ for tetrakis(triphenylphosphine)palladium
Pd(PPh$_3$)$_2$Cl$_2$ for Bis(triphenylphosphine)palladium(II) dichloride
POCl$_3$ for phosphorus oxychloride
PPh$_3$ for triphenylphosphine
PS-TsCl for polystyrene sulfonyl chloride
PS-PPh$_3$-Pd for polystyrene triphenylphosphine-Pd(0)
SCX-2 for a silica-based sorbent with a chemically bonded propylsulfonic acid functional group
TBAF for Tetra-n-butylammonium fluoride
TBDMS for tert-butyldimethylsilyl
TCA for trichloroacetic acid
TFA for trifluoroacetic acid
THF for tetrahydrofuran
TMS azide for trimethylsilyl azide
Xantphos for 4,5-Bis(diphenylphosphino)-9,9-dimethylxanthene
XPhos for 2-Dicyclohexylphosphino-2',4',6'-triisopropylbiphenyl LCMS Methods Samples analysed by High Performance Liquid Chromatography-Mass Spectrometry employed the following conditions. Unless otherwise noted, Method X was utilized.

Method 1

Method 1 employed Gilson 306 pumps, Gilson 811C mixer, Gilson 806 manometric module, and Gilson UV/VIS 152 detector at 254 nm wavelength. The mass spectrometer was a Finnigan AQA and the column used was a Waters SunFire, 5 μm pore size, C18 of dimensions 50×4.60 mm. The injection volume was 10 μl. The mobile phase consisted of a mixture of water and acetonitrile containing 0.1% formic acid. The eluent flow rate was 1.5 mL/min, using 95% water: 5% acetonitrile, changed linearly to 5% water: 95% acetonitrile over 5.5 minutes and then maintained at this mixture for 2 minutes.

Method 2

Method 2 employed Waters 515 pumps, a Waters 2525 mixer and a Waters 2996 diode array detector. The detection was performed between 210 nm and 650 nm. The mass spectrometer was a Waters micromass ZQ and the column used was a Waters SunFire, 5 μm pore size, C18 of dimensions 50×4.60 mm. The injection volume was 10 μl. The mobile phase consisted of a mixture of water and acetonitrile containing 0.1% formic acid. The eluent flow rate was 1.5 mL/min, using 95% water: 5% acetonitrile, changed linearly to 5% water: 95% acetonitrile over 5.5 minutes and then maintained at this mixture for 2 minutes.

Method 3

Method 3 employed Waters 515 pumps, a Waters 2525 mixer and a Waters 2487 UV detector (single wavelength 254 nm). The mass spectrometer was a Waters micromass ZQ and the column used was a Waters SunFire, 5 μm pore size, C18 of dimensions 50×4.60 mm. The injection volume was 10 μl. The mobile phase consisted of a mixture of water and acetonitrile containing 0.1% formic acid. The eluent flow rate was 1.5 mL/min, using 95% water: 5% acetonitrile, changed linearly to 5% water: 95% acetonitrile over 5.5 minutes and then maintained at this mixture for 2 minutes.

Method 4

Method 4 employed Waters 515 pumps, a Waters 2545 mixer with valves directing to the different columns and a Waters 2996 diode array detector. The detection was performed between 210 nm and 650 nm. The mass spectrometer used was a Waters 3100 which detected masses between 100 and 700 g/mol. The column used was a XBridge, 5 micron pore size, C18, 50×4.60 mm. The injection volume was 10 μl of a solution (around 1 mg/ml). The flow rate was 1.5 mL/min and the mobile phases of water pH 10 0.03% ammonium hydroxide) (3 ml/10 l) and acetonitrile 0.03% ammonium hydroxide (3 ml/10 l). The elution was started at 95% water: 5% acetonitrile ramping up to 5% water:95% acetonitrile over 5.50 minutes. The eluent level was returned to the starting conditions of 95% water: 5% acetonitrile over 6 seconds. These conditions were held for 1.4 minutes to allow equilibration of the column before the next sample was injected. The run lasted 7 minutes in total.

Method 5

Method 5 employed Waters 515 pumps, a Waters 2525 mixer with valves directing to the different columns and a Waters 2487 UV detector. The detection was done between at 254 nm. The mass spectrometer used was a Waters micromass ZQ which detected masses between 100 and 700 g/mol. The column used was a SunFire, 5 micron pore size, C18 column of dimensions 50×4.60 mm was used. The injection volume was 10 μL of a solution (around 1 mg/mL). The flow rate was 1.5 mL/min and the mobile phases of water and methanol contained 0.1% formic acid. The elution was started at 85% water:15% methanol ramping up to 15% water:85% methanol over 4.5 minutes, these conditions were held for 1 minute before the eluent level was returned to the starting conditions of 85% water:15% methanol over 6 seconds. These conditions were held for 1.4 minutes to allow equilibration of the column before the next sample was injected. The run lasted 7 minutes in total.

Method 6

Method 6 employed Waters 515 pumps, a Waters 2545 mixer with valves directing to the different columns and a Waters 2996 diode array detector. The detection was done between 210 nm and 650 nm. The mass spectrometer used was a Waters 3100 which detected masses between 100 and 700 g/mol. The column used was a XBridge, 5 micron pore size, C18, 50×4.60 mm. The injection volume was 10 µL of a solution (around 1 mg/mL). The flow rate was 1.5 mL/min and the mobile phases of water pH 10 0.03% ammonium hydroxide) (3 ml/10 l) and methanol 0.03% ammonium hydroxide (3 ml/10 l). The elution was started at 85% water:15% methanol ramping up to 15% water:85% methanol over 4.5 minutes. These conditions were held for 1 minute before the eluent level was returned to the starting conditions of 85% water:15% methanol over 6 seconds. These conditions were held for 1.4 minutes to allow equilibration of the column before the next sample was injected. The run lasted 7 minutes in total.

Method 7

Method 7 employed Waters 515 pumps, a Waters 2545 mixer with valves directing to the different columns and a Waters 2487 UV detector. The detection was done between at 254 nm. The mass spectrometer used was a Waters micromass ZQ which detected masses between 100 and 700 g/mol. The column used was a SunFire, 5 micron pore size, C18 column of dimensions 50×4.60 mm was used. The injection volume was 10 µL of a solution (around 1 mg/mL). The flow rate was 1.5 mL/min and the mobile phases of water and methanol contained 0.1% formic acid. The elution was started at 85% water:15% methanol ramping up to 15% water:85% methanol over 4.5 minutes., these conditions were held for 1 minute before the eluent level was returned to the starting conditions of 85% water:15% methanol over 6 seconds. These conditions were held for 1.4 minutes to allow equilibration of the column before the next sample was injected. The run lasted 7 minutes in total.

Method 8

Method 8 employed Waters 515 pumps, a Waters 2525 mixer with valves directing to the different columns and a Waters 2487 UV detector. The detection was done between at 254 nm. The mass spectrometer used was a Waters micromass ZQ which detected masses between 100 and 700 g/mol. The column used was a SunFire, 5 micron pore size, C18 column of dimensions 50×4.60 mm was used. The injection volume was 10 µL of a solution (around 1 mg/mL). The flow rate was 1.5 mL/min and the mobile phases of water and methanol contained 0.1% formic acid. The elution was started at 85% water:15% methanol ramping up to 15% water:85% methanol over 3 minutes., these conditions were held for 2.5 minute before the eluent level was returned to the starting conditions of 85% water:15% methanol over 6 seconds. These conditions were held for 1.4 minutes to allow equilibration of the column before the next sample was injected. The run lasted 7 minutes in total.

Method 9

Method 9 employed Waters 515 pumps, a Waters 2545 mixer with valves directing to the different columns and a Waters 2487 UV detector. The detection was done between at 254 nm. The mass spectrometer used was a Waters micromass ZQ which detected masses between 100 and 700 g/mol. The column used was a XBridge, 5 micron pore size, C18, 50×4.60 mm. The injection volume was 10 µL of a solution (around 1 mg/mL). The flow rate was 1.5 mL/min and the mobile phases of water pH 10 0.03% ammonium hydroxide) (3 ml/10 l) and methanol 0.03% ammonium hydroxide (3 ml/10 l). The elution was started at 85% water:15% methanol ramping up to 15% water:85% methanol over 4.5 minutes. These conditions were held for 1 minute before the eluent level was returned to the starting conditions of 85% water:15% methanol over 6 seconds. These conditions were held for 1.4 minutes to allow equilibration of the column before the next sample was injected. The run lasted 7 minutes in total.

Method 10

LCMS results were obtained on either of two instruments. LCMS analysis was performed on a Waters Aquity Ultra Performance LC with a 2.1 mm×50 mm Waters Aquity UPLC BEH C18 1.7 µm column. The target column temperature was 45° C., with a run time of two (2) minutes, a flow rate of 0.600 mL/min, and a solvent mixture of 5% (0.1% formic acid/water):95% (acetonitrile/0.1% formic acid). The mass spectrometry data was acquired on a Micromass LC-ZQ 2000 quadrupole mass spectrometer. Alternatively, LCMS analysis was performed on a Bruker Esquire 200 ion trap.

Preparative HPLC Methods

Samples purified by Mass Spectrometry directed High Performance Liquid Chromatography employed the following conditions.

Method A

Method A employed Waters 515 pumps, a Waters 2525 mixer and a Waters 2487 UV detector (single wavelength 254 nm). The mass spectrometer was a Waters micromass ZQ and the column used was a Waters SunFire, 5 µm pore size, C18 of dimensions 50×19 mm. The injection volume was up to 500 µL of solution at a maximum concentration of 50 mg/mL. The mobile phase consisted of a mixture of water and acetonitrile containing 0.1% formic acid. The eluent flow rate was 25 mL/min using 95% water, 5% acetonitrile, changing linearly over 5.3 minutes to 95% acetonitrile, 5% water, and maintaining for 0.5 minutes.

Method B

Method B employed Waters 515 pumps a Waters 2545 mixer with valves directing to the different columns and a Waters 2996 diode array detector. The detection was performed between 210 nm and 650 nm. The mass spectrometer used was a Waters 3100 which detected masses between 100 and 700 g/mol. The column used was a XBridge, 5 micron pore size, C18, 50×19 mm. The injection volume was chosen by the user and can be up to 500 µL of the solution (max 50 mg/mL). The flow rate was 25 mL/min and the mobile phases of water pH 10 0.03% ammonium hydroxide (3 ml/10 l) and acetonitrile 0.03% ammonium hydroxide (3 ml/10 l). The elution was started at 95% water:5% acetonitrile ramping up to 5% water:95% acetonitrile over 5.30 minutes. The eluent level was returned to the starting conditions of 95% water: 5% acetonitrile over 0.6 minutes. These conditions were held for 1.4 minutes to allow equilibration of the column before the next sample was injected. The run lasted 7 minutes in total.

Analytical HPLC Methods

Method X

Method X employs gradient elution (0 to 100%) acetonitrile (containing 0.1% trifluoroacetic acid):water (containing 0.1% trifluoroacetic acid) over five minutes on a 4.6×75 mm (2.5 micron) Zorbax XDB-C8 column at 2.5 ml/min on an Agilent 1100 series HPLC.

Synthesis

Several methods for the chemical synthesis of 4-substituted-2-(pyridin-4-yl)-azaquinazoline compounds (for convenience, collectively referred to herein as "4PAZ compounds") of the present application are described herein. These and/or other well known methods may be modified and/or adapted in known ways in order to facilitate the synthesis of additional compounds within the scope of the present application. Methods of making compounds of the present disclosure can also be found in WO 2014/052699, the disclosure of which is incorporated by reference herein.

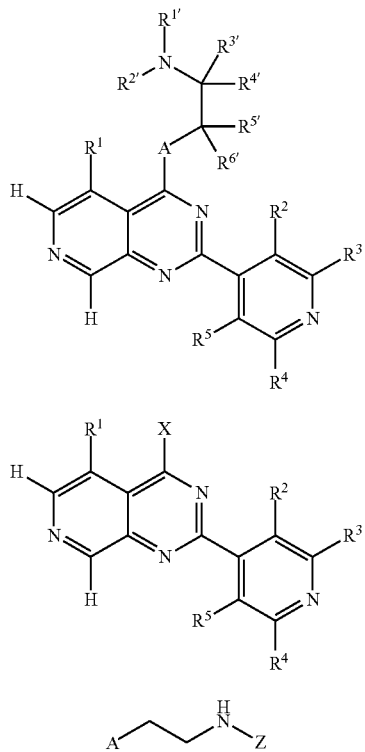

In one approach, 4PAZ compounds of general formula [F-001] (where A=NH or N alkyl) are prepared by reacting a compound of formula [F-002] (where X is a halogen such as chlorine or a sulfonate) with a compound of formula [F-003] (where A is NH or NH2 and Z on the terminal nitrogen is H, alkyl or a suitable nitrogen protecting group, such as Boc, Alloc, Cbz or Fmoc) in a suitable solvent such as DMF in the presence of a suitable base such as triethylamine. The reaction is suitably conducted at an elevated temperature for example 40° C. Where Z is a suitable nitrogen protecting group, such as Boc, Alloc, Cbz or Fmoc, compounds of formula [F-001] are prepared by a suitable deprotection reaction. For example: where Z is a Boc protecting group reaction with an acid such as TFA in a suitable solvent such as DCM. The reaction is suitably conducted at ambient temperature. In one approach, compounds of formula [F-001] (where A=0) are prepared by reacting a compound of formula [F-002] (where X is a halogen such as chlorine or sulfonate) with a compound of formula [F-003] (where A is OH and Z on the terminal nitrogen is H, alkyl or a suitable nitrogen protecting group, such as Boc, Alloc, Cbz or Fmoc) in a suitable solvent such as DMA in the presence of a suitable base such as sodium hydride. The reaction is suitably conducted at ambient temperature. Where Z is a suitable nitrogen protecting group, such as Boc, Alloc, Cbz or Fmoc, compounds of formula [F-001] are prepared by a suitable deprotection reaction. For example: where Z is a Boc protecting group reaction with an acid such as TFA in a suitable solvent such as DCM.

The reaction is suitably conducted at ambient temperature.

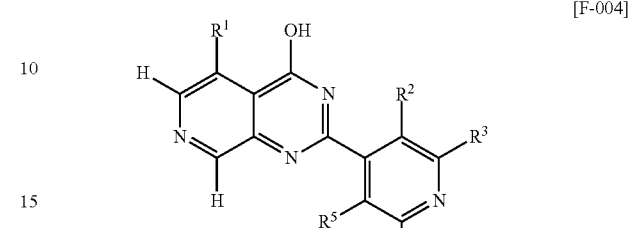

In one approach, compounds of formula [F-002] (where X is a halogen such as chlorine) are prepared by reacting a compound of formula [F-004] with a suitable halogenating agent such as phosphorous oxychloride. The reaction is suitably conducted at elevated temperature such as 125° C. Compounds of formula [F-002] (where X is a sulfonate) are prepared by reacting a compound of formula [F-004] with a suitably substituted sulfonyl chloride in a suitable solvent such as DMA in the presence of a suitable base such as triethylamine and a catalytic amount of DMAP. The reaction is suitably conducted at ambient temperature.

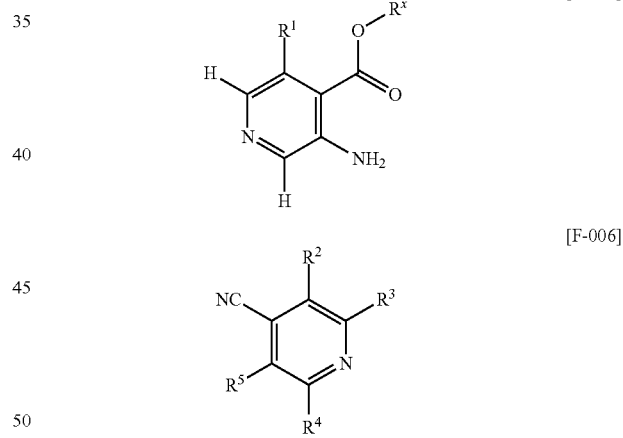

In one approach, compounds of formula [F-004] are prepared by reacting a compound of formula [F-005] (where Rx is an alkyl group such as methyl or ethyl) with a compound of formula [F-006] in a suitable solvent in a dry non-aprotic solvent such as dioxane or THF in the presence of a hindered alkoxide base such as potassium-tert-pentylate 1.7M in toluene or potassium-tert-butoxide. The reaction is suitably conducted at ambient temperature.

In one approach, compounds of formula [F-004] are prepared by reacting a compound of formula [F-007] with a compound of formula [F-006] in a suitable solvent in a protic solvent such as methanol in the presence of a base such as sodium methoxide. The reaction is suitably conducted first at ambient temperature then at reflux overnight.

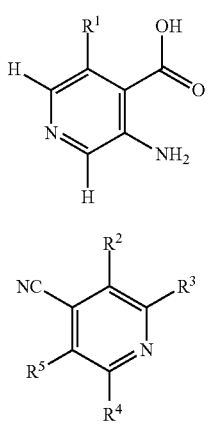

An example of a method as described above is illustrated in the following scheme.

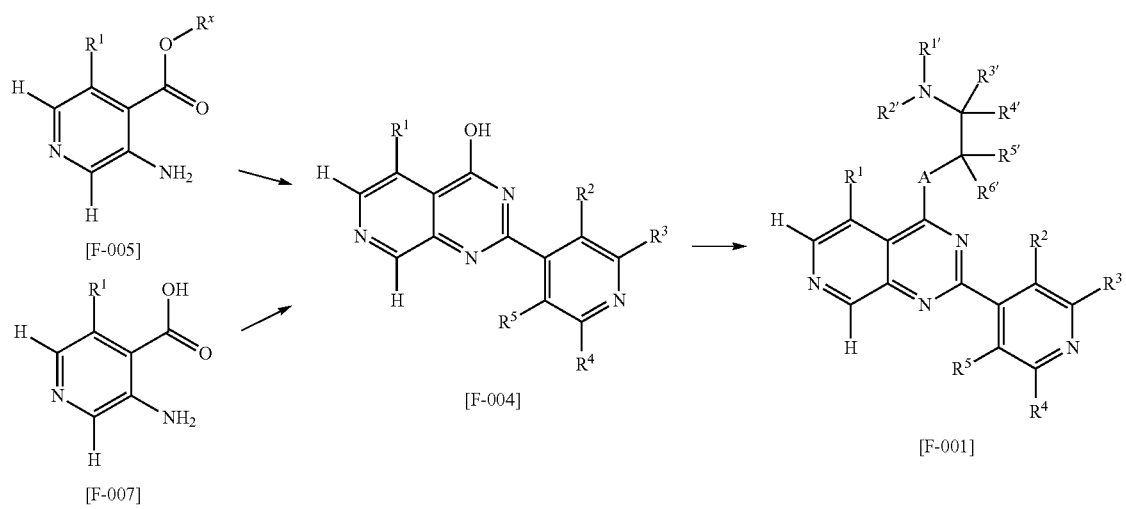

General Synthesis of 4-substituted-1-yl-2-pyridin-4-yl-pyrido[3,4-d]pyrimidine Derivatives of General Formula [F-001] Scheme A1

Substituted 2-Pyridin-4-yl-pyrido[3,4-d]pyrimidin-4-ol derivatives of general formula [F-001] were prepared by the reaction of a 2-amino-pyridyl derivative of general formula [F-005] with a 4-cyanopyridyl derivative of general formula [F-006] in the presence of a base such as sodium methoxide in a polar aprotic solvent such as methanol. The reaction is suitably conducted at elevated temperature to yield the cyclised 2-Pyridin-4-yl-pyrido[3,4-d]pyrimidin-4-ol product of general formula [F-004]. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivatives of general formula [F-004] with a chlorinatation agent such as phosphorous oxychloride to yield 4-chloro-1-yl-2-pyridin-4-yl-pyrido[3,4-d]pyrimidine derivatives of general formula [F-008] which were reacted with primary or secondary amino derivative of general formula [F-003], in a polar aprotic solvent such as DMA, DMF, NMP in the presence of a tertiary amine base such as Et3N, DIPEA or NMM at ambient temperature [method A]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by normal phase silica gel chromatography or reverse phase preparative HPLC. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivatives of general formula [F-004] with 2,4,6-triisopropylbenzenesulfonyl chloride in a polar aprotic solvent such as DMA, DMF, NMP with a tertiary alkylamine base such as Et3N, DIPEA or NMM and a catalytic amount of DMAP [method B]. The intermediate 6,7-substituted-(2,4,6-triisopropyl-benzenesulfonic acid)-2-pyridin-4-yl-thieno[3,2-d]pyrimidin-4-yl ester was then reacted with a primary or secondary amino derivative, of general formula [F-003], in a polar aprotic solvent such as DMA, DMF, NMP in the presence of a tertiary amine base such as Et3N, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC Scheme A1
Method A
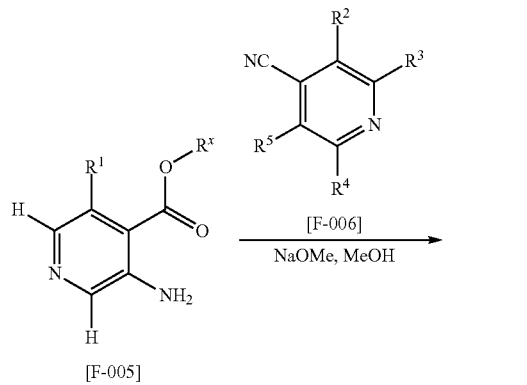
[F-005] + [F-006] →(NaOMe, MeOH)
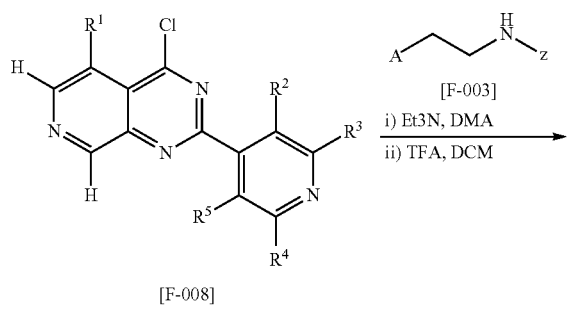
[F-004] →(POCl₃)
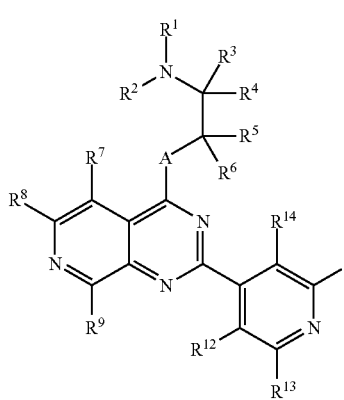
[F-008] + [F-003] i) Et₃N, DMA ii) TFA, DCM →
[F-001]
Method B
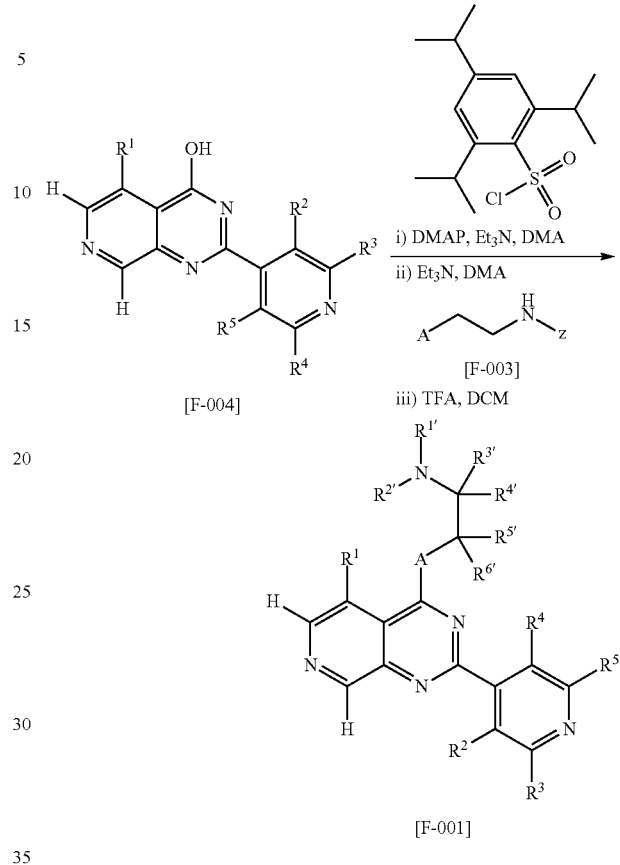
[F-004] i) DMAP, Et₃N, DMA ii) Et₃N, DMA + [F-003] iii) TFA, DCM →
[F-001]
Synthesis of 4-Piperazin-1-yl-2-pyridin-4-yl-pyrido[3,4-d]pyrimidine[1] Method A
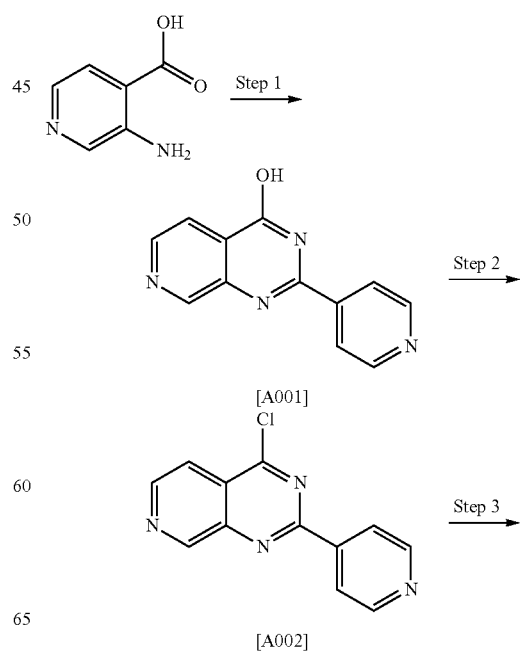
[A001] Step 2 →
[A002] Step 3 →

-continued

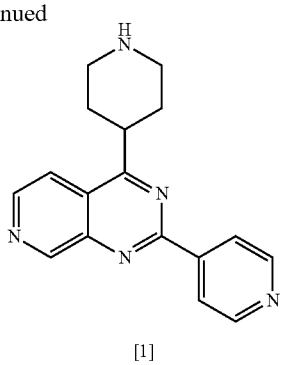

[1]

Synthesis of 2-Pyridin-4-yl-pyrido[3,4-d]pyrimidin-4-ol [A001]

A mixture of 4-Cyanopyridine (8.25 g, 79.2 mmol), sodium methoxide (891 mg, 16.5 mmol) and methanol (400 mL) was stirred at room temperature for 60 minutes. 3-Amino-isonicotinic acid (9.12 g, 66.0 mmol) was added and the mixture heated to reflux for 3 days. After cooling to room temperature the solid precipitate was collected by filtration then dried in the vacuum oven to yield the title compound as an off-white solid (6.02 g): (1H, 300 MHz, d6-dmso) 13.10 (1H, br s), 9.16 (1H, s), 8.80 (2H, dd), 8.70 (1H, d), 8.10 (2H, dd), 8.00 (1H, dd)

Synthesis of 4-Chloro-2-pyridin-4-yl-pyrido[3,4-d]pyrimidine [A002]

2-Pyridin-4-yl-pyrido[3,4-d]pyrimidin-4-ol [A001] (4 g, 17.8 mmol) in POCl$_3$ (50 mL, 538 mmol) was heated to 110° C. for 3 hours. The reaction mixture was concentrated under vacuum, quenched with saturated NaHCO$_3$ solution, extracted into DCM, washed with water then brine, passed through a phase separator cartridge and evaporated to yield the title compound [A002] (2.6 g) as a yellow/brown solid which was used without further purification: LCMS method: 1, RT:4.09 min, MI 243 [M+H].

Synthesis of 1-[2-(pyridin-4-yl)pyrido[3,4-d]pyrimidin-4-yl]piperazine[1]

A solution of 4-Chloro-2-pyridin-4-yl-pyrido[3,4-d]pyrimidine [A002] (100 mg, 0.43 mmol), piperazine (172 mg, 2 mmol) in anhydrous DMA (5 mL) was stirred at room temperature for 3 days. The reaction mixture was partitioned between NaOH (2M aqueous solution) and ethyl acetate. The organic layer was further washed with water then brine, dried (MgSO$_4$), passed through a phase separator cartridge and evaporated to yield the crude material, which was purified by preparative HPLC (method A) to yield the title compound (1.87 mg). LCMS method: 1, RT:3.49 min, MI 293 [M+H]; 1H-NMR (300 MHz; DMSO-d6): 9.26 (1H, s), 8.76 (2H, d), 8.58 (1H, d),8.32 (2H, d), 8.24 (1H, s), 7.92 (1H, d), 3.96 (4H, br tr), 2.99 (4H, br tr)

Synthesis of (5-Methoxy-2-pyridin-4-yl-pyrido[3,4-d]pyrimidin-4-yl)-(R)-pyrrolidin-3-yl-amine[2] method B

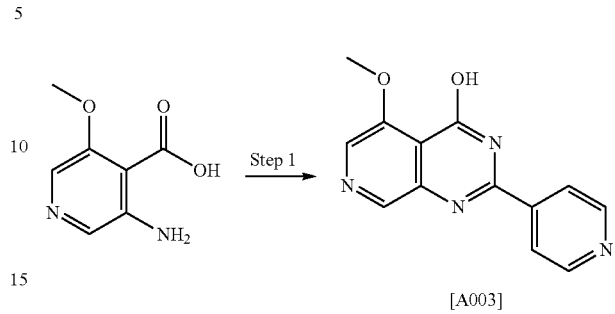

[A003]

Synthesis of 5-Methoxy-2-pyridin-4-yl-3H-pyrido[3,4-d]pyrimidin-4-one [A003]

To a stirred solution of 2-chloro-4-pyridinecarbonitrile (1 g, 9.6 mmol) in MeOH (20 mL) was added 0.5 M NaOMe (2 mmol, 4 mL) followed by 3-Amino-5-methoxy-isonicotinic acid (1.35 g, 8 mmol). The RM was heated at 75° C. over night. The RM was left to cool and a solid ppt formed which was collected by filtration, washed with cold MeOH and dried in a vac oven to give the title compound as a pale brown solid (610 mg, 30% yield). LCMS method: 1, RT:3.82 min, MI 255.09 [M+H].

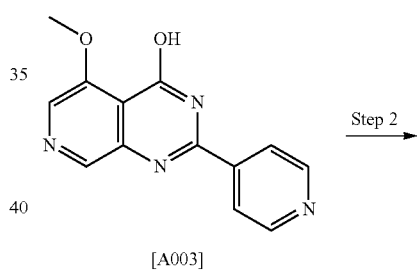

[A003]

[2]

Synthesis of (5-Methoxy-2-pyridin-4-yl-pyrido[3,4-d]pyrimidin-4-yl)-(R)-pyrrolidin-3-yl-amine[2]

5-methoxy-2-pyridin-4-yl-pyrido[3,4-d]pyrimidin-4-[A003] (0.157 mmol, 0.04 g), 2,4,6-triisopropylbenzenesulfonyl chloride (0.173 mmol, 0.052 g), were dissolved in anhydrous DMA (2 mL), and Et$_3$N (0.314 mmol, 0.045 mL), and DMAP (5 mg) were added sequentially. The mixture was stirred at room temperature for 1 hour and (R)-3-amino-pyrrolidine-1-carboxylic acid tert-butyl ester (0.236 mmol, 0.044 g) was added. The mixture was stirred at room temperature overnight. The solvent was then removed under reduced pressure and the residue was stirred in trifluoroacetic acid (1 mL) at room temperature for 3 h. The solution was poured on to an SCX-2 cartridge (5 g), washed with methanol (10 mL) and then washed with ammonia (2N in methanol, 20 mL). The ammonia washes were concentrated in vacuo to a brown residue that was purified by preparative HPLC (method A) to yield the title compound (0.016 g). LCMS method: 1, RT:1.47 min, MI 323 [M+H]; 1H-NMR 300 MHz (1H d6-dmso) 8.81 (1H, s), 8.76 (2H, dd), 8.35 (1H, s), 8.32 (2H, dd), 8.23 (1H, d), 6.42 (1H, s), 4.98 (1H, m), 4.14 (3H, s), 3.19-3.07 (2H, m), 2.41-2.29 (2H, m), 2.07-1.95 (2H, m).

General Synthesis of Substituted 5-substituted-1-yl-2-pyridin-4-yl-pyrido[3,4-d]pyrimidine Derivatives of General Formula [F-001] Scheme A7

2-Pyridin-4-yl-pyrido[3,4-d]pyrimidin-4-ol derivatives of general formula [F-004] were prepared by coupling of a ortho-halo-isonicotinic acid derivative of general formula [F-016] with an appropriately substituted 4-carbamimidoyl-pyridines of general formula [F-018] with a suitable coupling agent such as O-(7-Azabenzotriazol-1-yl)-N,N,N',N'-tetramethyluronium hexafluorophosphate (HATU) in a polar aprotic solvent such as DMA or DMF. The isonicotinoyl-amidine derivative of general formula [F-017] were then cyclised to displace the relevant halogen group to yield the desired 2-Pyridin-4-yl-pyrido[3,4-d]pyrimidin-4-ol derivatives of general formula [F-004]. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivatives of general formula [F-004] with a chlorinatation agent such as phosphorous oxychloride and the intermediate 4-chloro derivative was then reacted with primary or secondary amino derivative of general formula [F-015], in a polar aprotic solvent such as DMA, DMF, NMP in the presence of a tertiary amine base such as Et$_3$N, DIPEA or NMM at ambient temperature [method A]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or H$_2$SO$_4$ in a solvent such as DCM, DCE, THF, EtOH or MeOH and the crude reaction product was purified by normal phase silica gel chromatography or reverse phase preparative HPLC. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivatives of general formula [F-004] with 2,4,6-triisopropylbenzenesulfonyl chloride in a polar aprotic solvent such as DMA, DMF, NMP with a tertiary alkylamine base such as Et$_3$N, DIPEA or NMM and a catalytic amount of DMAP [method B]. The intermediate 6,7-substituted-(2,4,6-triisopropyl-benzenesulfonic acid)-2-pyridin-4-yl-thieno[3,2-d]pyrimidin-4-yl ester was then reacted with a primary or secondary amino derivative, of general formula [F-015], in a polar aprotic solvent such as DMA, DMF, NMP in the presence of a tertiary amine base such as Et$_3$N, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or H$_2$SO$_4$ in a solvent such as DCM, DCE, THF, EtOH or MeOH and the crude reaction product was purified by reverse phase preparative HPLC.

Schemed A7

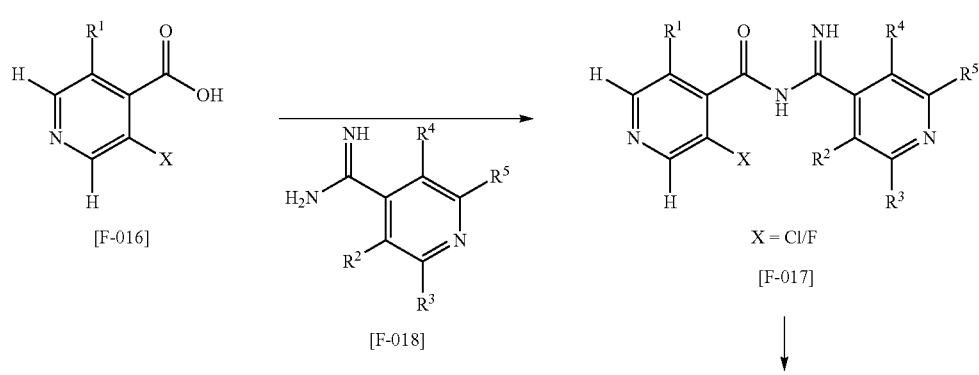

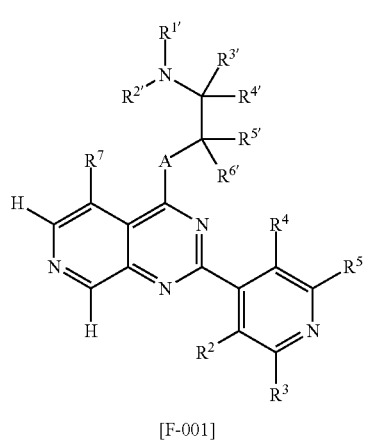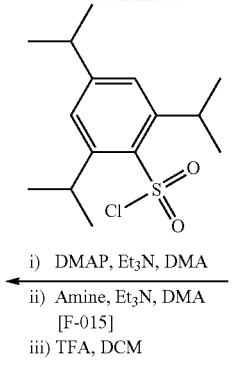
[F-001]
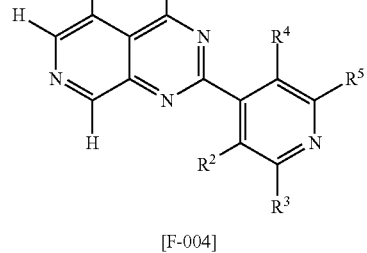
i) DMAP, Et₃N, DMA
ii) Amine, Et₃N, DMA [F-015]
iii) TFA, DCM
Method B
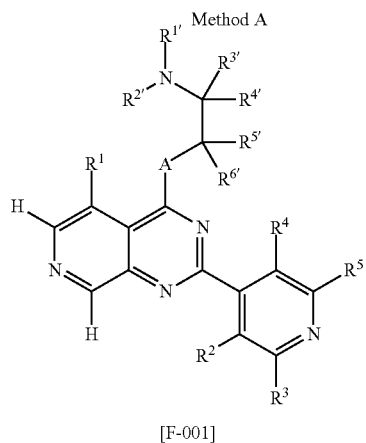
[F-004]
i) POCl₃
ii) Amine, Et₃N, DMA [F-015]
iii) TFA, DCM
Method A
[F-001]
Synthesis of 5-Chloro-4-piperazin-1-yl-2-pyridin-4-yl-pyrido[3,4-d]pyrimidine [132]
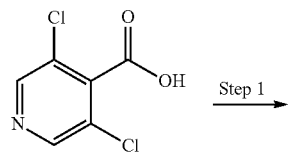
Step 1
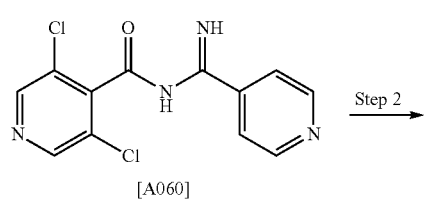
[A060]
Step 2
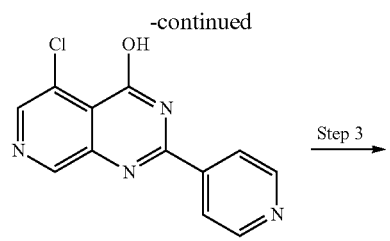
[A061]
Step 3
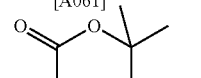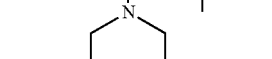
[A062]
Step 4

-continued

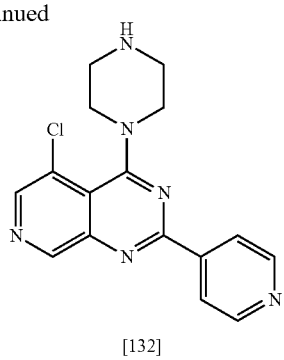

[132]

Synthesis of 3,5-Dichloro-N-(imino-pyridin-4-yl-methyl)-isonicotinamide [A060]

3,5-Dichloro-isonicotinic acid (10.4 mmol, 1.997 g), was dissolved in anhydrous DMF (50 mL) at room temperature and HATU (10.4 mmol, 3.95 g), added in one portion and the mixture stirred for 5 mins. Then DIPEA (28.6 mmol, 5.0 mL) was added in one portion and reaction stirred for 40 minutes. Pyridine-4-carboximidamide hydrochloride (9.52 mmol, 1.5 g) was added in one portion and reaction stirred at room temperature for 18 hours.

The reaction mixture was then poured into water (~250 mL in total including rinses of reaction vessel) in a conical flask. The resultant mixture was stirred at room temperature for 90 minutes and the precipitate formed was filtered, washed with water (×2) and ether (×2). Then the solid was dried in vac oven for 4 hrs to yield the title compound [A060] (2.359 g), as a pale brown powder. LCMS method: 1, RT:3.31 min, MI 295 [M+H].

Synthesis of 5-Chloro-2-pyridin-4-yl-3H-pyrido[3,4-d]pyrimidin-4-one [A061]

In a 25 mL Biotage microwave vessel, under nitrogen, was added 3,5-Dichloro-N-(imino-pyridin-4-yl-methyl)-isonicotinamide [A060] (1.5 mmol, 0.443 g), cesium carbonate (3.0 mmol, 0.978 g) and N,N'-Dibenzylethylenediamine (0.3 mmol, 0.071 mL). The mixture was stirred in anhydrous DMA (10 mL), vigorously and iron (III) chloride (0.15 mmol, 0.024 g) added in one portion. Then the mixture was heated in the microwave at 120° C. for 90 mins. The reaction was allowed to cool to room temperature and acetic acid (12.0 mmol, 0.69 mL), added dropwise over about 5 minutes and the resulting mixture diluted with MeOH (10 mL) and stirred at RT for 30 mins. The mixture was added to a 10 g SCX-2 cartridge and washed with methanol (~25-30 mL). The cartridge was then washed with ammonia (2N in MeOH, 40 mL) and the ammonia washes concentrated in vacuo to yield 5-Chloro-2-pyridin-4-yl-3H-pyrido[3,4-d]pyrimidin-4-one (130 mg). The non-basic methanol washes of the SCX-2 cartridge were left standing overnight, forming a precipitate. This was filtered, washed with methanol (×1), and dried in a vacuum oven overnight to yield the title compound [A061] (13 mg) as an off-white solid. LCMS method: 1, RT:2.12 min, MI 259 [M+H].

Synthesis of 4-(5-Chloro-2-pyridin-4-yl-pyrido[3,4-d]pyrimidin-4-yl)-piperazine-1-carboxylic acid tert-butyl ester [A062]

5-Chloro-2-pyridin-4-yl-3H-pyrido[3,4-d]pyrimidin-4-one [A061] (0.553 mmol, 0.143 g), was suspended in anhydrous DCM (14 mL) at RT under nitrogen and triethylamine (1.38 mmol, 0.193 mL), DMAP (approximately 0.005 g) and 2,4,6-triisopropylbenzene sulfonyl chloride (0.663 mmol, 0.201 g) were added sequentially. The reaction was stirred at room temperature as an off-white suspension for 2 hrs. Slowly the mixture becomes a pale green suspension, that was left stirring overnight. Then pyridine (4 mL) was added and the reaction vessel sonicated for 5 minutes to try to improve the dissolution causing the reaction to change colour from green to brown suspension. The resultant mixture was stirred at room temperature for 1 hour. Boc-piperazine (0.608 mmol, 0.113 g) was added in one portion and the mixture left stirring for 18 hours.

The reaction was diluted with water and extracted with DCM (×3). Combined organics washed with brine (×1), dried (MgSO$_4$), filtered and concentrated in vacuo. To yield the title compound [A062] which was used in the next reaction without further purification: LCMS method: 1, RT:5.69 min, MI 427 [M+H].

Synthesis of 5-Chloro-4-piperazin-1-yl-2-pyridin-4-yl-pyrido[3,4-d]pyrimidine[132]

To a solution of 4-(5-Chloro-2-pyridin-4-yl-pyrido[3,4-d]pyrimidin-4-yl)-piperazine-1-carboxylic acid tert-butyl ester [A062] (0.47 mmol, 0.201 g), in anhydrous DCM (8 mL), at room temperature was added HCl (4.0N in dioxane, 2 mL) to yield an orange suspension that was stirred at room temperature for 3 hours. The mixture was then concentrated in vacuo, redissolved in DCM/MeOH (1:1, 6 mL total) and added to an SCX-2.10 g cartridge.

The cartridge was washed with DCM and MeOH (~35 mL total ~2:3 ratio respectively). Then the cartridge was washed with ammonia in methanol (2N, 40 mL) and the ammonia washes were concentrated in vacuo to yield 92 mg brown oil. The crude material was purified by column chromatography (SP1 4 g VWR column with 0-20% MeOH/DCM 15 volumes) to yield the title compound [138] (0.044 g) as an orangey-yellow foam. LCMS method: 1, RT:1.60 min, MI 327 [M+H]; NMR: (1H, 300 MHz, d6-dmso); 9.15 (1H, s), 8.77 (2H, d), 8.61 (1H, s), 8.29 (2H, d), 3.69 (4H, br s), 2.85 (4H, br s)

Synthesis of 3-Bromo-5-fluoro-N-(imino-pyridin-4-yl-methyl)-isonicotinamide [A065]

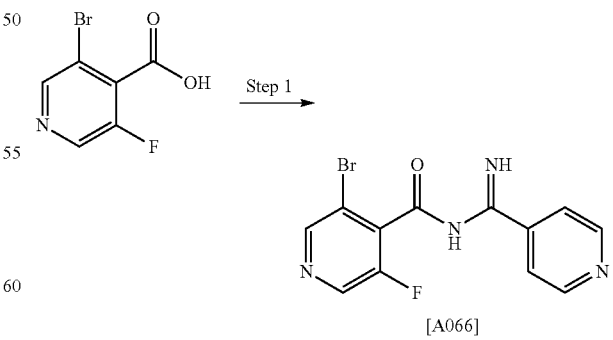

[A066]

2-Bromo-5-fluoro-N-(imino-pyridin-4-yl-methyl)-isonicotinamide [A066] was prepare by reaction of 3-Bromo-4-carboxy-5-fluoro-pyridinium; chloride, pyridine-4-carboximidamide hydrochloride, HATU, DIPEA and DMF at room temperature to give the title compound. LCMS method: 1, RT:3.20 min, MI 325 [M+H].

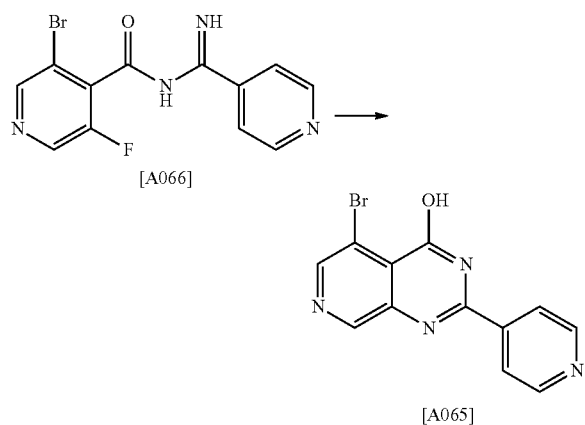

2-Bromo-5-fluoro-N-(imino-pyridin-4-yl-methyl)-isonicotinamide [A066] (0.05 g, 0.155 mmol), DMA (0.5 mL), K₂CO₃ (0.022 g, 0.16 mmol), DIPEA (0.28 mL, 0.16 mmol) and DBA (0.024 mL, 0.16 mmol) wa heated at 150° C. in μwave for 45 mins. The crude reaction mixture was evaporated under reduced pressure and the crude material was purified by column chromatography (SP1 4 g VWR column in 0.5% Et3N/DCM/0-20% MeOH) to yield the title compound [A065] (0.044 g, 80% yield) as an orangey-yellow foam: LCMS method: 1, RT:11.57 min, MI 304 [M+H].

General Synthesis of Substituted 5-substituted-1-yl-2-pyridin-4-yl-pyrido[3,4-d]pyrimidine Derivatives of General Formula [F-001] Scheme A8

Ortho-halo-isonicotinic acid derivatives of general formula [F-020] were prepared by reaction of a dihalo isonicotinic acid derivative of general formula [F-019] with a grindard reagent of general formula [F-021] in a polar aprotic solvent such as THF or Et₂O. 2-Pyridin-4-yl-pyrido[3,4-d]pyrimidin-4-ol derivatives of general formula [F-004] were prepared by coupling of a ortho-halo-isonicotinic acid derivative of general formula [F-020] with an appropriately substituted 4-carbamimidoyl-pyridines of general formula [F-018] with a suitable coupling agent such as 0-(7-Azabenzotriazol-1-yl)-N,N,N',N'-tetramethyluronium hexafluorophosphate (HATU) in a polar aprotic solvent such as DMA or DMF. The isonicotinoyl-amidine derivative of general formula [F-022] were cyclised to displace the relevant halogen group to yield the desired- Pyridin-4-yl-pyrido[3,4-d]pyrimidin-4-ol derivatives of general formula [F-004]. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivative of general formula [F-004] with a chlorinatation agent such as phosphorous oxychloride and the intermediate 4-chloro derivative was then reacted with primary or secondary amino derivative of general formula [F-015], in a polar aprotic solvent such as DMA, DMF, NMP in the presence of a tertiary amine base such as Et₃N, DIPEA or NMM at ambient temperature [method A]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or H₂SO₄ in a solvent such as DCM, DCE, THF, EtOH or MeOH and the crude reaction product was purified by normal phase silica gel chromatography or reverse phase preparative HPLC. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivatives of general formula [F-004] with 2,4,6-triisopropylbenzenesulfonyl chloride in a polar aprotic solvent such as DMA, DMF, NMP with a tertiary alkylamine base such as Et₃N, DIPEA or NMM and a catalytic amount of DMAP [method B]. The intermediate 6,7-substituted-(2,4,6-triisopropyl-benzenesulfonic acid)-2-pyridin-4-yl-thieno[3,2-d]pyrimidin-4-yl ester was then reacted with a primary or secondary amino derivative, of general formula [F-015], in a polar aprotic solvent such as DMA, DMF, NMP in the presence of a tertiary amine base such as Et₃N, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or H₂SO₄ in a solvent such as DCM, DCE, THF, EtOH or MeOH and the crude reaction product was purified by reverse phase preparative HPLC.

Scheme A8

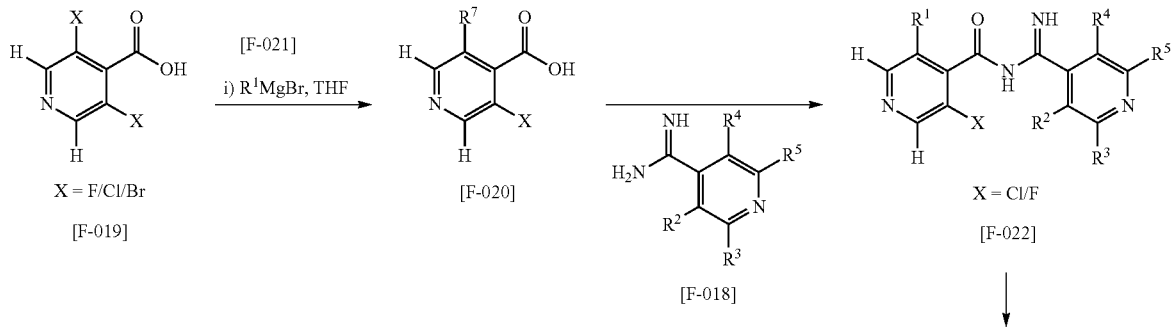

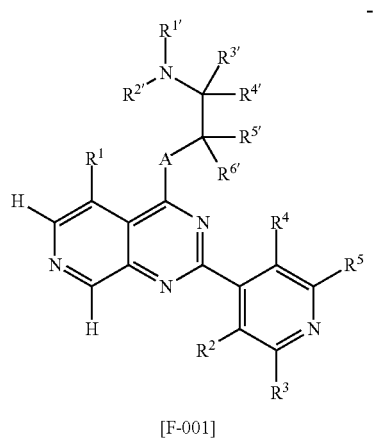
[F-001]
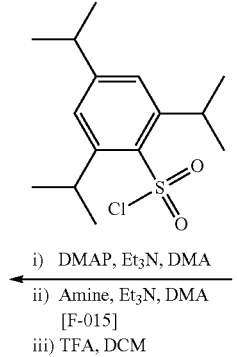
i) DMAP, Et₃N, DMA
ii) Amine, Et₃N, DMA [F-015]
iii) TFA, DCM
Method B
-continued
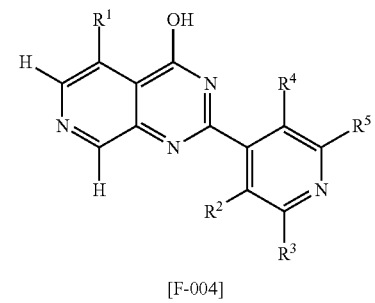
[F-004]
i) POCl3
ii) Amine, Et₃N, DMA [F-015]
iii) TFA, DCM
Method A
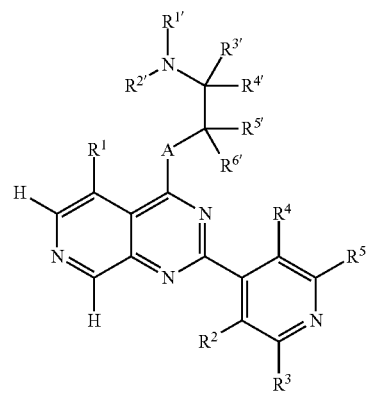
[F-001]
Synthesis of 5-Butyl-4-piperazin-1-yl-2-pyridin-4-yl-pyrido[3,4-d]pyrimidine [135]
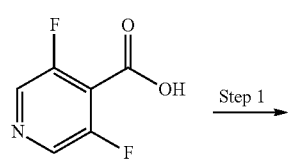
Step 1
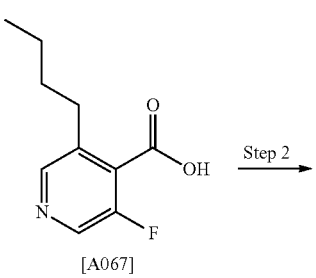
[A067]
Step 2
-continued
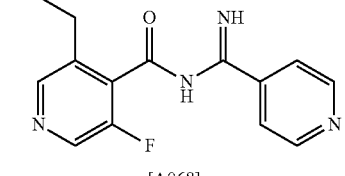
[A068]
Step 3
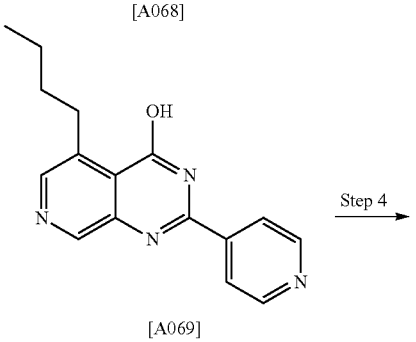
[A069]
Step 4

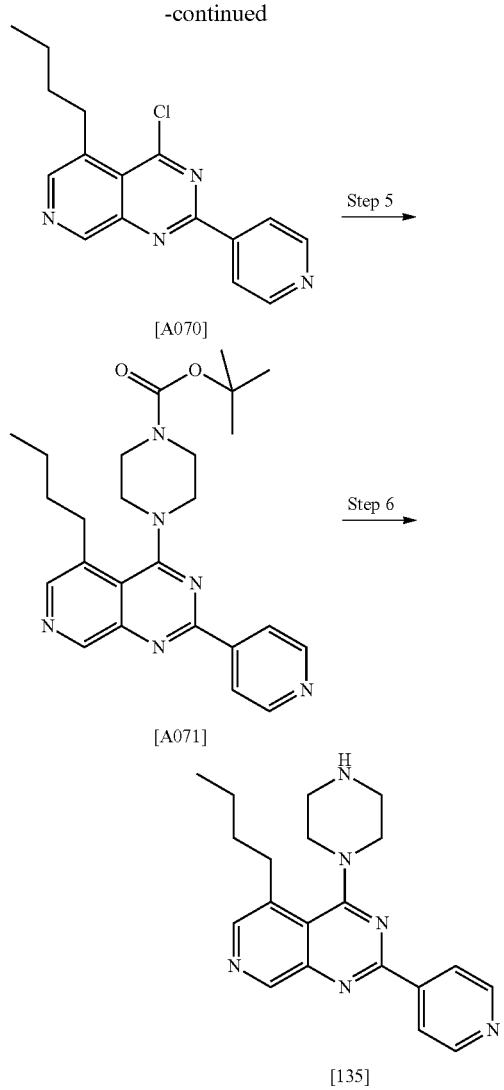

Synthesis of 3-Butyl-5-fluoro-isonicotinic acid [A067]

3,5-Difluoro-isonicotinic acid (0.557 g, 3.5 mmol) was suspended in anhydrous THF (8 mL) at 0° C., under an atmosphere of nitrogen. To this was added butyl magnesium chloride (2.0 M in diethyl ether, 5.25 mL, 10.5 mmol) dropwise over 10 minutes. The suspension slowly changed form during the slow addition with preliminary agglomeration of solid then the solid started to dissolve slowly, achieving full solution around completion of addition of reagent. The reaction mixture was allowed to warm to room temperature and stirred over 72 hours to form a thick yellow suspension. Diluted with water and transferred into a single neck flask and concentrated in vacuo. The yellow solid was diluted with water (10 mL) and EtOAc (10 mL). The pH was adjusted pH-2, by dropwise addition of HCl (conc.) and extracted with EtOAc (×3—some of the yellow colour goes into organics). Combined organics were washed with brine (×1), dried (MgSO$_4$) and concentrated in vacuo to yield the title compound [A067] as an orange gum/solid (0.402 g) that solidifies slowly: NMR: (1H, 300 MHz, d6-dmso); 8.52 (1H, s), 8.42 (1H, s), 2.67 (2H, t), 1.58-1.48 (2H, m), 1.35-1.22 (2H, m), 0.87 (3H, t); LCMS method: 1, RT:1.22 min, MI 198 [M+H].

Synthesis of 3-Butyl-5-fluoro-N-(imino-pyridin-4-yl-methyl)-isonicotinamide [A068]

3-Butyl-5-fluoro-isonicotinic acid [A067] (2.05 mmol, 0.402 g) was dissolved in anhydrous DMF (8 mL) and diisopropylethylamine (DIPEA) (5.95 mmol, 1.04 mL) was added and the mixture stirred at room temperature for 5 minutes. Then O-(7-Azabenzotriazol-1-yl)-N,N,N',N'-tetramethyluronium hexafluorophosphate (HATU) (2.0 5 mmol, 0.78 g) was added in one portion and the resultant mixture stirred for 1 hour. pyridine-4-carboximidamide hydrochloride (1.95 mmol, 0.307 g) was then added portionwise over 5 minutes to the reaction. The resultant solution was stirred at room temperature for 18 hours. The reaction mixture was poured into water (85 mL) and stirred for 30 minutes and then extracted with EtOAc (×3). The combined organics washed with water (×4), brine (×1), dried (MgSO$_4$), filtered and concentrated in vacuo to yield the title compound [A068] (480 mg) as a brown solid. The material was used crude in next reaction: NMR: (1H, 300 MHz, d6-dmso); 10.28 (1H, br s), 9.93 (1H, br s), 8.74 (2H, d), 8.45 (1H, s), 8.37 (1H, s), 7.90 (2H, d), 2.72-2.66 (2H, m), 1.58-1.48 (2H, m), 1.28-1.15 (2H, m), 0.79 (3H, t); LCMS method: 1, RT:3.90 min, MI 301 [M+H].

Synthesis of 5-Butyl-2-pyridin-4-yl-3H-pyrido[3,4-d]pyrimidin-4-one [A069]

3-butyl-5-fluoro-N-(imino-pyridin-4-yl-methyl)-isonicotinamide [A068] was placed into 25 mL Biotage microwave vessel in solution in anhydrous DMA (5 mL) and heated at 150° C. in the microwave for 45 mins. The reaction mixture was filtered material through an SCX-2 25 g cartridge. The cartridge was washed with methanol (50 mL). Then the cartridge was washed with ammonia (2N, 40 mL) and the ammonia washes concentrated in vacuo to yield the title compound [A069] (390 mg) as a pale brown solid: NMR: (1H, 300 MHz, d6-dmso); 8.95 (1H, s), 8.79 (2H, dd), 8.46 (1H, s), 8.10 (2H, dd), 3.21 (2H, t), 1.63-1.50 (2H, m), 1.43-1.27 (2H, m), 0.91 (3H, t)—also shows one equivalent of DMA; LCMS method: 1, RT:3.29 min, MI 281 [M+H].

Synthesis of 5-Butyl-4-chloro-2-pyridin-4-yl-pyrido[3,4-d]pyrimidine [A070]

5-Butyl-2-pyridin-4-yl-3H-pyrido[3,4-d]pyrimidin-4-one [A069] (1.35 mmol, 0.378 g) was suspended in anhydrous 1,2-dichloroethane (DCE) (10 mL) and phosphorus oxychloride (POCl$_3$) (1.4 mmol, 0.131 mL) was added dropwise over 2-3 minutes. Finally DIPEA (2.0 mmol, 0.348 mL) was added and the mixture stirred at RT under nitrogen overnight. The brown solid slowly to change appearance after POCl$_3$ addition, then darkens further on addition of DIPEA to become a dark brown apparent solution. The reaction was left stirring at room temperature overnight under nitrogen. After 20 hours POCl$_3$ (65 µL) was added and stirred at room temperature overnight. The crude mixture was concentrated in vacuo, then azeotroped with toluene (×2) to dryness. The residue was diluted with sodium carbonate (aq. soln., 2N, 20 mL) and extracted with DCM (×2), EtOAc (×1). Combined organics washed with brine (×1), dried (MgSO$_4$), filtered through a pad of silica and concentrated in vacuo to yield the title compound [A070] (180 mg) as a of a pale brown solid which was used in the next reaction without further purification: LCMS method: 1, RT:5.66 min, MI 299 [M+H].

Synthesis of 4-(5-Butyl-2-pyridin-4-yl-pyrido[3,4-d]pyrimidin-4-yl)-piperazine-1-carboxylic acid tert-butyl ester [A071]

5-Butyl-4-chloro-2-pyridin-4-yl-pyrido[3,4-d]pyrimidine [A070] (0.615 mmol, 0.180 g), was dissolved in anhydrous DCM (5 mL), under nitrogen at room temperature and treated with triethylamine (0.868 mmol, 0.121 mL) and N-Boc-piperazine (0.682 mmol, 0.127 g) in one portion. The resulting mixture was stirred at room temperature for 2 hours. Then sodium carbonate (1N aq. soln, 20 mL) was added and extracted with DCM (×2) and EtOAc (×1). Combined organics washed with brine (×1), dried (MgSO$_4$), filtered and concentrated in vacuo to a dark brown solid, which was purified by column chromatography (SP1 on 25 g VWR cartridge in 0-10% MeOH/DCM, 15 col vols) to yield the title compound [A071] as a brown gum (0.092 g) which was used in the next reaction without further purification: NMR: (1H, 300 MHz, d6-dmso); 9.24 (1H, s), 8.79 (2H, d), 8.49 (1H, s), 8.36 (2H, d), 3.77-3.48 (8H, m), 3.19-3.07 (2H, m), 1.64-1.23 (4H, m), 1.48 (9H, s), 0.96-0.87 (3H, t).

Synthesis of 5-Butyl-4-piperazin-1-yl-2-pyridin-4-yl-pyrido[3,4-d]pyrimidine[135]

4-(5-Butyl-2-pyridin-4-yl-pyrido[3,4-d]pyrimidin-4-yl)-piperazine-1-carboxylic acid tert-butyl ester [A071] (0.20 mmol, 0.09 g) was dissolved in anhydrous DCM (4 mL) and treated with hydrogen chloride (4N in dioxane, 4 mL) at room temperature and stirred for 2 hours. The reaction was diluted with methanol and poured onto SCX-2 cartridge (5 g), washing with MeOH/DCM (20 mL). The cartridge was then washed with ammonia (2N, 20 mL) and the ammonia washes concentrated in vacuo to yield a brown gum (0.059 g). The residue was purified by column chromatography (SP 1 4 g column, in a gradient 5-20% MeOH/DCM 15 col vols) to yield the title compound [133] as an orangey-brown gum (0.020 g); NMR: (1H, 300 MHz, d6-dmso); 9.09 (1H, s), 8.76 (2H, d), 8.51 (1H, s), 8.31 (2H, d), 3.73-3.58 (2H, br s), 3.50-3.37 (2H, br s), 3.07 (2H, t), 2.90-2.79 (4H, br s), 1.51-1.38 (2H, m), 1.28-1.15 pm (2H, m), 0.84 (3H, t); LCMS method: 1, RT:2.58 min, MI 349 [M+H].

General Synthesis of Substituted 2-amino pyridyl substituted 2-(2-amino-pyridin-4-yl)-pyrido[3,4-d]pyrimidin-4-yl amine Derivatives of General Formula [G-003] Scheme B1

2-(2-chloro-pyridin-4-yl)-pyrido[3,4-d]pyrimidin-4-yl amine derivatives of general formula [G-002] were prepared by the reaction of a 2-(2-chloro-pyridin-4-yl)-pyrido[3,4-d]pyrimidin-4-ol derivative of general formula [G-001] with 2,4,6-triisopropylbenzenesulfonyl chloride in a polar aprotic solvent such as DMA, DMF, NMP with a tertiary alkylamine base such as Et$_3$N, DIPEA or NMM and a catalytic amount of DMAP. The intermediate 6,7-substituted-(2,4,6-triisopropyl-benzenesulfonic acid)-2-(2-chloro-pyridin-4-yl)-pyrido[3,4-d]pyrimidin-4-yl ester was then reacted with a primary or secondary amino derivative, of general formula [G-004], in a polar aprotic solvent such as DMA, DMF, NMP in the presence of a tertiary amine base such as Et$_3$N, DIPEA or NMM at ambient temperature. The 2-(2-chloro-pyridin-4-yl)-pyrido[3,4-d]pyrimidin-4-yl amine derivatives of general formula [G-002] was involved in a Buchwald type reaction utilising a suitable amine, of general formula [G-005], a palladium catalyst such as Pd(dba)$_2$ or Pd(OAc)$_2$, a ligand such as Xantphos and a base such as NaOtBu or Cs$_2$CO$_3$ in a polar solvent such as dioxane or a combination of dioxane and DMA at high temperature either by heating thermally or using a microwave reactor, to yield substituted 2-amino pyridyl substituted 2-(2-amino-pyridin-4-yl)-pyrido[3,4-d]pyrimidin-4-yl amine derivatives of general formula [G-003]. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

Scheme B1

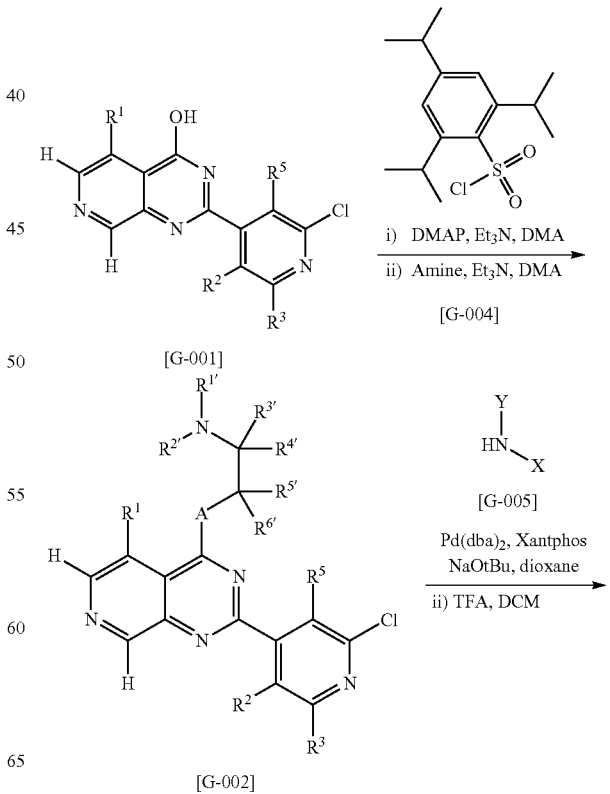

-continued

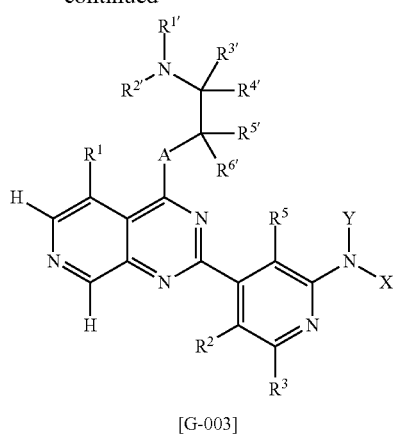

[G-003]

Synthesis of [4-(5-Methoxy-4-piperazin-1-yl-pyrido[3,4-d]pyrimidin-2-yl)-pyridin-2-yl]-phenyl-amine [200]

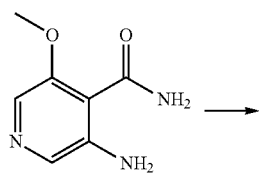

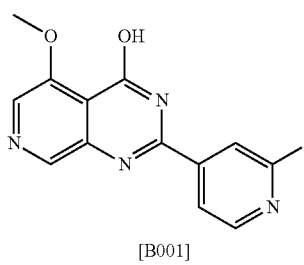

2-(2-Chloro-pyridin-4-yl)-5-methoxy-pyrido[3,4-d]pyrimidin-4-ol [B001]

To a solution of 2-chloro-4-pyridinecarbonitrile (0.97 g, 7.03 mmol) in MeOH (35 mL) at RT, under nitrogen, was added NaOMe (0.08 g, 1.46 mmol) and left to stir for 60 mins. Then a solution of 3-Amino-5-methoxy-isonicotinic acid (1 g, 5.86 mmol) in MeOH (15 mL) was added to the dark brown mixture dropwise over 5-10 mins (via syringe). The solution was stirred at rt for 2 h and then overnight at 85° C. After cooling down, the solid was filtered and, washed with methanol and used without further purification to yield the title compound [B001] (0.97 g 57% yield: LCMS: method: 5, RT:6.32 min, MI 287.34 [M+H].

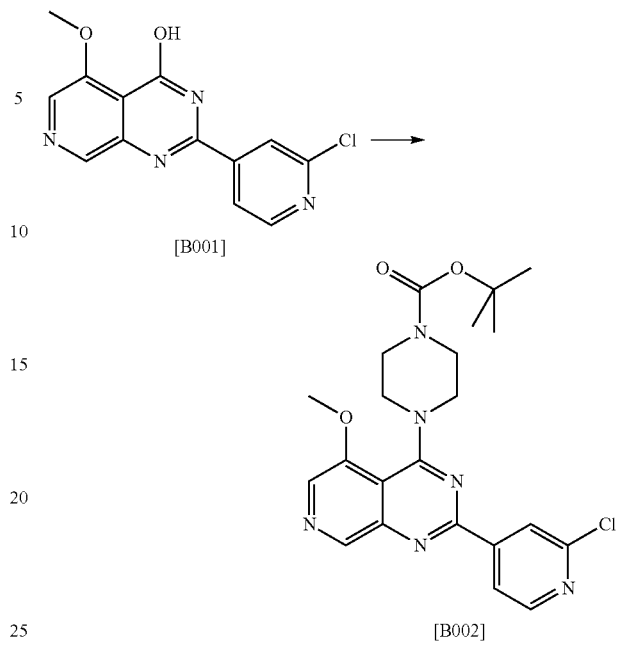

4-[2-(2-Chloro-pyridin-4-yl)-5-methoxy-pyrido[3,4-d]pyrimidin-4-yl]-piperazine-1-carboxylic acid tert-butyl ester [B002]

A mixture of 2-(2-chloro-pyridin-4-yl)-5-methoxy-pyrido[3,4-d]pyrimidin-4-ol [B001] (0.58 g, 2 mmol), anhydrous DMA (5 mL), triethylamine (0.58 mL, 4 mmol) and DMAP (20 mg, 0.16 mmol) was sonicated for 10 min then stirred at room temperature for 10 min. 2,4,6-Triisopropyl-benzene-sulfonyl chloride (0.67 g, 2.2 mmol) was added and the mixture was sonicated for 5 min then left to stir at room temperature for 2 hours. During this time the material went into solution to form a viscous solution. A solution of Boc piperazine (0.56 g, 3 mmol) in anhydrous DMA (1 mL) was added and the reaction mixture was left to stir at room temperature overnight. Water (20 mL) was added and the reaction mixture was extracted with DCM (2×30 mL), the extracts were combined and washed with water (20 mL), saturated bicarbonate solution (2×20 mL) and water (20 mL), dried (MgSO$_4$) filtered and evaporated under reduced pressure to give a pale yellow oil, which was purified by flash column chromatography (SP1, 50 g SiO$_2$ cartridge 100% EtOAc up to 95% EtOAc: 5% MeOH gradient) to give the title compound [B002] as a colourless solid (0.22 g 24% yield). LCMS: method: 5, RT:10.86 min, MI 457 [M+H]; NMR: (1H, 500 MHz, CDCl$_3$); 9.0 (1H, s), 8.53 (1H, d), 8.35 (1H, s), 8.28 (1H, 1H, d), 8.23 (1H, s), 3.70 (4H, br s), 3.64 (4H, br s), 1.50 (9H, s)

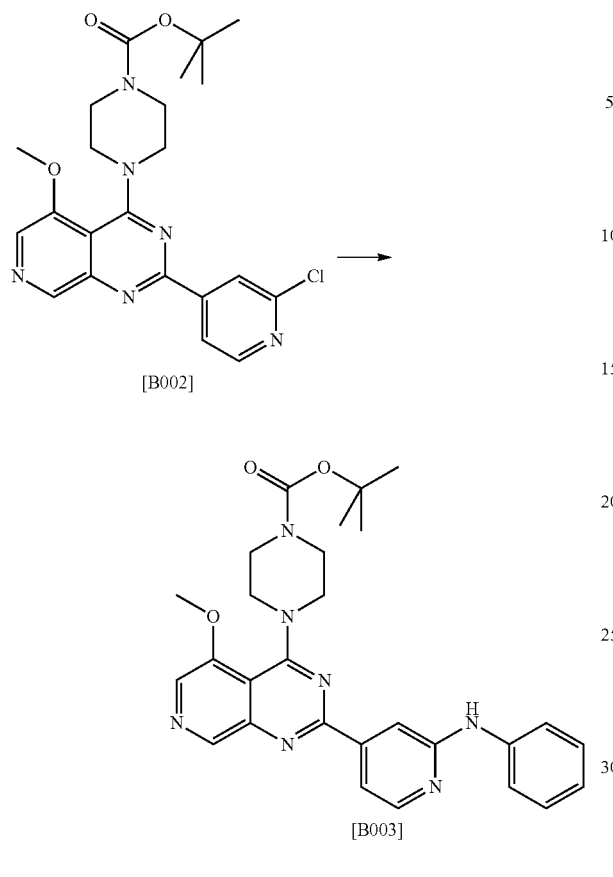

[B002]

[B003]

[B003]

4-[5-Methoxy-2-(2-phenylamino-pyridin-4-yl)-pyrido[3,4-d]pyrimidin-4-yl]-piperazine-1-carboxylic acid tert-butyl ester [B003]

A mixture of 4-[2-(2-Chloro-pyridin-4-yl)-5-methoxy-pyrido[3,4-d]pyrimidin-4-yl]-piperazine-1-carboxylic acid tert-butyl ester [B002] (0.100 g, 0.22 mmol), Pd(dba)$_2$ (10 mg, 0.013 mmol), Xantphos (17.5 mg, 0.025 mmol), NaOtBu (43 mg, 0.440 mmol) and anhydrous dioxane (4 ml) was added to a microwave vial. Aniline was then added the vial was sealed and heated at 150° C. for 20 min. Water (10 mL) was added and the reaction mixture was extracted with DCM (2×10 mL), the extracts were combined and washed with water (10 mL), saturated bicarbonate (2×10 mL) and water (10 mL), dried with MgSO4 filtered and evaporated to give a pale yellow oil, which was purified by flash column chromatography (SP1, 25 g SiO2 cartridge 100% EtOAc up to 95% EtOAc: 5% MeOH gradient) to give the title compound [B003] as a colourless solid (0.04 g 36% yield). LCMS: method: 5, RT:7.80 min, MI 514 [M+H]; NMR: (1H, 500 MHz, CDCl$_3$); 8.93 (1H, s), 8.65 (1H, d), 8.41 (1H, s), 7.39 (1H, d), 7.58 (5H, m), 6.55 (1H, br s), 3.63 (4H, m), 3.57 (4H, m), 1.49 (9H, s).

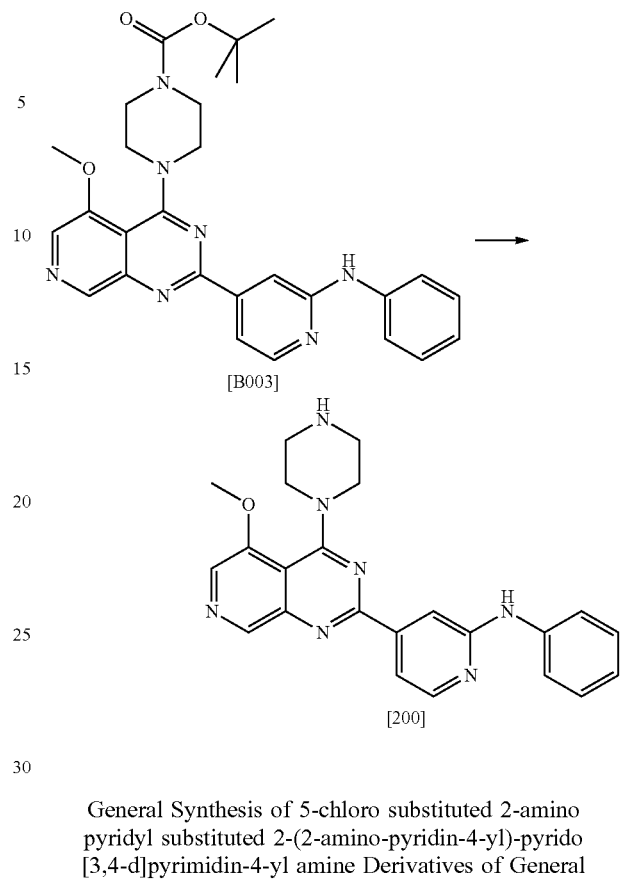

[B003]

[200]

General Synthesis of 5-chloro substituted 2-amino pyridyl substituted 2-(2-amino-pyridin-4-yl)-pyrido[3,4-d]pyrimidin-4-yl amine Derivatives of General Formula [G-008] Scheme B2

5-chloro 2-(2-chloro-pyridin-4-yl)-pyrido[3,4-d]pyrimidin-4-yl amine derivatives of general formula [G-007] were prepared by the reaction of a 5-chloro 2-(2-chloro-pyridin-4-yl)-pyrido[3,4-d]pyrimidin-4-ol derivative of general formula [G-006] with 2,4,6-triisopropylbenzenesulfonyl chloride in a polar aprotic solvent such as DMA, DMF, NMP with a tertiary alkylamine base such as Et$_3$N, DIPEA or NMM and a catalytic amount of DMAP. The intermediate 6,7-substituted-(2,4,6-triisopropyl-benzenesulfonic acid)-2-(2-chloro-pyridin-4-yl)-pyrido[3,4-d]pyrimidin-4-yl ester was then reacted with a primary or secondary amino derivative, of general formula [G-004], in a polar aprotic solvent such as DMA, DMF, NMP in the presence of a tertiary amine base such as Et$_3$N, DIPEA or NMM at ambient temperature. 5-chloro 2-(2-chloro-pyridin-4-yl)-pyrido[3,4-d]pyrimidin-4-yl amine derivatives of general formula [G-007] was involved in a Buchwald type reaction utilising a suitable amine, of general formula [G-005], a palladium catalyst such as Pd(dba)$_2$ or Pd(OAc)$_2$, a ligand such as Xantphos and a base such as NaOtBu or Cs$_2$CO$_3$ in a polar solvent such as dioxane or a combination of dioxane and DMA at high temperature either by heating thermally or using a microwave reactor. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

Scheme B2

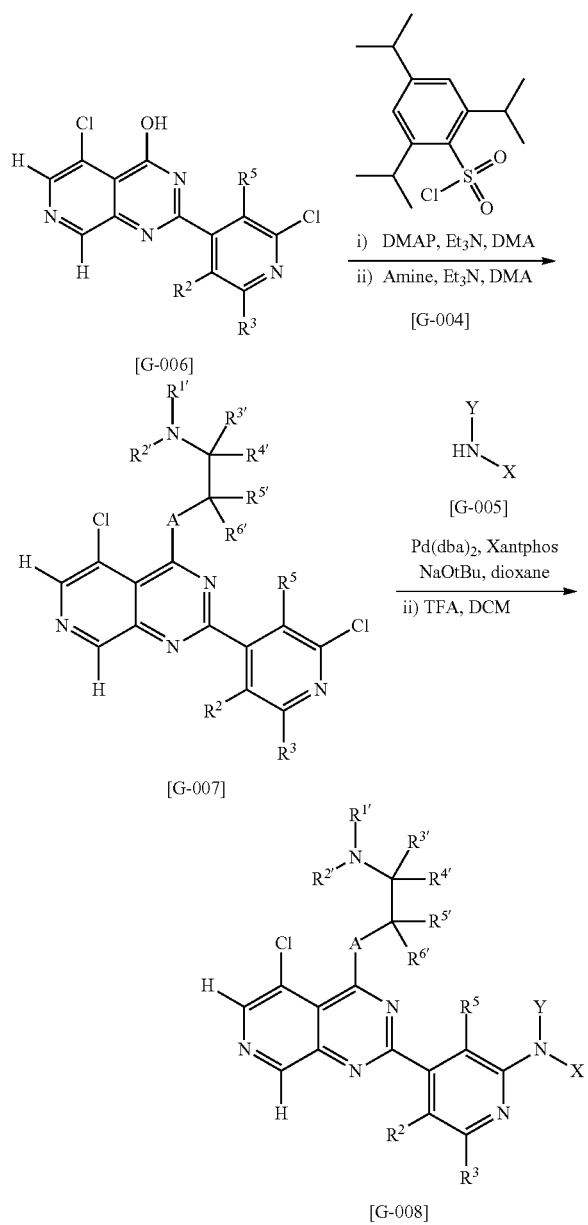

Synthesis of [4-(5-Chloro-4-piperazin-1-yl-pyrido[3,4-d]pyrimidin-2-yl)-pyridin-2-yl]-phenyl-amine [246]

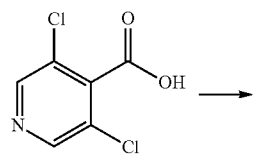

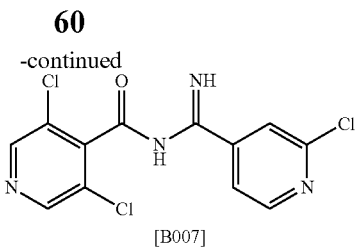

3,5-Dichloro-N-[(2-chloro-pyridin-4-yl)-imino-methyl]-isonicotinamide [B007]

A mixture of 3,5-dichloropyridine-4-carboxylic acid (15 g, 78.12 mmol), DIPEA (37.5 mL, 214 mmol) in DMF (400 mL) was stirred at room temperature then HATU (29.7 g, 78.12 mmol) was added in one portion and the mixture was left to stir for 45 min. 2-Chloro-isonicotinamide (14.25 g, 74.2 mmol) was added and the mixture left to stir for a further 2 hours. The crude reaction mixture was then poured onto water (800 mL) and left to stir overnight. The crude reaction mixture was filtered and the solid washed with water, then dried in in a vacuum oven over night to give the title compound (22 g, 85% yield) as an off white solid: LCMS method: 1, RT:4.89 min, MI 330 [M+H]; NMR: (1H, 300 MHz, d6-dmso); 10.25 (1H, br s), 10.10 (1H, br s), 8.70 (2H, s), 8.57 (1H, s), 7.99 (1H, s), 7.88 (1H, s).

5-Chloro-2-(2-chloro-pyridin-4-yl)-pyrido[3,4-d]pyrimidin-4-ol [B008]

3,5-Dichloro-N-[(2-chloro-pyridin-4-yl)-imino-methyl]-isonicotinamide [B007] (10 g, 30.34 mmol) cesium carbonate (19.8 g, 60.69 mmol) and DMA (180 mL) were stirred at room temperature. The mixture was flushed with nitrogen then iron(III) chloride (0.98 g, 6.07 mmol) was added and the mixture heated at 140 C overnight under an atmosphere of nitrogen. The crude reaction mixture was cooled then poured onto a mixture of ice water, the mixture was then acidified by the addition of glacial acetic acid, and the mixture was then left to stir at room temperature for 2 hours. The solid precipitate was collected by filtration, washed with water then dried in a vacuum oven over night to give the title compound (5.26 g, 59% yield) as a pale brown solid: LCMS method: 1, RT:4.83 min, MI 293 [M+H];

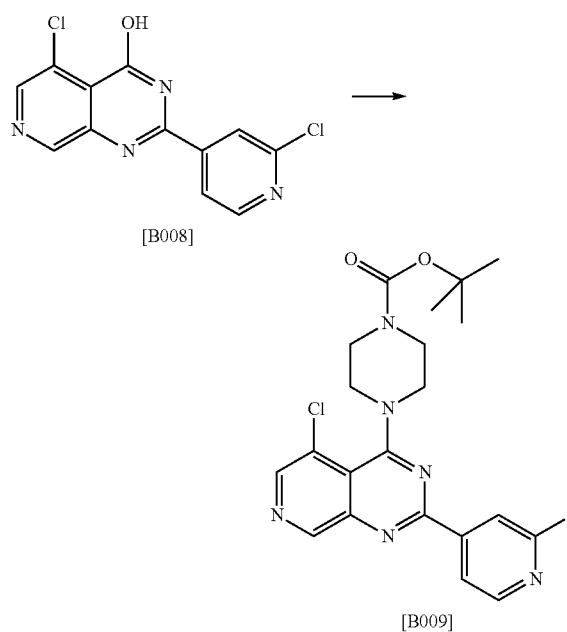

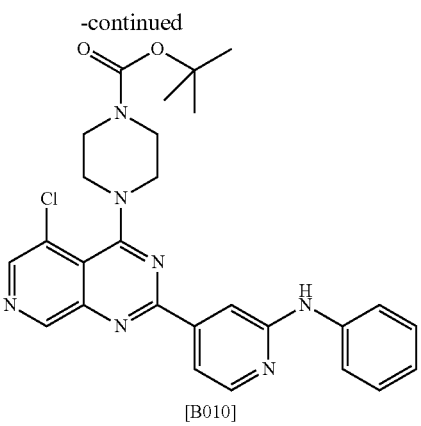

4-[5-Chloro-2-(2-chloro-pyridin-4-yl)-pyrido[3,4-d]pyrimidin-4-yl]-piperazine-1-carboxylic acid tert-butyl ester [B009]

A mixture of 5-Chloro-2-(2-chloro-pyridin-4-yl)-pyrido[3,4-d]pyrimidin-4-ol [B008] (1.05 g, 3.58 mmol), anhydrous DMF (40 mL), triethylamine (1.5 mL, 10.7 mmol) and DMAP (440 mg, 3.58 mmol) was sonicated for 45 min. 2,4,6-Triisopropyl-benzenesulfonyl chloride (1.3 g, 4.3 mmol) was added and the reaction mixture left to stir at room temperature for 2 hr. During this time the material went into solution to form a viscous solution. 1-Boc-piperazine (0.800 g, 4.3 mmol) was added and the reaction mixture was left to stir at room temperature overnight. The solvent was evaporated under reduced pressure and residue triturated in DCM to give brown solid, which was purified by flash column chromatography (SP1, 20 g SiO₂ cartridge 100% DCM up to 95% DCM: 5% MeOH gradient) to give the title compound [B009] as a beige solid (1.1 g, 67% yield). LCMS method: 1, RT:5.50 min, MI: 461 [M+H]; NMR: (1H, 300 MHz, d6-dmso); 9.20 (1H, s), 8.67 (1H, s), 8.62 (1H, d), 8.33 (1H, d), 8.32 (1H, s), 7.94 (1H, s), 3.72 (4H, m, br), 3.53 (4H, m, br), 1.41 (9H, s).

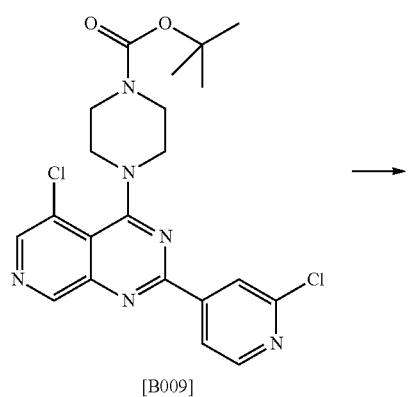

4-[5-Chloro-2-(2-phenylamino-pyridin-4-yl)-pyrido[3,4-d]pyrimidin-4-yl]-piperazine-1-carboxylic acid tert-butyl ester [B010]

A mixture of 4-[5-Chloro-2-(2-chloro-pyridin-4-yl)-pyrido[3,4-d]pyrimidin-4-yl]-piperazine-1-carboxylic acid tert-butyl ester [B009] (0.150 g, 0.325 mmol), Aniline (61 µL, 0.650 mmol), Pd(OAc)₂ (4 mg, 0.017 mmol), Xantphos (19 mg, 0.033 mmol), cesium carbonate (212 mg, 0.650 mmol) and anhydrous dioxane (1 ml) was heated at 90° overnight. Solvent evaporated under reduced pressure and residue purified by flash column chromatography (SP1, 20 g SiO₂ cartridge 100% DCM up to 97% DCM: 3% MeOH gradient) to give the title compound [B010] as a beige solid (65 mg, 39% yield). LCMS method: 1, RT:4.34 min, MI: 518.31 [M+H].

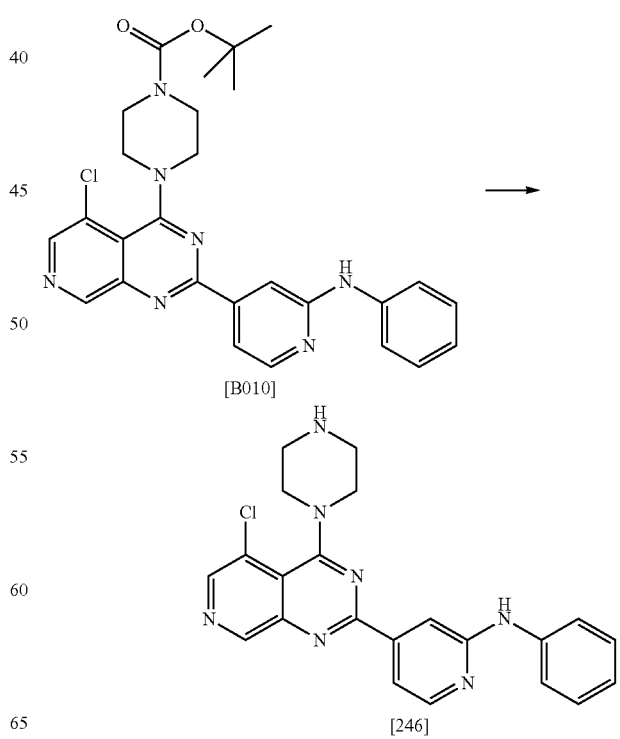

[4-(5-Chloro-4-piperazin-1-yl-pyrido[3,4-d]pyrimidin-2-yl)-pyridin-2-yl]-phenyl-amine[246]

A mixture of 4-[5-Chloro-2-(2-phenylamino-pyridin-4-yl)-pyrido[3,4-d]pyrimidin-4-yl]-piperazine-1-carboxylic acid tert-butyl ester [B010] (60 mg, 0.125 mmol) in 4N HCl in dioxane (1 mL) was stirred at room temperature for 2 hours. After completion solvent was evaporated in vacuo and residue diluted with MeOH (5 mL) and poured onto a 1 g SCX-2 cartridge and washed with DCM and MeOH before eluting with 2N NH3/MeOH which was evaporated evaporated under reduced pressure. The residue purified by flash column chromatography (SP1, 20 g SiO$_2$ cartridge 100% DCM up to 90% DCM: 10% MeOH gradient) to give the title compound [246] as a yellow solid (23 mg, 44% yield). LCMS method: 1, RT:5.48 min, MI: 418.29 [M+H]; NMR: (1H, 300 MHz, d6-dmso); 9.33 (1H, s), 9.12 (1H, s), 8.60 (1H, s), 8.32 (1H, d), 7.89 (1H, s), 7.74 (2H, d), 7.65 (1H, dd), 7.27 (2H, t), 6.89 (1H, t), 3.68 (4H, m), 3.15 (1H, d), 2.86 (4H, m).

General Synthesis of Substituted 2-amino pyridyl substituted 2-(2-amino-pyridin-4-yl)-pyrido[3,4-d]pyrimidin-4-yl amine Derivatives of General Formula [G-003] Scheme B3

5-chloro 2-(2-chloro-pyridin-4-yl)-pyrido[3,4-d]pyrimidin-4-yl amine derivatives of general formula [G-007] were prepared by the reaction of a 5-chloro 2-(2-chloro-pyridin-4-yl)-pyrido[3,4-d]pyrimidin-4-ol derivative of general formula [G-006] with 2,4,6-triisopropylbenzenesulfonyl chloride in a polar aprotic solvent such as DMA, DMF, NMP with a tertiary alkylamine base such as Et$_3$N, DIPEA or NMM and a catalytic amount of DMAP. The intermediate 6,7-substituted-(2,4,6-triisopropyl-benzenesulfonic acid)-2-(2-chloro-pyridin-4-yl)-pyrido[3,4-d]pyrimidin-4-yl ester was then reacted with a primary or secondary amino derivative, of general formula [G-004], in a polar aprotic solvent such as DMA, DMF, NMP in the presence of a tertiary amine base such as Et$_3$N, DIPEA or NMM at ambient temperature. 5-chloro 2-(2-chloro-pyridin-4-yl)-pyrido[3,4-d]pyrimidin-4-yl amine derivatives of general formula [G-007] was involved in a Buchwald type reaction utilising a suitable amine, of general formula [G-005], a palladium catalyst such as Pd(dba)$_2$ or Pd(OAc)$_2$, a ligand such as Xantphos and a base such as NaOtBu or Cs$_2$CO$_3$ in a polar solvent such as dioxane or a combination of dioxane and DMA at high temperature either by heating thermally or using a microwave reactor. The 5-chloro 2-amino-pyridyl substituted 2-(2-amino-pyridin-4-yl)-pyrido[3,4-d]pyrimidin-4-yl amine derivatives of general formula [G-008]. were reacted in a Suzuki type reaction utilising a suitable boronic acid or boronic ester, of general formula [G-009], a palladium catalyst such as Pd(PPh$_3$)$_4$ or Pd(PPh$_3$)$_2$Cl$_2$ a base such as Et$_3$N, KOH, Na$_2$CO$_3$ or NaOH in a polar solvent such as EtOH, THF, DMA or dioxane at high temperature either by heating thermally or using a microwave reactor. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

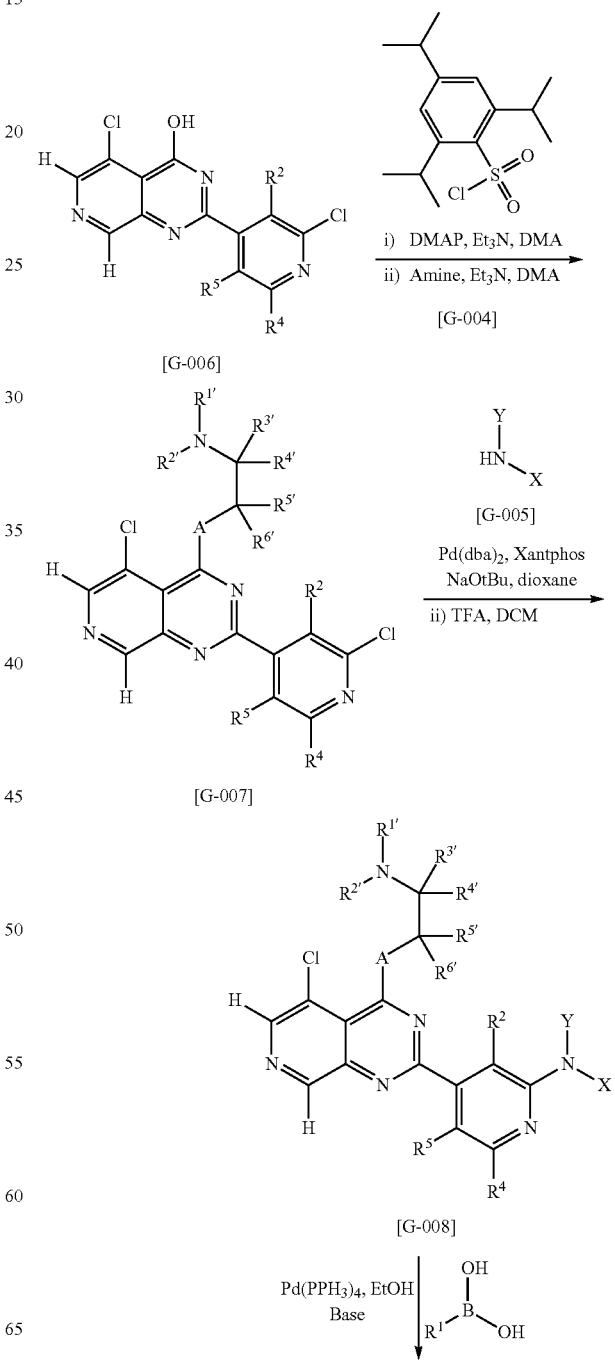

Scheme B3

-continued

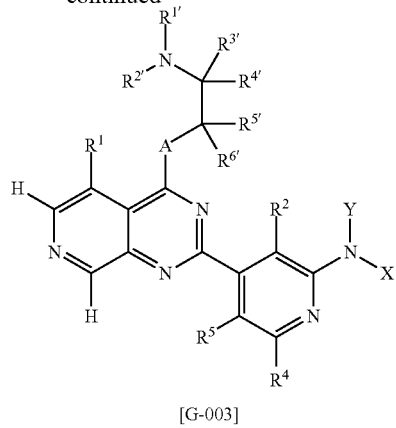

[G-003]

Synthesis of [4-(5-Cyclopropyl-4-piperazin-1-yl-pyrido[3,4-d]pyrimidin-2-yl)-pyridin-2-yl]-(2-fluoro-phenyl)-amine[263]

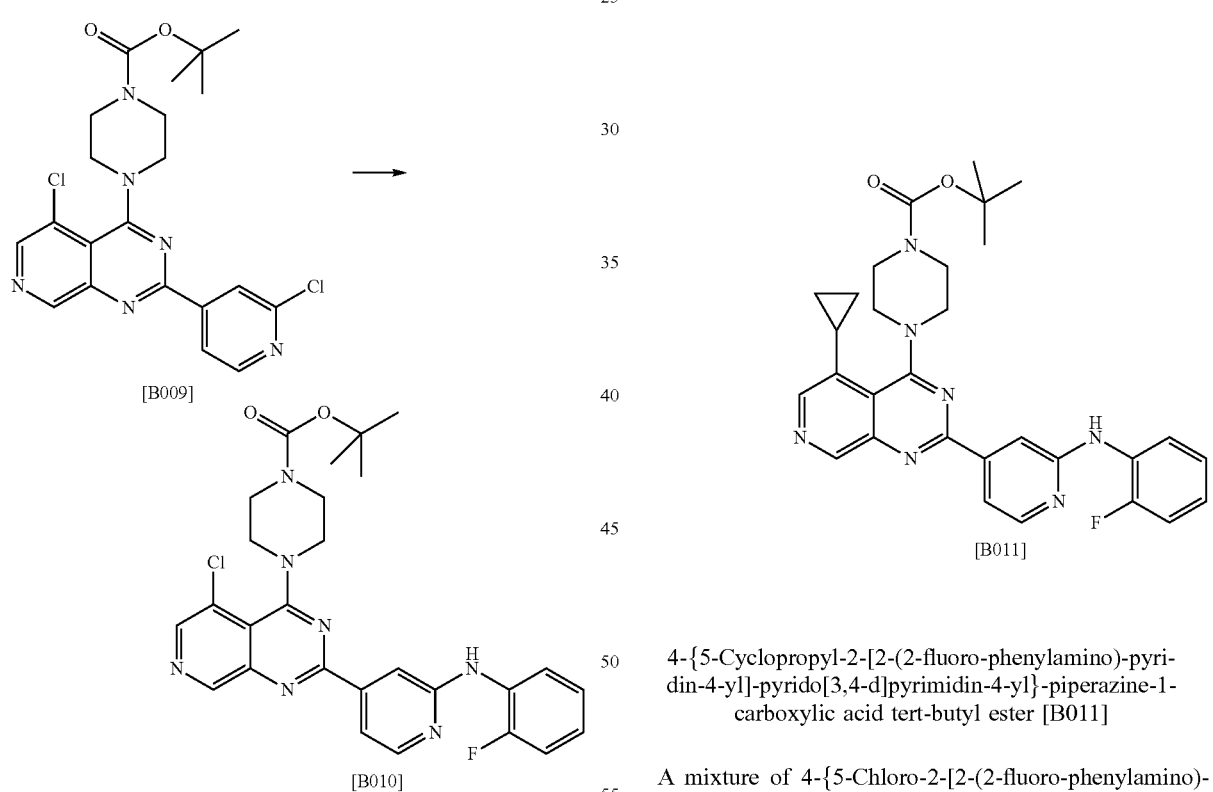

4-{5-Chloro-2-[2-(2-fluoro-phenylamino)-pyridin-4-yl]-pyrido[3,4-d]pyrimidin-4-yl}-piperazine-1-carboxylic acid tert-butyl ester [B010]

A mixture of 4-[5-Chloro-2-(2-chloro-pyridin-4-yl)-pyrido[3,4-d]pyrimidin-4-yl]-piperazine-1-carboxylic acid tert-butyl ester [B009] (3 g, 6.48 mmol), 2-fluoroaniline (654 μL, 6.48 mml), Pd(OAc)$_2$ (79 mg, 0.324 mmol), Xantphos (375 mg, 0.648 mmol), ceasium carbonate (4.11 g, 12.6 mmol) and anhydrous dioxane (20 ml) was heated at 90° overnight. Solvent was evaporated under reduced pressure and residue purified by flash column chromatography (ISCO, 120 g SiO$_2$ cartridge 100% cyclohexane up to 70% cyclohexane: 30% Ethylacetate gradient) to give the title compound [B010] as a yellow solid (1.2 g, 52% yield). LCMS method: 5, RT:4.19 min, MI 516.57 [M+H].

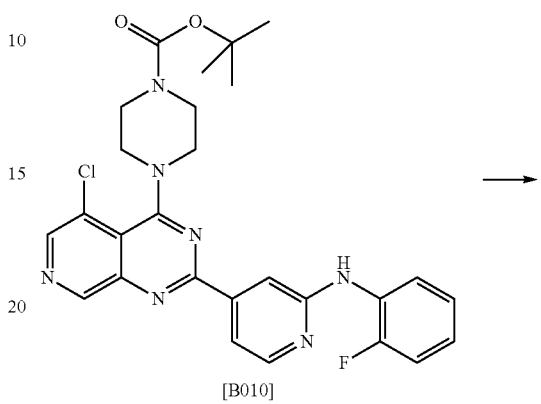

[B010]

4-{5-Cyclopropyl-2-[2-(2-fluoro-phenylamino)-pyridin-4-yl]-pyrido[3,4-d]pyrimidin-4-yl}-piperazine-1-carboxylic acid tert-butyl ester [B011]

A mixture of 4-{5-Chloro-2-[2-(2-fluoro-phenylamino)-pyridin-4-yl]-pyrido[3,4-d]pyrimidin-4-yl}-piperazine-1-carboxylic acid tert-butyl ester [B010] (1.8 g, 3.36 mmol), Pd(dppf)Cl$_2$.CH$_2$Cl$_2$ (137 mg, 0.168 mmol), K$_3$PO$_4$ (2.14 g, 10.075 mmol), cyclopropyl boronic acid (578 mg, 6.72 mmol) and anhydrous dioxane (30 ml) plus few drops of DMA was added to a microwave vial. Solvent was evaporated under reduced pressure and residue purified by flash column chromatography (ISCO, 40 g SiO$_2$ cartridge 100% cyclohexane up to 70% cyclohexane: 30% Ethylacetate gradient) to give the title compound [B011] as a yellow solid (950 mg, 52% yield). LCMS method: 5, RT:4.72 min, MI 542 [M+H].

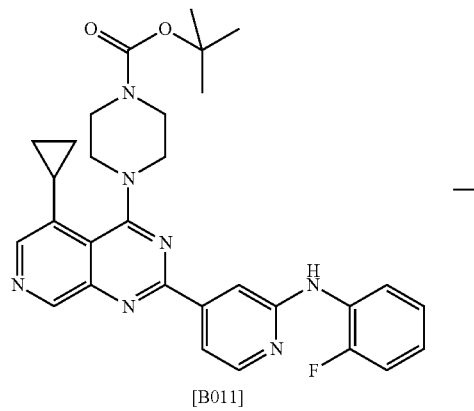

[B011]

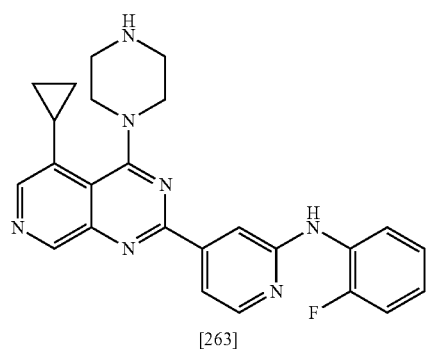

[263]

[4-(5-Cyclopropyl-4-piperazin-1-yl-pyrido[3,4-d]pyrimidin-2-yl)-pyridin-2-yl]-(2-fluoro-phenyl)-amine[263]

A mixture of 4-{5-Cyclopropyl-2-[2-(2-fluoro-phenylamino)-pyridin-4-yl]-pyrido[3,4-d]pyrimidin-4-yl}-piperazine-1-carboxylic acid tert-butyl ester [B011] (300 mg, 0.554 mmol) in 4N HCl in dioxane (1.5 mL) was stirred at room temperature for 2 hours. Solvent was evaporated under reduced pressure and residue purified by reverse phase flash column chromatography (ISCO, 24 g SiO$_2$ cartridge, 100% H$_2$O:0.1% formic acid up to 20% H$_2$O:0.1% formic acid: 80% MeOH: 0.1% formic acid gradient) The residue was diluted with MeOH (5 mL) and poured onto a 1 g SCX-2 cartridge and washed with DCM and MeOH before eluting with 2N NH3/MeOH which was evaporated under reduced pressure to give the title compound [263] as a yellow solid (110 mg, 45% yield). LCMS method: 1, RT:4.03 min, MI 442 [M+H]; NMR: (1H, 500 MHz, d6-dmso); 8.95 (1H, s), 8.27 (1H, d), 8.21 (1H, m), 8.08 (1H, s), 8.03 (1H, s), 7.70-7.69 (1H, dd), 7.23 (1H, m), 7.14 (1H, m), 6.99 (1H, m), 3.78-3.62 (4H, m), 2.84 (4H, s), 2.61 (1H, m), 1.25-1.24 (2H, m), 1.02-1.01 (2H, m).

General Synthesis of 5-cyclopropyl substituted 2-amino pyridyl substituted 2-(2-amino-pyridin-4-yl)-pyrido[3,4-d]pyrimidin-4-yl amine Derivatives of General Formula [G-012]

Scheme B4

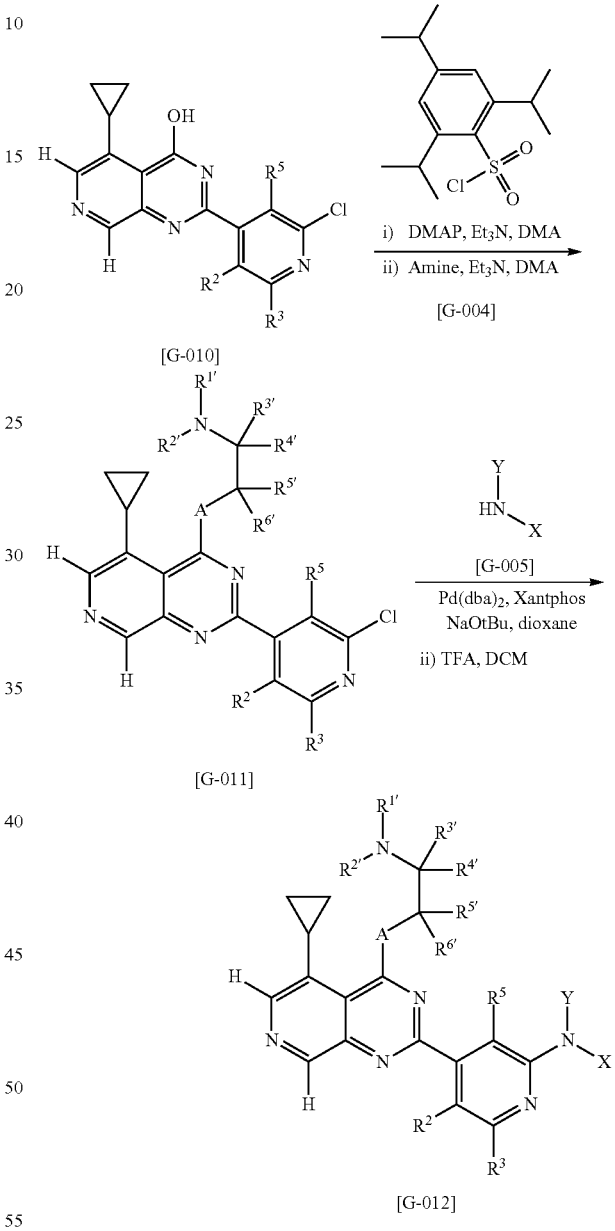

5-cyclopropyl 2-(2-chloro-pyridin-4-yl)-pyrido[3,4-d]pyrimidin-4-yl amine derivatives of general formula [G-011] were prepared by the reaction of a 5-cyclopropylo 2-(2-chloro-pyridin-4-yl)-pyrido[3,4-d]pyrimidin-4-ol derivative of general formula [G-010] with 2,4,6-triisopropylbenzenesulfonyl chloride in a polar aprotic solvent such as DMA, DMF, NMP with a tertiary alkylamine base such as Et$_3$N, DIPEA or NMM and a catalytic amount of DMAP. The intermediate 6,7-substituted-(2,4,6-triisopropyl-benzenesulfonic acid)-2-(2-chloro-pyridin-4-yl)-pyrido[3,4-d]pyrimidin-4-yl ester was then reacted with a primary or secondary amino derivative, of general formula [G-004], in a polar aprotic solvent such as DMA, DMF, NMP in the presence of a tertiary amine base such as Et$_3$N, DIPEA or NMM at ambient temperature. 5-cyclopropyl 2-(2-chloro-pyridin-4-yl)-pyrido[3,4-d]pyrimidin-4-yl amine derivatives of general formula [G-011] was involved in a Buchwald type reaction utilising a suitable amine, of general formula [G-005], a palladium catalyst such as Pd(dba)$_2$ or Pd(OAc)$_2$, a ligand such as Xantphos and a base such as NaOtBu or Cs$_2$CO$_3$ in a polar solvent such as dioxane or a combination of dioxane and DMA at high temperature either by heating thermally or using a microwave reactor. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

Synthesis of [4-(5-Cyclopropyl-4-piperazin-1-yl-pyrido[3,4-d]pyrimidin-2-yl)-pyridin-2-yl]-(4,5-dimethyl-oxazol-2-yl)-amine[272]

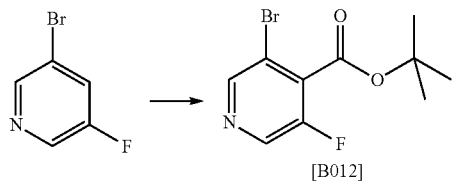

Synthesis of 3-Bromo-5-fluoro-isonicotinic acid test-butyl ester [B012]

To a solution of LDA (2M, 72 mL, 144 mmol) in THF (100 mL) cooled to approximately −70° C. was added dropwise via cannula a solution of 3-bromo-5-fluoropyridine (21.12 g, 120 mmol) in anhydrous THF (50 mL) pre-cooled to −70° C. The rate of addition was controlled such that the internal temperature did not rise above −65° C. The dark red-brown solution was stirred for 1 hour. Di-tert-butyldicarbonate (52.4 g, 240 mmol) in THF (50 mL) was cooled to −10° C. in a methanol/ice bath then added dropwise via cannula to the dark red-brown solution. The mixture was stirred for 2 hours then allowed to warm to room temperature and stirred for another 1 hour. Saturated aqueous ammonium chloride (100 mL) was added slowly and then water (200 mL) and EtOAc (200 mL) and the mixture was vigorously stirred for 45 minutes. The mixture was transferred to a separatory funnel and the layers were separated. The aqueous layer was extracted with EtOAc (200 mL). The THF and EtOAc layers were combined, dried over magnesium sulfate, filtered and evaporated. The recovered dark red-brown oil was purified by column chromatography (Cyclohexane/AcOEt: 1/0 to 97/3). Fractions containing desired material were concentrated in vacuo to yield the title compound [B012] as a pale yellow oil (14 g, 85%). LCMS method: 1, RT:5.44 min, MI: 277 [M+H]; NMR: (1H, 300 MHz, d6-dmso); 8.56 (s, 1H), 8.43 (s, 1H), 1.62 (s, 9H).

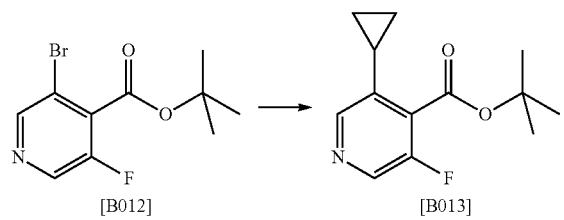

Synthesis of 3-Cyclopropyl-5-fluoro-isonicotinic acid test-butyl ester 1B0131

A solution containing 3-Bromo-5-fluoro-isonicotinic acid tert-butyl ester [B012] (5.52 g, 20 mmol), potassium phosphate tribasic (12.74 g, 60 mmol) and cyclopropyl boronic acid (2.58 g, 30 mmol), in anhydrous dioxane (100 mL) was subjected to vacuum/argon balloon (three times). Dichloro [1,1'-bis(diphenylphosphino)ferrocene]palladium (II) dichloromethane adduct (0.408 g, 0.5 mmol) was added and the reaction heated at 96° C. overnight under positive pressure of nitrogen. The mixture was cooled to room temperature and was filtered through a pad of 200 g silica and washed with EtOAc (1 L). The filtrate was concentrated in vacuo and the crude was purified by column chromatography (Cyclohexane/AcOEt: 98:2 to 96:4). The combined fractions were concentrated under reduced pressure to yield the title compound [B013] as a colourless oil (3.42 g, 72%). LCMS method: 1, RT: 5.36 min, MI: 238 [M+H].

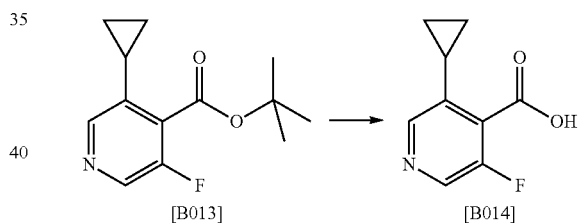

Synthesis of 3-Cyclopropyl-5-fluoro-isonicotinic acid [B014]

In a microwave vial, 3-cyclopropyl-5-fluoro-isonicotinic acid tert-butyl ester [B013] (1.186 g, 5 mmol) was dissolved in anhydrous methanol and then heated in microwave at 140° C. for 1 hr. The reaction was concentrated in vacuo to give the title compound [B014] 0.84 g (92%) as a white crystalline solid. LCMS method: 1, RT:1.51 min, MI: 182 [M+H].

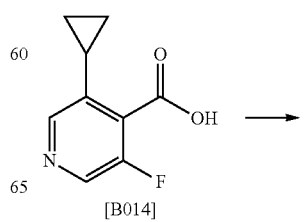

-continued

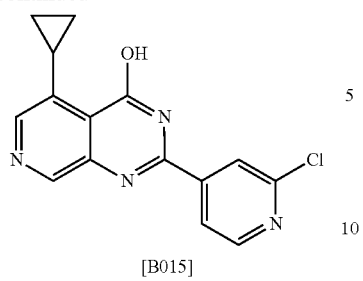
[B015]

Synthesis of 2-(2-Chloro-pyridin-4-yl)-5-cyclopropyl-pyrido[3,4-d]pyrimidin-4-ol [B015]

A mixture of 3-Cyclopropyl-5-fluoro-isonicotinic acid [B014] (5 g, 27.6 mmol) and HATU (10.5 g, 82.86 mmol) was stirred in DMF (35 mL) and DIPEA (14.5 mL, 82.86 mmol) was added. The mixture was left to stir at rt for 1 hour then 2-Chloro-isonicotinamidine hydrochloride (5.3 g, 27.52 mmol) was added in one portion and the mixture was left to stir at rt for 18 hours. The crude reaction mixture was poured onto water (180 mL) and left to stir for stirred for 2 hours and then the beige solid was collected by filtration, washed with water and dried in a vacuum oven to give N-[(2-Chloro-pyridin-4-yl)-imino-methyl]-3-cyclopropyl-5-fluoro-isonicotinamide (6.60 g, 75% yield) which was used in the next step without further purification: LCMS method: 1, RT:3.45 min, MI: 319 [M+H]; NMR: (1H, 300 MHz, d6-dmso); 10.25 (s, br, 1H), 9.92 (s, br, 1H), 8.59 (d, 1H), 8.42 (s, 1H), 8.11 (s, 1H), 8.00 (s, 1H), 7.92 (dd, 1H), 2.01 (m, 1H), 0.98 (m, 2H), 0.85 (m, 2H).

A mixture of N-[(2-Chloro-pyridin-4-yl)-imino-methyl]-3-cyclopropyl-5-fluoro-isonicotinamide (6.60 g, 20.70 mmol) and Cs2CO3 (6.7 g, 20.7 mmol) and DMA (90 mL) was heated at 90° C. overnight. The reaction mixture was poured into ice/water (100 ml), then acidified by the dropwise addition of glacial acetic acid and the mixture was left to stir at 0° C. for 1 hour. The beige precipitate was collected by filtration and washed with water then dried in a vacuum oven to give the title compound [B015] (4.8 g, 78% yield). LCMS method: 1, RT: 3.90 min, MI: 299 [M+H]; NMR: (1H, 300 MHz, d6-dmso); 12.92 (s, 1H), 8.88 (s, 1H), 8.66 (d, 1H), 8.25 (dd, 2H), 8.16 (dd, 1H), 3.39 (m, 1H), 1.11 (m, 2H), 0.94 (m, 2H).

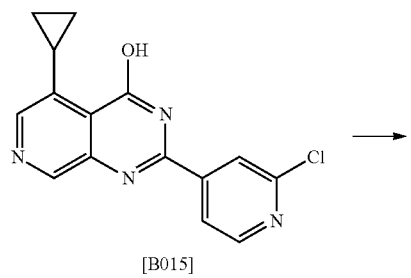
[B015] →

-continued

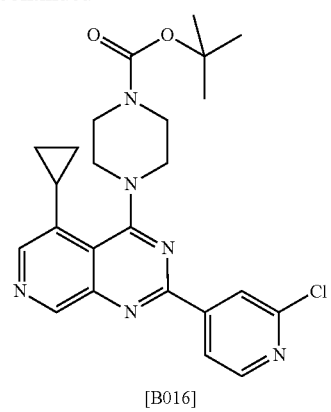
[B016]

4-[2-(2-Chloro-pyridin-4-yl)-5-cyclopropyl-pyrido[3,4-d]pyrimidin-4-yl]-piperazine-1-carboxylic acid tert-butyl ester [B016]

A mixture of 2-(2-Chloro-pyridin-4-yl)-5-cyclopropyl-pyrido[3,4-d]pyrimidin-4-ol [B015] (280 mg, 0.937 mmol), anhydrous DMF (9 mL), triethylamine (0.390 mL, 2.81 mmol) and DMAP (115 mg, 0.937 mmol) was sonicated for 10 min then stirred at room temperature for 10 min. 2,4,6-Triisopropyl-benzenesulfonyl chloride (340 mg, 1.12 mmol) was added and the mixture was sonicated for 5 min then left to stir at room temperature for 2 hours. During this time the material went into solution to form a viscous solution. 1-Boc-piperazine (190 mg, 1.03 mmol) was added and the reaction mixture was left to stir at room temperature overnight. Solvent was evaporated under reduced pressure and residue purified by flash column chromatography (SP1, 20 g SiO2 cartridge 100% DCM up to 95% DCM: 5% MeOH gradient) to give the title compound [B016] as a yellow solid (276 mg, 63% yield). LCMS method: 5, RT:5.16 min, MI: 467 [M+H]; NMR: (1H, 500 MHz, d6-dmso); 9.02 (1H, s), 8.61 (1H, dd), 8.34 (2H, m), 8.15 (1H, s), 3.68-3.83 (4H, very broad s), 3.51 (4H, br s), 2.59 (1H, m), 1.24 (2H, m), 1.16 (2H, m).

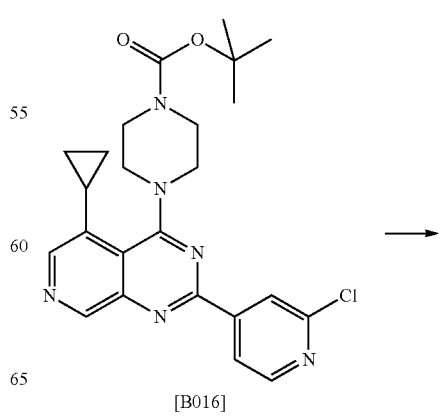
[B016] →

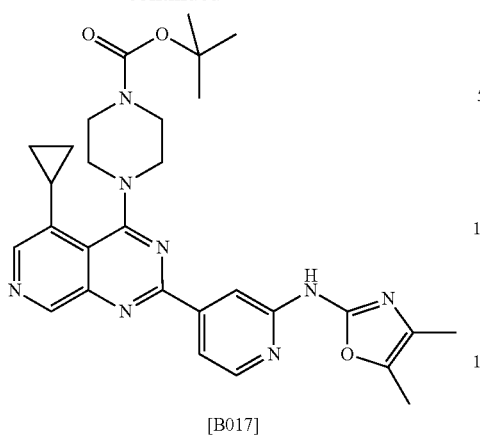

[B017]

4-{5-Cyclopropyl-2-[2-(4,5-dimethyl-oxazol-2-ylamino)-pyridin-4-yl]-pyrido[3,4-d]pyrimidin-4-yl}-piperazine-1-carboxylic acid tert-butyl ester [B017]

A mixture of 4-[2-(2-Chloro-pyridin-4-yl)-5-cyclopropyl-pyrido[3,4-d]pyrimidin-4-yl]-piperazine-1-carboxylic acid tert-butyl ester [B016] (280 mg, 0.591 mmol), 4,5-dimethyl-oxazol-2-ylamine (132 mg, 1.18 mml), Pd(OAc)$_2$ (7 mg, 0.030 mmol), Xantphos (35 mg, 0.060 mmol), ceasium carbonate (384 mg, 1.18 mmol) and anhydrous dioxane (1.5 ml) was heated at 90° overnight. Solvent was evaporated under reduced pressure and residue purified by flash column chromatography (SP1, 20 g SiO$_2$ cartridge 100% DCM up to 96% DCM: 4% MeOH gradient) to give the title compound [B017] as a beige solid (61 mg, 19% yield). LCMS method: 5, RT: 4.07 min, MI: 543 [M+H].

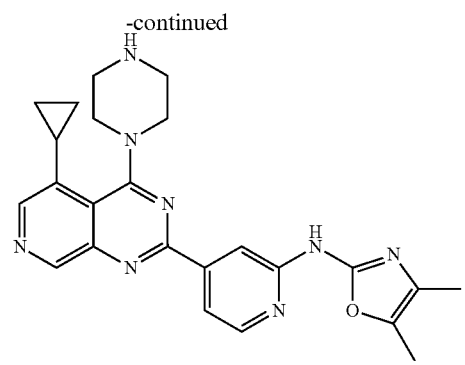

[272]

[4-(5-Cyclopropyl-4-piperazin-1-yl-pyrido[3,4-d]pyrimidin-2-yl)-pyridin-2-yl]-(4,5-dimethyl-oxazol-2-yl)-amine[272]

A mixture of 4-{5-Cyclopropyl-2-[2-(4,5-dimethyl-oxazol-2-ylamino)-pyridin-4-yl]-pyrido[3,4-d]pyrimidin-4-yl}-piperazine-1-carboxylic acid tert-butyl ester [B017] (60 mg, 0.112 mmol) in 4N HCl in dioxane (1 mL) was stirred at room temperature for 2 hours. After completion solvent was evaporated under reduced pressure and residue diluted with MeOH (5 mL) and poured onto a 1 g SCX-2 cartridge and washed with DCM and MeOH before eluting with 2N NH3/MeOH which was evaporated under reduced pressure. The residue was then purified by flash column chromatography (SP1, 10 g SiO$_2$ cartridge 100% DCM up to 90% DCM: 10% MeOH gradient) to give the title compound [272] as a yellow solid (22 mg, 44% yield). LCMS method: 5, RT:2.70 min, MI: 443 [M+H]; NMR: (1H, 500 MHz, d6-dmso); 10.61 (1H, s), 9.17 (1H, s), 9.05 (1H, s), 8.38 (1H, d), 8.16 (1H, s), 7.87 (1H, d), 3.94 (1H, s, br), 3.26 (4H, m, br), 2.69 (2H, m), 2.19 (3H, s), 2.04 (3H, s), 1.25-1.22 (3H, m), 1.06-1.05 (2H, m).

Synthesis of Cyclopentyl-[4-(5-cyclopropyl-4-piperazin-1-yl-pyrido[3,4-d]pyrimidin-2-yl)-pyridin-2-yl]-amine[281]

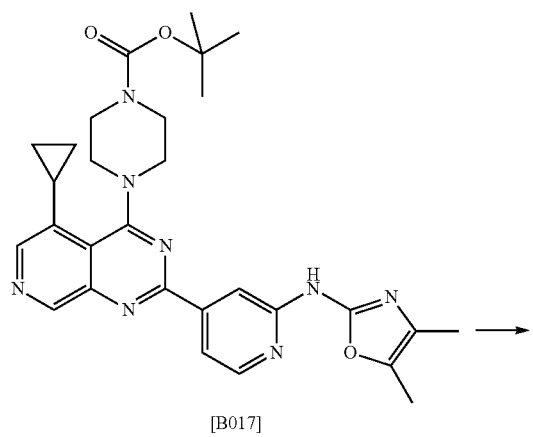

[B017]

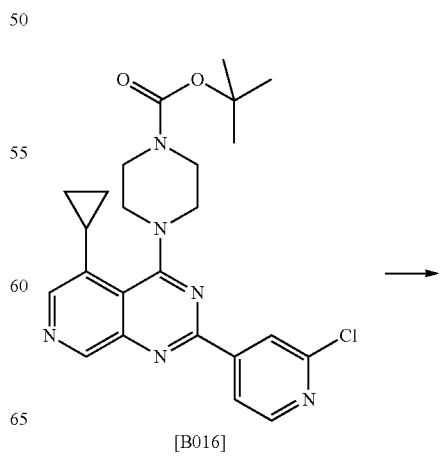

[B016]

-continued

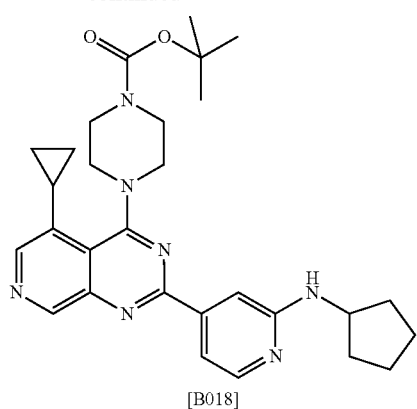

[B018]

4-[2-(2-Cyclopentylamino-pyridin-4-yl)-5-cyclopropyl-pyrido[3,4-d]pyrimidin-4-yl]-piperazine-1-carboxylic acid tert-butyl ester [B018]

A mixture of 4-[2-(2-Chloro-pyridin-4-yl)-5-cyclopropyl-pyrido[3,4-d]pyrimidin-4-yl]-piperazine-1-carboxylic acid tert-butyl ester [B016] [prepared according to the general synthesis shown in Scheme B4] (170 mg, 0.364 mmol), cyclopentylamine (73 μL, 0.728 mmol), Pd(t-Bu₃P)₂ (38 mg, 0.073 mmol), sodium tert-butoxide (54 mg, 0.546 mmol) and anhydrous dioxane (2 ml) was heated at 110° C. overnight. Solvent was evaporated under reduced pressure and residue purified by flash column chromatography (SP1, 20 g SiO₂ cartridge 100% DCM up to 96% DCM: 4% MeOH gradient) to give the title compound [B018] as a yellow solid (92 mg, 48% yield). LCMS: method: 5, RT: 4.19 min, MI 516.57 [M+H].

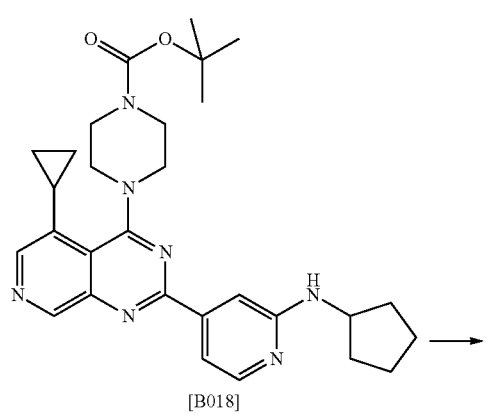

[B018]

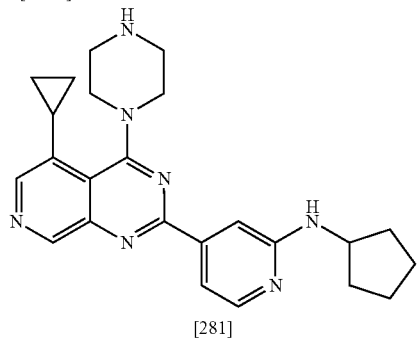

[281]

Cyclopentyl-[4-(5-cyclopropyl-4-piperazin-1-yl-pyrido[3,4-d]pyrimidin-2-yl)-pyridin-2-yl]-amine [281]

A mixture of 4-[2-(2-Cyclopentylamino-pyridin-4-yl)-5-cyclopropyl-pyrido[3,4-d]pyrimidin-4-yl]-piperazine-1-carboxylic acid tert-butyl ester [B018] (90 mg, 0.178 mmol) in 4N HCl in dioxane (2 mL) was stirred at room temperature for 2 hours. Solvent was evaporated under reduced pressure and residue diluted with MeOH (5 mL) and poured onto a 1 g SCX-2 cartridge and washed with DCM and MeOH before eluting with 2N NH3/MeOH which was evaporated under reduced pressure. The residue was then purified by flash column chromatography (SP1, 10 g SiO₂ cartridge 100% DCM up to 95% DCM: 5% MeOH gradient) to give the title compound [281] as a yellow solid to give the title compound as a yellow solid (26 mg, 37% yield). LCMS: method: 5, RT:2.22 min, MI 416.25 [M+H]; NMR: (1H, 500 MHz, d6-dmso); 8.95 (1H, s), 8.10 (2H, d), 8.08 (1H, s), 7.51 (1H, s), 7.38 (1H, dd), 6.75 (1H, d), 4.17 (1H, m), 3.84-3.65 (4H, m), 3.11 (4H, m), 2.91 (1H, m), 2.62 (2H, m), 1.98-1.92 (2H, m), 1.69 (2H, m), 1.55 (2H, m), 1.46 (2H, m), 1.24-1.22 (2H, m), 1.03 (2H, m).

4PPAZ Compounds

Several methods for the chemical synthesis of 4-substituted-2-(1H-pyrrolo[2,3-b]pyridin-4-yl)-azaquinazoline compounds (for convenience, collectively referred to herein as "4PPAZ compounds") of the present application are described herein, of general formula [I-001]. These and/or other well known methods may be modified and/or adapted in known ways in order to facilitate the synthesis of additional compounds within the scope of the present application.

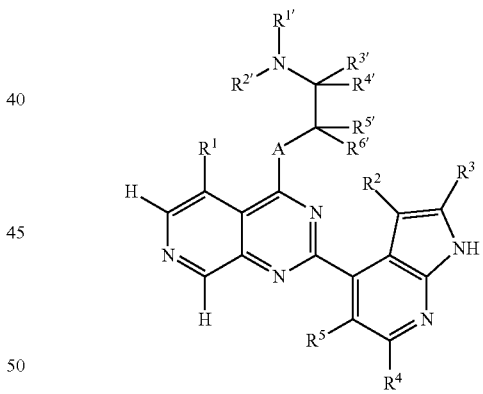

[I-001]

General Synthesis of Substituted Substituted 4-Substituted-2-(1H-pyrrolo[2,3-b]pyridin-4-yl)-azaquinazoline Derivatives of General Formula [I-001]
Scheme D1

The 4-substituted-2-(1H-pyrrolo[2,3-b]pyridin-4-yl)-azaquinazoline derivatives of general formula [I-003] were prepared by the reaction of a 2-Chloro-pyrido[3,4-d]pyrimidine derivative of general formula [I-002], prepared in scheme C2, in a Suzuki type palladium catalysed cross coupling reaction with boronic acid or boronate ester derivative of general formula [I-004] a palladium catalyst such as Pd(PPh₃)₄, a base such as K₂PO₄ in a polar aprotic solvent such as DMA or DMF at elevated temperature either by heating thermally or using a microwave reactor, to yield 4PPAZ derivative of general formula [I-003]. After reaction work up, typically by a liquid-liquid extraction or purification by acidic ion exchange catch-release, the intermediate was purified by column chromatography. The intermediate arylsulphonate protected derivative of general formula [I-003] was then subjected to a deprotection reaction in the presence of a base such as sodium hydroxide in a polar protic solvent such as ethanol. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

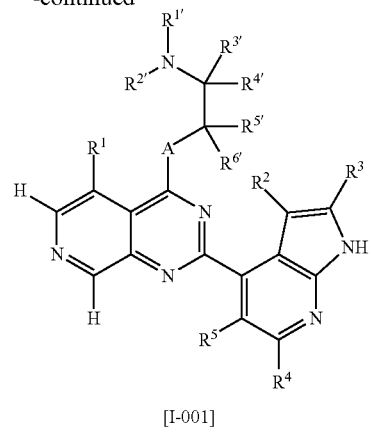

Synthesis of 5-Methoxy-4-piperazin-1-yl-2-(1H-pyrrolo[2,3-b]pyridin-4-yl)-pyrido[3,4-d]pyrimidine [1200]

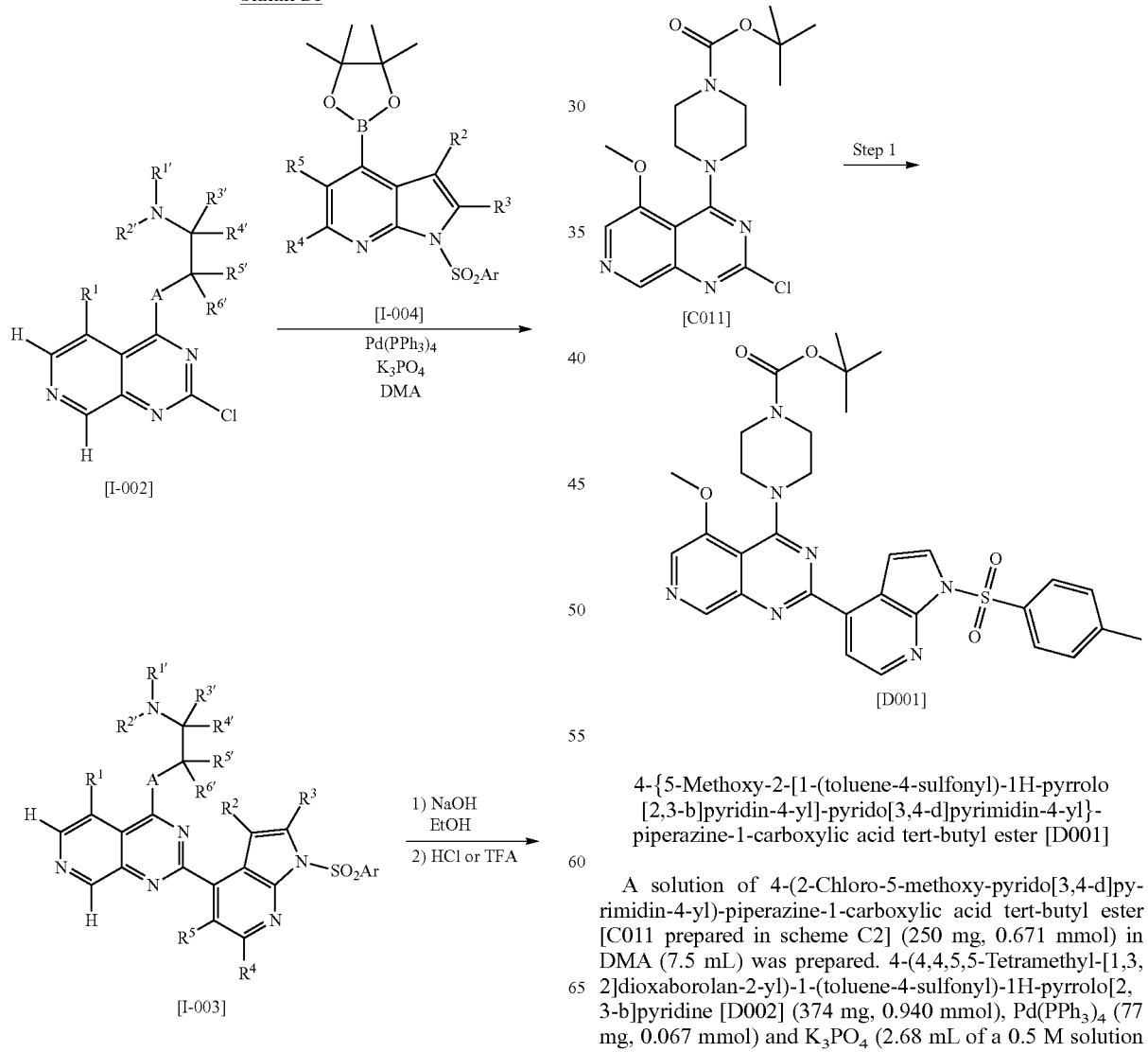

4-{5-Methoxy-2-[1-(toluene-4-sulfonyl)-1H-pyrrolo[2,3-b]pyridin-4-yl]-pyrido[3,4-d]pyrimidin-4-yl}-piperazine-1-carboxylic acid tert-butyl ester [D001]

A solution of 4-(2-Chloro-5-methoxy-pyrido[3,4-d]pyrimidin-4-yl)-piperazine-1-carboxylic acid tert-butyl ester [C011 prepared in scheme C2] (250 mg, 0.671 mmol) in DMA (7.5 mL) was prepared. 4-(4,4,5,5-Tetramethyl-[1,3,2]dioxaborolan-2-yl)-1-(toluene-4-sulfonyl)-1H-pyrrolo[2,3-b]pyridine [D002] (374 mg, 0.940 mmol), Pd(PPh$_3$)$_4$ (77 mg, 0.067 mmol) and K$_3$PO$_4$ (2.68 mL of a 0.5 M solution in water) were added. The reaction mixture was heated to 150° C. in the microwave for 10 min. The reaction mixture was concentrated by rotovap and purified by column chromatography on silica, eluting with cyclohexane containing 0-100% EtOAc. The appropriate fractions were combined and concentrated to give the title compound [D001]] (115 mg, 28%) as a yellow solid. LCMS method: 5, RT 5.13 min, MI 616 [M+H]; NMR: (1H, 500 MHz, d6-dmso) 8.92 (s, 1H), 8.53 (d, 1H), 8.37 (s, 1H), 8.26 (d, 1H), 8.05 (d, 1H), 8.02 (d, 1H), 7.77 (d, 1H), 7.64-7.60 (m, 1H), 7.57-7.53 (m, 1H), 7.43 (d, 2H), 4.09 (s, 3H), 3.67 (br. m, 4H), 3.56 (br. m, 4H), 1.43 (s, 9H).

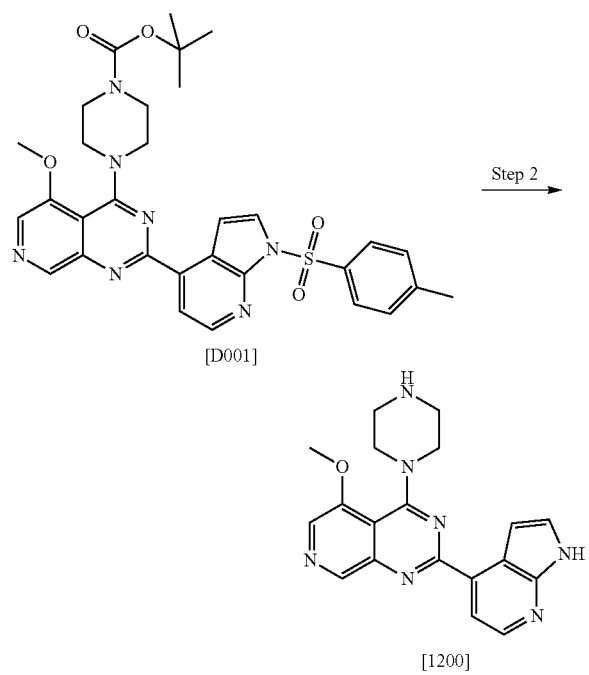

[D001]

[1200]

5-Methoxy-4-piperazin-1-yl-2-(1H-pyrrolo[2,3-b]pyridin-4-yl)-pyrido[3,4-d]pyrimidine[1200]

A solution of 4-{5-Methoxy-2-[1-(toluene-4-sulfonyl)-1H-pyrrolo[2,3-b]pyridin-4-yl]-pyrido[3,4-d]pyrimidin-4-yl}-piperazine-1-carboxylic acid tert-butyl ester [D001] (100 mg, 0.162 mmol) in ethanol (4 mL) was prepared and NaOH (1 mL of a 5 M solution) was added. The reaction mixture was stirred at room temperature overnight. The reaction mixture was concentrated by rotary evaporation and the residue dissolved in DCM (10 mL) and water (10 mL). The pH was adjusted to approx 7 by addition of ammonium chloride and the mixture extracted with DCM (3×10 mL). The combined organic extracts were dried (phase separator) and concentrated by rotary evaporation. The residue was purified by column chromatography on silica, eluting with cyclohexane containing 75-100% EtOAc. The appropriate fractions were combined and concentrated to give intermediate 4-[5-Methoxy-2-(1H-pyrrolo[2,3-b]pyridin-4-yl)-pyrido[3,4-d]pyrimidin-4-yl]-piperazine-1-carboxylic acid tert-butyl ester which was stirred in 4M HCl in dioxane (2 mL) at room temperature for 1 hour. The reaction mixture was concentrated by rotary evaporation, loaded onto a SCX cartridge, washed with methanol and eluted with 7N ammonia in methanol. The ammonia fraction was concentrated by rotary evaporation to give the title compound [1200] (29 mg, 49%) as a yellow solid. LCMS method: 5, RT 2.23 min, MI 362 [M+H]; NMR: (1H, 500 MHz, d6-dmso) 11.81 (1H, s), 8.89 (1H, s), 8.37 (1H, d, J=5.0 Hz), 8.31 (1H, s), 8.09 (1H, d, J=5.0 Hz), 7.63-7.62 (1H, m), 7.43 (1H, dd, J=3.3, 1.8 Hz), 4.07 (3H, s), 3.66-3.64 (4H, m), 2.91-2.89 (4H, m).

General Synthesis of Substituted Boronic Acid or Boronate Ester Derivative of General Formula [I-004] Scheme D2

The substituted boronic acid or boronate ester derivatives of general formula [I-004] were prepared by the reaction of a 4-Bromo-1H-pyrrolo[2,3-b]pyridine derivative of general formula [I-005] with an arylsuphonyl chloride derivative of general formula [I-008] with a base such as NaH in a polar aprotic solvent such as THF at low temperature. The 1-arylsulfonyl-4-bromo-1H-pyrrolo[2,3-b]pyridine derivative of general formula [I-006] was then reacted with a strong base such as LDA, in a polar aprotic solvent such as THF at low temperature and a alkylhalide derivative of general formula [I-009]. The C2 substituted 4-bromo-1H-pyrrolo[2,3-b]pyridine derivative of general formula [I-007] was then reacted in a palladium catalysed cross coupling reaction with a palladium catalyst such as PdCl$_2$ dppf, a boron agent such as bispinocolatodiboron, potassium acetate in a polar aprotic solvent such as dioxane at elevated temperature either by heating thermally or using a microwave reactor, to yield the substituted boronate ester derivative of general formula [I-004] which after reaction work up, typically by a liquid-liquid extraction was purified by column chromatography.

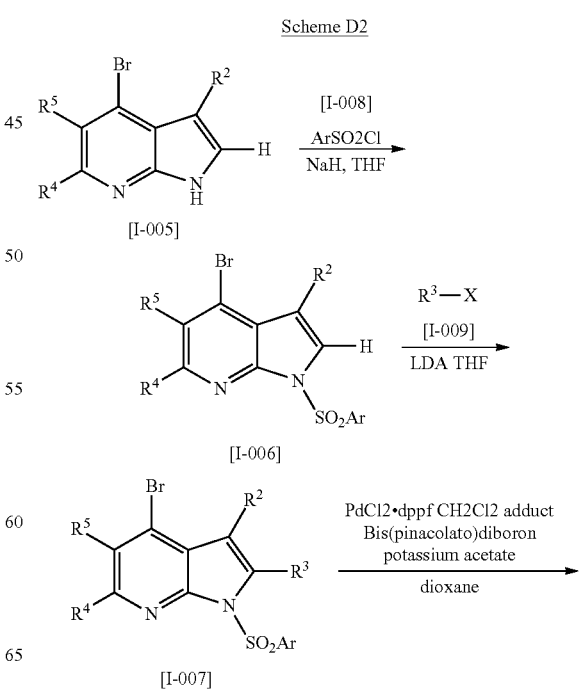

Scheme D2

-continued

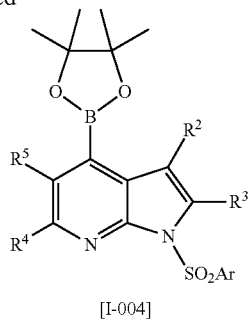

[I-004]

Synthesis of 4-(4,4,5,5-Tetramethyl-[1,3,2]dioxaborolan-2-yl)-1-(toluene-4-sulfonyl)-1H-pyrrolo[2,3-b]pyridine [D002]

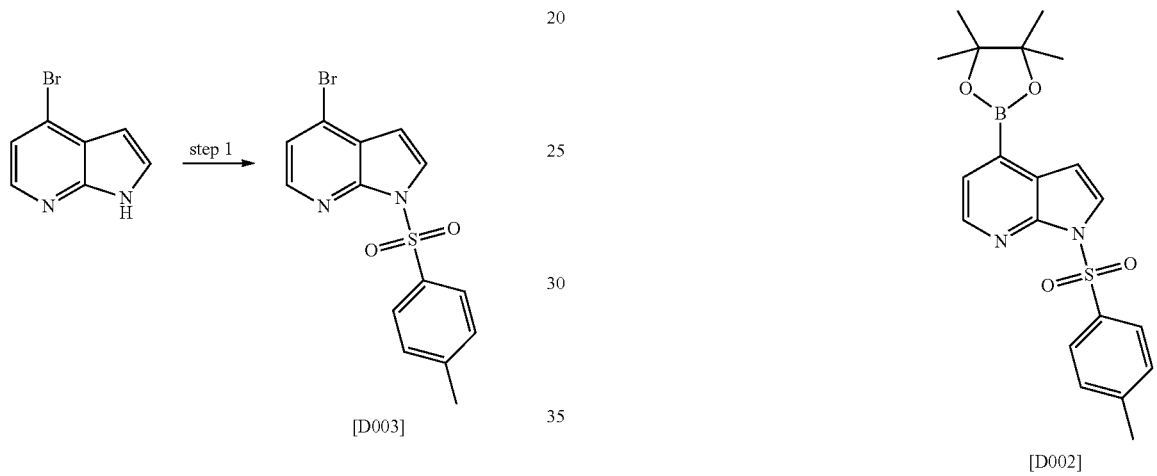

[D003]

4-Bromo-1-(toluene-4-sulfonyl)-1H-pyrrolo[2,3-b]pyridine [D003]

4-Bromo-7-azaindole (3 g, 15.22 mmol) was weighed into a round bottom flask and dissolved in THF (50 mL) under nitrogen. The reaction mixture was cooled to 0° C. and treated portionwise with sodium hydride (60% in mineral oil, 0.67 g, 16.75 mmol), the addition was accompanied by fizzing. After the addition the reaction mixture was allowed to stir for 30 minutes at room temperature and then treated with benzenesulfonyl chloride (2.14 mL, 16.75 mmol). The reaction mixture was allowed to warm to room temperature and stirred for 2 hours. The reaction mixture was evaporated under reduced pressure and dissolved in DCM 30 mL, the organics were washed with 2×30 mL portions of 2M sodium carbonate, dried with MgSO4, filtered and evaporated to an orange oil. Purified by flash column chromatography eluting with 1:9 ethyl acetate:cyclohexane to provide the title compound as an off white solid (92%). LCMS method: 5, RT 5.36 min, MI 337 [M+H]; NMR: (1H, 500 MHz, CDCl₃) 8.22 (d, 1H), 8.18 (d, 2H), 7.78 (d, 1H), 7.58 (t, 1H), 7.48 (t, 2H), 7.35 (d, 1H), 6.63 (d, 1H).

4-(4,4,5,5-Tetramethyl-[1,3,2]dioxaborolan-2-yl)-1-(toluene-4-sulfonyl)-1H-pyrrolo[2,3-b]pyridine [D002]

4-Bromo-1-(toluene-4-sulfonyl)-1H-pyrrolo[2,3-b]pyridine (1.57 g, 4.47 mmol), Bis(pinacolato)diboron [D003] (2.71 g, 10.72 mmol), PdCl2.dppf CH2Cl2 adduct (0.365 g, 0.45 mmol) and potassium acetate (0.876 g, 8.94 mmol) were weighed into a microwave vial. Dioxane (30 mL) was added and the reaction mixture was capped and heated at 130° C. in a microwave reactor for 30 minutes. The solvent was removed under reduced pressure and the residue was partitioned between ammonium chloride 20 mL and ethyl acetate 20 mL. The organics were dried with MgSO4, filtered and evaporated under reduced pressure to a brown oil. This was passed through a short column of silica eluting with 1:4 ethyl acetate:cyclohexane. The fractions were pooled and evaporated to yield the title compound [D002] as a pale yellow solid: LCMS method: 5, RT 4.77 min, MI 317 [M+H for boronic acid intermediate]

Synthesis of Benzenesulfonyl-2-methyl-4-(4,4,5,5-tetramethyl-[1,3,2]dioxaborolan-2-yl)-1H-pyrrolo[2,3-b]pyridine [D004]

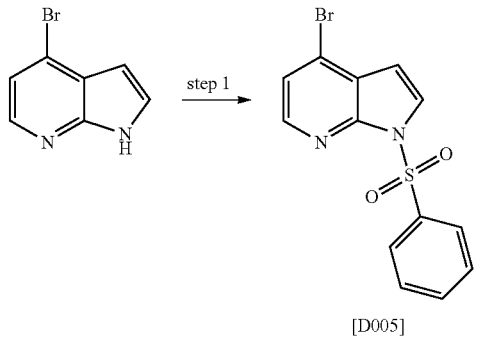

[D005]

1-Benzenesulfonyl-4-bromo-1H-pyrrolo[2,3-b]pyridine [D005]

4-Bromo-7-azaindole (3 g, 15.22 mmol) was weighed into a round bottom flask and dissolved in THF (50 mL) under nitrogen. The reaction mixture was cooled to 0° C. and treated portionwise with sodium hydride (60% in mineral oil, 0.67 g, 16.75 mmol), the addition was accompanied by fizzing. After the addition the reaction mixture was allowed to stir for 30 minutes at room temperature and then treated with benzenesulfonyl chloride (2.14 mL, 16.75 mmol). The reaction mixture was allowed to warm to room temperature and stirred for 2 hours. The reaction mixture was evaporated under reduced pressure and dissolved in DCM 30 mL, the organics were washed with 2×30 mL portions of 2M sodium carbonate, dried with MgSO4, filtered and evaporated to an orange oil. Purified by flash column chromatography eluting with 1:9 ethyl acetate: cyclohexane to provide the title compound [D005] as an off white solid (92%): LCMS method: 5, RT 5.36 min, MI 337 [M+H]; NMR: (1H, 500 MHz, CDCl₃) 8.22 (d, 1H), 8.18 (d, 2H), 7.78 (d, 1H), 7.58 (t, 1H), 7.48 (t, 2H), 7.35 (d, 1H), 6.63 (d, 1H).

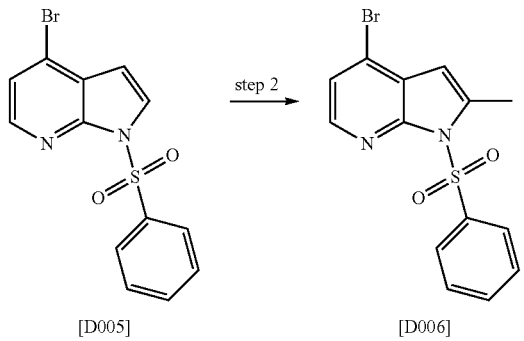

[D005]　　　　　　　　[D006]

1-Benzenesulfonyl-4-bromo-2-methyl-1H-pyrrolo[2,3-b]pyridine [D006]

To a solution of 1-Benzenesulfonyl-4-bromo-1H-pyrrolo[2,3-b]pyridine [D005] (2 g, 5.93 mmol) in THF (50 mL) at −78° C., LDA (2M, 5.9 mL, 11.86 mmol) was added dropwise. The solution was stirred 30 min. The temperature was allowed to warm to 0° C. and Methyl iodide (3.67 mL, 59 mmol) was then added dropwise and the solution was stirred 3 h at 0° C. and was allowed to stir to room temperature overnight. The reaction was quenched with aqueous ammonium chloride solution and extracted with DCM. The combined organic layers were dried over MgSO4 and concentrated in vacuo. The crude was purified by SP 1 (eluent, gradiant: Cyclohexane/AcOEt: 1/0 to 8/2). The fractions were collected and concentrated under reduced pressure to yield the title compound [D006] a white solid (87%). LCMS method: 5, RT 5.80 min, MI 351 [M+H]; NMR: (1H, 500 MHz, CDCl₃) 8.12-8.15 (m, 3H), 7.56 (t, 1H), 7.47 (t, 2H), 7.29 (d, 1H), 6.34 (s, 1H), 2.74 (s, 3H).

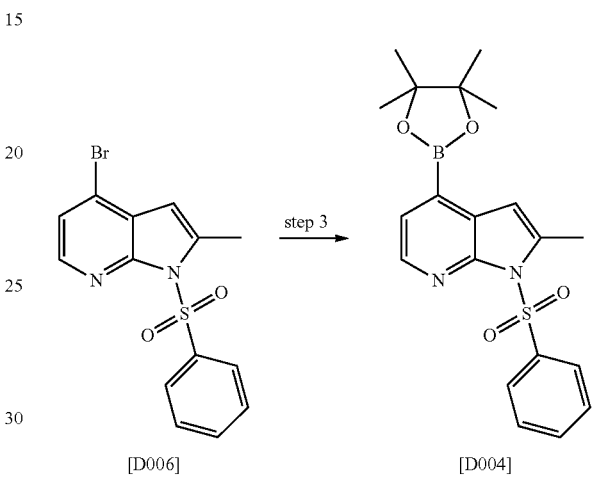

[D006]　　　　　　　　[D004]

Benzenesulfonyl-2-methyl-4-(4,4,5,5-tetramethyl-[1,3,2]dioxaborolan-2-yl)-1H-pyrrolo[2,3-b]pyridine [D004]

Following the procedure described in scheme D2 replacing 1-Benzenesulfonyl-4-bromo-1H-pyrrolo[2,3-b]pyridine with 1-Benzenesulfonyl-4-bromo-2-methyl-1H-pyrrolo[2,3-b]pyridine gave the title compound [D004] (72%%) as a pale yellow solid. LCMS method: 5, RT 6.19 min, MI 399 [M+H]; NMR: (1H, 500 MHz, CDCl₃) 8.34 (d, 1H), 8.07 (d, 2H), 7.50 (t, 1H), 7.46 (d, 1H), 7.41 (t, 2H), 6.70 (s, 1H), 2.73 (s, 3H), 1.33 (s, 12H). The following compounds were prepared according to Scheme D2:

1-Benzenesulfonyl-2-benzyl-4-(4,4,5,5-tetramethyl-[1,3,2]dioxaborolan-2-yl)-1H-pyrrolo[2,3-b]pyridine [D007]

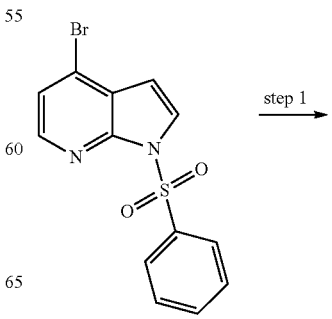

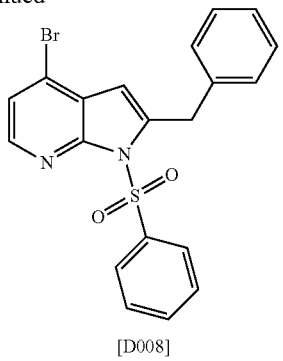

[D008]

1-Benzenesulfonyl-2-benzyl-4-bromo-1H-pyrrolo[2,3-b]pyridine [D008]

Following the procedure described in scheme D2, 1-Benzenesulfonyl-4-bromo-1H-pyrrolo[2,3-b]pyridine was reacted with benzyl bromide to give the title compound [D008] which was used crude in the next step. LCMS method: 5, RT 6.62 min, MI 427 [M+H].

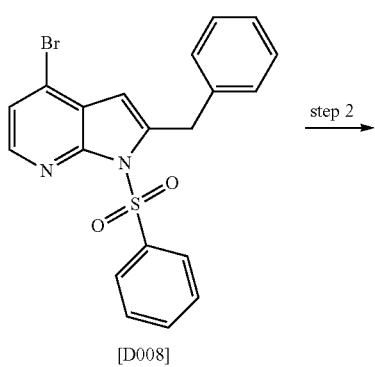

[D008]

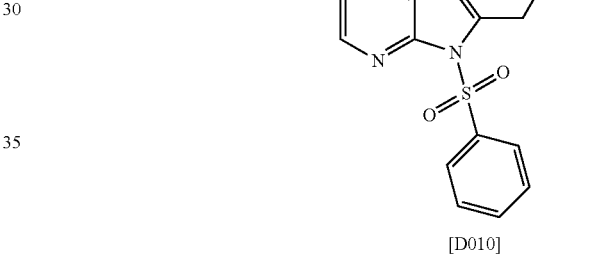

[D007]

1-Benzenesulfonyl-2-benzyl-4-(4,4,5,5-tetramethyl-[1,3,2]dioxaborolan-2-yl)-1H-pyrrolo[2,3-b]pyridine [D007]

Following the procedure described in scheme D2 replacing 1-Benzenesulfonyl-4-bromo-1H-pyrrolo[2,3-b]pyridine with 1-Benzenesulfonyl-2-benzyl-4-bromo-1H-pyrrolo[2,3-b]pyridine gave the title compound [D007] as a pale yellow solid: LCMS method: 5, RT 5.59 min, MI 392 [M+H, Boronic ester hydrolysed into the corresponding boronic acid in the LCMS conditions]; NMR: (1H, 500 MHz, d6-dmso) 8.38 (d, 1H), 7.70 (dd, 1H), 7.49 (d, 1H), 7.42 (t, 1H), 7.23-7.30 (m, 7H), 6.75 (s, 1H), 4.54 (d, 2H), 1.34 (s, 12H).

Synthesis of 1-Benzenesulfonyl-2-(2-fluoro-benzyl)-4-(4,4,5,5-tetramethyl-[1,3,2]dioxaborolan-2-yl)-1H-pyrrolo[2,3-b]pyridine [D009]

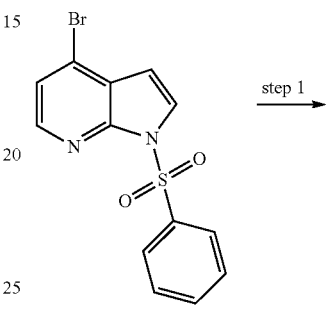

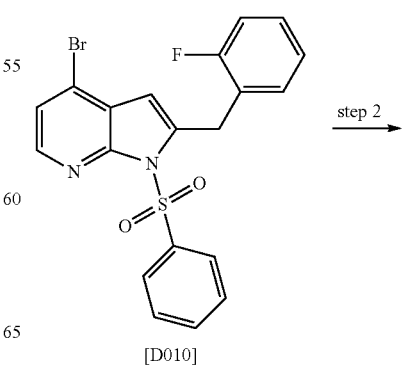

[D010]

Step 1: 1-Benzenesulfonyl-4-bromo-2-(2-fluoro-benzyl)-1H-pyrrolo[2,3-b]pyridine [D010]

Following the procedure described in scheme D2, 1-Benzenesulfonyl-4-bromo-1H-pyrrolo[2,3-b]pyridine was reacted with 2-fluorobenzylbromide to give the title compound [D010] (75%): LCMS method: 5, RT 6.45 min, MI 445 [M+H].

[D010]

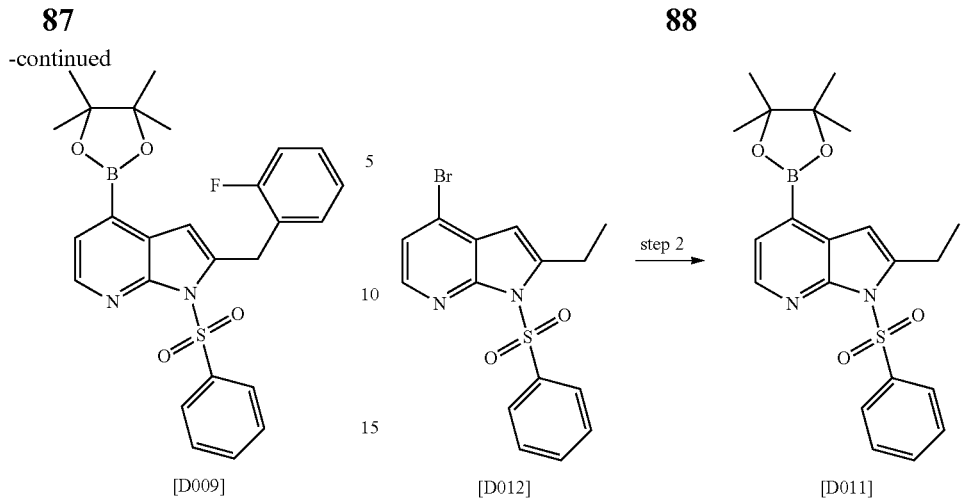

[D009]　　　　　[D012]　　　　　[D011]

Step 2: 1-Benzenesulfonyl-2-(2-fluoro-benzyl)-4-(4,4,5,5-tetramethyl-[1,3,2]dioxaborolan-2-yl)-1H-pyrrolo[2,3-b]pyridine [D009]

Following the procedure described in scheme D2 replacing 1-Benzenesulfonyl-4-bromo-1H-pyrrolo[2,3-b]pyridine with 1-Benzenesulfonyl-4-bromo-2-(2-fluoro-benzyl)-1H-pyrrolo[2,3-b]pyridine gave the title compound [D009] as a white solid. LCMS method: 5, RT 5.50 min, MI 411 [M+1, hydrolysed boronic ester to its corresponding boronic acid].

Synthesis of 1-Benzenesulfonyl-2-ethyl-4-(4,4,5,5-tetramethyl-[1,3,2]dioxaborolan-2-yl)-1H-pyrrolo[2,3-b]pyridine [D011]

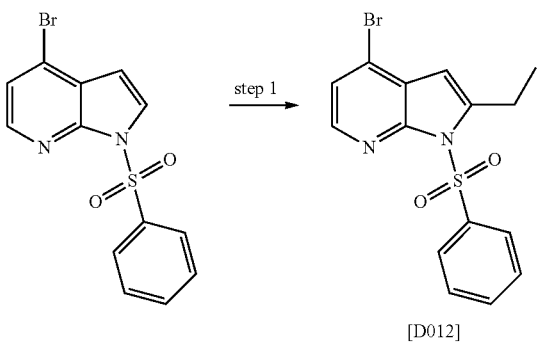

[D012]

1-Benzenesulfonyl-4-bromo-2-ethyl-1H-pyrrolo[2,3-b]pyridine [D012]

Following the procedure described in scheme D 2,1-Benzenesulfonyl-4-bromo-1H-pyrrolo[2,3-b]pyridine was reacted with iodoethane to give the title compound [D012] as a white solid: LCMS method: 5, RT 6.01 min, MI 351 [M+H]; NMR: (1H, 500 MHz, d6-dmso) 8.11-8.15 (m, 3H), 7.56 (d, 1H), 7.45-7.48 (m, 2H), 7.30 (d, 1H), 6.39 (s, 1H), 3.19 (q, 2H), 1.42 (t, 3H).

1-Benzenesulfonyl-2-ethyl-4-(4,4,5,5-tetramethyl-[1,3,2]dioxaborolan-2-yl)-1H-pyrrolo[2,3-b]pyridine [D011]

Following the procedure described in scheme D2 replacing 1-Benzenesulfonyl-4-bromo-1H-pyrrolo[2,3-b]pyridine with 1-Benzenesulfonyl-4-bromo-2-ethyl-1H-pyrrolo[2,3-b]pyridine gave the title compound [D011] as a pale yellow solid. LCMS method: 5, RT 6.42 min, MI 413 [M+H]; LCMS Method 1LCMS5, 6.42 min, MI: 413 [M+1].

General Synthesis of Substituted 4-substituted-2-(1H-pyrrolo[2,3-b]pyridin-4-yl)-azaquinazoline Derivatives of General Formula [I-001] Scheme D3

The 4-substituted-2-(1H-pyrrolo[2,3-b]pyridin-4-yl)-azaquinazoline derivatives of general formula [I-001] were prepared by the reaction of a halogenated pyridine derivative of general formula [I-010] with a strong base such as LDA, in a polar aprotic solvent such as THF, a symmetrical anhydride such as Di-tert-butyl dicarbonate at low temperature to yield halo-substituted-isonicotinic acid tert-butyl ester derivatives of general formula [I-011]. After reaction work up, typically by a liquid-liquid extraction the intermediate was purified by column chromatography. The halo-substituted-isonicotinic acid tert-butyl ester derivative of general formula [I-011] was then subjected to a Suzuki type palladium catalysed cross coupling reaction with boronic acid or boronate ester derivative of general formula [I-018] a palladium catalyst such as Pd(PPh$_3$)$_4$, a base such as K$_2$PO$_4$ in a polar aprotic solvent such as DMA or DMF at elevated temperature either by heating thermally or using a microwave reactor, to yield the substituted-isonicotinic acid tert-butyl ester derivative of general formula [I-012]. After reaction work up, typically by a liquid-liquid extraction the intermediate was purified by column chromatography. The t-butylester inter intermediate [I-012] was then subjected to a deprotection reaction in the presence of a base such as sodium hydroxide in a polar protic solvent such as ethanol to yield the substituted-isonicotinic acid derivative of general formula [I-013], which was then subjected to a coupling reaction with a substituted 1H-pyrrolo[2,3-b]pyridine-4-carboxamidine derivative of general formula [I-014], with a suitable coupling agent such as O-(7-Azabenzotriazol-1-yl)-N,N,N',N'-tetramethyluronium hexafluorophosphate (HATU) in a polar aprotic solvent such as DMA or DMF. The isonicotinoyl-amidine derivative of general formula

[I-015] can then be cyclised to displace the relevant halogen group to yield the desired 2-(1H-pyrrolo[2,3-b]pyridine-4-yl)-pyrido[3,4-d]pyrimidin-4-ol derivative of general formula [I-016]. The 4-substituted-2-(1H-pyrrolo[2,3-b]pyridin-4-yl)-azaquinazoline derivatives of general formula [I-001] were prepared by the reaction of a 2-(1H-pyrrolo[2,3-b]pyridine-4-yl)-pyrido[3,4-d]pyrimidin-4-ol derivative of general formula [I-016] with a chlorinatation agent such as phosphorous oxychloride to give compounds of general formula and the intermediate 4-chloro derivative was then further reacted with primary or secondary amino derivative of general formula [I-017], in a polar aprotic solvent such as DMA, DMF, NMP in the presence of a tertiary amine base such as $Et_3N$, DIPEA or NMM at ambient temperature [method A]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by normal phase silica gel chromatography or reverse phase preparative HPLC. 4-substituted-2-(1H-pyrrolo[2,3-b]pyridin-4-yl)-azaquinazoline derivatives of general formula [I-001] were prepared by the reaction of a -(1H-pyrrolo[2,3-b]pyridine-4-yl)-pyrido[3,4-d]pyrimidin-4-ol derivative of general formula [I-016] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP [method B]. The intermediate 6,7-substituted-(2, 4,6-triisopropyl-benzenesulfonic acid)-(1H-pyrrolo[2,3-b]pyridine-4-yl)-pyrido[3,4-d]pyrimidin-4-yl ester was then reacted with a primary or secondary amino derivative, of general formula [G-117], in a polar aprotic solvent such as DMA, DMF, NMP in the presence of a tertiary amine base such as $Et_3N$, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

Scheme D3

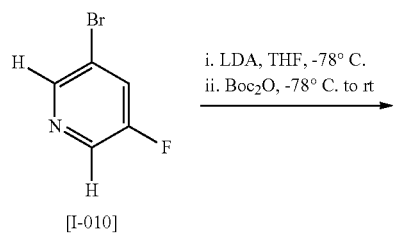

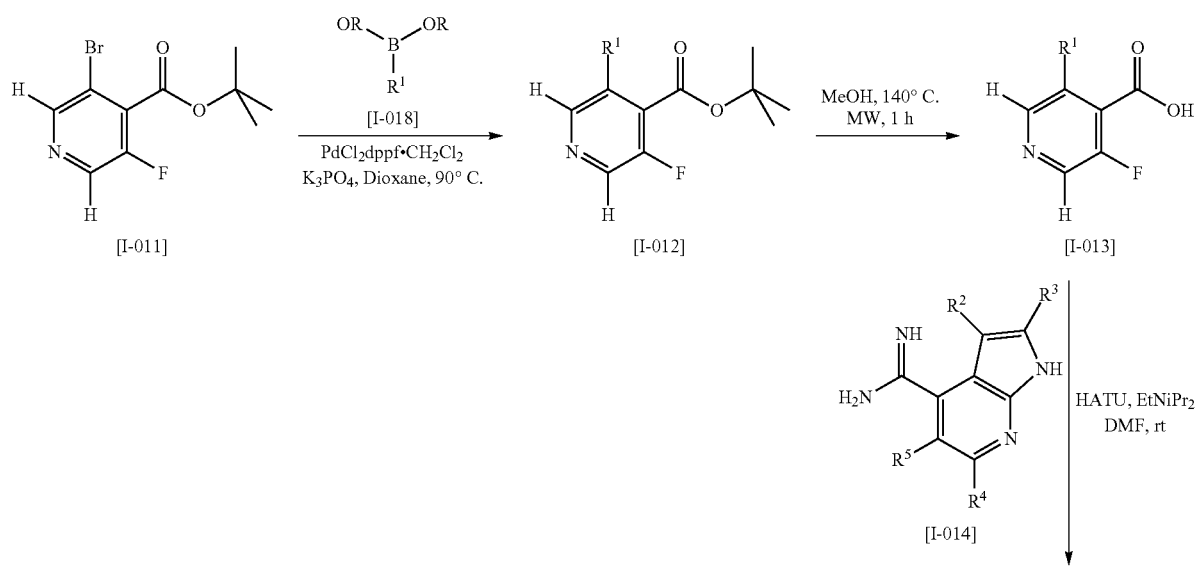

-continued
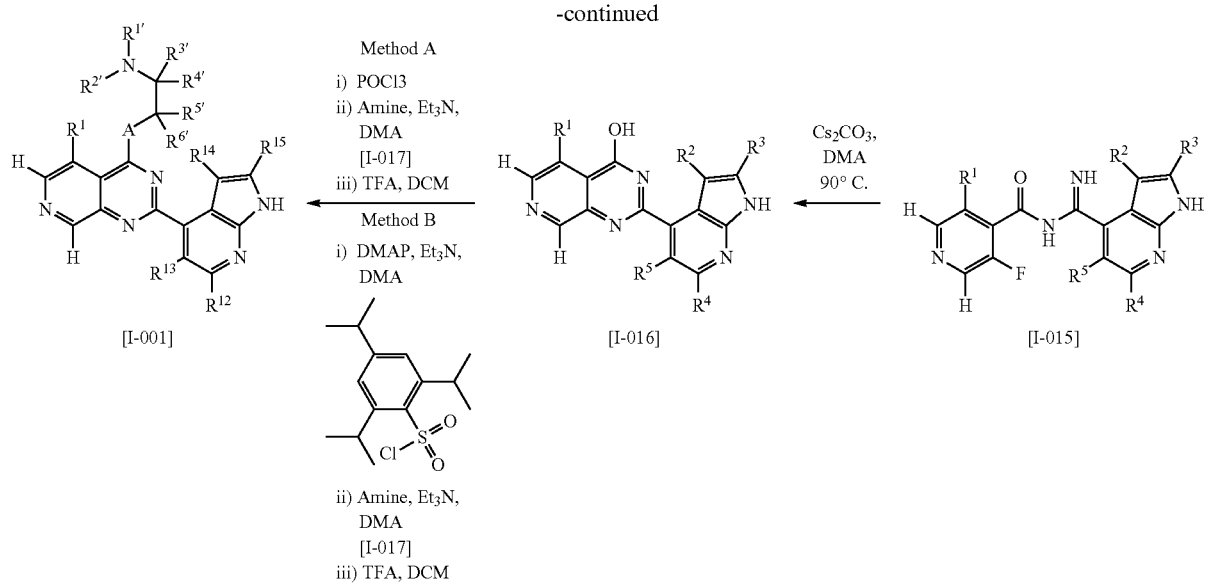
Synthesis of 5-Cyclopropyl-4-piperazin-1-yl-2-(1H-pyrrolo[2,3-b]pyridin-4-yl)-pyrido[3,4-d]pyrimidine [1209]
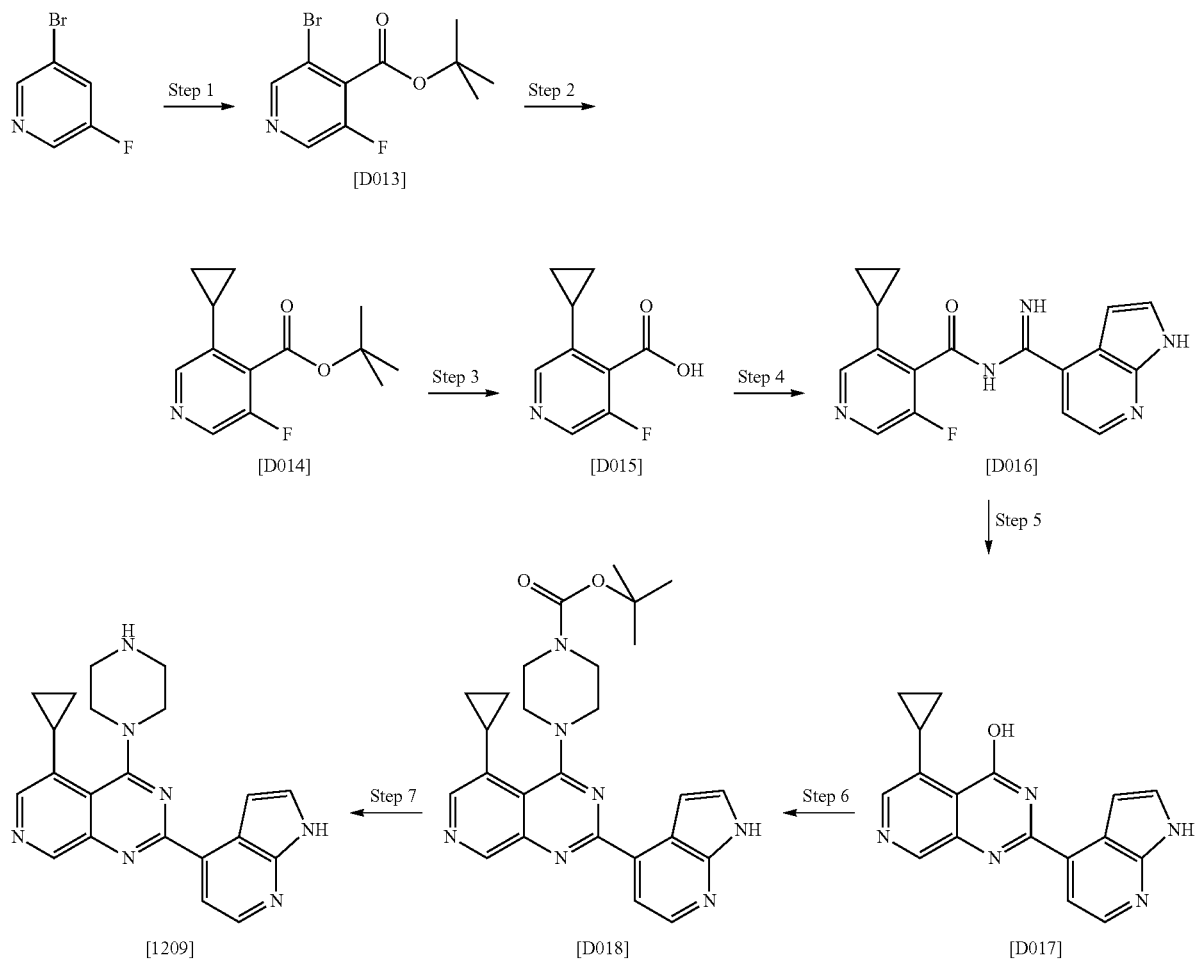

3-Bromo-5-fluoro-isonicotinic acid test-butyl ester [D013]

To a solution of LDA (2M, 72 mL, 144 mmol) in THF (100 mL) at −78° C. was added dropwise via cannula a solution of 3-bromo-5-fluoropyridine (21.12 g, 120 mmol) in THF (50 mL) pre-cooled at −78° C. During the addition the internal temperature did not rise above −65° C. The dark red-brown solution was stirred for 1 hour. Di-tert-butyldicarbonate (52.4 g, 240 mmol) in THF (50 mL) was cooled to −10° C. in a methanol/ice bath then added dropwise via cannula to the dark red-brown solution. The mixture was stirred for 2 hours then allowed to warm to room temperature and stir for 1 hour. Saturated aqueous ammonium chloride (100 mL) was added slowly and then water (200 mL) and EtOAc (200 mL) and the mixture was vigorously stirred for 45 minutes. The mixture was transferred to a separatory funnel and the layers were separated. The aqueous layer was extracted with EtOAc (200 mL). The THF and EtOAc layers were combined, dried over magnesium sulfate, filtered and evaporated. The recovered dark red-brown oil was purified by column chromatography (Cyclohexane/AcOEt: 1/0 to 97/3). Fractions containing desired material were concentrated in vacuo (14 g, 85%). LCMS method: 5, RT 5.44 min, MI 277 [M+H]; NMR: (1H, 500 MHz, CDCl3) 8.56 (s, 1H), 8.43 (s, 1H), 1.62 (s, 9H).

3-Cyclopropyl-5-fluoro-isonicotinic acid tert-butyl ester [D014]

A solution containing 3-Bromo-5-fluoro-isonicotinic acid tert-butyl ester [D013] (5.52 g, 20 mmol), potassium phosphate tribasic (12.74 g, 60 mmol) and cyclopropyl boronic acid (2.58 g, 30 mmol), in dioxane (100 mL) was subjected to vacuum/argon balloon (three times). Dichloro[1,1'-bis (diphenylphosphino)ferrocene]palladium (II) dichloromethane adduct (0.408 g, 0.5 mmol) was added and the reaction heated at 96° C. overnight under positive pressure of nitrogen. The mixture was cooled to room temperature and was filtered through a pad of 200 g silica and washed with EtOAc (1 L). The filtrate was concentrated in vacuo and the crude was purified by column chromatography (Cyclohexane/AcOEt: 98:2 to 96:4). The combined fractions were concentrated under reduced pressure to give the title compound [D014] as a colourless oil (3.42 g, 72%). LCMS method: 5, RT 5.36 min, MI 238 [M+H]; NMR: (1H, 500 MHz, CDCl3) 8.33 (s, 1H), 8.15 (s, 1H), 2.05-2.00 (m, 1H), 1.62 (s, 9H), 1.04-1.00 9m, 2H), 0.82-0.78 (m, 2H).

3-Cyclopropyl-5-fluoro-isonicotinic acid [D015]

In a microwave vial, 3-cyclopropyl-5-fluoro-isonicotinic acid tert-butyl ester [D014] (1.186 g, 5 mmol) was dissolved in methanol and then heated in microwave at 140° C. for 1 hr. The reaction was concentrated in vacuo to yield the title compound [D015] 0.84 g (92%) of white crystalline solid. LC-MS: 1NJM406_1_28 Jul. 2011; 1.51 min, 87%; 182+; 1LCMS5.

3-Cyclopropyl-5-fluoro-N-[imino-(1H-pyrrolo[2,3-b]pyridin-4-yl)-methyl]-isonicotinamide [D016]

3-Cyclopropyl-5-fluoro-isonicotinic acid [D015] (0.681 g, 3.76 mmol), HATU (1.43 g, 3.76 mmol) and diisopropylethylamine (2.29 mL, 13.16 mmol) were stirred in DMF (5 mL). After 1 hr, 1H-Pyrrolo[2,3-b]pyridine-4-carboxamidine; acetic acid salt (0.92 g, 3.76 mmol) was added. Having stirred for 18 hr the mixture was poured into water (180 ml), stirred for 2 hours and then a white solid collected by filtration and washed with H₂O to yield the title compound [D016] as a white solid (1.17 g) was used without further purification. LCMS method: 5, RT 3.22 min, MI 324 [M+H].

5-Cyclopropyl-2-pyridin-4-yl-pyrido[3,4-d]pyrimidin-4-ol [D017]

A mixture of N-[(2-Chloro-pyridin-4-yl)-imino-methyl]-3-cyclopropyl-5-fluoro-isonicotinamide [D016] (1.164 g, 3.6 mmol) and Cs2CO3 (1.18 g, 3.60 mmol) in DMA (12 mL) was heated thermally at 90° C. overnight. The reaction mixture was poured into H₂O (20 ml) and acidified with dropwise addition of acetic acid at 0° C. The beige precipitate (0.474, 43%) was collected by filtration and washed with H₂O to yield the title compound [D017] which was used without further purification. LCMS method: 5, RT 4.58 min, MI 304 [M+H]; NMR: (1H, 500 MHz, d6-dmso) 12.12 (brs, 1H), 9.09 (s, 1H), 8.54 (d, 1H), 8.37 (s, 1H), 7.90 (d, 1H), 7.83 (s, 1H), 7.36 (s, 1H), 3.56-3.64 (m, 1H), 1.24-1.30 (m, 2H), 1.08-1.14 (m, 2H).

4-[5-Cyclopropyl-2-(1H-pyrrolo[2,3-b]pyridin-4-yl)-pyrido[3,4-d]pyrimidin-4-yl]-piperazine-1-carboxylic acid tert-butyl ester [D018]

To a solution of 5-Cyclopropyl-2-pyridin-4-yl-pyrido[3,4-d]pyrimidin-4-o [D017]1 (0.47 g, 1.55 mmol) in DMF (25 mL) was added DIPEA (0.809 mL, 4.65 mmol) and DMAP (5 mg). 2,4,6-Triisopropylbenzenesulfonyl chloride (0.563 g, 1.86 mmol) was then added and the mixture was stirred 2 hours. N-Boc-Piperazine (0.318 g, 1.705 mmol) was then added and the mixture was the stirred overnight. Water was added water (60-70 mL) and the solution was stirred at RT for 15 mins. The resulting solid was collected and washed twice with water. The solid was dissolved in DCM and purified by column chromatography (eluent: DCM/MeOH gradient 0% to 10% MeOH) to yield the title compound [D018] as a dark brown gum (0.6 g, 82%) was used without further purification in the next step. LCMS method: 5, RT 5.85 min, MI 472 [M+H].

5-Cyclopropyl-4-piperazin-1-yl-2-(1H-pyrrolo[2,3-b]pyridin-4-yl)-pyrido[3,4-d]pyrimidine[1209]

To a solution of 4-[5-Cyclopropyl-2-(1H-pyrrolo[2,3-b]pyridin-4-yl)-pyrido[3,4-d]pyrimidin-4-yl]-piperazine-1-carboxylic acid tert-butyl ester [D018] (0.6 g, 1.27 mmol) in DCM (15 mL) was added HCl (4N, dioxane, 2 mL) and the resultant bright yellow suspension was stirred at RT for 90 mins. The solution was concentrated under reduced pressure and dissolved in MeOH and added to SCX-2 cartridge (10 g), washed with MeOH/DCM (1:1, 40 mL) and MeOH (20 mL). Then the SCX-2 cartridge was washed with ammonia (7N in MeOH, 30 mL). The ammonia washes were concentrated in vacuo and the material purified on the column chromatography (eluent DCM/MeOH gradient 0-20% MeOH/DCM). The fractions were combined and concentrated under reduced pressure to yield the title compound [1009]: LCMS method: 5, RT 2.65 min, MI 372 [M+H]; NMR: (1H, 500 MHz, d6-dmso) 11.82 (brs, 1H), 9.13 (s, 1H), 8.36 (d, 1H), 8.10 (d, 1H), 7.62 (t, 1H), 7.45 (dd, 1H), 3.50-3.90 (m, 4H), 2.88-2.91 (m, 4H), 2.66-2.69 (m, 1H), 1.22-1.27 (m, 2H), 1.02-1.06

General Synthesis of Substituted 1H-pyrrolo[2,3-b]pyridine-4-carboxamidine Derivative of General Formula [I-012] Scheme D4

The substituted 1H-pyrrolo[2,3-b]pyridine-4-carboxamidine derivatives of general formula [I-012] were prepared by the reaction of 2-methyl pyridine-2-yl carbamic acid tert butyl ester derivative of general formula [I-019] with a strong base such as nBuLi, in a polar aprotic solvent such as THF, and a substituted Weinreb amide derivative of general formula [I-025] at low temperature followed by reaction with a mineral acid such as hydrochloric acid at elevated temperature to yield the 1-H-pyrrolo[2,3-b]pyridine derivative of general formula [I-020], after reaction work up, typically by a liquid-liquid extraction the intermediate was purified by column chromatography. The 1-H-pyrrolo[2,3-b]pyridine derivative of general formula [I-020] was then subjected to a pyridine N-oxidation reaction with an oxidising reagent such as mCPBA in a solvent such as DCM. The intermediate 1-H-pyrrolo[2,3-b]pyridine-7-oxide derivative of general formula [I-021] was then reacted with a chlorinating agent such as methansulfonyl chloride, in a polar aprotic solvent such as DMF at elevated temperature, after reaction work up, typically by a liquid-liquid extraction the intermediate was purified by column chromatography. The intermediate 4-chloro-1H-pyrrolo[2,3-b]pyridine derivative of general formula [I-022] was then submitted to a palladium catalysed cross coupling reaction with a cyanide species such as zinc cyanide, a palladium catalyst such as dichloro[1,1'-bis(diphenylphosphino)ferrocene]palladium (II) dichloromethane adduct, zinc dust, in a polar aprotic solvent such as DMF at elevated temperature, after reaction work up, typically by a liquid-liquid extraction the intermediate was purified by column chromatography. The intermediate 1H-pyrrolo[2,3-b]pyridine-4-carbonitrile derivative of general formula [I-023] was then reacted with hydroxylamine (50% wt/wt in water) and a polar protic solvent such as EtOH at elevated temperature. The intermediate N-hydroxy-1H-pyrrolo[2,3-b]pyridine-4-carboxamide of general formula [I-024] was then subjected to a hydrogenolysis reaction with acetic anhydride in a polar protic solvent such as methanol a palladium catalyst such as palladium on activated charcoal under a atmosphere of hydrogen gas, to yield the substituted 1H-pyrrolo[2,3-b]pyridine-4-carboxamidine derivative of general formula [I-012] Scheme D4.

Scheme D4

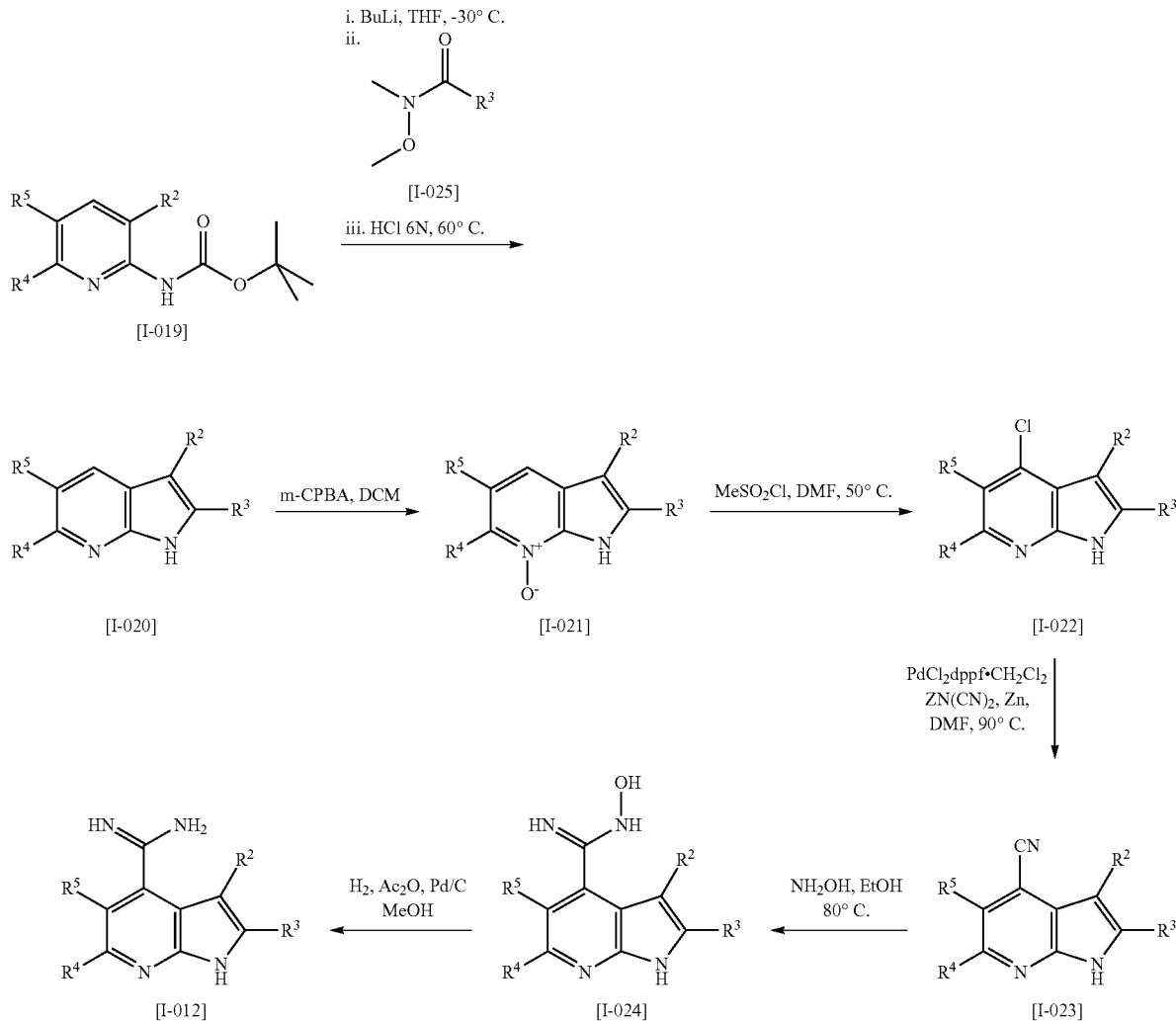

Synthesis of 2-Trifluoromethyl-1H-pyrrolo[2,3-b]pyridine-4-carboxamidine; Acetic Acid Salt [D036]

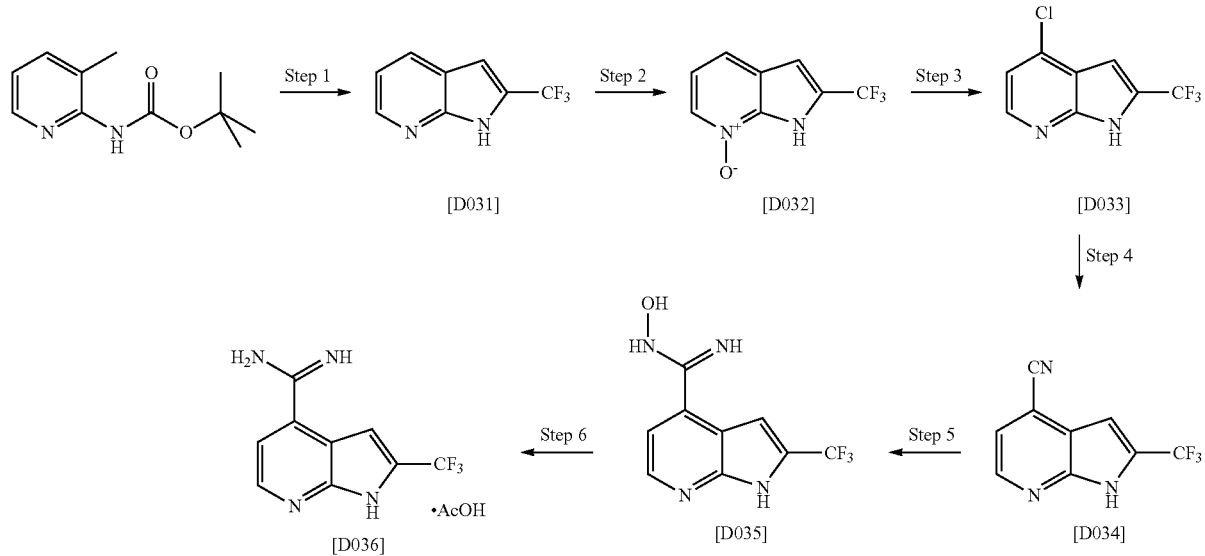

Step 1: 2-Trifluoromethyl-1H-pyrrolo[2,3-b]pyridine [D031]

To a solution of (3-Methyl-pyridin-2-yl)-carbamic acid tert-butyl ester (5 g, 24 mmol) in THF (50 mL) at −30° C. was added BuLi (2.5M, 28.5 mL, 72 mmol) and the reaction mixture was warmed to 0° C. and stirred for 90 min. A solution of 2,2,2-Trifluoro-N-methoxy-N-methyl-acetamide (2.9 mL, 24 mmol) in THF (10 mL) was slowly added and the reaction was stirred at 0° C. for 3 h. The reaction mixture was slowly treated with HCl (30 mL, 6M) followed by heating at 60° C. for 18 h. The reaction mixture was cooled, the layers were separated and the aqueous layer was made basic with NaOH (5M) and extracted twice with AcOEt. The combined organic layers (plus the one from the first extraction) were dried over MgSO4, concentrated and the residue was purified by Column chromatography (eluent Cyclohexane/AcOEt 1/0 to 8/2) to afford the title compound [D031] as a yellow solid (1.2 g, 27%): LCMS method: 5, RT 4.44 min, MI 187 [M+H], NMR: (1H, 500 MHz, d6-dmso) 14.33 (brs, 1H), 8.49 (d, 1H), 8.09 (d, 1H), 7.27 (dd, 1H), 6.90 (s, 1H).

2-Trifluoromethyl-1H-pyrrolo[2,3-b]pyridine 7-oxide [D032]

To a solution of 2-Trifluoromethyl-1H-pyrrolo[2,3-b]pyridine [D031] (1.2 g, 6.45 mmol) in DCM (10 mL), 3-Chloroperoxybenzoic acid (1.22 g, 7.09 mmol) was added and the mixture was stirred overnight. A saturated solution of NaHCO3 was added and the layers were separated. The organic was dried over MgSO4 and concentrated under reduced pressure. To yield the title compound [D032] as yellow solid (0.82 g, 63%) was used without further purification. LCMS method: 5, RT 3.43 min, MI 203 [M+H], NMR: (1H, 500 MHz, d6-dmso) 8.34 (d, 1H), 7.76 (d, 1H), 7.19 (d, 1H), 7.18 (s, 1H),

4-Chloro-2-trifluoromethyl-1H-pyrrolo[2,3-b]pyridine [D033]

To a solution of 2-Trifluoromethyl-1H-pyrrolo[2,3-b]pyridine 7-oxide [D032] (0.82 g, 4.05 mmol) in DMF (10 mL) at 50° C., methane sulfonyl chloride (1.57 mL, 20.28 mmol) was added dropwise. The solution was stirred 3 h at 50° C. The reaction was then cooled to room temperature and water (5 mL) was added. A solution of 5M NaOH was added and the solid was collected, dried using an azeotrope with toluene to yield the title compound [D032] which was used without further purification. LCMS: 1LCMS5 5.77 min, 221-223 [M+1, Cl pattern].

2-Trifluoromethyl-1H-pyrrolo[2,3-b]pyridine-4-carbonitrile [D034]

A sealable vial was charged with 4-Chloro-2-trifluoromethyl-1H-pyrrolo[2,3-b]pyridine [D033] (0.6 g, 2.72 mmol), Dichloro[1,1'-bis(diphenylphosphino)ferrocene]palladium (II) dichloromethane adduct (0.222 g, 0.27 mmol), zinc cyanide (0.958 g, 8.16 mmol), zinc (dust, 0.036 g, 0.54 mmol) and DMF (15 mL). The vial was capped and heated at 90° C. overnight. The reaction was poured in water and extracted with AcOEt. The aqueous layer was extracted again with AcOEt and the organics were combined, washed with water and brine and dried over MgSO4 to yield the title compound [D043] which was used without further purification: LCMS method: 5, RT 4.98 min, MI 212 [M+H].

N-Hydroxy-2-trifluoromethyl-1H-pyrrolo[2,3-b]pyridine-4-carboxamidine [D035]

A mixture of 2-Trifluoromethyl-1H-pyrrolo[2,3-b]pyridine-4-carbonitrile [D034] (0.68 g, 3.22 mmol) and hydroxylamine (50% wt/wt in water, 0.205 mL, 6.44 mmol) and EtOH (5 mL) was heated at 80° C. overnight. Solvent was then evaporated and the mixture azeotroped twice with toluene under vacuum. To yield the title compound [D035] as a yellow solid (0.78 g, 99%) which was used in the next step without further purification: LCMS method: 5, RT 2.22 min, MI 245 [M+H], NMR: (1H, 500 MHz, d6-dmso): 13.14 (brs, 1H), 10.40 (s, 1H), 8.70 (s, 1H), 7.70 (s, 1H), 7.56 (d, 1H), 6.27 (s, 2H).

2-Trifluoromethyl-1H-pyrrolo[2,3-b]pyridine-4-carboxamidine; Compound with Acetic Acid [D036]

To a suspension of N-Hydroxy-2-trifluoromethyl-1H-pyrrolo[2,3-b]pyridine-4-carboxamidine [D035] (0.43 g, 1.76 mmol) in MeOH (10 mL) was added dropwise acetic anhydride (0.175 mL, 1.85 mmol) at room temperature. The suspension was stirred 15 min and palladium on charcoal (5% wt/wt, 0.1 g) was added. The vessel was seal and hydrogen (balloon) was bubble in the mixture for 10 min and left stirring at RT under hydrogen atmosphere overnight. The mixture was filtered through celite and concentrated in vacuo to yield the title compound [D036] as a yellow solid (0.51 g, 100%) which was used without further purification. LCMS method: 5, RT 4.45 min, MI 229 [M+H], NMR: (1H, 500 MHz, d6-dmso) 1.79 (s, 3H, $CH_3CO_2H$), 8.50 (s, 1H), 7.35 (s, 1H), 7.03 (s, 1H).

Synthesis of 2-Thiophen-2-yl-1H-pyrrolo[2,3-b] pyridine-4-carboxamidine acetic acid salt [D042]

2-Thiophen-2-yl-1H-pyrrolo[2,3-b] pyridine-4-carbonitrile [D040]

Was prepared, following the procedure described in scheme D4, step 4, by reaction of 4-Chloro-2-thiophen-2-yl-1H-pyrrolo[2,3-b]pyridine [D039], PdCl2dppf:CH2Cl2, Zinc cyanide, zinc dust and DMA to give the title compound as a yellow solid. LCMS method: 5, RT 5.28 min, MI 226 [M+H].

N-Hydroxy-2-thiophen-2-yl-1H-pyrrolo[2,3-b]pyridine-4-carboxamidine [D041]

Was prepared, following the procedure described in scheme D4, step 5, by reaction of 2-thiophen-2-yl-1H-pyrrolo[2,3-b]pyridine-4-carbonitrile [D040], hydroxylam-

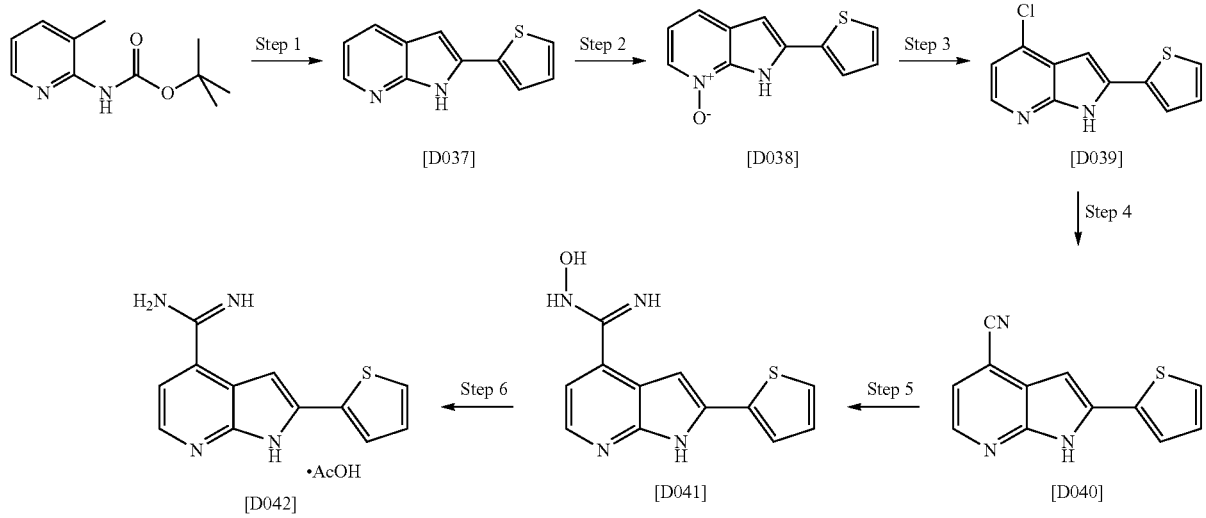

2-Thiophen-2-yl-1H-pyrrolo[2,3-b]pyridine [D037]

Was prepared, following the procedure described in scheme D4, step 1, by reaction of (3-Methyl-pyridin-2-yl)-carbamic acid tert-butyl ester, thiophene-2-carboxylic acid methoxy-methyl-amide, BuLi and THF to give the title compound as a yellow solid. LCMS method: 5, RT 4.79 min, MI 201 [M+H].

2-Thiophen-2-yl-1H-pyrrolo[2,3-b]pyridine 7-oxide [D038]

Was prepared, following the procedure described in scheme D4, step 2, by reaction of 2-Thiophen-2-yl-1H-pyrrolo[2,3-b]pyridine [D037], m-CPBA and DCM to give the title compound as a yellow solid. LCMS method: 5, RT 3.38 min, MI 217 [M+H].

4-Chloro-2-thiophen-2-yl-1H-pyrrolo[2,3-b]pyridine [D039]

Was prepared, following the procedure described in scheme D4, step 3, by reaction of 2-Thiophen-2-yl-1H-pyrrolo[2,3-b]pyridine 7-oxide [D038], methane sulfonyl chloride and DMF to give the title compound as a yellow solid. LCMS method: 5, RT 6.05 min, MI 235 [M+H].

ine and EtOH to give the title compound as a yellow solid. LCMS method: 5, RT 2.38 min, MI 259 [M+H].

2-Thiophen-2-yl-1H-pyrrolo[2,3-b]pyridine-4-carboxamidine acetic acid salt [D042]

Was prepared, following the procedure described in scheme D4, step 6, by reaction of N-Hydroxy-2-thiophen-2-yl-1H-pyrrolo[2,3-b]pyridine-4-carboxamidineacetic anhydride [D041], Pd/C, hydrogen and MeOH to give the title compound as a yellow solid. LCMS method: 5, RT 4.45 min, MI 243 [M+H].

Synthesis of 2-methyl-1H-pyrrolo[2,3-b]pyridine-4-carboxamidine acetic acid salt [D045]

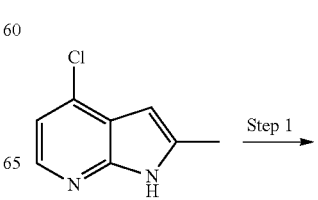

-continued

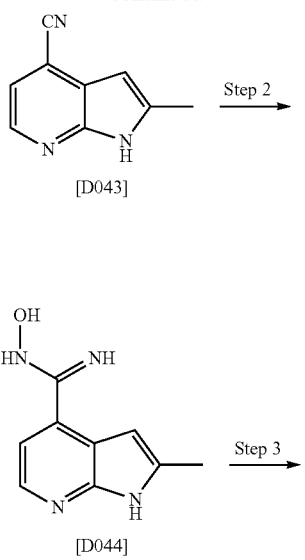

[D043]

[D044]

[D045]

2-Methyl-1H-pyrrolo[2,3-b]pyridine-4-carbonitrile [D043]

Was prepared, following the procedure described in scheme D4, step 4, by reaction of 4-Chloro-2-methyl-1H-pyrrolo[2,3-b]pyridine, PdCl2dppf:CH2Cl2, Zinc cyanide, zinc dust and DMA to give the title compound as a white solid. LCMS method: 5, RT 4.17 min, MI 158 [M+H].

N-Hydroxy-2-methyl-1H-pyrrolo[2,3-b]pyridine-4-carboxamidine [D044]

Was prepared, following the procedure described in scheme D4, step 5, by reaction of 2-Methyl-1H-pyrrolo[2,3-b]pyridine-4-carbonitrile [D043], hydroxylamine and EtOH to give the title compound as a yellow solid. LCMS method: 5, RT 1.92 min, MI 191 [M+H].

2-methyl-1H-pyrrolo[2,3-b]pyridine-4-carboxamidine acetic acid salt [D045]

Was prepared, following the procedure described in scheme D4, step 6, by reaction of N-Hydroxy-2-methyl-1H-pyrrolo[2,3-b]pyridine-4-carboxamidine [D044], acetic anhydride, Pd/C, hydrogen and MeOH to give the title compound as a yellow solid. LCMS method: 5, RT 2.44 min, MI 175 [M+H].

For Example Synthesis of 21H-pyrrolo[2,3-b]pyridine-4-carboxamidine acetic acid Salt [D047]

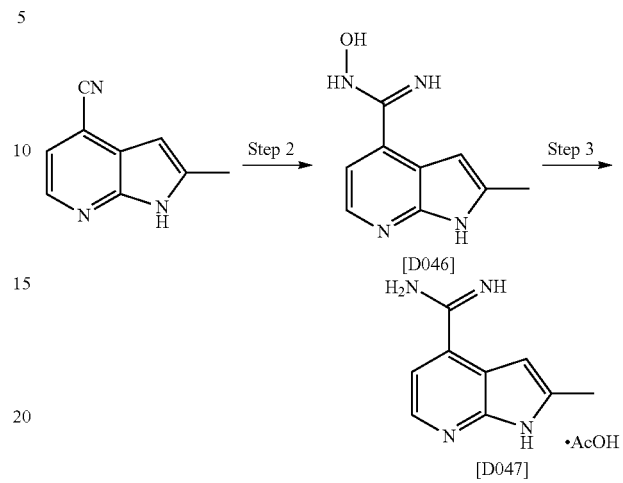

[D046]

[D047]

N-Hydroxy-1H-pyrrolo[2,3-b]pyridine-4-carboxamidine [D047]

Was prepared, following the procedure described in scheme D4, step 5, by reaction of 1H-pyrrolo[2,3-b]pyridine-4-carbonitrile, hydroxylamine and EtOH to give the title compound as a yellow solid. LCMS method: 5, RT 1.24 min, MI 162 [M+H].

2-1H-pyrrolo[2,3-b]pyridine-4-carboxamidine acetic acid salt [D047]

Was prepared, following the procedure described in scheme D4, step 6, by reaction of N-Hydroxy-1H-pyrrolo[2,3-b]pyridine-4-carboxamidine [D047], acetic anhydride, Pd/C, hydrogen and MeOH to give the title compound as a yellow solid. LCMS method: 5, RT 1.23 min, MI 161 [M+H], NMR: (1H, 500 MHz, d6-dmso) 8.38 (1H, d), 7.71 (1H, d), 7.30 (1H, d), 6.58 (1H, d), 1.80 (8H, s)

General Synthesis of 2-Substituted-Azaindole Derivatives of General Formula [I-034] Scheme D5

The 2-substituted azaindole derivatives of general formula [I-034] were prepared by the reaction of a 1-benzenesulfonyl-4-bromo-1H-pyrrolo[2,3-b]pyridine derivative of general formula [I-030] in a palladium catalysed cross coupling reaction with a palladium catalyst such as PdCl$_2$dppf:CH$_2$Cl$_2$, a cyanide reagent such as Zn(CN)$_2$, zinc dust, in a polar aprotic solvent such as DMF at high temperature either by heating thermally or using a microwave reactor. The crude product was purified by column chromatography. The 1-benzenesulfonyl-1H-pyrrolo[2,3-b]pyridine-4-carbonitrile derivative of general formula [I-031] was then reacted with a strong base such as LDA in a polar aprotic solvent such as THF at a low reaction temperature such as −78° C. with an electrophile such as a ketone, a disulfide or a halogenating agent such as NIS or NCS of general formula [I-035] to yield the 2-substituted 1-benzenesulfonyl-1H-pyrrolo[2,3-b]pyridine-4-carbonitrile derivative of general formula [I-032] following reaction work up, typically by a liquid-liquid extraction and purification by column chromatography. The intermediate of general formula [I-032] was deprotected by reaction with fluoride reagent such as TBAF in a polar aprotic solvent such as THF to yield the reaction intermediate of general formula [I-033]. The reaction intermediate of general formula [I-033] was then reacted with hydroxylamine (50% wt/wt in water) and a polar protic solvent such as EtOH at elevated temperature.

The intermediate N-Hydroxy-1H-pyrazolo[3,4-b]pyridine-4-carboxamidine was then subjected to a hydrogenolysis reaction with acetic anhydride in a polar protic solvent such as methanol a palladium catalyst such as palladium on activated charcoal under a atmosphere of hydrogen gas, to yield the 2-substituted 1H-pyrazolo[3,4-b]pyridine-4-carboxamidine derivative of general formula [I-034]

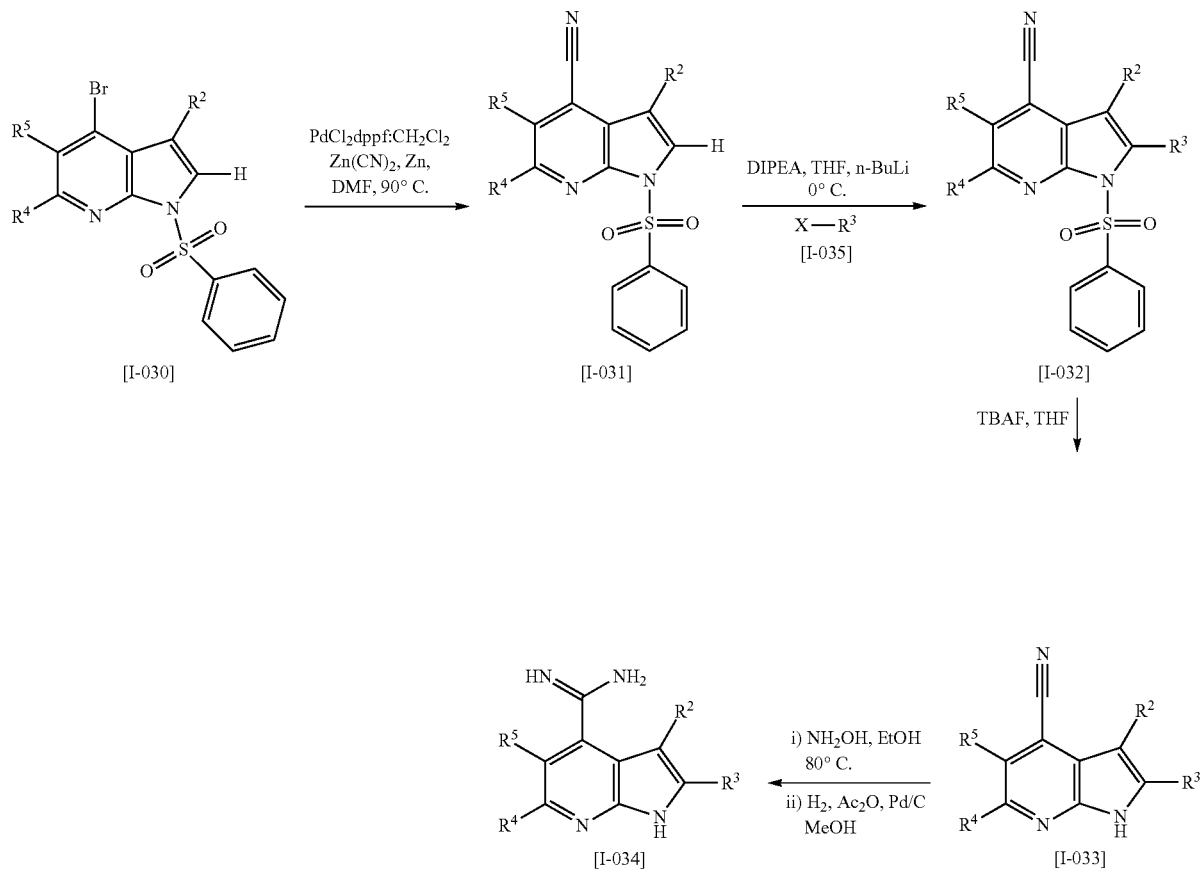

Synthesis of 2-(1-Hydroxy-cyclobutyl)-1H-pyrrolo[2,3-b]pyridine-4-carboxamidine [D054]

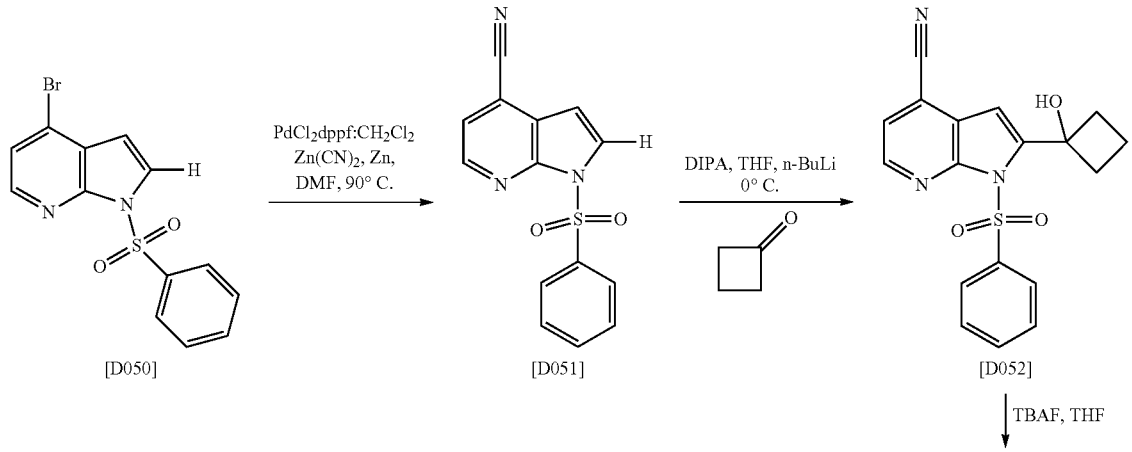

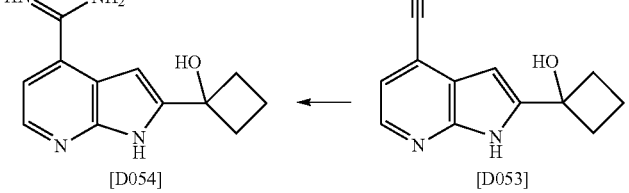

[D054]  ←  [D053]

1-(benzenesulfonyl)pyrrolo[2,3-b]pyridine-4-carbonitrile 1 [D051]

A suspension of 1-(benzenesulfonyl)-4-bromo-pyrrolo[2,3-b]pyridine [D050] (15.24 g, 45.2 mmol), zinc cyanide (7.96 g, 67.8 mmol), dichloro[1,1'-bis(diphenylphosphino)ferrocene]palladium (II) dichloromethane adduct (1.85 g, 2.26 mmol) and activated zinc dust (0.59 g, 9.04 mmol) in DMF (90 mL) was prepared equally divided between 6 microwave vials which were sealed and heated (thermally) to 85° C. overnight. The reaction mixture was diluted with water and the resulting precipitate filtered, washed with water and dried in the sinter. The precipitate was then washed with CH$_2$Cl$_2$ and the filtrate dried over MgSO$_4$, filtered and concentrated by rotary evaporation. The resulting orange residue was purified by column chromatography on silica gel, eluting with cyclohexane containing 5-50% EtOAc. The appropriate fractions were combined and concentrated to give 1-(benzenesulfonyl)pyrrolo[2,3-b]pyridine-4-carbonitrile [D051] (9.159 g, 72%) as an off-white solid. LCMS method 6 RT=3.62 min, MI+1=284.

1-(benzenesulfonyl)-2-(1-hydroxycyclobutyl)pyrrolo[2,3-b]pyridine-4-carbonitrile [D052]

A stirred solution of diisopropylamine (0.62 mL, 4.41 mmol) in THF (20 mL) was prepared under nitrogen and cooled to −78° C. nBuLi (1.6 M) (2.65 mL, 4.24 mmol) was added and the reaction mixture warmed to 0° C. and stirred at this temperature for 10 min then cooled back to −78° C. The solution was added dropwise to a −78° C. solution of 1-(benzenesulfonyl)pyrrolo[2,3-b]pyridine-4-carbonitrile [D051] (1.0 g, 3.53 mmol) in THF (20 mL) and the reaction mixture stirred at −78° C. for 45 min. Cyclobutanone (0.4 mL, 5.29 mmol) was added dropwise as a solution in THF (5 mL). The reaction mixture was allowed to warm slowly (dry-ice/acetone bath was not removed) over 2 h. The reaction mixture was quenched with NH$_4$Cl (aq) (20 mL), allowed to warm to room temperature and extracted with EtOAc (3×10 mL). The combined organic extracts were combined, dried over MgSO$_4$, filtered and concentrated by rotary evaporation. The crude residue was purified by column chromatography on silica gel, eluting with cyclohexane containing 5-40% EtOAc. The appropriate fractions were combined and concentrated to give 1-(benzenesulfonyl)-2-(1-hydroxycyclobutyl)pyrrolo[2,3-b]pyridine-4-carbonitrile [D052] (0.835 g, 67%) as a beige solid. LCMS method 6 RT=3.81 min, MI+1=354.

2-(1-hydroxycyclobutyl)-1H-pyrrolo[2,3-b]pyridine-4-carbonitrile [D053]

A solution of 1-(benzenesulfonyl)-2-(1-hydroxycyclobutyl)pyrrolo[2,3-b]pyridine-4-carbonitrile [D052] (1.92 g, 5.44 mmol) in THF (30 mL) was prepared and TBAF (8.15 mL of a 1 M solution in THF, 8.15 mmol) added drop-wise. The reaction mixture was stirred at room temperature overnight. The reaction mixture was poured into sat. NH$_4$Cl (aq) (50 mL) and extracted with EtOAc (3×20 mL). The organic phase was dried over MgSO$_4$, filtered and concentrated by rotary evaporation. The residue was purified by column chromatography on silica gel, eluting with cyclohexane containing 10-100% EtOAc. The appropriate fractions were combined and concentrated to give 2-(1-hydroxycyclobutyl)-1H-pyrrolo[2,3-b]pyridine-4-carbonitrile [D052] (0.799 g, 69%) as a beige solid. LCMS method 6 RT 3.32 min, MI+1=214.

2-(1-Hydroxy-cyclobutyl)-1H-pyrrolo[2,3-b]pyridine-4-carboxamidine [D054]

Amidine was prepared via hydroxylamine/hydrogenation route (scheme D4): LCMS: method 5 RT=0.67, MI+1=231.

General Synthesis of 3-Substituted-Azaindole Derivatives of General Formula [I-041] Scheme D6

The 3-substituted azaindole derivatives of general formula [I-041] were prepared by the reaction of 2-(1H-pyrrolo[2,3-b]pyridin-4-yl)-pyrido[3,4-d]pyrimidin-4-ol derivative of general formula [I-036] with a halogenating reagent such as NCS or NBS, in a polar aprotic solvent such as DMF, to yield the 2-(3-halo-1H-pyrrolo[2,3-b]pyridin-4-yl)-pyrido

[3,4-d]pyrimidin-4-ol derivatives of general formula [I-037], after reaction work up, typically by a liquid-liquid extraction the intermediates were purified by column chromatography. 2-(3-Halo-1H-pyrrolo[2,3-b]pyridin-4-yl)-pyrido[3,4-d]pyrimidin-4-ylamine derivatives of general formula [I-038] were prepared by the reaction of a 2-(3-halo-1H-pyrrolo[2,3-b]pyridin-4-yl)-pyrido[3,4-d]pyrimidin-4-ol derivatives of general formula [I-037] with 2,4,6-triisopropylbenzenesulfonyl chloride in a polar aprotic solvent such as DMA, DMF, NMP with a tertiary alkylamine base such as Et$_3$N, DIPEA or NMM and a catalytic amount of DMAP. The intermediates were then reacted with a primary or secondary amino derivative, of general formula [I-017], in a polar aprotic solvent such as DMA, DMF, NMP in the presence of a tertiary amine base such as Et$_3$N, DIPEA or NMM at ambient temperature. After reaction work up, typically by a liquid-liquid extraction the 2-(3-halo-1H-pyrrolo[2,3-b]pyridin-4-yl)-pyrido[3,4-d]pyrimidin-4-ylamine derivatives of general formula [I-038] were purified by column chromatography. The 2-(1-Benzenesulfonyl-3-halo-1H-pyrrolo[2,3-b]pyridin-4-yl)-pyrido[3,4-d]pyrimidin-4-ylamine derivatives of general formula [I-039] were prepared by reaction of 2-(3-halo-1H-pyrrolo[2,3-b]pyridin-4-yl)-pyrido[3,4-d]pyrimidin-4-ylamine derivatives of general formula [I-038] with a strong base such as NaH in a polar aprotic solvent such as THF with benzenesulphonyl chloride at low reaction temperature such as 0° C., followed by reaction work up, typically by a liquid-liquid extraction and purification by column chromatography. The 2-(1-Benzenesulfonyl-3-halo-1H-pyrrolo[2,3-b]pyridin-4-yl)-pyrido[3,4-d]pyrimidin-4-ylamine derivatives of general formula [I-039] were reacted in a Suzuki type reaction utilising a suitable boronic acid or boronic ester, of general formula [I-042], a palladium catalyst such as Pd(PPh$_3$)$_4$ or PdCl$_2$dppf:CH$_2$Cl$_2$ a base such as Et$_3$N, KOH, Na$_2$CO$_3$ or NaOH in a polar solvent such as EtOH, THF, DMA or dioxane at high temperature either by heating thermally or using a microwave reactor. After reaction work up, typically by a liquid-liquid extraction or purification by acidic ion exchange catch-release, the intermediate derivatives of general formula [I-040] were deprotected in a two step procedure firstly by reaction with fluoride reagent such as TBAF in a polar aprotic solvent such as THF then the N-Boc derivatives were deprotected under acidic conditions with a strong acid such as TFA, TCA, methanesulfonic acid, HCl or H$_2$SO$_4$ in a solvent such as DCM, DCE, THF, EtOH or MeOH and the crude reaction product was purified by normal phase chromatography or reverse phase preparative HPLC.

Scheme D6

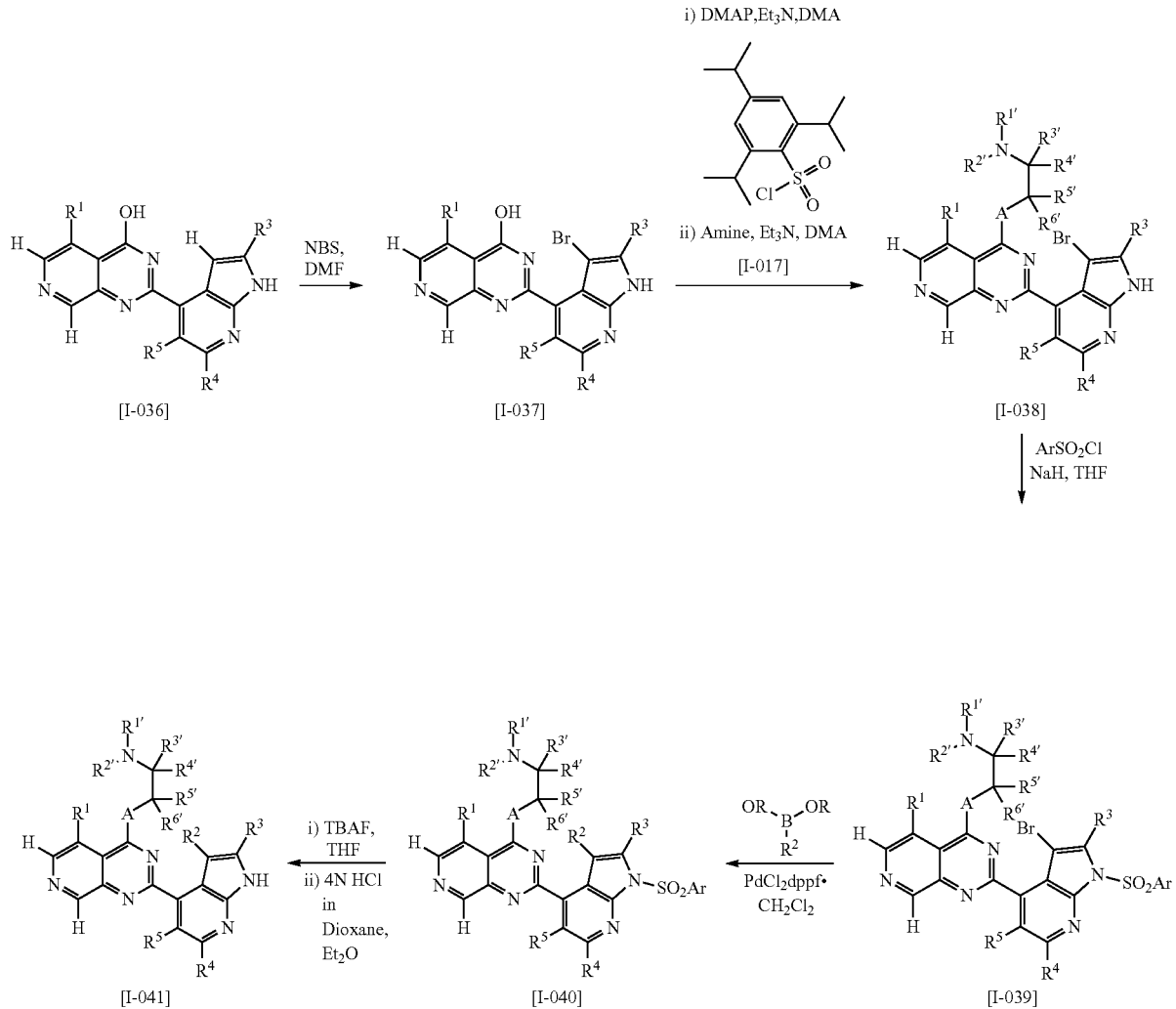

Synthesis of 5-Cyclopropyl-2-(3-phenyl-1H-pyrrolo[2,3-b]pyridin-4-yl)-4-piperazin-1-yl-pyrido[3,4-d]pyrimidine with water then diethyl ether. The solid was purified by chromatography on silica gel eluting with 10-100% EtOAc in cyclohexane to afford the title compound as a dark brown

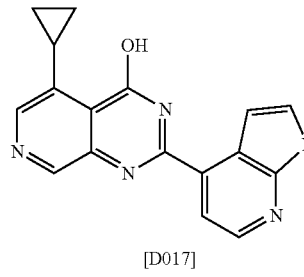

[D017]

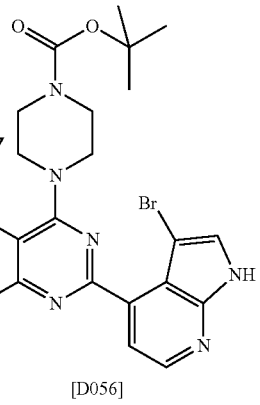

[D056]

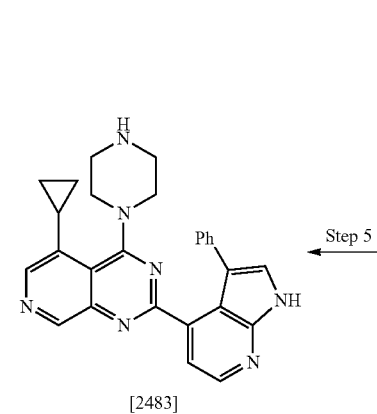

[2483]      [D058]      [D057]

Step 1: Synthesis of 2-(3-Bromo-1H-pyrrolo[2,3-b]pyridin-4-yl)-5-cyclopropyl-pyrido[3,4-d]pyrimidin-4-ol [D055]

5-Cyclopropyl-2-(1H-pyrrolo[2,3-b]pyridin-4-yl)pyrido[3,4-d]pyrimidin-4-ol [D017] (50 mg, 0.160 mmol) and 1-bromopyrrolidine-2,5-dione (44.01 mg, 0.250 mmol) were combined in DMF (11 mL) and the mixture allowed to stir at room temperature under nitrogen for 5 h. Water (15 mL) was added to the mixture and the resulting light brown precipitate was collected by filtration. The solid was washed with water and dried under vacuum at 40° C. to afford the title compound (30 mg, 48%). LCMS method 5 RT: 4.55 min, MI: 384 (MH)+.

Step 2: Synthesis of tert-Butyl 4-[2-(3-bromo-1H-pyrrolo[2,3-b]pyridin-4-yl)-5-cyclopropyl-pyrido[3,4-d]pyrimidin-4-yl]piperazine-1-carboxylate [D056]

To a suspension of 2-(3-bromo-1H-pyrrolo[2,3-b]pyridin-4-yl)-5-cyclopropyl-3H-pyrido[3,4-d]pyrimidin-4-one [D055] (0.9 g, 2.35 mmol) in DMA (20 mL) was added DIPEA (1.23 mL, 7.06 mmol) followed by 2,4,6-triisopropylbenzenesulfonyl chloride (0.73 g, 2.4 mmol) and DMAP (14.38 mg, 0.120 mmol). The reaction mixture was stirred at room temperature for 2 h then piperazine-1-carboxylic acid tert-butyl ester (0.53 g, 2.83 mmol) was added and stirring continued overnight. The mixture was diluted with water and resulting solid was collected by filtration and washed solid (200 mg, 15%). LCMS method 5 RT: 5.53 min, MI: 552.35 (MH)+. $^1$H NMR (500 MHz, d6-DMSO) 12.29 (1H, s), 8.99 (1H, s), 8.39 (1H, d), 8.16 (1H, s), 7.75 (1H, d), 7.46 (1H, d), 3.93-3.64 (4H, br m), 3.49 (4H, br s), 2.73-2.66 (1H, m), 1.39 (9H, s), 1.31-1.24 (2H, m), 1.07-1.01 (2H, m).

Step 3: Synthesis of tert-Butyl 4-[2-[1-(benzenesulfonyl)-3-bromo-pyrrolo[2,3-b]pyridin-4-yl]-5-cyclopropyl-pyrido[3,4-d]pyrimidin-4-yl]piperazine-1-carboxylate [D057]

A solution of tert-butyl 4-[2-(3-bromo-1H-pyrrolo[2,3-b]pyridin-4-yl)-5-cyclopropyl-pyrido[3,4-d]pyrimidin-4-yl]piperazine-1-carboxylate [D056] (200 mg, 0.360 mmol) in anhydrous THF (5 mL) was cooled to 0° C. and NaH (60% dispersion in mineral oil, 0.02 mL, 0.400 mmol) added. The mixture was allowed to stir at 0° C. for 30 min before the addition of benzenesulfonyl chloride (0.05 mL, 0.400 mmol). The mixture was allowed to warm to room temperature and stirred for 5 h. The reaction was quenched with water and extracted with ethyl acetate (×3). The organics were washed with brine, dried over magnesium sulfate and concentrated in vacuo. The residue was purified by flash chromatography on silica gel (eluting with 5%-90% ethyl acetate/cyclohexane) to afford the title compound as a dark orange solid (128 mg, 51%). LCMS method 5 RT: 6.26 min, MI: 692.53 (MH)+.

Step 4: Synthesis of tert-Butyl 4-[2-[1-(benzenesulfonyl)-3-phenyl-pyrrolo[2,3-b]pyridin-4-yl]-5-cyclopropyl-pyrido[3,4-d]pyrimidin-4-yl]piperazine-1-carboxylate [D058]

tert-Butyl 4-[2-[1-(benzenesulfonyl)-3-bromo-pyrrolo[2,3-b]pyridin-4-yl]-5-cyclopropyl-pyrido[3,4-d]pyrimidin-4-yl]piperazine-1-carboxylate [D057] (120 mg, 0.170 mmol), phenylboronic acid (31.59 mg, 0.260 mmol), freshly ground potassium phosphate tribasic (73.8 mg, 0.350 mmol) and dichloro[1,1'-bis(diphenylphosphino)ferrocene]palladium (II) dichloromethane adduct (7.09 mg, 0.010 mmol) were combined in a vial and purged with nitrogen (×3). Anhydrous 1,4-dioxane (0.55 mL) was added and the mixture heated to 90° C. overnight. The mixture was diluted with ethyl acetate and washed with water followed by brine. The organics were dried over magnesium sulfate and concentrated in vacuo. The residue was purified by flash chromatography on silica gel (eluting with 0-50% EtOAc/cyclohexane) to afford the title compound as a yellow solid (48 mg, 40%). LCMS method 5 RT: 6.32 min, MI: 688.58 (MH)$^+$.

Step 5: Synthesis of 5-Cyclopropyl-2-(3-phenyl-1H-pyrrolo[2,3-b]pyridin-4-yl)-4-piperazin-1-yl-pyrido[3,4-d]pyrimidine[2483]

To a solution of tert-butyl 4-[2-[1-(benzenesulfonyl)-3-phenyl-pyrrolo[2,3-b]pyridin-4-yl]-5-cyclopropyl-pyrido[3,4-d]pyrimidin-4-yl]piperazine-1-carboxylate [D058] (45 mg, 0.070 mmol) in THF (1 mL) was added TBAF (1M solution in THF, 0.1 mL, 0.100 mmol) drop-wise. The reaction mixture was stirred at room temperature for 6 h. The reaction mixture was quenched with a saturated aqueous solution of NH$_4$Cl, diluted with EtOAc and the organic phase separated. The aqueous phase was extracted with EtOAc. The combined organic phases were dried over magnesium sulfate, filtered and concentrated in vacuo. The residue was purified by flash chromatography on silica gel (eluting with 20% EtOAc/DCM-100% EtOAc) to afford tert-butyl 4-[5-cyclopropyl-2-(3-phenyl-1H-pyrrolo[2,3-b]pyridin-4-yl)pyrido[3,4-d]pyrimidin-4-yl]piperazine-1-carboxylate (23 mg, 64%). LCMS method 5 RT: 5.64 min, MI: 548.52 (MH)$^+$.

To a solution of tert-butyl 4-[5-cyclopropyl-2-(3-phenyl-1H-pyrrolo[2,3-b]pyridin-4-yl)pyrido[3,4-d]pyrimidin-4-yl]piperazine-1-carboxylate (15 mg, 0.030 mmol) in diethyl ether (2 mL) was added 4 M HCl in dioxane (0.14 mL, 0.550 mmol) and the mixture allowed to stir at room temperature for 4 h before concentrating in vacuo. The residue was dissolved in water and washed with ethyl acetate followed by cyclohexane. A saturated solution of sodium carbonate was then added to the aqueous layer until basic and the product extracted with ethyl acetate (×3). The organics were dried over magnesium sulfate, filtered and concentrated to afford the title compound as a pale yellow solid (11 mg, 91%). LCMS method 5 RT: 2.97 min, MI: 448.4 (MH)$^+$. $^1$H NMR (500 MHz, d6-DMSO) 12.04 (1H, s), 8.69 (1H, s), 8.39 (1H, d), 8.01 (1H, s), 7.61 (1H, d), 7.52 (1H, d), 7.00-6.92 (1H, m), 6.84-6.77 (4H, m), 3.19-2.89 (4H, m), 2.71-2.59 (4H, m), 2.45-2.38 (1H, m), 1.32-1.23 (2H, m), 1.05-1.00 (2H, m).

General Synthesis of 3-Substituted-Azaindole Derivatives of General Formula [I-045] Scheme D7

The 3-substituted azaindole derivatives of general formula [I-045] were prepared by the reaction of 2-(1H-pyrrolo[2,3-b]pyridin-4-yl)-pyrido[3,4-d]pyrimidin-4-ylamine derivatives of general formula [I-043] with a halogenating reagent such as NCS or NBS, in a polar aprotic solovent such as DMF, to yield the 2-(3-halo-1H-pyrrolo[2,3-b]pyridin-4-yl)-pyrido[3,4-d]pyrimidin-4-ylamine derivatives of general formula [I-044], after reaction work up, typically by a liquid-liquid extraction the intermediate was purified by column chromatography. The intermediate derivative of general formula [I-044] were deprotected under acidic conditions with a strong acid such as TFA, TCA, methanesulfonic acid, HCl or H$_2$SO$_4$ in a solvent such as DCM, DCE, THF, EtOH or MeOH and the crude reaction product was purified by normal phase chromatography or reverse phase preparative HPLC.

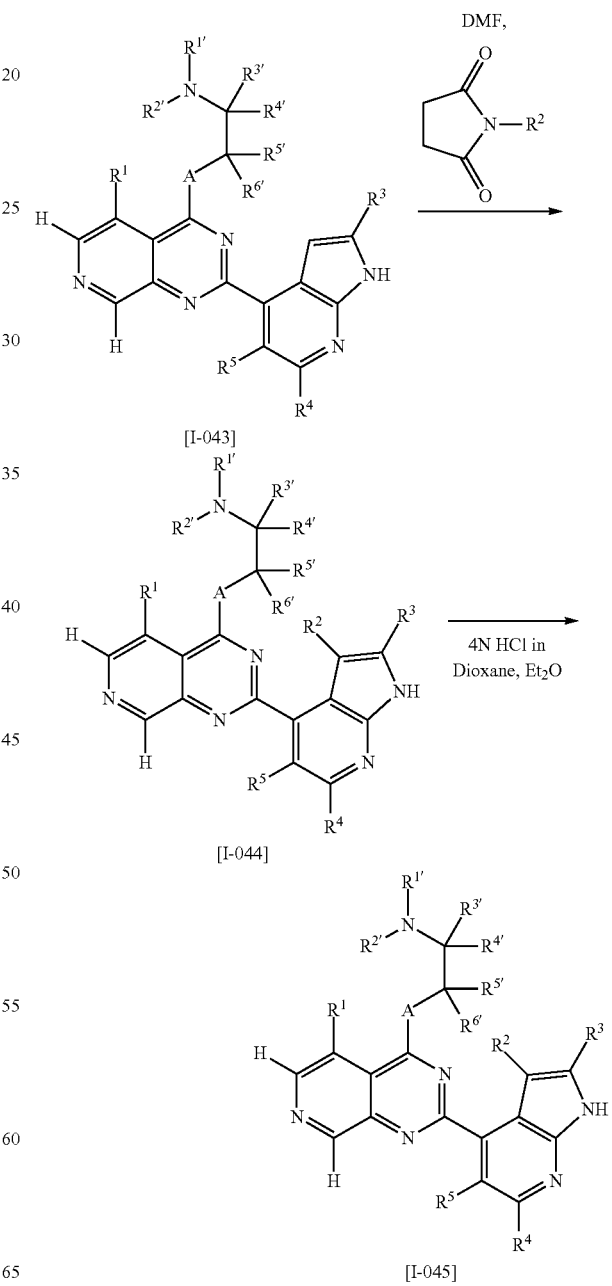

Scheme D7

Synthesis of 2-(3-Chloro-2-methyl-1H-pyrrolo[2,3-b]pyridin-4-yl)-5-cyclopropyl-4-piperazin-1-yl-pyrido[3,4-d]pyrimidine[2209]

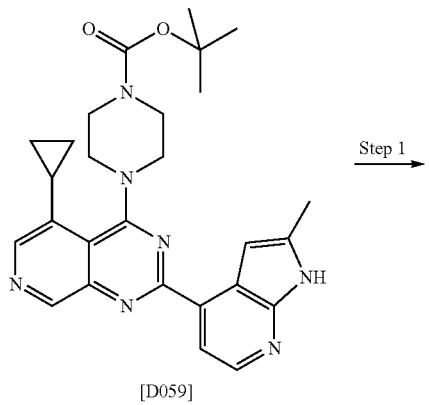

Step 1: Synthesis of tert-Butyl 4-[2-(3-chloro-2-methyl-1H-pyrrolo[2,3-b]pyridin-4-yl)-5-cyclopropyl-pyrido[3,4-d]pyrimidin-4-yl]piperazine-1-carboxylate [D060]

To a solution of tert-butyl 4-[5-cyclopropyl-2-(2-methyl-1H-pyrrolo[2,3-b]pyridin-4-yl)pyrido[3,4-d]pyrimidin-4-yl]piperazine-1-carboxylate [D059, prepared according to scheme D4] (317 mg, 0.650 mmol) in DMF (4.53 mL) was added 1-chloropyrrolidine-2,5-dione (87.17 mg, 0.650 mmol) and the mixture allowed to stir at room temperature under nitrogen overnight. The mixture was diluted with ethyl acetate and washed with water (×4). The organics were dried over magnesium sulfate, filtered and the filtrate concentrated in vacuo. The residue was purified by chromatography on silica gel, eluting with 10%-100% EtOAc/cyclohexane to afford tert-butyl 4-[2-(3-chloro-2-methyl-1H-pyrrolo[2,3-b]pyridin-4-yl)-5-cyclopropyl-pyrido[3,4-d]pyrimidin-4-yl]piperazine-1-carboxylate as an orange solid (201 mg, 59%). LCMS method 5 RT: 5.75 min, MI: 520.25 (MH)$^+$.

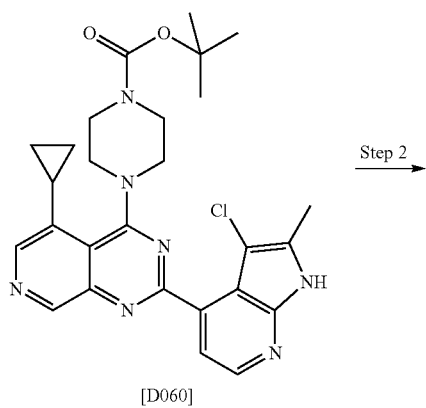

Step 2: Synthesis of 2-(3-Chloro-2-methyl-1H-pyrrolo[2,3-b]pyridin-4-yl)-5-cyclopropyl-4-piperazin-1-yl-pyrido[3,4-d]pyrimidine[2209]

tert-Butyl 4-[2-(3-chloro-2-methyl-1H-pyrrolo[2,3-b]pyridin-4-yl)-5-cyclopropyl-pyrido[3,4-d]pyrimidin-4-yl]piperazine-1-carboxylate [D060] (188 mg, 0.360 mmol) and 4M HCl in dioxane solution (1.81 mL, 7.23 mmol) were combined under nitrogen and the mixture allowed to stir at room temperature for 2 h. The mixture was concentrated in vacuo to yield an orange solid. The solid was dissolved in methanol and passed through a SCX column, eluting with methanol and then 7N ammonia in methanol solution. The solution was concentrated in vacuo and the residue purified by chromatography on silica gel eluting with 0-10% MeOH/DCM to yield a yellow solid. The solid was triturated with ether, filtered and dried under vacuum to afford 2-(3-chloro-2-methyl-1H-pyrrolo[2,3-b]pyridin-4-yl)-5-cyclopropyl-4-piperazin-1-yl-pyrido[3,4-d]pyrimidine (67 mg, 44%). LCMS method 5 RT: 3.00 min, MI: 420.14 (MH)$^+$. 1H NMR (500 MHz, d6-DMSO) 12.12 (1H, s), 8.96 (1H, s), 8.29 (1H, d), 8.11 (1H, s), 7.45 (1H, d), 3.88-3.41 (4 h, m), 2.90 (4H, s), 2.71-2.64 (1H, m), 2.38 (3H, s), 1.31-1.23 (2H, m), 1.07-1.01 (2H, m).

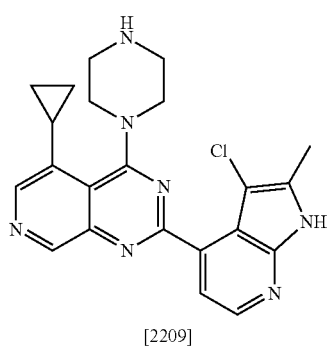

Synthesis of give 2-(difluoromethyl)-1H-pyrrolo[2,3-b]pyridine-4-carboxamidine dihydrochloride [D067] Scheme D8

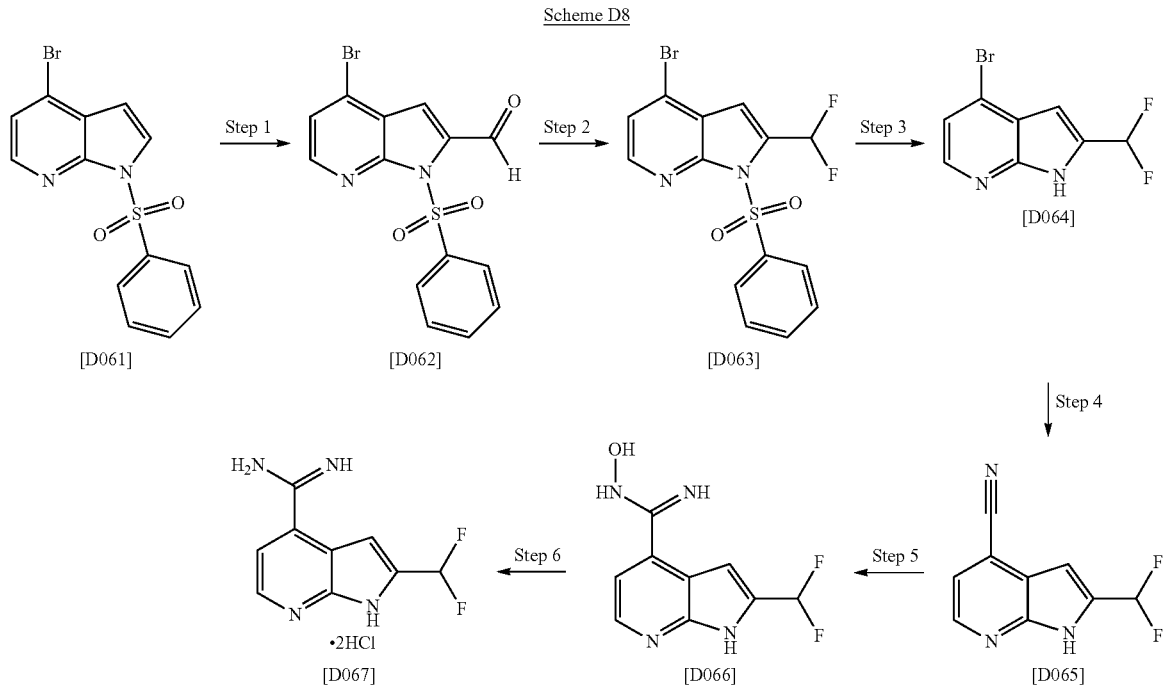

Step 1: synthesis of 1-(benzenesulfonyl)-4-bromo-pyrrolo[2,3-b]pyridine-2-carbaldehyde [D062]

A stirred solution of N,N-diisopropylamine (0.36 g, 3.56 mmol) in anhydrous THF (10 mL) was prepared under nitrogen and cooled to −78° C. n-BuLi (1.6 M in hexanes) (2.22 mL, 3.56 mmol) was added and the reaction mixture stirred at −78° C. for 2-3 min, then 0° C. for 10 min then re-cooled to −78° C. 1-(Benzenesulfonyl)-4-bromo-pyrrolo[2,3-b]pyridine [D061] (1.0 g, 2.97 mmol) was added drop-wise as a solution in anhydrous THF (3 mL) and the reaction mixture stirred at −78° C. for 2 h. N,N-dimethylformamide (0.92 mL, 11.86 mmol) was added drop-wise and the reaction mixture stirred at −78° C. for a further 2 hours then quenched with sat. NH$_4$Cl (aq) (20 mL). The mixture was diluted with EtOAc (10 mL) and the organic phase separated. The aqueous was extracted with EtOAc (2×10 mL) and the combined organic portions dried over MgSO$_4$, filtered and concentrated by rotary evaporation. The residue was purified by column chromatography on silica gel, eluting with cyclohexane containing 50-100% dichloromethane. The appropriate fractions were combined and concentrated to give 1-(benzenesulfonyl)-4-bromo-pyrrolo[2,3-b]pyridine-2-carbaldehyde (798 mg, 74%) as a colourless solid. LCMS method 5 RT=3.77 min, MI+1=365/367); 1H NMR (500 MHz, d6-DMSO) 10.45 (1H, s), 8.45 (1H, d, J=5.2 Hz), 8.24-8.22 (2H, m), 7.79-7.76 (1H, m), 7.75 (1H, d, J=5.2 Hz), 7.68-7.64 (2H, m), 7.45 (1H, s).

Step 2: Synthesis of 1-(benzenesulfonyl)-4-bromo-2-(difluoromethyl)pyrrolo[2,3-b]pyridine [D063]

A solution of 1-(benzenesulfonyl)-4-bromo-pyrrolo[2,3-b]pyridine-2-carbaldehyde [D062] (3.82 g, 10.47 mmol) in CH$_2$Cl$_2$ (50 mL) was prepared and deoxyfluor (R) (13.62 mL, 31.41 mmol) was added dropwise. The reaction mixture was stirred at room temperature overnight. The reaction mixture was poured carefully into sat NaHCO$_3$ (aq) and the organic phase separated and washed with 1 M HCl. The organic phase was dried through a phase separator and concentrated by rotary evaporation. The crude residue was combined with a second batch of crude residue (prepared following the same procedure on a 0.5 g scale) and purified by chromatography on silica, eluting with cyclohexane containing 10-50% EtOAc. The appropriate fractions were combined and concentrated to give 1-(benzenesulfonyl)-4-bromo-2-(difluoromethyl)pyrrolo[2,3-b]pyridine (2.625 g, 65%) as an off-white solid. LCMS method 5 RT=4.63 min, MI+1=387/389).

Step 3: synthesis of 4-bromo-2-(difluoromethyl)-1H-pyrrolo[2,3-b]pyridine [D064]

A solution of 1-(benzenesulfonyl)-4-bromo-2-(difluoromethyl)pyrrolo[2,3-b]pyridine [D063] (2.59 g, 6.7 mmol) in THF (50 mL) was prepared and TBAF (10.05 mL of a 1M solution in THF, 10.05 mmol) added drop-wise. The reaction mixture was stirred at room temperature overnight. The reaction mixture was concentrated by rotary evaporation and the residue purified by chromatography on silica, eluting with cyclohexane containing 10-70% EtOAc. The appropriate fractions were combined and concentrated to give 4-bromo-2-(difluoromethyl)-1H-pyrrolo[2,3-b]pyridine (1.466 g, 89%) as an off-white solid. LCMS method 5 (RT=5.14 min, MI+1=247/249). $^1$H NMR (500 MHz, d$_6$-DMSO) 12.82 (1H, s), 8.21 (1H, d, J=5.0 Hz), 7.44 (1H, d, J=5.0 Hz), 7.24 (1H, t, J=54.0 Hz), 6.77 (1H, s).

Step 4: Synthesis of 2-(difluoromethyl)-1H-pyrrolo[2,3-b]pyridine-4-carbonitrile [D065]

A solution of 4-bromo-2-(difluoromethyl)-1H-pyrrolo[2,3-b]pyridine [D064] (1.46 g, 5.91 mmol), zinc cyanide (1.04 g, 8.87 mmol) and dichloro[1,1'-bis(diphenylphosphino)fer rocene]palladium (II) dichloromethane adduct (0.24 g, 0.300 mmol) in DMF (20 mL) was prepared. Activated zinc dust (0.08 g, 1.18 mmol) was added and the microwave vials sealed and heated to 85° C. overnight.

LCMS showed complete conversion to desired product. The reaction mixture was cooled to room temperature and poured into water. The resulting precipitate was filtered and washed with $CH_2Cl_2$ and MeOH. The filtrate was dried through a phase separator and concentrated by rotary evaporation. Crude mass recovery was low (ca. 60%) therefore the precipitate was stirred in a mixture of EtOAc, $CH_2Cl_2$ and MeOH for 1 hour then filtered. The combined filtrates were concentrated by rotary evaporation to give crude mass return of 1.04 g (91%). The crude residue was purified by chromatography on silica, eluting with 10-100% EtOAc in cyclohexane. The appropriate fractions were combined and columned to give 2-(difluoromethyl)-1H-pyrrolo[2,3-b]pyridine-4-carbonitrile (0.774 g, 68%) as a beige solid. LCMS method 5 (RT=3.21 min, MI+1=194).

Step 5: synthesis of 2-(difluoromethyl)-N-hydroxy-1H-pyrrolo[2,3-b]pyridine-4-carboxamidine [D066]

A suspension of 2-(difluoromethyl)-1H-pyrrolo[2,3-b]pyridine-4-carbonitrile [D065] (0.77 g, 4.01 mmol) in ethanol (20 mL) was prepared in a microwave vial. Hydroxylamine 50% w/w in water (0.49 mL, 8.01 mmol) was added and the vial sealed and heated (thermally) to 85° C. for 3 h. The reaction mixture was concentrated by rotary evaporation to give a crude solid residue assumed to contain 2-(difluoromethyl)-N-hydroxy-1H-pyrrolo[2,3-b]pyridine-4-carboxamidine (0.906 g, 99.96%) which was used in the next step without purification.

Step 6: Synthesis of 2-(difluoromethyl)-1H-pyrrolo[2,3-b]pyridine-4-carboxamidine dihydrochloride [D067]

A suspension of 2-(difluoromethyl)-N-hydroxy-1H-pyrrolo[2,3-b]pyridine-4-carboxamidine [D066] (0.91 g, 4.01 mmol) in methanol (20 mL) was prepared. Acetic anhydride (0.45 mL, 4.81 mmol) was added and the reaction mixture stirred at room temperature for 1.5 h. 10% Pd/C (50 mg) was added and the reaction mixture stirred under an atmosphere of hydrogen (balloon) for 3 h. The reaction mixture was filtered through celite, washing with MeOH and the filtrate concentrated by rotary evaporation. The residue was stirred in 4M HCl in dioxane and the resulting solid filtered and dried under vacuum to give 2-(difluoromethyl)-1H-pyrrolo[2,3-b]pyridine-4-carboxamidine dihydrochloride (1.022 g, 90%). LCMS method 5 (RT=0.55 min, MI+1=211).

General Synthesis of [4-(4-Amino-5-cyclopropyl-pyrido[3,4-d]pyrimidin-2-yl)-pyridin-2-yl]-urea Derivatives of General Formula [I-053] Scheme D11

The [4-(4-Amino-5-cyclopropyl-pyrido[3,4-d]pyrimidin-2-yl)-pyridin-2-yl]-urea derivatives of general formula [I-053] were prepared by the reaction of a 2-(2-chloropyridin-4-yl)-5-cyclopropyl-pyrido[3,4-d]pyrimidin-4-ylamine derivative of general formula [I-052], prepared in scheme B4, in a Buchwald type reaction with sodium isocyanate, a palladium catalyst such as $Pd_2(dba)_3$ a ligand such as t-BuBrettPhos, a base such as $Et_3N$, in a polar solvent such as EtOH, THF, DMA or dioxane at high temperature either by heating thermally or using a microwave reactor, with a suitable amine of general formula [I-054]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by normal phase chromatography or reverse phase preparative HPLC.

Scheme D11

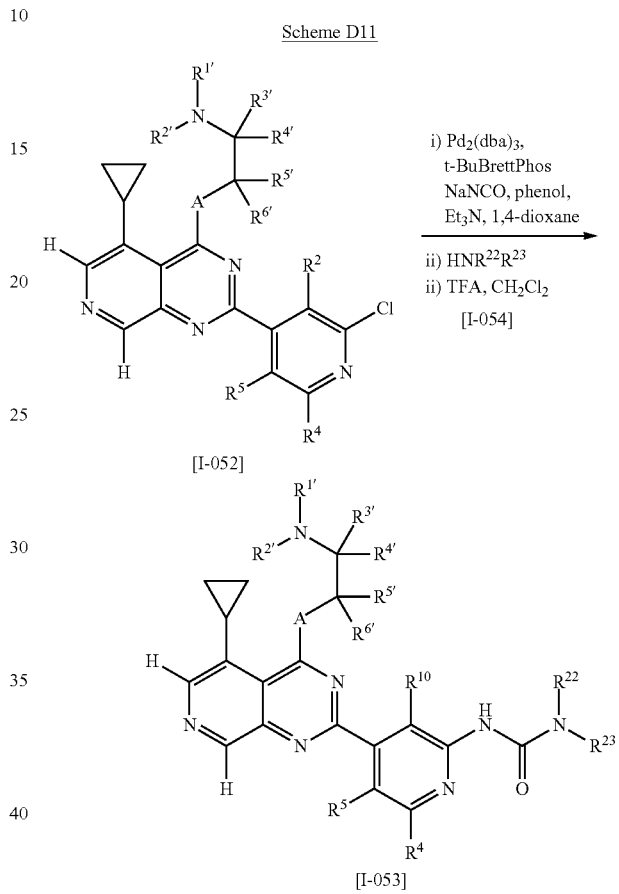

Synthesis of 1-[4-(5-Cyclopropyl-4-piperazin-1-yl-pyrido[3,4-d]pyrimidin-2-yl)-2-pyridyl]-3-phenyl-urea[2420]

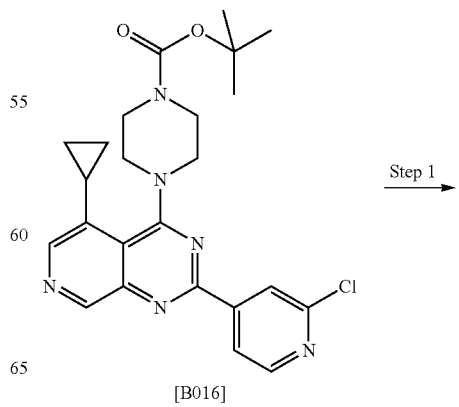

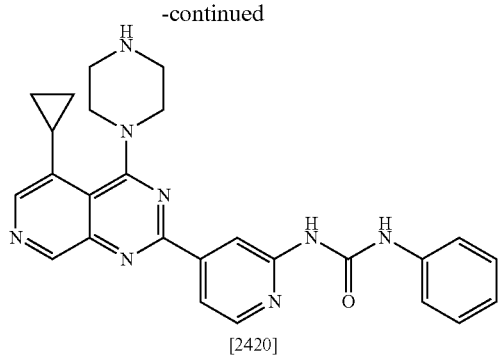

[2420]

Step 1: Synthesis of 1-[4-(5-Cyclopropyl-4-piperazin-1-yl-pyrido[3,4-d]pyrimidin-2-yl)-2-pyridyl]-3-phenyl-urea[2420]

An oven-dried microwave vial, which was equipped with a magnetic stir bar and fitted with a screw cap septum, was charged with tris(dibenzylideneacetone)dipalladium(0) (24.5 mg, 0.030 mmol) and t-BuBrettPhos (25.93 mg, 0.050 mmol). The vial was evacuated and backfilled with nitrogen and subsequently 1,4-dioxane (2.5 mL) was added via syringe. The resulting purple slurry was heated at 120° C. for 3 min at which point the colour of the resulting mixture turned dark orange-brown. A second oven-dried microwave vial, equipped with a magnetic stir bar and fitted with a screw cap septum, was charged with sodium isocyanate (69.56 mg, 1.07 mmol), phenol (0.09 mL, 1.07 mmol) and tert-butyl 4-[2-(2-chloro-4-pyridyl)-5-cyclopropyl-pyrido[3,4-d]pyrimidin-4-yl]piperazine-1-carboxylate [B016, prepared according to scheme B4] (0.25 g, 0.540 mmol) and backfilled with nitrogen and triethylamine (0.02 mL, 0.130 mmol) was added via syringe. The premixed catalyst solution was then transferred to the vial via cannula under nitrogen. The screw cap septum was replaced with an un-punctured septum under continuous nitrogen flow and the solution was heated to 120° C. for 16 h. The reaction mixture was then cooled to room temperature after which time aniline (0.06 mL, 0.640 mmol) and 1,4-dioxane were added into the vial under continuous nitrogen flow and the resulting mixture was stirred at 80° C. for 15 h. The reaction mixture was then cooled to room temperature and filtered through a pad of celite. The solvent was removed under reduced pressure and the crude product was purified by flash chromatography eluting with 5-10% dichloromethane/methanol to afford the N-boc protected desired product which was stirred in 50% TFA/DCM at room temperature for 1 hour to cleave off the Boc group. The compound was washed through a SCX-2 cartridge and purified by prep-HPLC to afford 1-[4-(5-cyclopropyl-4-piperazin-1-yl-pyrido[3,4-d]pyrimidin-2-yl)-2-pyridyl]-3-phenyl-urea (15 mg, 6%). LCMS method 6 RT: 2.95 min, MI: 467 (MH)$^+$. $^1$H NMR (500 MHz, d6-DMSO) 9.65 (1H, s), 9.00 (1H, s), 8.56 (1H, s), 8.46 (1H, dd), 8.12 (1H, s), 7.95 (1H, dd), 7.56 (2H, d), 7.33 (2H, t), 7.04 (1H, t), 3.78 (4H, m), 2.92 (4H, s), 2.63 (1H, m), 1.23 (2H, m), 1.03 (2H, m).

General Synthesis of 2-Arylsulfonylamino-Isonicotinamidine Derivatives of General Formula [I-059] Scheme D12

The 2-arylsulfonylamino-isonicotinamidine derivatives of general formula [I-059] were prepared by the reaction of a 2-amino-isonicotinonitrile derivative of general formula [I-055] with a substituted benzenesulphonyl chloride derivative of general formula [I-056] in a basic solvent such as pyridine at elevated temperature. The crude reaction intermediate of general formula [I-057] was then reacted with hydroxylamine (50% wt/wt in water) and a polar protic solvent such as EtOH at elevated temperature. The intermediate 2-arylsulfonylamino-isonicotinimidic acid of general formula [I-058] was then subjected to a hydrogenolysis reaction with acetic anhydride in a polar protic solvent such as methanol a palladium catalyst such as palladium on activated charcoal under a atmosphere of hydrogen gas, to yield the 2-arylsulfonylamino-isonicotinamidine derivative of general formula [I-059].

Scheme D12

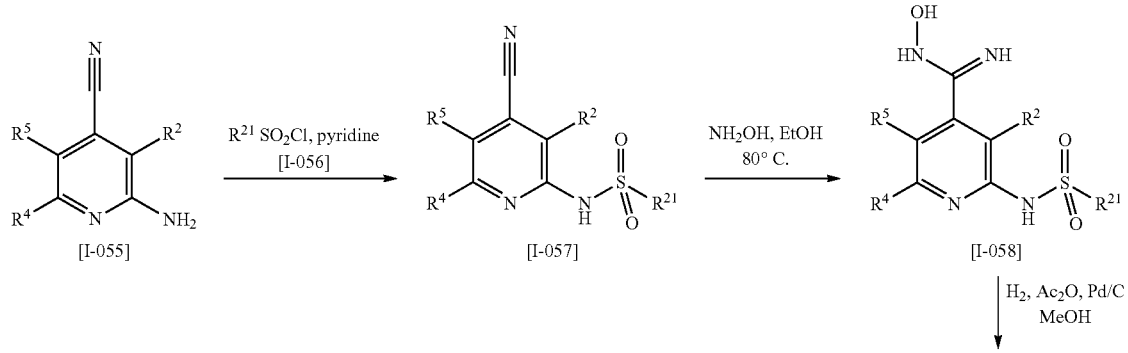

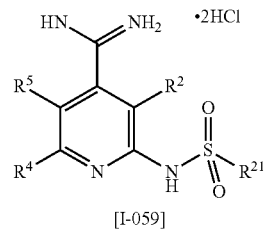

[I-059]

Synthesis of 2-(Benzenesulfonamido)pyridine-4-carboxamidine Dihydrochloride [D081]

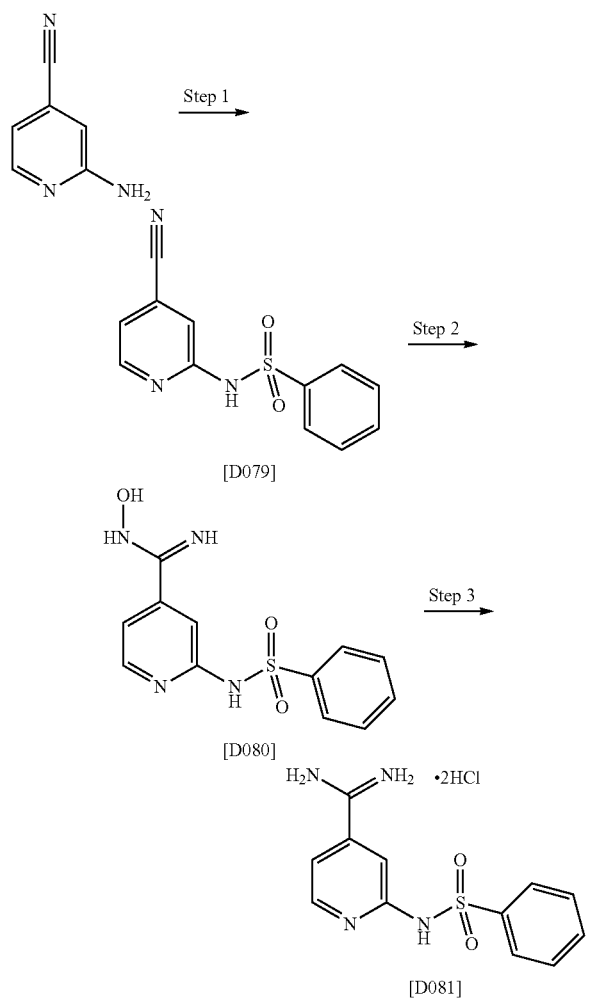

Step 1: Synthesis of N-(4-Cyano-2-pyridyl)benzenesulfonamide [D079]

A round bottom flask charged with a magnetic stir bar, 2-aminopyridine-4-carbonitrile (2 g, 16.79 mmol), benzenesulfonyl chloride (2.15 mL, 16.79 mmol) and pyridine (20 mL) was stirred and heated under reflux conditions at 140° C. for 48 hours. After reaction completion, the solution was allowed to cool down to room temperature and washed with water and extracted with ethyl acetate. The separated organic layer was dried over anhydrous magnesium sulphate and the solvent removed under reduced pressure. Dichloromethane was added to the oil obtained and a white solid precipitate was formed which was washed with copious amounts of dichloromethane, methanol and diethyl ether. The solid was dried under suction to afford N-(4-cyano-2-pyridyl)benzenesulfonamide, (2.21 g, 51%) as a fluffy white solid. LCMS method 6 RT: 2.87 min, MI: 260 (MH)$^+$.

Step 2: Synthesis of 2-(Benzenesulfonamido)-N-hydroxy-pyridine-4-carboxamidine [D080]

To a solution of N-(4-cyano-2-pyridyl)benzenesulfonamide [D079] (2 g, 7.71 mmol) in ethanol (40 mL) was added hydroxylamine (50% w/w in water, 0.94 mL, 15.43 mmol) dropwise. The mixture was then stirred at 80° C. overnight. The reaction mixture was allowed to cool down to room temperature and the solution evaporated to complete dryness under reduced pressure to afford 2-(benzenesulfonamido)-N-hydroxy-pyridine-4-carboxamidine (2.25 g, 100%). LCMS method 5 RT: 1.79 min, MI: 293 (MH)$^+$.

Step 3: Synthesis of 2-(Benzenesulfonamido)pyridine-4-carboxamidine Dihydrochloride [D081]

Acetic anhydride (0.47 mL, 4.96 mmol) was added to a stirred solution of 2-(benzenesulfonamido)-N-hydroxy-pyridine-4-carboxamidine [D080] (1.45 g, 4.96 mmol) in methanol (40 mL). The reaction mixture was stirred for 2 hours at room temperature. Palladium (5% on carbon, 263.9 mg, 2.48 mmol) was added to the mixture and the flask was evacuated and back filled with hydrogen. The reaction mixture was stirred for 18 hours at room temperature under an atmosphere of hydrogen (hydrogen balloon). The mixture was filtered over a plug of celite and the solvent evaporated under reduced pressure. The crude oil obtained was azeotroped several times with toluene. The crude material obtained was dissolved in a 4M HCl in 1,4-dioxane solution (10 mL) and the solvent was evaporated to dryness to afford 2-(benzenesulfonamido)pyridine-4-carboxamidine dihydrochloride (1.06 g, 61%). Analysis by LC-MS over a period of time (typical 24 hours) showed a slow degradation of the compound. LCMS method 5 RT: 1.11 min, MI: 277 (MH)$^+$.

General Synthesis of 1H-Pyrazolo[3,4-b]pyridine-4-carboxamidine Derivatives of General Formula [I-063] Scheme D13

The 1H-pyrazolo[3,4-b]pyridine-4-carboxamidine derivatives of general formula [I-063] were prepared by the reaction of a 4-bromo-1H-pyrazolo[3,4-b]pyridine derivative of general formula [I-060] in a palladium catalysed cross coupling reaction with a palladium catalyst such as Pd$_2$(dba)$_3$, a ligand such as dppf, a cyanide reagent such as Zn(CN)$_2$, zinc dust, in a polar aprotic solvent such as DMF at high temperature either by heating thermally or using a microwave reactor. The crude product was purified by column chromatography. The reaction intermediate of general formula [I-061] was then reacted with hydroxylamine (50% wt/wt in water) and a polar protic solvent such as EtOH at elevated temperature. The intermediate N-hydroxy-1H-pyrazolo[3,4-b]pyridine-4-carboxamidine of general formula [I-062] was then subjected to a hydrogenolysis reaction with acetic anhydride in a polar protic solvent such as methanol a palladium catalyst such as palladium on activated charcoal under a atmosphere of hydrogen gas, to yield the 1H-pyrazolo[3,4-b]pyridine-4-carboxamidine derivative of general formula [I-063]

Step 1: Synthesis of 1H-Pyrazolo[3,4-b]pyridine-4-carbonitrile [D081]

A microwave vial was charged with 4-bromo-1H-pyrazolo[3,4-b]pyridine (1 g, 5.05 mmol), Zn(CN)$_2$ (0.71 g, 6.06 mmol), Zn dust (0.07 g, 1.01 mmol), Pd$_2$(dba)$_3$ (0.46 g, 0.510 mmol), dppf (0.28 g, 0.510 mmol) and DMF (10 mL). The vial was sealed and heated at 90° C. overnight. The mixture was cooled and filtered through a celite pad, the celite pad was then washed with AcOEt. The filtrate was concentrated under reduced pressure. The crude residue was dissolved in DCM and diethyl ether was added. The resulting solid was collected and used without further purification. The filtrate was purified by column chromatography (eluting with cyclohexane/AcOEt 0 to 100%) to afford 1H-pyrazolo Scheme D13

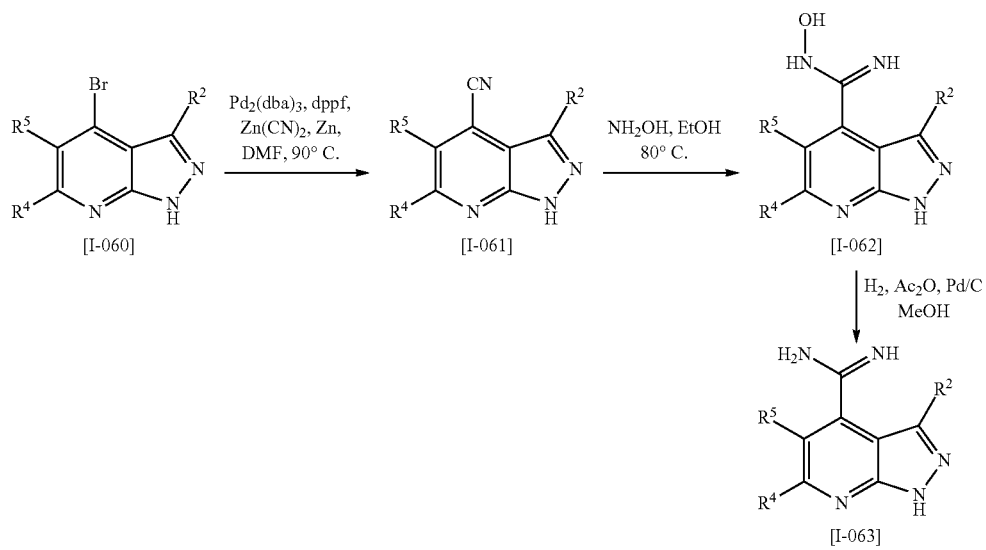

Synthesis of 1H-Pyrazolo[3,4-b]pyridine-4-carboxamidine Dihydrochloride [D084]

[3,4-b]pyridine-4-carbonitrile as a white solid (0.500 g, 69%). LCMS method 5 RT: 2.90 min, MI: 145 (MH)$^+$.

Step 2: Synthesis of N-Hydroxy-1H-pyrazolo[3,4-b]pyridine-4-carboxamidine [D083]

A mixture of 1H-pyrazolo[3,4-b]pyridine-4-carbonitrile [D082] (1.64 g, 11.38 mmol), hydroxylamine (50% wt/wt in water, 1.11 mL) and EtOH (20 mL) was stirred at 60° C. overnight. The solvent was then evaporated and the mixture azeotroped with toluene (×2) under vacuum to afford N-hydroxy-1H-pyrazolo[3,4-b]pyridine-4-carboxamidine (2.00 g, 99%). LCMS method 5 RT: 0.91 min, MI: 178 (MH)$^+$.

Step 3: Synthesis of 1H-Pyrazolo[3,4-b]pyridine-4-carboxamidine Dihydrochloride [D084]

N-Hydroxy-1H-pyrazolo[3,4-b]pyridine-4-carboxamidine [D083] (2.0 g, 11.40 mmol) was stirred at room temperature in methanol (30 mL) and then acetic anhydride (1.7 mL, 17.10 mmol) added dropwise. The mixture was stirred at room temperature for 30 mins, and then 5% palladium on charcoal (0.20 mg) added. Hydrogen was bubbled through the mixture for 5 min with a needle outlet and then the mixture was stirred at room temperature under a hydrogen atmosphere overnight. The mixture was filtered

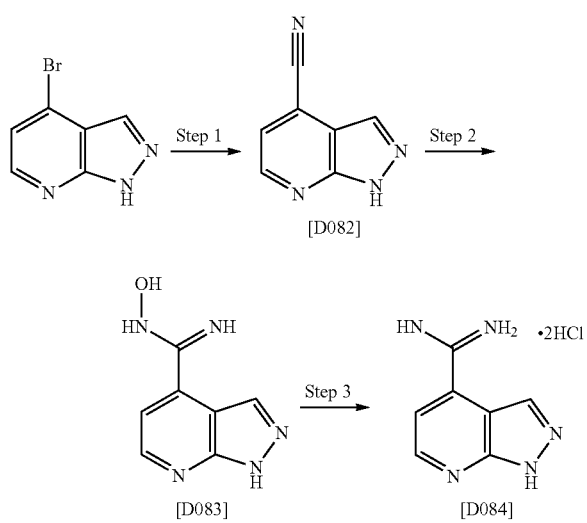

through celite and concentrated in vacuo to afford a pale beige solid. 4 N HCl in 1,4-dioxane (5 mL) was added and the solid was triturated. The solvent was removed under reduced pressure and further 4 N HCl in 1,4-dioxane (5 mL) was added, the solid triturated and the solvent was removed under reduced pressure to afford 1H-pyrazolo[3,4-b]pyridine-4-carboxamidine dihydrochloride as a brown solid (2.60 g, 97%). LCMS method 5 RT: 0.52 min, MI: 162 (MH)+.

General Synthesis of 2-substituted-sulfonyl-1H-pyrrolo[2,3-b]pyridine-4-carbonitrile Derivatives of General Formula [I-065] Scheme D14

The 2-substituted-sulfonyl-1H-pyrrolo[2,3-b]pyridine-4-carbonitrile derivatives of general formula [I-065] were prepared by the reaction of a 2-substituted sulfanyl-1H-pyrrolo[2,3-b]pyridine-4-carbonitrile derivative of general formula [I-064], prepared in scheme D5, with an oxidising agent such as m-CPBA in a halogenated solvent such as DCM. After reaction work up, typically by a liquid-liquid extraction the crude reaction mixture was purified by column chromatography.

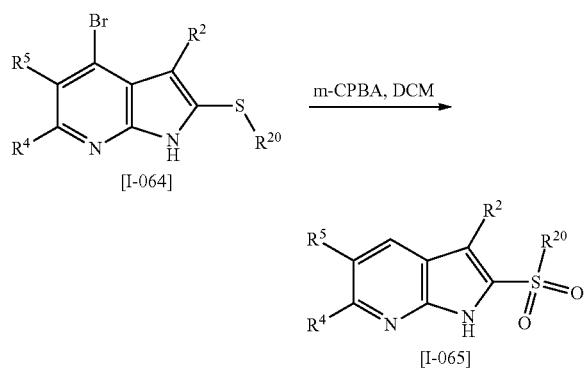

Synthesis of 2-(benzenesulfonyl)-1H-pyrrolo[2,3-b]pyridine-4-carbonitrile [D086]

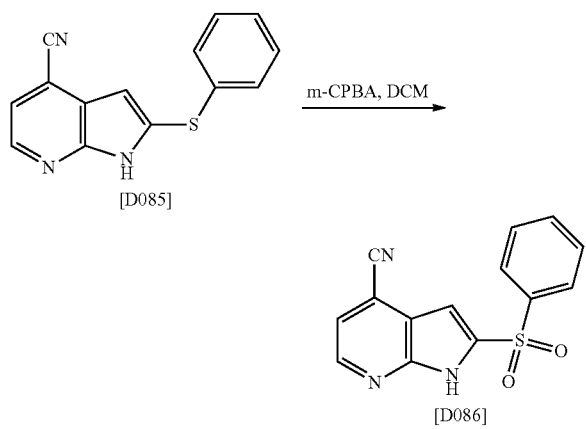

A solution of 2-phenylsulfanyl-1H-pyrrolo[2,3-b]pyridine-4-carbonitrile [D086, prepared according to scheme D5] (0.5 g, 1.99 mmol) in $CH_2Cl_2$ (20 mL) was prepared and cooled to 0° C. mCPBA (0.46 g, 1.99 mmol) was added and the reaction mixture stirred at 0° C. for 2 h. A further portion of mCPBA (0.46 g, 1.99 mmol) was added and stirring continued for a further 3 h. A further 5 mol % mCPBA was added and the reaction mixture stirred overnight at room temperature followed by a further 5 mol % mCPBA. The reaction mixture was stirred at room temperature for 2 h then filtered and the precipitate washed with $CH_2Cl_2$ and dried under vacuum. The precipitate was triturated in diethyl ether to give 2-(benzenesulfonyl)-1H-pyrrolo[2,3-b]pyridine-4-carbonitrile (0.445 g, 75%) as an off-white solid. LCMS method 6 (RT=3.67 min, MI+1=284): $^1$H NMR (500 MHz, d6-DMSO) 13.81 (1H, s), 8.66 (1H, d, J=4.8 Hz), 8.12-8.10 (2H, m), 7.76-7.74 (2H, m), 7.69-7.66 (2H, m), 7.37 (1H, s).

General Synthesis of 5-Cyclopropyl-2-(2-arylamino-pyridin-4-yl)-pyrido[3,4-d]pyrimidin-4-ylamine Derivatives of General Formula [1068] Scheme D15

The 5-cyclopropyl-2-(2-arylamino-pyridin-4-yl)-pyrido[3,4-d]pyrimidin-4-ylamine derivatives of general formula [I-068] were prepared by the reaction of a 2-(2-chloro-pyridin-4-yl)-5-cyclopropyl-pyrido[3,4-d]pyrimidin-4-ylamine derivative of general formula [I-066], prepared in scheme B4, in a Buchwald type reaction with sodium isocyanate, a palladium catalyst such as $Pd_2(dba)_3$ a ligand such as t-BuBrettPhos, a base such as $Et_3N$, in a polar protic solvent such as t-BuOH at high temperature either by heating thermally or using a microwave reactor. After reaction work up, typically by a liquid-liquid extraction the crude reaction mixture was purified by column chromatography and the intermediate was reacted with a strong acid such as TFA in a solvent such as DCM to yield the intermediate of general formula [I-067], that was reacted in a Buchwald type reaction with a palladium catalyst such as $Pd(OAc)_2$, a ligand such as Xantphos a base such as $Cs_2CO_3$ in a polar solvent such as 1,4-dioxane with a halo aromatic derivative of general formula [I-069] at high temperature either by heating thermally or using a microwave reactor. After reaction work up, typically by a liquid-liquid extraction the crude reaction mixture was purified by column chromatography and the reaction product subjected to a hydrogenolysis reaction with in a polar protic solvent such as methanol a palladium catalyst such as palladium on activated charcoal under a atmosphere of hydrogen gas, to yield 5-cyclopropyl-2-(2-arylamino-pyridin-4-yl)-pyrido[3,4-d]pyrimidin-4-ylamine derivatives of general formula [I-068].

Scheme D15

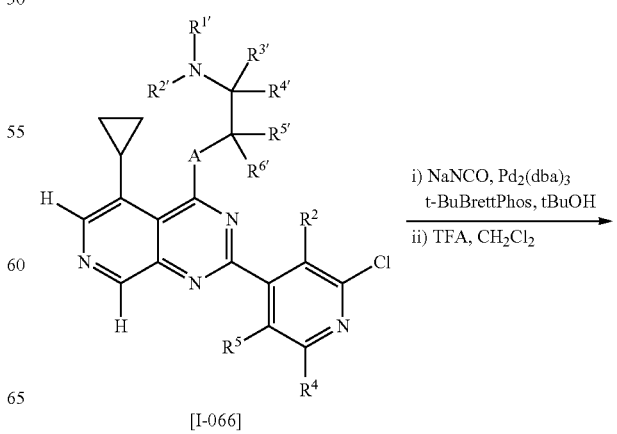

127

-continued

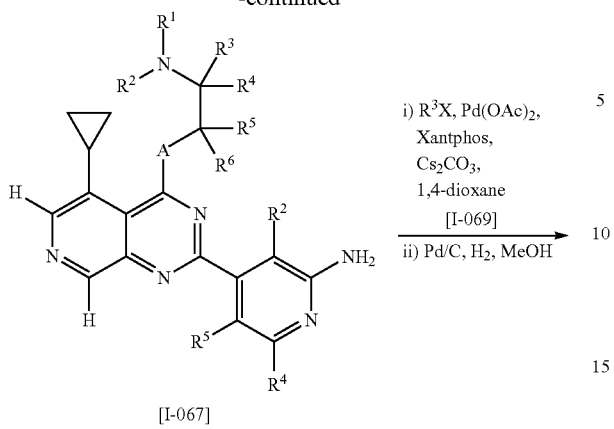

Synthesis of 4-(5-Cyclopropyl-4-piperazin-1-yl-pyrido[3,4-d]pyrimidin-2-yl)-N-[4-(oxetan-3-yl)phenyl]pyridin-2-amine [2454]

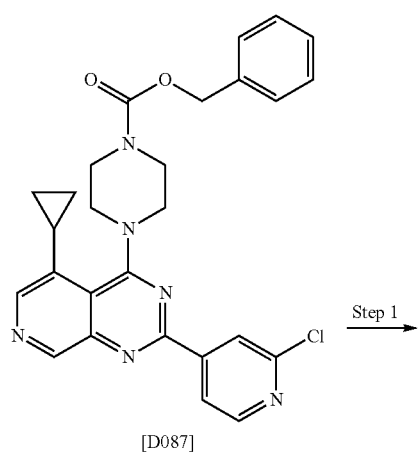

128

-continued

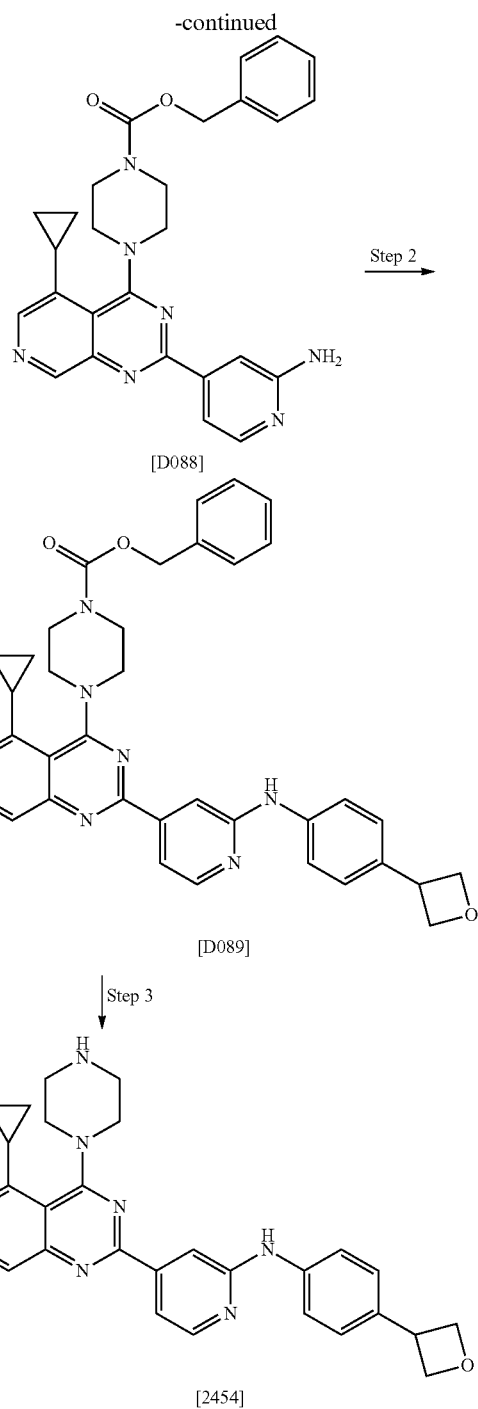

Step 1: Synthesis of Benzyl 4-[2-(2-amino-4-pyridyl)-5-cyclopropyl-pyrido[3,4-d]pyrimidin-4-yl]piperazine-1-carboxylate [D088]

An oven dried microwave vial, which was equipped with a magnetic stirrer bar and fitted with a re-sealable screwcap septum, was charged with sodium isocyanate (0.26 g, 3.99 mmol), benzyl 4-[2-(2-chloro-4-pyridyl)-5-cyclopropyl-pyrido[3,4-d]pyrimidin-4-yl]piperazine-1-carboxylate [D087, prepared according to scheme??] (1 g, 2 mmol), Pd$_2$(dba)$_3$ (91.4 mg, 0.10 mmol), and tBu Brett-phos (96.7 mg, 0.20 mmol). The tube was evacuated and backfilled with nitrogen three times and tert-butanol (5 mL) was added via syringe. The re-sealable screwcap septum was replaced with an unpunctured septum under continuous nitrogen flow and the solution was heated to 100° C. for 18 hours. The reaction mixture was allowed to cool to room temperature, and was then filtered through a pad of celite, washing with excess EtOAc. The crude product was purified by flash chromatography to afford the Boc-protected amino derivative which was stirred at room temperature in a 50% TFA/DCM solution for 2 hours. The free amine was purified by SCX-2 ion exchange to afford benzyl 4-[2-(2-amino-4-pyridyl)-5-cyclopropyl-pyrido[3,4-d]pyrimidin-4-yl]piperazine-1-carboxylate as a pale yellow solid (0.821 g, 85%). LCMS method 6 RT: 2.74 min, MI: 482 (MH)+.

Step 2: Synthesis of Benzyl 4-[5-cyclopropyl-2-[2-[4-(oxetan-3-yl)anilino]-4-pyridyl]pyrido[3,4-d]pyrimidin-4-yl]piperazine-1-carboxylate [D089]

Benzyl 4-[2-(2-amino-4-pyridyl)-5-cyclopropyl-pyrido[3,4-d]pyrimidin-4-yl]piperazine-1-carboxylate [D088] (0.25 g, 0.520 mmol), 3-(4-bromophenyl)oxetane (0.22 g, 1.04 mmol), Pd(OAc)$_2$ (5.83 mg, 0.030 mmol), xantphos (30.04 mg, 0.050 mmol) and caesium carbonate (0.34 g, 1.04 mmol) were all combined into a 2.5 mL biotage microwave vial which was flushed with nitrogen and capped tightly with a screw cap septum. 1,4-Dioxane (1.25 mL) was added and the mixture was stirred at 95° C. for 18 hours. The reaction mixture was taken up in dichloromethane and washed with brine. The layers were separated and the organic layer dried over anhydrous magnesium sulphate, filtered and concentrated under reduced pressure. The crude oil obtained was purified by chromatography eluting with 5-10% dichloromethane/methanol to afford benzyl 4-[5-cyclopropyl-2-[2-[4-(oxetan-3-yl)anilino]-4-pyridyl]pyrido[3,4-d]pyrimidin-4-yl]piperazine-1-carboxylate (0.221 g, 69%). LCMS method 6 RT: 4.31 min, MI: 614 (MH)+.

Step 3: Synthesis of 4-(5-Cyclopropyl-4-piperazin-1-yl-pyrido[3,4-d]pyrimidin-2-yl)-N-[4-(oxetan-3-yl)phenyl]pyridin-2-amine [2454]

A solution of benzyl 4-[5-cyclopropyl-2-[2-[4-(oxetan-3-yl)anilino]-4-pyridyl]pyrido[3,4-d]pyrimidin-4-yl]piperazine-1-carboxylate [D089] (0.22 g, 0.360 mmol), dissolved in methanol (20 mL) was passed through the H-Cube hydrogenation reactor at 50° C., 80 bar for 2 hours (continuous flow). The solvent was removed by reduced pressure and the oil obtained was purified by chromatography to afford 4-(5-cyclopropyl-4-piperazin-1-yl-pyrido[3,4-d]pyrimidin-2-yl)-N-[4-(oxetan-3-yl)phenyl]pyridin-2-amine (0.051 g, 29.7%). LCMS method 6 RT: 2.02 min, MI: 480 (MH)+. $^1$H NMR (500 MHz, DMSO) 9.34 (1H, s), 8.96 (1H, s), 8.31 (1H, d), 8.09 (1H, s), 7.91 (1H, s), 7.76 (2H, d), 7.67 (1H, dd), 7.33 (2H, m), 4.92 (2H, m), 4.61 (2H, m), 4.19 (1H, m), 3.17 (4H, m), 2.86 (4H, s), 2.62 (1H, m), 1.26 (2H, m), 1.03 (2H, m).

The synthesis of analogues containing a 2-methyl-8H-1,3a,7,8-tetraaza-cyclopent[a]indene moiety can be found in Scheme D17. A compound of formula [J001] can be benzylated and reduced to give compounds of formula [J003]. Cyclization with cyanogens bromide yield compounds of formula [J004]. Another ring cyclization with bromoacetone provides compounds of formula [J005]. A sequence similar to that described in Schemes D4 provides the nitrile [J006] and amidine [J007]. And a sequence similar to that described in Scheme D3 provides [J010] which can be deprotected to give Example 3. The synthesis of Example 3 is described in detail below.

Scheme [D17]

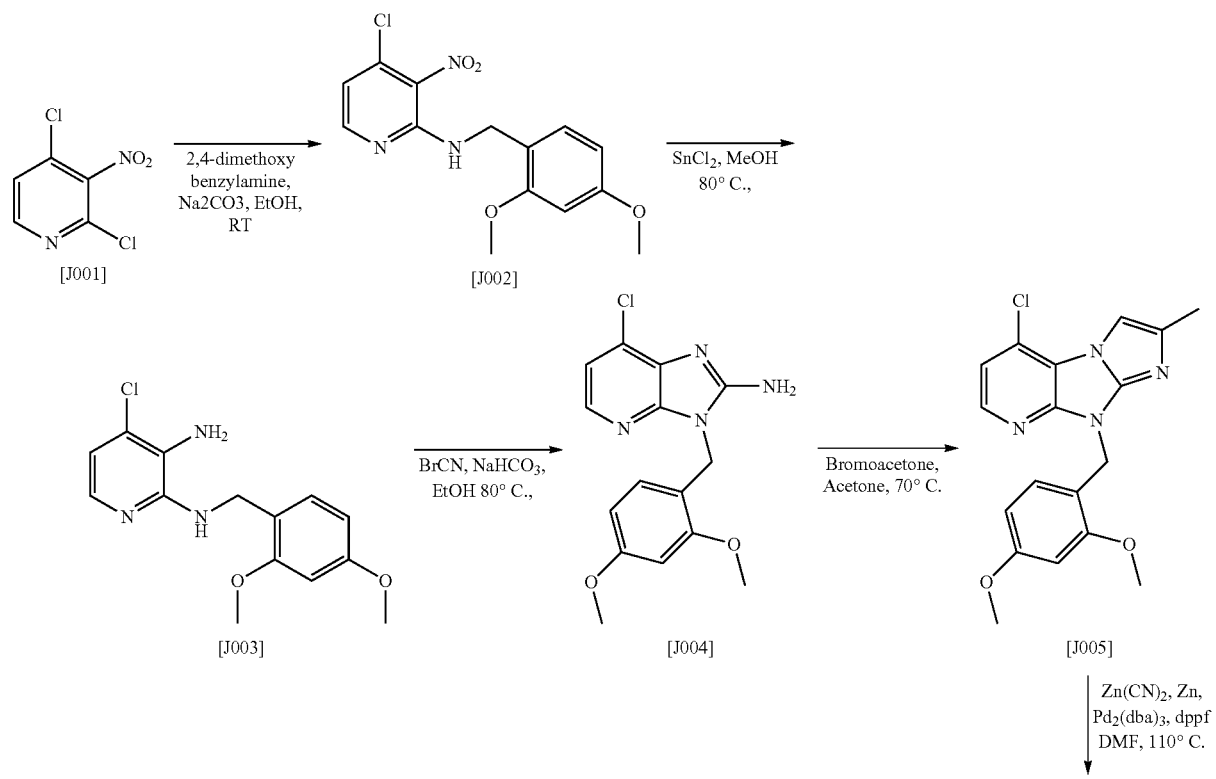

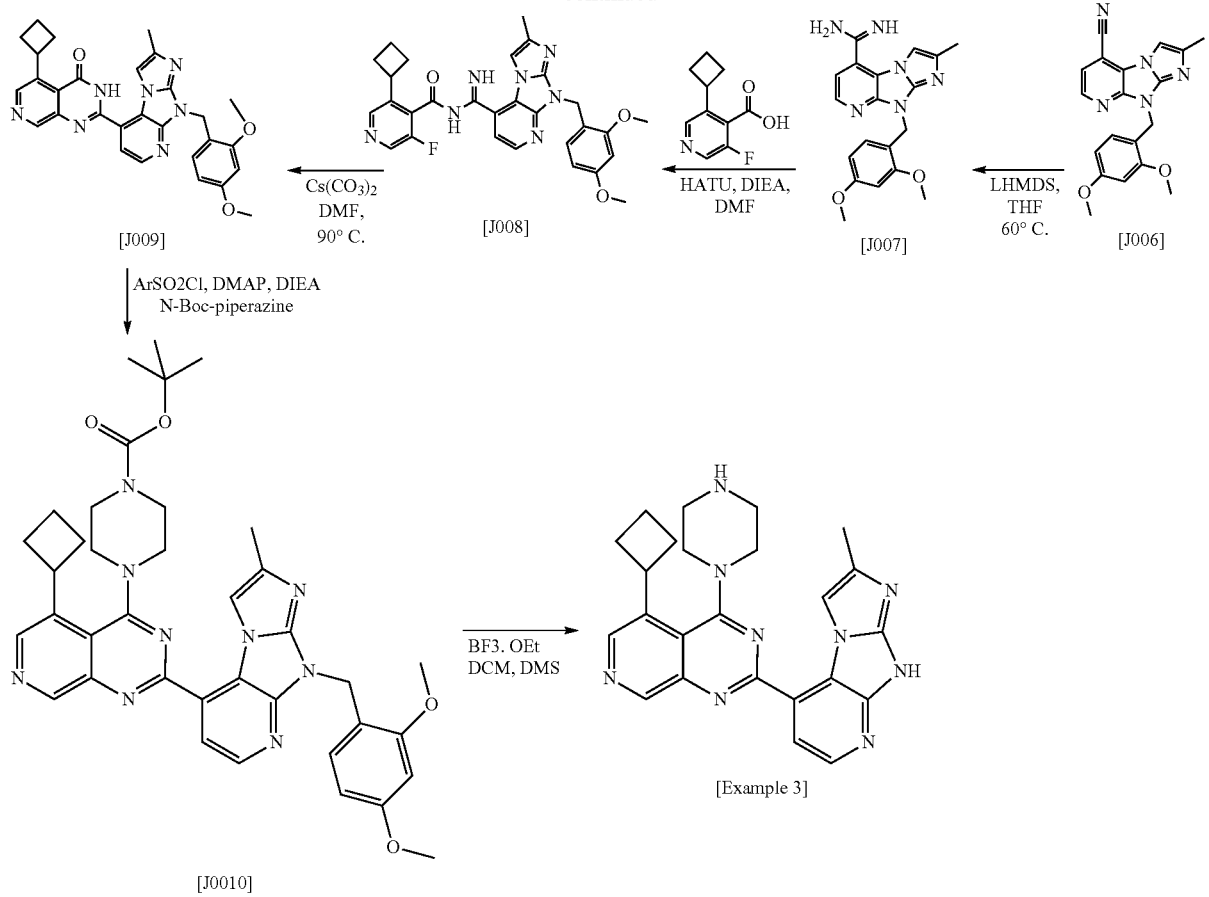

[Example 3]

4-Chloro-3-nitro-pyridin-2-yl)-(2,4-dimethoxy-benzyl [1J002]

To the 2,4-dichloro-3-nitropyridine (8.2 g, 42 mmol) in 200 mL of methanol was added the sodium carbonate (9.01 g, 85.0 mmol), followed by the 2,4-dimethoxybenzyl amine (7.81 g, 46.7 mmol) and stirred at room temp for 18 h. The reaction mixture was concentrated and the crude extracted with EtOAc. The ethylacetate layer was washed with water, brine and dried over anhydrous sodium sulfate, filtered and concentrated. The crude was chromatographed on 330 g ISCO silica gel column using a gradient of Hexane:EtOAc (0-30%) to give 9.9 g of the compound [J002] (72% yield).

4-Chloro-N(2)-(2,4-dimethoxy-benzyl)-pyridine-2,3-diamine [J003]

To [J002] (4-Chloro-3-nitro-pyridin-2-yl)-(2,4-dimethoxy-benzyl)-amine (9.9 g, 30.6 mmol) in 100 mL of methanol was added the tin chloride dihydrate (14.0 g, 61 mmol) and heated at 80° C. for 5 h. The methanol was removed under reduced pressure and the residue suspended in ethyl acetate. The reaction was quenched with saturated bicarbonate, and organic layer separated. The EtOAc layer was washed with water, brine and dried over anhy.Na2SO4, filtered and concentrated. The crude was chromatographed on Isco 220 g column using 10:1 DCM:MeOH gradient to give 3.7 g of pure material [J003] in 41% yield.

7-Chloro-3-(2,4-dimethoxy-benzyl)-3H-imidazo[4,5-b]pyridin-2-ylamine [J004]

To [J003] 4-Chloro-N(2)-(2,4-dimethoxy-benzyl)-pyridine-2,3-diamine (3.2 g, 5.8 mmol) in 200 mL of ethanol was added the sodium bicarbonate (3.29 g, 19.8 mmol) and cooled to 0° C. To this was added a solution of the cyanogen bromide (2.08 g, 19.8 mmol) in 5.0 mL of anhydrous DCM and the reaction was stirred at room temp for 8 h and then heated at 80° C. for 8 h. After 8 h heating, the reaction mixture was cooled to room temperature and another aliquot of sodium bicarbonate (19.8 mmol) and cyanogen bromide (19.8 mmol) in 5 mL of DCM was added. The reaction was heated at 80° C. for additional 14 h. The reaction mixture was concentrated and the crude extracted with DCM, washed with water, brine and dried over anhy. sodium sulfate. The organic layer was filtered, concentrated and the crude was triturated with DCM to give 1.42 g of the solid [J004] in 41% yield. $^1$H NMR (CDCl$_3$): δ 8.01 (d, J=5.36 Hz, 1H), 7.17-7.12 (m, 2H), 6.49-6.21 (m, 2H), 5.02 (s, 2H), 3.862 (s, 3H), 3.79 (s, 3H).

4-Chloro-8-(2,4-dimethoxy-benzyl)-2-methyl-8H-1,3a,7,8-tetraaza-cyclopent[a]indene [J005]

To [J004] 7-Chloro-3-(2,4-dimethoxy-benzyl)-3H-imidazo[4,5-b]pyridin-2-ylamine (0.80 g, 2.0 mmol) in 80 mL of acetone was added the bromoacetone (2.4 g, 18 mmol) and the solution was heated at 65° C. for 16 h. The reaction mixture was concentrated and the crude was chromatographed on a 40 g ISCO silica gel column using 10:1 DCM:MeOH to give the 0.39 g of product [J005]. $^1$H NMR (400 MHz, CDCl$_3$) δ ppm 8.12 (1H, d, J=5.5 Hz) 7.38 (1H, d, J=1.3 Hz) 7.29 (1H, d, J=8.3 Hz) 7.18 (1H, d, J=5.5 Hz) 6.44 (2H, d, J=1.8 Hz) 3.73-3.81 (4H, m) 3.80 (9H, d, J=18.1 Hz) 2.41 (3H, d, J=1.0 Hz).

8-(2,4-Dimethoxy-benzyl)-2-methyl-8H-1,3a,7,8-tetraaza-cyclopent[a]indene-4-carbonitrile [J006]

To [J005] 4-Chloro-8-(2,4-dimethoxy-benzyl)-2-methyl-8H-1,3a,7,8-tetraaza-cyclopent[a]indene (0.25 g, 0.70 mmol), Zinc Cyanide (0.14 g, 1.2 mmol), Zinc (0.018 g, 0.28 mmol), Tris(dibenzylideneacetone)dipalladium(0) (0.019 g, 0.021 mmol) and 1,1'-Bis(diphenylphosphino)ferrocene (0.012 g, 0.021 mmol) was added 10 mL of anhydrous DMF. The reaction mixture was sparged with argon and heated at 110° C. for 3 h. The reaction mixture was cooled to room temperature, diluted with 100 mL of EtOAc, and washed with water, brine and dried. The crude was chromatographed on 40 g silica gel Isco column using 10:1 DCM:MeOH to give 110 mg of pure product [J006]. $^1$H NMR (400 MHz, CDCl3) δ 8.41 (d, J=5.52 Hz, 1H), 7.46 (d, J=1.12 Hz, 1H), 7.40 (d, J=5.52 Hz, 1H), 7.35 (d, J=8.96 Hz, 1H), 6.46-6.44 (m, 2H), 5.32 (s, 2H), 3.81 (s, 3H), 3.78 (s, 3H), 2.42 (d, J=1.04 Hz, 3H).

8-(2,4-Dimethoxy-benzyl)-2-methyl-8H-1,3a,7,8-tetraaza-cyclopent[a]indene-4-carboxamidine [J007]

To [J006] 8-(2,4-Dimethoxy-benzyl)-2-methyl-8H-1,3a,7,8-tetraaza-cyclopent[a]indene-4-carbonitrile (0.13 g, 0.37 mmol) in 10 mL of anhydrous THF was added the 1.0 M solution of lithium hexamethylsilazide in THF (1.5 mL, 1.5 mmol). The reaction was heated at 50° C. for 8 h and then cooled to room temperature and stirred overnight. The reaction was quenched with water, extracted with EtOAc, dried, filtered and used with out further purification.

3-Cyclobutyl-N-{[8-(2,4-dimethoxy-benzyl)-2-methyl-8H-1,3a,7,8-tetraaza-cyclopent[a]inden-4-yl]-imino-methyl}-5-fluoro-isonicotinamide [J008]

To a mixture of 3-Cyclobutyl-5-fluoro-isonicotinic acid (0.07 g, 0.36 mmol) in 6 mL of anhydrous DMF was added the DIEA (0.14 g, 1.1 mmol), followed by the HATU (0.14 g, 0.36 mmol) and stirred at room temperature for 1 hour. To the reaction mixture was added [J007] 8-(2,4-Dimethoxy-benzyl)-2-methyl-8H-1,3a,7,8-tetraaza-cyclopent[a]indene-4-carboxamidine (0.13 g, 0.36 mmol) and stirred for 18 hours. The reaction mixture was diluted with water (10 mL) and then extracted with DCM, the organic layer was separated, washed with water, brine and dried over anhydrous sodium sulfate. The DCM layer was filtered, concentrated and the crude was chromatographed on silica gel using 10:1 DCM:MeOH to give the 0.12 g of pure amide [J008] in 62% yield. 1H NMR (400 MHz, CDCl$_3$) δ ppm 10.46 (1H, br. s.) 9.07 (1H, br. s.) 8.48 (3H, d, J=19.3 Hz) 8.37 (1H, d, J=5.3 Hz) 7.58 (1H, d, J=1.3 Hz) 7.35-7.36 (1H, m) 7.43 (2H, d, J=5.3 Hz) 6.31-6.48 (3H, m) 5.26-5.29 (1H, m) 5.35 (3H, s) 3.70-3.89 (10H, m) 2.19-2.35 (6H, m) 2.07 (4H, d, J=1.3 Hz) 1.15-1.36 (3H, m).

5-Cyclobutyl-2-[8-(2,4-dimethoxy-benzyl)-2-methyl-8H-1,3a,7,8-tetraaza-cyclopent[a]inden-4-yl]-3H-pyrido[3,4-d]pyrimidin-4-one [J009]

To a solution of [J008] 3-Cyclobutyl-N-{[8-(2,4-dimethoxy-benzyl)-2-methyl-8H-1,3a,7,8-tetraaza-cyclopent[a]inden-4-yl]-imino-methyl}-5-fluoro-isonicotinamide (0.12 g, 0.22 mmol) in 4 mL of DMF was added the cesium carbonate (0.076 g, 0.23 mmol) and the mixture heated at 90° C. for 6 h. The mixture was cooled to room temperature and saturated aqueous ammonium chloride 10 mL was added. The reaction mixture was extracted with DCM, washed with water brine and dried over anhy sodium sulfate. The DCM layer was filtered, concentrated and the crude chromatographed on a 12 g Isco column using 10:1 DCM: MeOH to give 80 mg of product [J009] in 70% yield. $^1$H NMR (400 MHz, CDCl$_3$) δ ppm 11.15 (1H, br. s.) 9.24 (1H, s) 8.72 (1H, s) 8.48 (1H, d, J=1.0 Hz) 8.40 (2H, d, J=5.3 Hz) 7.44 (1H, d, J=5.5 Hz) 7.30 (4H, d, J=8.5 Hz) 6.34-6.50 (3H, m) 3.72-3.89 (10H, m) 1.77-2.65 (15H, m) 1.17-1.35 (4H, m).

4-(5-Cyclobutyl-4-piperazin-1-yl-pyrido[3,4-d]pyrimidin-2-yl)-2-methyl-8H-1,3a,7,8-tetraaza-cyclopent[a]indene [J010]

To [J009] 5-Cyclobutyl-2-[8-(2,4-dimethoxy-benzyl)-2-methyl-8H-1,3a,7,8-tetraaza-cyclopent[a]inden-4-yl]-3H-pyrido[3,4-d]pyrimidin-4-one (0.05 g, 0.1 mmol) in 2.0 mL of DMF was added the DMAP (1 mg, 0.009 mmol), TEA (0.036 mL, 0.26 mmol) and the 2,4,6-triisopropylbenzenesulfonyl chloride (0.029 g, 0.0961 mmol) and stirred at room temp for 1 h. To the reaction mixture was added the 1-N Boc piperazine [A] (0.018 g, 0.096 mmol) and stirred at room temp for 3 h. The LC/MS showed formation of product, the reaction was allowed to stir at room temp for 18 h. The reaction mixture was diluted with 30 mL of DCM, washed with water, brine and dried over anhy sodium sulfate. The DCM layer was filtered, concentrated and the crude was chromatographed on silica gel using 10:1 DCM:MeOH to give 0.02 g of product [J010]. $^1$H NMR (400 MHz, CDCl$_3$) δ ppm 9.32 (s, 1H) 8.74 (s, 1H) 8.53 (d, J=5.52 Hz, 1H) 7.58 (d, J=1.00 Hz, 1H) 7.34 (d, J=5.52 Hz, 1H) 7.22-7.30 (m, 3H) 6.37-6.50 (m, 2H) 5.38 (s, 2H) 3.86 (s, 3H) 3.78 (bs, 5H) 3.58 (br. s, 5H) 2.46-2.60 (m, 2H) 2.40 (s, 3H) 1.94-2.34 (m, 5H) 1.82-1.59 (m. 3H) 1.49 (s, 9H) 1.19-1.33 (m, 3H)

4-(5-Cyclobutyl-4-piperazin-1-yl-pyrido[3,4-d]pyrimidin-2-yl)-2-methyl-8H-1,3a,7,8-tetraaza-cyclopent[a]indene Example 3

To [J010] 4-{5-Cyclobutyl-2-[8-(2,4-dimethoxy-benzyl)-2-methyl-8H-1,3a,7,8-tetraaza-cyclopent[a]inden-4-yl]-pyrido[3,4-d]pyrimidin-4-yl}-piperazine-1-carboxylic acid tert-butyl ester (0.02 g, 0.03 mmol) in 2 mL of DCM and 1 mL of dimethyl sulfide at 0° C. was added the boron trifluoride etherate (0.02 mL) dropwise and stirred for 18 h. The reaction mixture was concentrated under vacuum and the crude was chromatographed on the C-18 reverse phase HPLC column, using 10-50% acetonitrile in water at 50 mL/min to give 5 mg of the title compound. $^1$H NMR (400 MHz, CD$_3$OD) δ ppm 9.50 (1H, s) 8.90 (1H, s) 8.78 (1H, d, J=1.3 Hz) 8.56 (1H, d, J=6.8 Hz) 8.03 (1H, d, J=6.8 Hz) 4.36 (3H, t, J=8.3 Hz) 4.01-4.18 (2H, m) 3.45-3.59 (3H, m) 2.53-2.72 (5H, m) 2.21-2.41 (3H, m) 2.07 (1H, t, J=7.5 Hz).

The synthesis of analogues containing a 9H-dipyrido[2,3-b;3',2'-d]pyrrole moiety can be found in Scheme D18. A compound of formula [J012] can be synthesized via Pd-catalyzed amination/cyclization from compounds of formula [J011] and an aminopyridine. A sequence similar to that described in Scheme D4 provides [J016] which can be taken on using a sequence similar to that described in Scheme [D3] to give Example 145 (and other). The synthesis of Example 145 is described in detail below.

Scheme [D18]

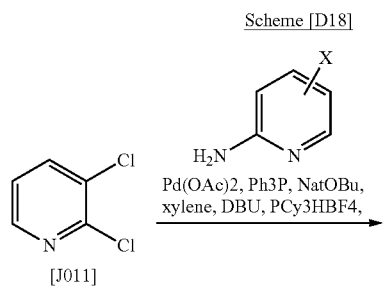

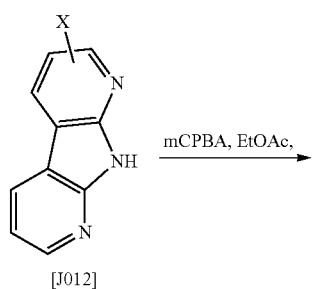

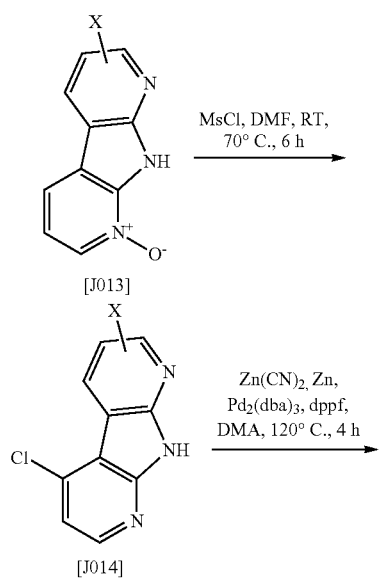

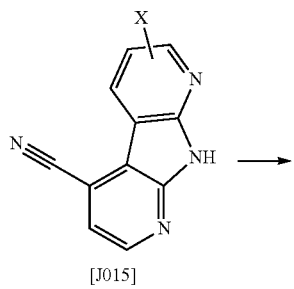

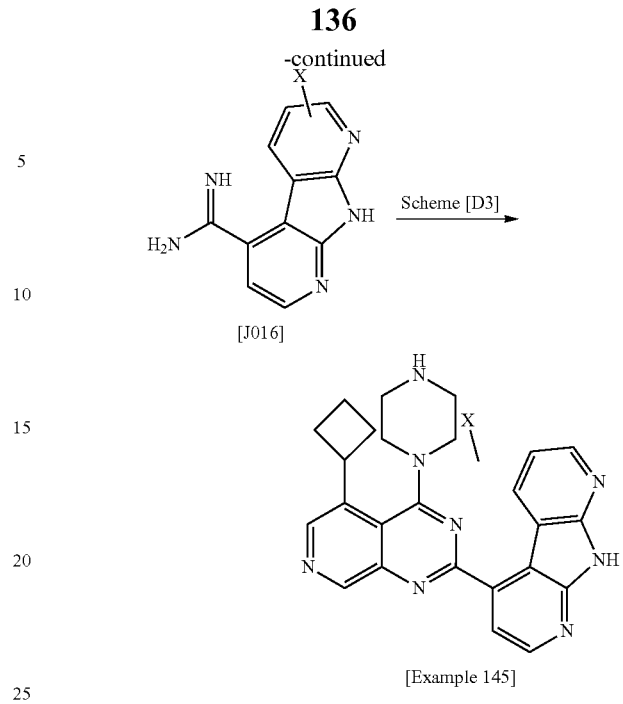

Example 145. 5-(5-Cyclobutyl-4-piperazin-1-yl-pyrido[3,4-d]pyrimidin-2-yl)-3-fluoro-9H-dipyrido[2,3-b;3',2'-d]pyrrole 145a) To a solution of 2,3-dichloropyridine (0.5 g, 3.38 mmol) and 2-amino-5-fluoropyridine (0.45 g, 4.0 mmol) in xylene was added NaOtBu (0.38 g, 4.0 mmol), PPh3 (0.088 g, 0.3 mmol) and the mixture was degassed with Argon. Palladium acetate (0.037 g, 0.16 mmol) was added to reaction mixture which was then heated at 120° C. for 4 h. The reaction mixture was cooled to rt and DMF was added to reaction mixture followed by DBU (1.0 g, 6.7 mmol) and Cy3P.HBF4 (0.12 g, 0.3 mmol) and the mixture was degassed with argon. Palladium acetate (0.037 g, 0.16 mmol) was added to reaction mixture which was heated at 150° C. for 15 h. Reaction was quenched with water and extracted with ethyl acetate. Organic layer was washed with water and then brine solution, dried over sodium sulfate and concentrated. The residue was purified by silica gel column chromatography to afford 3-Fluoro-9H-dipyrido[2,3-b;3',2'-d]pyrrole (0.2 g).

145b) To a stirred solution of 3-Fluoro-9H-dipyrido[2,3-b;3',2'-d]pyrrole (0.1 g, 0.53 mmol) in EtOAc (100 mL), mCPBA (0.135 g, 0.79 mmol) was added at 0° C. and the reaction mixture was stirred at rt for 6 h. The reaction mixture was evaporated and the residue was triturated with ether and then with pentane to afford 3-Fluoro-9H-dipyrido [2,3-b;3',2'-d]pyrrole 8-oxide (60 mg).

145c) A mixture of 3-Fluoro-9H-dipyrido[2,3-b;3',2'-d]pyrrole 8-oxide (60 mg, 0.29 mmol), methanesulfonyl chloride (0.1 mL, 1.4 mmol) in DMF (1 mL) was heated at 60° C. for 4 h. After complete consumption of starting material, reaction was cooled and quenched with ice water. Precipitate formed was filtered, dried, and triturated with diethyl ether to provide 5-Chloro-3-fluoro-9H-dipyrido[2,3-b;3',2'-d]pyrrole as white solid (25 mg).

145d) To a solution of 5-Chloro-3-fluoro-9H-dipyrido[2,3-b;3',2'-d]pyrrole (0.2 g, 0.9 mmol) in anhydrous DMA (5 mL) was added Zinc cyanide (63 mg, 0.54 mmol), activated zinc dust (5.8 mg, 0.09 mmol) and reaction mixture was degassed by argon for 20 min. Dichloro[1,1'-bis(diphenylphosphino)ferrocene] palladium(II) dichloromethane adduct (19 mg, 0.02 mmol) and Pd2(dba)3 (16 mg, 0.018 mmol) were added to the reaction mixture which was then heated to 120° C. for 2 h. The mixture was cooled to rt, water was added and the precipitate formed was filtered and dried. The crude solid was dissolved in ethyl acetate. Solvent was evaporated and the residue was triturated with diethyl ether to afford 6-Fluoro-9H-dipyrido[2,3-b;3',2'-d]pyrrole-4-carbonitrile (110 mg).

145e) A stirred suspension of 6-Fluoro-9H-dipyrido[2,3-b:3',2'-d]pyrrole-4-carbonitrile (0.9092 g, 4.285 mmol) in 1.0 M of Sodium hexamethyldisilazane in Tetrahydrofuran (18.0 mL, 18.0 mmol) under an atmosphere of Nitrogen was heated at 50° C. The reaction mixture was heated over weekend then cooled to room temperature. The volatiles were evaporated and the residue was suspended in water (50 mL) and stirred. The solid was filtered and washed with water. The aqueous filtrate was evaporated under reduced pressure to dryness. 6-Fluoro-9H-dipyrido[2,3-b:3',2'-d]pyrrole-4-carboxamidine was isolated as an orange-brown foam (0.98 g) and was used without further purification. $^1$H NMR (400 MHz, d6-DMSO, δ): 8.43 (s, 1H), 8.29 (d, J=4.8 Hz, 1H), 8.24-8.18 (m, 2H), 8.10 (dd, J=10.0, 3.0 Hz, 1H), 6.69 (d, J=4.8 Hz, 1H), 6.43 (br s, 2H). LC/MS=229.95 (MH)+.

145f) Intermediate 3-Cyclobutyl-5-fluoro-N-[(6-fluoro-9H-dipyrido[2,3-b:3',2'-d]pyrrol-4-yl)-imino-methyl]-isonicotinamide was prepared from 3-Cyclobutyl-5-fluoro-isonicotinic acid (0.58 g, 3.0 mmol) and 6-Fluoro-9H-dipyrido[2,3-b:3',2'-d]pyrrole-4-carboxamidine (0.98 g, 4.3 mmol) in an analogous manner previously described. Product was isolated as a light gray solid (0.809 g) used without further purification. $^1$H NMR (400 MHz, d6-DMSO, δ): 10.23 (br s, 1H), 8.65 (d, J=5.0 Hz, 1H), 8.53-8.46 (m, 3H), 8.36-8.31 (m, 1H), 7.52-7.48 (m, 1H), 3.73-3.63 (m, 1H), 2.27-2.13 (m, 3H), 1.99-1.72 (m, 2H). LC/MS=407.04 (MH)+.

5-Cyclobutyl-2-(6-fluoro-9H-dipyrido[2,3-b:3',2'-d]pyrrol-4-yl)-3H-pyrido[3,4-d]pyrimidin-4-one was prepared from 3-Cyclobutyl-5-fluoro-N-[(6-fluoro-9H-dipyrido[2,3-b:3',2'-d]pyrrol-4-yl)-imino-methyl]-isonicotinamide and Cesium Carbonate (2.0 g, 6.0 mmol) in an analogous manner previously described. Product was isolated as a brown solid (1.2 g) and was used without further purification. $^1$H NMR (400 MHz, d6-DMSO, δ): 12.84 (br s, 1H), 8.98 (s, 1H), 8.74-8.67 (m, 2H), 8.57 (s, 1H), 8.52-8.45 (m, 1H), 7.67-7.20 (m, 2H), 4.70-4.60 (m, 1H), 2.52-2.42 (m, 2H), 2.36-2.20 (m, 2H), 2.10-2.00 (m, 1H), 1.90-1.80 (m, 1H). LC/MS=387.04 (MH)+.

145g) 5-(5-Cyclobutyl-4-piperazin-1-yl-pyrido[3,4-d]pyrimidin-2-yl)-3-fluoro-9H-dipyrido[2,3-b:3',2'-d]pyrrole was prepared from 5-Cyclobutyl-2-(6-fluoro-9H-dipyrido[2,3-b:3',2'-d]pyrrol-4-yl)-3H-pyrido[3,4-d]pyrimidin-4-one (100.0 mg, 0.2588 mmol), 2,4,6-Triisopropylbenzenesulfonyl Chloride (71.0 mg, 0.234 mmol) and tert-Butyl 1-Piperazinecarboxylate (48.0 mg, 0.258 mmol) then Trifluoroacetic Acid (1 mL, 10 mmol) in an analogous manner previous described. 5-(5-Cyclobutyl-4-piperazin-1-yl-pyrido[3,4-d]pyrimidin-2-yl)-3-fluoro-9H-dipyrido[2,3-b:3',2'-d]pyrrole (0.0129 g, 8%) was isolated as a yellow lyophilate as the trifluoroacetic acid salt. $^1$H NMR (400 MHz, d6-DMSO, δ): 12.81 (s, 1H), 9.27 (s, 1H), 9.23 (dd, J=10.3, 2.8 Hz, 1H), 8.95-8.80 (m, 2H), 8.72 (d, J=5.1 Hz, 1H), 8.58 (dd, J=2.8, 1.1 Hz, 1H), 8.12 (d, J=5.1 Hz, 1H), 4.35-4.25 (m, 1H), 3.95-3.77 (m, 4H), 3.40-3.20 (m, 4H), 2.55-2.45 (m, 2H), 2.33-2.22 (m, 2H), 2.20-2.07 (m, 1H), 2.00-1.90 (m, 1H). LC/MS=455.15 (MH)+.

The synthesis of analogues containing a 2,2,2-trifluoro-1-methyl-ethyl)-pyrido[3,4-d]pyrimidin-2-yl structure can be found in Scheme D19. A compound of formula [J017] is formed via Suzuki coupling of 3-Bromo-5-fluoro-isonicotinic acid tert-butyl ester. Reduction gives compounds of formula [J018] and acid-hydrolysis gives compounds of formula [J019], which can be taken on using a sequence similar to that described in Scheme [D3] to give Example 146 (and others). The synthesis of Example 146 is described in detail below.

Scheme [D19]

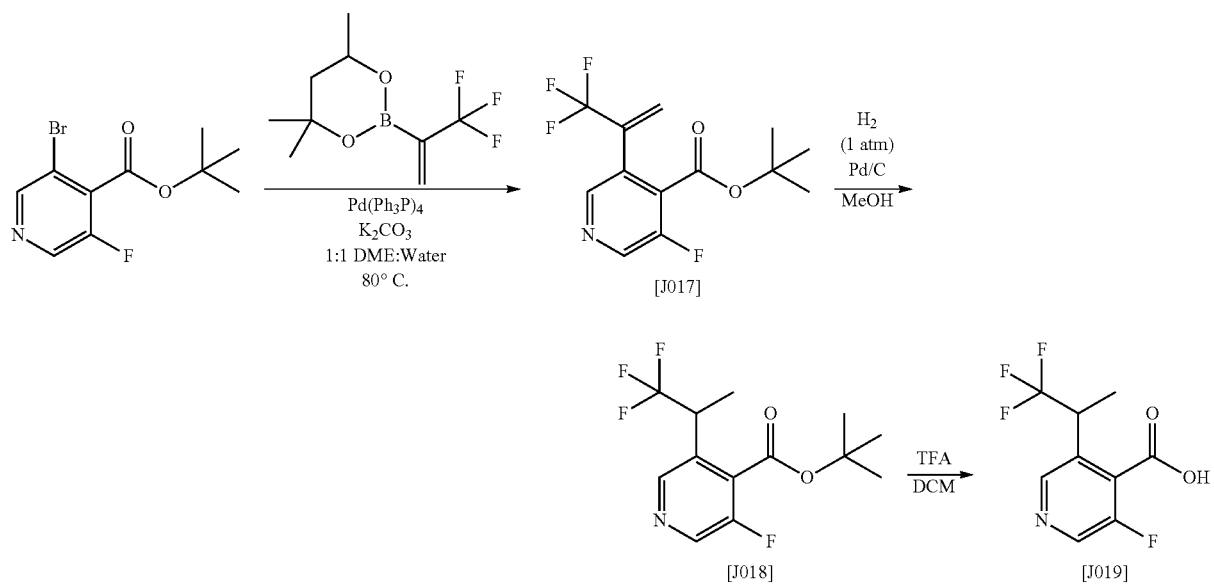

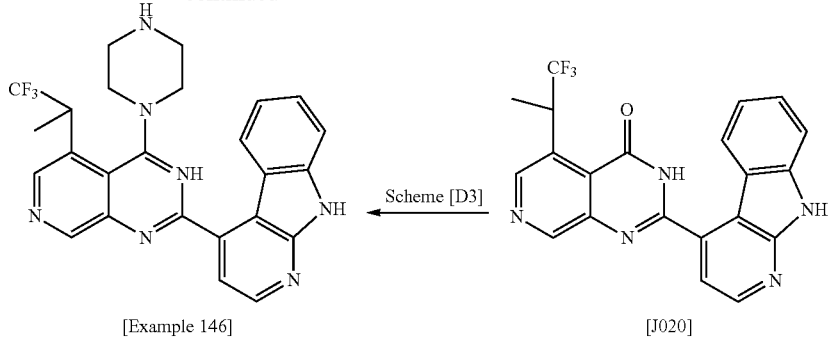

[Example 146]              [J020]

Example 146. 4-[4-Piperazin-1-yl-5-(2,2,2-trifluoro-1-methyl-ethyl)-pyrido[3,4-d]pyrimidin-2-yl]-9H-pyrido[2,3-b]indole 146a) To a solution of 3-Bromo-5-fluoro-isonicotinic acid tert-butyl ester (0.5 g, 1.8 mmol) and 4,4,6-Trimethyl-2-(1-trifluoromethyl-vinyl)-[1,3,2]dioxaborinane (0.486 g, 2.1 mmol) in 1,2-Dimethoxyethane:water (2:1) was added potassium carbonate (1 g, 7.2 mmol). The mixture was degassed with argon gas for 10 min followed by addition of Pd(PPh3)4 (0.104 g, 0.09 mmol) then reaction mixture was heated at 80° C. for 8 h. The reaction mixture was cooled to rt and filtered through diatomaceous earth. Water was added to filtrate and the mixture was extracted with ethyl acetate. The organic layer was washed with brine and dried over sodium sulfate and concentrated. The residue was purified by silica gel column chromatography to afford 3-Fluoro-5-(1-trifluoromethyl-vinyl)-isonicotinic acid tert-butyl ester (50 mg).

146b) To a stirred solution of 3-Fluoro-5-(1-trifluoromethyl-vinyl)-isonicotinic acid tert-butyl ester (0.1 g, 0.34 mmol) in methanol (10 mL) was added Pd/C and reaction was stirred under Hydrogen gas (1 atm) at rt for 3 h. The mixture was filtered through celite, washed with methanol, and the filtrate was concentrated to provide 3-Fluoro-5-(2,2,2-trifluoro-1-methyl-ethyl)-isonicotinic acid tert-butyl ester (80 mg).

146c) To a stirred solution of 3-Fluoro-5-(2,2,2-trifluoro-1-methyl-ethyl)-isonicotinic acid tert-butyl ester (0.08 g, 0.27 mmol) in DCM (1 mL) was added TFA (1 mL) and reaction was stirred at rt for 12 h. The reaction mixture was concentrated and azeotroped with DCM to provide a solid which was triturated with ether and n-pentane to provide 3-Fluoro-5-(2,2,2-trifluoro-1-methyl-ethyl)-isonicotinic acid (45 mg).

146d) A solution of 3-Fluoro-5-(2,2,2-trifluoro-1-methyl-ethyl)-isonicotinic acid (0.65 g, 2.7 mmol), N,N-Diisopropylethylamine (2.1 mL, 12 mmol) and N,N,N',N'-Tetramethyl-O-(7-azabenzotriazol-1-yl)uronium Hexafluorophosphate (1.1 g, 3.0 mmol) in N,N-Dimethylformamide (10 mL) was stirred at room temperature for 1 hour. 9H-Pyrido[2,3-b]indole-4-carboxamidine (0.52 g, 2.5 mmol) was added and the mixture was stirred overnight. The reaction was complete by LC/MS. Water (25 mL) was added. The mixture was stirred for 30 minutes and cooled in an ice-water bath. The resulting suspension was filtered, rinsed with water and dried by suction then under high vacuum for 4 hours. The recovered brown solid was consistent for desired intermediate and used without further purification. LC/MS=430.02 (MH)+.

The brown solid and Cesium Carbonate (1.6 g, 4.9 mmol) in N,N-Dimethylacetamide (10 mL) was heated at 90° C. overnight. The mixture was cooled to room temperature then in an ice-water bath. Water (10 mL) and saturated aqueous ammonium chloride (10 mL) was added. The mixture was stirred for 30 minutes. The resulting solid was filtered, rinsed with water and dried by suction. The solid was triturated with ethanol (25 mL) then filtered, rinsed with ethanol. The ethanolic filtrate was evaporated to dryness. Crude 2-(9H-Pyrido[2,3-b]indol-4-yl)-5-(2,2,2-trifluoro-1-methyl-ethyl)-3H-pyrido[3,4-d]pyrimidin-4-one (0.59 g) was isolated as a brown resin and was used without further purification. LC/MS=410.03 (MH)+.

146e) To a stirred suspension of crude 2-(9H-Pyrido[2,3-b]indol-4-yl)-5-(2,2,2-trifluoro-1-methyl-ethyl)-3H-pyrido[3,4-d]pyrimidin-4-one (100.0 mg, 0.2443 mmol), 4-Dimethylaminopyridine (1.0 mg, 0.0082 mmol) and N,N-Diisopropylethylamine (135.0 uL, 0.7750 mmol) in N,N-Dimethylformamide (1 mL, 10 mmol) was added 2,4,6-Triisopropylbenzenesulfonyl Chloride (60.0 mg, 0.198 mmol). The mixture was stirred for 2 hours. The reaction mixture was purified via silica gel chromatography (12 g, 0%→10% Methanol:Dichloromethane). The desired fractions were combined and evaporated. The recovered material was consistent for desired intermediate as a brown resin. The brown resin was dissolved in Methylene chloride (1 mL, 20 mmol) and Trifluoroacetic Acid (1 mL, 10 mmol) was added. The mixture was stirred at room temperature for 30 minutes. The volatiles were evaporated. The residue was purified via reverse phase chromatography (5%→50% Acetonitrile:Water with 0.1% TFA as modifier). The desired fractions were combined, frozen and lyophilized. 4-[4-Piperazin-1-yl-5-(2,2,2-trifluoro-1-methyl-ethyl)-pyrido[3,4-d]pyrimidin-2-yl]-9H-pyrido[2,3-b]indole (0.0546 g, 37%) was isolated as a yellow lyophilate as the trifluoroacetic acid salt. $^1$H NMR (400 MHz, d6-DMSO, δ): 12.12 (s, 1H), 9.48 (s, 1H), 8.94 (s, 1H), 8.93-8.70 (m, 2H), 8.62-8.57 (m, 2H), 7.92 (d, J=5.2 Hz, 1H), 7.56 (d, J=8.2 Hz, 1H), 7.52-7.47 (m, 1H), 7.21-7.16 (m, 1H), 4.81-4.71 (m, 1H), 4.20-3.08 (m, 8H), 1.86 (d, J=7.2 Hz, 3H). LC/MS=478.14 (MH)+.

Shown in Scheme [D20], Similar to Scheme [D19], compounds of formula [J023] can be synthesized and taken on to Example 215.

The synthesis of analogues containing a 1H-pyrrolo[2,3-b]pyridine-2-carboxylic acid amide structure can be found in Scheme D21. A compound of formula [J024] can be synthesized according to procedures found in Adams, Nicholas D. et al; J. Med. Chem. 2010, 53, 3973-4001. Oxidation, chlorination and cyanation gives compounds of [J027]; analogous procedures have been described herewithin. Base mediated hydrolysis gives compounds of formula [J028] and amide formation can be effected with standard HATU conditions to give compounds of formula [J029] which can be taken on using a sequence similar to that described in Scheme [D4] and [D3] to give Example 162 (and others).

A general synthesis of analogues containing a 1H-pyrrolo[2,3-b]pyridine-2-(hetero)aryl structure is described in Scheme D22. A 2-iodo compound of general formula [J030] can be converted to a compound of general formula [J031] by a Stille coupling with a reagent of general formula [J032]. [J031] can be converted using a sequence similar to that described in Schemes [D5] and [D3] to give Example 356 (and, similarly, Examples 362, 364, 365, 367, 369-372, 385, 395).

Scheme [D22]

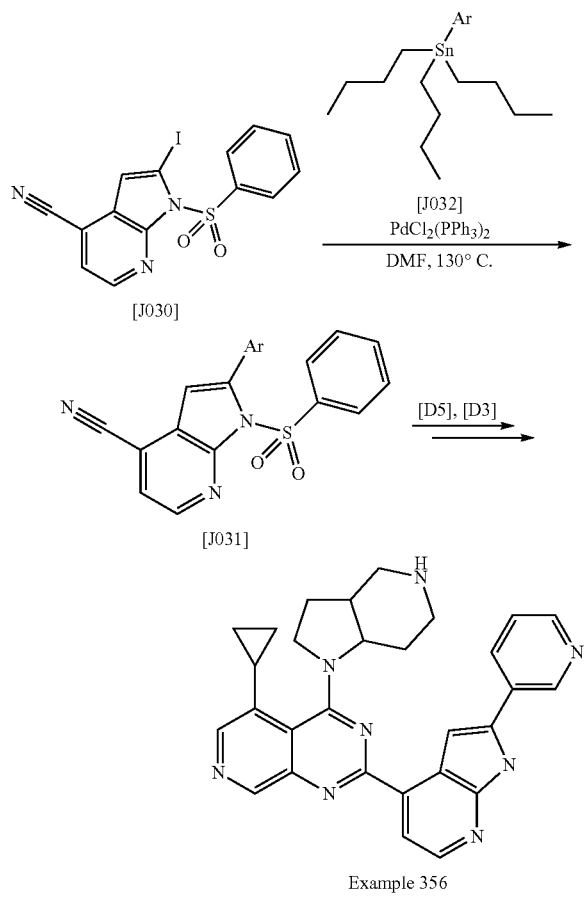

Example 356

Example 356. 5-Cyclopropyl-4-(octahydro-pyrrolo[3,2-c]pyridin-1-yl)-2-(2-pyridin-3-yl-1H-pyrrolo[2,3-b]pyridin-4-yl)-pyrido[3,4-d]pyrimidine 1-Benzenesulfonyl-2-iodo-1H-pyrrolo[2,3-b]pyridine-4-carbonitrile (2.002 g, 4.892 mmol), tributyl(3-pyridyl)stannane (6.878 g, 18.69 mmol), bis(triphenylphosphine)palladium(II) chloride (0.647 g, 0.9218 mmol) and anhydrous DMF (80 mL) were combined in an oven dried flask. The reaction was purged with argon and heated at 130° C. under nitrogen for 3 hours. The hot reaction was filtered through Celite, concentrated and purified by normal phase chromatography eluting with ethyl acetate/heptane to yield 1.07 g (61%) of 1-(benzenesulfonyl)-2-(3-pyridyl)pyrrolo[2,3-b]pyridine-4-carbonitrile: LC/MS 361.08 [M+H]; 1H NMR (400 MHz, DMSO-d6) δ 8.83 (m, 1H), 8.72 (m, 1H), 8.61 (d, 1H, J=5.0 Hz), 8.10 (m, 1H), 7.85 (m, 3H), 7.72 (m, 1H), 7.59 (m, 3H), 7.22 (s, 1H). Following the general procedures described in Schemes [D5] and [D3], 1-(benzenesulfonyl)-2-(3-pyridyl)pyrrolo[2,3-b]pyridine-4-carbonitrile was converted to the target compound, 5-cyclopropyl-4-(octahydro-pyrrolo[3,2-c]pyridin-1-yl)-2-(2-pyridin-3-yl-1H-pyrrolo[2,3-b]pyridin-4-yl)-pyrido[3,4-d]pyrimidine as a salt with trifluoroacetic acid: lyophilate, LC/MS 489.3 [M+H], 1H NMR (400 MHz, DMSO-d6) δ 12.58 (s, 1H), 9.33 (d, 1H, J=1.4 Hz), 9.24 (s, 1H), 8.65 (m, 3H), 8.54 (m, 1H), 8.46 (d, 1H, J=5.0 Hz), 8.22 (s, 1H), 8.11 (d, 1H, J=5.0 Hz), 8.08 (d, 1H, J=2.1 Hz), 7.68-7.64 (m, 1H), 4.64 (m, 1H), 4.44-4.37 (m, 2H), 3.44-3.26 (m, 3H), 2.99 (m, 2H), 2.82-2.73 (m, 2H), 2.24-2.21 (m, 1H), 1.94-1.91 (m, 1H), 1.79-1.76 (m, 1H), 1.48-1.44 (m, 1H), 1.22-1.15 (m, 1H), 1.12-1.06 (m, 1H), 0.96-0.90 (m, 1H).

Synthesis of amine building blocks are shown below Schemes [E1]-[E5] Amines of formula [K008] can be synthesized from compounds of formula [K001] via protection (BOC₂O) and pyridine benzylation to give compounds of formula [K003]. Reduction with NaBH₄ gives compounds of formula [K004] which is cyclopropanated and then the protecting groups manipulated to give compounds of formula [K008]. This can be taken on utilizing procedures analogous to those found in Scheme [D3] to give Example 198 (and others). The detailed description of the synthesis of Example 198 is shown below.

Scheme [E1]

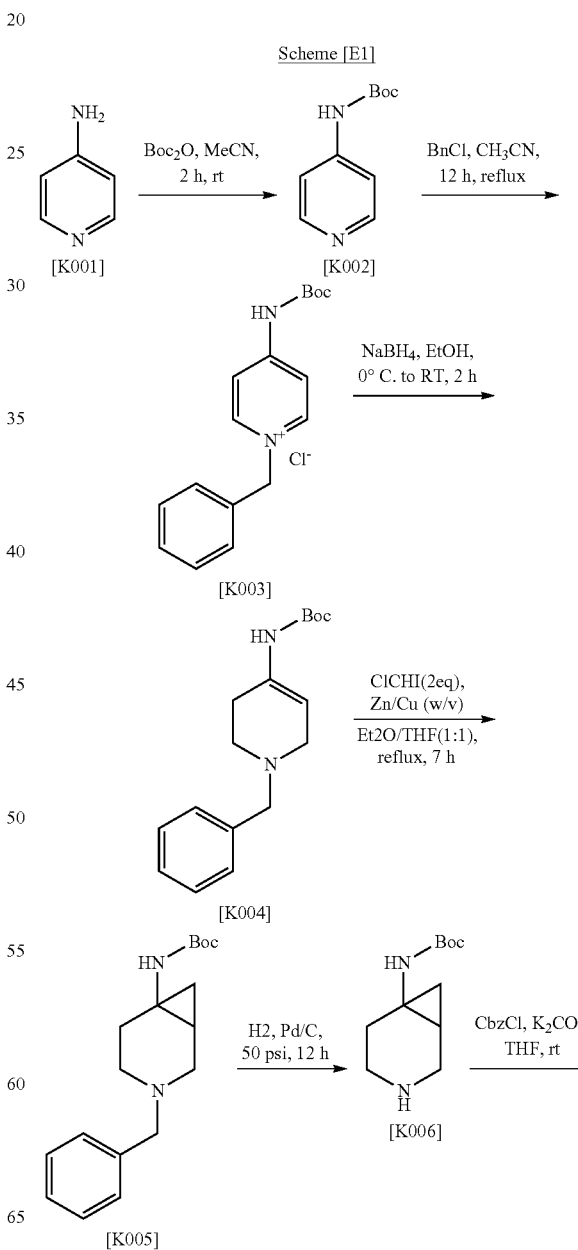

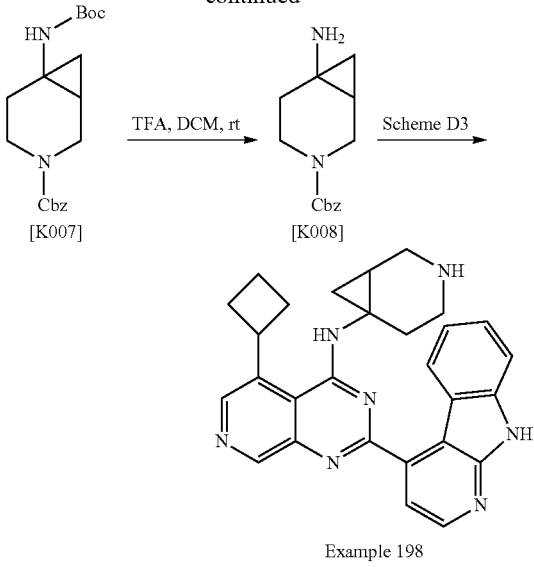

Example 198

Example 198

(3-Aza-bicyclo[4.1.0]hept-6-yl)-[5-cyclobutyl-2-(9H-pyrido[2,3-b]indol-4-yl)-pyrido[3,4-d]pyrimidin-4-yl]-amine 198a) To a solution of (3-Aza-bicyclo[4.1.0]hept-6-yl)-carbamic acid tert-butyl ester (0.65 g, 3.1 mmol) [prepared as described in Miller, W. H. et al, WO2006/010040] in THF (5 mL) at 0° C. was added $K_2CO_3$ (1.28 g, 9.3 mmol) followed by Cbz-Cl (0.63 g, 3.72 mmol) and stirred at rt for 12 h. Reaction mixture was concentrated and residue was diluted with water and extracted with DCM. The organic layer was washed with aq. sat. sodium bicarbonate, dried ($N_{a2}SO_4$) and concentrated to afford 6-tert-Butoxycarbonylamino-3-aza-bicyclo[4.1.0]heptane-3-carboxylic acid benzyl ester (0.55 g, 55%) as clear oil. The compound was characterized by MS and 1H-NMR. $^1$H NMR (400 MHz, d6-DMSO, δ): 7.41-7.27 (m, 5H), 5.05 (s, 2H), 3.61 (d, J=8.3 Hz, 2H), 3.19 (d, J=11.9 Hz, 2H), 1.89 (q, J=5.8 Hz, 1H), 1.98-1.95 (m, 2H) 1.37 (s, 9H), 1.12 (s, 1H), 0.76 (dd, J=9.5, 5.4 Hz, 1H), 0.45-0.43 (m, 1H). LC/MS=303 (M+H)+.

198b) To a solution of 6-tert-Butoxycarbonylamino-3-aza-bicyclo[4.1.0]heptane-3-carboxylic acid benzyl ester (0.55 g, 1.59 mmol) in THF (5 mL) at 0° C. was added TFA (1 mL) and stirred at rt for 5 h. Reaction mixture was concentrated and residue was triturated with diethyl ether to afford 6-Amino-3-aza-bicyclo[4.1.0]heptane-3-carboxylic acid benzyl ester (0.35 g, 90%) as clear oil. The compound was characterized by MS and 1H-NMR. $^1$H NMR (400 MHz, d6-DMSO, δ): 8.23 (s, 2H), 7.37-7.35 (m, 5H), 5.06 (d, J=1.4 Hz, 2H), 3.53-3.33 (m, 2H), 3.12 (s, 1H), 1.97 (p, J=7.2, 6.6 Hz, 2H), 1.56-1.46 (m, 1H), 1.12-1.00 (m, 1H), 0.76-0.68 (m, 2H). LC/MS=247 (M+H)+.

198c) To a mixture of 2,4,6-Triisopropyl-benzenesulfonic acid 5-cyclobutyl-2-(9H-pyrido[2,3-b]indol-4-yl)-pyrido[3,4-d]pyrimidin-4-yl ester (150.0 mg, 0.2367 mmol) and N,N-Diisopropylethylamine (125.0 uL, 0.7176 mmol) in N,N-Dimethylformamide (1 mL) was added a solution of 6-tert-Butoxycarbonylamino-3-aza-bicyclo[4.1.0]heptane-3-carboxylic acid benzyl ester (140.0 mg, 0.56 mmol) in DMF (0.5 mL). The mixture was stirred at room temperature over the weekend. The reaction was poured into water (20 mL) and extracted with ethyl acetate (15 mL). The organic was washed with water (2×10 mL) and saturated aqueous sodium chloride (10 mL). The organic was dried over magnesium sulfate, filtered and the filtrate was evaporated to a brown resin consistent for desired intermediate.

The brown resin was dissolved in Methylene chloride (5 mL) and stirred at room temperature. Dimethyl sulfide (1 mL) followed by Boron trifluoride etherate (200.0 uL, 1.578 mmol) was added and the yellow suspension was stirred at room temperature overnight. The volatiles were evaporated to a yellow solid. Methanol (10 mL) was added and then evaporated. The residue purified via reverse phase chromatography (5%→50% acetonitrile:Water with 0.1% TFA as modifier). The desired fractions were combined, frozen and lyophilized. (±)-(3-Aza-bicyclo[4.1.0]hept-6-yl)-[5-cyclobutyl-2-(9H-pyrido[2,3-b]indol-4-yl)-pyrido[3,4-d]pyrimidin-4-yl]-amine (0.0614 g, 45%) was recovered as yellow lyophilate as the trifluoroacetic acid salt. $^1$H NMR (400 MHz, d6-DMSO, δ): 12.06 (s, 1H), 9.12 (s, 1H), 8.58 (d, J=5.0 Hz, 1H), 8.53-8.41 (m, 3H), 8.05 (br s, 1H), 7.81 (s, 1H), 7.76 (d, J=5.1 Hz, 1H), 7.55 (d, J=8.0 Hz, 1H), 7.50-7.45 (m, 1H), 7.18-7.12 (m, 1H), 4.54-4.44 (m, 1H), 3.27-3.13 (m, 2H), 2.90-2.72 (m, 2H), 2.57-2.47 (m, 2H), 2.38-2.04 (m, 6H), 1.90-1.80 (m, 1H), 1.62-1.54 (m, 1H), 1.36-1.30 (m, 1H), 1.13-1.08 (m, 1H). LC/MS=462.16 (MH)+.

Amines of formula [K016] can be synthesized from compounds of formula [K009] as found in Scheme [E2]. Protection (TBDMSC1) and pyridine benzylation followed by reduction with $NaBH_4$ gives compounds of formula [K010] which can be converted via benzoylation, desilylation and azide formation to give compounds of formula [K013]. This can be epoxidized and the azide reduced which is followed by concomitant cyclization to give compounds of formula [K016]. Utilizing procedures analogous to those found in Scheme [D3], [K016] can be used to give Example 76 (and others). A detailed description of the synthesis of Example 76 is outlined below.

Scheme [E2]

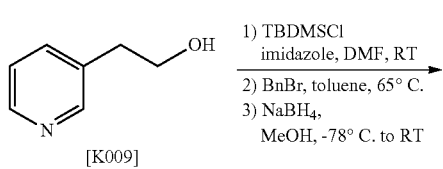

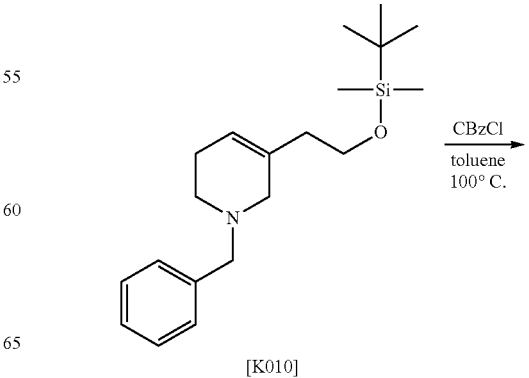

-continued

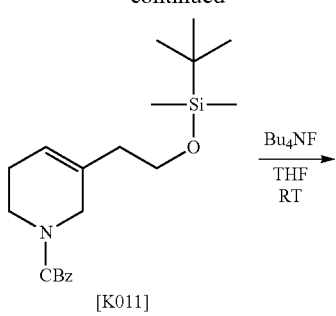
[K011]

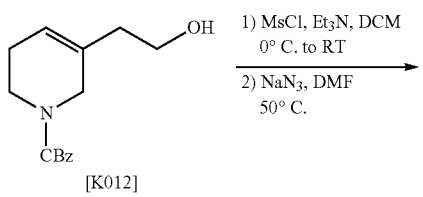
[K012]

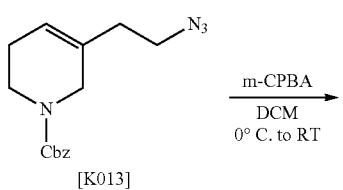
[K013]

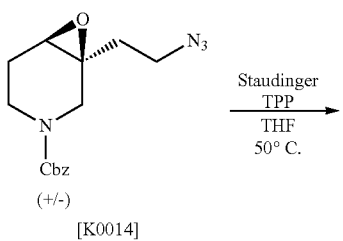
(+/-)
[K0014]

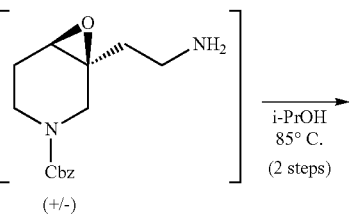
(+/-)
[K015]

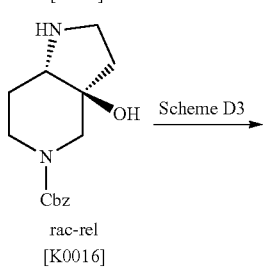
rac-rel
[K0016]

-continued

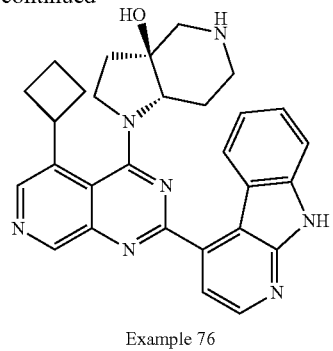

Example 76

Example 76. (±)-(3aS,7aS)-1-[5-Cyclobutyl-2-(9H-pyrido[2,3-b]indol-4-yl)-pyrido[3,4-d]pyrimidin-4-yl]-octahydro-pyrrolo[3,2-c]pyridin-3a-ol 76a) To a stirred solution of 1-Benzyl-5-[2-(tert-butyl-dimethyl-silanyloxy)-ethyl]-1,2,3,6-tetrahydro-pyridine (4.0 g, 12 mmol) [prepared as described in Marazano, C.; et. al., J. Org. Chem., 2002, 67, 1890-1897] in Toluene (100 mL) was added dropwise, via addition funnel, Benzyl chloroformate (2.1 mL, 14 mmol) in Toluene (100 mL). The mixture was stirred at room temperature until addition was complete. The reaction mixture was warmed to 65° C. and heated overnight under an atmosphere of Nitrogen. The volatiles were evaporated, the residue was triturated with hexanes (150 mL), filtered through a plug of diatomaceous earth and the filtrate was evaporated. The residue was purified via silica gel chromatography (40 g, 0%→25% Ethyl Acetate:Hexane). The products were visualized on TLC with iodine. 5-[2-(tert-Butyl-dimethyl-silanyloxy)-ethyl]-3,6-dihydro-2H-pyridine-1-carboxylic acid benzyl ester (3.66 g) was isolated as a clear oil. $^1$H NMR (400 MHz, CDCl3, δ): 7.39-7.28 (m, 5H), 5.58 (br s, 1H), 5.15 (s, 2H), 3.91-3.88 (m, 2H), 3.68 (t, J=6.6 Hz, 2H), 3.51 (t, J=5.7 Hz, 2H), 2.23-2.07 (m, 4H), 0.88 (s, 9H), 0.03 (s, 6H). LC/MS=346.06 (MH)+ and 398.09 (M+Na)+.

76b) To a stirred solution of 5-[2-(tert-Butyl-dimethyl-silanyloxy)-ethyl]-3,6-dihydro-2H-pyridine-1-carboxylic acid benzyl ester (3.16 g, 8.41 mmol) in Tetrahydrofuran (6 mL) was added 1.0 M of Tetra-n-butylammonium fluoride in Tetrahydrofuran(9.5 mL, 9.5 mmol). The mixture was stirred at room temperature overnight. The reaction was complete by TLC (Iodine stain, 3:2 Ethyl Acetate:Hexane). The mixture was diluted with water (15 mL) and stirred for 15 minutes. The mixture was extracted with ether (2×50 mL). The combined ether layers were washed with water (2×15 mL), saturated aqueous sodium chloride (15 mL) and then dried over magnesium sulfate, filtered and the filtrate was evaporated. The residue was purified via silica gel chromatography (12 g, 25%→75% Ethyl Acetate:Hexane). The products were visualized on TLC with iodine and LC/MS. 5-(2-Hydroxy-ethyl)-3,6-dihydro-2H-pyridine-1-carboxylic acid benzyl ester (1.84 g) was recovered as a clear oil (1.84 g). $^1$H NMR (400 MHz, CDCl3, δ): 7.39-7.28 (m, 5H), 5.66 (br s, 1H), 5.15 (s, 2H), 3.90 (br s, 2H), 3.71 (t, J=6.0 Hz, 2H), 3.54 (t, J=5.8 Hz, 2H), 2.25 (br s, 2H), 2.15 (br s, 2H). LC/MS=283.95 (M+Na)+.

76c) To a cooled, stirred mixture of 5-(2-Hydroxy-ethyl)-3,6-dihydro-2H-pyridine-1-carboxylic acid benzyl ester (1.84 g, 7.04 mmol) and Triethylamine (1974 uL, 14.16 mmol) in Methylene chloride (60 mL) at −5° C. in brine-ice bath was added Methanesulfonyl chloride (819.8 uL, 10.59 mmol; Supplier=Aldrich) dropwise. The mixture was stirred at −5° C. for 1 hour then allowed to warm to room temperature and stirred for 1 hour. The mixture was partitioned between ether (100 mL) and water (50 mL). The layers were separated. The organic layer was dried over magnesium sulfate, filtered and the filtrate evaporated. The mixture was triturated with ether (25 mL), filtered through a plug of diatomaceous earth and the filtrate was evaporated. Intermediate 5-(2-Methanesulfonyloxy-ethyl)-3,6-dihydro-2H-pyridine-1-carboxylic acid benzyl ester was isolated as pale yellow oil and was used without further purification. $^1$H NMR (400 MHz, CDCl3, δ): 7.38-7.29 (m, 5H), 5.69 (br s, 1H), 5.15 (s, 2H), 4.29 (t, J=6.4 Hz, 2H), 3.90 (br s, 2H), 3.53 (t, J=5.8 Hz, 2H), 3.04-2.90 (m, 3H), 2.42 (br s, 2H), 2.15 (br s, 2H). LC/MS=361.95 (M+Na)+.

To a stirred solution of 5-(2-Methanesulfonyloxy-ethyl)-3,6-dihydro-2H-pyridine-1-carboxylic acid benzyl ester in N,N-Dimethylformamide (30 mL) was added Sodium azide (0.911 g, 14.0 mmol). The mixture was stirred and warmed to 50° C. under an atmosphere of Nitrogen for 6 hours then cooled and stirred at room temperature overnight. The mixture was partitioned between ether (50 mL) and water (50 mL). The aqueous was extracted with ether (2×50 mL). The combined organic layers were washed with water (2×50 mL), saturated aqueous sodium chloride (25 mL) then dried over magnesium sulfate, filtered and the filtrate was evaporated then placed under high vacuum for 30 minutes. 5-(2-Azido-ethyl)-3,6-dihydro-2H-pyridine-1-carboxylic acid benzyl ester (1.84 g) was isolated as a pale yellow oil. $^1$H NMR (400 MHz, CDCl3, δ): 7.38-7.29 (m, 5H), 5.67 (br s, 1H), 5.16 (s, 2H), 3.89 (br s, 2H), 3.53 (t, J=5.7 Hz, 2H), 3.36 (t, J=6.7 Hz, 2H), 2.27 (br s, 2H), 2.15 (br s, 2H). LC/MS=308.95 (M+Na)+.

76d) To a cooled solution of 5-(2-Azido-ethyl)-3,6-dihydro-2H-pyridine-1-carboxylic acid benzyl ester (1.84 g, 6.43 mmol) in Methylene chloride (50 mL) in an ice-water bath at 5° C. was added m-CPBA 70-75%(70:30, m-Chloroperbenzoic acid:3-Chlorobenzoic acid, 3.0 g, 12 mmol). The mixture was stirred for 30 minutes at 5° C. then warmed to room temperature over 30 minutes and stirred at room temperature overnight. The mixture was diluted with dichloromethane (50 mL) and water (25 mL) then saturated aqueous sodium thiosulfate (15 mL) was added and stirred for 15 minutes. The layers were separated. The organic layer was washed with saturated aqueous sodium bicarbonate (50 mL) then dried over magnesium sulfate, filtered and the filtrate was evaporated. (±)-1-(2-Azido-ethyl)-7-oxa-3-azabicyclo[4.1.0]heptane-3-carboxylic acid benzyl ester (2.03 g) was isolated as a pale yellow oil and was used without further purification.

76e) A round bottom flask with stir bar, reflux condenser and gas inlet adapter was charged with (±)-1-(2-Azido-ethyl)-7-oxa-3-aza-bicyclo[4.1.0]heptane-3-carboxylic acid benzyl ester (2.02 g, 6.68 mmol), Water (4 mL, 200 mmol) and Tetrahydrofuran (75 mL) followed by Triphenylphosphine (1.93 g, 7.35 mmol). The mixture was stirred and heated at 60° C. under an atmosphere of Nitrogen for 2 hours. Gas evolution was observed. The reaction was complete by LC/MS and TLC (Iodine stain, 5:95 MeOH:DCM). The mixture was cooled to room temperature and the volatiles were evaporated under reduced pressure. Crude 1-(2-Amino-ethyl)-7-oxa-3-aza-bicyclo[4.1.0]heptane-3-carboxylic acid benzyl ester was isolated to a pale yellow oil and was UV visible at 215 nm.

The pale yellow oil was dissolved in Isopropyl alcohol (75 mL) and heated at 85° C. overnight. The reaction was complete by LC/MS and HPLC (UV at 215 nm) and TLC (iodine stain, 15:85 MeOH:DCM). The mixture was cooled to room temperature and the volatiles were evaporated. The pale yellow oil was purified via silica gel chromatography (40 g, 5%→25% [10% NH4OH in MeOH]:Dichlormethane). (±)-(3,4-trans)-4-{[5-Cyclobutyl-2-(9H-pyrido[2,3-b]indol-4-yl)-pyrido[3,4-d]pyrimidin-4-yl]-methyl-amino}-3-methyl-piperidin-3-ol (1.23 g) was isolated as pale yellow viscous oil. Structure was confirmed by variable temperature $^1$H NMR, $^{13}$C NMR, COSY and HMQC at 298 and 368K. $^1$H NMR (400 MHz, d6-DMSO, δ, 298K): 7.40-7.28 (m, 5H), 5.10-5.00 (m, 2H), 4.78 (br s, 1H), 3.55-3.10 (m, 10H), 2.91-2.73 (m, 3H), 1.76-1.66 (m, 1H), 1.60-1.54 (m, 2H), 1.39-1.27 (m, 1H). LC/MS=277.00 (MH)+.

76f) A tube with stir bar was charged with 4-(4-Chloro-5-cyclobutyl-pyrido[3,4-d]pyrimidin-2-yl)-9H-pyrido[2,3-b]indole (100.0 mg, 0.2592 mmol), (±)-(3,4-trans)-4-{[5-Cyclobutyl-2-(9H-pyrido[2,3-b]indol-4-yl)-pyrido[3,4-d]pyrimidin-4-yl]-methyl-amino}-3-methyl-piperidin-3-ol (100.0 mg, 0.3619 mmol), N,N-Diisopropylethylamine (136.0 uL, 0.7808 mmol), 4-Dimethylaminopyridine (3 mg, 0.02 mmol) and N,N-Dimethylformamide (1 mL). The tube was sealed and the mixture was stirred at room temperature overnight. DMF was evaporated under reduced pressure. The residue was purified via silica gel chromatography (12 g, 0%→5% Methanol:Dichloromethane). The desired fractions were combined and evaporated to a red-brown resin (0.124 g) was consistent for desired intermediate and used without further purification. $^1$H NMR (400 MHz, d6-DMSO, δ): 12.02 (s, 1H), 9.08 (s, 1H), 8.74-8.67 (m, 2H), 8.56 (d, J=5.1 Hz, 1H), 7.88 (d, J=5.1 Hz, 1H), 7.53 (d, J=7.9 Hz, 1H), 7.49-7.44 (m, 1H), 7.41-7.29 (m, 5H), 7.18-7.13 (m, 1H), 5.30-5.05 (m, 3H), 4.65-4.45 (m, 1H), 4.33-4.15 (m, 1H), 4.05-3.95 (m, 1H), 3.88-3.58 (m, 3H), 3.50-3.10 (m, 2H), 2.72-2.62 (m, 1H), 2.48-2.34 (m, 2H), 2.20-1.70 (m, 7H). LC/MS=626.28 (MH)+.

The red-brown resin was dissolved in Methylene chloride (1 mL) and Dimethyl sulfide (1 mL) and cooled to 0° C. then Boron trifluoride etherate (320.0 uL, 2.50 mmol) was added dropwise. The stirred mixture immediately formed a suspension, was warmed to room temperature and stirred overnight. The mixture was evaporated to a yellow solid. The solid was dissolved in methanol (10 mL) and evaporated under reduced pressure. The residue was purified via reverse phase chromatography (5%→50% Acetonitrile: Water with 0.1% TFA as modifier). The desired fractions were combined, frozen and lyophilized. Racemic, rel-(3aS,7aS)-1-[5-Cyclobutyl-2-(9H-pyrido[2,3-b]indol-4-yl)-pyrido[3,4-d]pyrimidin-4-yl]-octahydro-pyrrolo[3,2-c]pyridin-3a-ol (0.0759 g, 48%) was isolated as yellow lyophilate as the trifluoroacetic acid salt. $^1$H NMR (400 MHz, d6-DMSO, δ): 12.07 (s, 1H), 9.15 (s, 1H), 8.80-8.70 (m, 4H), 8.58 (d, J=5.1 Hz, 1H), 7.86 (d, J=5.1 Hz, 1H), 7.54 (d, J=7.9 Hz, 1H), 7.51-7.46 (m, 1H), 7.21-7.16 (m, 1H), 5.80 (br s, 1H), 4.33-4.22 (m, 3H), 4.05-3.95 (m, 1H), 3.35-2.94 (m, 5H), 2.79-2.69 (m, 1H), 2.52-2.38 (m, 2H), 2.30-1.80 (m, 6H). LC/MS=492.18 (MH)+.

Amines of formula [K023] can be synthesized from compounds of formula [K017] as found in Scheme [E4]. Pyridine benzylation followed by reduction with NaBH4 and then benzoylyation gives compounds of formula [K021] which can be converted via epoxidation and methylamine eposide opening to give compounds of formula [K023]. Utilizing procedures analogous to those found in Scheme [D3], [K023] can be used to give Example 77 (and others). A detailed description of the synthesis of Example 77 is outlined below.

Scheme [E3]

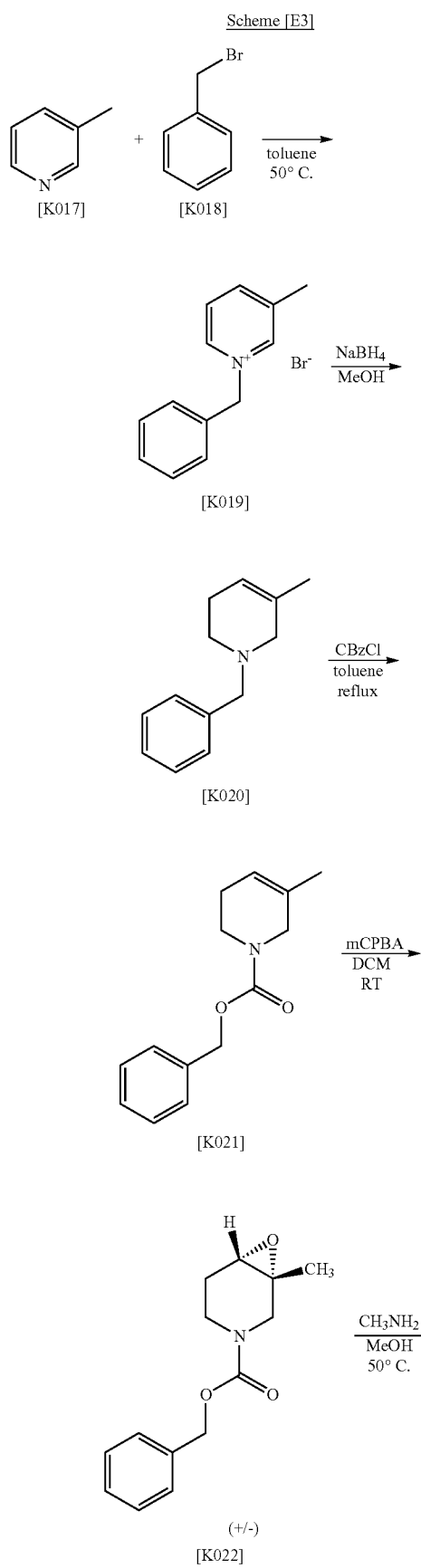

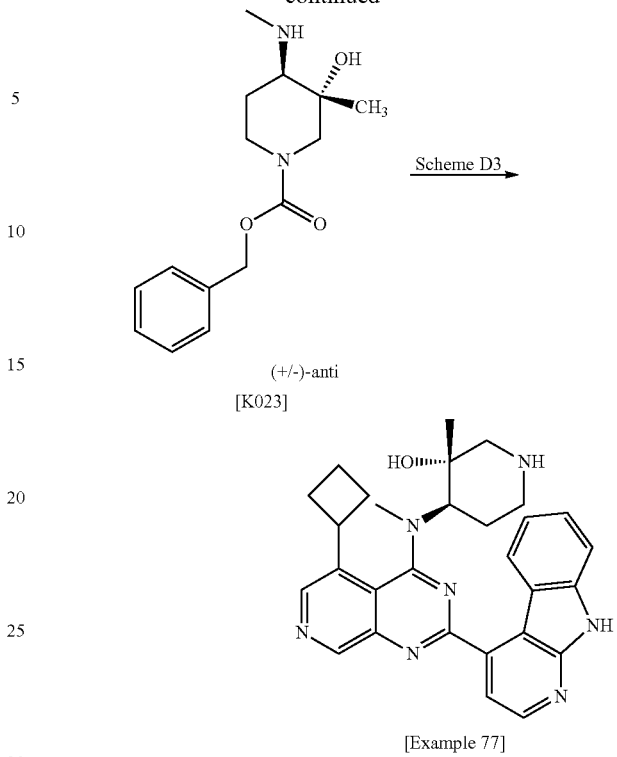

[Example 77]

Example 77. (±)-(3,4-trans)-4-{[5-Cyclobutyl-2-(9H-pyrido[2,3-b] indol-4-yl)-pyrido[3,4-d]pyrimidin-4-yl]-methyl-amino}-3-methyl-piperidin-3-ol 77a) A solution of 3-Methyl-pyridine (5.0 mL, 51 mmol) and Benzyl bromide (6.1 mL, 51 mmol) in Toluene (10 mL, 90 mmol) was heated at 50° C. for 3 hours. The bi-phasic mixture was cooled and the toluene was evaporated under reduced pressure. Crude 1-benzyl-3-methyl-pyridin-1-ium bromide (16 g) was used without further purification. $^1$H NMR (400 MHz, d6-DMSO, δ): 9.15 (s, 1H), 9.04 (d, J=6.1 Hz, 1H), 8.47 (d, J=8.0 Hz, 1H), 8.08 (dd, J=7.9, 6.1 Hz, 1H), 7.56-7.40 (m, 5H), 5.80 (s, 2H), 2.51 (s, 3H). LC/MS=183.98 (M)+.

77b) A 500 mL round bottom flask with stir bar, reflux condenser and gas inlet adapter was added a solution of 1-benzyl-3-methyl-pyridin-1-ium bromide (14 g, 53 mmol) in methanol (100 mL) under an atmosphere of Nitrogen. The mixture was cooled to 5° C. in an ice-water bath. Sodium borohydride (6.0 g, 160 mmol) was added portionwise (0.50 g x 12) to the vigorously stirred solution. Vigorous gas evolution was noted during each addition. The yellow solution was stirred at room temperature overnight then evaporated to dryness. Water (300 mL) was added and the mixture was stirred at room temperature for 30 minutes. The mixture was transferred to a separatory funnel and extracted with dichloromethane (3×100 mL). The combined organic layer was dried over magnesium sulfate, filtered and the filtrate was evaporated. Crude 1-Benzyl-5-methyl-1,2,3,6-tetrahydro-pyridine (10.3 g) was isolated as an orange oil and was used without further purification. $^1$H NMR (400 MHz, d6-DMSO, δ): 7.40-7.15 (m, 5H), 5.41-5.36 (m, 1H), 3.52 (s, 2H), 2.74-2.71 (m, 2H), 2.42 (t, J=5.7 Hz, 2H), 2.05-1.99 (m, 2H), 1.57-1.55 (m, 3H). LC/MS=188.01 (MH)+.

77c) To a solution of 1-Benzyl-5-methyl-1,2,3,6-tetrahydro-pyridine (6.78 g, 36.2 mmol) in Toluene (100 mL) was added dropwise, via addition funnel, a solution of Benzyl chloroformate (7.8 mL, 54 mmol) in Toluene (100 mL) at room temperature. Once addition was complete, the mixture was heated at 100° C. for 18 hours under dry nitrogen. The mixture was cooled to room temperature and the volatiles were evaporated. The residue was purified via silica gel chromatography (24 g, 0%→20% Ethyl Acetate: Hexane). The desired fractions were combined and evaporated. 5-Methyl-3,6-dihydro-2H-pyridine-1-carboxylic acid benzyl ester (6.46 g) was recovered as a yellow oil. $^1$H NMR (400 MHz, d6-DMSO, δ): 7.40-7.28 (m, 5H), 5.52 (br s, 1H), 5.09 (s, 2H), 3.76 (br s, 2H), 3.42 (br s, 2H), 2.07-2.00 (m, 2H), 1.64 (s, 3H). LC/MS=231.96 (MH)+ and 253.95 (M+Na)+.

77d) To a stirred, cooled solution of 5-Methyl-3,6-dihydro-2H-pyridine-1-carboxylic acid benzyl ester (1.0 g, 4.3 mmol) in Methylene chloride (10 mL) at 0° C. in an ice-water bath was added m-CPBA 70-75%(70:30, m-Chloroperbenzoic acid:3-Chlorobenzoic acid, 1.5 g, 6.0 mmol). The mixture was stirred and warmed to room temperature. After 30 minutes, the mixture was partitioned between dichloromethane (50 mL) and water (25 mL). The organic was washed with water (25 mL) then saturated aqueous sodium bicarbonate (2×25 mL) then saturated aqueous sodium chloride (10 mL). The organic layer was dried over magnesium sulfate, filtered and the filtrate was evaporated. (±)-1-Methyl-7-oxa-3-aza-bicyclo[4.1.0]heptane-3-carboxylic acid benzyl ester (1.0 g) was recovered as a yellow oil (1.083 g) and used without further purification. $^1$H NMR (400 MHz, d6-DMSO, δ): 7.40-7.28 (m, 5H), 5.06 (s, 2H), 3.84-3.76 (m, 1H), 3.52-3.34 (m, 2H), 3.16-3.02 (m, 2H), 1.89-1.81 (m, 2H), 1.26 (s, 3H). LC/MS=247.96 (MH)+ and 269.95 (M+Na)+.

77e) To a thick walled pressure vessel with pressure gauge and stir bar was added (±)-1-Methyl-7-oxa-3-aza-bicyclo[4.1.0]heptane-3-carboxylic acid benzyl ester (0.63 g, 2.5 mmol) and 2.0 M of Methylamine in Methanol (10 mL, 20 mmol). The vessel was sealed and the mixture was warmed to 50° C. overnight behind a blast shield. Pressure increased 5 psi during heating. The mixture was cooled to room temperature, the contents were transferred to a round bottom flask and the volatiles were evaporated. The mixture was loaded onto Phenomenex SX-C cartridges (2×2 g), rinsed with methanol (2×10 mL, each) and product was released with 2N ammonia in methanol (2×10 mL, each). The ammonical filtrates were combined and evaporated under reduced pressure. anti-(±)-3-Hydroxy-3-methyl-4-methylamino-piperidine-1-carboxylic acid benzyl ester (0.38 g) was recovered as a yellow viscous oil that solidifies upon standing at room temperature after several days. $^1$H NMR (400 MHz, d6-DMSO, δ): 7.40-7.28 (m, 5H), 5.10-4.98 (m, 2H), 4.67 (s, 1H), 3.90-3.82 (m, 1H), 3.65 (dd, J=12.7, 1.3 Hz, 1H), 3.00-2.62 (m, 2H), 2.31-2.25 (m, 4H), 1.79 (dddd, J=16.7, 3.6, 3.6, 3.6 Hz, 1H), 1.65 (br s, 1H), 1.13-1.01 (m, 1H), 0.97 (s, 3H). LC/MS=278.96 (MH)+.

77f) A tube with stir bar was charged with 4-(4-Chloro-5-cyclobutyl-pyrido[3,4-d]pyrimidin-2-yl)-9H-pyrido[2,3-b]indole (100.0 mg, 0.2592 mmol), anti-(±)-3-Hydroxy-3-methyl-4-methylamino-piperidine-1-carboxylic acid benzyl ester (100.0 mg, 0.3593 mmol), N,N-Diisopropylethylamine (135.0 uL, 0.7750 mmol), 4-Dimethylaminopyridine (3.0 mg, 0.024 mmol) and N,N-Dimethylformamide (1 mL). The tube was sealed and the mixture was stirred at room temperature overnight. DMF was evaporated under reduced pressure. The residue was purified via silica gel chromatography (12 g, 0%→5% Methanol:Dichloromethane). The desired fractions were combined and evaporated. The recovered red-brown resin (0.096 g) was consistent for desired intermediate by LC/MS. The recovered red-brown resin was dissolved in Methylene chloride (1 mL, 20 mmol) then Dimethyl sulfide (1 mL, 10 mmol) followed by Boron trifluoride etherate (98.53 uL, 0.7775 mmol) was added. The mixture was stirred at room temperature overnight. The volatiles were evaporated. The recovered yellow solid was dissolved in methanol (10 mL) and evaporated under reduced pressure to an oil. The residue was purified via reverse phase chromatography (5%→50% Acetonitrile:Water with 0.1% TFA as modifier). The desired fractions were combined, frozen and lyophilized. (±)-(3,4-trans)-4-{[5-Cyclobutyl-2-(9H-pyrido[2,3-b]indol-4-yl)-pyrido[3,4-d]pyrimidin-4-yl]-methyl-amino}-3-methyl-piperidin-3-ol (0.06652 g, 42%) was recovered as yellow lyophilate as the trifluoroacetic acid salt. The recovered product showed a very complex $^1$H NMR most likely due to atropisomerism. Isolated material was single peak in HPLC. $^1$H NMR (400 MHz, d6-DMSO, δ): 12.19-12.03 (m, 1H), 9.50-8.20 (m, 6H), 7.85-7.75 (m, 1H), 7.60-7.45 (m, 2H), 7.23-7.12 (m, 1H), 5.62-1.12 (m, 21H). LC/MS=494.20 (MH)+.

The following amines were synthesized using procedures found in the indicated references. Amine [K024] was synthesized using the procedures analogous to those found in US2013/0079321. [K024] was utilized for the synthesis of Examples 230, 231 (and others) using procedures analogous to those outlined in Scheme D3. Amine [K025] was synthesized using the procedures analogous to those found in 2006/081178. [K025] was utilized for the synthesis of Examples 135 (and others) using procedures analogous to those outlined in Scheme D3. Amine [K026] was synthesized using the procedures analogous to those found in J. AM. CHEM. SOC. 2010, 132, 13111-13113. [K024] was utilized for the synthesis of Examples 207 (and others) using procedures analogous to those outlined in Scheme D3.

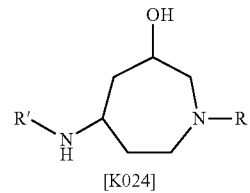

[K024]

Scheme D3 ↓

[Examples 230, 231]

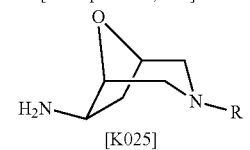

[K025]

Scheme D3 ↓

[Examples 135]

-continued

[K026]

Scheme D3 ↓

[Examples 207]

Intermediate amines [K032], [K034] and [K038] were prepared as described in the Scheme [E4] below, starting with either S or R α-methylbenzylamine, by a modified procedure from W. Qian et al., Bioorg. Med. Chem. Lett. 2012 (22), 1061-1067. The first step, condensation to an imine, was performed in toluene under reflux, in presence of molecular sieves and magnesium sulfate as dehydrating agents to give [K030] which was reduced to give [K031] which was hydrogenated to give [K032] which was taken on via Scheme D3 to Example 153 (and others). Intermediate [K034] was prepared from intermediate 1 via a 2-step, alkylation/hydrogenolysis procedure and taken on via Scheme D3 to Examples 212 (and others). The other enantiomer [K038] was prepared in the same manner utilizing [K035] and was taken on to Example 154 (and others)

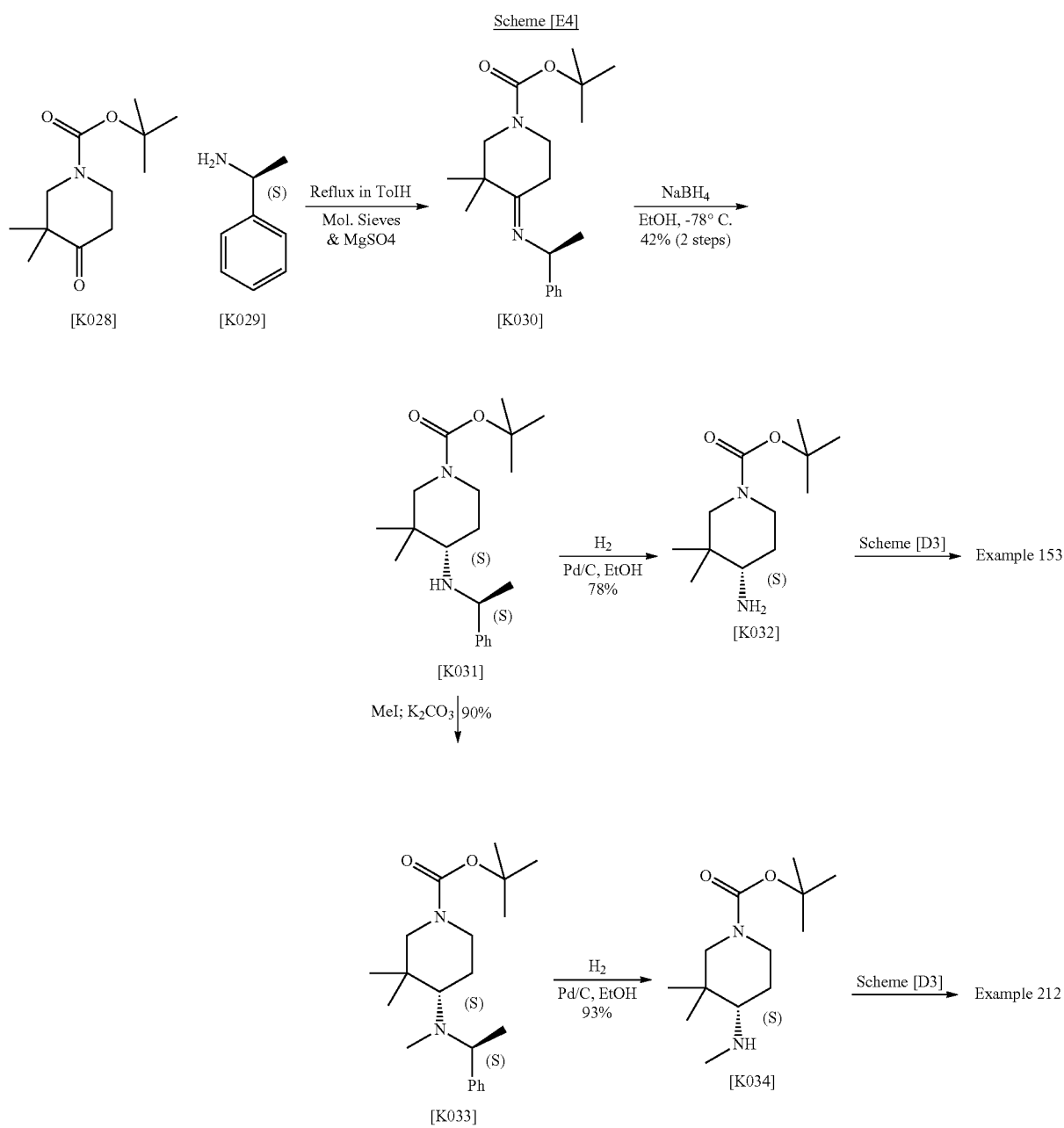

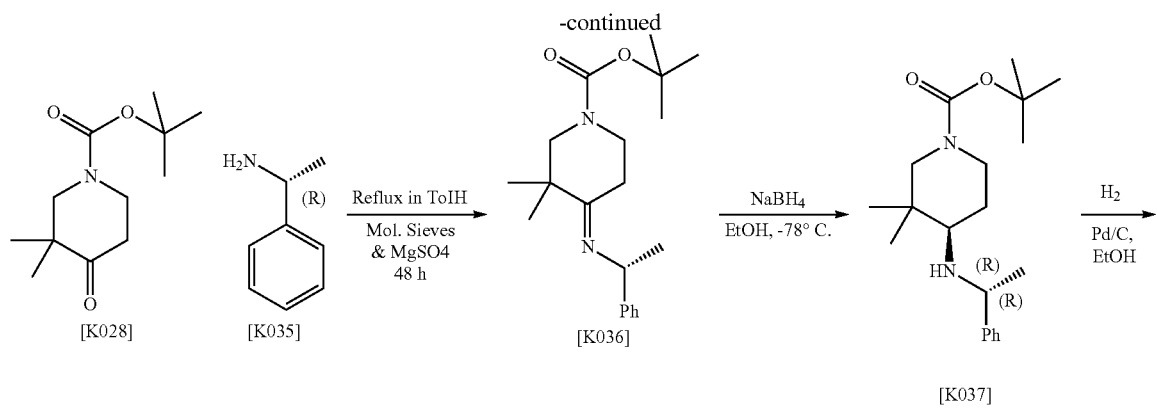

[K028]  [K035]  [K036]  [K037]

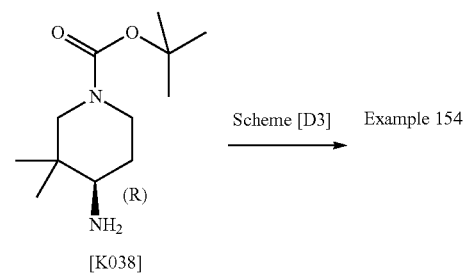

[K038]

Scheme [D3] → Example 154

Intermediate [K042] in Scheme [E5] was prepared according to the Scheme below, in a 2-step procedure: Boc-protection/benzyl hydrogenolysis and taken on via Scheme [D3] to example 155 (and others)

Scheme [E5]

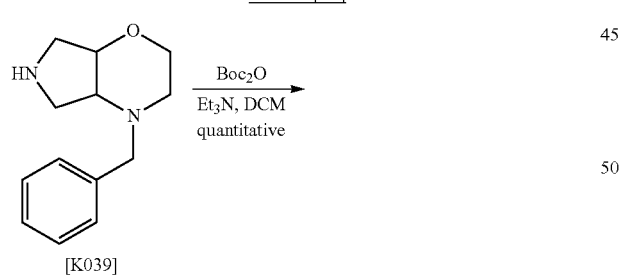

[K039]

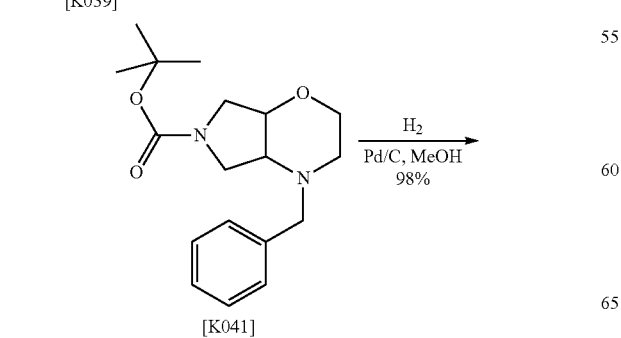

[K041]

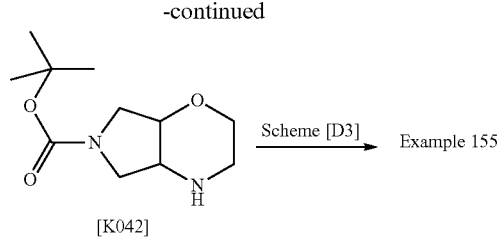

[K042]

Scheme [D3] → Example 155

The following compounds in Table A were synthesized according to the general syntheses shown in the Scheme(s) using procedures and intermediates analogous to those described therein.

TABLE A

| Ex | Structure | Scheme | Analysis LCMS | 1H-NMR | Name |
|---|---|---|---|---|---|
| 1 | 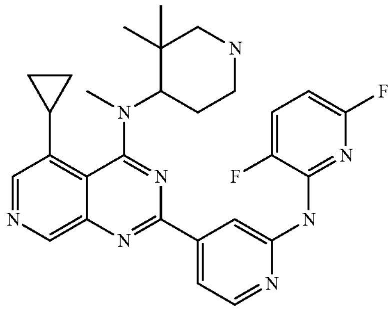 [SMILES: CN(c1nc(-c2ccnc(Nc3nc(F)ccc3F)c2)nc2cncc(C3CC3)c12)C1CCNCC1(C)C] | [B4] | 517 (M + H)+ | 1H NMR (400 MHz, METHANOL-d4) d ppm 9.07 (1 H, s) 8.51 (1 H, d, J = 6.0 Hz) 8.29 (1 H, d, J = 4.8 Hz) 8.16 (1 H, br. s.) 7.87 (1 H, td, J = 9.1, 5.9 Hz) 6.80 (1 H, d, J = 8.3 Hz) 3.64 (1 H, d, J = 10.8 Hz) 2.58 (1 H, br. s.) 1.13-1.56 (5 H, m) | {5-Cyclopropyl-2-[2-(3,6-difluoro-pyridin-2-ylamino)-pyridin-4-yl]-pyrido[3,4-d]pyrimidin-4-yl}-(3,3-dimethyl-piperidin-4-yl)-methyl-amine |
| 2 | 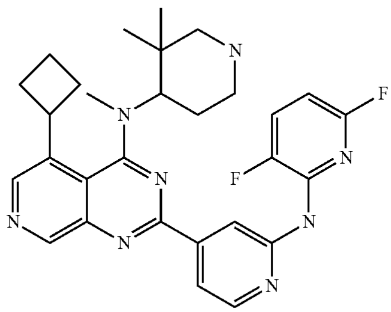 [SMILES: CN(c1nc(-c2ccnc(Nc3nc(F)ccc3F)c2)nc2cncc(C3CCC3)c12)C1CCNCC1(C)C] | [B4] | 531 (M + H)+ | 1H NMR(400 MHz, METHANOL-d4) d ppm 8.68-9.21 (3 H, m) 8.40 (1 H, br. s.) 8.21 (1 H, d, J = 5.0 Hz) 7.78 (1 H, td, J = 9.1, 5.9 Hz) 6.73 (1 H, br. s.) 5.67 (1 H, d, J = 9.0 Hz) 3.51 (1 H, d, J = 12.5 Hz) 2.55-2.88 (2 H, m) 2.22-2.41 (2 H, m) 1.76-1.97 (4 H, m) 1.44 (3 H, s) 1.23 (4 H, s) | {5-Cyclobutyl-2-[2-(3,6-difluoro-pyridin-2-ylamino)-pyridin-4-yl]-pyrido[3,4-d]pyrimidin-4-yl}-(3,3-dimethyl-piperidin-4-yl)-methyl-amine |
| 3 | 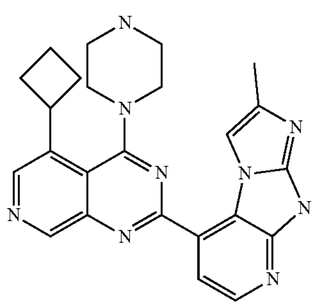 [SMILES: Cc1cn2c(n1)[nH]c1nccc(-c3nc(N4CCNCC4)c4c(C5CCC5)cncc4n3)c12] | [D17] | 440 (M + H)+ | 1H NMR (400 MHz, CD3OD) δ ppm 9.50 (1 H, s) 8.90 (1 H, s) 8.78 (1 H, d, J = 1.3 Hz) 8.56 (1 H, d, J = 6.8 Hz) 8.03 (1 H, d, J = 6.8 Hz) 4.36 (3 H, t, J = 8.3 Hz) 4.01-4.18 (2 H, m) 3.45-3.59 (3 H, m) 2.53-2.72 (5 H, m) 2.21-2.41 (3 H, m) 2.07 (1 H, t, J = 7.5 Hz). | 4-(5-Cyclobutyl-4-piperazin-1-yl-pyrido[3,4-d]pyrimidin-2-yl)-2-methyl-8H-1,3a,7,8-tetraaza-cyclopenta[a]indene |
| 4 | Chiral | [D4], [D3] | 470.04 (M + H)+ | 1H NMR (400 MHz, DMSO-d6) δ ppm 13.25 (1 H, br. s.), 9.60 (2 H, br. s), 9.42 (1 H, s), 8.67 (1 H, d, J = 5.02 Hz), 8.54 (1 H, s), 8.38 (1 H, d, J = 4.77 Hz), 8.04 (1 H, s), 5.28 (1 H, dd, J = 12.05, 5.02 Hz), 4.97 (1 H, dd, J = 12.05, 5.77 Hz), 4.11-4.24 (2 H, m), 3.85 (1 H, br. d, J = 11.00 Hz), 3.48-3.67 (3 H, m), 3.12-3.41 (3 H, m), 2.70-2.89 (1 H, m), 1.08-1.14 (2 H, m), 1.00-1.08 (1 H, m), 0.85-0.93 (1 H, m) | {(S)-1-[5-Cyclopropyl-2-(2-trifluoromethyl-1H-pyrrolo[2,3-b]pyridin-4-yl)-pyrido[3,4-d]pyrimidin-4-yl]-piperazin-2-yl}-methanol |

TABLE A-continued

| Ex | Structure | Scheme | LCMS | 1H-NMR | Name |
|---|---|---|---|---|---|
| 5 | 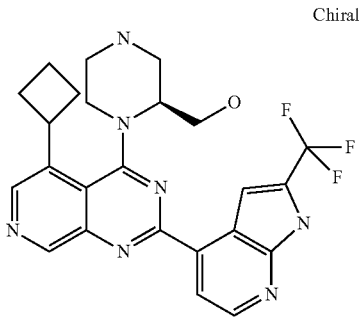 [SMILES: OC[C@@H]1CNCCN1c1nc(-c2ccnc3[nH]c(C(F)(F)F)cc23)nc2cncc(C3CCC3)c12] | Chiral | [D4], [D3] 484.07 (M + H)+ | H NMR (400 MHz, DMSO-d6) δ ppm 13.25 (br. s., 1 H), 9.48-9.81 (br s, 2 H), 9.46 (s, 1 H), 8.74 (s, 1 H), 8.67 (d, J = 5.0 Hz, 1 H), 8.37 (d, J = 5.0 Hz, 1 H), 8.04 (s, 1 H), 5.30 (dd, J = 12.0, 4.3 Hz, 1 H), 4.95 (dd, J = 12.2, 6.4 Hz, 1 H), 4.37-4.51 (m, 1 H), 4.16 (br. s., 1 H), 3.87 (d, J = 11.3 Hz, 2H), 3.57 (dd, J = 16.1, 11.3 Hz, 2 H), 3.17-3.36 (m, 4 H), 2.38-2.48 (m, 3 H), 2.15-2.27 (m, 1 H), 2.03-2.15 (m, 1 H), 1.76-1.97 (m, 1 H) | {(S)-1-[5-Cyclobutyl-2-(2-trifluoromethyl-1H-pyrrolo[2,3-b]pyridin-4-yl)-pyrido[3,4-d]pyrimidin-4-yl]-piperazin-2-yl}-methanol |
| 6 | 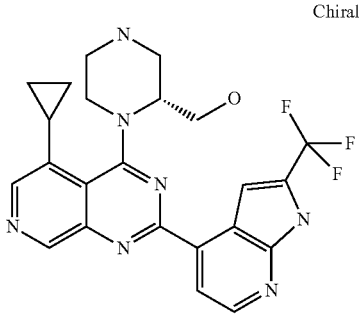 [SMILES: OC[C@H]1CNCCN1c1nc(-c2ccnc3[nH]c(C(F)(F)F)cc23)nc2cncc(C3CC3)c12] | Chiral | [D4], [D3] 470.05 (M + H)+ | 1H NMR (400 MHz, DMSO-d6) δ ppm 13.26 (br. s., 1 H), 9.65 (br. s., 2 H), 9.42 (s, 1 H), 8.68 (d, J = 5.0 Hz, 1 H), 8.55 (s, 1 H), 8.37 (d, J = 4.8 Hz, 1 H), 8.04 (s, 1 H), 5.27 (dd, J = 11.9, 4.9 Hz, 1 H), 4.96 (dd, J = 12.0, 5.8 Hz, 1 H), 4.15 (br. s., 2 H), 3.84 (d, J = 11.5 Hz, 2 H), 3.51-3.66 (m, 2 H), 3.15-3.34 (m, 3 H), 2.75-2.85 (m, 1 H), 1.01-1.15 (m, 3 H), 0.85-1.01 (m, 1 H) | {(R)-1-[5-Cyclopropyl-2-(2-trifluoromethyl-1H-pyrrolo[2,3-b]pyridin-4-yl)-pyrido[3,4-d]pyrimidin-4-yl]-piperazin-2-yl}-methanol |
| 7 | 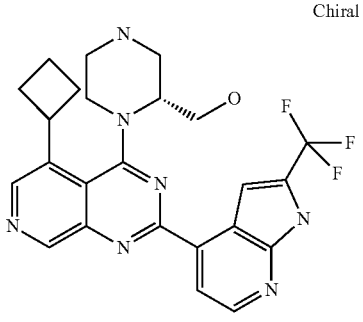 [SMILES: OC[C@H]1CNCCN1c1nc(-c2ccnc3[nH]c(C(F)(F)F)cc23)nc2cncc(C3CCC3)c12] | Chiral | [D4], [D3] 484.07 (M + H)+ | 1H NMR (400 MHz, DMSO-d6) δ ppm 13.25 (br. s., 1 H), 9.70 (br. s, 2 H), 9.38-9.52 (m, 1 H), 8.74 (s, 1 H), 8.67 (d, J = 4.8 Hz, 1 H), 8.37 (d, J = 5.0 Hz, 1 H), 8.05 (s, 1 H), 5.32 (dd, J = 12.0, 4.3 Hz, 1 H), 4.9 5(dd, J = 12.3, 6.3 Hz, 1 H), 4.43 (quin, J = 8.5 Hz, 2 H), 4.17 (br. s., 2 H), 3.89 (d, J = 11.3 Hz, 2H), 3.58 (dd, J = 17.9, 11.4 Hz, 2 H), 3.16-3.36 (m, 3 H), 2.39-2.48 (m, 3 H), 2.16-2.27 (m, 1 H), 2.02-2.16 (m, 1 H), 1.87 (d, J = 6.3 Hz, 1 H) | {(R)-1-[5-Cyclobutyl-2-(2-trifluoromethyl-1H-pyrrolo[2,3-b]pyridin-4-yl)-pyrido[3,4-d]pyrimidin-4-yl]-piperazin-2-yl}-methanol |
| 8 | 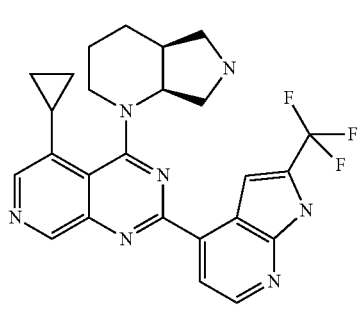 [SMILES: FC(F)(F)c1cc2c(-c3nc(N4CCC[C@H]5CNC[C@H]54)c4c(C5CC5)cncc4n3)ccnc2[nH]1] | | [D4], [D3] 480.14 (M + H)+ | 1H NMR (400 MHz, DMSO-d6) δ ppm 13.19 (br. s., 1H) 13.12-13.27 (m, 3 H), 9.22 (br. s., 1 H), 8.85-9.15 (m, 2 H), 8.65 (d, J = 4.8 Hz, 1 H), 8.24-8.32 (m, 1 H) 8.19 (br. s., 1 H), 8.02 (br. s., 1 H), 5.13 (br. s., 1 H), 4.85 (br. s., 1 H), 3.97 (br. s., 1 H), 3.75 (br. s., 2 H), 3.29-3.46 (m, 1 H), 3.21 (br. s., 1 H), 3.06 (br. s., 1 H), 2.65 (br. s., 1 H), 1.85 (br. s., 3 H), 1.22-1.62 (m, 1 H), 1.10-1.22 (m, 1 H), 1.05 (br. s., 1 H) | (±)-5-Cyclopropyl-4-(4,7-cis)-octahydro-pyrrolo[3,4-b]pyridin-1-yl-2-(2-trifluoromethyl-1H-pyrrolo[2,3-b]pyridin-4-yl)-pyrido[3,4-d]pyrimidine |

TABLE A-continued

| Ex | Structure | Scheme | Analysis LCMS | 1H-NMR | Name |
|---|---|---|---|---|---|
| 9 | 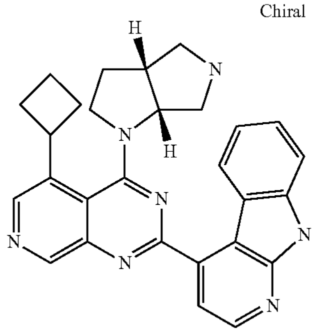 [SMILES: c1ccc2c(c1)[nH]c1nccc(-c3nc(N4CC[C@@H]5CNC[C@@H]54)c4c(C5CCC5)cncc4n3)c12] | Chiral [D3] | 462 (M + H)+ | 1H NMR (400 MHz, DMSO-d6) δ ppm 12.07 (1 H, s) 9.12 (2 H, br. s.) 8.99 (1 H, br. s.) 8.86 (1 H, br. s.) 8.53-8.66 (2 H, m) 7.89 (1 H, d, J = 5.0 Hz) 7.40-7.60 (2 H, m) 7.17 (1 H, td, J = 7.5, 1.3 Hz) 5.15 (1 H, br. s.) 4.22 (1 H, t, J = 8.4 Hz) 4.03 (1 H, br. s.) 3.19-3.75 (5 H, m) 3.06 (1 H, br. s.) 2.67 (1 H, dd, J = 3.8, 1.8 Hz) 2.45 (3 H, br. s.) 1.82-2.05 (3 H, m) | 4-((R)-5-Cyclobutyl-4-(R)-hexahydro-pyrrolo[3,4-b]pyrrol-1-yl-pyrido[3,4-d]pyrimidin-2-yl)-9H-pyrido[2,3-b]indole |
| 10 | 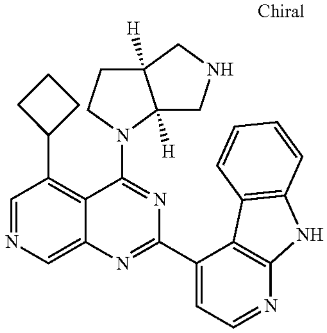 [SMILES: c1ccc2c(c1)[nH]c1nccc(-c3nc(N4CC[C@H]5CNC[C@H]54)c4c(C5CCC5)cncc4n3)c12] | Chiral [D3] | 462 (M + H)+ | 1H NMR (400 MHz, DMSO-d6) δ ppm 12.07 (1 H, s) 9.12 (1 H, s) 8.72-8.98 (1 H, m) 8.48-8.67 (1 H, m) 7.89 (1 H, d, J = 5.0 Hz) 7.41-7.59 (1 H, m) 7.17 (1 H, ddd, J = 8.2, 7.0, 1.1 Hz) 5.14 (1 H, br. s.) 4.22 (1 H, t, J = 8.4 Hz) 4.01 (1 H, br. s.) 3.60-3.76 (1 H, m) 2.95-3.59 (2 H, m) 2.59-2.75 (1 H, m) 1.82-2.20 (4 H, m) | 4-((S)-5-Cyclobutyl-4-(S)-hexahydro-pyrrolo[3,4-b]pyrrol-1-yl-pyrido[3,4-d]pyrimidin-2-yl)-9H-pyrido[2,3-b]indole |
| 11 | 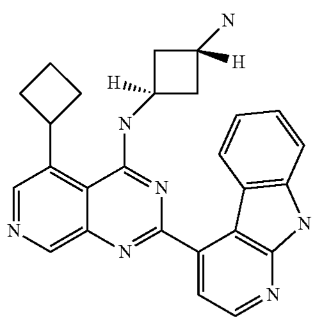 [SMILES: N[C@H]1C[C@H](Nc2nc(-c3ccnc4[nH]c5ccccc5c34)nc3cncc(C4CCC4)c23)C1] | [D3] | 436 (M + H)+ | 1H NMR (400 MHz, DMSO-d6) δ ppm 12.05 (1 H, s) 9.13 (1 H, br. s.) 8.42-8.66 (3 H, m) 8.05 (3 H, d, J = 4.0 Hz) 7.78 (1 H, d, J = 5.3 Hz) 7.40-7.60 (3 H, m) 7.15 (1 H, ddd, J = 8.1, 7.0, 1.3 Hz) 4.96-5.11 (2 H, m) 4.52-4.76 (2 H, m) 3.85 (1 H, d, J = 4.5 Hz) 2.52-2.79 (6 H, m) 1.73-2.42 (5 H, m) | trans-N-[5-Cyclobutyl-2-(9H-pyrido[2,3-b]indol-4-yl)-pyrido[3,4-d]pyrimidin-4-yl]-cyclobutane-1,3-diamine |
| 12 | 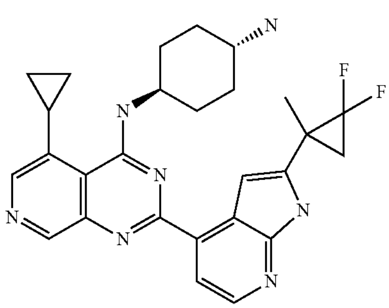 [SMILES: CC1(c2cc3c(-c4nc(N[C@H]5CC[C@H](N)CC5)c5c(C6CC6)cncc5n4)ccnc3[nH]2)CC1(F)F] | [D4], [D3] | 491 (M + H)+ | | trans-N-{5-Cyclopropyl-2-[2-(2,2-difluoro-1-methyl-cyclopropyl)-1H-pyrrolo[2,3-b]pyridin-4-yl]-pyrido[3,4-d]pyrimidin-4-yl}-cyclohexane-1,4-diamine |

TABLE A-continued

| Ex | Structure | Scheme | Analysis LCMS | 1H-NMR | Name |
|---|---|---|---|---|---|
| 13 | 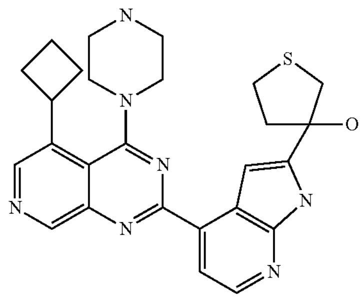 [SMILES: OC1(c2cc3c(-c4nc(N5CCNCC5)c5c(C6CCC6)cncc5n4)ccnc3[nH]2)CCSC1] | [D4], [D3] | 488 (M + H)+ | | 3-[4-(5-Cyclobutyl-4-piperazin-1-yl-pyrido[3,4-d]pyrimidin-2-yl)-1H-pyrrolo[2,3-b]pyridin-2-yl]-tetrahydro-thiophen-3-ol |
| 14 | 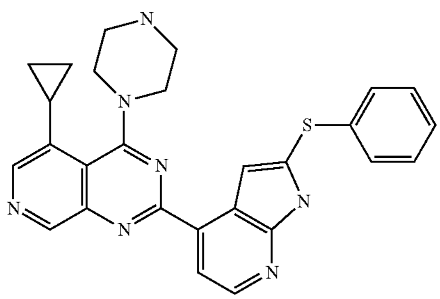 [SMILES: c1ccc(Sc2cc3c(-c4nc(N5CCNCC5)c5c(C6CC6)cncc5n4)ccnc3[nH]2)cc1] | [D4], [D3] | 480 (M + H)+ | | 5-Cyclopropyl-2-(2-phenylsulfanyl-1H-pyrrolo[2,3-b]pyridin-4-yl)-4-piperdzin-1-yl-pyrido[3,4-d]pyrimidine |
| 15 | 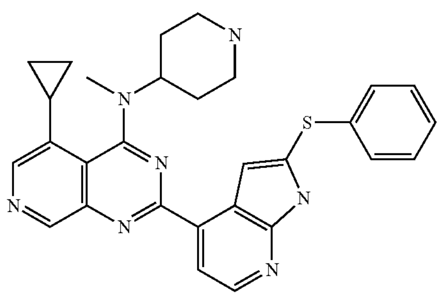 [SMILES: CN(c1nc(-c2ccnc3[nH]c(Sc4ccccc4)cc23)nc2cncc(C3CC3)c12)C1CCNCC1] | [D4], [D3] | 508 (M + H)+ | | [5-Cyclopropyl-2-(2-phenylsulfanyl-1H-pyrrolo[2,3-b]pyridin-4-yl)-pyrido[3,4-d]pyrimidin-4-yl]-methyl-piperidin-4-yl amine |
| 16 | 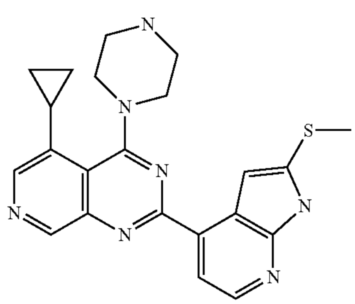 [SMILES: CSc1cc2c(-c3nc(N4CCNCC4)c4c(C5CC5)cncc4n3)ccnc2[nH]1] | [D4], [D3] | 418 (M + H)+ | | 5-Cyclopropyl-2-(2-methylsulfanyl-1H-pyrrolo[2,3-b]pyridin-4-yl)-4-piperazin-1-yl pyrido[3,4-d]pyrimidine |
| 17 | 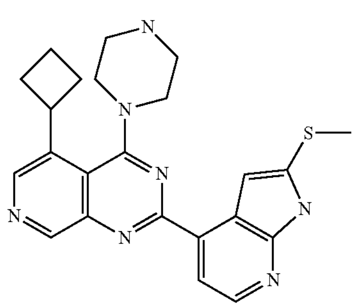 [SMILES: CSc1cc2c(-c3nc(N4CCNCC4)c4c(C5CCC5)cncc4n3)ccnc2[nH]1] | [D4], [D3] | 432 (M + H)+ | | 5-Cyclobutyl-2-(2-methylsulfanyl-1H-pyrrolo[2,3-b]pyridin-4-yl)-4-piperazin-1-yl pyrido[3,4-d] pyrimidine |

TABLE A-continued

| Ex | Structure | Scheme | Analysis | | Name |
| --- | --- | --- | --- | --- | --- |
| | | | LCMS | 1H-NMR | |
| 18 | 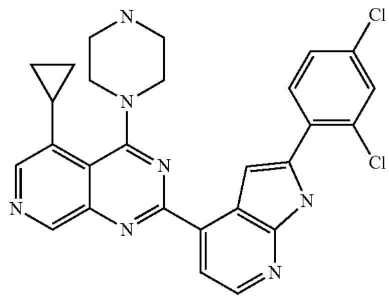 | [D4], [D3] | 516.08 (M + H)+ | 1H NMR (400 MHz, DMSO-d6) δ 12.37 (s, 1H), 9.14 (s, 1H),, 9.00-8.94 (br s, 2H), 8.48 (d, 1H, J = 5.0 Hz), 8.20-8.19 (m, 2H), 7.96 (d, 1H, J = 1.8 Hz), 7.88-7.84 (m, 2H), 7.64-7.62 (m, 1H), 3.78 (m, 4H), 3.37 (m, 4H), 2.79-2.73 (m, 1H), 1.29-1.26 (m, 2H), 1.10-1.08 (m, 2H) | 5-Cyclopropyl-2-[2-(2,4-dichloro-phenyl)-1H-pyrrolo[2,3-b]pyridin-4-yl]-4-piperazin-1-yl-pyrido[3,4-d]pyrimidine |
| 19 | 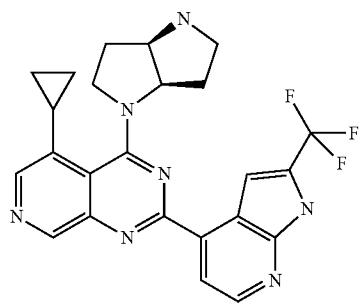 [SMILES: FC(F)(F)c1cc2c(-c3nc(N4CC[C@H]5NCC[C@H]54)c4c(C5CC5)cncc4n3)ccnc2[nH]1] | [D4], [D3] | 466.13 (M + H)+ | 1H NMR (400 MHz, DMSO-d6) δ ppm 13.16 (br. s., 1 H), 9.39 (br. s., 1 H), 9.26 (br. s., 1 H), 9.09 (s, 1 H), 8.64 (d, J = 4.8 Hz, 1 H), 8.28 (d, J = 4.8 Hz, 1 H), 7.94 (s, 1 H), 5.32-5.42 (m, 1 H), 4.28-4.44 (m, 2 H), 3.45-3.65 (m, 2 H), 3.38 (d, J = 6.3 Hz, 1 H), 2.44-2.50 (m, 2 H), 2.33-2.43 (m, 1 H), 2.24-2.33 (m, 1 H), 2.05-2.24 (m, 1 H), 1.35-1.44 (m, 1 H), 1.11-1.22 (m, 1 H), 1.01-1.11 (m, 1 H), 0.91-1.01 (m, 1 H) | (±)-5-Cyclopropyl-4-(3,6-cis)-hexahydro-pyrrolo[3,2-b]pyrrol-1-yl-2-(2-trifluoromethyl-1H-pyrrolo[2,3-b]pyridin-4-yl)-pyrido[3,4-d]pyrimidine |
| 20 | Chiral | [D4], [D3] | 466.13 (M + H)+ | 1H NMR (400 MHz, DMSO-d6) δ ppm 13.16 (br. s., 1 H), 9.31 (br. s., 2 H), 9.10 (s, 1 H), 8.64 (d, J = 5.0 Hz, 1 H), 8.25 (d, J = 5.0 Hz, 1 H), 8.15 (s, 1 H), 7.91 (d, J = 1.0 Hz, 1 H), 5.17-5.23 (m, 1 H), 4.24-4.40 (m, 1 H), 3.72-3.84 (m, 2 H), 3.39-3.63 (m, 2 H), 3.26-3.36 (m, 1 H), 3.12-3.22 (m, 1 H), 1.90- 2.04 (m, 2H), 1.37-1.46 (m, 1 H), 1.08-1.26 (m, 2 H), 0.91-1.07 (m, 1 H) | 5-Cyclopropyl-4-(3aS,6aS)-hexahydro-pyrrolo[3,4-b]pyrrol-1-yl-2-(2-trifluoromethyl-1H-pyrrolo[2,3-b]pyridin-4-yl)-pyrido[3,4-d]pyrimidine |
| 21 | Chiral | [D4], [D3] | 466.12 (M + H)+ | 1H NMR (400 MHz, DMSO-d6) δ ppm 13.16 (br. s., 1 H), 9.30 (br. s., 2 H), 9.10 (s, 1 H), 8.64 (d, J = 5.0 Hz, 1 H), 8.25 (d, J = 5.0 Hz, 1 H), 8.15 (s, 1 H), 7.91 (br. d, J = 1.3 Hz, 1 H), 5.14-5.27 (m, 1 H), 4.27-4.37 (m, 2 H), 3.70-3.86 (m, 2 H), 3.43-3.62 (m, 2 H), 3.23-3.38 (m, 1 H), 3.10-3.23 (m, 1 H), 2.48 (d, J = 2.8 Hz, 1 H), 1.91-2.04 (m, 2H), 1.37-1.46 (m, 1 H), 1.10-1.27 (m, 2 H), 0.90-1.07 (m, 1 H) | 5-Cyclopropyl-4-(3aR,6aR)-hexahydro-pyrrolo[3,4-b]pyrrol-1-yl-2-(2-trifluoromethyl-1H-pyrrolo[2,3-b]pyridin-4-yl)-pyrido[3,4-d]pyrimidine |

TABLE A-continued

| Ex | Structure | Scheme | LCMS | 1H-NMR | Name |
|---|---|---|---|---|---|
| 22 | 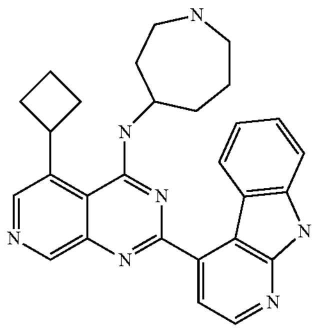 [SMILES: c1ccc2c(c1)[nH]c1nccc(-c3nc(NC4CCCNCC4)c4c(C5CCC5)cncc4n3)c12] | [D3] | 464 (M + H)+ | 1H NMR (400 MHz, DMSO-d6) δ ppm 12.03 (1 H, s) 9.12 (1 H, s) 8.44-8.66 (5 H, m) 7.82 (1 H, d, J = 5.0 Hz) 7.42-7.61 (2 H, m) 6.99-7.24 (2 H, m) 4.58 (3 H, dd, J = 17.3, 8.5 Hz) 2.98-3.39 (5 H, m) 2.12-2.42 (7 H, m) 1.63-2.00 (5 H, m) | Azepan-4-yl-[5-cyclobutyl-2-(9H-pyrido[2,3-b]indol-4-yl)-pyrido[3,4-d]pyrimidin-4-yl]-amine |
| 23 | 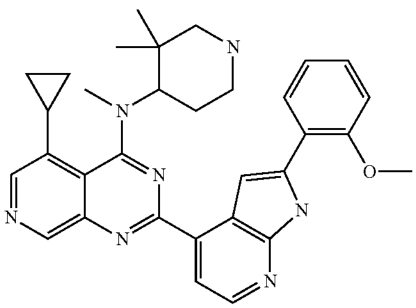 [SMILES: COc1ccccc1-c1cc2c(-c3nc(N(C)C4CCNCC4(C)C)c4c(C5CC5)cncc4n3)ccnc2[nH]1] | [D4], [D3] | 534.25 (M + H)+ | 1H NMR (400 MHz, DMSO-d6) δ 12.07 (br s, 1H), 9.12 (m, 2H), 8.42-8.35 (m, 2H), 8.16 (br s, 2H), 7.99-7.94 (m, 2H), 7.44-7.40 (m, 1H), 7.23 (d, 1H, J = 7.9 Hz), 7.14-7.10 (m, 1H), 5.61 (m, 1H), 4.19 (m, 2H), 3.99 (s, 3H), 3.49-2.68 (m, 7H), 2.23-1.96 (m, 2H), 1.47-0.92 (m, 9H) | {5-Cyclopropyl-2-[2-(2-methoxy-phenyl)-1H-pyrrolo[2,3-b]pyridin-4-yl]-pyrido[3,4-d]pyrimidin-4-yl}-(3,3-dimethyl-piperidin-4-yl)-methyl-amine |
| 24 | 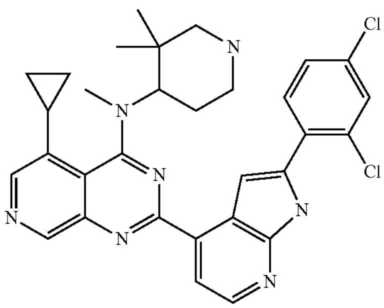 [SMILES: CN(c1nc(-c2ccnc3[nH]c(-c4ccc(Cl)cc4Cl)cc23)nc2cncc(C3CC3)c12)C1CCNCC1(C)C] | [D4], [D3] | 572.17 (M + H)+ | 1H NMR (400 MHz, DMSO-d6) δ 12.34 (br s, 1H), 9.07 (m, 2H), 8.47 (d, 1H, J = 5.0 Hz), 8.28-8.14 (m, 3H), 7.95-7.84 (m, 3H), 7.64-7.61 (m, 1H), 5.59 (br s, 1H), 3.49-2.67 (m, 8H), 2.33-1.95 (m, 2H), 1.46-0.82 (m, 10H) | {5-Cyclopropyl-2-[2-(2,4-dichloro-phenyl)-1H-pyrrolo[2,3-b]pyridin-4-yl]-pyrido[3,4-d]pyrimidin-4-yl}-(3,3-dimethyl-piperidin-4-yl)-methyl-amine |
| 25 | 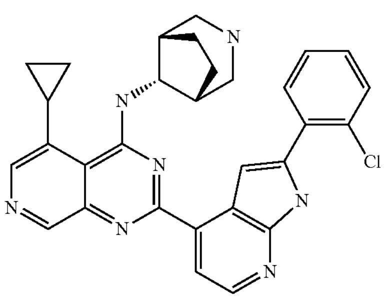 [SMILES: Clc1ccccc1-c1cc2c(-c3nc(N[C@H]4[C@@H]5CC[C@H]4CNC5)c4c(C5CC5)cncc4n3)ccnc2[nH]1] | [D4], [D3] | 522.18 (M + H)+ | 1H NMR (400 MHz, DMSO-d6) δ 12.27 (d, 1H, J = 1.6 Hz), 9.16 (s, 1H), 8.89 (m, 1H), 8.54 (s, 1H), 8.49-8.44 (m, 2H), 8.14 (d, 1H, J = 5.0 Hz), 7.93 (m, 1H), 7.85-7.81 (m, 2H), 7.68-7.66 (m, 1H), 7.55-7.46 (m, 2H), 4.33-4.31 (m, 1H), 3.31-3.26 (m, 2H), 3.11-3.08 (m, 2H), 2.85-2.80 (m, 3H), 2.02-1.99 (m, 2H), 1.88-1.84 (m, 2H), 1.26-1.21 (m, 2H), 1.13-1.10 (m, 2H) | (1R,5S,8R)-3-Aza-bicyclo[3.2.1]oct-8-yl-{2-[2-(2-chloro-phenyl)-1H-pyrrolo[2,3-b]pyridin-4-yl]-5-cyclopropyl-pyrido[3,4-d]pyrimidin-4-yl}-amine |
| 26 | 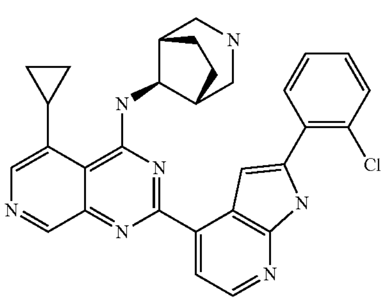 [SMILES: Clc1ccccc1-c1cc2c(-c3nc(N[C@@H]4[C@@H]5CC[C@H]4CNC5)c4c(C5CC5)cncc4n3)ccnc2[nH]1] | [D4], [D3] | 522.18 (M + H)+ | 1H NMR (400 MHz, DMSO-d6) δ 12.25 (d, 1H, J = 1.8 Hz), 9.16-9.06 (m, 2H), 8.46 (m, 3H), 8.20 (d, 1H, J = 5.0 Hz), 7.93 (d, 2H, J = 2.2 Hz), 7.83 (m, 1H), 7.66 (m, 1H), 7.59 (m, 1H), 7.51 (m, 2H), 4.62 (m, 1H), 3.33 (m, 4H), 2.79 (m, 2H), 2.59 (m, 1H), 2.10 (m, 2H), 1.88 (m, 2H), 1.15 (m, 4H) | (1R,5S,8S)-3-Aza-bicyclo[3.2.1]oct-8-yl-{2-[2-(2-chloro-phenyl)-1H-pyrrolo[2,3-b]pyridin-4-yl]-5-cyclopropyl-pyrido[3,4-d]pyrimidin-4-yl}-amine |

TABLE A-continued

| Ex | Structure | Scheme | LCMS | 1H-NMR | Name |
|---|---|---|---|---|---|
| 27 | 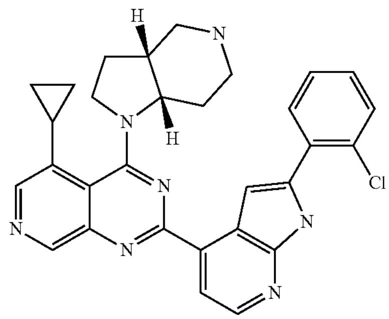 [SMILES: Clc1ccccc1-c1cc2c(-c3nc(N4CC[C@@H]5CNCC[C@@H]54)c4c(C5CC5)cncc4n3)ccnc2[nH]1] | [D4], [D3] | 523.15 (M + H)+ | 1H NMR (400 MHz, DMSO-d6) δ 12.29 (d, 1H, J = 1.6 Hz), 9.05 (s, 1H), 8.66 (m, 2H), 8.45 (d, 1H, J = 5.0 Hz), 8.12 (d, 1H, J = 5.0 Hz), 7.89 (d, 1H, J = 2.1 Hz), 7.84-7.82 (m, 1H), 7.69-7.66 (m, 1H), 7.55-7.45 (m, 2H), 4.63-4.37 (m, 3H), 3.41-3.23 (m, 3H), 2.97 (m, 2H), 2.75-2.67 (m, 2H), 2.20 (m, 1H), 1.92-1.87 (m, 1H), 1.50-1.44 (m, 1H), 1.22-1.15 (m, 1H), 1.13-1.06 (m, 1H), 0.96-0.90 (m, 1H) | (±)-2-[2-(2-Chloro-phenyl)-1H-pyrrolo[2,3-b]pyridin-4-yl]-5-cyclopropyl-4-(3aR,7aS)-octahydro-pyrrolo[3,2-c]pyridin-1-yl-pyrido[3,4-d]pyrimidine |
| 28 | 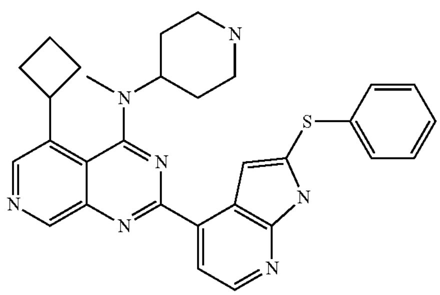 [SMILES: CN(c1nc(-c2ccnc3[nH]c(Sc4ccccc4)cc23)nc2cncc(C3CCC3)c12)C1CCNCC1] | [D4], [D3] | 522 (M + H)+ | | [5-Cyclobutyl-2-(2-phenylsulfanyl-1H-pyrrolo[2,3-b]pyridin-4-yl)-pyrido[3,4-d]pyrimidin-4-yl]-methyl-piperidin-4-yl-amine |
| 29 | 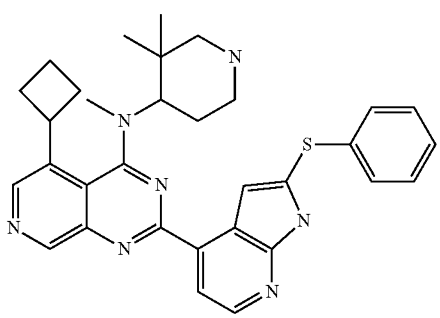 | [D4], [D3] | 536 (M + H)+ | | [5-Cyclopropyl-2-(2-phenylsulfanyl-1H-pyrrolo[2,3-b]pyridin-4-yl)-pyrido[3,4-d]pyrimidin-4-yl]-(3,3-dimethyl-piperidin-4-yl)-methyl-amine |
| 30 | 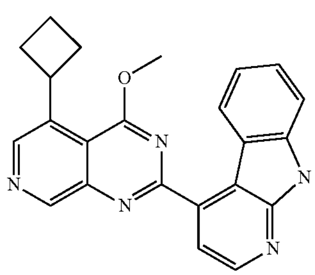 [SMILES: COc1nc(-c2ccnc3[nH]c4ccccc4c23)nc2cncc(C3CCC3)c12] | [D3] | 382.03 (M + H)+ | (400 MHz, d6-DMSO, δ): 12.10 (s, 1H), 9.35 (s, 1H), 8.77 (d, J = 0.9 Hz, 1H), 8.68 (d, J = 8.2 Hz, 1H), 8.60 (d, J = 5.0 Hz, 1H), 7.91 (d, J = 5.1 Hz, 1H), 7.59 (d, J = 8.0 Hz, 1H), 7.52-7.47 (m, 1H), 7.22-7.17 (m, 1H), 4.45-4.35 (m, 1H), 4.29 (s, 3H), 2.54-2.45 (m, 1H), 2.41-2.29 (m, 3H), 2.16-2.04 (m, 1H), 1.92-1.83 (m, 1H). | 4-(5-Cyclobutyl-4-methoxy-pyrido[3,4-d]pyrimidin-2-yl)-9H-pyrido[2,3-b]indole |
| 31 | 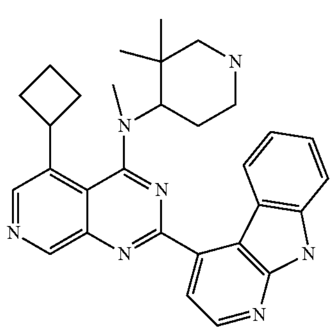 [SMILES: CN(c1nc(-c2ccnc3[nH]c4ccccc4c23)nc2cncc(C3CCC3)c12)C1CCNCC1(C)C] | [D3] | 492.22 (M + H)+ | (400 MHz, d6-DMSO, δ): 12.06 (s, 1H), 9.17 (s, 1H), 9.07 (s, 1H), 8.91-8.81 (m, 1H), 8.62 (d, J = 8.1 Hz, 1H), 8.57 (d, J = 5.1 Hz, 1H), 8.27-8.14 (m, 1H), 7.77 (d, J = 5.1 Hz, 1H), 7.54 (d, J = 8.0 Hz, 1H), 7.51-7.46 (m, 1H), 7.19-7.13 (m, 1H), 5.54-5.47 (m, 1H), 4.41-4.431 (m, 1H), 3.43-3.36 (m, 1H), 3.26-3.09 (m, 2H), 3.04-2.83 (m, 4H), 2.77-2.67 (m, 2H), 2.33-1.88 (m, 6H), 1.40 (s, 3H), 1.16 (s, 3H) | [5-Cyclobutyl-2-(9H-pyrido[2,3-b]indol-4-yl)-pyrido[3,4-d]pyrimidin-4-yl]-(3,3-dimethyl-piperidin-4-yl)-methyl-amine |

TABLE A-continued

| Ex | Structure | Scheme | Analysis | | Name |
| --- | --- | --- | --- | --- | --- |
| | | | LCMS | 1H-NMR | |
| 32 | 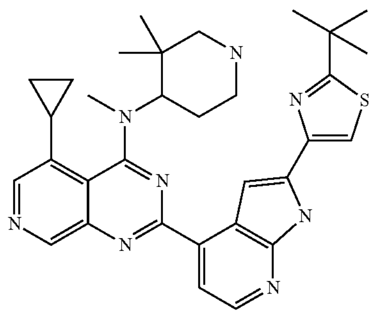 [SMILES: CN(c1nc(-c2ccnc3[nH]c(-c4csc(C(C)(C)C)n4)cc23)nc2cncc(C3CC3)c12)C1CCNCC1(C)C] | [D4], [D3] | 567.26 (M + H)+ | 1H NMR (400 MHz, DMSO-d6) δ ppm 12.35 (s, 1 H), 9.08 (br. s., 1 H), 8.94 (d, J = 11.8 Hz, 1 H), 8.40 (d, J = 5.0 Hz, 1 H), 8.18-8.33 (m, 1 H), 8.15 (br. s., 1H), 8.08-8.13 (m, 2 H), 7.81 (br. s., 1 H), 5.63 (br. s., 1H), 2.96-3.26 (m, 5H), 2.22 (br. s., 1 H), 1.91 (s, 1 H), 1.48 (s, 9 H), 1.14-1.40 (m, 6 H), 1.12 (s, 2 H), 0.99 (br. s., 1 H) | {2-[2-(2-tert-Butyl-thiazol-4-yl)-1H-pyrrolo[2,3-b]pyridin-4-yl]-5-cyclopropyl-pyrido[3,4-d]pyrimidin-4-yl}-(3,3-dimethyl-piperidin-4-yl)-methyl-amine |
| 33 | 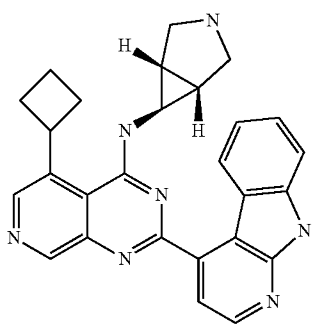 [SMILES: c1ccc2c(c1)[nH]c1nccc(-c3nc(N[C@H]4[C@@H]5CNC[C@@H]54)c4c(C5CCC5)cncc4n3)c12] | [D3] | 448 (M + H)+ | 1H NMR (400 MHz, DMSO-d6) δ ppm 12.04 (1 H, s) 9.16 (1 H, s) 9.00 (1 H, br. s.) 8.70 (1H, d, J = 8.0 Hz) 8.41-8.59 (2 H, m) 7.93 (1H, d, J = 5.0 Hz) 7.40-7.63 (3 H, m) 7.20 (1H, ddd, J = 8.1, 7.0, 1.3 Hz) 4.45-4.64 (2 H, m) 3.14-3.47 (5 H, m) 3.02 (1 H, d, J = 2.5 Hz) 1.71-2.16 (2 H, m) | (2R,6S)-3-Aza-bicyclo[3.1.0]hex-6-yl-[(S)-5-cyclobutyl-2-(9H-pyrido[2,3-b]indol-4-yl)-pyrido[3,4-d]pyrimidin-4-yl]-amine |
| 34 | 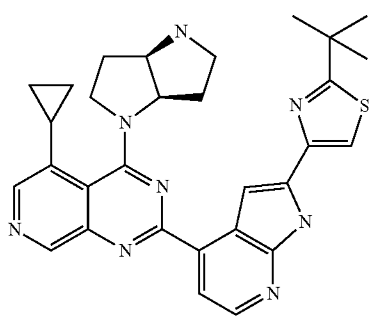 [SMILES: CC(C)(C)c1nc(-c2cc3c(-c4nc(N5CC[C@H]6NCC[C@H]65)c5c(C6CC6)cncc5n4)ccnc3[nH]2)cs1] | [D4], [D3] | 537.23 (M + H)+ | 1H NMR (400 MHz, DMSO-d6) δ ppm 12.37 (d, J = 1.8 Hz, 1H), 9.35 (br. s., 1 H), 9.10 (br. s., 1 H), 9.04 (s, 1 H), 8.40 (d, J = 5.3 Hz, 1 H), 8.21 (s, 1 H), 8.17 (d, J = 5.0 Hz, 1 H), 8.08 (s, 1 H), 7.88 (d, J = 2.0 Hz, 1 H), 5.43 (t, J = 5.3 Hz, 1 H), 4.35 (br. s., 2 H), 3.53-3.63 (m, 1 H), 3.45 (br. s., 2 H), 2.65-2.80 (m, 1 H), 2.53-2.64 (m, 1 H), 2.34-2.46 (m, 1 H), 2.20-2.32 (m, 1 H), 2.03-2.20 (m, 1 H), 1.48 (s, 9 H), 1.34-1.44 (m, 1 H), 1.12-1.24 (m, 1 H), 1.03-1.11 (m, 1H), 0.92-1.03 (m, 1 H) | (±)-2-[2-(2-tert-Butyl-thiazol-4-yl)-1H-pyrrolo[2,3-b]pyridin-4-yl]-5-cyclopropyl-4-(3,6-cis)-hexahydro-pyrrolo[3,2-b]pyrrol-1-yl-pyrido[3,4-d]pyrimidine |
| 35 | 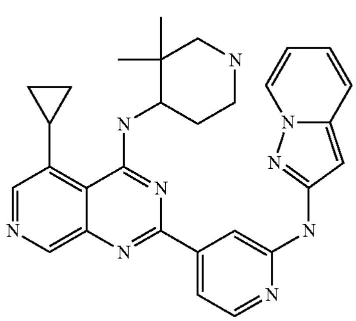 [SMILES: CC1(C)CNCCC1Nc1nc(-c2ccnc(Nc3cc4ccccn4n3)c2)nc2cncc(C3CC3)c12] | [B4] | 506.24 (M + H)+ | (400 MHz, d6-DMSO, δ): 10.40 (br s, 1H), 9.10 (s, 1H), 9.09-9.01 (m, 1H), 8.54 (dd, J = 7.0, 0.7 Hz, 1H), 8.52 (d, J = 0.7 Hz, 1H), 8.40 (d, J = 5.6 Hz, 1H), 8.33-8.20 (m, 2H), 7.87 (d, J = 5.3 Hz, 1H), 7.63 (d, J = 8.8 Hz, 1H), 7.57 (d, J = 8.8 Hz, 1H), 7.23-7.18 (m, 1H), 6.88 (s, 1H), 6.80 (t, J = 6.8 Hz, 1H), 4.89-4.81 (m, 1H), 3.41-3.33 (m, 1H), 3.26-3.05 (m, 3H), 2.65-2.55 (m, 1H), 2.17-2.09 (m, 1H), 2.02-1.89 (m, 1H), 1.31-1.10 (m, 9H). | {5-Cyclopropyl-2-[2-(pyrazolo[1,5-a]pyridin-2-ylamino)-pyridin-4-yl]-pyrido[3,4-d]pyrimidin-4-yl}-(3,3-dimethyl-piperidin-4-yl)-amine |

TABLE A-continued

| Ex | Structure | Scheme | LCMS | 1H-NMR | Name |
|---|---|---|---|---|---|
| 36 | 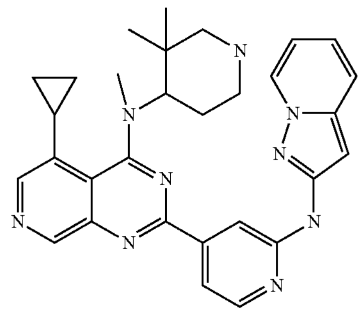 [SMILES: CN(c1nc(-c2ccnc(Nc3cc4ccccn4n3)c2)nc2cncc(C3CC3)c12)C1CCNCC1(C)C] | [B4] | 520.23 (M + H)+ | (400 MHz, d6-DMSO, δ): 10.58 (br s, 1H), 9.18-8.99 (m, 2H), 8.55 (dd, J = 6.9 0.7 Hz, 1H), 8.40 (d, J = 5.6 Hz, 1H), 8.27 (br s, 2H), 8.15 (s, 1H), 7.87(d, J = 5.3 Hz, 1H), 7.59 (d, J = 8.8 Hz, 1H), 7.25-7.19 (m, 1H), 6.91-6.77 (m, 2H), 5.65-5.53 (m, 1H), 3.51-3.43 (m, 1H), 3.40-3.00 (m, 6H), 2.47-2.37 (m, 1H), 2.32-1.75 (m, 2H), 1.55-0.90 (m, 9H). | {5-Cyclopropyl-2-[2-(pyrazolo[1,5-a]pyridin-2-ylamino)-pyridin-4-yl]-pyrido[3,4-d]pyrimidin-4-yl}-(3,3-dimethyl-piperidin-4-yl)-methyl-amine |
| 37 | 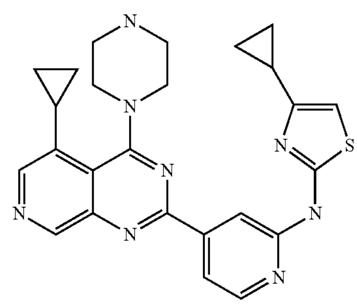 [SMILES: c1cc(-c2nc(N3CCNCC3)c3c(C4CC4)cncc3n2)cc(Nc2nc(C3CC3)cs2)n1] | [B4] | 471.15 (M + H)+ | 1H NMR (400 MHz, DMSO-d6) δ ppm 11.42 (br. s., 1 H), 9.07 (s, 1 H), 9.00 (br. s., 2 H), 8.45 (d, J = 5.3 Hz, 1 H), 8.19 (s, 2 H), 7.85 (dd, J = 5.4, 1.4 Hz, 1 H), 6.63 (s, 1 H), 3.95 (br. s., 4 H), 3.33 (br. s., 4 H), 2.63-2.74 (m, 1 H), 1.91-2.03 (m, 1 H), 1.22-1.30 (m, 2 H), 1.02-1.15 (m, 2 H), 0.73 -0.94 (m, 4 H) | [4-(5-Cyclopropyl-4 piperazin-1-yl-pyrido[3,4-d]pyrimidin-2-yl)-pyridin-2-yl]-(4-cyclopropyl-thiazol-2-yl)-amine |
| 38 | 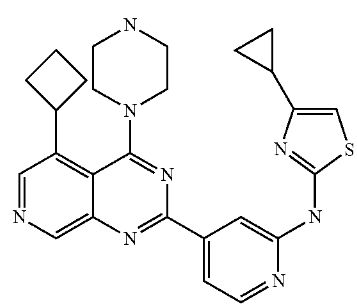 [SMILES: c1cc(-c2nc(N3CCNCC3)c3c(C4CCC4)cncc3n2)cc(Nc2nc(C3CC3)cs2)n1] | [B4] | 485.17 (M + H)+ | 1H NMR (400 MHz, DMSO-d6) δ ppm 11.42 (br. s., 1 H), 9.15 (s, 1 H), 8.89-9.13 (m, 2 H), 8.79 (s, 1 H), 8.39-8.50 (m, 1 H), 8.18 (s, 1 H), 7.84 (dd, J = 5.4, 1.4 Hz, 1 H), 6.63 (s, 1 H), 4.25 (dt, J = 17.3, 8.7 Hz, 1 H), 3.86 (br. s., 4 H), 3.33 (br. s., 2 H), 3.25 (br. s., 2 H), 2.40-2.49 (m, 2 H), 2.15-2.29 (m, 2 H), 2.11 (s, 1 H), 1.87-2.01 (m, 2 H), 0.84-0.91 (m, 2 H), 0.76-0.84 (m, 2H) | [4-(5-Cyclobutyl-4-piperazin-1-yl-pyrido[3,4-d]pyrimidin-2-yl)-pyridin-2-yl]-(4-cyclopropyl-thiazol-2-yl)-amine |
| 39 | 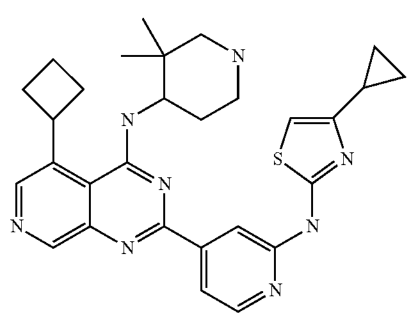 | [B4] | 513.23 (M + H)+ | 1H NMR (400 MHz, DMSO-d6) δ ppm 11.47 (br. s., 1 H), 9.20 (d, J = 11.3 Hz, 1 H), 9.07 (s, 1 H), 8.51 (d, J = 0.8 Hz, 1 H), 8.42-8.47 (m, 1 H), 8.40 (d, J = 9.5 Hz, 1 H), 8.11 (s, 1 H), 7.90 (dd, J = 5.4, 1.4 Hz, 1 H), 7.63 (d, J = 8.8 Hz, 1 H), 6.63 (s, 1 H), 4.79-4.89 (m, 2 H), 3.40 (d, J = 12.0 Hz, 1 H), 3.26 (d, J = 13.1 Hz, 1 H), 3.18 (d, J = 10.5 Hz, 1 H), 3.03-3.14 (m, 1 H), 2.55-2.65 (m, 1 H), 2.07-2.17 (m, 1 H), 1.94-2.03 (m, 2 H), 1.26 (dq, J = 8.3, 5.3 Hz, 1 H), 1.20 (s, 3 H), 1.14-1.19 (m, 2 H), 1.12 (s, 3 H), 0.84-0.91 (m, 2 H), 0.78-0.84 (m, 2 H) | {5-Cyclopropyl-2-[2-(4-cyclopropyl-thiazol-2-ylamino)-pyridin-4-yl]-pyrido[3,4-d]pyrimidin-4-yl}-(3,3-dimethyl-piperidin-4-yl)-amine |

TABLE A-continued

| Ex | Structure | Scheme | Analysis LCMS | 1H-NMR | Name |
|---|---|---|---|---|---|
| 40 | 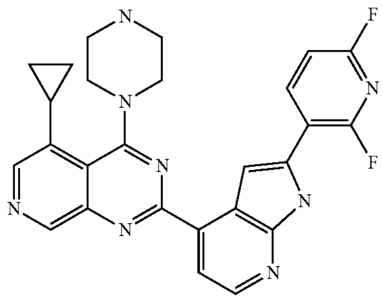 [SMILES: Fc1ccc(-c2cc3c(-c4nc(N5CCNCC5)c5c(C6CC6)cncc5n4)ccnc3[nH]2)c(F)n1] | [D4], [D3] | 486 (M + H)+ | | 5-Cyclopropyl-2-[2-(2,6-difluoro-pyridin-3-yl)-1H-pyrrolo[2,3-b]pyridin-4-yl]-4-piperazin-1-yl-pyrido[3,4-d]pyrimidine |
| 41 | 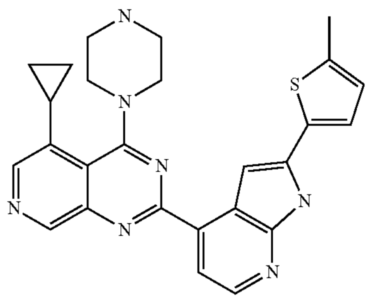 [SMILES: Cc1ccc(-c2cc3c(-c4nc(N5CCNCC5)c5c(C6CC6)cncc5n4)ccnc3[nH]2)s1] | [D4], [D3] | 469 (M + H)+ | | 5-Cyclopropyl-2-[2-(5-methyl-thiophen-2-yl)-1H-pyrrolo[2,3-b]pyridin-4-yl]-4-piperazin-1-yl-pyrido[3,4-d]pyrimidine |
| 42 | 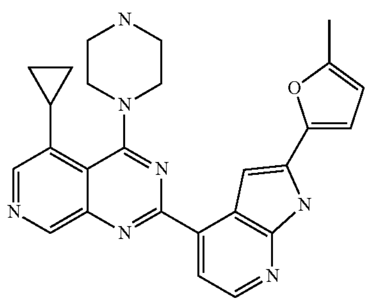 [SMILES: Cc1ccc(-c2cc3c(-c4nc(N5CCNCC5)c5c(C6CC6)cncc5n4)ccnc3[nH]2)o1] | [D4], [D3] | 452.9 (M + H)+ | | 5-Cyclopropyl-2-[2-(5-methyl-furan-2-yl)-1H-pyrrolo[2,3-b]pyridin-4-yl]-4-piperazin-1-yl-pyrido[3,4-d]pyrimidine |
| 43 | 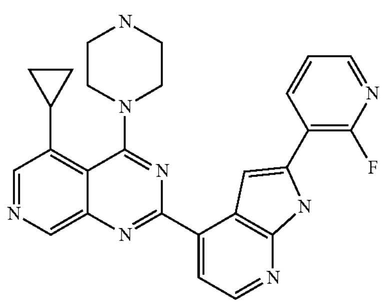 [SMILES: Fc1ncccc1-c1cc2c(-c3nc(N4CCNCC4)c4c(C5CC5)cncc4n3)ccnc2[nH]1] | [D4], [D3] | 468 (M + H)+ | | 5-Cyclopropyl-2-[2-(2-fluoro-pyridin-3-yl)-1H-pyrrolo[2,3-b]pyridin-4-yl]-4-piperazin-1-yl-pyrido[3,4-d]pyrimidine |
| 44 | 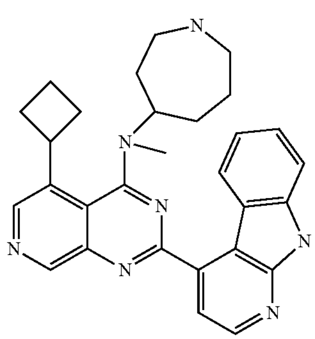 [SMILES: CN(c1nc(-c2ccnc3[nH]c4ccccc4c23)nc2cncc(C3CCC3)c12)C1CCCNCC1] | [D3] | 478 (M + H)+ | 1H NMR (400 MHz, DMSO-d6) δ ppm 12.06 (1 H, s) 9.13 (1 H, s) 8.41-8.79 (5 H, m) 7.87 (1 H, d, J = 5.0 Hz) 7.41-7.59 (2 H, m) 7.09-7.28 (1 H, m) 4.74 (1 H, br. s.) 4.21 (1 H, br. s.) 3.17 (3 H, br. s.) 3.03 (5 H, s) 2.58-2.75 (1 H, m) 1.77-2.27 (9 H, m) | Azepan-4-yl-[5-cyclobutyl-2-(9H-pyrido[2,3-b]indol-4-yl)-pyrido[3,4-d]pyrimidin-4-yl]-methyl-amine |

TABLE A-continued

| Ex | Structure | Scheme | Analysis | | Name |
| --- | --- | --- | --- | --- | --- |
| | | | LCMS | 1H-NMR | |
| 45 | 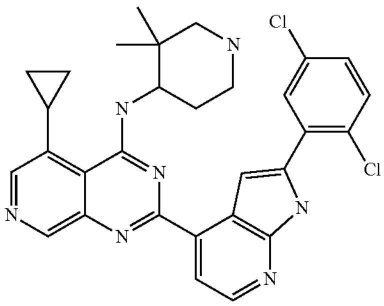 | [D4], [D3] | 572.16 (M + H)+ | 1H NMR (400 MHz, DMSO-d6) δ 12.35 (br s, 1H), 9.07-9.04 (m, 2H), 8.49 (d, 1H, J = 5.0 Hz), 8.26-8.19 (m, 2H), 8.14 (br s, 1H), 8.03 (m, 1H), 7.94 (d, 1H, J = 2.4 Hz), 7.70 (d, 1H, J = 8.6 Hz), 7.54 (m, 1H), 4.22-4.01 (m, 3H), 3.48-2.67 (m, 7H), 2.34-1.94 (m, 2H), 1.48-0.91 (m, 9H) | {5-Cyclopropyl-2-[2-(2,5-dichloro-phenyl)-1H-pyrrolo[2,3-b]pyridin-4-yl]-pyrido[3,4-d]pyrimidin-4-yl}-(3,3-dimethyl-piperidin-4-yl)-methyl-amine |
| 46 | 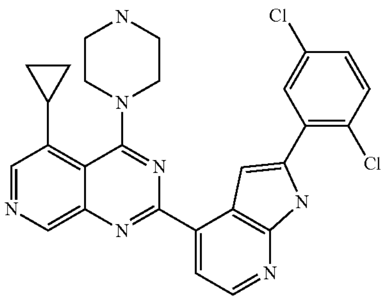 | [D4], [D3] | 518.08 (M + H)+ | 1H NMR (400 MHz, DMSO-d6) δ 12.39 (d, 1H, J = 1.6 Hz), 9.15-8.92 (m, 3H), 8.50 (d, 1H, J = 5.0 Hz), 8.20 (m, 2H), 8.03 (d, 1H, J = 2.1 Hz), 7.95 (d, 1H, J = 2.6 Hz), 7.70 (d, 1H, J = 8.6 Hz), 7.54 (m, 1H), 4.13-3.92 (m, 4H), 3.38 (m, 4H), 2.80-2.73 (m, 1H), 1.30-1.25 (m, 2H), 1.12-1.08 (m, 2H) | 5-Cyclopropyl-2-[2-(2,5-dichloro-phenyl)-1H-pyrrolo[2,3-b]pyridin-4-yl]-4-piperazin-1-yl-pyrido[3,4-d]pyrimidine |
| 47 | 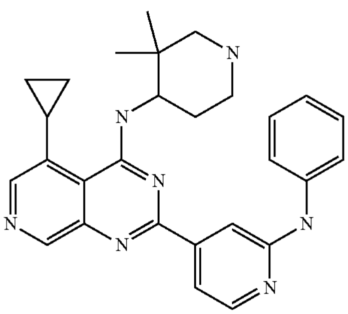 [SMILES: CC1(C)CNCCC1Nc1nc(-c2ccnc(Nc3ccccc3)c2)nc2cncc(C3CC3)c12] | [B4] | 466.24 (M + H)+ | | [5-Cyclopropyl-2-(2-phenylamino-pyridin-4-yl)-pyrido[3,4-d]pyrimidin-4-yl]-(3,3-dimethyl-piperidin-4-yl)-amine |
| 48 | 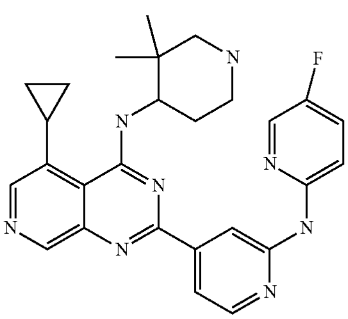 [SMILES: CC1(C)CNCCC1Nc1nc(-c2ccnc(Nc3ccc(F)cn3)c2)nc2cncc(C3CC3)c12] | [B4] | 486 (M + H)+ | | {5-Cyclopropyl-2-[2-(5-fluoro-pyridin-2-ylamino)-pyridin-4-yl]-pyrido[3,4-d]pyrimidin-4-yl}-(3,3-dimethyl-piperidin-4-yl)-amine |
| 49 | 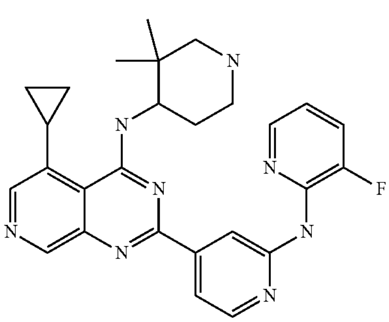 | [B4] | 185.18 (M + H)+ | | {5-Cyclopropyl-2-[2-(3-fluoro-pyridin-2-ylamino)-pyridin-4-yl]-pyrido[3,4-d]pyrimidin-4-yl}-(3,3-dimethyl-piperidin-4-yl)-amine |

TABLE A-continued

| Ex | Structure | Scheme | LCMS | 1H-NMR | Name |
|---|---|---|---|---|---|
| 50 | 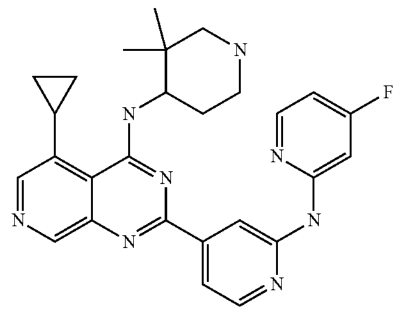 [SMILES: CC1(C)CNCCC1Nc1nc(-c2ccnc(Nc3cc(F)ccn3)c2)nc2cncc(C3CC3)c12] | [B4] | 485 (M + H)+ | | {5-Cyclopropyl-2-[2-(4-fluoro-pyridin-2-ylamino)-pyridin-4-yl]-pyrido[3,4-d]pyrimidin-4-yl}-(3,3-dimethyl-piperidin-4-yl)-amine |
| 51 | 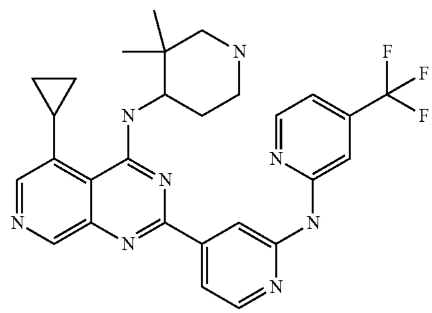 [SMILES: CC1(C)CNCCC1Nc1nc(-c2ccnc(Nc3cc(C(F)(F)F)ccn3)c2)nc2cncc(C3CC3)c12] | [B4] | 535 (M + H)+ | | {5-Cyclopropyl-2-[2-(4-trifluoromethyl-pyridin-2-ylamino)-pyridin-4-yl]-pyrido[3,4-d]pyrimidin-4-yl}-(3,3-dimethyl-piperidin-4-yl)-amine |
| 52 | 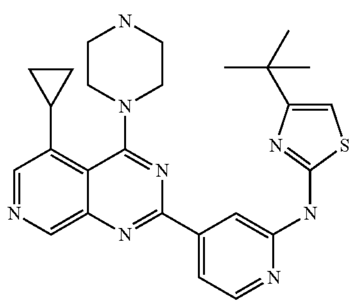 [SMILES: CC(C)(C)c1csc(Nc2cc(-c3nc(N4CCNCC4)c4c(C5CC5)cncc4n3)ccn2)n1] | [B4] | 487.18 (M + H)+ | 1H NMR (400 MHz, DMSO-d6) δ ppm 11.53 (br. s., 1 H), 9.07 (s, 3 H), 8.46 (d, J = 5.3 Hz, 1 H), 8.23 (s, 1 H), 8.19 (s, 1 H), 7.85 (dd, J = 5.3, 1.3 Hz, 1 H), 6.59 (s, 1 H), 3.95 (br. s., 4 H), 3.33 (br. s., 4 H), 2.61-2.76 (m, 1 H), 1.30 (s, 9 H), 1.21-1.29 (m, 2 H), 1.02-1.16 (m, 2 H); LC/MS (ESI+): 487.18 (M + H) | (4-tert-Butyl-thiazol-2-yl)-[4-(5-cyclopropyl-4-piperazin-1-yl-pyrido[3,4-d]pyrimidin-2-yl)-pyridin-2-yl]-amine |
| 53 | 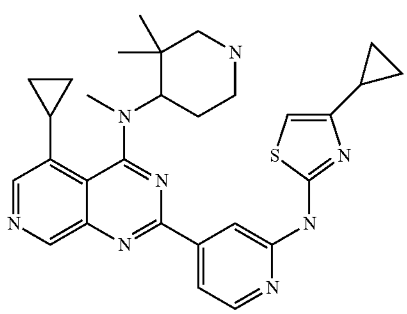 [SMILES: CN(c1nc(-c2ccnc(Nc3nc(C4CC4)cs3)c2)nc2cncc(C3CC3)c12)C1CCNCC1(C)C] | [B4] | 527.25 (M + H)+ | 1H NMR (400 MHz, DMSO-d6) δ ppm 11.47 (br. s, 1 H), 9.15 (br. s, 1 H), 8.99 (s, 1 H), 8.44 (d, J = 5.5 Hz, 1 H), 8.35 (br. s., 1 H), 8.13 (s, 1 H), 8.06 (br. s., 1 H), 7.87 (d, J = 5.3 Hz, 1 H), 6.63 (s, 1 H), 5.60 (br. s., 1 H), 3.50 (d, J = 11.3 Hz, 1 H), 3.16 (br. s., 7 H), 2.36-2.46 (m, 1 H), 2.22 (br. s., 1 H), 1.94-2.03 (m, 1 H), 1.45 (br. s., 1 H), 1.04-1.36 (m, 8 H), 0.98 (br. s., 1 H), 0.84-0.89 (m, 2 H), 0.78-0.84 (m, 2 H) | {5-Cyclopropyl-2-[2-(4-cyclopropyl-thiazol-2-ylamino)-pyridin-4-yl]-pyrido[3,4-d]pyrimidin-4-yl}-(3,3-dimethyl-piperidin-4-yl)-methyl-amine |
| 54 | 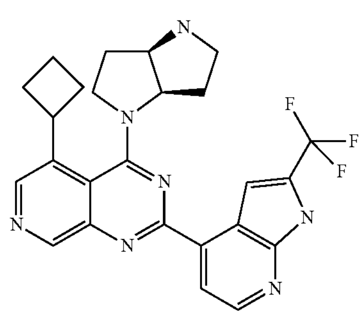 [SMILES: FC(F)(F)c1cc2c(-c3nc(N4CC[C@H]5NCC[C@H]54)c4c(C5CCC5)cncc4n3)ccnc2[nH]1] | [D4], [D3] | 480.16 (M + H)+ | 1H NMR (400 MHz, DMSO-d6) δ ppm 13.15 (br. s., 1 H), 9.40 (br. s., 1 H), 9.28 (br. s., 1 H), 9.14 (s, 1 H), 8.74 (s, 1 H), 8.63 (d, J = 5.0 Hz, 1 H), 8.25-8.31 (m, 1 H), 8.28 (d, J = 5.0 Hz, 1 H), 7.94 (s, 1 H), 5.34 (br. s., 1 H), 4.35 (br. s., 1 H), 4.00-4.16 (m, 2 H), 3.53 (br. s., 1 H), 3.40 (br. s., 2 H), 2.60-2.72 (m, 1 H), 2.34-2.44 (m, 2 H), 2.26 (dd, J = 13.7, 5.4 Hz, 1 H), 2.01-2.15 (m, 2 H), 1.89-2.01 (m, 2 H) | (±)-5-Cyclobutyl-4-(3,6-cis)-hexahydro-pyrrolo[3,2-b]pyrrol-1-yl-2-(2-trifluoromethyl-1H-pyrrolo[2,3-b]pyridin-4-yl)-pyrido[3,4-d]pyrimidine |

TABLE A-continued

| Ex | Structure | Scheme | LCMS | 1H-NMR | Name |
|---|---|---|---|---|---|
| 55 | 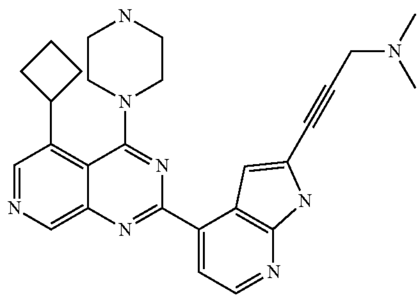 [SMILES: CN(C)CC#Cc1cc2c(-c3nc(N4CCNCC4)c4c(C5CCC5)cncc4n3)ccnc2[nH]1] | [D4], [D3] | 467 (M + H)+ | | {3-[4-(5-Cyclobutyl-4-piperazin-1-yl-pyrido[3,4-d]pyrimidin-2-yl)-1H-pyrrolo[2,3-b]pyridin-2-yl]-prop-2-ynyl}-dimethyl-amine |
| 56 | 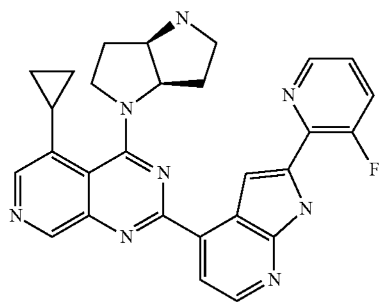 [SMILES: Fc1cccnc1-c1cc2c(-c3nc(N4CC[C@H]5NCC[C@H]54)c4c(C5CC5)cncc4n3)ccnc2[nH]1] | [D4], [D3] | 493.18 (M + H)+ | 1 H NMR (400 MHz, DMSO-d6) δ ppm 12.45 (s, 1 H), 9.40 (br. s., 1 H), 9.23 (br. s., 1 H), 9.04 (s, 1 H), 8.62 (dt, J = 4.5, 1.5 Hz, 1 H), 8.51 (d, J = 5.0 Hz, 1 H), 8.17-8.28 (m, 2 H), 8.14 (dd, J = 4.3, 2.0 Hz, 1 H), 7.91 (ddd, J = 11.7, 8.3, 1.3 Hz, 1 H), 7.53 (dt, J = 8.5, 4.3 Hz, 1 H), 5.42-5.49 (m, 1 H), 4.29-4.42 (m, 2 H), 3.60 (t, J = 8.8 Hz, 1 H), 3.48 (br. s., 1 H), 3.38 (d, J = 5.0 Hz, 1 H), 2.53-2.64 (m, 1 H), 2.35-2.49 (m, 2 H), 2.23-2.35 (m, 1 H), 2.09-2.23 (m, 1 H), 1.37-1.45 (m, 1 H), 1.13-1.22 (m, 1H), 1.03-1.13 (m, 1 H), 0.99 (dt, J = 9.5, 4.7 Hz, 1 H) | (±)-5-Cyclopropyl-2-[2-(3-fluoro-pyridin-2-yl)-1H-pyrrolo[2,3-b]pyridin-4-yl]-4-(3,6-cis)-hexahydro-pyrrolo[3,2-b]pyrrol-1-yl-pyrido[3,4-d]pyrimidine |
| 57 | 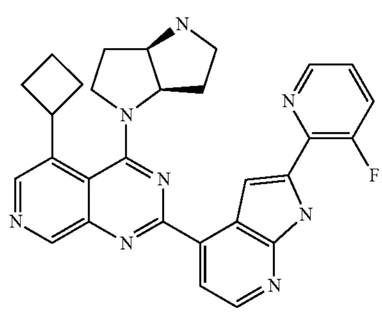 [SMILES: Fc1cccnc1-c1cc2c(-c3nc(N4CC[C@H]5NCC[C@H]54)c4c(C5CCC5)cncc4n3)ccnc2[nH]1] | [D4], [D3] | 507.20 (M + H)+ | 1H NMR (400 MHz, DMSO-d6) δ ppm 12.42 (s, 1 H), 9.33 (br. s., 1 H), 9.17 (br. s., 1 H), 9.09 (s, 1 H), 8.74 (s, 1 H), 8.61 (dt, J = 3.1, 1.6 Hz, 1 H), 8.50 (d, J = 4.5 Hz, 1 H), 8.20 (d, J = 5.0 Hz, 1 H), 8.13 (d, J = 2.0 Hz, 1 H), 7.92 (ddd, J = 11.7, 8.4, 1.0 Hz, 1 H), 7.53 (dt, J = 8.3, 4.2 Hz, 1 H), 5.42 (br. s., 1 H), 3.97-4.17 (m, 4 H), 3.42 (br. s., 3 H), 2.59-2.72 (m, 2 H), 2.34-2.47 (m, 3 H), 2.20-2.30 (m, 1 H), 2.00-2.16 (m, 2 H), 1.86-2.00 (m, 2 H) | (±)-5-Cyclobutyl-2-[2-(3-fluoro-pyridin-2-yl)-1H-pyrrolo[2,3-b]pyridin-4-yl]-4-(3,6-cis)-hexahydro-pyrrolo[3,2-b]pyrrol-1-yl-pyrido[3,4-d]pyrimidine |
| 58 | 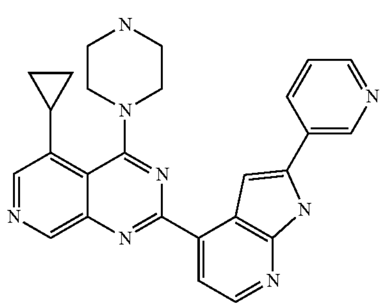 [SMILES: c1cncc(-c2cc3c(-c4nc(N5CCNCC5)c5c(C6CC6)cncc5n4)ccnc3[nH]2)c1] | [D4], [D3] | 449.13 (M + H)+ | 1H NMR (400 MHz, DMSO-d6) δ 12.63 (br s, 1H), 9.35 (m, 2H), 8.99 (br s, 2H), 8.67 (m, 1H), 8.60 (m, 1H), 8.48 (d, 1H, J = 5.0 Hz), 8.19 (m, 2H), 8.12 (d, 1H, J = 2.0 Hz), 7.70 (m, 1H), 4.40-3.95 (m, 4H), 3.39 (m, 4H), 2.80-2.73 (m, 1H), 1.31-1.26 (m, 2H), 1.13-1.09 (m, 2H) | 5-Cyclopropyl-4-piperazin-1-yl-2-(2-pyridin-3-yl-1H-pyrrolo[2,3-b]pyridin-4-yl)-pyrido[3,4-d]pyrimidine |

TABLE A-continued

| Ex | Structure | Scheme | Analysis LCMS | 1H-NMR | Name |
|---|---|---|---|---|---|
| 59 | 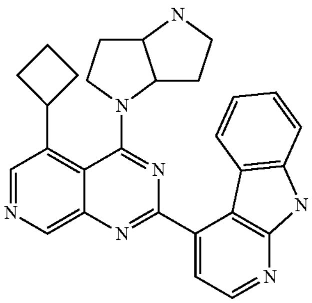 [SMILES: c1ccc2c(c1)[nH]c1nccc(-c3nc(N4CCC5NCCC54)c4c(C5CCC5)cncc4n3)c12] | [D3] | 462 (M + H)+ | 1H NMR (400 MHz, DMSO-d6) δ ppm 12.05 (1 H, s) 9.12 (2 H, s) 9.00 (1 H, br. s.) 8.78 (1 H, s) 8.52-8.67 (2 H, m) 7.91 (1 H, d, J = 5.0 Hz) 7.38-7.60 (2 H, m) 7.17 (1 H, td, J = 7.6, 1.1 Hz) 5.37 (1 H, br. s.) 3.93-4.30 (5 H, m) 3.26-3.54 (3 H, m) 2.67 (1 H, dd, J = 3.8, 1.8 Hz) 1.85-2.23 (6 H, m) | 4-[5-Cyclobutyl-4-(hexahydro-pyrrolo[3,2-b]pyrrol-1-yl)-pyrido[3,4-d]pyrimidin-2-yl]-9H-pyrido[2,3-b]indole |
| 60 | 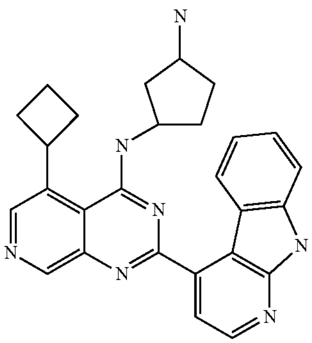 [SMILES: NC1CCC(Nc2nc(-c3ccnc4[nH]c5ccccc5c34)nc3cncc(C4CCC4)c23)C1] | [D3] | 450 (M + H)+ | 1H NMR (400 MHz, DMSO-d6) δ ppm 12.03 (1 H, s) 9.12 (1 H, s) 8.45-8.68 (3 H, m) 7.76-7.97 (4 H, m) 7.39-7.60 (2 H, m) 7.10-7.22 (2 H, m) 4.49-4.84 (3 H, m) 3.56 (2 H, d, J = 5.5 Hz) 2.51-2.70 (4 H, m) 1.63-2.38 (11 H, m) | N-[5-Cyclobutyl-2-(9H-pyrido[2,3-b]indol-4-yl)-pyrido[3,4-d]pyrimidin-4-yl]-cyclopentane-1,3-diamine |
| 61 | 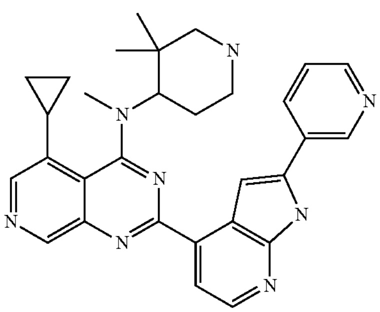 [SMILES: CN(c1nc(-c2ccnc3[nH]c(-c4cccnc4)cc23)nc2cncc(C3CC3)c12)C1CCNCC1(C)C] | [D4], [D3] | 505.22 (M + H)+ | 1H NMR (400 MHz, DMSO-d6) δ 12.57 (s, 1H), 9.34-9.27 (m, 2H), 9.06-8.91 (br s, 1H), 8.64 (m, 1H), 8.55 (m, 1H), 8.45 (m, 1H), 8.30-8.12 (m, 3H), 7.66 (m, 1H), 5.60 (br s, 1H), 4.28 (m, 4H), 3.56-2.78 (m, 7H), 2.28-1.87 (m, 1H), 1.47-0.91 (m, 8H) | [5-Cyclopropyl-2-(2-pyridin-3-yl-1H-pyrrolo[2,3-b]pyridin-4-yl)-pyrido[3,4-d]pyrimidin-4-yl]-(3,3-dimethyl-piperidin-4-yl)-methyl-amine |
| 62 | 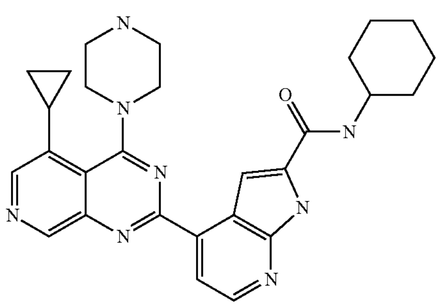 [SMILES: O=C(NC1CCCCC1)c1cc2c(-c3nc(N4CCNCC4)c4c(C5CC5)cncc4n3)ccnc2[nH]1] | [D21] | 497.2 (M + H)+ | 1H NMR (400 MHz, DMSO-d6) δ ppm 12.30 (d, 1H, J = 1.5 Hz), 9.25 (s, 1H), 9.04-8.98 (br s, 2H), 8.53 (d, 1H, J = 4.9 Hz), 8.37 (d, 1H, J = 7.9 Hz), 8.20 (m, 2H), 8.10 (d, 1H, J = 2.0 Hz), 3.96-3.83 (m, 5H), 3.37 (m, 4H), 2.78-2.71 (m, 1H), 1.91 (m, 2H), 1.77 (m, 2H), 1.66-1.63 (m, 1H), 1.45-1.08 (m, 9H) | 4-(5-Cyclopropyl-4-piperazin-1-yl-pyrido[3,4-d]pyrimidin-2-yl)-1H-pyrrolo[2,3-b]pyridine-2-carboxylic acid cyclohexylamide |
| 63 | 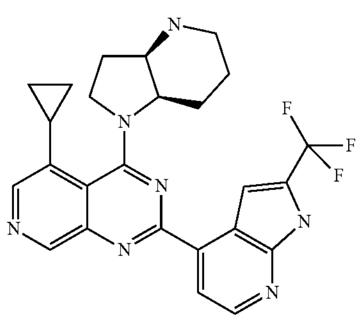 [SMILES: FC(F)(F)c1cc2c(-c3nc(N4CC[C@H]5NCCC[C@H]54)c4c(C5CC5)cncc4n3)ccnc2[nH]1] | [D4], [D3] | 480.14 (M + H)+ | 1H NMR (400 MHz, DMSO-d6) ppm 13.16 (br. s., 1 H), 9.51 (d, J = 8.8 Hz, 1 H), 9.12 (s, 1 H), 8.64 (d, J = 5.0 Hz, 1 H), 8.49 (d, J = 9.3 Hz, 1 H), 8.22 (d, J = 5.0 Hz, 2H), 7.97 (s, 1 H), 4.74 (d, J = 3.3 Hz, 1 H), 4.59 (td, J = 11.0, 6.5 Hz, 1 H), 4.06 (d, J = 4.8 Hz, 1 H), 3.43 (t, J = 9.7 Hz, 1 H), 3.35 (d, J = 11.5 Hz, 1 H), 3.07 (d, J = 10.5 Hz, 1 H), 3.00-3.13 (m, 1 H), 2.59-2.73 (m, 1 H), 2.40-2.50 (m, 1 H), 2.07- | (±)-5-Cyclopropyl-4-(3,7-cis)-octahydro-pyrrolo[3,2-b]pyridin-1-yl-2-(2-trifluoromethyl-1H-pyrrolo[2,3-b]pyridin-4-yl)-pyrido[3,4-d]pyrimidine |

TABLE A-continued

| Ex | Structure | Scheme | Analysis LCMS | 1H-NMR | Name |
|---|---|---|---|---|---|
| | | | | 2.20 (m, 2 H), 1.94-2.07 (m, 1 H), 1.65-1.88 (m, 2 H), 1.47-1.56 (m, 1 H), 1.16-1.25 (m, 1 H), 1.10 (td, J = 9.5, 5.6 Hz, 1 H), 0.92 (dq, J = 10.0, 5.0 Hz, 1 H) | |
| 64 | 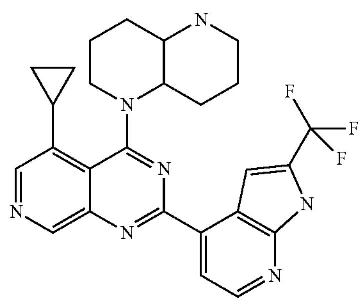 [SMILES: FC(F)(F)c1cc2c(-c3nc(N4CCCC5NCCCC54)c4c(C5CC5)cncc4n3)ccnc2[nH]1] | [D4], [D3] | 494.17 (M + H)+ | 1H NMR (400 MHz, DMSO-d6, signals at coalescence) ppm 13.17 (br. s., 1 H), 9.29 - 9.53 (m, 1 H), 9.18 (br. s., 2 H), 8.79 (br. s., 1 H), 8.65 (d, J = 5.0 Hz, 1 H), 8.43 (br. s., 1 H), 8.20 (s, 1 H), 8.03 (br. s., 1 H), 5.22 (br. s., 1 H), 4.73-4.93 (m, 1 H), 3.53-4.05 (m, 3H), 2.92-3.31 (m, 2 H), 2.37-2.67 (m, 1 H), 2.13-2.34 (m, 1 H), 1.61-2.10 (m, 6 H), 1.23-1.42 (m, 2 H), 1.02 (br. s., 2 H) | 5-Cyclopropyl-4-(octahydro-[1,5]naphthyridin-1-yl)-2-(2-trifluoromethyl-1H-pyrrolo[2,3-b]pyridin-4-yl)-pyrido[3,4-d]pyrimidine |
| 65 | 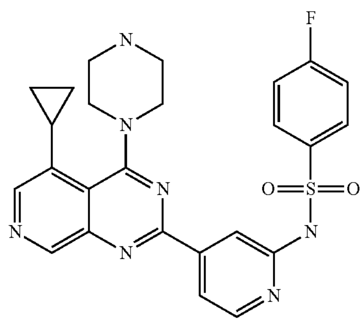 [SMILES: O=S(=O)(Nc1cc(-c2nc(N3CCNCC3)c3c(C4CC4)cncc3n2)ccn1)c1ccc(F)cc1] | [D3], [D12] | 506 (M + H)+ | | N-[4-(5-Cyclopropyl-4-piperazin-1-yl-pyrido[3,4-d]pyrimidin-2-yl)-pyridin-2-yl]-4-fluoro-benzenesulfonamide |
| 66 | 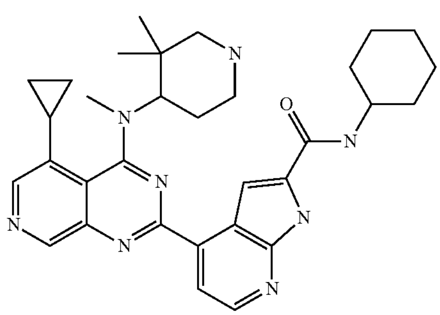 [SMILES: CN(c1nc(-c2ccnc3[nH]c(C(=O)NC4CCCCC4)cc23)nc2cncc(C3CC3)c12)C1CCNCC1(C)C] | [D12] | 553.28 (M + H)+ | 1H NMR (400 MHz, DMSO-d6) δ ppm 12.28 (s, 1H), 9.16 (m, 2H), 8.53 (d, 1H, J = 5.0 Hz), 8.34 (m, 2H), 8.19 (d, 1H, J = 5.0 Hz), 8.15 (s, 1H), 8.08 (m, 1H), 3.48 (m, 1H), 3.17 (m, 6H), 2.33-2.23 (m, 1H), 1.91 (m, 3H), 1.77 (m, 2H), 1.64 (m, 1H), 1.51-0.94 (m, 14H) | 4-{5-Cyclopropyl-4-[(3,3-dimethyl-piperidin-4-yl)-methyl-amino]-pyrido[3,4-d]pyrimidin-2-yl}-1H-pyrrolo[2,3-b]pyridine-2-carboxylic acid cyclohexylamide |
| 67 | 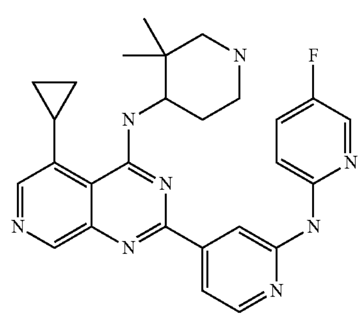 | [B4] | 499 (M + H)+ | 1H NMR (400 MHz, METHANOL-d4) δ ppm 9.13 (s, 1 H) 8.63 (s, 1 H) 8.52 (d, J = 0.75 Hz, 1 H) 8.38-8.45 (m, 2 H) 8.35 (d, J = 1.51 Hz, 1 H) 7.76-7.91 (m, 1 H) 7.28-7.40 (m, 1 H) 4.96-5.05 (m, 1 H) 4.22-4.37 (m, 1 H) 3.43-3.58 (m, 1 H) 3.35 (s, 2 H) 3.26 (s, 1 H) 2.36-2.70 (m, 4 H) 2.00-2.28 (m, 4 H) 1.37 (s, 3 H) 1.20-1.24 (m, 3 H) | {5-Cyclobutyl-2-[2-(5-fluoro-pyridin-2-ylamino)-pyridin-4-yl]-pyrido[3,4-d]pyrimidin-4-yl}-(3,3-dimethyl-piperidin-4-yl)-amine |

TABLE A-continued

| Ex | Structure | Scheme | LCMS | 1H-NMR | Name |
|---|---|---|---|---|---|
| 68 | 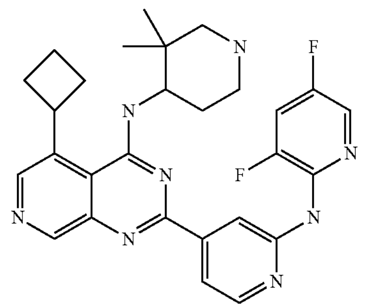 [SMILES: CC1(C)CNCCC1Nc1nc(-c2ccnc(Nc3ncc(F)cc3F)c2)nc2cncc(C3CCC3)c12] | [B4] | 517 (M + H)+ | 1H NMR (400 MHz, METHANOL-d4) δ ppm 9.15 (s, 1 H) 8.57-8.84 (m, 2 H) 8.38-8.50 (m, 2 H) 8.32 (d, J = 2.51 Hz, 1 H) 7.96 (ddd, J = 10.35, 8.22, 2.51 Hz, 1 H) 5.01 (dd, J = 11.80, 4.52 Hz, 1 H) 4.32 (t, J = 8.28 Hz, 1 H) 3.51 (br. s., 1 H) 3.32-3.39 (m, 2 H) 3.15-3.26 (m, 1 H) 2.35-2.72 (m, 4 H) 1.98-2.27 (m, 4 H) 1.38 (s, 3 H) 1.22 (s, 3 H) | {5-Cyclobutyl-2-[2-(3,5-difluoro-pyridin-2-ylamino)-pyridin-4-yl]-pyrido[3,4-d]pyrimidin-4-yl}-(3,3-dimethyl-piperidin-4-yl)-amine |
| 69 | 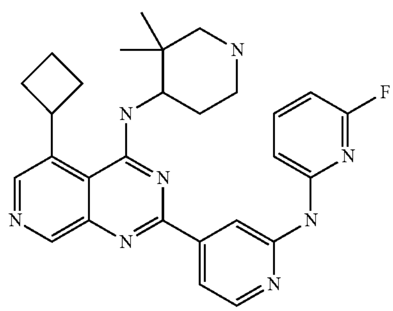 | [B4] | 599.3 (M + H)+ | 1H NMR (400 MHz, METHANOL-d4) δ ppm 9.12 (s, 1 H) 8.63 (s, 1 H) 8.43-8.55 (m, 3 H) 8.38 (d, J = 1.51 Hz, 1 H) 7.05-7.19 (m, 2 H) 5.01 (dd, J = 11.80, 4.27 Hz, 1 H) 4.30 (s, 1 H) 3.44-3.57 (m, 1 H) 3.35 (s, 2 H) 3.17-3.27 (m, 1 H) 2.35-2.71 (m, 4 H) 2.01-2.29 (m, 4 H) 1.37 (s, 3 H) 1.22 (s, 3 H) | {5-Cyclobutyl-2-[2-(4-fluoro-pyridin-2-ylamino)-pyridin-4-yl]-pyrido[3,4-d]pyrimidin-4-yl}-(3,3-dimethyl-piperidin-4-yl)-amine |
| 70 | 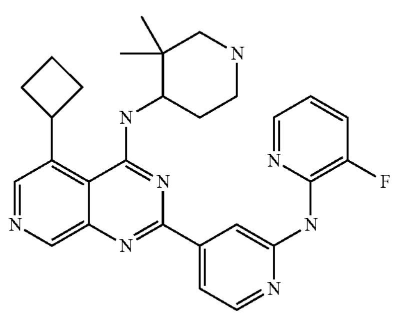 | [B4] | 599.5 (M + H)+ | 1H NMR (400 MHz, METHANOL-d4) δ ppm 9.15 (s, 1 H) 8.77 (d, J = 1.00 Hz, 1 H) 8.64 (s, 1 H) 8.47-8.53 (m, 1 H) 8.39-8.46 (m, 1 H) 8.34 (dd, J = 5.14, 1.13 Hz, 1 H) 7.89 (ddd, J = 10.79, 8.28, 1.25 Hz, 1 H) 7.35 (ddd, J = 8.28, 4.89, 3.89 Hz, 1 H) 5.01 (dd, J = 11.67, 4.39 Hz, 1H) 4.32 (t, J = 8.16 Hz, 1 H) 3.53 (d, J = 13.05 Hz, 1 H) 3.32-3.39 (m, 2 H) 3.20 (d, J = 13.05 Hz, 1 H) 2.34-2.70 (m, 4H) 1.99-2.29 (m, 4 H) 1.38 (s, 3 H) 1.22 (s, 3 H) | {5-Cyclobutyl-2-[2-(3-fluoro-pyridin-2-ylamino)-pyridin-4-yl]-pyrido[3,4-d]pyrimidin-4-yl}-(3,3-dimethyl-piperidin-4-yl)-amine |
| 71 | 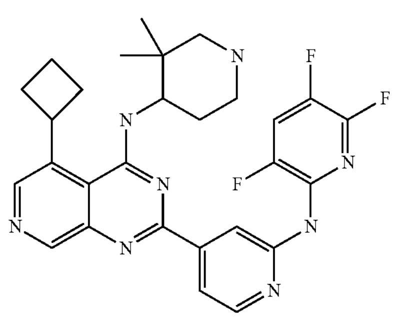 [SMILES: CC1(C)CNCCC1Nc1nc(-c2ccnc(Nc3nc(F)c(F)cc3F)c2)nc2cncc(C3CCC3)c12] | [B4] | 535 (M + H)+ | 1H NMR (400 MHz, METHANOL-d4) δ ppm 9.13 (s, 1 H) 8.92 (d, J = 0.75 Hz, 1 H) 8.62 (s, 1 H) 8.46 (d, J = 6.27 Hz, 1 H) 8.33 (dd, J = 6.27, 1.51 Hz, 1 H) 8.02-8.18 (m, 1 H) 5.02 (dd, J = 11.67, 4.39 Hz, 1 H) 4.31 (t, J = 8.16 Hz, 1 H) 3.51 (d, J = 12.80 Hz, 1H) 3.32-3.39 (m, 2 H) 3.12-3.24 (m, 1 H) 2.33-2.71 (m, 4H) 2.03 (s, 4 H) 1.37 (s, 3 H) 1.22 (s, 3 H) | {5-Cyclobutyl-2-[2-(3,5,6-trifluoro-pyridin-2-ylamino)-pyridin-4-yl]-pyrido[3,4-d]pyrimidin-4-yl}-(3,3-dimethyl-piperidin-4-yl)-amine |

TABLE A-continued

| Ex | Structure | Scheme | LCMS | 1H-NMR | Name |
|---|---|---|---|---|---|
| 72 | 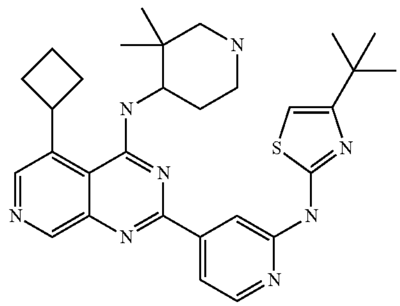 [SMILES: CC(C)(C)c1csc(Nc2cc(-c3nc(NC4CCNCC4(C)C)c4c(C5CCC5)cncc4n3)ccn2)n1] | [B4] | 543.8 (M + H)+ | 1H NMR (400 MHz, METHANOL-d4) δ ppm 9.11 (s, 1 H) 8.55-8.61 (m, 2H) 8.50 (s, 1 H) 8.23 (d, J = 5.27 Hz, 1 H) 6.81 (s, 1 H) 5.11 (d, J = 8.53 Hz, 1 H) 4.30 (t, J = 7.91 Hz, 1 H) 3.58-3.81 (m, 2H) 3.22 (t, J = 7.40 Hz, 2 H) 2.55-2.66 (m, 2 H) 2.33-2.54 (m, 2 H) 1.98-2.25 (m, 4 H) 1.43 (s, 9 H) 1.38 (br. s., 3 H) 1.23 (s, 3 H) | {2-[2-(4-tert-Butyl-thiazol-2-ylamino)-pyridin-4-yl]-5-cyclobutyl-pyrido[3,4-d]pyrimidin-4-yl}-(3,3-dimethyl-piperidin-4-yl)-amine |
| 73 | 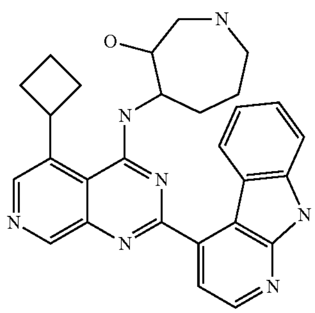 [SMILES: OC1CNCCCC1Nc1nc(-c2ccnc3[nH]c4ccccc4c23)nc2cncc(C3CCC3)c12] | [D3] | 480 (M + H)+ | 1H NMR (400 MHz, DMSO-d6) δ ppm 12.03 (1 H, s) 9.14 (1 H, s) 8.86 (1 H, br. s.) 8.52-8.73 (3 H, m) 8.43 (1 H, br. s.) 7.87 (1 H, d, J = 5.0 Hz) 7.39-7.60 (2 H, m) 6.98-7.22 (2 H, m) 5.80 (1 H, br. s.) 4.55 (3 H, dd, J = 16.9, 8.4 Hz) 4.30 (2 H, d, J = 4.5 Hz) 2.94-3.45 (5 H, m) 2.54-2.72 (2 H, m) 1.72-2.41 (10 H, m) | 4-[5-Cyclobutyl-2-(9H-pyrido[2,3-b]indol-4-yl)-pyrido[3,4-d]pyrimidin-4-ylamino]-azepan-3-ol |
| 74 | 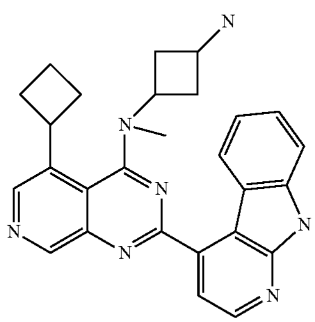 [SMILES: CN(c1nc(-c2ccnc3[nH]c4ccccc4c23)nc2cncc(C3CCC3)c12)C1CC(N)C1] | [D3] | 450 (M + H)+ | 1H NMR(400 MHz, METHANOL-d4) δ ppm 9.13 (1 H, s) 8.71 (1 H, s) 8.51 (1 H, d, J = 5.3 Hz) 8.28 (1 H, d, J = 8.0 Hz) 7.77 (1 H, d, J = 5.0 Hz) 7.40-7.62 (2 H, m) 7.15 (1H, td, J = 7.7, 1.3 Hz) 4.22-4.50 (2 H, m) 3.57 (1 H, t, J = 7.9 Hz) 3.12 (s, 3H) 2.81-2.67 (3 H, m) 2.50-1.99 (6 H, m) | N-[5-Cyclobutyl-2-(9H-pyrido[2,3-b]indol-4-yl)-pyrido[3,4-d]pyrimidin-4-yl]-N-methyl-cyclobutane-1,3-diamine |
| 75 | 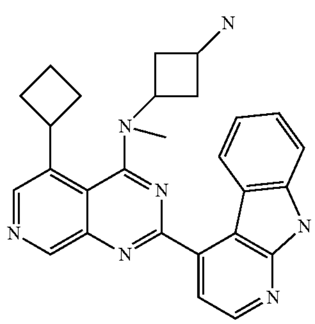 [SMILES: CN(c1nc(-c2ccnc3[nH]c4ccccc4c23)nc2cncc(C3CCC3)c12)C1CC(N)C1] | [D3] | 450 (M + H)+ | 1H NMR (400 MHz, METHANOL-d4) δ ppm 9.14 (1 H, s) 8.69 (1 H, s) 8.50 (1 H, d, J = 5.3 Hz) 8.25 (1 H, d, J = 8.0 Hz) 7.75 (1 H, d, J = 5.3 Hz) 7.42-7.62 (2 H, m) 7.15 (1 H, t, J = 7.7 Hz) 4.46 (1H, d, J = 8.3 Hz) 3.87 (1 H, s) 3.13 (3 H, s) 1.95-2.94 (9 H, m) | N-[5-Cyclobutyl-2-(9H-pyrido[2,3-b]indol-4-yl)-pyrido[3,4-d]pyrimidin-4-yl]-N-methyl-cyclobutane-1,3-diamine |
| 76 | 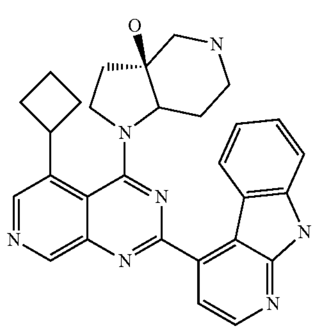 | [D3] | 492.18 (M + H)+ | (400 MHz, d6-DMSO, δ): 12.07 (s, 1H), 9.15 (s, 1H), 8.80-8.70 (m, 4H), 8.58 (d, J = 5.1 Hz, 1H), 7.86 (d, J = 5.1 Hz, 1H), 7.54 (d, J = 7.9 Hz, 1H), 7.51-7.46 (m, 1H), 7.21-7.16 (m, 1H), 5.80 (br s, 1H), 4.33-4.22 (m, 3H), 4.05-3.95 (m, 1H), 3.35-2.94 (m, 5H), 2.79-2.69 (m, 1H), 2.52-2.38 (m, 2H), 2.30-1.80 (m, 6H). | (±)-(3aS,7aS)-1-[5-Cyclobutyl-2-(9H-pyrido[2,3-b]indol-4-yl)-pyrido[3,4-d]pyrimidin-4-yl]-octahydro-pyrrolo[3,2-c]pyridin-3a-ol |

TABLE A-continued

| Ex | Structure | Scheme | LCMS | 1H-NMR | Name |
|---|---|---|---|---|---|
| 77 | 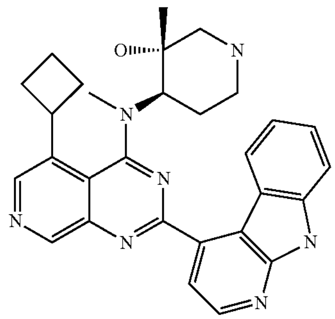 [SMILES: CN(c1nc(-c2ccnc3[nH]c4ccccc4c23)nc2cncc(C3CCC3)c12)[C@@H]1CCNC[C@@]1(C)O] | [D3] | 494.20 (M + H)+ | 12.19-12.03 (m, 1H), 9.50-8.20 (m, 6H), 7.85-7.75 (m, 1H), 7.60-7.45 (m, 2H), 7.23-7.12 (m, 1H), 5.62-1.12 (m, 21H). | (±)-(3,4-trans)-4-{[5-Cyclobutyl-2-(9H-pyrido[2,3-b]indol-4-yl)-pyrido[3,4-d]pyrimidin-4-yl]-methyl-amino}-3-methyl-piperidin-3-ol |
| 78 | 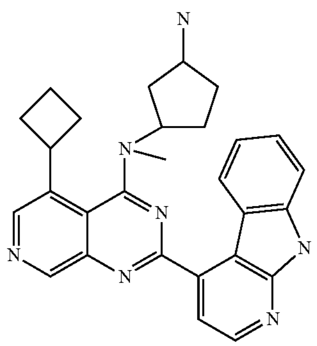 [SMILES: CN(c1nc(-c2ccnc3[nH]c4ccccc4c23)nc2cncc(C3CCC3)c12)C1CCC(N)C1] | [D3] | 464 (M + H)+ | 1H NMR (400 MHz, METHANOL-d4) δ ppm 9.10 (1 H, s) 8.66 (1H, s) 8.51 (1 H, d, J = 5.3 Hz) 8.25 (1 H, d, J = 8.8 Hz) 7.78 (1 H, br. s.) 7.41-7.66 (2 H, m) 7.15 (1 H, t, J = 7.0 Hz) 5.03 (1 H, br.s.) 4.27-4.48 (1 H, m) 3.50-3.71 (2 H, m) 3.17 (3 H, s) 2.49-2.84 (3 H, m) 1.61-2.27 (8 H, m) | N-[5-Cyclobutyl-2-(9H-pyrido[2,3-b]indol-4-yl)-pyrido[3,4-d]pyrimidin-4-yl]-N-methyl-cyclopentane-1,3-diamine |
| 79 | 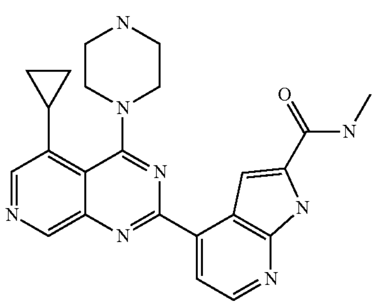 [SMILES: CNC(=O)c1cc2c(-c3nc(N4CCNCC4)c4c(C5CC5)cncc4n3)ccnc2[nH]1] | [D21] | 429.11 (M + H)+ | 1H NMR (400 MHz, DMSO-d6) δ ppm 12.32 (d, 1H, J = 1.2 Hz), 9.27 (s, 1H), 9.04-8.99 (br s, 1H), 8.67-8.64 (m, 1H), 8.53 (d, 1H, J = 5.0 Hz), 8.19 (m, 2H), 8.13 (d, 1H, J = 2.0 Hz), 3.94 (m, 4H), 3.37 (m, 4H), 2.89 (d, 3H, J = 4.6 Hz), 2.78-2.71 (m, 1H), 1.30-1.25 (m, 2H), 1.12-1.08 (m, 2H) | 4-(5-Cyclopropyl-4-piperazin-1-yl-pyrido[3,4-d]pyrimidin-2-yl)-1H-pyrrolo[2,3-b]pyridine-2-carboxylic acid methylamide |
| 80 | 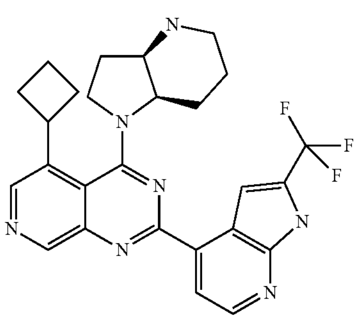 [SMILES: FC(F)(F)c1cc2c(-c3nc(N4CC[C@H]5NCCC[C@H]54)c4c(C5CCC5)cncc4n3)ccnc2[nH]1] | [D4], [D3] | 494.17 (M + H)+ | 1H NMR (400 MHz, DMSO-d6) δ ppm 13.16 (br. s., 1 H), 9.48 (br. s., 1 H), 9.19 (s, 1 H), 8.74 (s, 1 H), 8.63 (d, J = 5.0 Hz, 2H), 8.21 (d, J = 5.0 Hz, 1 H), 7.96 (s, 1 H), 4.71 (br. s., 1 H), 4.28-4.36 (m, 1 H), 4.21 (dt, J = 17.1, 8.6 Hz, 2 H), 3.37 (br. s., 1 H), 3.25 (br. s., 1 H), 3.08 (m, 1 H), 2.67-2.79 (m, 1 H), 2.61 (br. s., 1 H), 2.36-2.48 (m, 2 H), 2.03-2.21 (m, 3 H), 1.68-2.02 (m, 6 H) | (±)-5-Cyclobutyl-4-(3,7-cis)-octahydro-pyrrolo[3,2-b]pyridin-1-yl-2-(2-trifluoromethyl-1H-pyrrolo[2,3-b]pyridin-4-yl)-pyrido[3,4-d]pyrimidine |

TABLE A-continued

| Ex | Structure | Scheme | Analysis | | Name |
| --- | --- | --- | --- | --- | --- |
| | | | LCMS | 1H-NMR | |
| 81 | 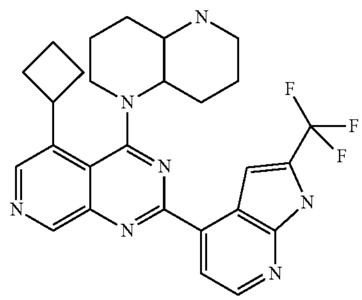 [SMILES: FC(F)(F)c1cc2c(-c3nc(N4CCCC5NCCCC54)c4c(C5CCC5)cncc4n3)ccnc2[nH]1] | [D4], [D3] | 508.20 (M + H)+ | 1H NMR (400 MHz, DMSO-d 6, mixture of racemic diastereomers, ~3:2 ratio) δ ppm 13.08-13.28 (m, 2 H), 9.49 (br. s., 1 H), 9.28 (d, J = 8.5 Hz, 2 H), 8.99-9.23 (m, 1 H), 8.70-8.90 (m, 3 H), 8.70-8.90 (m, 3 H), 8.65 (d, J = 5.0 Hz, 2 H), 8.45 (d, J = 5.0 Hz, 1 H), 8.22 (d, J = 4.8 Hz, 1 H), 8.05 (s, 1 H), 7.96 (s, 1 H), 5.28 (d, J = 12.5 Hz, 2 H), 4.74 (d, J = 12.0 Hz, 1 H), 4.14-4.26 (m, 2 H), 4.04 (d, J = 12.0 Hz, 1 H), 3.62-3.76 (m, 2 H), 3.57 (d, J = 13.3 Hz, 1H), 3.44 (d, J = 12.8 Hz, 1 H), 3.00-3.23 (m, 4 H), 2.53 -2.66 (m, 2 H), 2.20-2.49 (m, 6 H), 1.78-2.18 (m, 13 H), 1.66-1.75 (m, 2 H), 1.49-1.65 (m, 2H), 1.08-1.29 (m, 1 H) | 5-Cyclobutyl-4-(octahydro-[1,5]naphthyridin-1-yl)-2-(2-trifluoromethyl-1H-pyrrolo[2,3-b]pyridin-4-yl)-pyrido[3,4-d]pyrimidine |
| 82 | 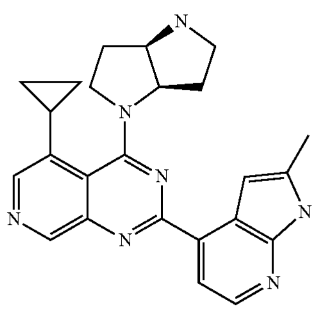 [SMILES: Cc1cc2c(-c3nc(N4CC[C@H]5NCC[C@H]54)c4c(C5CC5)cncc4n3)ccnc2[nH]1] | [D4], [D3] | 412.15 (M + H)+ | 1H NMR (400 MHz, DMSO-d6) ppm 11.89 (s, 1 H), 9.42 (br. s., 1 H), 9.25 (br. s., 1 H), 9.07 (s, 1 H), 8.30 (d, J = 5.3 Hz, 1 H), 8.22 (s, 1 H), 8.10 (d, J = 5.0 Hz, 1 H), 7.16-7.21 (m, 1H), 5.35-5.41 (m, 1H), 4.28-4.42 (m, 2H), 3.57 (t, J = 8.9 Hz, 1H), 3.47 (br. s., 1 H), 3.38 (d, J = 5.8 Hz, 1 H), 2.55 (d, J = 1.8 Hz, 1 H), 2.51 (d, J = 0.8 Hz, 3 H), 2.42-2.48 (m, 1 H), 2.34-2.42 (m, 2 H), 2.23-2.33 (m, 1H), 2.16 (dd, J = 9.8, 7.0 Hz, 1 H), 1.36-1.44 (m, 1 H), 1.13-1.22 (m, 1 H), 1.02-1.11 (m, 1 H), 0.98 (dt, J = 9.7, 4.8 Hz, 1H) | (±)-5-Cyclopropyl-4-(3,6-cis)-hexahydro-pyrrolo[3,2-b]pyrrol-1-yl-2-(2-methyl-1H-pyrrolo[2,3-b]pyridin-4-yl)-pyrido[3,4-d]pyrimidine |
| 83 | 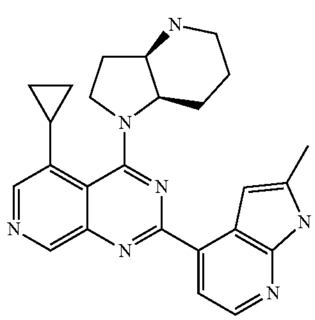 [SMILES: Cc1cc2c(-c3nc(N4CC[C@H]5NCCC[C@H]54)c4c(C5CC5)cncc4n3)ccnc2[nH]1] | [D4], [D3] | 426.15 (M + H)+ | 1H NMR (400 MHz, DMSO-d6) ppm 11.87 (s, 1 H), 9.55 (d, J = 9.0 Hz, 1 H), 9.09 (s, 1 H), 8.53 (d, J = 9.3 Hz, 1 H), 8.30 (d, J = 5.0 Hz, 1 H), 8.18 (s, 1 H), 8.05 (d, J = 5.3 Hz, 1 H), 7.20-7.25 (m, 1 H), 4.75 (d, J = 3.3 Hz, 1 H), 4.58 (td, J = 11.1, 6.7 Hz, 1 H), 4.06 (d, J = 4.5 Hz, 1 H), 3.42 (t, J = 9.8 Hz, 1 H), 3.36 (d, J = 11.8 Hz, 1 H), 3.05 (q, J = 10.0 Hz, 1 H), 2.65 (d, J = 15.6 Hz, 1 H), 2.52 (s, 3 H), 2.41-2.49 (m, 1 H), 2.07-2.21 (m, 2H), 1.97-2.07 (m, 1 H), 1.65-1.85 (m, 2H), 1.46-1.57 (m, 1 H), 1.15-1.26 (m, 1 H), 1.10 (td, J = 9.5, 5.8 Hz, 1H), 0.87-0.96 (m, 1 H) | (±)-5-Cyclopropyl-2-(2-methyl-1H-pyrrolo[2,3-b]pyridin-4-yl)-4-(3,7-cis)-octahydro-pyrrolo[3,2-b]pyridin-1-yl-pyrido[3,4-d]pyrimidine |

TABLE A-continued

| Ex | Structure | Scheme | LCMS | 1H-NMR | Name |
|---|---|---|---|---|---|
| 84 | 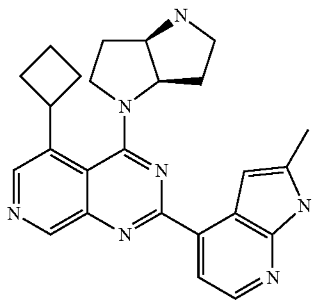 [SMILES: Cc1cc2c(-c3nc(N4CC[C@H]5NCC[C@H]54)c4c(C5CCC5)cncc4n3)ccnc2[nH]1] | [D4], [D3] | 426.14 (M + H)+ | 1H NMR (400 MHz, DMSO-d6) ppm 11.91 (s, 1 H), 9.49 (br. s., 1 H), 9.33 (br. s., 1 H), 9.13 (s, 1 H), 8.73 (s, 1 H), 8.30 (d, J = 5.3 Hz, 1 H), 8.10 (d, J = 5.3 Hz, 1 H), 7.18 (s, 1 H), 5.34 (br. s., 1 H), 4.35 (br. s., 1 H), 3.98-4.18 (m, 2 H), 3.28-3.61 (m, 3 H), 2.54-2.74 (m, 2 H), 2.51 (s, 3 H), 2.34-2.44 (m, 2 H), 2.27 (dd, J = 13.7, 5.6 Hz, 1 H), 2.02-2.16 (m, 2 H), 1.87-2.01 (m, 2 H) | (±)-5-Cyclobutyl-4-(3,6-cis)-hexahydro-pyrrolo[3,2-b]pyrrol-1-yl-2-(2-methyl-1H-pyrrolo[2,3-b]pyridin-4-yl)-pyrido[3,4-d]pyrimidine |
| 85 | 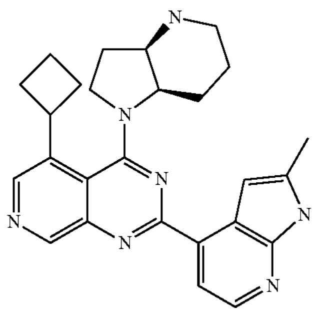 [SMILES: Cc1cc2c(-c3nc(N4CC[C@H]5NCCC[C@H]54)c4c(C5CCC5)cncc4n3)ccnc2[nH]1] | [D4], [D3] | 440.16 (M + H)+ | 1H NMR (400 MHz, DMSO-d6) ä ppm 11.89 (s, 1 H), 9.55-9.64 (m, 1 H), 9.16 (s, 1 H), 8.73 (s, 2 H), 8.30 (d, J = 5.3 Hz, 1 H), 8.04 (d, J = 5.3 Hz, 1 H), 7.20-7.24 (m, 1 H), 4.71 (br. s., 1 H), 4.28-4.44 (m, 1 H), 4.21 (quin, J = 8.5 Hz, 1 H), 4.04 (br. s., 1 H), 3.38 (br. s., 1 H), 3.25 (br. s., 1 H), 3.07 (d, J = 10.3 Hz, 1 H), 2.66- 2.78 (m, 1 H), 2.55 (br. s., 1 H), 2.52 (s, 3 H), 2.34-2.49 (m, 2 H), 2.04-2.24 (m, 3 H), 1.66- 2.03 (m, 5 H) | (±)-5-Cyclobutyl-2-(2-methyl-1H-pyrrolo[2,3-b]pyridin-4-yl)-4-(3,7-cis)-octahydro-pyrrolo[3,2-b]pyridin-1-yl-pyrido[3,4-d]pyrimidine |
| 86 | 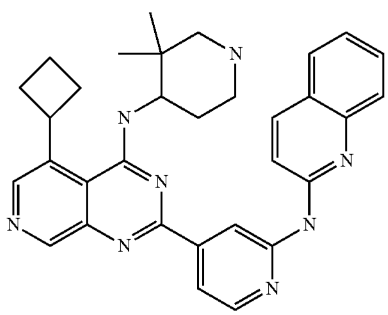 [SMILES: CC1(C)CNCCC1Nc1nc(-c2ccnc(Nc3ccc4ccccc4n3)c2)nc2cncc(C3CCC3)c12] | [B4] | 531 (M + H)+ | 1H NMR (400 MHz, METHANOL-d4) δ ppm 9.12 (s, 1 H) 8.73-8.82 (m, 1H) 8.58-8.69 (m, 2 H) 8.40-8.49 (m, 2H) 8.17(d, J = 8.03 Hz, 1 H) 8.05 (d, J = 8.03 Hz, 1 H) 7.96 (d, J = 1.26 Hz, 1 H) 7.65-7.74 (m, 1 H) 7.46 (d, J = 9.29 Hz, 1H) 5.03(d, J = 7.53 Hz, 1H) 4.24-4.36 (m, 1 H) 3.48-3.58 (m, 1 H) 3.33-3.38 (m, 2 H) 3.20-3.28 (m, 1 H) 2.36-2.70 (m, 4 H) 2.05-2.31 (m, 4 H) 1.38 (s, 3 H) 1.23 (s, 3 H) | {5-Cyclobutyl-2-[2-(quinolin-2-ylamino)-pyridin-4-yl]-pyrido[3,4-d]pyrimidin-4-yl}-(3,3-dimethyl-piperidin-4-yl)-amine |
| 87 | 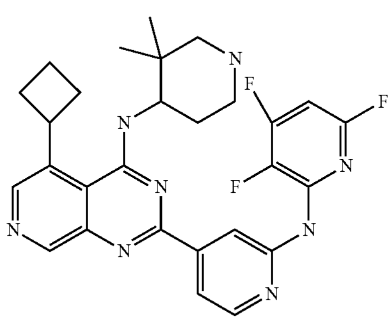 [SMILES: CC1(C)CNCCC1Nc1nc(-c2ccnc(Nc3nc(F)cc(F)c3F)c2)nc2cncc(C3CCC3)c12] | [B4] | 535 (M + H)+ | 1H NMR (400 MHz, METHANOL-d4) δ ppm 9.15 (s, 1 H) 8.90-8.94 (m, 1 H) 8.63 (s, 1 H) 8.49-8.54 (m, 1 H) 8.39 (dd, J = 6.27, 1.51 Hz, 1 H) 6.90-6.98 (m, 1 H) 4.95-5.03 (m, 1 H) 4.27-4.37 (m, 1 H) 3.45-3.55 (m, 1 H) 3.32-3.37 (m, 2 H) 3.14-3.20 (m, 1 H) 2.38-2.68 (m, 4 H) 2.04-2.28 (m, 4 H) 1.37 (s, 3 H) 1.22 (s, 3 H) | {5-Cyclobutyl-2-[2-(3,4,6-trifluoro-pyridin-2-ylamino)-pyridin-4-yl]-pyrido[3,4-d]pyrimidin-4-yl}-(3,3-dimethyl-piperidin-4-yl)-amine |

TABLE A-continued

| Ex | Structure | Scheme | LCMS | 1H-NMR | Name |
|---|---|---|---|---|---|
| 88 | 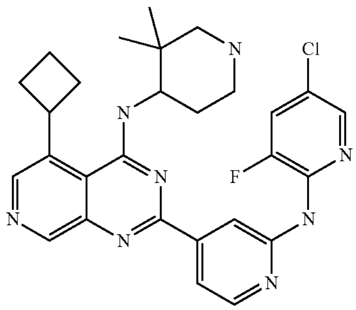 [SMILES: CC1(C)CNCCC1Nc1nc(-c2ccnc(Nc3ncc(Cl)cc3F)c2)nc2cncc(C3CCC3)c12] | [B4] | 534 (M + H)+ | 1H NMR (400 MHz, METHANOL-d4) δ ppm 9.14 (s, 1 H) 8.80 (d, J = 0.75 Hz, 1 H) 8.64 (d, J = 1.00 Hz, 1 H) 8.41-8.51 (m, 2 H) 8.36 (d, J = 2.26 Hz, 1 H) 8.07 (dd, J = 10.29, 2.01 Hz, 1 H) 5.00 (dd, J = 11.67, 4.39 Hz, 1 H) 4.31 (t, J = 8.28 Hz, 1 H) 3.51 (br. s., 1 H) 3.32-3.39 (m, 2 H) 3.19 (d, J = 13.05 Hz, 1 H) 2.65 (s, 4 H) 2.04-2.28 (m, 4 H) 1.37 (s, 3 H) 1.22 (s, 3 H) | {2-[2-(5-Chloro-3-fluoro-pyridin-2-ylamino)-pyridin-4-yl]-5-cyclobutyl-pyrido[3,4-d]pyrimidin-4-yl}-(3,3-dimethyl-piperidin-4-yl)-amine |
| 89 | 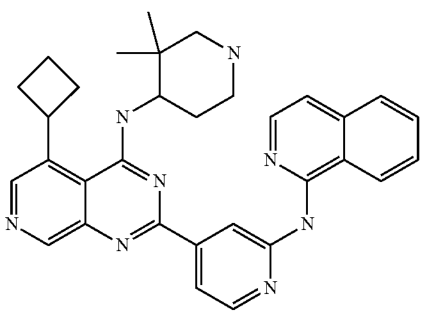 [SMILES: CC1(C)CNCCC1Nc1nc(-c2ccnc(Nc3nccc4ccccc34)c2)nc2cncc(C3CCC3)c12] | [B4] | 531 (M + H)+ | 1H NMR (400 MHz, METHANOL-d4) δ ppm 9.12 (s, 1 H) 8.94 (dd, J = 8.53, 0.75 Hz, 1 H) 8.79-8.84 (m, 1 H) 8.73 (dd, J = 5.52, 0.75 Hz, 1 H) 8.61 (d, J = 1.00 Hz, 1 H) 8.44 (dd, J = 5.52, 1.51 Hz, 1 H) 8.08-8.14 (m, 3 H) 7.94-8.02 (m, 1 H) 7.65-7.71 (m, 1 H) 5.00-5.10 (m, 1 H) 4.24-4.36 (m, 1 H) 3.48-3.57 (m, 1 H) 3.33 (br. s., 2 H) 3.26 (d, 1 H) 2.36-2.70 (m, 4 H) 2.00-2.30 (m, 4 H) 1.38 (s, 3 H) 1.23 (s, 3 H) | {5-Cyclobutyl-2-[2-(isoquinolin-1-ylamino)-pyridin-4-yl]-pyrido[3,4-d]pyrimidin-4-yl}-(3,3-dimethyl-piperidin-4-yl)-amine |
| 90 | 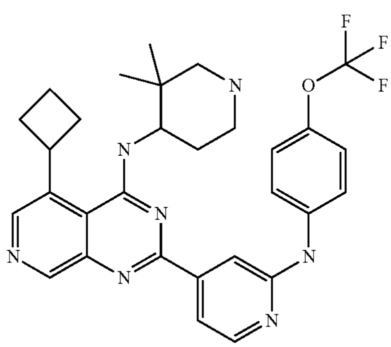 [SMILES: CC1(C)CNCCC1Nc1nc(-c2ccnc(Nc3ccc(OC(F)(F)F)cc3)c2)nc2cncc(C3CCC3)c12] | [B4] | 564 (M + H)+ | 1H NMR (400 MHz, METHANOL-d4) δ ppm 9.11 (s, 1 H) 8.62 (s, 1 H) 8.35 (s, 1 H) 7.99-8.10 (m, 2 H) 7.58-7.65 (m, 2 H) 7.46 (d, J = 8.03 Hz, 2 H) 4.95-5.02 (m, 1 H) 4.24-4.35 (m, 1 H) 3.48 (d, J = 1.76 Hz, 1 H) 3.32-3.40 (m, 2 H) 3.19-3.25 (m, 1 H) 2.34-2.69 (m, 4 H) 1.99-2.25 (m, 4 H) 1.36 (s, 3 H) 1.19 (s, 3 H) | {5-Cyclobutyl-2-[2-(4-trifluoromethoxy-phenylamino)-pyridin-4-yl]-pyrido[3,4-d]pyrimidin-4-yl}-(3,3-dimethyl-piperidin-4-yl)-amine |
| 91 | 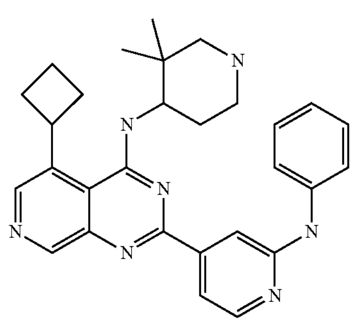 | [B4] | 480 (M + H)+ | 1H NMR (400 MHz, METHANOL-d4) δ ppm 9.12 (br. s., 1 H) 8.62 (s, 1 H) 8.28 (dd, J = 1.51, 0.75 Hz, 1 H) 8.06-8.11 (m, 1 H) 8.01 (d, J = 6.78 Hz, 1 H) 7.55-7.63 (m, 2 H) 7.43-7.52 (m, 3 H) 4.82 (d, J = 4.27 Hz, 1 H) 4.29 (t, J = 8.16 Hz, 1 H) 3.47 (d, J = 2.01 Hz, 1 H) 3.33 (d, J = 1.51 Hz, 1 H) 3.10-3.22 (m, 1 H) 3.06 (d, J = 13.05 Hz, 1 H) 2.34-2.64 (m, 4 H) 1.99-2.24 (m, 4 H) 1.34 (s, 3 H) 1.14 (s, 3 H) | [5-Cyclobutyl-2-(2-phenylamino-pyridin-4-yl)-pyrido[3,4-d]pyrimidin-4-yl]-(3,3-dimethyl-piperidin-4-yl)-amine |

TABLE A-continued

| Ex | Structure | Scheme | LCMS | 1H-NMR | Name |
|---|---|---|---|---|---|
| 92 | 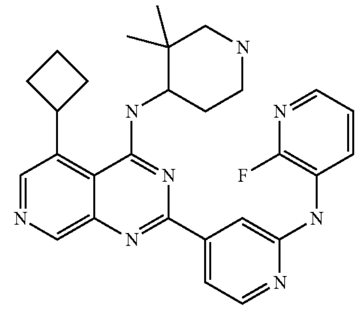 [SMILES: CC1(C)CNCCC1Nc1nc(-c2ccnc(Nc3cccnc3F)c2)nc2cncc(C3CCC3)c12] | [B4] | 499 (M + H)+ | 1H NMR(400 MHz, METHANOL-d4) δ ppm 9.10 (s, 1 H) 8.63 (s, 1 H) 8.58 (s, 1 H) 8.27-8.31 (m, 1 H) 8.08 (s, 1 H) 7.98 (dd, J = 5.65, 1.38 Hz, 1 H) 7.89-7.94 (m, 1 H) 7.32-7.38 (m, 1H) 4.97 (dd, J = 12.05, 4.52 Hz, 1 H) 4.29 (s, 1 H) 3.51 (d, J = 13.05 Hz, 1 H) 3.32-3.38 (m, 2 H) 3.16-3.23 (m, 1 H) 2.33-2.68 (m, 4 H) 2.00-2.26 (m, 4 H) 1.36 (s, 3 H) 1.19 (s, 3 H) | {5-Cyclobutyl-2-[2-(2-fluoro-pyridin-3-ylamino)-pyridin-4-yl]-pyrido[3,4-d]pyrimidin-4-yl}-(3,3-dimethyl-piperidin-4-yl)-amine |
| 93 | 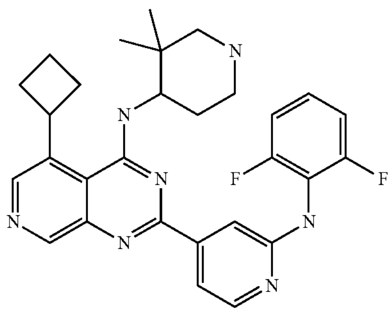 [SMILES: CC1(C)CNCCC1Nc1nc(-c2ccnc(Nc3c(F)cccc3F)c2)nc2cncc(C3CCC3)c12] | [B4] | 516 (M + H)+ | 1H NMR (400 MHz, METHANOL-d4) δ ppm 9.12 (s, 1 H) 8.62 (d, J = 0.75 Hz, 1 H) 8.23 (s, 1 H) 8.08-8.18 (m, 2 H) 7.48-7.59 (m, 1 H) 7.22-7.32 (m, 2 H) 4.88-4.94 (m, 1 H) 4.30 (t, J = 8.16 Hz, 1 H) 3.45-3.55 (m, 1 H) 3.32-3.37 (m, 1 H) 3.19-3.26 (m, 1 H) 3.11 (d, J = 13.30 Hz, 1 H) 2.33-2.69 (m, 4 H) 2.01-2.26 (m, 4 H) 1.36 (s, 3 H) 1.18 (s, 3 H) | {5-Cyclobutyl-2-[2-(2,6-difluoro-phenylamino)-pyridin-4-yl]-pyrido[3,4-d]pyrimidin-4-yl}-(3,3-dimethyl-piperidin-4-yl)-amine |
| 94 | 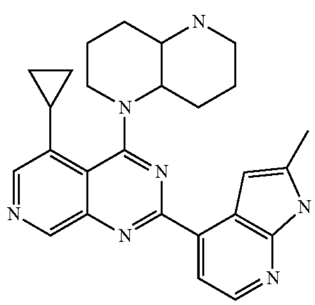 [SMILES: Cc1cc2c(-c3nc(N4CCCC5NCCCC54)c4c(C5CC5)cncc4n3)ccnc2[nH]1] | [D4], [D3] | 440.17 (M + H)+ | 1H NMR (400 MHz, DMSO-d6, 95 C) ppm 11.39 (br. s., 1 H), 9.12-9.47 (m, 1 H), 9.09 (s, 1 H), 8.58-8.98 (m, 1 H), 8.26(d, J = 5.0 Hz, 1 H), 8.16 (s, 1 H), 8.09 (d, J = 5.3 Hz, 1 H), 7.19 (s, 1 H), 4.94-5.03 (br s, exch. H), 3.85 (d, J = 12.8 Hz, 2 H), 3.44 (t, J = 12.3 Hz, 1 H), 3.03-3.18 (m, 2 H), 2.60 (tt, J = 8.4, 5.2 Hz, 1 H), 2.51 (d, J = 0.8 Hz, 3 H), 2.12-2.32 (m, 2H), 1.76-1.97 (m, 6 H), 1.68 (br. s., 1 H), 1.23-1.32 (m, 1 H), 1.15-1.23 (m, 1 H), 0.90-1.01 (m, 2 H) | 5-Cyclopropyl-2-(2-methyl-1H-pyrrolo[2,3-b]pyridin-4-yl)-4-(octahydro-[1,5]naphthyridin-1-yl)-pyrido[3,4-d]pyrimidine |
| 95 | 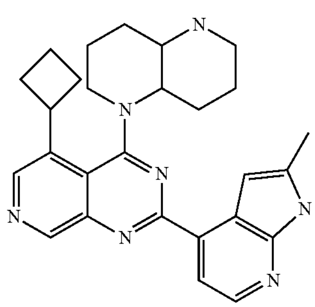 [SMILES: Cc1cc2c(-c3nc(N4CCCC5NCCCC54)c4c(C5CCC5)cncc4n3)ccnc2[nH]1] | [D4], [D3] | 454.19 (M + H)+ | 1H NMR (400 MHz, DMSO-d6, 95C) ppm 11.40 (br. s., 1 H), 9.22 (d, J = 8.3 Hz, 1 H), 9.16 (s, 1 H), 8.74-9.03 (m, 1 H), 8.68 (s, 1 H), 8.25 (d, J = 5.3 Hz, 1 H), 8.03-8.16 (m, 1 H), 7.19 (s, 1 H), 4.25 (s, 1 H), 3.72-4.02 (m, 1 H), 3.51 (br. s., 1 H), 2.98-3.20 (m, 2 H), 2.52-2.61 (m, 2 H), 2.51 (s, 3 H), 2.16-2.33 (m, 3 H), 2.01-2.16 (m, 3 H), 1.93 (d, J = 7.8 Hz, 7 H) | 5-Cyclobutyl-2-(2-methyl-1H-pyrrolo[2,3-b]pyridin-4-yl)-4-(octahydro-[1,5]naphthyridin-1-yl)-pyrido[3,4-d]pyrimidine |

TABLE A-continued

| Ex | Structure | Scheme | LCMS | 1H-NMR | Name |
|---|---|---|---|---|---|
| 96 | 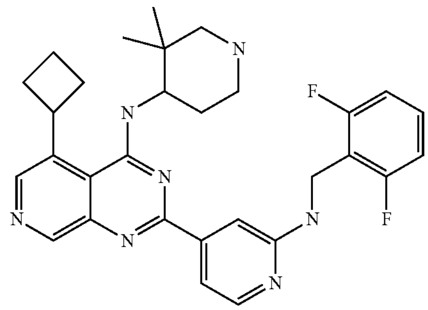 [SMILES: CC1(C)CNCCC1Nc1nc(-c2ccnc(NCc3c(F)cccc3F)c2)nc2cncc(C3CCC3)c12] | [B4] | 531 (M + H)+ | 1H NMR (400 MHz, METHANOL-d4) δ ppm 9.10 (s, 1 H) 8.61 (s, 1 H) 8.18 (s, 1 H) 7.96-8.09 (m, 2 H) 7.49 (s, 1 H) 7.12 (t, J = 8.16 Hz, 2 H) 4.94 (s, 1 H) 4.79 (s, 2 H) 4.20-4.34 (m, 1 H) 3.44-3.54 (m, 1 H) 3.33 (d, J = 1.76 Hz, 1 H) 3.20-3.29 (m, 1 H) 3.13 (d, J = 12.80 Hz, 1 H) 2.35-2.67 (m, 4 H) 1.97-2.25 (m, 4 H) 1.35 (s, 3 H) 1.18 (s, 3 H) | {5-Cyclobutyl-2-[2-(2,6-difluoro-benzylamino)-pyridin-4-yl]-pyrido[3,4-d]pyrimidin-4-yl}-(3,3-dimethyl-piperidin-4-yl)-amine |
| 97 | 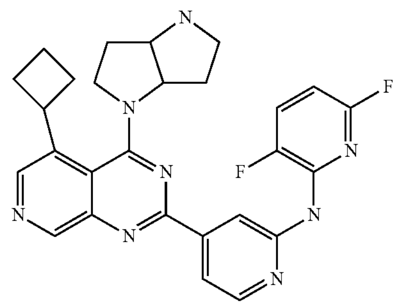 [SMILES: Fc1ccc(F)c(Nc2cc(-c3nc(N4CCC5NCCC54)c4c(C5CCC5)cncc4n3)ccn2)n1] | [B4] | 501 (M + H)+ | 1H NMR (400 MHz, METHANOL-d4) δ ppm 9.12 (s, 1 H) 8.98 (d, J = 1.00 Hz, 1 H) 8.75 (s, 1 H) 8.55-8.57 (m, 1 H) 8.48-8.54 (m, 1 H) 8.35 (dd, J = 6.27, 1.51 Hz, 1 H) 7.88-7.99 (m, 1 H) 6.83-6.92 (m, 1 H) 5.45-5.58 (m, 1 H) 4.41-4.50 (m, 1 H) 4.08-4.28 (m, 2 H) 3.46-3.68 (m, 3 H) 2.69-2.86 (m, 2 H) 2.35-2.62 (m, 4 H) 2.13-2.32 (m, 2 H) 2.03 (d, J = 2.76 Hz, 2 H) | {4-[5-Cyclobutyl-4-(hexahydro-pyrrolo[3,2-b]pyrrol-1-yl)-pyrido[3,4-d]pyrimidin-2-yl]-pyridin-2-yl}-(3,6-difluoro-pyridin-2-yl)-amine |
| 98 | 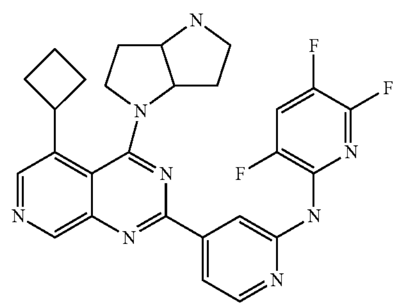 [SMILES: Fc1cc(F)c(Nc2cc(-c3nc(N4CCC5NCCC54)c4c(C5CCC5)cncc4n3)ccn2)nc1F] | [B4] | 519 (M + H)+ | 1H NMR (400 MHz, METHANOL-d4) δ ppm 9.11 (s, 1 H) 8.93-8.98 (m, 1 H) 8.74 (s, 1 H) 8.46 (d, J = 6.27 Hz, 1 H) 8.29 (dd, J = 6.15, 1.63 Hz, 1 H) 8.05-8.13 (m, 1 H) 5.49-5.57 (m, 1 H) 4.46 (br. s., 1 H) 4.20 (d, J = 8.53 Hz, 2 H) 3.57 (br. s., 3 H) 2.70-2.84 (m, 2 H) 2.35-2.61 (m, 4 H) 2.14-2.31 (m, 2H) 1.96-2.10 (m, 2 H) | {4-[5-Cyclobutyl-4-(hexahydro-pyrrolo[3,2-b]pyrrol-1-yl)-pyrido[3,4-d]pyrimidin-2-yl]-pyridin-2-yl}-(3,5,6-trifluoro-pyridin-2-yl)-amine |
| 99 | 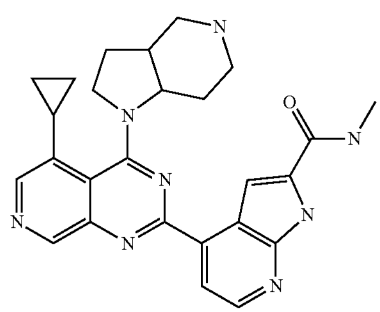 [SMILES: CNC(=O)c1cc2c(-c3nc(N4CCC5CNCCC54)c4c(C5CC5)cncc4n3)ccnc2[nH]1] | [D21] | 469.17 (M + H)+ | 1H NMR (400 MHz, DMSO-d6) δ ppm 12.28 (br s, 1H), 9.18 (s, 1H), 8.72-8.61 (m, 3H), 8.52 (d, 1H, J = 4.9 Hz), 8.23 (s, 1H), 8.13 (d, 1H, J = 1.8 Hz), 8.10 (d, 1H, J = 5.0 Hz), 4.60 (m, 1H), 4.43-4.36 (m, 1H), 3.44-3.26 (m, 3H), 3.03-2.95 (m, 2H), 2.89 (d, 3H, J = 4.6 Hz), 2.75-2.71 (m, 2H), 2.48 (m, 1H), 2.26 (m, 1H), 1.96-1.87 (m, 1H), 1.79-1.75 (m, 1H), 1.51-1.43 (m, 1H), 1.22-1.15 (m, 1H), 1.12-1.05 (m, 1H), 0.96-0.89 (m, 1H) | 4-[5-Cyclopropyl-4-(octahydro-pyrrolo[3,2-c]pyridin-1-yl)-pyrido[3,4-d]pyrimidin-2-yl]-1H-pyrrolo[2,3-b]pyridine-2-carboxylic acid methylamide |
| 100 | 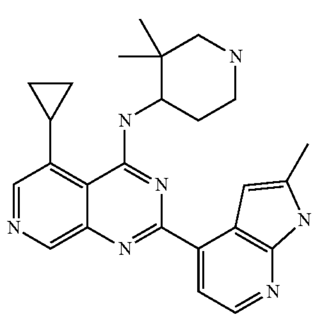 [SMILES: Cc1cc2c(-c3nc(NC4CCNCC4(C)C)c4c(C5CC5)cncc4n3)ccnc2[nH]1] | [D4], [D3] | 428.20 (M + H)+ | 1H NMR (400 MHz, DMSO-d6) ppm 11.79 (s, 1 H), 9.16 (s, 1 H), 9.02-9.11 (m, 1 H), 8.49 (s, 1 H), 8.32-8.43 (m, 1 H), 8.29 (d, J = 5.0 Hz, 1 H), 8.16 (s, 1 H), 7.58 (d, J = 8.8 Hz, 1 H), 7.22-7.28 (m, 1 H), 4.76-4.96 (m, 1 H), 3.33-3.45 (m, 2 H), 3.06-3.28 (m, 3 H), 2.60 (t, J = 6.1 Hz, 1 H), 2.09-2.24 (m, 1 H), 1.86-2.04 (m, 1 H), 1.23-1.32 (m, 1 H), 1.21 (s, 3 H), 1.18 (d, J = 6.0 Hz, 2 H), 1.12 (s, 3 H) | [5-Cyclopropyl-2-(2-methyl-1H-pyrrolo[2,3-b]pyridin-4-yl)-pyrido[3,4-d]pyrimidin-4-yl]-(3,3-dimethyl-piperidin-4-yl)-amine |

TABLE A-continued

| Ex | Structure | Scheme | LCMS | 1H-NMR | Name |
|---|---|---|---|---|---|
| 101 | 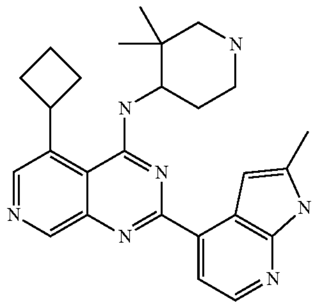 [SMILES: Cc1cc2c(-c3nc(NC4CCNCC4(C)C)c4c(C5CCC5)cncc4n3)ccnc2[nH]1] | [D4], [D3] | 442.18 (M + H)+ | 1H NMR (400 MHz, DMSO-d6) ppm 11.82 (s, 1 H), 9.16 (s, 1 H), 9.09 (d, J = 10.0 Hz, 1 H), 8.55 (s, 1 H), 8.32-8.46 (m, 1 H), 8.29 (d, J = 5.3 Hz, 1 H), 8.13 (d, J = 5.3 Hz, 1 H), 7.19-7.27 (m, 1 H), 6.54 (d, J = 8.5 Hz, 1 H), 4.70-4.87 (m, 2 H), 4.43 (t, J = 8.2 Hz, 1 H), 3.33-3.43 (m, 1 H), 3.19-3.27 (m, 1 H), 3.08-3.19 (m, 2 H), 2.22-2.42 (m, 2 H), 1.82-2.15 (m, 5 H), 1.27 (s, 3 H), 1.12 (s, 3 H) | [5-Cyclobutyl-2-(2-methyl-1H-pyrrolo[2,3-b]pyridin-4-yl)-pyrido[3,4-d]pyrimidin-4-yl]-(3,3-dimethyl-piperidin-4-yl)-amine |
| 102 | 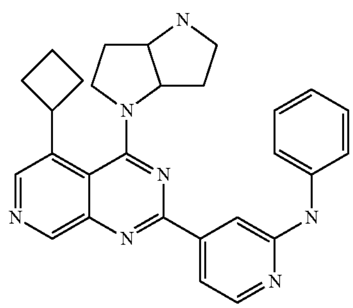 [SMILES: c1ccc(Nc2cc(-c3nc(N4CCC5NCCC54)c4c(C5CCC5)cncc4n3)ccn2)cc1] | [B4] | 464 (M + H)+ | 1H NMR (400 MHz, METHANOL-d4) δ ppm 9.07 (s, 1 H) 8.73 (s, 1 H) 8.23-8.30 (m, 1 H) 8.00-8.06 (m, 2 H) 7.54-7.62 (m, 2 H) 7.39-7.51 (m, 3 H) 5.30-5.38 (m, 1 H) 4.37-4.46 (m, 1 H) 3.99-4.23 (m, 2 H) 3.44-3.65 (m, 3 H) 2.67-2.80 (m, 1 H) 2.29-2.61 (m, 5 H) 2.11-2.28 (m, 2 H) 2.01 (s, 2 H) | {4-[5-Cyclobutyl-4-(hexahydro-pyrrolo[3,2-b]pyrrol-1-yl)-pyrido[3,4-d]pyrimidin-2-yl]-pyridin-2-yl}-phenyl-amine |
| 103 | 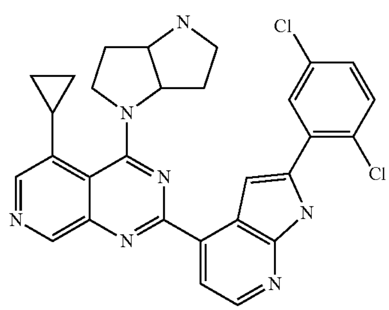 [SMILES: Clc1ccc(Cl)c(-c2cc3c(-c4nc(N5CCC6NCCC65)c5c(C6CC6)cncc5n4)ccnc3[nH]2)c1] | [D4], [D3] | 542.14 (M + H)+ | 1H NMR (400 MHz, DMSO-d6) δ ppm 12.35 (d, 1H, J = 1.6 Hz), 9.26 (m, 1H), 9.09-9.05 (m, 2H), 8.48 (d, 1H, J = 5.0 Hz), 8.20 (m, 2H), 7.97 (d, 1H, J = 2.1 Hz), 7.92 (d, 1H, J = 2.5 Hz), 7.70 (d, 1H, J = 8.6 Hz), 7.54 (m, 1H), 5.42 (m, 1H), 4.37-4.27 (m, 2H), 3.61-3.33 (m, 3H), 2.47-2.36 (m, 3H), 2.28-2.23 (m, 1H), 2.19-2.10(m, 1H), 1.42-1.36 (m, 1H), 1.20-1.13 (m, 1H), 1.09-1.03 (m, 1H), 1.00-0.94 (m, 1H) | 5-Cyclopropyl-2-[2-(2,5-dichloro-phenyl)-1H-pyrrolo[2,3-b]pyridin-4-yl]-4-(hexahydro-pyrrolo[3,2-b]pyrrol-1-yl)-pyrido[3,4-d]pyrimidine |
| 104 | 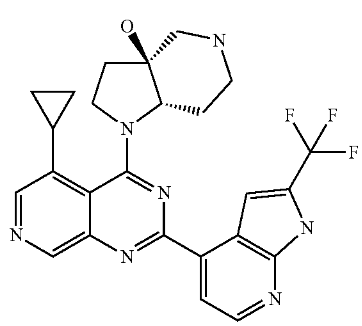 [SMILES: O[C@]12CCN(c3nc(-c4ccnc5[nH]c(C(F)(F)F)cc45)nc4cncc(C5CC5)c34)[C@H]1CCNC2] | [D4], [D3] | 496.16 (M + H)+ | 1H NMR (400 MHz, DMSO-d6) ppm 13.17 (br. s., 1 H), 9.13 (s, 1 H), 8.91-9.11 (m, 1 H), 8.76 (br. s., 1 H), 8.65 (d, J = 5.0 Hz, 1 H), 8.21 (s, 2 H), 7.95 (s, 1 H), 4.38 (br. s., 1 H), 4.27-4.36 (m, 1 H), 3.37 (d, J = 9.8 Hz, 1 H), 3.30 (br. s., 2 H), 3.21 (d, J = 12.5 Hz, 1 H), 3.06 (q, J = 10.3 Hz, 1 H), 2.59-2.78 (m, 1 H), 2.23-2.41 (m, 1H), 1.97-2.09 (m, 1 H), 1.82-1.97 (m, 1 H), 1.42-1.52 (m, 1 H), 1.14-1.23 (m, 1 H), 1.09 (td, J = 9.4, 5.8 Hz, 1 H), 0.84-1.03 (m, 1 H) | (±)-(3aS,7aS)-1-[5-Cyclopropyl-2-(2-trifluoromethyl-1H-pyrrolo[2,3-b]pyridin-4-yl)-pyrido[3,4-d]pyrimidin-4-yl]-octahydro-pyrrolo[3,2-c]pyridin-3a-ol |

TABLE A-continued

| Ex | Structure | Scheme | LCMS | 1H-NMR | Name |
|---|---|---|---|---|---|
| 105 | 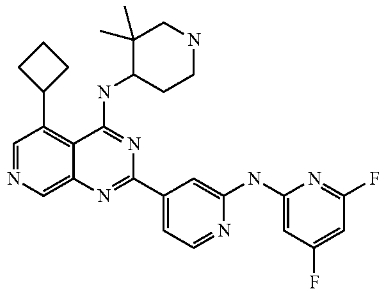 [SMILES: CC1(C)CNCCC1Nc1nc(-c2ccnc(Nc3cc(F)cc(F)n3)c2)nc2cncc(C3CCC3)c12] | [B4] | 517 (M + H)+ | 1H NMR (400 MHz, METHANOL-d4) δ ppm 9.08 (s, 1 H) 8.56 (s, 1 H) 8.48 (d, J = 5.77 Hz, 1 H) 7.96-8.03 (m, 2 H) 7.30 (s, 2 H) 4.94-5.02 (m, 1 H) 4.22-4.34 (m, 1 H) 3.48-3.55 (m, 1 H) 3.35 (br. s., 1 H) 3.25-3.29 (m, 1 H) 3.15-3.23 (m, 1 H) 2.63 (d, J = 2.51 Hz, 4 H) 1.98-2.30 (m, 4H) 1.37 (s, 3 H) 1.22 (s, m | {5-Cyclobutyl-2-[2-(4,6-difluoro-pyridin-2-ylamino)-pyridin-4-yl]-pyrido[3,4-d]pyrimidin-4-yl}-(3,3-dimethyl-piperidin-4-yl)-amine |
| 106 | 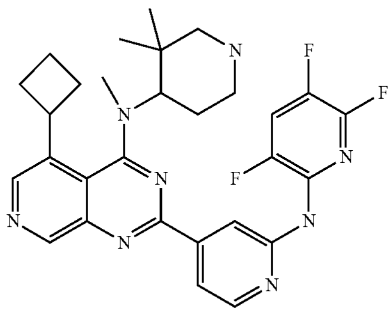 [SMILES: CN(c1nc(-c2ccnc(Nc3nc(F)c(F)cc3F)c2)nc2cncc(C3CCC3)c12)C1CCNCC1(C)C] | [B4] | 549 (M + H)+ | 1H NMR (400 MHz, METHANOL-d4) δ ppm 9.12 (s, 1 H) 8.97 (s, 1 H) 8.63-8.83 (m, 1 H) 8.45 (dd, J = 6.02, 0.75 Hz, 1 H) 8.26 (d, J = 5.77 Hz, 1 H) 8.06 (td, J = 8.91,7.28 Hz, 1 H) 5.72-5.81 (m, 1 H) 4.11 (s, 1 H) 3.51-3.65 (m, 1 H) 3.33-3.46 (m, 2 H) 3.17-3.28 (m, 1 H) 3.09 (s, 3 H) 2.68-2.81 (m, 2 H) 2.32-2.62 (m, 2 H) 2.01 (s, 4) 1.53 (s, 3 H) 1.33 (s, 3 H) | {5-Cyclobutyl-2-[2-(3,5,6-trifluoro-pyridin-2-ylamino)-pyridin-4-yl]-pyrido[3,4-d]pyrimidin-4-yl}-(3,3-dimethyl-piperidin-4-yl)-methyl-amine |
| 107 | 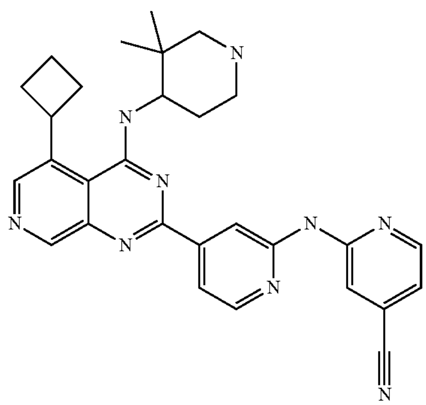 [SMILES: CC1(C)CNCCC1Nc1nc(-c2ccnc(Nc3cc(C#N)ccn3)c2)nc2cncc(C3CCC3)c12] | [B4] | 506 (M + H)+ | 1H NMR (400 MHz, METHANOL-d4) δ ppm 9.14 (s, 1 H) 8.67 (dd, J = 5.27, 0.75 Hz, 1 H) 8.64 (s, 1 H) 8.60 (d, J = 0.75 Hz, 1 H) 8.46-8.50 (m, 1 H) 8.39-8.44 (m, 1 H) 7.61 (t, J = 1.00 Hz, 1 H) 7.54 (dd, J = 5.27, 1.25 Hz, 1 H) 5.03 (dd, J = 11.80, 4.27 Hz, 1 H) 4.31 (s, 1 H) 3.45-3.56 (m, 1 H) 3.32-3.43 (m, 2 H) 3.20-3.28 (m, 1 H) 2.37-2.70 (m, 4 H) 2.03-2.28 (m, 4 H) 1.37 (s, 3 H) 1.22 (s, 3 H) | 2-{4-[5-Cyclobutyl-4-(3,3-dimethyl-piperidin-4-ylamino)-pyrido[3,4-d]pyrimidin-2-yl]-pyridin-2-ylamino}-isonicotinonitrile |
| 108 | 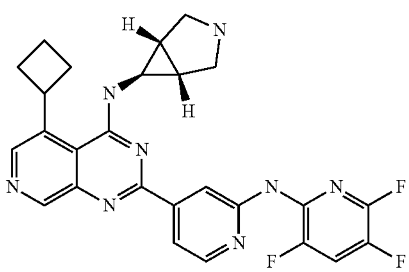 [SMILES: Fc1cc(F)c(Nc2cc(-c3nc(N[C@H]4[C@@H]5CNC[C@@H]54)c4c(C5CCC5)cncc4n3)ccn2)nc1F] | [B4] | 505 (M + H)+ | 1H NMR (400 MHz, CHLOROFORM-d) δ ppm 13.03-13.28 (m, 1 H) 10.26-10.44 (m, 1 H) 10.06-10.25 (m, 1 H) 9.28 (s, 1 H) 9.23 (s, 1 H) 8.63 (s, 1 H) 8.44 (dd, J = 6.65, 1.38 Hz, 1 H) 8.23(d, J = 6.52 Hz, 1 H) 7.72 (d, J = 7.53 Hz, 1 H) 4.03 (dd, J = 10.92, 5.90 Hz, 4 H) 2.51-2.62 (m, 4 H) 2.37-2.50 (m, 4 H) 2.18-2.30 (m, 2 H) | (1S,6S)-3-Aza-bicyclo[3.1.0]hex-6-yl-{(R)-5-cyclobutyl-2-[2-(3,5,6-trifluoro-pyridin-2-ylamino)-pyridin-4-yl]-pyrido[3,4-d]pyrimidin-4-yl}-amine |
| 109 | 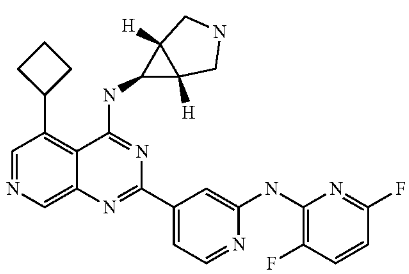 [SMILES: Fc1ccc(F)c(Nc2cc(-c3nc(N[C@H]4[C@@H]5CNC[C@@H]54)c4c(C5CCC5)cncc4n3)ccn2)n1] | [B4] | 487 (M + H)+ | 1H NMR (400 MHz, CHLOROFORM-d) δ ppm 13.08-13.37 (m, 1 H) 10.39 (br. s., 2 H) 9.27 (s, 2 H) 8.64 (s, 1 H) 8.46 (d, J = 6.53 Hz, 1 H) 8.22 (d, J = 6.52 Hz, 1 H) 7.77 (d, J = 5.77 Hz, 1 H) 6.82 (d, J = 8.78 Hz, 1 H) 6.55 (br. s., 1 H) 4.04 (d, J = 8.03 Hz, 4 H) 2.56 (br. s., 4 H) 2.36-2.50 (m, 4 H) 2.18-2.31 (m, 2 H) | (1S,6S)-3-Aza-bicyclo[3.1.0]hex-6-yl-{(R)-5-cyclobutyl-2-[2-(3,6-difluoro-pyridin-2-ylamino)-pyridin-4-yl]-pyrido[3,4-d]pyrimidin-4-yl}-amine |

TABLE A-continued

| Ex | Structure | Scheme | LCMS | 1H-NMR | Name |
|---|---|---|---|---|---|
| 110 | 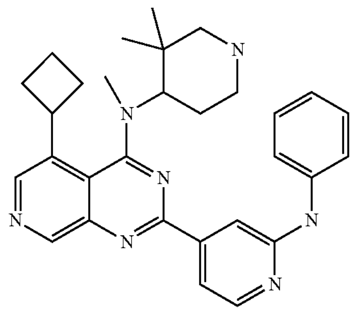 [SMILES: CN(c1nc(-c2ccnc(Nc3ccccc3)c2)nc2cncc(C3CCC3)c12)C1CCNCC1(C)C] | [B4] | 494 {M + H} | 1H NMR (400 MHz, METHANOL-d4) δ ppm 9.09 (s, 1 H) 8.96 (s, 1 H) 8.15 (s, 1 H) 7.97-8.07 (m, 2 H) 7.52-7.60 (m, 2 H) 7.46-7.52 (m, 2 H) 7.34-7.44 (m, 1 H) 5.60-5.68 (m, 1 H) 4.37 (br. s., 1 H) 3.54-3.64 (m, 1 H) 3.07 (s, 4 H) 3.00-3.07 (m, 1 H) 2.74 (br. s., 2 H) 2.45-2.63 (m, 1 H) 2.29-2.45 (m, 2 H) 2.04-2.20 (m, 3 H) 1.88-2.01 (m, 1 H) 1.50 (s, 3 H) 1.25 (s, 3 H) | [5-Cyclobutyl-2-(2-phenylamino-pyridin-4-yl)-pyrido[3,4-d]pyrimidin-4-yl]-(3,3-dimethyl-piperidin-4-yl)-methyl-amine |
| 111 | 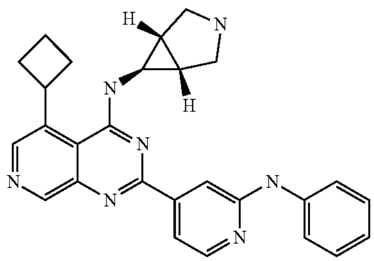 [SMILES: c1ccc(Nc2cc(-c3nc(N[C@H]4[C@@H]5CNC[C@@H]54)c4c(C5CCC5)cncc4n3)ccn2)cc1] | [B4] | 450 (M + H)+ | 1H NMR(400 MHz, METHANOL-d4) δ ppm 9.09 (s, 1 H) 8.48 (s, 1 H) 8.30 (d, J = 0.75 Hz, 1 H) 7.99-8.10 (m, 2 H) 7.54-7.60 (m, 2 H) 7.46-7.51 (m, 2 H) 7.42 (s, 1 H) 4.34 (s, 1 H) 3.52-3.68 (m, 4 H) 3.02 (s, 1 H) 2.57 (dd, J = 7.91, 2.89 Hz, 2 H) 2.13-2.34 (m, 5 H) 1.84-1.97 (m, 1 H) | (1S,6S)-3-Aza-bicyclo[3.1.0]hex-6-yl-[(R)-5-cyclobutyl-2-(2-phenylamino-pyridin-4-yl)-pyrido[3,4-d]pyrimidin-4-yl]-amine |
| 112 | 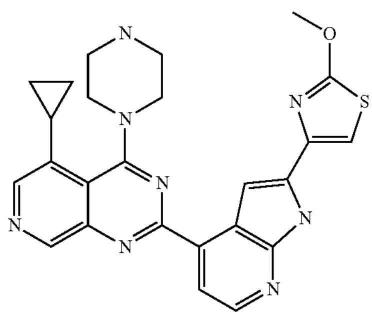 [SMILES: COc1nc(-c2cc3c(-c4nc(N5CCNCC5)c5c(C6CC6)cncc5n4)ccnc3[nH]2)cs1] | [D4], [D3] | 485.13 (M + H)+ | 1H NMR (400 MHz, DMSO-d6) δ 12.36 (d, 1H, J = 1.7 Hz), 9.17 (s, 1H), 8.96 (br s, 2H), 8.41 (d, 1H, J = 5.1 Hz), 8.19 (s, 1H), 8.15 (d, 1H, J = 5.1 Hz), 7.83 (d, 1H, J = 2.1 Hz), 7.65 (s, 1H), 4.19 (s, 3H), 4.00 (m, 4H), 3.38 (m, 4H), 2.78-2.72 (m, 1H), 1.30-1.25 (m, 2H), 1.12-1.08 (m, 2H) | 5-Cyclopropyl-2-[2-(2-methoxy-thiazol-4-yl)-1H-pyrrolo[2,3-b]pyridin-4-yl]-4-piperazin-1-yl-pyrido[3,4-d]pyrimidine |
| 113 | 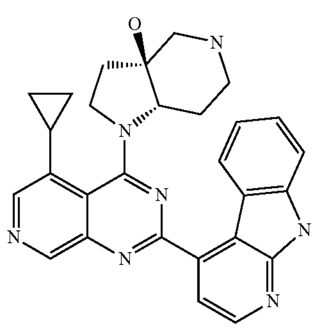 [SMILES: O[C@]12CCN(c3nc(-c4ccnc5[nH]c6ccccc6c45)nc4cncc(C5CC5)c34)[C@H]1CCNC2] | [D3] | 478.17 (M + H)+ | (400 MHz, d6-DMSO, δ): 12.07 (s, 1H), 9.08 (s, 1H), 8.75 (d, J = 8.0 Hz, 1H), 8.73-8.63 (m, 2H), 8.59 (d, J = 5.1 Hz, 1H), 8.27 (s, 1H), 7.85 (d, J = 5.1 Hz, 1H), 7.55 (d, J = 7.9 Hz, 1H), 7.51-7.46 (m, 1H), 7.21-7.16 (m, 1H), 5.81 (br s, 1H), 4.38-4.28 (m, 2H), 3.48-3.38 (m, 1H), 3.32-2.97 (m, 4H), 2.65-2.48 (m, 2H), 2.25-2.10 (m, 1H), 2.07-1.99 (m, 1H), 1.94-1.84 (m, 1H), 1.52-1.43 (m, 1H), 1.25-1.09 (m, 2H), 1.01-0.94 (m, 1H). | (±)-(3aS,7aS)-1-[5-Cyclopropyl-2-(9H-pyrido[2,3-b]indol-4-yl)-pyrido[3,4-d]pyrimidin-4-yl]-octahydro-pyrrolo[3,2-c]pyridin-3a-ol |
| 114 | 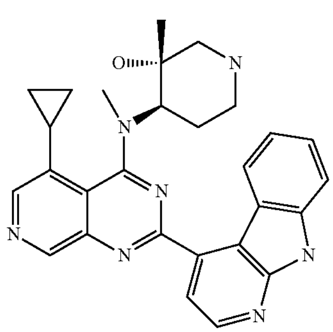 [SMILES: CN(c1nc(-c2ccnc3[nH]c4ccccc4c23)nc2cncc(C3CC3)c12)[C@@H]1CCNC[C@@]1(C)O] | [D3] | 480.14 (M + H)+ | (400 MHz, d6-DMSO, δ): 12.20-12.00 (m, 1H), 9.42-8.15 (m, 6H), 7.85-7.78 (m, 1H), 7.60-7.45 (m, 2H), 7.23-7.13 (m, 1H), 5.66-0.88 (m, 19H) | (±)-(3,4-trans)-4-{[5-Cyclopropyl-2-(9H-pyrido[2,3-b]indol-4-yl)-pyrido[3,4-d]pyrimidin-4-yl]-methyl-amino}-3-methyl-piperidin-3-ol |

TABLE A-continued

| Ex | Structure | Scheme | LCMS | 1H-NMR | Name |
|---|---|---|---|---|---|
| 115 | 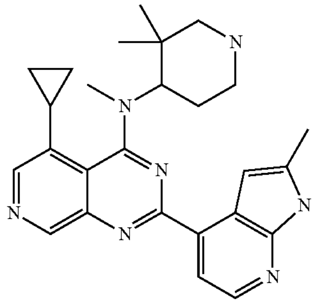 [SMILES: Cc1cc2c(-c3nc(N(C)C4CCNCC4(C)C)c4c(C5CC5)cncc4n3)ccnc2[nH]1] | [D4], [D3] | 442.17 (M + H)+ | 1H NMR (400 MHz, DMSO-d6, ppm): 11.79 (s, 1 H), 9.08 (s, 2 H), 8.28 (d, J = 5.3 Hz, 2 H), 8.03-8.16 (m, 2 H), 7.20 (s, 1 H), 3.42-3.53 (m, 2 H), 2.96-3.38 (m, 6 H), 2.67-2.90 (m, 1 H), 2.06-2.34 (m, 1 H), 1.74-2.04 (m, 1 H), 1.39-1.60 (m, 1 H), 1.22 (d, J = 8.3 Hz, 7 H), 0.89-1.03 (m, 1 H) | [5-Cyclopropyl-2-(2-methyl-1H-pyrrolo[2,3-b]pyridin-4-yl)-pyrido[3,4-d]pyrimidin-4-yl]-(3,3-dimethyl-piperidin-4-yl)-methyl-amine |
| 116 | 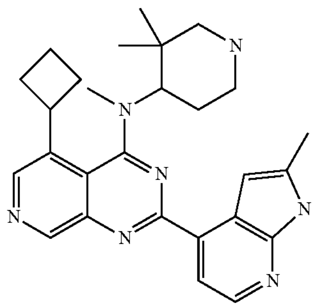 [SMILES: Cc1cc2c(-c3nc(N(C)C4CCNCC4(C)C)c4c(C5CCC5)cncc4n3)ccnc2[nH]1] | [D4], [D3] | 456.19 (M + H)+ | 1H NMR (400 MHz, DMSO-d6, ppm): 11.72 (s, 1 H), 9.16 (s, 1 H), 8.97 (s, 1 H), 8.27 (d, J = 5.0 Hz, 2 H), 8.07 (s, 1 H), 7.17 (s, 1 H), 5.57 (d, J = 9.8 Hz, 1 H), 4.35 (d, J = 8.0 Hz, 1 H), 3.48-3.53 (m, 1 H), 3.07-3.35 (m, 4 H), 2.95 (s, 3 H), 2.67 (d, J = 1.8 Hz, 2 H), 2.13-2.31 (m, 2 H), 1.82-2.09 (m, 4 H), 1.42 (s, 3 H), 1.18 (s, 3 H), 1.05 (br. s., 1 H) | [5-Cyclobutyl-2-(2-methyl-1H-pyrrolo[2,3-b]pyridin-4-yl)-pyrido[3,4-d]pyrimidin-4-yl]-(3,3-dimethyl-piperidin-4-yl)-methyl-amine |
| 117 | 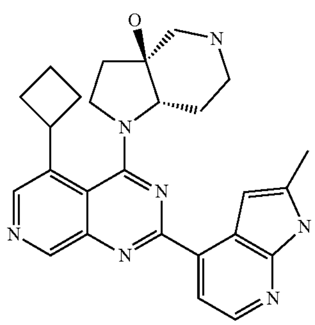 [SMILES: Cc1cc2c(-c3nc(N4CC[C@]5(O)CNCC[C@H]45)c4c(C5CCC5)cncc4n3)ccnc2[nH]1] | [D4], [D3] | 456.19 (M + H)+ | 1H NMR (400 MHz, DMSO-d6, ppm): 11.84 (s, 1 H), 9.15 (s, 1 H), 8.92-9.08 (m, 1 H), 8.78-8.90 (m, 1 H), 8.73 (s, 1 H), 8.29 (d, J = 5.0 Hz, 1 H), 8.02 (d, J = 5.3 Hz, 1 H), 7.20 (s, 1 H), 4.36 (t, J = 4.5 Hz, 1 H), 4.17-4.32 (m, 1 H), 3.95 (d, J = 7.5 Hz, 1 H), 3.32 (br. s., 3 H), 3.25 (br. s., 2 H), 3.03 (d, J = 9.3 Hz, 1 H), 2.63-2.79 (m, 1 H), 2.17-2.45 (m, 3 H), 2.10 (d, J = 9.0 Hz, 1 H), 1.76-2.02 (m, 3 H) | (±)-(3aS,7aS)-1-[5-Cyclobutyl-2-(2-methyl-1H-pyrrolo[2,3-b]pyridin-4-yl)-pyrido[3,4-d]pyrimidin-4-yl]-octahydro-pyrrolo[3,2-c]pyridin-3a-ol |
| 118 | 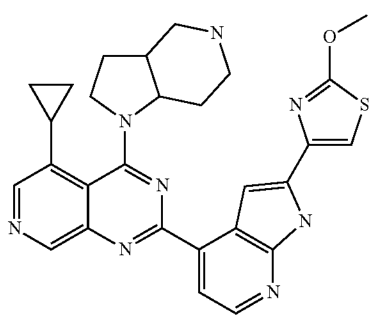 [SMILES: COc1nc(-c2cc3c(-c4nc(N5CCC6CNCCC65)c5c(C6CC6)cncc5n4)ccnc3[nH]2)cs1] | [D4], [D3] | 525.17 (M + H)+ | 1H NMR (400 MHz, DMSO-d6) δ 12.32 (d, 1H, J = 1.7 Hz), 9.07 (s, 1H), 8.64 (m, 2H), 8.39 (d, 1H, J = 5.1 Hz), 8.20 (s, 1H), 8.09 (m, 1H, J = 5.0 Hz), 7.80 (d, 1H, J = 2.1 Hz), 7.62 (s, 1H), 4.62 (m, 1H), 4.41-4.36 (m, 1H), 4.19 (s, 3H), 3.42-3.25 (m, 4H), 3.01-2.72 (m, 4H), 2.33-2.28 (m, 1H), 1.97-1.88 (m, 1H), 1.77 (m, 1H), 1.50-1.43 (m, 1H), 1.22-1.06 (m, 2H), 0.96-0.92 (m, 1H) | 5-Cyclopropyl-2-[2-(2-methoxy-thiazol-4-yl)-1H-pyrrolo[2,3-b]pyridin-4-yl]-4-(octahydro-pyrrolo[3,2-c]pyridin-1-yl)-pyrido[3,4-d]pyrimidine |
| 119 | 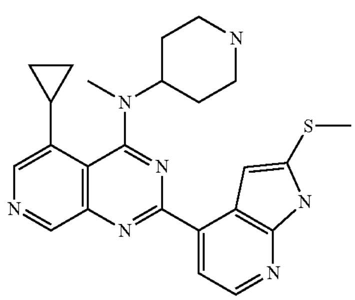 [SMILES: CSc1cc2c(-c3nc(N(C)C4CCNCC4)c4c(C5CC5)cncc4n3)ccnc2[nH]1] | [D4], [D3] | 446 (M + H)+ | | [5-Cyclopropyl-2-(2-methylsulfanyl-1H-pyrrolo[2,3-b]pyridin-4-yl)-pyrido[3,4-d]pyrimidin-4-yl]-methyl-piperidin-4-yl-amine |

TABLE A-continued

| Ex | Structure | Scheme | LCMS | 1H-NMR | Name |
|---|---|---|---|---|---|
| 120 | 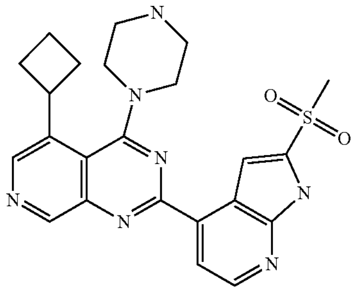 [SMILES: CS(=O)(=O)c1cc2c(-c3nc(N4CCNCC4)c4c(C5CCC5)cncc4n3)ccnc2[nH]1] | [D4], [D3] | 464 (M + H)+ | | 5-Cyclobutyl-2-(2-methanesulfonyl-1H-pyrrolo[2,3-b]pyridin-4-yl)-4-piperazin-1-yl-pyrido[3,4-d]pyrimidine |
| 121 | 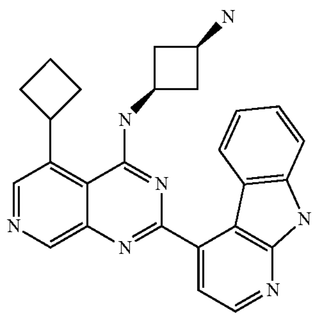 [SMILES: N[C@H]1C[C@@H](Nc2nc(-c3ccnc4[nH]c5ccccc5c34)nc3cncc(C4CCC4)c23)C1] | [D3] | 436 (M + H)+ | 1H NMR (400 MHz, DMSO-d6) δ ppm 12.04 (1 H, s) 9.12 (1 H, s) 8.43-8.64 (3 H, m) 8.00 (3 H, br. s.) 7.79 (1 H, d, J = 5.0 Hz) 7.31-7.58 (3 H, m) 7.15 (1 H, ddd, J = 8.1, 7.0, 1.3 Hz) 4.44-4.72 (3 H, m) 3.53 (1 H, d, J = 5.8 Hz) 2.57-2.81 (4 H, m) 2.22-2.38 (5 H, m) 2.05-2.23 (2 H, m) 1.81-1.98 (1 H, m) | cis-[5-Cyclobutyl-2-(9H-pyrido[2,3-b]indol-4-yl)-pyrido[3,4-d]pyrimidin-4-yl]-cyclobutane-1,3-diamine |
| 122 | 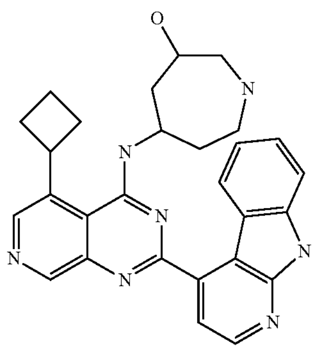 [SMILES: OC1CNCCC(Nc2nc(-c3ccnc4[nH]c5ccccc5c34)nc3cncc(C4CCC4)c23)C1] | [D3] | 480 (M + H)+ | 1H NMR (400 MHz, DMSO-d6) δ ppm 12.03 (1 H, s) 9.12 (1 H, s) 8.86 (1 H, br. s.) 8.49-8.67 (3 H, m) 8.38 (1 H, br. s.) 7.81 (1 H, d, J = 5.0 Hz) 7.42-7.65 (3 H, m) 7.06-7.24 (1 H, m) 6.21 (1 H, br. s.) 4.86 (1H, br. s.) 4.26-4.43 (2 H, m) 3.01-3.28 (6 H, m) 1.78-2.33 (9 H, m) | 5-[5-Cyclobutyl-2-(9H-pyrido[2,3-b]indol-4-yl)-pyrido[3,4-d]pyrimidin-4-ylamino]-azepan-3-ol |
| 123 | 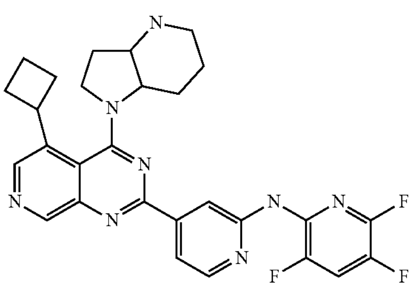 [SMILES: Fc1cc(F)c(Nc2cc(-c3nc(N4CCC5NCCCC54)c4c(C5CCC5)cncc4n3)ccn2)nc1F] | [B4] | 533 (M + H)+ | 1H NMR (400 MHz, METHANOL-d4) δ ppm 9.13 (s, 1 H) 8.88 (d, J = 0.75 Hz, 1 H) 8.75 (s, 1 H) 8.46 (d, J = 6.27 Hz, 1 H) 8.28 (dd, J = 6.27, 1.51 Hz, 1 H) 8.02-8.15 (m, 1 H) 4.25-4.43 (m, 2 H) 4.04-4.10 (m, 1 H) 3.37-3.57 (m, 2 H) 3.09-3.24 (m, 1 H) 2.69-2.85 (m, 2 H) 2.41-2.61 (m, 2 H) 2.11-2.32 (m, 4 H) 1.84-2.07 (m, 4 H) | {4-[5-Cyclobutyl-4-(octahydro-pyrrolo[3,2-b]pyridin-1-yl)-pyrido[3,4-d]pyrimidin-2-yl]-pyridin-2-yl}-(3,5,6-trifluoro-pyridin-2-yl)-amine |
| 124 | 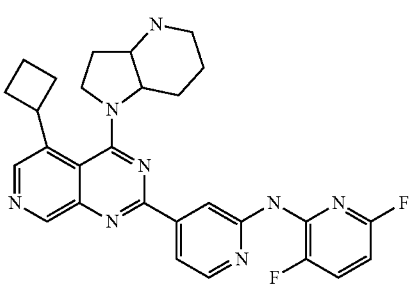 [SMILES: Fc1ccc(F)c(Nc2cc(-c3nc(N4CCC5NCCCC54)c4c(C5CCC5)cncc4n3)ccn2)n1] | [B4] | 515 (M + H)+ | 1H NMR (400 MHz, METHANOL-d4) δ ppm 9.12 (s, 1 H) 8.97 (s, 1 H) 8.74 (s, 1 H) 8.49 (d, J = 6.02 Hz, 1 H) 8.28 (dd, J = 6.27, 1.51 Hz, 1 H) 7.88 (d, J = 6.02 Hz, 1 H) 6.82 (d, J = 8.78 Hz, 1 H) 4.32 (d, J = 17.57 Hz, 2 H) 4.08 (d, J = 7.03 Hz, 1 H) 3.40-3.57 (m, 2 H) 3.08-3.25 (m, 1 H) 2.80 (d, J = 6.02 Hz, 2 H) 2.43-2.61 (m, 2 H) 1.78-2.32 (m, 9 H) | {4-[5-Cyclobutyl-4-(octahydro-pyrrolo[3,2-b]pyridin-1-yl)-pyrido[3,4-d]pyrimidin-2-yl]-pyridin-2-yl}-(3,6-difluoro-pyridin-2-yl)-amine |

TABLE A-continued

| Ex | Structure | Scheme | LCMS | 1H-NMR | Name |
|---|---|---|---|---|---|
| 125 | 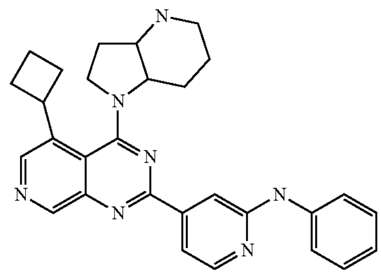 [SMILES: c1ccc(Nc2cc(-c3nc(N4CCC5NCCCC54)c4c(C5CCC5)cncc4n3)ccn2)cc1] | [B4] | 478 (M + H)+ | 1H NMR (400 MHz, METHANOL-d4) δ ppm 9.10 (s, 1 H) 8.74 (s, 1 H) 8.24 (t, J = 1.00 Hz, 1 H) 8.03 (d, J = 0.75 Hz, 2 H) 7.55-7.62 (m, 2 H) 7.43-7.50 (m, 3 H) 4.70 (d, J = 3.51 Hz, 1 H) 4.21-4.40 (m, 2 H) 4.00-4.07 (m, 1 H) 3.36-3.55 (m, 2 H) 3.10-3.21 (m, 1 H) 2.71-2.85 (m, 1 H) 2.49 (d, J = 9.54 Hz, 2 H) 1.79-2.30 (m, 9 H) | {4-[5-Cyclobutyl-4-(octahydro-pyrrolo[3,2-b]pyridin-1-yl)-pyrido[3,4-d]pyrimidin-2-yl]-pyridin-2-yl}-phenyl-amine |
| 126 | 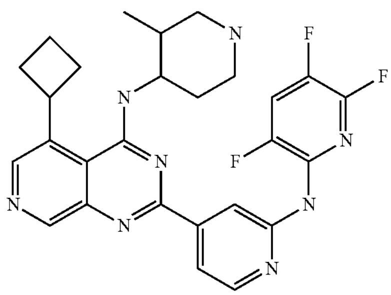 [SMILES: CC1CNCCC1Nc1nc(-c2ccnc(Nc3nc(F)c(F)cc3F)c2)nc2cncc(C3CCC3)c12] | [B4] | 521 (M + H)+ | 1H NMR (400 MHz, METHANOL-d4) δ ppm 9.09-9.16 (m, 1 H) 8.85-8.94 (m, 1 H) 8.61 (d, J = 1.00 Hz, 1 H) 8.46 (d, J = 6.27 Hz, 1 H) 8.33 (d, J = 1.51 Hz, 1 H) 8.05-8.17 (m, 1 H) 4.95-5.05 (m, 1 H) 4.69-4.84 (m, 1 H) 4.31-4.49 (m, 1 H) 3.34-3.63 (m, 3 H) 2.61-2.84 (m, 3 H) 2.17-2.49 (m, 5H) 1.95-2.07 (m, 1 H) 1.05-1.26 (m, 3 H) | {5-Cyclobutyl-2-[2-(3,5,6-trifluoro-pyridin-2-ylamino)-pyridin-4-yl]-pyrido[3,4-d]pyrimidin-4-yl}-(3-methyl-piperidin-4-yl)-amine |
| 127 | 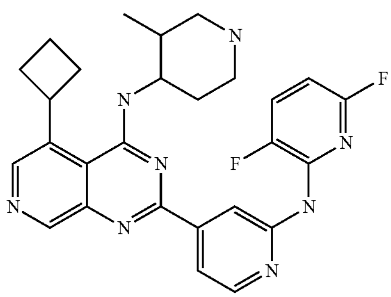 [SMILES: CC1CNCCC1Nc1nc(-c2ccnc(Nc3nc(F)ccc3F)c2)nc2cncc(C3CCC3)c12] | [B4] | 503 (M + H)+ | 1H NMR (400 MHz, METHANOL-d4) δ ppm 9.08-9.18 (m, 1 H) 8.86-8.96 (m, 1 H) 8.54-8.63 (m, 1 H) 8.46-8.54 (m, 1 H) 8.32-8.43 (m, 1 H) 7.87-8.01 (m, 1 H) 6.81-6.93 (m, 1 H) 4.92-5.04 (m, 1 H) 4.69-4.85 (m, 1 H) 4.26-4.49 (m, 1 H) 3.33-3.63 (m, 3 H) 2.73-2.84 (m, 1 H) 2.66 (dd, J = 7.03, 4.02 Hz, 2 H) 2.18-2.50 (m, 5 H) 2.02-2.08 (m, 1 H) 1.05-1.27 (m, 3 H) | {5-Cyclobutyl-2-[2-(3,6-difluoro-pyridin-2-ylamino)-pyridin-4-yl]-pyrido[3,4-d]pyrimidin-4-yl}-(3-methyl-piperidin-4-yl)-amine |
| 128 | 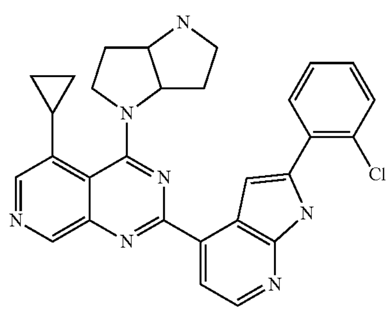 [SMILES: Clc1ccccc1-c1cc2c(-c3nc(N4CCC5NCCC54)c4c(C5CC5)cncc4n3)ccnc2[nH]1] | [D4], [D3] | 508.17 (M + H)+ | 1H NMR (400 MHz, DMSO-d6) δ 12.30 (d, 1H, J = 1.4 Hz), 9.27 (m, 1H), 9.13 (m, 1H), 9.05 (s, 1H), 8.45 (d, 1H, J = 5.0 Hz), 8.20 (m, 2H), 7.87 (d, 1H, J = 2.1 Hz), 7.82 (m, 1H), 7.66 (m, 1H), 7.55-7.45 (m, 2H), 5.44-5.41 (m, 1H), 4.37-4.27 (m, 2H), 3.60-3.33 (m, 3H), 2.45-2.10 (m, 1H), 1.43-1.36 (m, 1H), 1.20-0.94 (m, 3H) | 2-[2-(2-Chloro-phenyl)-1H-pyrrolo[2,3-b]pyridin-4-yl]-5-cyclopropyl-4-(hexahydro-pyrrolo[3,2-b]pyrrol-1-yl)-pyrido[3,4-d]pyrimidine |
| 129 | 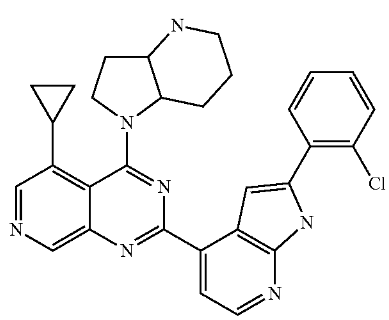 [SMILES: Clc1ccccc1-c1cc2c(-c3nc(N4CCC5NCCCC54)c4c(C5CC5)cncc4n3)ccnc2[nH]1] | [D4], [D3] | 522.17 (M + H)+ | 1H NMR (400 MHz, DMSO-d6) δ 12.28 (m, 1H), 9.37 (m, 1H), 9.06 (s, 1H), 8.46-8.37 (m, 2H), 8.19 (s, 1H), 8.11 (d, 1H, J = 5.0 Hz), 7.89 (d, 1H, J = 2.2 Hz), 7.82 (m, 1H), 7.66 (m, 1H), 7.55 -7.45 (m, 2H), 4.76 (m, 2H), 4.59-4.53 (m, 2H), 4.03 (m, 1H), 3.45-3.31 (m, 2H), 3.03 (m, 1H), 2.17-1.98 (m, 3H), 1.81-1.70 (m, 2H), 1.54-1.47 (m, 1H), 1.25 -1.07 (m, 2H), 0.95-0.89 (m, 1H) | 2-[2-(2-Chloro-phenyl)-1H-pyrrolo[2,3-b]pyridin-4-yl]-5-cyclopropyl-4-(octahydro-pyrrolo[3,2-b]pyridin-1-yl)-pyrido[3,4-d]pyrimidine |

TABLE A-continued

| Ex | Structure | Scheme | Analysis LCMS | 1H-NMR | Name |
|---|---|---|---|---|---|
| 130 | 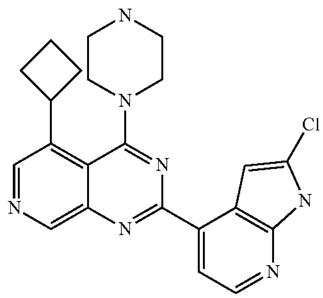 [SMILES: Clc1cc2c(-c3nc(N4CCNCC4)c4c(C5CCC5)cncc4n3)ccnc2[nH]1] | [D4], [D3] | 420 (M + H)+ | | 2-(2-Chloro-1H-pyrrolo[2,3-b]pyridin-4-yl)-5-cyclobutyl-4-piperazin-1-yl-pyrido[3,4-d]pyrimidine |
| 131 | 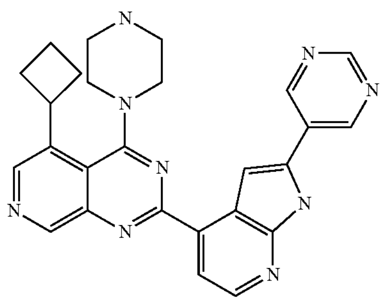 [SMILES: c1ncc(-c2cc3c(-c4nc(N5CCNCC5)c5c(C6CCC6)cncc5n4)ccnc3[nH]2)cn1] | [D4], [D3] | 464 (M + H)+ | | 5-Cyclobutyl-4-piperazin-1-yl-2-(2-pyrimidin-5-yl-1H-pyrrolo[2,3-b]pyridin-4-yl)-pyrido[3,4-d]pyrimidine |
| 132 | 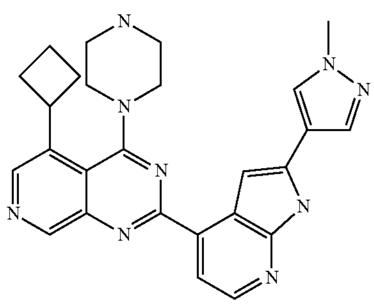 [SMILES: Cn1cc(-c2cc3c(-c4nc(N5CCNCC5)c5c(C6CCC6)cncc5n4)ccnc3[nH]2)cn1] | [D4], [D3] | 466 (M + H)+ | | 5-Cyclobutyl-2-[2-(1-methyl-1H-pyrazol-4-yl)-1H-pyrrolo[2,3-b]pyridin-4-yl]-4-piperazin-1-yl-pyrido[3,4-d]pyrimidine |
| 133 | 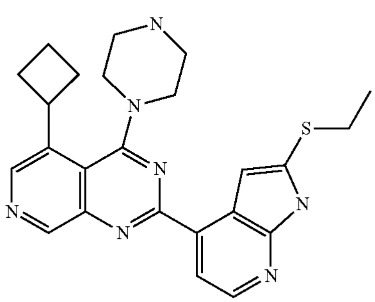 [SMILES: CCSc1cc2c(-c3nc(N4CCNCC4)c4c(C5CCC5)cncc4n3)ccnc2[nH]1] | [D4], [D3] | 446 (M + H)+ | | 5-Cyclobutyl-2-(2-ethylsulfanyl-1H-pyrrolo[2,3-b]pyridin-4-yl)-4-piperazin-1-yl-pyrido[3,4-d]pyrimidine |
| 134 | 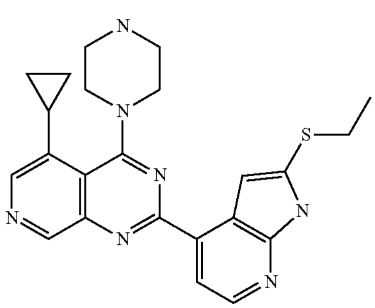 [SMILES: CCSc1cc2c(-c3nc(N4CCNCC4)c4c(C5CC5)cncc4n3)ccnc2[nH]1] | [D4], [D3] | 432 (M + H)+ | | 5-Cyclopropyl-2-(2-ethylsulfanyl-1H-pyrrolo[2,3-b]pyridin-4-yl)-4-piperazin-1-yl-pyrido[3,4-d]pyrimidine |

TABLE A-continued

| Ex | Structure | Scheme | Analysis LCMS | 1H-NMR | Name |
|---|---|---|---|---|---|
| 135 | 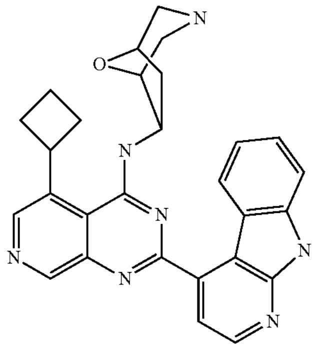 [SMILES: c1ccc2c(c1)[nH]c1nccc(-c3nc(NC4CC5CNCC4O5)c4c(C5CCC5)cncc4n3)c12] | [D3] | 478 (M + H)+ | 1H NMR (400 MHz, DMSO-d6) δ ppm 12.04 (1 H, s) 9.14 (1 H, s) 8.99 (1 H, br. s.) 8.67 (1 H, br. s.) 8.44-8.59 (3 H, m) 7.83 (1 H, d, J = 5.0 Hz) 7.42-7.59 (2 H, m) 7.10-7.27 (2 H, m) 4.92-5.06 (1 H, m) 4.49-4.76 (3 H, m) 3.01-3.27 (5 H, m) 1.75-2.36 (6 H, m) | [5-Cyclobutyl-2-(9H-pyrido[2,3-b]indol-4-yl)-pyrido[3,4-d]pyrimidin-4-yl]-(8-oxa-3-aza-bicyclo[3.2.1]oct-6-yl)-amine |
| 136 | 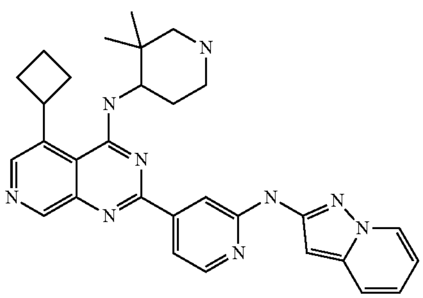 | [B4] | 520 (M + H)+ | 1H NMR (400 MHz, METHANOL-d4) δ ppm 9.14 (s, 1 H) 8.64 (d, J = 1.00 Hz, 2 H) 8.49 (d, J = 1.00 Hz, 1 H) 8.41 (s, 1 H) 8.29 (s, 1 H) 7.61-7.69 (m, 1 H) 7.29-7.40 (m, 1 H) 6.90-7.01 (m, 1 H) 6.44 (s, 1 H) 4.95-5.04 (m, 1 H) 4.23-4.37 (m, 1 H) 3.48-3.58 (m, 1 H) 3.34-3.37 (m, 2 H) 3.19-3.24 (m, 1 H) 2.37-2.69 (m, 4 H) 2.00-2.32 (m, 4 H) 1.38 (s, 3H) 1.22 (s, 3 H) | {5-Cyclobutyl-2-[2-(pyrazolo[1,5-a]pyridin-2-ylamino)-pyridin-4-yl]-pyrido[3,4-d]pyrimidin-4-yl}-(3,3-dimethyl-piperidin-4-yl)-amine |
| 137 | 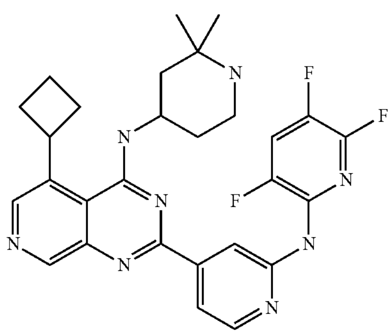 [SMILES: CC1(C)CC(Nc2nc(-c3ccnc(Nc4nc(F)c(F)cc4F)c3)nc3cncc(C4CCC4)c23)CCN1] | [B4] | 535 (M + H)+ | 1H NMR (400 MHz, METHANOL-d4) δ ppm 9.10 (s, 1 H) 8.83 (d, J = 0.75 Hz, 1 H) 8.51 (s, 1 H) 8.46 (d, J = 5.52 Hz, 1 H) 8.25 (dd, J = 6.27, 1.51 Hz, 1 H) 8.08 (d, J = 7.53 Hz, 1 H) 4.90-5.02 (m, 1 H) 4.43 (t, J = 8.41 Hz, 1 H) 3.47 (d, J = 3.01 Hz, 2 H) 2.49-2.71 (m, 3 H) 2.13-2.44 (m, 4 H) 1.76-2.03 (m, 3 H) 1.60 (s, 3 H) 1.50 (s, 3 H) | {5-Cyclobutyl-2-[2-(3,5,6-trifluoro-pyridin-2-ylamino)-pyridin-4-yl]-pyrido[3,4-d]pyrimidin-4-yl}-(2,2-dimethyl-piperidin-4-yl)-amine |
| 138 | 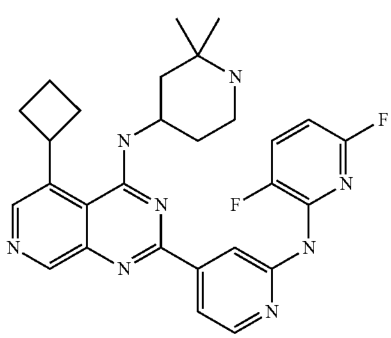 [SMILES: CC1(C)CC(Nc2nc(-c3ccnc(Nc4nc(F)ccc4F)c3)nc3cncc(C4CCC4)c23)CCN1] | [B4] | 517 (M + H)+ | 1H NMR (400 MHz, METHANOL-d4) δ ppm 9.10 (d, J = 0.75 Hz, 1H) 8.90 (d, J = 1.00 Hz, 1 H) 8.46-8.54 (m, 2 H) 8.28 (dd, J = 6.27, 1.51 Hz, 1 H) 7.88 (d, J = 6.02 Hz, 1 H) 6.77-6.85 (m, 1 H) 4.90-5.02 (m, 1 H) 4.42 (t, J = 8.41 Hz, 1 H) 3.41-3.56 (m, 2 H) 2.50-2.71 (m, 3 H) 2.15-2.43 (m, 4 H) 1.75-2.03 (m, 3 H) 1.60 (s, 3 H) 1.50 (s, 3 H) | {5-Cyclobutyl-2-[2-(3,6-difluoro-pyridin-2-ylamino)-pyridin-4-yl]-pyrido[3,4-d]pyrimidin-4-yl}-(2,2-dimethyl-piperidin-4-yl)-amine |

TABLE A-continued

| Ex | Structure | Scheme | LCMS | 1H-NMR | Name |
|---|---|---|---|---|---|
| 139 | 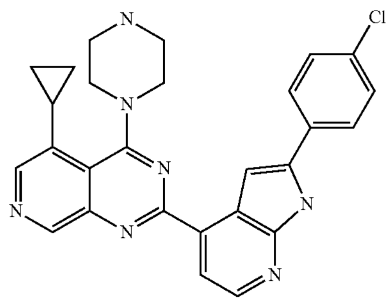 [SMILES: Clc1ccc(-c2cc3c(-c4nc(N5CCNCC5)c5c(C6CC6)cncc5n4)ccnc3[nH]2)cc1] | [D4], [D3] | 482.15 (M + H)+ | 1H NMR (400 MHz, DMSO-d6) δ 12.46 (d, 1H, J = 1.7 Hz), 9.31 (s, 1H), 8.96 (br s, 2H), 8.42 (d, 1H, J = 5.0 Hz), 8.20 (s, 1H), 8.16 (d, 1H, J = 5.0 Hz), 8.10 (m, 2H), 7.97 (d, 1H, J = 2.2 Hz), 7.58 (m, 2H), 3.96 (m, 4H), 3.38 (m, 4H), 2.80-2.73 (m, 1H), 1.30-1.25 (m, 2H), 1.12-1.08 (m, 2H) | 2-[2-(4-Chloro-phenyl)-1H-pyrrolo[2,3-b]pyridin-4-yl]-5-cyclopropyl-4-piperazin-1-yl-pyrido[3,4-d]pyrimidine |
| 140 | 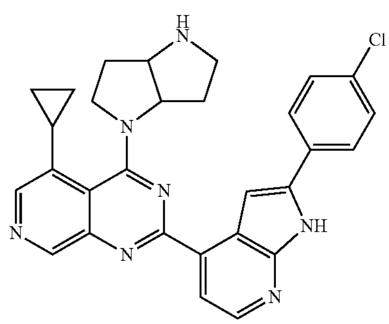 [SMILES: Clc1ccc(-c2cc3c(-c4nc(N5CCC6NCCC65)c5c(C6CC6)cncc5n4)ccnc3[nH]2)cc1] | [D4], [D3] | 508.18 (M + H)+ | 1H NMR (400 MHz, DMSO-d6) δ 12.44 (d, 1H, J = 1.6 Hz), 9.27 (m, 1H), 9.17 (s, 1H), 9.07 (m, 1H), 8.41 (d, 1H, J = 5.0 Hz), 8.23 (s, 1H), 8.15 (d, 1H, J = 5.0 Hz), 8.07 (d, 2H, J = 8.6 Hz), 7.92 (d, 1H, J = 2.2 Hz), 7.58 (d, 2H, J = 8.6 Hz), 5.41 (m, 1H), 4.36-4.28 (m, 3H), 3.61-3.36 (m, 4H), 2.44-2.12 (m, 3H), 1.42-1.36 (m, 1H), 1.21-0.95 (m, 3H) | 2-[2-(4-Chloro-phenyl)-1H-pyrrolo[2,3-b]pyridin-4-yl]-5-cyclopropyl-4-(hexahydro-pyrrolo[3,2-b]pyrrol-1-yl)-pyrido[3,4-d]pyrimidine |
| 141 | 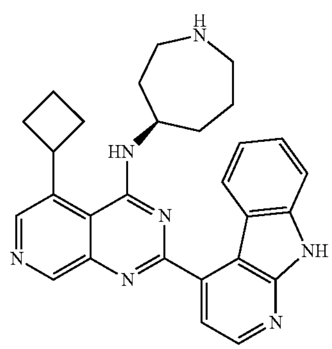 [SMILES: c1ccc2c(c1)[nH]c1nccc(-c3nc(N[C@@H]4CCCNCC4)c4c(C5CCC5)cncc4n3)c12] | [D3] | 464 (M + H)+ | 1H NMR (400 MHz, DMSO-d6) δ ppm 12.04 (1 H, s) 9.12 (1 H, s) 8.41-8.69 (5 H, m) 7.82 (1 H, d, J = 5.3 Hz) 7.39-7.61 (2 H, m) 6.98-7.24 (2 H, m) 4.59 (2 H, dd, J = 17.1, 8.8 Hz) 2.95-3.37 (4 H, m) 2.52-2.65 (3 H, m) 1.62 -2.39 (11 H, m) | (R)-Azepan-4-yl-[5-cyclobutyl-2-(9H-pyrido[2,3-b]indol-4-yl)-pyrido[3,4-d]pyrimidin-4-yl]-amine |
| 142 | 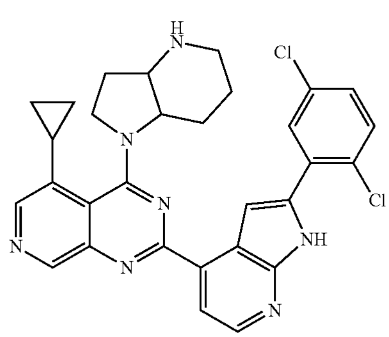 [SMILES: Clc1ccc(Cl)c(-c2cc3c(-c4nc(N5CCC6NCCCC65)c5c(C6CC6)cncc5n4)ccnc3[nH]2)c1] | [D4], [D3] | 556.16 (M + H)+ | 1H NMR (400 MHz, DMSO-d6) δ 12.35 (d, 1H, J = 1.7 Hz), 9.39 (m, 1H), 9.07 (s, 1H), 8.48 (d, 1H, J = 5.0 Hz), 8.40 (m, 1H), 8.19 (s, 1H), 8.12 (d, 1H, J = 5.0 Hz), 7.99 (d, 1H, J = 2.2 Hz), 7.93 (d, 1H, J = 2.6 Hz), 7.70 (d, 1H, J = 8.6 Hz), 7.54 (m, 1H), 4.76 (m, 1H), 4.60-4.53 (m, 1H), 4.05 (m, 1H), 3.45-3.32 (m, 2H), 3.07-3.01 (m, 1H), 2.67-2.63 (m, 1H), 2.48-2.44 (m, 1H), 2.20-1.99 (m, 3H), 1.77-1.70 (m, 2H), 1.54-1.47 (m, 1H), 1.25-1.07 (m, 2H), 0.95-0.89 (m, 1H) | 5-Cyclopropyl-2-[2-(2,5-dichloro-phenyl)-1H-pyrrolo[2,3-b]pyridin-4-yl]-4-(octahydro-pyrrolo[3,2-b]pyridin-1-yl)-pyrido[3,4-d]pyrimidine |

TABLE A-continued

| Ex | Structure | Scheme | LCMS | 1H-NMR | Name |
|---|---|---|---|---|---|
| 143 | 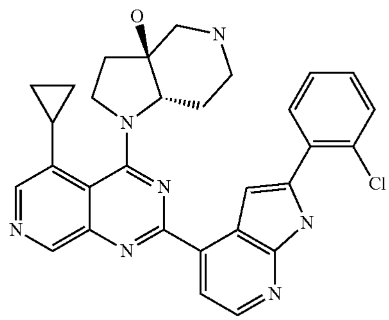 [SMILES: O[C@]12CCN(c3nc(-c4ccnc5[nH]c(-c6ccccc6Cl)cc45)nc4cncc(C5CC5)c34)[C@H]1CCNC2] | [D4], [D3] | 538.19 (M + H)+ | 1H NMR (400 MHz, DMSO-d6) δ 12.31 (d, 1H, J = 1.6 Hz), 9.08 (s, 1H), 8.93 (m, 1H), 8.74 (m, 1H), 8.46 (d, 1H, J = 5.0 Hz), 8.20 (s, 1H), 8.12 (d, 1H, J = 5.0 Hz), 7.88 (d, 1H, J = 2.1 Hz), 7.83 (m, 1H), 7.67 (m, 1H), 7.55-7.46 (m, 2H), 4.40 (m, 1H), 4.35-4.28 (m, 1H), 3.38-3.01 (m, 5H), 2.67 (m, 1H), 2.54 (m, 1H), 2.32 (m, 1H), 2.05-1.87 (m, 2H), 1.50-1.43 (m, 1H), 1.22-1.07 (m, 2H), 0.96-0.90 (m, 1H) | (±)-(3aS,7aS)-1-{2-[2-(2-Chloro-phenyl)-1H-pyrrolo[2,3-b]pyridin-4-yl]-5-cyclopropyl-pyrido[3,4-d]pyrimidin-4-yl}-octahydro-pyrrolo[3,2-c]pyridin-3a-ol |
| 144 | 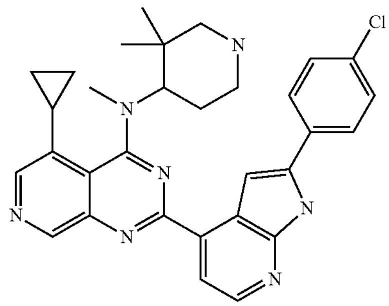 [SMILES: CN(c1nc(-c2ccnc3[nH]c(-c4ccc(Cl)cc4)cc23)nc2cncc(C3CC3)c12)C1CCNCC1(C)C] | [D4], [D3] | 538.2 (M + H)+ | 1H NMR (400 MHz, DMSO-d6) δ 12.42 (m, 1H), 9.22 (br s, 1H), 8.98 (m, 1H), 8.41 (d, 1H, J = 5.0 Hz), 8.31-7.96 (m, 6H), 7.62-7.54 (m, 2H), 3.71 (m, 4H), 3.50-3.46 (m, 2H), 3.19-3.16 (m, 5H), 2.33-1.91 (m, 1H), 1.38-0.84 (m, 9H) | {2-[2-(4-Chloro-phenyl)-1H-pyrrolo[2,3-b]pyridin-4-yl]-5-cyclopropyl-pyrido[3,4-d]pyrimidin-4-yl}-(3,3-dimethyl-piperidin-4-yl)-methyl-amine |
| 145 | 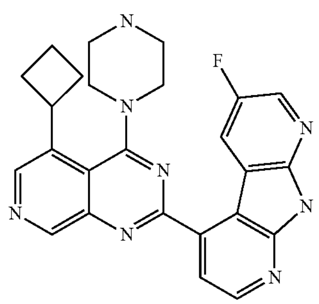 [SMILES: Fc1cnc2[nH]c3nccc(-c4nc(N5CCNCC5)c5c(C6CCC6)cncc5n4)c3c2c1] | [D18] | 455.15 (M + H)+ | (400 MHz, d6-DMSO, δ): 12.81 (s, 1H), 9.27 (s, 1H), 9.23 (dd, J = 10.3, 2.8 Hz, 1H), 8.95-8.80 (m, 2H), 8.72 (d, J = 5.1 Hz, 1H), 8.58 (dd, J = 2.8, 1.1 Hz, 1H), 8.12 (d, J = 5.1 Hz, 1H), 4.35-4.25 (m, 1H), 3.95-3.77 (m, 4H), 3.40-3.20 (m, 4H), 2.55-2.45 (m, 2H), 2.33-2.22 (m, 2H), 2.20-2.07 (m, 1H), 2.00-1.90 (m, 1H). | 5-(5-Cyclobutyl-4-piperazin-1-yl-pyrido[3,4-d]pyrimidin-2-yl)-3-fluoro-9H-dipyrido[2,3-b;3',2'-d]pyrrole |
| 146 | 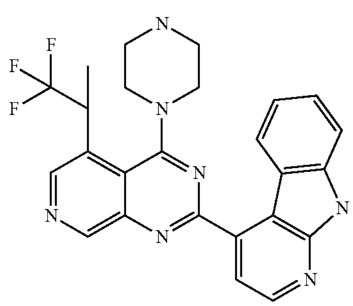 [SMILES: CC(c1cncc2nc(-c3ccnc4[nH]c5ccccc5c34)nc(N3CCNCC3)c12)C(F)(F)F] | [D19] | 478.14 (M + H)+ | (400 MHz, d6-DMSO, δ): 12.12 (s, 1H), 9.48 (s, 1H), 8.94 (s, 1H), 8.93-8.70 (m, 2H), 8.62-8.57 (m, 2H), 7.92 (d, J = 5.2 Hz, 1H), 7.56 (d, J = 8.2 Hz, 1H), 7.52-7.47 (m, 1H), 7.21-7.16 (m, 1H), 4.81-4.71 (m, 1H), 4.20-3.08 (m, 8H), 1.86 (d, J = 1.2 Hz, 3H). | 4-[4-Piperazin-1-yl-5-(2,2,2-trifluoro-1-methyl-ethyl)-pyrido[3,4-d]pyrimidin-2-yl]-9H-pyrido[2,3-b]indole |
| 147 | 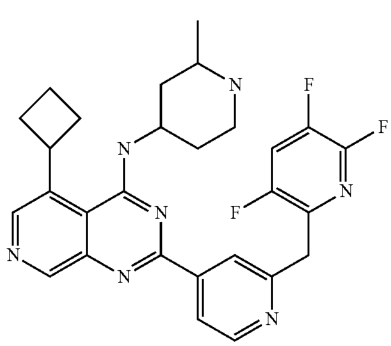 [SMILES: CC1CC(Nc2nc(-c3ccnc(Cc4nc(F)c(F)cc4F)c3)nc3cncc(C4CCC4)c23)CCN1] | [B4] | 521 (M + H)+ | 1H NMR (400 MHz, METHANOL-d4) δ ppm 9.07-9.13 (m, 1 H) 8.91-9.04 (m, 1 H) 8.48-8.58 (m, 1 H) 8.41-8.46 (m, 1 H) 8.23 (dd, J = 5.77, 1.51 Hz, 1 H) 7.96-8.08 (m, 1 H) 4.36-4.48 (m, 1 H) 3.46-3.77 (m, 3 H) 2.49-2.73 (m, 4H) 2.15-2.49 (m, 4H) 1.75 (d, J = 13.55 Hz, 4 H) 1.41-1.47 (m, 3 H) | {5-Cyclobutyl-2-[2-(3,5,6-trifluoro-pyridin-2-ylamino)-pyridin-4-yl]-pyrido[3,4-d]pyrimidin-4-yl}-(2-methyl-piperidin-4-yl)-amine |

TABLE A-continued

| Ex | Structure | Scheme | Analysis | | Name |
| --- | --- | --- | --- | --- | --- |
| | | | LCMS | 1H-NMR | |
| 148 | 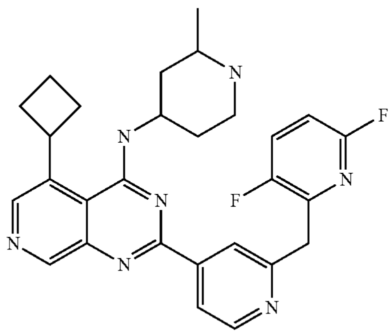 [SMILES: CC1CC(Nc2nc(-c3ccnc(Cc4nc(F)ccc4F)c3)nc3cncc(C4CCC4)c23)CCN1] | [B4] | 503 (M + H)+ | 1H NMR (400 MHz, METHANOL-d4) δ ppm 9.08-9.15 (m, 1 H) 8.91-9.01 (m, 1 H) 8.45-8.60 (m, 2 H) 8.28-8.37 (m, 1 H) 7.86-7.97 (m, 1H) 6.85 (dt, J = 8.78, 2.51 Hz, 1 H) 4.35-4.51 (m, 1 H) 3.44-3.72 (m, 2 H) 3.34 (d, J = 5.52 Hz, 1 H) 2.18-2.72 (m, 8 H) 1.69-2.04 (m, 3 H) 1.42-1.48 (m, 3 H) | (5-Cyclobutyl-2-[2-(3,6-difluoro-pyridin-2-ylamino)-pyridin-4-yl]-pyrido[3,4-d]pyrimidin-4-yl}-(2-methyl-piperidin-4-yl)-amine |
| 149 | 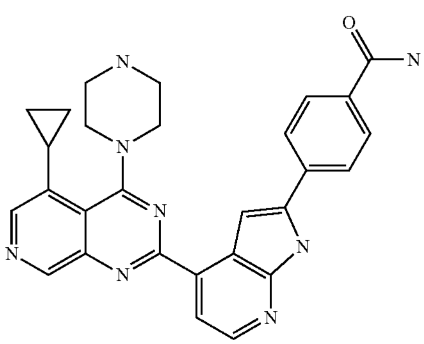 [SMILES: NC(=O)c1ccc(-c2cc3c(-c4nc(N5CCNCC5)c5c(C6CC6)cncc5n4)ccnc3[nH]2)cc1] | [D4], [D3] | 491.19 (M + H)+ | 1H NMR (400 MHz, DMSO-d6) δ 12.49 (d, 1H, J = 1.8 Hz), 9.33 (s, 1H), 8.95 (br s, 2H), 8.44 (d, 1H, J = 5.0 Hz), 8.20-8.15 (m, 4H), 8.06 (m, 4H), 7.44 (br s, 1H), 3.89 (m, 4H), 3.39 (m, 4H), 2.80-2.74 (m, 1H), 1.30-1.26 (m, 2H), 1.13-1.09 (m, 2H) | 4-[4-(5-Cyclopropyl-4-piperazin-1-yl-pyrido[3,4-d]pyrimidin-2-yl)-1H-pyrrolo[2,3-b]pyridin-2-yl]-benzamide |
| 150 | 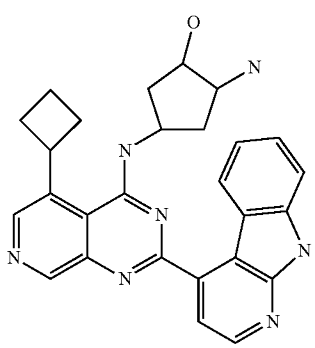 [SMILES: NC1CC(Nc2nc(-c3ccnc4[nH]c5ccccc5c34)nc3cncc(C4CCC4)c23)CC1O] | [D3] | 466 (M + H)+ | 1H NMR (400 MHz, DMSO-d6) δ ppm 12.04 (1 H, s) 9.13 (1 H, s) 8.47-8.68 (3 H, m) 7.75-7.94 (4 H, m) 7.33-7.60 (3 H, m) 7.17 (1 H, td, J = 7.6, 1.1 Hz) 6.14 (1 H, br. s.) 4.91 (1 H, br. s.) 4.17-4.41 (4 H, m) 3.49 (1 H, br. s.) 2.52-2.78 (3 H, m) 1.70-2.35 (9 H, m) | 2-Amino-4-[5-cyclobutyl-2-(9H-pyrido[2,3-b]indol-4-yl)-pyrido[3,4-d]pyrimidin-4-ylamino]-cyclopentanol |
| 151 | 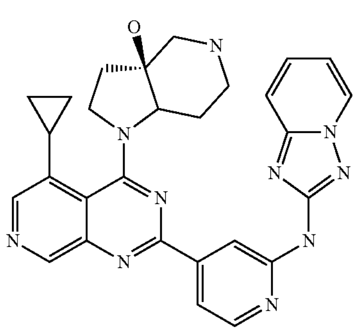 | [B4] | 521.24 (M + H)+ | (400 MHz, d6-DMSO, δ): 10.62 (br s, 1H), 9.12 (s, 1H), 9.05 (s, 1H), 8.87 (d, J = 6.7 Hz, 1H), 8.83-8.60 (m, 2H), 8.44 (d, J = 5.4 Hz, 1H), 8.22 (s, 1H), 7.92 (dd, J = 5.4, 1.2 Hz, 1H), 7.73 (d, J = 8.8 Hz, 1H), 7.70-7.64 (m, 1H), 7.16-7.11 (m, 1H), 5.95 (br s, 1H), 4.36-4.26 (m, 2H), 3.40-3.20 (m, 4H), 3.09-2.96 (m, 1H), 2.90-2.77 (m, 1H), 2.54-2.44 (m, 1H), 2.40-2.28 (m, 1H), 2.02-1.85 (m, 2H), 1.50-1.41 (m, 1H), 1.21-1.03 (m, 2H), 0.96-0.85 (m, 1H). | (±)-(3aS,7aS)-1-{5-Cyclopropyl-2-[2-([1,2,4]triazolo[1,5-a]pyridin-2-ylamino)-pyridin-4-yl]-pyrido[3,4-d]pyrimidin-4-yl}-octahydro-pyrrolo[3,2-c]pyridin-3a-ol |

TABLE A-continued

| Ex | Structure | Scheme | LCMS | 1H-NMR | Name |
|---|---|---|---|---|---|
| 152 | 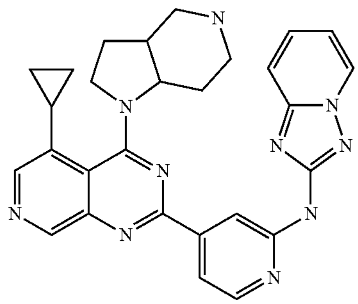 [SMILES: c1ccn2nc(Nc3cc(-c4nc(N5CCC6CNCCC65)c5c(C6CC6)cncc5n4)ccn3)nc2c1] | [B4] | 505.23 (M + H)+ | (400 MHz, d6-DMSO, δ): 10.91 (s, 1H), 9.04 (s, 1H), 9.00 (s, 1H), 8.87 (d, J = 6.7 Hz, 1H), 8.66 (br s, 2H), 8.46 (d, J = 5.5 Hz, 1H), 8.24 (s, 1H), 7.96 (dd, J = 5.5, 1.3 Hz, 1H), 7.76-7.66 (m, 2H), 7.21-7.16 (m, 1H), 4.56-4.51 (m, 1H), 4.45-4.35 (m, 1H), 3.46-3.38 (m, 1H), 3.36-3.26 (m, 2H), 3.05-2.85 (m, 3H), 2.77-2.68 (m, 1H), 2.55-2.44 (m, 1H), 2.30-2.18 (m, 1H), 1.96-1.84 (m, 1H), 1.78-1.70 (m, 1H), 1.51-1.42 (m, 1H), 1.23-1.03 (m, 2H), 0.96-0.88 (m, 1H). | {4-[5-Cyclopropyl-4-(octahydro-pyrrolo[3,2-c]pyridin-1-yl)-pyrido[3,4-d]pyrimidin-2-yl]-pyridin-2-yl}-[1,2,4]triazolo[1,5-a]pyridin-2-yl-amine |
| 153 | Chiral | [D4], [D3] | 428.18 (M + H)+ | 1H NMR (400 MHz, DMSO-d6, ppm): 11.85 (s, 1 H), 9.07-9.21 (m, 2 H), 8.49 (s, 1 H), 8.42 (d, J = 9.8 Hz, 1 H), 8.30 (d, J = 5.3 Hz, 1 H), 8.17 (d, J = 5.0 Hz, 1 H), 7.59 (d, J = 8.8 Hz, 1 H), 7.26 (d, J = 0.8 Hz, 1 H), 4.80-4.90 (m, 3 H), 3.34-3.44 (m, 1 H), 3.10-3.27 (m, 3H), 2.61 (t, J = 6.0 Hz, 1 H), 2.10-2.23 (m, 1 H), 1.84-2.05 (m, 1H), 1.23-1.32 (m, 1 H), 1.21 (s, 3 H), 1.13-1.20 (m, 3 H), 1.12 (s, 3 H) | [5-Cyclopropyl-2-(2-methyl-1H-pyrrolo[2,3-b]pyridin-4-yl)-pyrido[3,4-d]pyrimidin-4-yl]-((S)-3,3-dimethyl-piperidin-4-yl)-amine |
| 154 | Chiral | [D4], [D3] | 428.19 (M + H)+ | 1H NMR (400 MHz, DMSO-d6, ppm): 11.85 (s, 1 H), 9.10-9.19 (m, 2H), 8.50 (s, 1 H), 8.41 (d, J = 9.8 Hz, 1 H), 8.30 (d, J = 5.3 Hz, 1 H), 8.16 (d, J = 5.0 Hz, 1 H), 7.59 (d, J = 8.5 Hz, 1 H), 7.26 (s, 1 H), 4.82-4.91 (m, 1 H), 3.31-3.49 (m, 1 H), 3.08-3.26 (m, 3 H), 2.55-2.68 (m, 1 H), 2.17 (dd, J = 14.1, 3.0 Hz, 1 H), 1.88-2.04 (m, 1 H), 1.24-1.32 (m, 1H), 1.21 (s, 3 H), 1.14-1.20 (m, 3H), 1.09-1.14 (m, 4 H) | [5-Cyclopropyl-2-(2-methyl-1H-pyrrolo[2,3-b]pyridin-4-yl)-pyrido[3,4-d]pyrimidin-4-yl]-((R)-3,3-dimethyl-piperidin-4-yl)-amine |
| 155 | 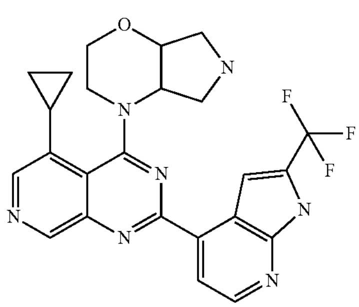 [SMILES: FC(F)(F)c1cc2c(-c3nc(N4CCOC5CNCC54)c4c(C5CC5)cncc4n3)ccnc2[nH]1] | [D4], [D3] | 482.12 (M + H)+ | 1H NMR (400 MHz, DMSO-d6, ppm): 11.85 (s, 1 H), 9.10-9.19 (m, 2H), 8.50 (s, 1 H), 8.41 (d, J = 9.8 Hz, 1 H), 8.30 (d, J = 5.3 Hz, 1 H), 8.16 (d, J = 5.0 Hz, 1 H), 7.59 (d, J = 8.5 Hz, 1 H), 7.26 (s, 1 H), 4.82-4.91 (m, 1 H), 3.31-3.49 (m, 1 H), 3.08-3.26 (m, 3 H), 2.55-2.68 (m, 1 H), 2.17 (dd, J = 14.1, 3.0 Hz, 1 H), 1.88-2.04 (m, 1H), 1.24-1.32 (m, 1H), 1.21 (s, 3 H), 1.14-1.20 (m, 3 H), 1.09-1.14 (m, 4 H) | 5-Cyclopropyl-4-(hexahydro-pyrrolo[3,4-b][1,4]oxazin-4-yl)-2-(2-trifluoromethyl-1H-pyrrolo[2,3-b]pyridin-4-yl)-pyrido[3,4-d]pyrimidine |

TABLE A-continued

| Ex | Structure | Scheme | Analysis | | Name |
| --- | --- | --- | --- | --- | --- |
| | | | LCMS | 1H-NMR | |
| 156 | 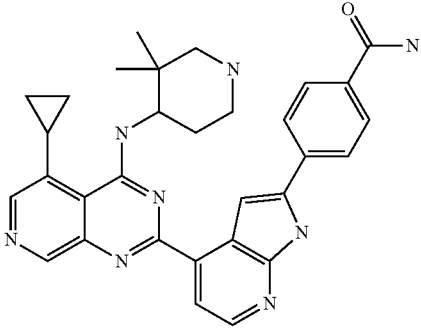 [SMILES: CC1(C)CNCCC1Nc1nc(-c2ccnc3[nH]c(-c4ccc(C(N)=O)cc4)cc23)nc2cncc(C3CC3)c12] | [D4], [D3] | 533.24 (M + H)+ | 1H NMR (400 MHz, MeOD) δ 9.16 (br s, 1H), 8.41-8.30 (m, 2H), 8.13 (d, 1H, J = 5.0 Hz), 7.97-7.91 (m, 6H), 4.98-4.94 (m, 1H), 3.45-3.38 (m, 1H), 3.11-3.08 (m, 1H), 2.45-2.42 (m, 1H), 2.26-2.23 (m, 1H), 2.06-1.95 (m, 1H), 1.33-1.02 (m, 12H) | 4-{4-[5-Cyclopropyl-4-(3,3-dimethyl-piperidin-4-ylamino)-pyrido[3,4-d]pyrimidin-2-yl]-1H-pyrrolo[2,3-b]pyridin-2-yl}-benzamide |
| 157 | 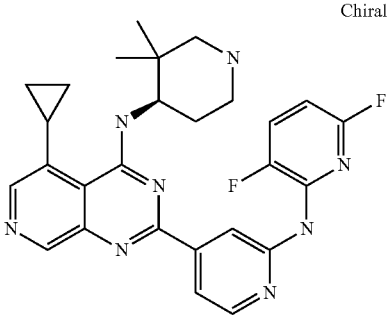 [SMILES: CC1(C)CNCC[C@H]1Nc1nc(-c2ccnc(Nc3nc(F)ccc3F)c2)nc2cncc(C3CC3)c12] Chiral | [B4] | 503 (M + H)+ | 1H NMR (400 MHz, METHANOL-d4) δ ppm 9.10-9.18 (m, 1 H) 8.90 (d, J = 1.00 Hz, 1 H) 8.56 (d, J = 1.00 Hz, 1 H) 8.52 (d, J = 6.27 Hz, 1 H) 8.44 (dd, J = 6.27, 1.51 Hz, 1 H) 7.95 (td, J = 9.10, 5.90 Hz, 1 H) 6.92 (dt, J = 8.66, 2.45 Hz, 1 H) 5.04 (dd, J = 11.80, 4.27 Hz, 1 H) 3.54 (d, J = 13.05 Hz, 1 H) 3.35 (d, J = 1.51 Hz, 1 H) 3.11-3.25 (m, 1 H) 2.55 (t, J = 6.15 Hz, 1 H) 2.02-2.36 (m, 2 H) 1.42 (td, J = 8.72, 3.14 Hz, 1 H) 1.25-1.36 (m, 5 H) 1.22 (s, 3 H) 1.02-1.18 (m, 1 H) 0.82-0.83 (m, 1 H) | {5-Cyclopropyl-2-[2-(3,6-difluoro-pyridin-2-ylamino)-pyridin-4-yl]-pyrido[3,4-d]pyrimidin-4-yl}-((R)-3,3-dimethyl-piperidin-4-yl)-amine |
| 158 | 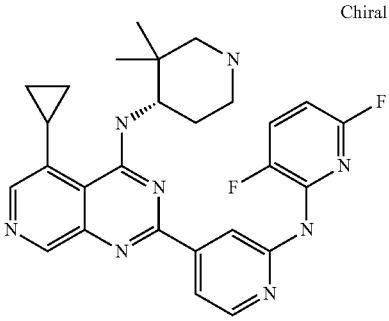 [SMILES: CC1(C)CNCC[C@@H]1Nc1nc(-c2ccnc(Nc3nc(F)ccc3F)c2)nc2cncc(C3CC3)c12] Chiral | [B4] | 503 (M + H)+ | 1H NMR(400 MHz, METHANOL-d4) δ ppm 9.14 (s, 1 H) 8.90 (d, J = 0.75 Hz, 1 H) 8.57 (s, 1 H) 8.52 (d, J = 6.53 Hz, 1 H) 8.39-8.47 (m, 1 H) 7.96 (td, J = 9.10, 5.90 Hz, 1 H) 6.82-6.97 (m, 1 H) 5.04 (dd, J = 11.80, 4.27 Hz, 1H) 4.93-4.96 (m, 1 H) 3.54 (d, J = 13.30 Hz, 1 H) 3.35 (br. s., 1 H) 3.08-3.25 (m, 1 H) 2.47-2.61 (m, 1 H) 2.02-2.33 (m, 2 H) 1.37-1.50 (m, 1 H) 1.26-1.37 (m, 5 H) 1.22 (s, 3H) 1.15 (d, J = 5.52 Hz, 1 H) | {5-Cyclopropyl-2-[2-(3,6-difluoro-pyridin-2-ylamino)-pyridin-4-yl]-pyrido[3,4-d]pyrimidin-4-yl}-((S)-3,3-dimethyl-piperidin-4-yl)-amine |
| 159 | 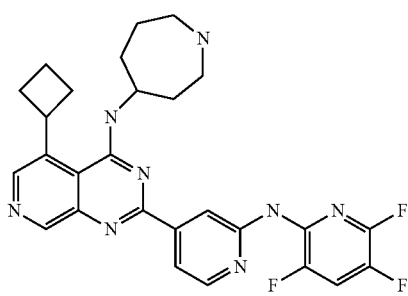 [SMILES: Fc1cc(F)c(Nc2cc(-c3nc(NC4CCCNCC4)c4c(C5CCC5)cncc4n3)ccn2)nc1F] | [B4] | 521 (M + H)+ | 1H NMR (400 MHz, METHANOL-d4) δ ppm 9.00 (s, 1 H) 8.81 (d, J = 0.75 Hz, 1 H) 8.42 (s, 1 H) 8.36 (s, 1 H) 8.15-8.22 (m, 1 H) 8.18 (dd, J = 6.27, 1.51 Hz, 1 H) 7.99 (td, J = 8.78, 7.28 Hz, 1 H) 4.32 (t, J = 8.28 Hz, 1 H) 3.23-3.46 (m, 4 H) 2.50-2.62 (m, 2 H) 1.88-2.45 (m, 11 H) | Azepan-4-yl-{5-cyclobutyl-2-[2-(3,5,6-trifluoro-pyridin-2-ylamino)-pyridin-4-yl]-pyrido[3,4-d]pyrimidin-4-yl}-amine |

TABLE A-continued

| Ex | Structure | Scheme | LCMS | 1H-NMR | Name |
|---|---|---|---|---|---|
| 160 | 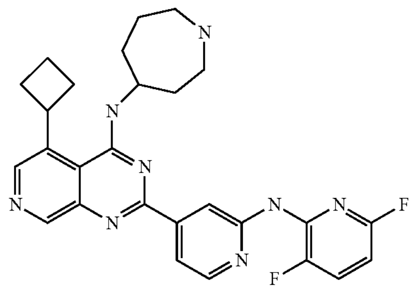 [SMILES: Fc1ccc(F)c(Nc2cc(-c3nc(NC4CCCNCC4)c4c(C5CCC5)cncc4n3)ccn2)n1] | [B4] | 503 (M + H)+ | 1H NMR (400 MHz, METHANOL-d4) δ ppm 9.10 (d, J = 0.75 Hz, 1 H) 8.93 (d, J = 1.51 Hz, 1 H) 8.45-8.57 (m, 2 H) 8.33 (dd, J = 6.27, 1.51 Hz, 1 H) 7.92 (td, J = 9.03, 6.02 Hz, 1 H) 6.88 (dt, J = 8.53, 2.51 Hz, 1 H) 4.42(t, J = 8.41 Hz, 1 H) 3.34-3.55 (m, 4 H) 2.59-2.72 (m, 2 H) 1.93-2.57 (m, 11 H) | Azepan-4-yl-{5-cyclobutyl-2-[2-(3,6-difluoro-pyridin-2-ylamino)-pyridin-4-yl]-pyrido[3,4-d]pyrimidin-4-yl}-amine |
| 161 | 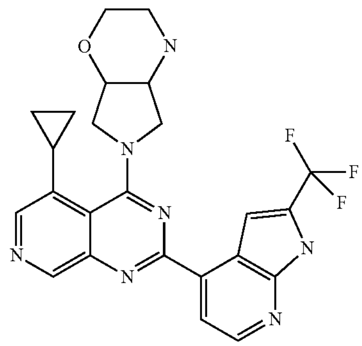 [SMILES: FC(F)(F)c1cc2c(-c3nc(N4CC5NCCOC5C4)c4c(C5CC5)cncc4n3)ccnc2[nH]1] | [D4], [D3] | 482.14 (M + H)+ | 1H NMR (400 MHz, DMSO-d6, ppm): 13.13 (br. s., 1 H), 9.41-9.59 (m, 1 H), 9.22-9.38 (m, 1 H), 9.09 (s, 1 H), 8.63 (d, J = 5.0 Hz, 1 H), 8.27 (d, J = 4.8 Hz, 1 H), 8.20 (s, 1 H), 7.94 (s, 1 H), 4.30-4.47 (m, 3 H), 4.01 (br. s., 1 H), 3.85-3.97 (m, 2 H), 3.72 (d, J = 13.3 Hz, 2 H), 3.09-3.18 (m, 1 H), 2.27-2.37 (m, 1 H), 1.39-1.49 (m, 1 H), 1.15-1.27 (m, 1 H), 1.06 (dt, J = 9.7, 5.1 Hz, 1 H), 0.98 (dt, J = 9.9, 5.0 Hz, 1 H) | 5-Cyclopropyl-4-(hexahydro-pyrrolo[3,4-b][1,4]oxazin-6-yl)-2-(2-trifluoromethyl-1H-pyrrolo[2,3-b]pyridin-4-yl)-pyrido[3,4-d]pyrimidine |
| 162 | 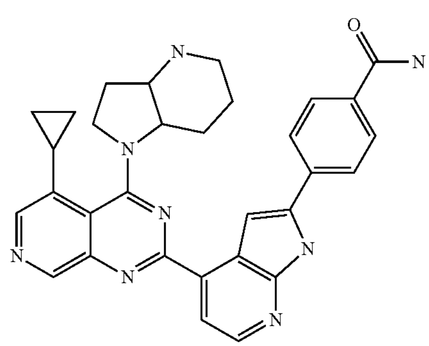 [SMILES: NC(=O)c1ccc(-c2cc3c(-c4nc(N5CCC6NCCCC65)c5c(C6CC6)cncc5n4)ccnc3[nH]2)cc1] | [D4], [D3] | 531.23 (M + H)+ | 1H NMR (400 MHz, DMSO-d6) δ 12.47 (d, 1H, J = 1.8 Hz), 9.38 (m, 1H), 9.24 (s, 1H), 8.44-8.33 (m, 2H), 8.20 (m, 1H), 8.15-8.10 (m, 3H), 8.06-8.01 (m, 4H), 7.44 (br s, 1H), 4.79 (m, 1H), 4.61-4.54 (m, 1H), 4.06 (m, 2H), 3.46-3.33 (m, 2H), 3.09-3.04 (m, 1H), 2.67 (m, 1H), 2.18-1.99 (m, 3H), 1.81-1.73 (m, 2H), 1.55-1.48 (m, 1H), 1.26-1.08 (m, 2H), 0.97-0.91 (m, 1H) | 4-{4-[5-Cyclopropyl-4-(octahydro-pyrrolo[3,2-b]pyridin-1-yl)-pyrido[3,4-d]pyrimidin-2-yl]-1H-pyrrolo[2,3-b]pyridin-2-yl}-benzamide |
| 163 | 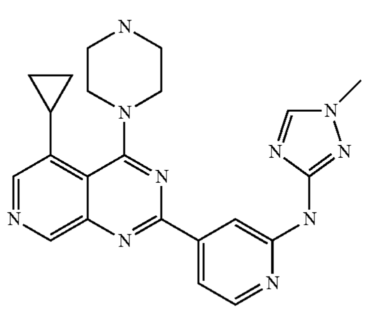 [SMILES: Cn1cnc(Nc2cc(-c3nc(N4CCNCC4)c4c(C5CC5)cncc4n3)ccn2)n1] | [B4] | 429.17 (M + H)+ | (400 MHz, d6-DMSO, δ): 11.00 (br s, 1H), 9.10 (s, 1H), 9.01 (br s, 2H), 8.81 (s, 1H), 8.50 (s, 1H), 8.42 (d, J = 5.8 Hz, 1H), 8.22 (s, 1H), 7.94 (dd, J = 5.7, 1.1 Hz, 1H), 4.10-3.80 (m, 7H), 3.35 (br s, 4H), 2.73-2.65 (m, 1H), 1.30-1.24 (m, 2H), 1.12-1.06 (m, 2H). | [4-(5-Cyclopropyl-4-piperazin-1-yl-pyrido[3,4-d]pyrimidin-2-yl)-pyridin-2-yl]-(1-methyl-1H-[1,2,4]triazol-3-yl)-amine |

TABLE A-continued

| Ex | Structure | Scheme | Analysis | | Name |
|---|---|---|---|---|---|
| | | | LCMS | 1H-NMR | |
| 164 | 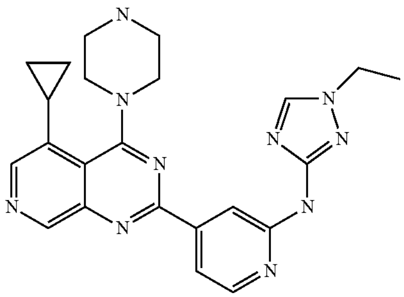 [SMILES: CCn1cnc(Nc2cc(-c3nc(N4CCNCC4)c4c(C5CC5)cncc4n3)ccn2)n1] | [B4] | 443.18 (M + H)+ | (400 MHz, d6-DMSO, δ): 11.07 (br s, 1H), 9.09 (s, 1H), 9.02 (br s, 2H), 8.79 (s, 1H), 8.56 (s, 1H), 8.42 (d, J = 5.8 Hz, 1H), 8.22 (s, 1H), 7.96 (dd, J = 5.8, 1.1 Hz, 1H), 4.22 (q, J = 7.3 Hz, 2H), 3.95 (br s, 4H), 3.34 (br s, 4H), 2.72-2.64 (m, 1H), 1.47 (t, J = 7.3 Hz, 3H), 1.30-1.24 (m, 2H), 1.12-1.06 (m, 2H). | [4-(5-Cyclopropyl-4-piperazin-1-yl-pyrido[3,4-d]pyrimidin-2-yl)-pyridin-2-yl]-(1-ethyl-1H-[1,2,4]triazol-3-yl)-amine |
| 165 | 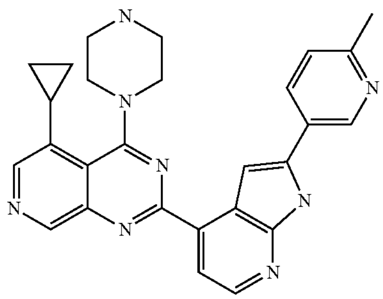 [SMILES: Cc1ccc(-c2cc3c(-c4nc(N5CCNCC5)c5c(C6CC6)cncc5n4)ccnc3[nH]2)cn1] | [D4], [D3] | 463.17 (M + H)+ | 1H NMR (400 MHz, DMSO-d6) δ 9.32 (s, 1H), 9.24 (d, 1H, J = 1.9 Hz), 8.86 (m, 1H), 8.48 (d, 1H, J = 5.2 Hz), 8.32 (d, 1H, J = 5.2 Hz), 8.27 (s, 1H), 8.19 (br s, 1H), 7.91 (d, 1H, J = 8.4 Hz), 4.09 (m, 4H), 3.50-3.47 (m, 4H), 2.91-2.77 (m, 4H), 1.42-1.37 (m, 2H), 1.16-1.12 (m, 2H) | 5-Cyclopropyl-2-[2-(6-methyl-pyridin-3-yl)-1H-pyrrolo[2,3-b]pyridin-4-yl]-4-piperazin-1-yl-pyrido[3,4-d]pyrimidine |
| 166 | Chiral | [D4], [D3] | 509.21 (M + H)+ | 1H NMR (400 MHz, DMSO-d6, ppm): 12.39 (s, 1 H), 9.06-9.17 (m, 2 H), 8.62 (dt, J = 2.9, 1.7 Hz, 1 H), 8.47-8.55 (m, 2 H), 8.37 (d, J = 10.0 Hz, 1 H), 8.22 (d, J = 5.0 Hz, 1 H), 8.19 (dd, J = 4.1, 2.1 Hz, 1 H), 7.92 (ddd, J = 11.8, 8.4, 1.1 Hz, 1 H), 7.64 (d, J = 8.8 Hz, 1 H), 7.54 (dt, J = 8.5, 4.2 Hz, 1 H), 4.82-4.95 (m, 1 H), 3.39 (d, J = 12.0 Hz, 1 H), 3.02-3.29 (m, 3 H), 2.63 (t, J = 5.8 Hz, 1 H), 2.18 (d, J = 11.0 Hz, 1 H), 1.91-2.08 (m, 1 H), 1.24-1.34 (m, 1 H), 1.22 (s, 3 H), 1.14-1.21 (m, 3 H), 1.13 (s, 3 H) | {5-Cyclopropyl-2-[2-(3-fluoro-pyridin-2-yl)-1H-pyrrolo[2,3-b]pyridin-4-yl]-pyrido[3,4-d]pyrimidin-4-yl}-((S)-3,3-dimethyl-piperidin-4-yl)-amine |
| 167 | Chiral | [D4], [D3] | 509.22 (M + H)+ | 1H NMR (400 MHz, DMSO-d6, ppm): 12.39 (s, 1 H), 9.06-9.15 (m, 2 H), 8.62 (dt, J = 4.5, 1.5 Hz, 1 H), 8.48-8.54 (m, 2 H), 8.35 (d, J = 10.0 Hz, 1 H), 8.22 (d, J = 5.2 Hz, 1 H), 8.19 (dd, J = 4.0, 2.0 Hz, 1 H), 7.92 (ddd, J = 11.8, 8.4, 1.1 Hz, 1 H), 7.64 (d, J = 8.8 Hz, 1 H), 7.54 (dt, J = 8.3, 4.2 Hz, 1 H), 4.81-4.98 (m, 1 H), 3.39 (d, J = 12.5 Hz, 1 H), 3.03-3.30 (m, 3 H), 2.63 (t, J = 6.4 Hz, 1 H), 2.13-2.25 (m, 1 H), 1.90-2.08 (m, 1 H), 1.24-1.33 (m, 1 H), 1.22 (s, 3 H), 1.14 -1.22 (m, 3 H), 1.13 (s, 3 H) | {5-Cyclopropyl-2-[2-(3-fluoro-pyridin-2-yl)-1H-pyrrolo[2,3-b]pyridin-4-yl]-pyrido[3,4-d]pyrimidin-4-yl}-((R)-3,3-dimethyl-piperidin-4-yl)-amine |

TABLE A-continued

| Ex | Structure | Scheme | Analysis | | Name |
|---|---|---|---|---|---|
| | | | LCMS | 1H-NMR | |
| 168 | 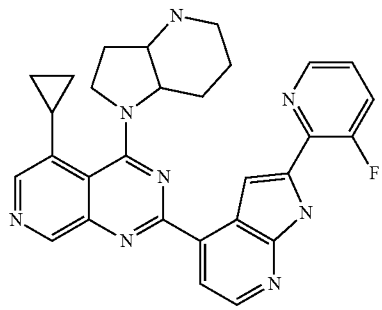 [SMILES: Fc1cccnc1-c1cc2c(-c3nc(N4CCC5NCCCC54)c4c(C5CC5)cncc4n3)ccnc2[nH]1] | [D4], [D3] | 507.20 (M + H)+ | 1H NMR (400 MHz, DMSO-d6, ppm): 12.43 (s, 1 H), 9.43 (d, J = 10.3 Hz, 1 H), 9.05 (s, 1 H), 8.61 (dt, J = 4.5, 1.5 Hz, 1 H), 8.51 (d, J = 5.0 Hz, 1 H), 8.45 (d, J = 9.3 Hz, 1 H), 8.20 (s, 1 H), 8.16 (dd, J = 4.3, 2.0 Hz, 1 H), 8.12 (d, J = 5.0 Hz, 1 H), 7.93 (ddd, J = 11.6, 8.3, 1.1 Hz, 1 H), 7.53 (dt, J = 8.5, 4.2 Hz, 1 H), 4.78 (d, J = 3.5 Hz, 1 H), 4.54-4.63 (m, 2 H), 4.04 (br. s., 1 H), 3.44 (t, J = 9.3 Hz, 1 H), 3.35(d, J = 11.8 Hz, 1 H), 3.06 (d, J = 10.3 Hz, 1 H), 2.67 (d, J = 2.0 Hz, 1 H), 2.16 (d, J = 11.0 Hz, 2 H), 1.97-2.06 (m, 1 H), 1.66-1.88 (m, 2 H), 1.46-1.58 (m, 1 H), 1.16-1.26 (m, 1H), 1.11 (dd, J = 9.3, 4.3 Hz, 1 H), 0.89-0.98 (m, 1 H) | 5-Cyclopropyl-2-[2-(3-fluoro-pyridin-2-yl)-1H-pyrrolo[2,3-b]pyridin-4-yl]-4-(octahydro-pyrrolo[3,2-b]pyridin-1-yl)-pyrido[3,4-d]pyrimidine |
| 169 | 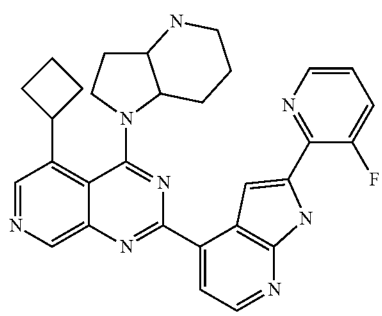 [SMILES: Fc1cccnc1-c1cc2c(-c3nc(N4CCC5NCCCC54)c4c(C5CCC5)cncc4n3)ccnc2[nH]1] | [D4], [D3] | 521.22 (M + H)+ | 1H NMR (400 MHz, DMSO-d6, ppm): 1H NMR (400 MHz, DMSO-d6) ä ppm 12.41 (s, 1 H), 9.40 (br. s., 1 H), 9.11 (s, 1 H), 8.73 (s, 1 H), 8.61 (dt, J = 4.5, 1.6 Hz, 2 H), 8.50 (d, J = 5.0 Hz, 1 H), 8.14 (dd, J = 4.0, 2.0 Hz, 1 H), 8.12 (d, J = 5.0 Hz, 1 H), 7.93 (ddd, J = 11.7, 8.3, 1.3 Hz, 1 H), 7.53 (dt, J = 8.5, 4.2 Hz, 1 H), 4.75 (br. s., 1 H), 4.34 (d, J = 6.3 Hz, 1 H), 4.17-4.28 (m, 1 H), 3.38 (br. s., 1 H), 3.26 (br. s., 1 H), 3.06 (d, J = 10.8 Hz, 1 H), 2.72 (d, J = 10.0 Hz, 2 H), 2.45 (d, J = 10.3 Hz, 2 H), 2.02-2.26 (m, 3 H), 1.91 (td, J = 18.4, 8.9 Hz, 5 H) | 5-Cyclobutyl-2-[2-(3-fluoro-pyridin-2-yl)-1H-pyrrolo[2,3-b]pyridin-4-yl]-4-(octahydro-pyrrolo[3,2-b]pyridin-1-yl)-pyrido[3,4-d]pyrimidine |
| 170 | 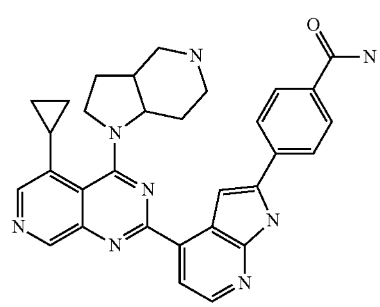 [SMILES: NC(=O)c1ccc(-c2cc3c(-c4nc(N5CCC6CNCCC65)c5c(C6CC6)cncc5n4)ccnc3[nH]2)cc1] | [D4], [D3] | 531.24 (M + H)+ | 1H NMR (400 MHz, DMSO-d6) δ 12.46 (d, 1H, J = 1.7 Hz), 9.21 (s, 1H), 8.60 (m, 2H), 8.43 (d, 1H, J = 5.0 Hz), 8.22 (s, 1H), 8.15-8.09 (m, 3H), 8.06-8.01 (m, 4H), 7.43 (br s, 1H), 4.64(m, 1H), 4.44-4.37 (m, 1H), 3.43-3.27 (m, 3H), 2.99-2.74 (m, 5H), 2.26 (m, 1H), 1.93 (m, 1H), 1.76 (m, 1H), 1.51-1.43 (m, 1H), 1.19-1.15 (m, 1H), 1.12-1.06 (m, 1H), 0.97-0.93 (m, 1H) | 4-{4-[5-Cyclopropyl-4-(octahydro-pyrrolo[3,2-c]pyridin-1-yl)-pyrido[3,4-d]pyrimidin-2-yl]-1H-pyrrolo[2,3-b]pyridin-2-yl}-benzamide |

TABLE A-continued

| Ex | Structure | Scheme | LCMS | 1H-NMR | Name |
|---|---|---|---|---|---|
| 171 | Chiral | [B4] | 537 (M + H)+ | 1H NMR (400 MHz, METHANOL-d4) δ ppm 9.10 (d, J = 0.75 Hz, 1 H) 8.93 (s, 1 H) 8.55 (d, J = 1.00 Hz, 1 H) 8.36-8.46 (m, 1 H) 8.22 (dd, J = 5.90, 1.38 Hz, 1 H) 8.02 (td, J = 8.91,7.28 Hz, 1 H) 4.89-4.97 (m, 2 H) 4.22 (quin, J = 8.41 Hz, 1 H) 4.05 (br. s., 1 H) 3.93 (d, J = 13.80 Hz, 1 H) 3.66-3.71 (m, 3 H) 3.41-3.53 (m, 1 H) 3.26 (s, 1 H) 2.37-2.77 (m, 5 H) 1.86-2.28 (m, 3 H) | (±)-{5-Cyclobutyl-2-[2-(3,5,6-trifluoro-pyridin-2-ylamino)-pyridin-4-yl]-pyrido[3,4-d]pyrimidin-4-yl}-((3,4-cis)-3-methoxy-piperidin-4-yl)-amine |
| 172 | Chiral | [B4] | 519 (M + H)+ | 1H NMR (400 MHz, METHANOL-d4) δ ppm 9.13 (s, 1 H) 8.90 (d, J = 0.75 Hz, 1 H) 8.58 (s, 1 H) 8.50 (d, J = 6.53 Hz, 1 H) 8.38 (dd, J = 6.53, 1.51 Hz, 1 H) 7.94 (dd, J = 9.16, 3.14 Hz, 1 H) 6.90 (d, J = 8.53 Hz, 1 H) 4.90-4.99 (m, 1 H) 4.23 (t, J = 8.28 Hz, 1 H) 4.05 (br. s., 1 H) 3.94 (d, J = 14.05 Hz, 1 H) 3.68 (s, 3 H) 3.42-3.55 (m, 1 H) 3.33 (d, J = 0.75 Hz, 2 H) 2.34-2.77 (m, 5H) 1.96-2.30 (m, 3 H) | (±)-{5-Cyclobutyl-2-[2-(3,6-difluoro-pyridin-2-ylamino)-pyridin-4-yl]-pyrido[3,4-d]pyrimidin-4-yl}-((3,4-cis)-3-methoxy-piperidin-4-yl)-amine |
| 173 | 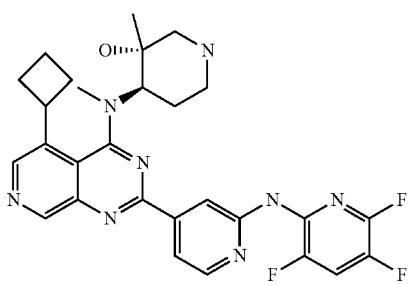 [SMILES: CN(c1nc(-c2ccnc(Nc3nc(F)c(F)cc3F)c2)nc2cncc(C3CCC3)c12)[C@@H]1CCNC[C@@]1(C)O] | [B4] | 551 (M + H)+ | 1H NMR (400 MHz, METHANOL-d4) δ ppm 9.30 (s, 1 H) 8.96 (s, 1 H) 8.78 (s, 1 H) 8.47 (d, J = 5.02 Hz, 1 H) 8.01-8.09 (m, 1 H) 7.85-7.98 (m, 1 H) 4.36-4.55 (m, 2 H) 3.94-4.15 (m, 2 H) 3.60 (d, J = 13.30 Hz, 1 H) 2.40-2.74 (m, 5 H) 2.25-2.32 (m, 1 H) 2.22 (s, 3 H) 2.10-2.20 (m, 2 H) 2.01 (m, 1 H) | (±)-(3,4-trans)-4-({5-Cyclobutyl-2-[2-(3,5,6-trifluoro-pyridin-2-ylamino)-pyridin-4-yl]-pyrido[3,4-d]pyrimidin-4-yl}-methyl-amino)-3-methyl-piperidin-3-ol |
| 174 | 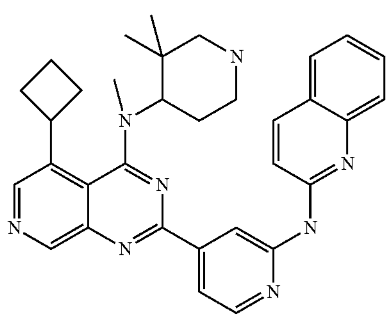 [SMILES: CN(c1nc(-c2ccnc(Nc3ccc4ccccc4n3)c2)nc2cncc(C3CCC3)c12)C1CCNCC1(C)C] | [B4] | 545 (M + H)+ | 1H NMR (400 MHz, METHANOL-d4) δ ppm 9.12 (s, 1 H) 8.96 (s, 1 H) 8.78 (d, J = 5.52 Hz, 1 H) 8.64 (d, J = 9.29 Hz, 1 H) 8.35-8.45 (m, 2 H) 8.18 (d, J = 8.28 Hz, 1 H) 8.06 (d, J = 7.28 Hz, 1 H) 7.96 (td, J = 7.78, 1.25 Hz, 1 H) 7.64-7.75 (m, 1 H) 7.46 (d, J = 9.29 Hz, 1 H) 5.73-5.85 (m, 1 H) 4.32-4.50 (m, 1 H) 3.53-3.70 (m, 1 H) 3.43 (d, J = 9.54 Hz, 1 H) 3.33 (br. s., 1 H) 3.17-3.26 (m, 1 H) 3.00-3.13 (m, 3 H) 2.76 (d, J = 6.53 Hz, 2 H) 2.28-2.65 (m, 3 H) 1.93 -2.27 (m, 4 H) 1.54 (s, 3 H) 1.33 (s, 3 H) | {5-Cyclobutyl-2-[2-(quinolin-2-ylamino)-pyridin-4-yl]-pyrido[3,4-d]pyrimidin-4-yl}-(3,3-dimethyl-piperidin-4-yl)-methyl-amine |

TABLE A-continued

| Ex | Structure | Scheme | Analysis | | Name |
| --- | --- | --- | --- | --- | --- |
| | | | LCMS | 1H-NMR | |
| 175 | 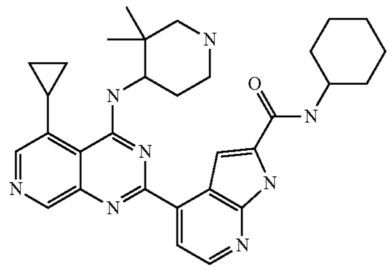 [SMILES: CC1(C)CNCCC1Nc1nc(-c2ccnc3[nH]c(C(=O)NC4CCCCC4)cc23)nc2cncc(C3CC3)c12] | [D21] | 539.29 (M + H)+ | 1H NMR (400 MHz, DMSO-d6) δ 12.23 (d, 1H, J = 1.8 Hz), 9.25 (s, 1H), 9.01 (m, 1H), 8.51 (m, 2H), 8.35 (m, 1H), 8.23 (m, 2H), 8.13 (d, 1H, J = 2.2 Hz), 7.60 (m, 1H), 4.91-4.85 (m, 1H), 3.84 (m, 1H), 3.24-3.08 (m, 4H), 2.66-2.58 (m, 1H), 2.18 (m, 1H), 1.99-1.91 (m, 3H), 1.77 (m, 2H), 1.64 (m, 1H), 1.43-1.09 (m, 15H) | 4-[5-Cyclopropyl-4-(3,3-dimethyl-piperidin-4-ylamino)-pyrido[3,4-d]pyrimidin-2-yl]-1H-pyrrolo[2,3-b]pyridine-2-carboxylic acid cyclohexylamide |
| 176 | 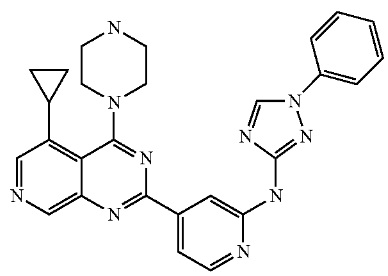 [SMILES: c1ccc(-n2cnc(Nc3cc(-c4nc(N5CCNCC5)c5c(C6CC6)cncc5n4)ccn3)n2)cc1] | [B4] | 491.16 (M + H)+ | (400 MHz, d6-DMSO, δ): 10.53 (br s, 1H), 9.24 (s, 1H), 9.10-8.71 (m, 4H), 8.44 (d, J = 5.6 Hz, 1H), 8.20 (s, 1H), 7.97-7.92 (m, 3H), 7.64-7.59 (m, 2H), 7.46-7.41 (m, 1H), 3.95 (br s, 4H), 3.28 (br s, 4H), 2.74-2.65 (m, 1H), 1.29-1.24 (m, 2H), 1.12-1.07 (m, 2H). | [4-(5-Cyclopropyl-4-piperazin-1-yl-pyrido[3,4-d]pyrimidin-2-yl)-pyridin-2-yl]-(1-phenyl-1H-[1,2,4]triazol-3-yl)-amine |
| 177 | 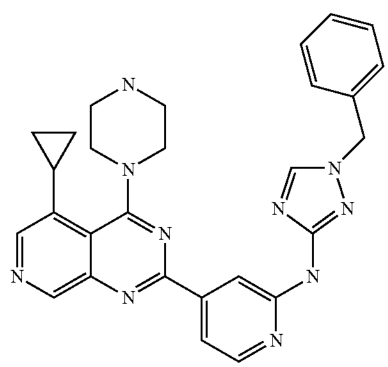 [SMILES: c1ccc(Cn2cnc(Nc3cc(-c4nc(N5CCNCC5)c5c(C6CC6)cncc5n4)ccn3)n2)cc1] | [B4] | 505.19 (M + H)+ | (400 MHz, d6-DMSO, δ): 11.04 (br s, 1H), 9.08 (s, 1H), 9.02 (br s, 2H), 8.77 (s, 1H), 8.71 (s, 1H), 8.41 (d, J = 5.7 Hz, 1H), 8.21 (s, 1H), 7.94 (dd, J = 5.8, 1.3 Hz, 1H), 7.42-7.31 (m, 5H), 5.43 (s, 2H), 3.93 (br s, 4H), 3.30 (br s, 4H), 2.71-2.63 (m, 1H), 1.29-1.24 (m, 2H), 1.11-1.06 (m, 2H). | (1-Benzyl-1H-[1,2,4]triazol-3-yl)-[4-(5-cyclopropyl-4-piperazin-1-yl-pyrido[3,4-d]pyrimidin-2-yl)-pyridin-2-yl]-amine |
| 178 | 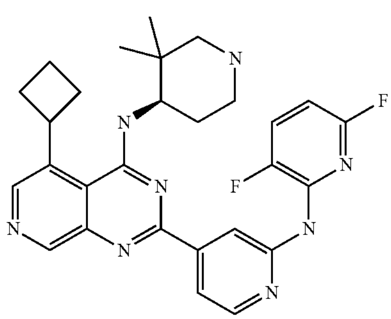 [SMILES: CC1(C)CNCC[C@H]1Nc1nc(-c2ccnc(Nc3nc(F)ccc3F)c2)nc2cncc(C3CCC3)c12] | [B4] | 517 (M + H)+ | 1H NMR (400 MHz, METHANOL-d4) δ ppm 9.14 (s, 1 H) 8.91 (d, J = 1.51 Hz, 1 H) 8.63 (s, 1 H) 8.51 (d, J = 6.53 Hz, 1 H) 8.40 (dd, J = 6.40, 1.63 Hz, 1 H) 7.94 (td, J = 9.03, 6.02 Hz, 1 H) 6.84-6.94 (m, 1 H) 5.00 (dd, J = 11.67, 4.39 Hz, 1 H) 4.31 (quin, J = 8.16 Hz, 1 H) 3.45-3.59 (m, 1 H) 3.32-3.40 (m, 2 H) 3.18 (d, J = 13.05 Hz, 1 H) 2.34-2.71 (m, 4 H) 1.97-2.31 (m, 4 H) 1.37 (s, 3 H) 1.22 (s, 3 H) | {5-Cyclobutyl-2-[2-(3,6-difluoro-pyridin-2-ylamino)-pyridin-4-yl]-pyrido[3,4-d]pyrimidin-4-yl}-((R)-3,3-dimethyl-piperidin-4-yl)-amine |

TABLE A-continued

| Ex | Structure | Scheme | LCMS | 1H-NMR | Name |
|---|---|---|---|---|---|
| 179 | 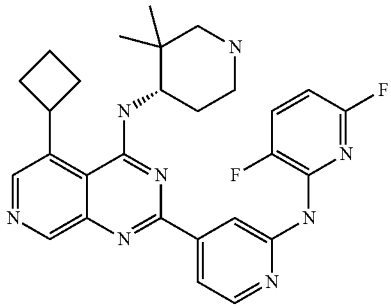 [SMILES: CC1(C)CNCC[C@@H]1Nc1nc(-c2ccnc(Nc3nc(F)ccc3F)c2)nc2cncc(C3CCC3)c12] | [B4] | 517 (M + H)+ | 1H NMR (400 MHz, METHANOL-d4) δ ppm 9.14 (s, 1 H) 8.91 (d, J = 0.75 Hz, 1 H) 8.63 (s, 1 H) 8.51 (d, J = 6.53 Hz, 1 H) 8.39 (dd, J = 6.52, 1.51 Hz, 1 H) 7.93 (td, J = 9.03, 6.02 Hz, 1 H) 6.89 (dt, J = 8.72, 2.42 Hz, 1 H) 5.00 (dd, J = 11.80, 4.52 Hz, 1 H) 4.31 (t, J = 8.16 Hz, 1 H) 3.43-3.59 (m, 1 H) 3.32- 3.39 (m, 2 H) 3.18 (d, J = 13.05 Hz, 1 H) 2.34-2.71 (m, 4 H) 1.96-2.30 (m, 4 H) 1.37 (s, 3 H) 1.22 (s, 3 H) | {5-Cyclobutyl-2-[2-(3,6-difluoro-pyridin-2-ylamino)-pyridin-4-yl]-pyrido[3,4-d]pyrimidin-4-yl}-((S)-3,3-dimethyl-piperidin-4-yl)-amine |
| 180 | 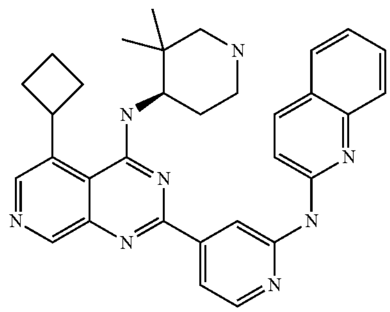 [SMILES: CC1(C)CNCC[C@H]1Nc1nc(-c2ccnc(Nc3ccc4ccccc4n3)c2)nc2cncc(C3CCC3)c12] | [B4] | 531 (M + H)+ | 1H NMR (400 MHz, METHANOL-d4) δ ppm 9.00 (s, 1 H) 8.63-8.68 (m, 1 H) 8.45-8.56 (m, 2 H) 8.35 (d, J = 0.75 Hz, 2 H) 8.06 (d, J = 8.53 Hz, 1 H) 7.93 (d, J = 8.03 Hz, 1 H) 7.85 (td, J = 7.84, 1.38 Hz, 1 H) 7.54-7.62 (m, 1 H) 7.37 (d, J = 9.29 Hz, 1 H) 4.94 (dd, J = 11.80, 4.27 Hz, 1 H) 4.20 (quin, J = 8.22 Hz, 1H) 3.45 (d, J = 12.80 Hz, 1 H) 3.24-3.34 (m, 2 H) 3.12-3.19 (m, 1 H) 2.23-2.62 (m, 4 H) 1.88-2.21 (m, 4H) 1.29 (s, 3 H) 1.15 (s, 3 H) | {5-Cyclobutyl-2-[2-(quinolin-2-ylamino)-pyridin-4-yl]-pyrido[3,4-d]pyrimidin-4-yl}-((R)-3,3-dimethyl-piperidin-4-yl)-amine |
| 181 | 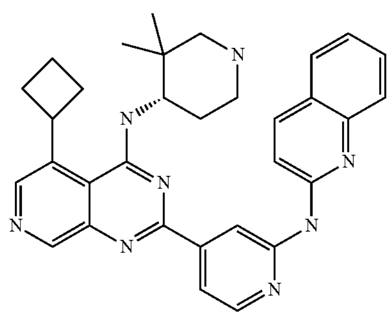 [SMILES: CC1(C)CNCC[C@@H]1Nc1nc(-c2ccnc(Nc3ccc4ccccc4n3)c2)nc2cncc(C3CCC3)c12] | [B4] | 531 (M + H)+ | 1H NMR (400 MHz, METHANOL-d4) δ ppm 9.11 (s, 1 H) 8.77 (dd, J = 5.77, 0.75 Hz, 1 H) 8.58-8.68 (m, 2 H)8.38-8.49 (m, 2 H) 8.17 (d, J = 8.28 Hz, 1 H) 8.05 (d, J = 8.28 Hz, 1 H) 7.96 (td, J = 7.84, 1.38 Hz, 1 H) 7.65-7.75 (m, 1 H) 7.45 (d, J = 9.03 Hz, 1 H) 5.03 (dd, J = 11.80, 4.27 Hz, 1 H) 4.30 (t, J = 8.28 Hz, 1 H) 3.53 (d, J = 13.05 Hz, 1 H) 3.33-3.41 (m, 2 H) 3.17-3.28 (m, 1 H) 2.36-2.71 (m, 4 H) 1.97-2.33 (m, 4 H) 1.38 (s, 3 H) 1.23 (s, 3 H) | {5-Cyclobutyl-2-[2-(quinolin-2-ylamino)-pyridin-4-yl]-pyrido[3,4-d]pyrimidin-4-yl}-((S)-3,3-dimethyl-piperidin-4-yl)-amine |
| 182 | 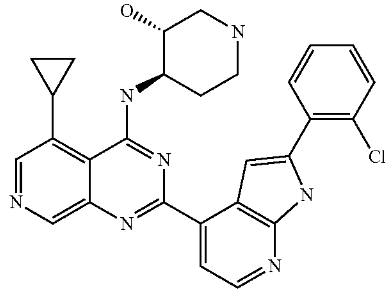 [SMILES: O[C@@H]1CNCC[C@H]1Nc1nc(-c2ccnc3[nH]c(-c4ccccc4Cl)cc23)nc2cncc(C3CC3)c12] | [D4], [D3] | 512.14 (M + H)+ | 1H NMR (400 MHz, DMSO-d6) δ 12.24 (d, 1H, J = 1.8 Hz), 9.13 (br s, 1H), 8.86 (m, 1H), 8.65 (m, 1H), 8.50 (br s, 1H), 8.44 (d, 1H, J = 5.0 Hz), 8.19 (d, 1H, J = 5.0 Hz), 7.93-7.89 (m, 2H), 7.84 (m, 1H), 7.66 (m, 1H), 7.50 (m, 2H), 4.58-4.51 (m, 1H), 4.09-4.04 (m, 1H), 3.43-3.32 (m, 2H), 3.13-2.95 (m, 2H), 2.69-2.57 (m, 2H), 1.88-1.79 (m, 1H), 1.28-1.10 (m, 4H) | (±)-(3,4-trans)-4-{2-[2-(2-Chloro-phenyl)-1H-pyrrolo[2,3-b]pyridin-4-yl]-5-cyclopropyl-pyrido[3,4-d]pyrimidin-4-ylamino}-piperidin-3-ol |

TABLE A-continued

| Ex | Structure | Scheme | Analysis | | Name |
| --- | --- | --- | --- | --- | --- |
| | | | LCMS | 1H-NMR | |
| 183 | 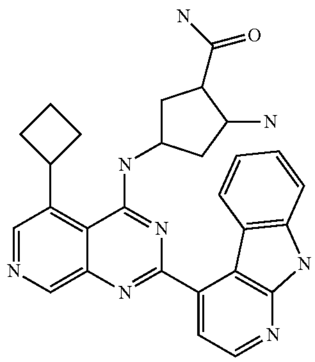 [SMILES: NC(=O)C1CC(Nc2nc(-c3ccnc4[nH]c5ccccc5c34)nc3cncc(C4CCC4)c23)CC1N] | [D3] | 493 (M + H)+ | 1H NMR (400 MHz, METHANOL-d4) δ ppm 9.11 (1 H, br. s.) 8.48-8.64 (2 H, m) 8.41 (1 H, d, J = 8.3 Hz) 7.87 (1 H, d, J = 5.5 Hz) 7.45-7.69 (2 H, m) 7.22 (1 H, ddd, J = 8.1, 7.1, 1.1 Hz) 4.89-5.00 (1 H, m) 4.42-4.61 (1 H, m) 3.89 (1 H, dt, J = 10.4, 7.6 Hz) 3.12 (1 H, dt, J = 10.0, 7.6 Hz) 2.80-2.92 (1 H, m) 2.61-2.74 (2 H, m) 2.33-2.51 (4 H, m) 2.21-2.32 (1 H, m) 1.86-2.06 (2 H, m) | 2-Amino-4-[5-cyclobutyl-2-(9H-pyrido[2,3-b]indol-4-yl)-pyrido[3,4-d]pyrimidin-4-ylamino]-cyclopentanecarboxylic acid amide |
| 184 | 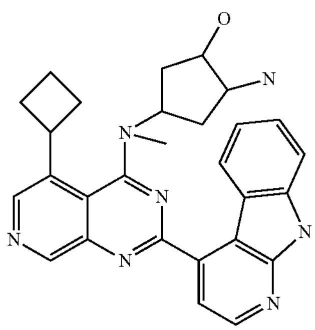 [SMILES: CN(c1nc(-c2ccnc3[nH]c4ccccc4c23)nc2cncc(C3CCC3)c12)C1CC(N)C(O)C1] | [D3] | 480 (M + H)+ | 1H NMR (400 MHz, METHANOL-d4) δ ppm 9.12 (1 H, br. s.) 8.71 (1 H, br. s.) 8.55 (1 H, d, J = 5.3 Hz) 8.14-8.37 (1 H, m) 7.80-7.93 (1 H, m) 7.47-7.66 (2 H, m) 7.13-7.29 (1 H, m) 5.01-5.44 (1 H, m) 3.99-4.43 (2 H, m) 3.41-3.67 (1 H, m) 3.13-3.26 (3 H, m) 1.92-2.85 (12 H, m) | 2-Amino-4-{[5-cyclobutyl-2-(9H-pyrido[2,3-b]indol-4-yl)-pyrido[3,4-d]pyrimidin-4-yl]-methyl-amino}-cyclopentanol |
| 185 | 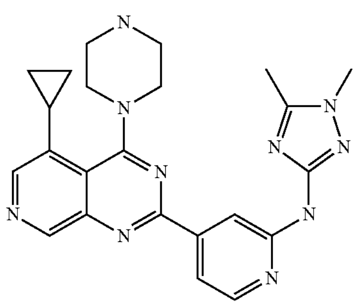 [SMILES: Cc1nc(Nc2cc(-c3nc(N4CCNCC4)c4c(C5CC5)cncc4n3)ccn2)nn1C] | [B4] | 443.17 (M + H)+ | (400 MHz, d6-DMSO, δ): 11.08 (br s, 1H), 9.10 (s, 1H), 9.04 (brs, 2H), 8.74 (s, 1H), 8.42 (d, J = 6.0 Hz, 1H), 8.22 (s, 1H), 7.96 (dd, J = 5.9, 1.3 Hz, 1H), 3.95 (br s, 4H), 3.81 (s, 3H), 3.34 (br s, 4H), 2.72-2.64 (m, 1H), 2.47 (s, 3H), 1.30-1.24 (m, 2H), 1.12-1.07 (m, 2H). | [4-(5-Cyclopropyl-4-piperazin-1-yl-pyrido[3,4-d]pyrimidin-2-yl)-pyridin-2-yl]-(1,5-dimethyl-1H-[1,2,4]triazol-3-yl)-amine |
| 186 | 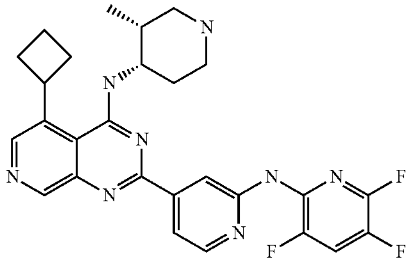 [SMILES: C[C@@H]1CNCC[C@@H]1Nc1nc(-c2ccnc(Nc3nc(F)c(F)cc3F)c2)nc2cncc(C3CCC3)c12] | [B4] | 521 (M + H)+ | 1H NMR (400 MHz, METHANOL-d4) δ ppm 9.04 (s, 1 H) 8.82 (d, J = 0.75 Hz, 1 H) 8.50 (s, 1 H) 8.36 (d, J = 6.27 Hz, 1 H) 8.21 (dd, J = 6.27, 1.51 Hz, 1 H) 8.00 (td, J = 8.85, 7.40 Hz, 1 H) 4.91 (dt, J = 8.22, 4.30 Hz, 1 H) 4.28 (t, J = 8.16 Hz, 1 H) 3.24-3.40 (m, 3 H) 3.18 (d, J = 6.78 Hz, 1 H) 2.70 (d, J = 3.51 Hz, 1 H) 2.47-2.61 (m, 2 H) 2.03-2.41 (m, 5 H) 1.86-2.00 (m, 1 H) 1.14 (d, J = 7.03 Hz, 3 H) | (±)-{5-Cyclobutyl-2-[2-(3,5,6-trifluoro-pyridin-2-ylamino)-pyridin-4-yl]-pyrido[3,4-d]pyrimidin-4-yl}-((3,4-cis)-3-methyl-piperidin-4-yl)-amine |

TABLE A-continued

| Ex | Structure | Scheme | LCMS | 1H-NMR | Name |
|---|---|---|---|---|---|
| 187 | 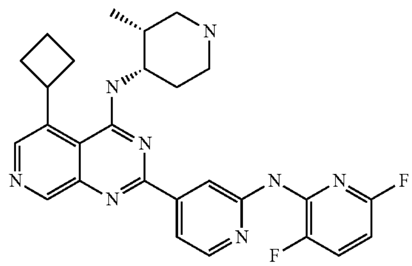 [SMILES: C[C@@H]1CNCC[C@@H]1Nc1nc(-c2ccnc(Nc3nc(F)ccc3F)c2)nc2cncc(C3CCC3)c12] | [B4] | 503 (M + H)+ | 1H NMR (400 MHz, METHANOL-d4) ppm 9.09 (s, 2 H) 8.56 (s, 1 H) 8.44 (d, J = 5.77 Hz, 1 H) 8.19 (dd, J = 5.77, 1.51 Hz, 1 H) 7.79 (ddd, J = 9.47, 8.60, 6.27 Hz, 1 H) 6.71 (d, J = 8.53 Hz, 1 H) 4.96-5.04 (m, 1 H) 4.35 (s, 1 H) 3.34-3.50 (m, 3 H) 3.15-3.29 (m, 1 H) 2.73-2.88 (m, 1 H) 2.65 (dt, J = 7.53, 3.51 Hz, 2 H) 2.14-2.51 (m, 5 H) 1.93-2.10 (m, 1 H) 1.23 (d, J = 7.28 Hz, 3 H) | (±)-{5-Cyclobutyl-2-[2-(3,6-difluoro-pyridin-2-ylamino)-pyridin-4-yl]-pyrido[3,4-d]pyrimidin-4-yl}-((3,4-cis)-3-methyl-piperidin-4-yl)-amine |
| 188 | 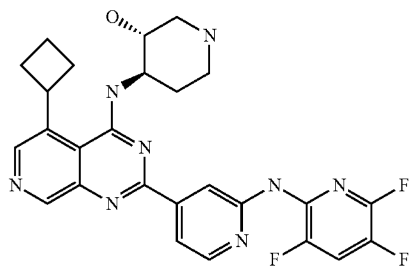 [SMILES: O[C@@H]1CNCC[C@H]1Nc1nc(-c2ccnc(Nc3nc(F)c(F)cc3F)c2)nc2cncc(C3CCC3)c12] | [B4] | 523 (M + H)+ | 1H NMR (400 MHz, METHANOL-d4) δ ppm 8.98-9.06 (m, 1 H) 8.71-8.80 (m, 1 H) 8.46 (d, J = 1.00 Hz, 1 H) 8.37 (d, J = 6.27 Hz, 1 H) 8.25 (dd, J = 6.27, 1.51 Hz, 1 H) 8.03 (td, J = 8.91, 7.28 Hz, 1 H) 4.56 (td, J = 9.54, 4.27 Hz, 1 H) 4.32 (quin, J = 8.16 Hz, 1 H) 4.15 (td, J = 9.35, 4.14 Hz, 1 H) 3.51 (dd, J = 12.42, 4.14 Hz, 1 H) 3.35-3.45 (m, 1 H) 3.23-3.29 (m, 1 H) 2.89-3.07 (m, 1 H) 2.47-2.78 (m, 3 H) 2.01-2.45 (m, 3 H) 1.72-1.97 (m, 2 H) | (±)-(3,4-trans)-4-{5-Cyclobutyl-2-[2-(3,5,6-trifluoro-pyridin-2-ylamino)-pyridin-4-yl]-pyrido[3,4-d]pyrimidin-4-ylamino}-piperidin-3-ol |
| 189 | 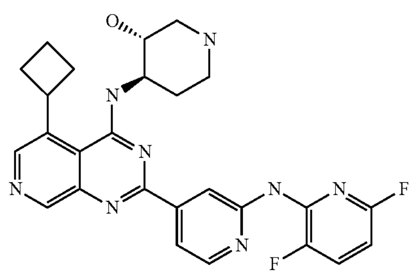 [SMILES: O[C@@H]1CNCC[C@H]1Nc1nc(-c2ccnc(Nc3nc(F)ccc3F)c2)nc2cncc(C3CCC3)c12] | [B4] | 505 (M + H)+ | 1H NMR (400 MHz, METHANOL-d4) δ ppm 9.01 (d, J = 1.51 Hz, 1 H) 8.86 (s, 1 H) 8.45 (s, 1 H) 8.39 (dd, J = 6.15, 1.63 Hz, 1 H) 8.21 (dt, J = 6.27, 1.88 Hz, 1 H) 7.67-7.86 (m, 1 H) 6.73 (dd, J = 8.66, 2.38 Hz, 1 H) 4.55 (d, J = 3.26 Hz, 1 H) 4.30 (t, J = 8.41 Hz, 1 H) 4.03-4.17 (m, 1 H) 3.45-3.54 (m, 1 H) 3.32-3.43 (m, 1 H) 3.25 (d, J = 2.26 Hz, 1 H) 2.91-3.06 (m, 1 H) 2.60-2.80 (m, 2 H) 2.48-2.59 (m, 1 H) 2.04-2.45 (m, 3 H) 1.70-1.98 (m, 2 H) | (±)-(3,4-trans)-4-{5-Cyclobutyl-2-[2-(3,6-difluoro-pyridin-2-ylamino)-pyridin-4-yl]-pyrido[3,4-d]pyrimidin-4-ylamino}-piperidin-3-ol |
| 190 | 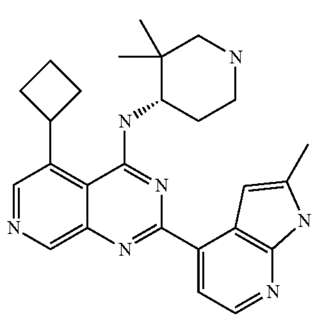 [SMILES: Cc1cc2c(-c3nc(N[C@H]4CCNCC4(C)C)c4c(C5CCC5)cncc4n3)ccnc2[nH]1] | [D4], [D3] | 442.18 (M + H)+ | 1H NMR (400 MHz, DMSO-d6) ppm 11.85 (s, 1 H), 9.04-9.25 (m, 2 H), 8.55 (br. s, 1 H), 8.41 (d, J = 9.8 Hz, 1 H), 8.29 (d, J = 5.3 Hz, 1 H), 8.14 (d, J = 5.3 Hz, 1 H), 7.24 (d, J = 0.8 Hz, 1 H), 6.56 (d, J = 8.5 Hz, 1 H), 4.78-4.88 (m, 1 H), 4.43 (t, J = 8.2 Hz, 1 H), 3.40 (d, J = 19.8 Hz, 1 H), 3.05-3.29 (m, 3 H), 2.54-2.45 (m, 1 H), 2.52 (s, 3 H), 2.22-2.41 (m, 2 H), 1.82-2.16 (m, 5 H), 1.27 (s, 3 H), 1.13 (s, 3 H) | [5-Cyclobutyl-2-(2-methyl-1H-pyrrolo[2,3-b]pyridin-4-yl)-pyrido[3,4-d]pyrimidin-4-yl]-((S)-3,3-dimethyl-piperidin-4-yl)-amine |

TABLE A-continued

| Ex | Structure | Scheme | Analysis | | Name |
|---|---|---|---|---|---|
| | | | LCMS | 1H-NMR | |
| 191 | Chiral | [D4], [D3] | 523.23 (M + H)+ | 1H NMR (400 MHz, DMSO-d6) ppm 12.41 (s, 1 H), 9.13 (br. s., 2 H), 8.62 (dt, J = 4.6, 1.5 Hz, 1 H), 8.57 (s, 1 H), 8.51 (d, J = 4.5 Hz, 1 H), 8.39 (d, J = 9.8 Hz, 1 H), 8.21 (d, J = 5.0 Hz, 1 H), 8.17 (d, J = 4.5 Hz, 1 H), 7.93 (ddd, J = 11.8, 8.4, 1.1 Hz, 1 H), 7.54 (dt, J = 8.5, 4.3 Hz, 1 H), 6.60 (d, J = 8.8 Hz, 1 H), 4.81-4.93 (m, 1 H), 4.40-4.51 (m, 3 H), 3.37 (d, J = 12.3 Hz, 1 H), 3.27 (d, J = 12.5 Hz, 1 H), 3.10 (q, J = 11.4 Hz, 2 H), 2.55 (dd, J = 7.3, 3.3 Hz, 1 H), 2.23-2.44 (m, 2 H), 1.97-2.14 (m, 3H), 1.85-1.97 (m, 1 H), 1.29 (s, 3 H), 1.11-1.18 (m, 3 H); | {5-Cyclobutyl-2-[2-(3-fluoro-pyridin-2-yl)-1H-pyrrolo[2,3-b]pyridin-4-yl]-pyrido[3,4-d]pyrimidin-4-yl}-((S)-3,3-dimethyl-piperidin-4-yl)-amine |
| 192 | 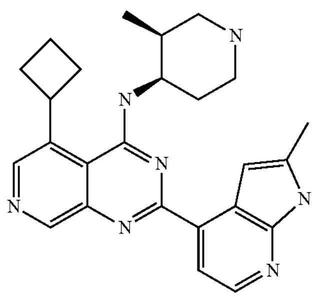 [SMILES: Cc1cc2c(-c3nc(N[C@@H]4CCNC[C@@H]4C)c4c(C5CCC5)cncc4n3)ccnc2[nH]1] | [D4], [D3] | 428.22 (M + H)+ | 1H NMR (400 MHz, DMSO-d6) ppm 11.81 (s, 1 H), 9.15 (s, 1 H), 8.83 (br. s., 1 H), 8.51 (s, 2 H), 8.28 (d, J = 5.3 Hz, 1 H), 8.10 (d, J = 5.0 Hz, 1 H), 7.19-7.29 (m, 1 H), 6.80 (d, J = 7.0 Hz, 1 H), 5.45-6.63 (m, 1 H), 4.83 (t, J = 7.5 Hz, 1 H), 4.51 (t, J = 8.3 Hz, 1 H), 3.18-3.36 (m, 4 H), 2.68 (d, J = 5.8 Hz, 1 H), 2.53 (br. s., 1 H), 2.51-2.52 (m, 3 H), 2.14-2.34 (m, 3 H), 2.02-2.14 (m, 2 H), 1.87 (d, J = 10.0 Hz, 1 H), 1.11 (d, J = 7.3 Hz, 3 H) | (±)-[5-Cyclobutyl-2-(2-methyl-1H-pyrrolo[2,3-b]pyridin-4-yl)-pyrido[3,4-d]pyrimidin-4-yl]-((3,4-cis)-3-methyl-piperidin-4-yl)-amine |
| 193 | 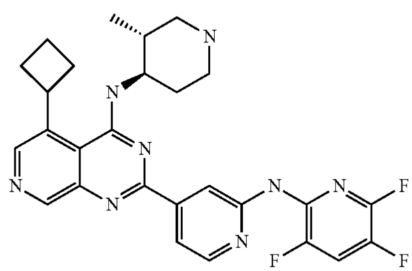 [SMILES: C[C@@H]1CNCC[C@H]1Nc1nc(-c2ccnc(Nc3nc(F)c(F)cc3F)c2)nc2cncc(C3CCC3)c12] | [B4] | 521 (M + H)+ | 1H NMR (400 MHz, METHANOL-d4) δ ppm 8.92-9.10 (m, 1 H) 8.79 (d, J = 0.75 Hz, 1 H) 8.45 (d, J = 1.00 Hz, 1 H) 8.36 (d, J = 6.27 Hz, 1 H) 8.24 (dd, J = 6.27, 1.51 Hz, 1 H) 8.01 (dd, J = 8.78, 1.51 Hz, 1 H) 4.67 (d, J = 4.02 Hz, 1 H) 4.34 (t, J = 8.28 Hz, 1 H) 3.38-3.52 (m, 2 H) 3.07-3.20 (m, 1 H) 2.90 (t, J = 12.55 Hz, 1 H) 2.49-2.63 (m, 2 H) 2.07-2.38 (m, 5 H) 1.81-1.94 (m, 2 H) 1.04 (d, J = 6.53 Hz, 3 H) | (±)-{5-Cyclobutyl-2-[2-(3,5,6-trifluoro-pyridin-2-ylamino)-pyridin-4-yl]-pyrido[3,4-d]pyrimidin-4-yl}-((3,4-trans)-3-methyl-piperidin-4-yl)-amine |
| 194 | 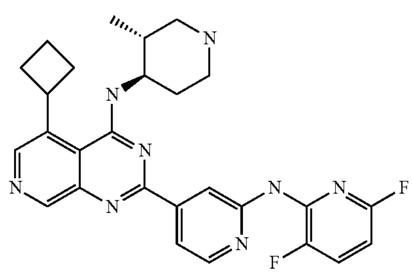 [SMILES: C[C@@H]1CNCC[C@H]1Nc1nc(-c2ccnc(Nc3nc(F)ccc3F)c2)nc2cncc(C3CCC3)c12] | [B4] | 503 (M + H)+ | 1H NMR (400 MHz, METHANOL-d4) δ ppm 8.98-9.10 (m, 2 H) 8.51 (s, 1 H) 8.45 (d, J = 5.52 Hz, 1 H) 8.23 (dd, J = 5.77, 1.51 Hz, 1 H) 7.71-7.88 (m, 1 H) 6.59-6.81 (m, 1 H) 4.77 (td, J = 11.23, 4.14 Hz, 1 H) 4.40 (quin, J = 8.22 Hz, 1 H) 3.49-3.62 (m, 2 H) 3.24 (td, J = 13.18, 3.01 Hz, 1 H) 2.98 (t, J = 12.55 Hz, 1 H) 2.57-2.72 (m, 2 H) 2.34-2.49 (m, 3 H) 2.17-2.31 (m, 2 H) 1.81-2.01 (m, 2 H) 1.14 (d, J = 6.53 Hz, 3 H) | (±)-{5-Cyclobutyl-2-[2-(3,6-difluoro-pyridin-2-ylamino)-pyridin-4-yl]-pyrido[3,4-d]pyrimidin-4-yl}-((3,4-trans)-3-methyl-piperidin-4-yl)-amine |

TABLE A-continued

| Ex | Structure | Scheme | Analysis | | Name |
|---|---|---|---|---|---|
| | | | LCMS | 1H-NMR | |
| 195 | 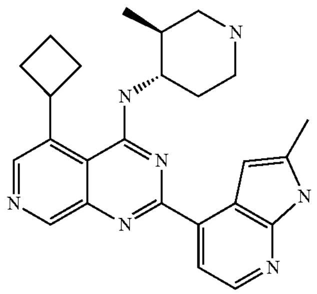 [SMILES: Cc1cc2c(-c3nc(N[C@H]4CCNC[C@@H]4C)c4c(C5CCC5)cncc4n3)ccnc2[nH]1] | [D4], [D3] | 428.17 (M + H)+ | 1H NMR (400 MHz, DMSO-d6) ppm 11.85 (s, 1 H), 9.14 (s, 1 H), 8.92 (d, J = 10.3 Hz, 1 H), 8.61 (d, J = 9.8 Hz, 1 H), 8.46 (s, 1 H), 8.29 (d, J = 5.3 Hz, 1 H), 8.13 (d, J = 5.3 Hz, 1 H), 7.23 (d, J = 1.0 Hz, 1 H), 6.99 (d, J = 8.3 Hz, 1 H), 4.56-4.64 (m, 3 H), 3.35-3.50 (m, 2 H), 3.15 (d, J = 11.0 Hz, 1 H), 2.95 (q, J = 11.5 Hz, 1 H), 2.53-2.57 (m, 1 H), 2.52 (s, 3 H), 2.18-2.34 (m, 4 H), 2.01-2.17 (m, 1 H), 1.76-1.97 (m, 2 H), 1.00 (d, J = 6.5 Hz, 3 H) | (±)-[5-Cyclobutyl-2-(2-methyl-1H-pyrrolo[2,3-b]pyridin-4-yl)-pyrido[3,4-d]pyrimidin-4-yl]-((3,4-trans)-3-methyl-piperidin-4-yl)-amine |
| 196 | 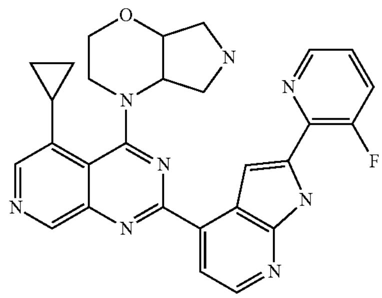 [SMILES: Fc1cccnc1-c1cc2c(-c3nc(N4CCOC5CNCC54)c4c(C5CC5)cncc4n3)ccnc2[nH]1] | [D4], [D3] | 509.19 (M + H)+ | 1H NMR (400 MHz, DMSO-d6) ppm 12.46 (s, 1 H), 9.40 (br. s., 1 H), 9.13 (s, 2 H), 8.61 (dt, J = 4.5, 1.6 Hz, 1 H), 8.51 (d, J = 5.0 Hz, 1 H), 8.22 (d, J = 5.0 Hz, 3 H), 7.93 (ddd, J = 11.8, 8.4, 1.1 Hz, 1 H), 7.53 (dt, J = 8.5, 4.3 Hz, 1 H), 4.50 (br. s., 2 H), 3.85-4.20 (m, 3 H), 3.77 (br. s., 2 H), 3.23-3.60 (m, 4 H), 2.63-2.83 (m, 1 H), 1.21-1.42 (m, 2 H), 0.99-1.20 (m, 2 H) | 5-Cyclopropyl-2-[2-(3-fluoro-pyridin-2-yl)-1H-pyrrolo[2,3-b]pyridin-4-yl]-4-(hexahydro-pyrrolo[3,4-b][1,4]oxazin-4-yl)-pyrido[3,4-d]pyrimidine |
| 197 | Chiral | [D4], [D3] | 525.19 (M + H)+ | 1H NMR (400 MHz, DMSO-d6) δ 12.25 (d, 1H, J = 1.8 Hz), 9.13 (s, 1H), 9.00 (m, 1H), 8.50 (s, 1H), 8.45 (d, 1H, J = 5.0 Hz), 8.29 (m, 1H), 8.21 (d, 1H, J = 5.0 Hz), 7.92 (d, 1H, J = 2.2 Hz), 7.83 (m, 1H), 7.66 (m, 1H), 7.60 (d, 1H, J = 8.8 Hz), 7.55-7.45 (m, 2H), 4.90-4.84 (m, 1H), 3.35 (m, 1H), 3.22-3.07 (m, 3H), 2.65-2.58 (m, 1H), 2.18 (m, 1H), 2.01-1.92 (m, 1H), 1.28-1.09 (m, 10H) | {2-[2-(2-Chloro-phenyl)-1H-pyrrolo[2,3-b]pyridin-4-yl]-5-cyclopropyl-pyrido[3,4-d]pyrimidin-4-yl}-((S)-3,3-dimethyl-piperidin-4-yl)-amine |
| 198 | 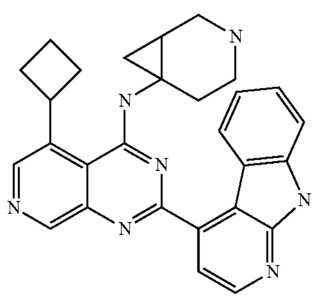 [SMILES: c1ccc2c(c1)[nH]c1nccc(-c3nc(NC45CCNCC4C5)c4c(C5CCC5)cncc4n3)c12] | [D3] | 462.16 (M + H)+ | (400 MHz, d6-DMSO, δ): 12.06 (s, 1H), 9.12 (s, 1H), 8.58 (d, J = 5.0 Hz, 1H), 8.53-8.41 (m, 3H), 8.05 (br s, 1H), 7.81 (s, 1H), 7.76 (d, J = 5.1 Hz, 1H), 7.55 (d, J = 8.0 Hz, 1H), 7.50-7.45 (m, 1H), 7.18-7.12 (m, 1H), 4.54-4.44 (m, 1H), 3.27-3.13 (m, 2H), 2.90-2.72 (m, 2H), 2.57-2.47 (m, 2H), 2.38-2.04 (m, 6H), 1.90-1.80 (m, 1H), 1.62-1.54 (m, 1H), 1.36-1.30 (m, 1H), 1.13-1.08 (m, 1H). | (3-Aza-bicyclo[4.1.0]hept-6-yl)-[5-cyclobutyl-2-(9H-pyrido[2,3-b]indol-4-yl)-pyrido[3,4-d]pyrimidin-4-yl]-amine |
| 199 | 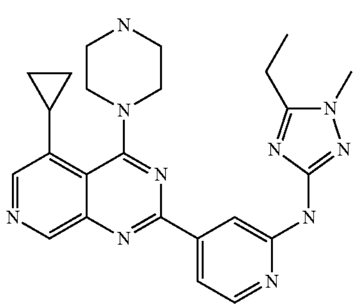 [SMILES: CCc1nc(Nc2cc(-c3nc(N4CCNCC4)c4c(C5CC5)cncc4n3)ccn2)nn1C] | [B4] | 457.19 (M + H)+ | (400 MHz, d6-DMSO, δ): 11.45 (br s, 1H), 9.20-8.95 (m, 3H), 8.71 (s, 1H), 8.45 (d, J = 6.1 Hz, 1H), 8.23 (s, 1H), 8.00 (dd, J = 6.1, 1.4 Hz, 1H), 3.96 (br s, 4H), 3.83 (s, 3H), 3.34 (br s, 4H), 2.83 (q, J = 7.6 Hz, 2H), 2.72-2.64 (m, 1H), 1.33-1.24 (m, 5H), 1.12-1.07 (m, 2H). | [4-(5-Cyclopropyl-4-piperazin-1-yl-pyrido[3,4-d]pyrimidin-2-yl)-pyridin-2-yl]-(5-ethyl-1-methyl-1H-[1,2,4]triazol-3-yl)-amine |

TABLE A-continued

| Ex | Structure | Scheme | Analysis | | Name |
| --- | --- | --- | --- | --- | --- |
| | | | LCMS | 1H-NMR | |
| 200 | Chiral | [D3] | 478 (M + H)+ | 1H NMR (400 MHz, METHANOL-d4) δ ppm 9.17 (1 H, br. s.) 8.70 (1 H, br. s.) 8.41-8.56 (2 H, m) 8.00 (1 H, d, J = 5.8 Hz) 7.49-7.68 (2 H, m) 7.16-7.29 (1 H, m) 4.91 (1 H, dd, J = 11.5, 4.5 Hz) 4.33 (1 H, t, J = 8.2 Hz) 3.46 (1 H, d, J = 13.1 Hz) 2.94-3.15 (2 H, m) 2.66 (3 H, m) 2.35-2.59 (2 H, m) 1.99-2.28 (4 H, m) 1.38 (3 H, s) 1.17 (3 H, s) | [5-Cyclobutyl-2-(9H-pyrido[2,3-b]indol-4-yl)-pyrido[3,4-d]pyrimidin-4-yl]-((S)-3,3-dimethyl-piperidin-4-yl)-amine |
| 201 | 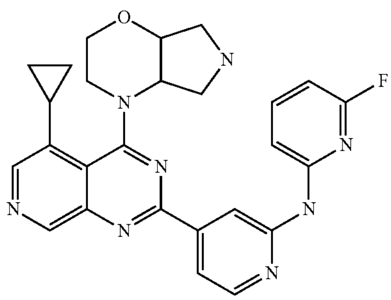 [SMILES: Fc1cccc(Nc2cc(-c3nc(N4CCOC5CNCC54)c4c(C5CC5)cncc4n3)ccn2)n1] | [B4] | 485.16 (M + H)+ | 1H NMR (400 MHz, DMSO-d6) ppm 10.38 (s, 1 H), 9.46 (br. s., 1 H), 9.20 (br. s., 1 H), 9.09 (s, 1 H), 8.67 (s, 1 H), 8.46 (d, J = 5.5 Hz, 1 H), 8.21 (s, 1 H), 7.95 (dd, J = 5.4, 1.4 Hz, 1 H), 7.90 (q, J = 8.0 Hz, 1 H), 7.76 (dd, J = 8.0, 2.0 Hz, 1 H), 6.66 (dd, J = 7.8, 2.3 Hz, 1 H), 4.48 (br. s., 1 H), 3.71-4.12 (m, 4 H), 3.47 (br. s., 2 H), 3.32-3.44 (m, 2 H), 2.60-2.74 (m, 1 H), 1.29 (br. s., 2 H), 1.09 (br. s., 2 H) | {4-[5-Cyclopropyl-4-(hexahydro-pyrrolo[3,4-b][1,4]oxazin-4-yl)-pyrido[3,4-d]pyrimidin-2-yl]-pyridin-2-yl}-(6-fluoro-pyridin-2-yl)-amine |
| 202 | 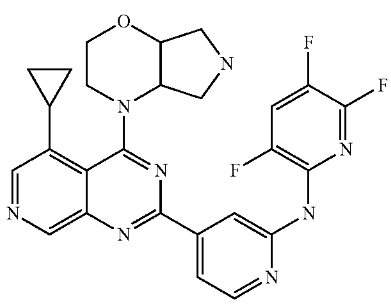 [SMILES: Fc1cc(F)c(Nc2cc(-c3nc(N4CCOC5CNCC54)c4c(C5CC5)cncc4n3)ccn2)nc1F] | [B4] | 521.16 (M + H)+ | 1H NMR (400 MHz, DMSO-d6) δ ppm 9.86 (br. s., 1 H), 9.45 (br. s., 1 H), 9.23 (br. s., 1 H), 9.08 (s, 1 H), 8.70 (s, 1 H), 8.44 (d, J = 5.3 Hz, 1 H), 8.24-8.33 (m, 1 H), 8.21 (br. s., 1 H), 7.99 (dd, J = 5.3, 1.3 Hz, 1 H), 4.86-5.12 (m, 1 H), 4.47 (br. s., 1 H), 3.64-4.13 (m, 4 H), 3.45 (br. s., 2H), 3.29-3.42 (m, 2 H), 2.60-2.73 (m, 1 H), 1.29 (br. s., 2H), 1.09 (br. s., 2 H) | {4-[5-Cyclopropyl-4-(hexahydro-pyrrolo[3,4-b][1,4]oxazin-4-yl)-pyrido[3,4-d]pyrimidin-2-yl]-pyridin-2-yl}-(3,5,6-trifluoro-pyridin-2-yl)-amine |
| 203 | 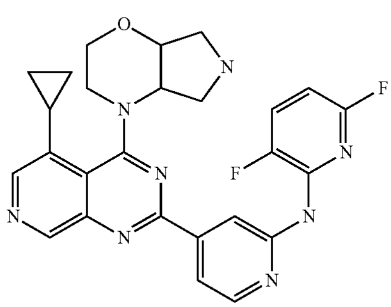 [SMILES: Fc1ccc(F)c(Nc2cc(-c3nc(N4CCOC5CNCC54)c4c(C5CC5)cncc4n3)ccn2)n1] | [B4] | 503.17 (M + H)+ | 1H NMR (400 MHz, DMSO-d6) ppm 9.79 (br. s., 1 H), 9.40 (br. s., 1 H), 9.08 (br. s., 2 H), 8.88 (s, 1 H), 8.47 (d, J = 5.3 Hz, 1 H), 8.21 (br. s., 1 H), 8.01 (dd, J = 5.3, 1.5 Hz, 1 H), 7.88 (ddd, J = 9.7, 8.6, 6.5 Hz, 1 H), 6.67-6.78 (m, 1 H), 4.86-5.22 (m, 1 H), 3.76 (br. s., 6 H), 3.30-3.51 (m, 4 H), 2.67 (br. s., 1 H), 1.28 (br. s., 2 H), 1.09 (br. s., 2 H) | {4-[5-Cyclopropyl-4-(hexahydro-pyrrolo[3,4-b][1,4]oxazin-4-yl)-pyrido[3,4-d]pyrimidin-2-yl]-pyridin-2-yl}-(3,6-difluoro-pyridin-2-yl)-amine |

TABLE A-continued

| Ex | Structure | Scheme | LCMS | 1H-NMR | Name |
|---|---|---|---|---|---|
| 204 | 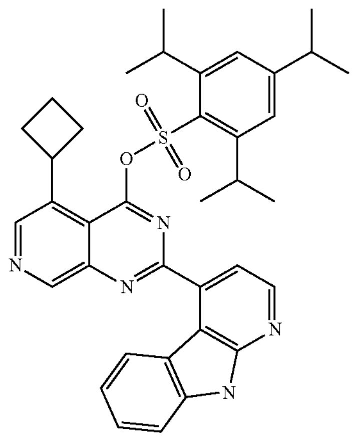 [SMILES: CC(C)c1cc(C(C)C)c(S(=O)(=O)Oc2nc(-c3ccnc4[nH]c5ccccc5c34)nc3cncc(C4CCC4)c23)c(C(C)C)c1] | [D3] | 634.28 (M + H)+ | (400 MHz, d6-DMSO, δ): 12.12 (s, 1H), 9.48 (s, 1H), 8.95 (s, 1H), 8.60 (d, J = 8.3 Hz, 1H), 8.38 (d, J = 5.1 Hz, 1H), 7.55-7.46 (m, 2H), 7.41 (s, 2H), 7.17-7.12 (m, 1H), 6.82 (d, J = 5.2 Hz, 1H), 4.42-4.33 (m, 1H), 4.11-4.03 (m, 2H), 3.06-2.98 (m, 1H), 2.63-2.55 (m, 2H), 2.50-2.40 (m, 2H), 2.10-1.88 (m, 2H). | 2,4,6-Triisopropyl-benzenesulfonic acid 5-cyclobutyl-2-(9H-pyrido[2,3-b]indol-4-yl)-pyrido[3,4-d]pyrimidin-4-yl ester |
| 205 | 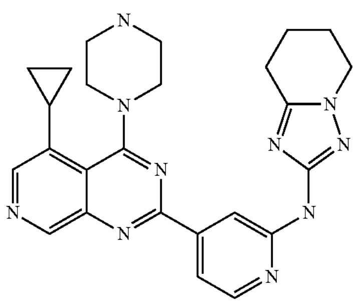 [SMILES: c1cc(-c2nc(N3CCNCC3)c3c(C4CC4)cncc3n2)cc(Nc2nc3n(n2)CCCC3)n1] | [B4] | 469.20 (M + H)+ | (400 MHz, d6-DMSO, δ): 11.07 (brs, 1H), 9.10 (s, 1H), 8.99 (brs, 2H), 8.78 (s, 1H), 8.93 (d, J = 5.5 Hz, 1H), 8.22 (s, 1H), 7.95 (dd, J = 6.0, 1.3 Hz, 1H), 4.11 (t, J = 5.8 Hz, 2H), 3.95 (brs, 4H), 3.34 (br s, 4H), 2.87 (t, J = 6.2 Hz, 2H), 2.72-2.64 (m, 1H), 2.09-1.89 (m, 4H), 1.30-1.24 (m, 2H), 1.12-1.06 (m, 2H). | [4-(5-Cyclopropyl-4-piperazin-1-yl-pyrido[3,4-d]pyrimidin-2-yl)-pyridin-2-yl]-(5,6,7,8-tetrahydro-[1,2,4]triazolo[1,5-a]pyridin-2-yl)-amine |
| 206 | 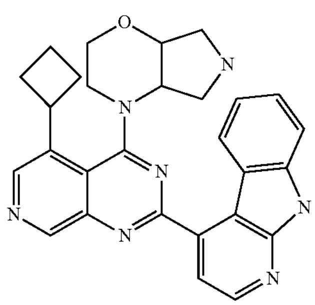 [SMILES: c1ccc2c(c1)[nH]c1nccc(-c3nc(N4CCOC5CNCC54)c4c(C5CCC5)cncc4n3)c12] | [D3] | 478 (M + H)+ | 1H NMR(400 MHz, METHANOL-d4) δ ppm 9.28 (1 H, br. s.) 8.95(1 H, br. s.) 8.51 (1 H, d, J = 7.5 Hz) 7.94 (1 H, d, J = 5.5 Hz) 7.43 -7.69(1 H, m) 7.22 (1 H, t, J = 7.4 Hz) 4.98 (1 H, d, J = 7.8 Hz) 4.06-4.69 (5 H, m) 3.40-3.96 (3 H, m) 2.11 -2.69 (5 H, m) 1.97-2.10 (2 H, m) | 4-[5-Cyclobutyl-4-(hexahydro-pyrrolo[3,4-b][1,4]oxazin-4-yl)-pyrido[3,4-d]pyrimidin-2-yl]-9H-pyrido[2,3-b]indole |
| 207 | 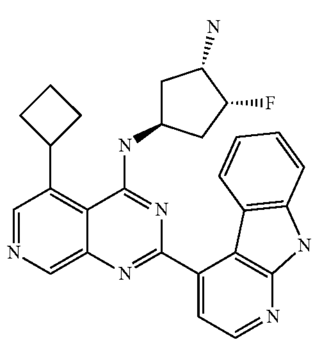 [SMILES: N[C@H]1C[C@H](Nc2nc(-c3ccnc4[nH]c5ccccc5c34)nc3cncc(C4CCC4)c23)C[C@H]1F] | [D3] | 468 (M + H)+ | 1H NMR (400 MHz, METHANOL-d4) δ ppm 9.13 (1 H, s) 8.44-8.64 (2 H, m) 8.34(1 H, d, J = 8.0Hz) 7.82(1 H, d, J = 5.3 Hz) 7.46-7.66 (2 H, m)7.21 (1H, ddd, J = 8.2, 7.2, 1.0 Hz) 5.06- 5.35 (2 H, m) 4.38(1 H, quin, J = 8.4 Hz) 3.96-4.13(1 H, m) 1.92-2.79(11 H, m) | (±)-(1S,3S,4S)-N*1*-[5-Cyclobutyl-2-(9H-pyrido[2,3-b]indol-4-yl)-pyrido[3,4-d]pyrimidin-4-yl]-4-fluoro-cyclopentane-1,3-diamine |

TABLE A-continued

| Ex | Structure | Scheme | LCMS | 1H-NMR | Name |
|---|---|---|---|---|---|
| 208 | 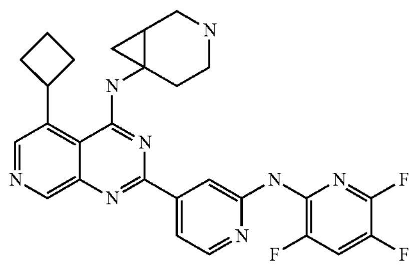 [SMILES: Fc1cc(F)c(Nc2cc(-c3nc(NC45CCNCC4C5)c4c(C5CCC5)cncc4n3)ccn2)nc1F] | [B4] | 519 (M + H)+ | 1H NMR (400 MHz, METHANOL-d4) δ ppm 9.15 (s, 1 H)8.86(d, J = 0.75 Hz, 1 H) 8.47-8.58 (m, 2 H) 8.30 (dd, J = 6.02, 1.51 Hz, 1 H) 8.00-8.19 (m, 1 H)4.29-4.47 (m, 1 H) 3.77-3.96 (m, 1 H) 3.37-3.45 (m, 1 H) 3.23 - 3.33 (m, 1 H) 2.96-3.11 (m, 1 H) 2.77- 2.91 (m, 1H) 2.69 (s, 2 H) 2.17-2.47 (m, 4 H) 1.97 (s, 1 H) 1.81-1.89 (m, 1 H) 1.45-1.55 (m, 1 H) 1.30-1.42 (m, 1 H) | (3-Aza-bicyclo[4.1.0]hept-6-yl)-{5-cyclobutyl-2-[2-(3,5,6-trifluoro-pyridin-2-ylamino)-pyridin-4-yl]-pyrido[3,4-d]pyrimidin-4-yl}-amine |
| 209 | 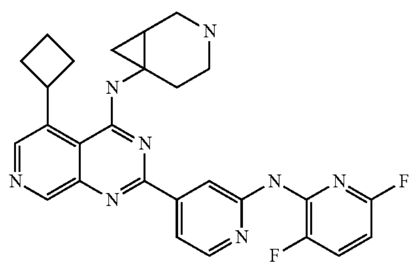 [SMILES: Fc1ccc(F)c(Nc2cc(-c3nc(NC45CCNCC4C5)c4c(C5CCC5)cncc4n3)ccn2)n1] | [B4] | 501 (M + H)+ | 1H NMR (400 MHz, METHANOL-d4) δ ppm 9.08-9.17(m, 1 H)8.92 (d, J = 0.75 Hz, 1 H) 8.49-8.64 (m, 2 H) 8.32 (dd, J = 6.27, 1.51 Hz, 1 H) 7.93 (td, J = 9.16, 6.02 Hz, 1 H) 6.88 (dt, J = 8.60, 2.48 Hz, 1 H) 4.31-4.45 (m, 1 H) 3.88-3.98 (m, 1 H) 3.38-3.44 (m, 1 H) 3.30 (d, J = 7.03 Hz, 1 H) 3.00-3.12 (m, 1 H) 2.79-2.91 (m, 1 H)2.69(s, 2 H) 2.16-2.48 (m, 4 H) 1.97 (s, 1 H) 1.72 -1.89 (m, 1 H) 1.49 (dd, J = 10.16, 6.15 Hz, 1 H) 1.31-1.42 (m, 1 H) | (3-Aza-bicyclo[4.1.0]hept-6-yl)-{5-cyclobutyl-2-[2-(3,6-difluoro-pyridin-2-ylamino)-pyridin-4-yl]-pyrido[3,4-d]pyrimidin-4-yl}-amine |
| 210 | 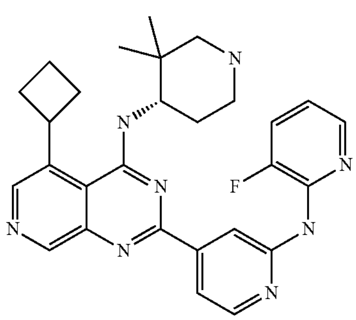 [SMILES: CC1(C)CNCC[C@@H]1Nc1nc(-c2ccnc(Nc3ncccc3F)c2)nc2cncc(C3CCC3)c12] | [B4] | 499 (M + H)+ | 1H NMR(400 MHz, METHANOL-d4) δ ppm 9.17 (s, 1 H) 8.80 (d, J = 1.00 Hz, 1 H) 8.67 (d, J = 0.75 Hz, 1 H) 8.53 (s, 1 H)8.48 (d, J = 1.76 Hz, 1 H)8.38(dd, J = 5.02, 1.25 Hz, 1 H) 7.86-7.97 (m, 1 H) 7.38 (ddd, J = 8.41, 4.89, 3.76 Hz, 1 H) 5.04 (dd, J = 11.80, 4.52 Hz, 1 H) 4.35 (quin, J = 8.22Hz, 1 H)3.52-3.61 (m, 1 H) 3.36- 3.44 (m, 2 H)3.23 (d, J = 13.05 Hz, 1 H) 2.38-2.75 (m, 4 H) 2.03-2.33 (m, 4 H) 1.41 (s, 3 H) 1.26 (s, 3 H) | {5-Cyclobutyl-2-[2-(3-fluoro-pyridin-2-ylamino)-pyridin-4-yl]-pyrido[3,4-d]pyrimidin-4-yl}-((S)-3,3-dimethyl-piperidin-4-yl)-amine |
| 211 | 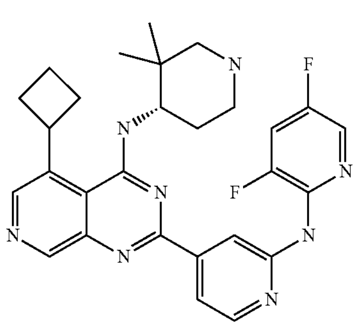 [SMILES: CC1(C)CNCC[C@@H]1Nc1nc(-c2ccnc(Nc3ncc(F)cc3F)c2)nc2cncc(C3CCC3)c12] | [B4] | 517 (M + H)+ | 1H NMR (400 MHz, METHANOL-d4) δ ppm 9.18 (s, 1 H) 8.81 (d, J = 1.00 Hz, 1 H) 8.67 (s, 1 H) 8.47 (d, J = 1.51 Hz, 2 H) 8.35 (d, J = 2.51 Hz, 1 H) 7.99 (s, 1 H) 5.04 (dd, J = 11.80, 4.27 Hz, 1 H) 4.35 (t, J = 8.16 Hz, 1 H) 3.48-3.62 (m, 1 H) 3.35-3.43 (m, 2 H) 3.24 (d, J = 13.05 Hz, 1 H) 2.36-2.76 (m, 4 H) 2.01-2.33 (m, 4 H) 1.41 (s, 3 H) 1.25 (s, 3 H) | {5-Cyclobutyl-2-[2-(3,5-difluoro-pyridin-2-ylamino)-pyridin-4-yl]-pyrido[3,4-d]pyrimidin-4-yl}-((S)-3,3-dimethyl-piperidin-4-yl)-amine |

TABLE A-continued

| Ex | Structure | Scheme | LCMS | 1H-NMR | Name |
|---|---|---|---|---|---|
| 212 | Chiral | [D4], [D3] | 442.16 (M + H)+ | 1H NMR (400 MHz, DMSO-d6) ppm 11.74 (s, 1 H), 9.07 (m, 2 H), 8.27 (d, J = 5.0 Hz, 2 H), 8.06-8.16 (m, 3 H), 7.19 (s, 1 H), 5.49-5.68 (m, 1 H), 3.05-3.24 (m, 6 H), 1.80-2.31 (m, 3 H), 1.06-1.52 (m, 7 H), 0.87-1.05 (m, 1 H) | [5-Cyclopropyl-2-(2-methyl-1H-pyrrolo[2,3-b]pyridin-4-yl)-pyrido[3,4-d]pyrimidin-4-yl]-((S)-3,3-dimethyl-piperidin-4-yl)-methyl-amine |
| 213 | 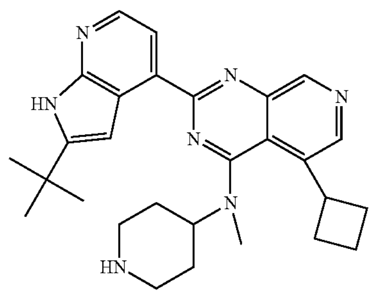 [SMILES: CN(c1nc(-c2ccnc3[nH]c(C(C)(C)C)cc23)nc2cncc(C3CCC3)c12)C1CCNCC1] | [D4], [D3] | 470 (M + H)+ | | [2-(2-tert-Butyl-1H-pyrrolo[2,3-b]pyridin-4-yl)-5-cyclobutyl-pyrido[3,4-d]pyrimidin-4-yl]-methyl-piperidin-4-yl-amine |
| 214 | 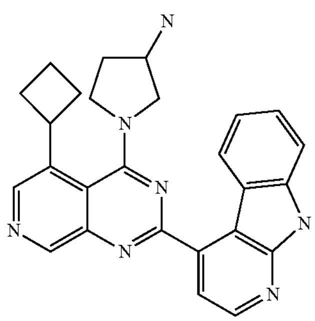 [SMILES: NC1CCN(c2nc(-c3ccnc4[nH]c5ccccc5c34)nc3cncc(C4CCC4)c23)C1] | [D3] | 436 (M + H)+ | 1H NMR(400 MHz, METHANOL-d4) δ 9.10 (s, 1H), 8.78 (s, 1H), 8.53(d, J = 5.3 Hz, 1H), 8.37 (d, J = 8.0 Hz, 1H), 7.92 (d, J = 5.3 Hz, 1H), 7.57-7.64 (m, 1H), 7.52 (td, J = 7.7, 1.0 Hz, 1H), 7.18 (td, J = 7.7, 1.0 Hz, 1H), 4.15-4.34 (m, 2H), 3.99 (br. s., 4H), 2.57-2.76 (m, 2H), 1.97-2.53 (m, 7H) | 1-[5-Cyclobutyl-2-(9H-pyrido[2,3-b]indol-4-yl)-pyrido[3,4-d]pyrimidin-4-yl]-pyrrolidin-3-ylamine |
| 215 | 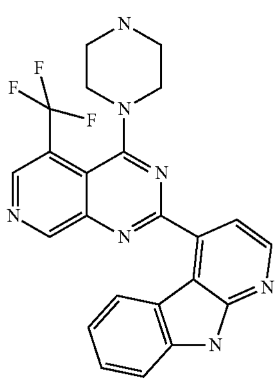 [SMILES: FC(F)(F)c1cncc2nc(-c3ccnc4[nH]c5ccccc5c34)nc(N3CCNCC3)c12] | [D20] | 450 (M + H)+ | 1H NMR (400 MHz, METHANOL-d4) δ 9.67 (s, 1H), 9.10 (s, 1H), 8.49-8.63 (m, 2H), 7.94 (d, J = 5.3 Hz, 1H), 7.47-7.63 (m, 2H), 7.22 (ddd, J = 8.2, 7.0, 1.1 Hz, 1H), 3.93 (br. s., 4H), 3.37(t, J = 5.3 Hz, 4H) | 4-(4-Piperazin-1-yl-5-trifluoromethyl-pyrido[3,4-d]pyrimidin-2-yl)-9H-pyrido[2,3-b]indole |

TABLE A-continued

| Ex | Structure | Scheme | Analysis | | Name |
|---|---|---|---|---|---|
| | | | LCMS | 1H-NMR | |
| 216 | Chiral | [D20] | 476 (M + H)+ | 1H NMR (400 MHz, METHANOL-d4) δ 9.48 (s, 1H), 9.01 (s, 1H), 8.52 (d, J = 5.3 Hz, 1H), 8.38 (d, J = 8.3 Hz, 1H), 7.87 (d, J = 5.0 Hz, 1H), 7.45-7.62 (m, 2H), 7.19 (ddd, J = 8.2, 7.1, 1.0 Hz, 1H), 5.28 (td, J = 7.3, 3.8 Hz, 1H), 4.02-4.16 (m, 1H), 3.87 (dd, J = 13.2, 6.9 Hz, 1H), 3.61-3.75 (m, 2H), 3.43-3.59 (m, 1H), 3.06-3.24 (m, 1H), 1.97-2.13 (m, 2H) | 4-((3R,6R)-4-Hexahydro-pyrrolo[3,4-b]pyrrol-1-yl-5-trifluoromethyl-pyrido[3,4-d]pyrimidin-2-yl)-9H-pyrido[2,3-b]indole |
| 217 | Chiral | [D20] | 492 (M + H)+ | 1H NMR (400 MHz, METHANOL-d4) δ 9.56 (s, 1H), 9.10 (s, 1H), 8.53 (d, J = 5.0 Hz, 1H), 8.34 (d, J = 8.0 Hz, 1H), 7.80 (d, J = 5.3 Hz, 1H), 7.45-7.62 (m, 2H), 7.16 (ddd, J = 8.1, 7.1, 1.1 Hz, 1H), 2.92-3.07 (m, 2H), 2.28 (dd, J = 14.7, 3.1 Hz, 1H), 1.87-2.04 (m, 1H), 1.28 (s, 3H), 1.17 (s, 3H) | ((S)-3,3-Dimethyl-piperidin-4-yl)-[2-(9H-pyrido[2,3-b]indol-4-yl)-5-trifluoromethyl-pyrido[3,4-d]pyrimidin-4-yl]-amine |
| 218 | 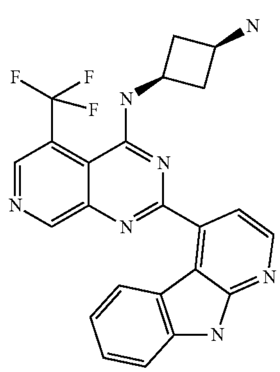 [SMILES: N[C@H]1C[C@@H](Nc2nc(-c3ccnc4[nH]c5ccccc5c34)nc3cncc(C(F)(F)F)c23)C1] | [D20] | 450 (M + H)+ | 1H NMR (400 MHz, METHANOL-d4) δ 9.52 (s, 1H), 9.07 (d, J = 0.8 Hz, 1H), 8.52 (d, J = 5.3 Hz, 1H), 8.37-8.46 (m, 1H), 7.85 (d, J = 5.3 Hz, 1H), 7.47-7.63 (m, 2H), 7.19 (ddd, J = 8.2, 7.0, 1.1 Hz, 1H), 4.75 (quin, J = 8.1 Hz, 1H), 3.43-3.68 (m, 1H), 2.92-3.05 (m, 2H), 2.18-2.30 (m, 2H) | cis-N-[2-(9H-Pyrido[2,3-b]indol-4-yl)-5-trifluoromethyl-pyrido[3,4-d]pyrimidin-4-yl]-cyclobutane-1,3-diamine |

TABLE A-continued

| Ex | Structure | Scheme | Analysis LCMS | 1H-NMR | Name |
|---|---|---|---|---|---|
| 219 | 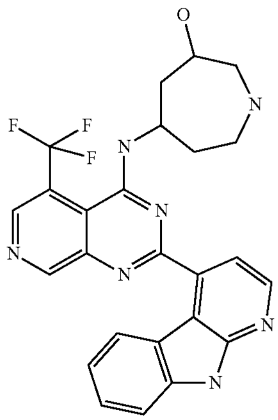 [SMILES: OC1CNCCC(Nc2nc(-c3ccnc4[nH]c5ccccc5c34)nc3cncc(C(F)(F)F)c23)C1] | [D20] | 494 (M + H)+ | 1H NMR (400 MHz, METHANOL-d4) δ 9.48-9.55 (m, 1H), 8.99-9.09 (m, 1H), 8.49-8.55 (m, 1H), 8.38 (d, J = 8.0 Hz, 1H), 7.82 (d, J = 5.3 Hz, 1H), 7.45-7.64 (m, 2H), 7.19 (ddd, J = 8.2, 7.1, 1.0 Hz, 1H), 5.11-5.26 (m, 1H), 4.45 (t, J = 5.9 Hz, 1H), 3.34-3.56 (m, 2H), 3.04-3.26 (m, 2H), 2.30-2.53 (m, 3H) | 5-[2-(9H-Pyrido[2,3-b]indol-4-yl)-5-trifluoromethyl-pyrido[3,4-d]pyrimidin-4-ylamino]-azepan-3-ol |
| 220 | 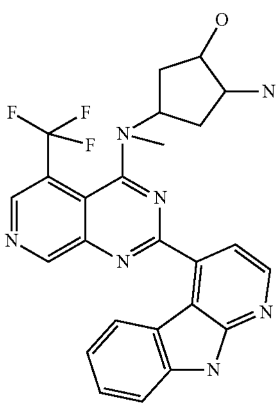 [SMILES: CN(c1nc(-c2ccnc3[nH]c4ccccc4c23)nc2cncc(C(F)(F)F)c12)C1CC(N)C(O)C1] | [D20] | 494 (M + H)+ | 1H NMR (400 MHz, METHANOL-d4) δ 9.47-9.54 (m, 1H), 8.99 (s, 1H), 8.48-8.56 (m, 1H), 7.79 (d, J = 5.3 Hz, 1H), 7.54-7.62 (m, 1H), 7.45-7.54 (m, 1H), 7.13-7.24 (m, 1H), 3.98-4.27 (m, 1H), 3.03-3.18 (m, 4H), 2.19 (d, J = 6.5 Hz, 2H) | 2-Amino-4-{methyl-[2-(9H-pyrido[2,3-b]indol-4-yl)-5-trifluoromethyl-pyrido[3,4-d]pyrimidin-4-yl]-amino}-cyclopentanol |
| 221 | 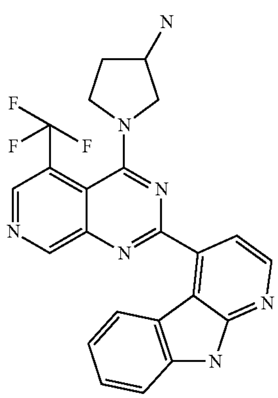 [SMILES: NC1CCN(c2nc(-c3ccnc4[nH]c5ccccc5c34)nc3cncc(C(F)(F)F)c23)C1] | [D20] | 450 (M + H)+ | 1H NMR (400 MHz, METHANOL-d4) δ 9.47 (s, 1H), 9.00 (s, 1H), 8.49-8.56 (m, 2H), 7.99 (d, J = 5.5 Hz, 1H), 7.57-7.61 (m, 1H), 7.51 (ddd, J = 8.2, 7.1, 1.3 Hz, 1H), 7.20 (ddd, J = 8.2, 7.2, 1.3 Hz, 1H), 4.24 (dd, J = 12.5, 6.5 Hz, 1H), 3.88-4.05 (m, 4H), 2.43 (dd, J = 13.3, 6.5 Hz, 1H), 2.06 (dd, J = 13.2, 6.4 Hz, 1H) | 1-[2-(9H-Pyrido[2,3-b]indol-4-yl)-5-trifluoromethyl-pyrido[3,4-d]pyrimidin-4-yl]-pyrrolidin-3-ylamine |
| 222 | 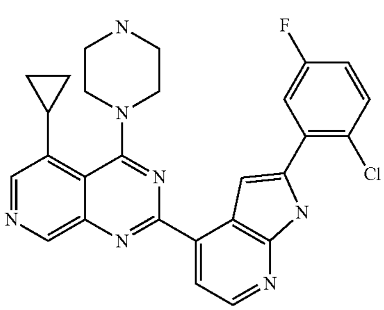 [SMILES: Fc1ccc(Cl)c(-c2cc3c(-c4nc(N5CCNCC5)c5c(C6CC6)cncc5n4)ccnc3[nH]2)c1] | [D4], [D3] | 500.13 (M + H)+ | 1H NMR (400 MHz, DMSO-d6) δ 12.37 (d, 1H, J = 1.8 Hz), 9.14 (s, 1H), 8.89 (br s, 2H), 8.50 (d, 1H, j = 5.0 Hz), 8.20 (m, 2H), 8.06 (d, 1H, J = 2.2 Hz), 7.73 (m, 2H), 7.35 (m, 1H), 4.13-3.96 (m, 4H), 3.37 (m, 4H), 2.79-2.73 (m, 1H), 1.29-1.25 (m, 2H), 1.12-1.08 (m, 2H) | 2-[2-(2-Chloro-5-fluoro-phenyl)-1H-pyrrolo[2,3-b]pyridin-4-yl]-5-cyclopropyl-4-piperazin-1-yl-pyrido[3,4-d]pyrimidine |

TABLE A-continued

| Ex | Structure | Scheme | LCMS | 1H-NMR | Name |
|---|---|---|---|---|---|
| 223 | 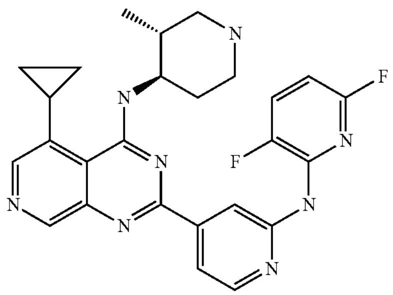 [SMILES: C[C@@H]1CNCC[C@H]1Nc1nc(-c2ccnc(Nc3nc(F)ccc3F)c2)nc2cncc(C3CC3)c12] | [B4] | 489 (M + H)+ | 1H NMR (400 MHz, METHANOL-d4) δ ppm 9.11 (s, 1 H) 8.94 (d, J = 0.75 Hz, 1 H) 8.55 (s, 1 H) 8.50 (d, J = 6.53 Hz, 1 H) 8.38 (dd, J = 6.40, 1.63 Hz, 1 H) 7.93 (td, J = 9.10, 5.90 Hz, 1H) 6.88 (dt, J = 8.60, 2.48 Hz, 1 H) 4.70 (td, J = 11.17, 4.27 Hz, 1 H) 3.50-3.64 (m, 2 H) 3.34 (d, J = 3.01 Hz, 1 H) 3.01 (t, J = 12.67 Hz, 1 H) 2.49-2.60 (m, 2 H) 2.14-2.29 (m, 1 H) 1.84-2.01 (m, 1 H) 1.31-1.40 (m, 2 H) 1.14-1.23 (m, 5 H) | (±)-{5-Cyclopropyl-2-[2-(3,6-difluoro-pyridin-2-ylamino)-pyridin-4-yl]-pyrido[3,4-d]pyrimidin-4-yl}-((3,4-trans)-3-methyl-piperidin-4-yl)-amine |
| 224 | 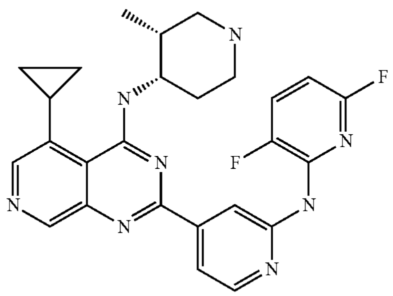 [SMILES: C[C@@H]1CNCC[C@@H]1Nc1nc(-c2ccnc(Nc3nc(F)ccc3F)c2)nc2cncc(C3CC3)c12] | [B4] | 489 (M + H)+ | 1H NMR (400 MHz, METHANOL-d4) δ ppm 9.13 (d, J = 0.75 Hz, 1 H) 9.11 (s, 1 H) 8.54 (d, J = 1.00 Hz, 1 H) 8.47 (dd, J = 6.02, 0.75 Hz, 1 H) 8.27 (dd, J = 5.77, 1.51 Hz, 1 H) 7.80-7.91 (m, 1 H) 6.72-6.81 (m, 1 H) 5.07 (s, 1 H) 3.41-3.51 (m, 1 H) 3.36 (t, J = 5.90 Hz, 2H) 3.21 (dd, J = 13.05, 7.78 Hz, 1H) 2.73-2.84 (m, 1 H) 2.53-2.64 (m, 1 H) 2.33-2.45 (m, 1 H) 2.18-2.31 (m, 1 H) 1.33-1.42 (m, 2 H) 1.20-1.26 (m, 5 H) | (±)-{5-Cyclopropyl-2-[2-(3,6-difluoro-pyridin-2-ylamino)-pyridin-4-yl]-pyrido[3,4-d]pyrimidin-4-yl}-((3,4-cis)-3-methyl-piperidin-4-yl)-amine |
| 225 | 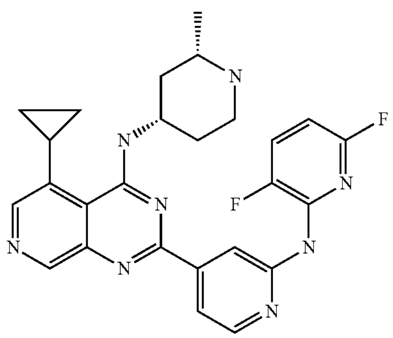 [SMILES: C[C@H]1C[C@@H](Nc2nc(-c3ccnc(Nc4nc(F)ccc4F)c3)nc3cncc(C4CC4)c23)CCN1] | [B4] | 489 (M + H)+ | 1H NMR (400 MHz, METHANOL-d4) δ ppm 9.11 (d, J = 0.75 Hz, 1 H) 8.95 (d, J = 0.75 Hz, 1 H) 8.54 (d, J = 1.25 Hz, 1 H) 8.49 (d, J = 6.27 Hz, 1 H) 8.34 (dd, J = 6.15, 1.63 Hz, 1 H) 7.90 (td, J = 9.03, 6.02 Hz, 1 H) 6.85 (dt, J = 8.66, 2.45 Hz, 1 H) 4.75-4.83 (m, 1 H) 3.45-3.66 (m, 2 H) 2.48-2.68 (m, 4H) 1.65-1.90 (m, 2 H) 1.44 (d, J = 6.53 Hz, 3H) 1.31-1.38 (m, 2 H) 1.06-1.19 (m, 2 H) | (±)-{5-Cyclopropyl-2-[2-(3,6-difluoro-pyridin-2-ylamino)-pyridin-4-yl]-pyrido[3,4-d]pyrimidin-4-yl}-((2,4-cis)-2-methyl-piperidin-4-yl)-amine |
| 226 | 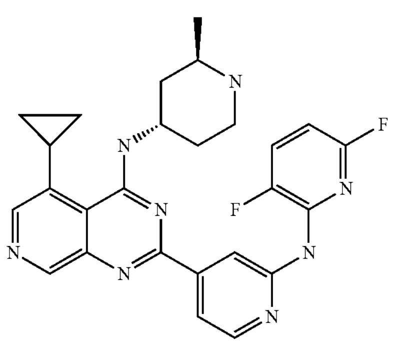 [SMILES: C[C@@H]1C[C@@H](Nc2nc(-c3ccnc(Nc4nc(F)ccc4F)c3)nc3cncc(C4CC4)c23)CCN1] | [B4] | 489 (M + H)+ | 1H NMR (400 MHz, METHANOL-d4) δ ppm 9.14 (s, 1 H) 8.97 (d, J = 1.51 Hz, 1 H) 8.56 (d, J = 1.00 Hz, 1 H) 8.48-8.53 (m, 1 H) 8.36 (dd, J = 6.27, 1.51 Hz, 1 H) 7.93 (td, J = 9.16, 6.02 Hz, 1H) 6.89 (dt, J = 8.78, 2.51 Hz, 1 H) 4.91-4.97 (m, 1 H) 3.62 (ddd, J = 10.42, 6.78, 3.39 Hz, 1 H) 3.50 (dt, J = 13.43, 4.20 Hz, 1 H) 3.32-3.40 (m, 1 H) 2.61-2.71 (m, 1 H) 2.38-2.54 (m, 2 H) 2.25-2.37 (m, 1 H) 2.12 (ddd, J = 14.87, 10.98, 3.76 Hz, 1 H) 1.44 (d, J = 6.53 Hz, 3 H) 1.34 (dt, J = 7.84, 3.73 Hz, 2 H) 1.15-1.25 (m, 2 H) | (±)-{5-Cyclopropyl-2-[2-(3,6-difluoro-pyridin-2-ylamino)-pyridin-4-yl]-pyrido[3,4-d]pyrimidin-4-yl}-((2,4-trans)-2-methyl-piperidin-4-yl)-amine |

TABLE A-continued

| Ex | Structure | Scheme | Analysis | | Name |
| --- | --- | --- | --- | --- | --- |
| | | | LCMS | 1H-NMR | |
| 227 | Chiral | [D4], [D3] | 482.13 (M + H)+ | 1H NMR (400 MHz, DMSO-d6) ppm 13.14 (br. s., 1 H), 9.21 (s, 1 H), 9.10 (d, J = 11.0 Hz, 1 H), 8.64 (d, J = 4.8 Hz, 1 H), 8.52 (s, 1 H), 8.38 (d, J = 10.0 Hz, 1 H), 8.32 (d, J = 5.0 Hz, 1 H), 7.99 (s, 1 H), 7.64 (d, J = 8.8 Hz, 1 H), 4.78-4.94 (m, 1 H), 3.34-3.43 (m, 1 H), 3.06-3.29 (m, 3 H), 2.55-2.71 (m, 1 H), 2.09-2.22 (m, 1 H), 1.88-2.05 (m, 1 H), 1.24-1.32 (m, 1 H), 1.21 (s, 3 H), 1.13-1.20 (m, 2 H), 1.12 (s, 3 H) | [5-Cyclopropyl-2-(2-trifluoromethyl-1H-pyrrolo[2,3-b]pyridin-4-yl)-pyrido[3,4-d]pyrimidin-4-yl]-((S)-3,3-dimethyl-piperidin-4-yl)-amine |
| 228 | Chiral | [D4], [D3] | 496.18 (M + H)+ | 1H NMR (400 MHz, DMSO-d6) ppm 10.38 (s, 1 H), 9.46 (br. s., 1 H), 9.20 (br. s., 1 H), 9.09 (s, 1 H), 8.67 (s, 1 H), 8.46 (d, J = 5.5 Hz, 1 H), 8.21 (s, 1 H), 7.95 (dd, J = 5.4, 1.4 Hz, 1 H), 7.90 (q, J = 8.0 Hz, 1 H), 7.76 (dd, J = 8.0, 2.0 Hz, 1 H), 6.66 (dd, J = 7.8, 2.3 Hz, 1 H), 4.48 (br. s., 1 H), 3.71-4.12 (m, 4 H), 3.47 (br. s., 2 H), 3.32-3.44 (m, 2 H), 2.60-2.74 (m, 1 H), 1.29 (br. s., 2 H), 1.09 (br. s., 2 H) | [5-Cyclobutyl-2-(2-trifluoromethyl-1H-pyrrolo[2,3-b]pyridin-4-yl)-pyrido[3,4-d]pyrimidin-4-yl]-((S)-3,3-dimethyl-piperidin-4-yl)-amine |
| 229 | 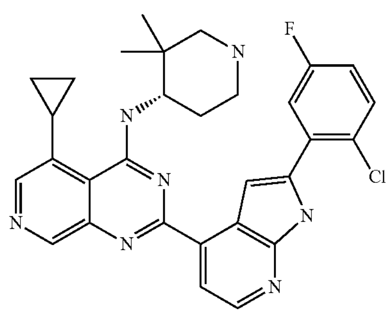 [SMILES: CC1(C)CNCC[C@@H]1Nc1nc(-c2ccnc3[nH]c(-c4cc(F)ccc4Cl)cc23)nc2cncc(C3CC3)c12] | [D4], [D3] | 542.18 (M + H)+ | 1H NMR (400 MHz, DMSO-d6) δ 12.30 (d, 1H, J = 1.8 Hz), 9.14 (s, 1H), 9.04 (m, 1H), 8.49 (m, 2H), 8.32 (m, 1H), 8.22 (d, 1H, J = 5.0 Hz), 8.05 (d, 1H, J = 2.2 Hz), 7.76-7.70 (m, 2H), 7.60 (d, 1H, J = 8.8 Hz), 7.38-7.33 (m, 1H), 4.87 (m, 1H), 3.35 (m, 1H), 3.22-3.07 (m, 3H), 2.62 (m, 1H), 2.18 (m, 1H), 2.02-1.91 (m, 1H), 1.30-1.24 (m, 1H), 1.20-1.12 (m, 9H) | {2-[2-(2-Chloro-5-fluoro-phenyl)-1H-pyrrolo[2,3-b]pyridin-4-yl]-5-cyclopropyl-pyrido[3,4-d]pyrimidin-4-yl}-((S)-3,3-dimethyl-piperidin-4-yl)-amine |
| 230 | 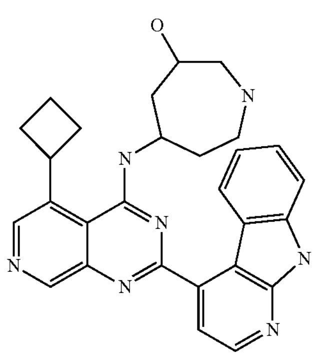 [SMILES: OC1CNCCC(Nc2nc(-c3ccnc4[nH]c5ccccc5c34)nc3cncc(C4CCC4)c23)C1] | [D3] | 480 (M + H)+ | 1H NMR (400 MHz, METHANOL-d4) δ 9.10 (br. s., 1H), 8.61 (br. s., 1H), 8.50-8.55 (m, 1H), 8.34 (d, J = 8.0 Hz, 1H), 7.78-7.88 (m, 1H), 7.59-7.66 (m, 1H), 7.51-7.58 (m, 1H), 7.22 (t, J = 7.7 Hz, 1H), 5.09 (br. s., 1H), 4.55 (t, J = 4.9 Hz, 1H), 4.23-4.42 (m, 1H), 3.34-3.50 (m, 2H), 3.14 (dt, J = 8.1, 5.7 Hz, 1H), 2.42-2.86 (m, 5H), 2.15-2.41 (m, 4H), 1.91-2.07 (m, 1H) | Cis- or trans- (±)-5-[5-Cyclobutyl-2-(9H-pyrido[2,3-b]indol-4-yl)-pyrido[3,4-d]pyrimidin-4-ylamino]-azepan-3-ol |

| Ex | Structure | Scheme | LCMS | 1H-NMR | Name |
|---|---|---|---|---|---|
| 231 | 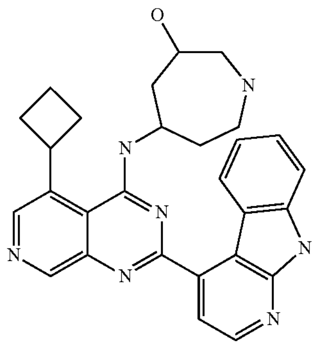 | [D3] | 480 (M + H)+ | 1H NMR (400 MHz, METHANOL-d4) δ 9.10 (s, 1H), 8.45-8.61 (m, 2H), 8.29 (d, J = 7.8 Hz, 1H), 7.79 (d, J = 5.3 Hz, 1H), 7.43-7.63 (m, 2H), 7.16 (td, J = 7.7, 1.0 Hz, 1H), 4.45 (quin, J = 8.5 Hz, 1H), 4.25-4.34 (m, 1H), 3.08-3.25 (m, 2H), 2.69 (td, J = 7.3, 3.9 Hz, 2H), 1.93-2.54 (m, 9H) | Trans- or cis- (±)-5-[5-Cyclobutyl-2-(9H-pyrido[2,3-b]indol-4-yl)-pyrido[3,4-d]pyrimidin-4-ylamino]-azepan-3-ol |
| 232 | 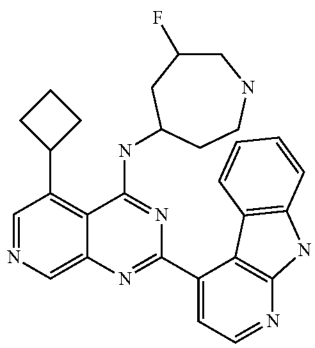 | [D3] | 482 (M + H)+ | 1H NMR(400 MHz, METHANOL-d4) δ 9.12 (s, 1H), 8.46-8.64 (m, 2H), 8.31 (dd, J = 17.4, 8.2 Hz, 1H), 7.73-7.88 (m, 1H), 7.46-7.63 (m, 2H), 7.18 (t, J = 7.5 Hz, 1H), 5.13-5.43 (m, 1H), 4.90-5.02 (m, 1H), 4.34-4.55 (m, 1H), 3.59-3.80 (m, 1H), 3.37-3.50 (m, 2H), 3.03-3.24 (m, 1H), 1.94-2.88 (m, 11H) | [5-Cyclobutyl-2-(9H-pyrido[2,3-b]indol-4-yl)-pyrido[3,4-d]pyrimidin-4-yl]-(6-fluoro-azepan-4-yl)-amine |
| 233 | 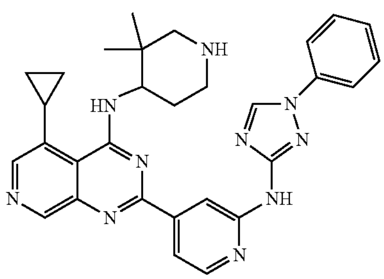 [SMILES: CC1(C)CNCCC1Nc1nc(-c2ccnc(Nc3ncn(-c4ccccc4)n3)c2)nc2cncc(C3CC3)c12] | [B4] | 533.25 (MH)+ | (400 MHz, d6-DMSO, δ): 10.61 (br s, 1H), 9.25 (s, 1H), 9.09 (s, 1H), 9.00-8.92 (m, 2H), 8.53 (s, 1H), 8.43 (d, J = 5.7 Hz, 1H), 8.30-8.16 (m, 1H), 7.99-7.94 (m, 3H), 7.66-7.58 (m, 3H), 7.46-7.41 (m, 1H), 4.85-4.78 (m, 1H), 3.35-3.28 (m, 1H), 3.22-2.99 (m, 3H), 2.64-2.57 (m, 1H), 2.17-2.10 (m, 1H), 1.98-1.86 (m, 1H), 1.30-1.08 (m, 10H). | rac-{5-Cyclopropyl-2-[2-(1-phenyl-1H-1,2,4-triazol-3-ylamino)-pyridin-4-yl]-pyrido[3,4-d]pyrimidin-4-yl}-(3,3-dimethyl-piperidin-4-yl)-amine |
| 234 | 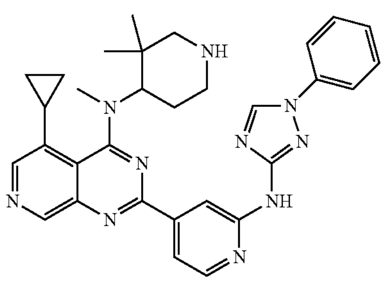 [SMILES: CN(c1nc(-c2ccnc(Nc3ncn(-c4ccccc4)n3)c2)nc2cncc(C3CC3)c12)C1CCNCC1(C)C] | [B4] | 547.28 (MH)+ | (400 MHz, d6-DMSO, δ): 10.61 (br s, 1H), 9.24 (s, 1H), 9.05-8.90 (m, 3H), 8.43 (d, J = 5.6 Hz, 1H), 8.27-8.13 (m, 2H), 7.97-7.93 (m, 3H), 7.63-7.58 (m, 2H), 7.46-7.41 (m, 1H), 5.57 (br s, 1H), 3.48-2.90 (m, 7H), 2.50-2.40 (m, 2H), 2.30-1.75 (m, 1H), 1.55-0.90 (m, 10H). | rac-{5-Cyclopropyl-2-[2-(1-phenyl-1H-1,2,4-triazol-3-ylamino)-pyridin-4-yl]-pyrido[3,4-d]pyrimidin-4-yl}-(3,3-dimethyl-piperidin-4-yl)-methyl-amine |
| 235 | 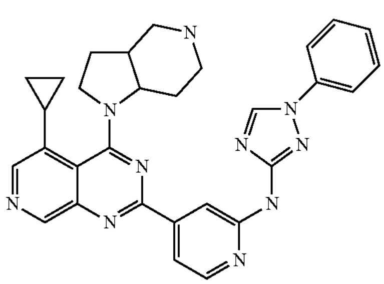 [SMILES: c1ccc(-n2cnc(Nc3cc(-c4nc(N5CCC6CNCCC65)c5c(C6CC6)cncc5n4)ccn3)n2)cc1] | [B4] | 531.26 (MH)+ | (400 MHz, d6-DMSO, ): 10.77 (br s, 1H), 9.27 (s, 1H), 9.00 (s, 1H), 8.95 (s, 1H), 8.65-8.50 (m, 2H), 8.44 (d, J = 5.6 Hz, 1H), 8.23 (s, 1H), 7.97-7.94 (m, 2H), 7.91-7.88 (m, 1H), 7.63-7.58 (m, 2H), 7.46-7.41 (m, 1H), 4.53-4.48 (m, 1H), 4.42-4.33 (m, 1H), 3.42-3.30 (m, 2H), 3.18-3.11 (m, 1H), 3.01-2.88 (m, 2H), 2.82-2.62 (m, 2H), 2.52-2.42 (m, 1H), 2.22-2.10 (m, 1H), 1.95-1.83 (m, 1H), 1.78-1.70 (m, 1H), 1.49-1.41 (m, 1H), | [4-[5-Cyclopropyl-4-(octahydro-pyrrolo[3,2-c]pyridin-1-yl)-pyrido[3,4-d]pyrimidin-2-yl]-pyridin-2-yl}-(1-phenyl-1H-1,2,4-triazol-3-yl)-amine |

TABLE A-continued

| Ex | Structure | Scheme | LCMS | 1H-NMR | Name |
|---|---|---|---|---|---|
| | | | | 1.21-1.13 (m, 1H), 1.11-1.03 (m, 1H), 0.95-0.88 (m, 1H). | |
| 236 | 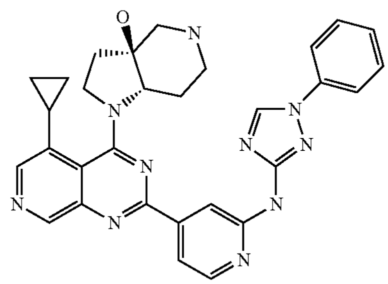 [SMILES: O[C@]12CCN(c3nc(-c4ccnc(Nc5ncn(-c6ccccc6)n5)c4)nc4cncc(C5CC5)c34)[C@H]1CCNC2] | [B4], [E2] | 547.25 (MH)+ | (400 MHz, d6-DMSO, δ): 10.68 (br s, 1H), 9.25 (s, 1H), 9.00 (s, 1H), 8.94 (s, 1H), 8.74 (br s, 1H), 8.63 (brs, 1H), 8.44 (d, J = 5.5 Hz, 1H), 8.21 (s, 1H), 7.97-7.93 (m, 2H), 7.89-7.87 (m, 1H), 7.64-7.58 (m, 2H), 7.46-7.41 (m, 1H), 5.86 (br s, 1H), 4.32-4.23 (m, 3H), 3.45-3.20 (m, 3H), 3.12-2.93 (m, 2H), 2.72-2.58 (m, 1H), 2.52-2.42 (m, 2H), 2.35-2.20 (m, 1H), 2.02-1.80 (m, 2H), 1.48-1.40 (m, 1H), 1.21-1.03 (m, 2H), 0.97-0.89 (m, 1H). | |
| 237 | 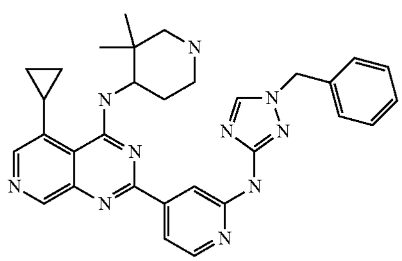 [SMILES: CC1(C)CNCCC1Nc1nc(-c2ccnc(Nc3ncn(Cc4ccccc4)n3)c2)nc2cncc(C3CC3)c12] | [B4] | 547.28 (MH)+ | (400 MHz, d6-DMSO, δ): 11.10 (br s, 1H), 9.15-9.04 (m, 2H), 8.75 (s, 1H), 8.67 (s, 1H), 8.54 (s, 1H), 8.40 (d, J = 6.0 Hz, 1H), 8.38-8.25 (m, 1H), 8.00 (d, J = 5.8 Hz, 1H), 7.67 (d, J = 8.7 Hz, 1H), 7.44-7.31 (m, 5H), 5.43 (s, 2H), 4.86-4.78 (m, 1H), 3.41-3.34 (m, 1H), 3.26-3.01 (m, 3H), 2.65-2.56 (m, 1H), 2.15-2.07 (m, 1H), 2.02-1.89 (m, 1H), 1.30-1.08 (m, 10H). | rac-{2-[2-(1-Benzyl-1H-1,2,4-triazol-3-ylamino)-pyridin-4-yl]-5-cyclopropyl-pyrido[3,4-d]pyrimidin-4-yl}-(3,3-dimethyl-piperidin-4-yl)-amine |
| 238 | 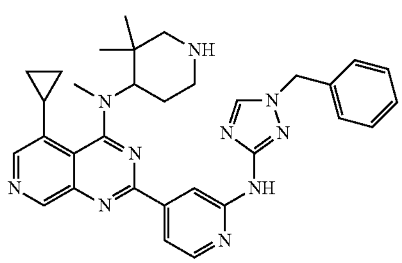 [SMILES: CN(c1nc(-c2ccnc(Nc3ncn(Cc4ccccc4)n3)c2)nc2cncc(C3CC3)c12)C1CCNCC1(C)C] | [B4] | 561.31 (MH)+ | (400 MHz, d6-DMSO, δ): 10.94 (brs, 1H), 9.13 (br s, 1H), 9.00 (s, 1H), 8.80-8.55 (m, 2H), 8.39 (d, J = 5.8 Hz, 1H), 8.28 (br s, 1H), 8.16 (s, 1H), 7.97-7.92 (m, 1H), 7.42-7.31 (m, 5H), 5.59 (br s, 1H), 5.42 (s, 2H), 3.51-3.44 (m, 1H), 3.30-2.95 (m, 6H), 2.45-2.35 (m, 1H), 2.30-1.80 (m, 2H), 1.55-0.90 (m, 10H). | rac-{2-[2-(1-Benzyl-1H-1,2,4-triazol-3-ylamino)-pyridin-4-yl]-5-cyclopropyl-pyrido[3,4-d]pyrimidin-4-yl}-(3,3-dimethyl-piperidin-4-yl)-methyl-amine |
| 239 | 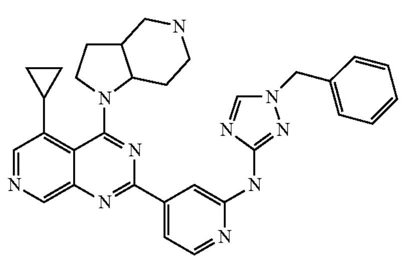 [SMILES: c1ccc(Cn2cnc(Nc3cc(-c4nc(N5CCC6CNCCC65)c5c(C6CC6)cncc5n4)ccn3)n2)cc1] | [B4] | 545.28 (MH)+ | (400 MHz, d6-DMSO, δ): 11.15 (br s, 1H), 9.00 (s, 1H), 8.77-8.63 (m, 4H), 8.40 (d, J = 5.9 Hz, 1H), 8.24 (s, 1H), 7.92 (d, J = 5.4Hz, 1H), 7.41-7.30 (m, 5H), 5.44 (s, 2H), 4.51-4.45 (m, 1H), 4.42-4.33 (m, 1H), 3.45-3.19 (m, 3H), 3.02-2.90 (m, 2H), 2.82-2.64 (m, 2H), 2.51-2.41 (m, 1H), 2.30-2.18 (m, 1H), 1.92-1.70 (m, 2H), 1.50-1.40 (m, 1H), 1.21-1.13 (m, 1H), 1.09-1.02 (m, 1H), 0.94-0.86 (m, 1H). | (1-Benzyl-1H-1,2,4-triazol-3-yl)-{4-[5-cyclopropyl-4-(octahydro-pyrrolo[3,2-c]pyridin-1-yl)-pyrido[3,4-d]pyrimidin-2-yl]-pyridin-2-yl}-amine |
| 240 | 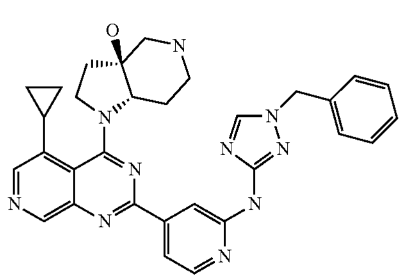 [SMILES: O[C@]12CCN(c3nc(-c4ccnc(Nc5ncn(Cc6ccccc6)n5)c4)nc4cncc(C5CC5)c34)[C@H]1CCNC2] | [B4], [E2] | 561.28 (MH)+ | (400 MHz, d6-DMSO) δ 10.96 (br s, 1H), 9.00 (s, 1H), 8.92-8.82 (m, 1H), 8.75-8.65 (m, 3H), 8.40 (d, J = 5.8 Hz, 1H), 8.22 (s, 1H), 7.89 (d, J = 5.7 Hz, 1H), 7.42-7.30 (m, 5H), 5.91 (br s, 1H), 5.43 (s, 2H), 4.34-4.24 (m, 2H), 3.42-2.95 (m, 5H), 2.74-2.60 (m, 1H), 2.51-2.41 (m, 1H), 2.40-2.28 (m, 1H), 2.03-1.95 (m, 1H), 1.92-1.82 (m, 1H), 1.49-1.40 (m, 1H), 1.21-1.12 (m, 1H), 1.10-1.03 (m, 1H), 0.95-0.87 (m, 1H). | rac-(3aS,7aS)-1-{2-[2-(1-Benzyl-1H-1,2,4-triazol-3-ylamino)-pyridin-4-yl]-5-cyclopropyl-pyrido[3,4-d]pyrimidin-4-yl}-octahydro-pyrrolo[3,2-c]pyridin-3a-ol |

TABLE A-continued

| Ex | Structure | Scheme | LCMS | 1H-NMR | Name |
|---|---|---|---|---|---|
| 241 | 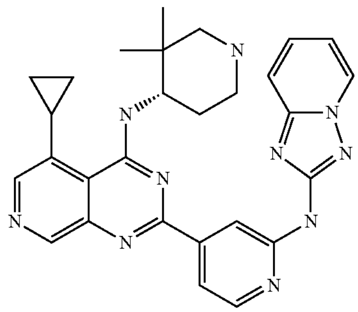 [SMILES: CC1(C)CNCC[C@@H]1Nc1nc(-c2ccnc(Nc3nc4ccccn4n3)c2)nc2cncc(C3CC3)c12] | [B4], [E4] | 507.20 (MH)+ | (400 MHz, d6-DMSO, δ): 10.95 (s, 1H), 9.16 (s, 1H), 9.07-8.98 (m, 1H), 8.94 (s, 1H), 8.92-8.89 (m, 1H), 8.54 (d, J = 0.7 Hz, 1H), 8.47 (d, J = 5.8 Hz, 1H), 8.37-8.23 (m, 1H), 8.04 (dd, J = 5.5, 1.3 Hz, 1H), 7.75-7.65 (m, 3H), 7.20-7.16 (m, 1H), 4.88-4.80 (m, 1H), 3.38-3.30 (m, 1H), 3.25-3.00 (m, 3H), 2.66-2.57 (m, 1H), 2.17-2.10 (m, 1H), 2.03-1.90 (m, 1H), 1.31-1.10 (m, 10H). | [5-Cyclopropyl-2-[2-([1,2,4]triazolo[1,5-a]pyridin-2-ylamino)-pyridin-4-yl]-pyrido[3,4-d]pyrimidin-4-yl]-((S)-3,3-dimethyl-piperidin-4-yl)-amine |
| 242 | 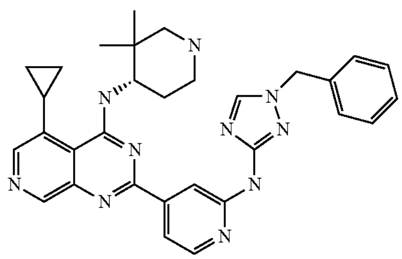 [SMILES: CC1(C)CNCC[C@@H]1Nc1nc(-c2ccnc(Nc3ncn(Cc4ccccc4)n3)c2)nc2cncc(C3CC3)c12] | [B4], [E4] | 547.28 (MH)+ | (400 MHz, d6-DMSO, δ): 11.18 (s, 1H), 9.19-9.11 (m, 1H), 9.09 (s, 1H), 8.76 (s, 1H), 8.66 (s, 1H), 8.54 (s, 1H), 8.41 (d, J = 6.0 Hz, 1H), 8.40-8.30 (m, 1H), 8.03-8.00 (m, 1H), 7.67 (d, J = 8.7 Hz, 1H), 7.43-7.31 (m, 5H), 5.43 (s, 2H), 4.86-4.78 (m, 1H), 3.42-3.34 (m, 1H), 3.26-3.01 (m, 3H), 2.65-2.56 (m, 1H), 2.15-2.06 (m, 1H), 2.02-1.90 (m, 1H), 1.30-1.08 (m, 10H). | {2-[2-(1-Benzyl-1H-1,2,4-triazol-3-ylamino)-pyridin-4-yl]-5-cyclopropyl-pyrido[3,4-d]pyrimidin-4-yl}-((S)-3,3-dimethyl-piperidin-4-yl)-amine |
| 243 | 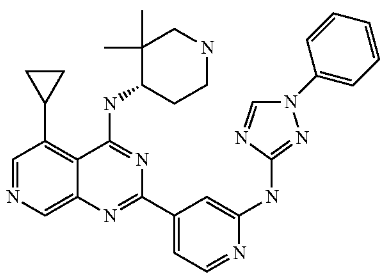 [SMILES: CC1(C)CNCC[C@@H]1Nc1nc(-c2ccnc(Nc3ncn(-c4ccccc4)n3)c2)nc2cncc(C3CC3)c12] | [B4], [E4] | 533.25 (MH)+ | (400 MHz, d6-DMSO, δ): 10.56 (br s, 1H), 9.24 (s, 1H), 9.08 (s, 1H), 9.01 -8.90 (m, 2H), 8.53 (s, 1H), 8.43 (d, J = 5.5 Hz, 1H), 8.27-8.15 (m, 1H), 7.98-7.93 (m, 3H), 7.65-7.58 (m, 3H), 7.46-7.41 (m, 1H), 4.86-4.78 (m, 1H), 3.35-3.27 (m, 1H), 3.22-2.99 (m, 3H), 2.65-2.56 (m, 1H), 2.17-2.09 (m, 1H), 1.99-1.86 (m, 1H), 1.30-1.06 (m, 10H). | {5-Cyclopropyl-2-[2-(1-phenyl-1H-1,2,4-triazol-3-ylamino)-pyridin-4-yl]-pyrido[3,4-d]pyrimidin-4-yl}-((S)-3,3-dimethyl-piperidin-4-yl)-amine |
| 244 | 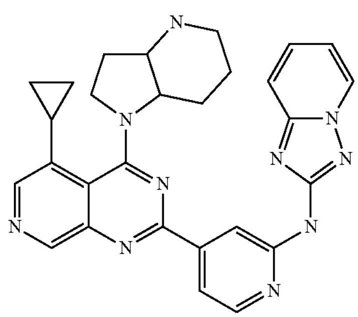 [SMILES: c1ccn2nc(Nc3cc(-c4nc(N5CCC6NCCCC65)c5c(C6CC6)cncc5n4)ccn3)nc2c1] | [B4] | 505.22 (MH)+ | (400 MHz, d6-DMSO, δ): 10.62 (br s, 1H), 9.36-9.27 (m, 1H), 9.08-9.04 (m, 2H), 8.85 (d, J = 6.7 Hz, 1H), 8.44 (d, J = 5.4 Hz, 1H), 8.32-8.19 (m, 2H), 7.92 (d, J = 5.3, 1.2 Hz, 1H), 7.72-7.64 (m, 2H), 7.18-7.13 (m, 1H), 4.70-4.65 (m, 1H), 4.61-4.52 (m, 1H), 3.45-3.30 (m, 2H), 3.09-2.98 (m, 1H), 2.83-2.75 (m, 1H), 2.50-2.40 (m, 1H), 2.20-1.95 (m, 3H), 1.85-1.65 (m, 2H), 1.54-1.45 (m, 1H), 1.26-1.06 (m, 2H), 0.96-0.89 (m, 1H). | {4-[5-Cyclopropyl-4-(octahydro-pyrrolo[3,2-b]pyridin-1-yl)-pyrido[3,4-d]pyrimidin-2-yl]-pyridin-2-yl}-[1,2,4]triazolo[1,5-a]pyridin-2-yl-amine |
| 245 | 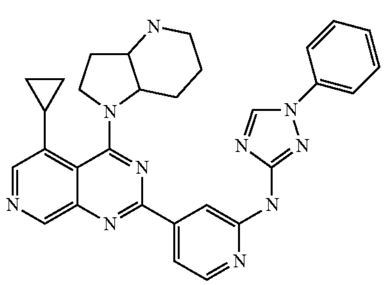 [SMILES: c1ccc(-n2cnc(Nc3cc(-c4nc(N5CCC6NCCCC65)c5c(C6CC6)cncc5n4)ccn3)n2)cc1] | [B4] | 531.25 (MH)+ | (400 MHz, d6-DMSO, δ): 10.42 (br s, 1H), 9.29-9.19 (m, 2H), 9.01-8.97 (m, 2H), 8.41 (d, J = 5.3 Hz, 1H), 8.27-8.17 (m, 2H), 7.95-7.90 (m, 1H), 7.87 (dd, J = 5.4, 1.1 Hz, 1H), 7.64-7.58 (m, 2H), 7.46-7.41 (m, 1H), 4.64-4.60 (m, 1H), 4.57-4.48 (m, 1H), 3.95-3.87 (m, 1H), 3.44-3.37 (m, 1H), 3.31-3.24 (m, 1H), 2.90-2.80 (m, 1H), 2.68-2.59 (m, 1H), 2.48-2.38 (m, 1H), 2.17-2.06 (m, 1H), 2.00-1.85 (m, 2H), 1.65-1.57 (m, 2H), 1.52-1.44 | {4-[5-Cyclopropyl-4-(octahydro-pyrrolo[3,2-b]pyridin-1-yl)-pyrido[3,4-d]pyrimidin-2-yl]-pyridin-2-yl}-(1-phenyl-1H-1,2,4-triazol-3-yl)-amine |

TABLE A-continued

| Ex | Structure | Scheme | LCMS | 1H-NMR | Name |
|---|---|---|---|---|---|
| | | | | (m, 1H), 1.25-1.05 (m, 2H), 0.96-0.88 (m, 1H). | |
| 246 | 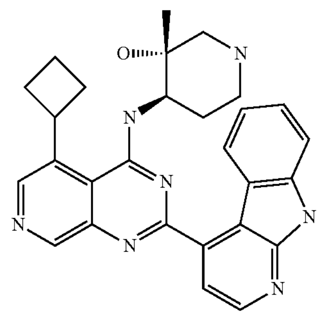 [SMILES: C[C@@]1(O)CNCC[C@H]1Nc1nc(-c2ccnc3[nH]c4ccccc4c23)nc2cncc(C3CCC3)c12] | [E3] | 480.17 (MH)+ | (400 MHz, d6-DMSO, δ): 12.05 (s, 1H), 9.16 (s, 1H), 8.75-8.50 (m, 5H), 7.87 (d, J = 5.1 Hz, 1H), 7.54 (d, J = 8.1 Hz, 1H), 7.50-7.45 (m, 1H), 7.19-7.14 (m, 1H), 6.86 (d, J = 8.3 Hz, 1H), 5.83-5.65 (m, 1H), 4.83-4.77 (m, 1H), 4.56-4.46 (m, 1H), 3.32-3.25 (m, 1H), 3.22-3.05 (m, 2H), 3.03-2.95 (m, 1H), 2.70-2.60 (m, 1H), 2.48-2.20 (m, 3H), 2.14-2.01 (m, 1H), 1.95-1.83 (m, 2H), 1.37 (s, 3H). | rac-(3R,4R)-4-[5-Cyclobutyl-2-(9H-pyrido[2,3-b]indol-4-yl)-pyrido[3,4-d]pyrimidin-4-ylamino]-3-methyl-piperidin-3-ol |
| 247 | 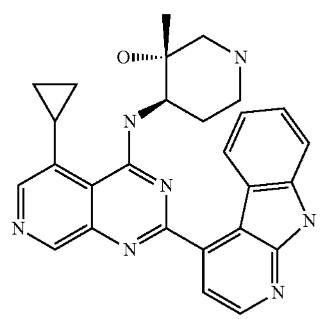 [SMILES: C[C@@]1(O)CNCC[C@H]1Nc1nc(-c2ccnc3[nH]c4ccccc4c23)nc2cncc(C3CC3)c12] | [E3] | 466.15 (MH)+ | (400 MHz, d6-DMSO, δ): 12.06 (s, 1H), 9.16 (s, 1H), 8.70-8.50 (m, 5H), 7.81 (d, J = 5.0 Hz, 1H), 7.78 (d, J = 8.4 Hz, 1H), 7.54 (d, J = 7.9 Hz, 1H), 7.50-7.45 (m, 1H), 7.18-7.13 (m, 1H), 5.85-5.70 (m, 1H), 4.87-4.81 (m, 1H), 3.19-3.00 (m, 4H), 2.79-2.70 (m, 1H), 2.45-2.35 (m, 1H), 1.98-1.89 (m, 1H), 1.36-1.18 (m, 7H). | rac-(3R,4R)-4-[5-Cyclopropyl-2-(9H-pyrido[2,3-b]indol-4-yl)-pyrido[3,4-d]pyrimidin-4-ylamino]-3-methyl-piperidin-3-ol |
| 248 | 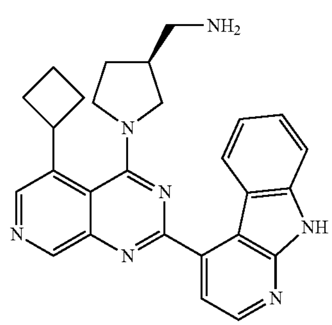 [SMILES: NC[C@@H]1CCN(c2nc(-c3ccnc4[nH]c5ccccc5c34)nc3cncc(C4CCC4)c23)C1] | [D3] | 450.3 (MH)+ | (400 MHz, d6-DMSO, δ): 12.07 (s, 1H), 9.06 (s, 1H), 8.68 (s, 1H), 8.59-8.52 (m, 2H), 7.87 (d, J = 5.1 Hz, 1H), 7.82-7.70 (m, 3H), 7.54 (d, J = 7.9 Hz, 1H), 7.50-7.45 (m, 1H), 7.18-7.13 (m, 1H), 4.23-4.13 (m, 1H), 3.90-3.50 (m, 4H), 3.00-2.85 (m, 2H), 2.65-2.55 (m, 1H), 2.28-2.05 (m, 4H), 1.95-1.85 (m, 1H), 1.80-1.65 (m, 1H). | C-{(S)-1-[5-Cyclobutyl-2-(9H-pyrido[2,3-b]indol-4-yl)-pyrido[3,4-d]pyrimidin-4-yl]-pyrrolidin-3-yl}-methylamine |
| 249 | 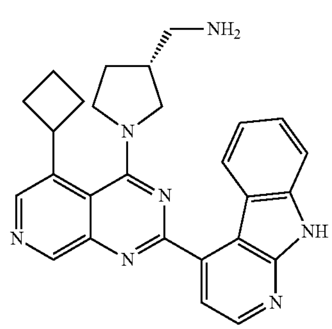 [SMILES: NC[C@H]1CCN(c2nc(-c3ccnc4[nH]c5ccccc5c34)nc3cncc(C4CCC4)c23)C1] | [D3] | 450.3 (MH)+ | (400 MHz, d6-DMSO, δ): 12.07 (s, 1H), 9.06 (s, 1H), 8.68 (s, 1H), 8.59-8.53 (m, 2H), 7.87 (d, J = 5.1 Hz, 1H), 7.82-7.70 (m, 3H), 7.54 (d, J = 8.0 Hz, 1H), 7.50-7.45 (m, 1H), 7.18-7.13 (m, 1H), 4.23-4.13 (m, 1H), 3.90-3.50 (m, 4H), 3.00-2.85 (m, 2H), 2.65-2.55 (m, 1H), 2.28-2.05 (m, 5H), 1.95-1.85 (m, 1H), 1.80-1.65 (m, 1H). | C-{(R)-1-[5-Cyclobutyl-2-(9H-pyrido[2,3-b]indol-4-yl)-pyrido[3,4-d]pyrimidin-4-yl]-pyrrolidin-3-yl}-methylamine |

TABLE A-continued

| Ex | Structure | Scheme | Analysis | | Name |
| --- | --- | --- | --- | --- | --- |
| | | | LCMS | 1H-NMR | |
| 250 | 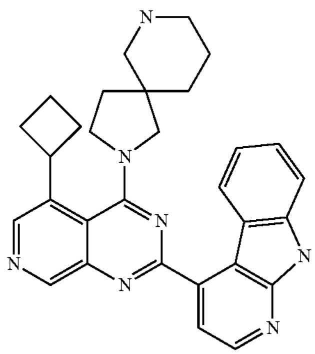 [SMILES: c1ccc2c(c1)[nH]c1nccc(-c3nc(N4CCC5(CCCNC5)C4)c4c(C5CCC5)cncc4n3)c12] | [D3] | 490.4 (MH)+ | (400 MHz, d6-DMSO, δ): 12.05 (br s, 1H), 9.07 (s, 1H), 8.69 (s, 1H), 8.62-8.55 (m, 2H), 8.49-8.26 (m, 2H), 7.89 (d, J = 5.0 Hz, 1H), 7.54 (d, J = 8.0 Hz, 1H), 7.50-7.45 (m, 1H), 7.18-7.13 (m, 1H), 4.22-4.12 (m, 1H), 3.85-3.79 (m, 2H), 3.72-3.57 (m, 2H), 3.15-2.85 (m, 4H), 2.62-2.48 (m, 3H), 2.25-2.05 (m, 3H), 2.00-1.50 (m, 6H). | 4-[5-Cyclobutyl-4-(2,7-diaza-spiro[4.5]dec-2-yl)-pyrido[3,4-d]pyrimidin-2-yl]-9H-pyrido[2,3-b]indole |
| 251 | 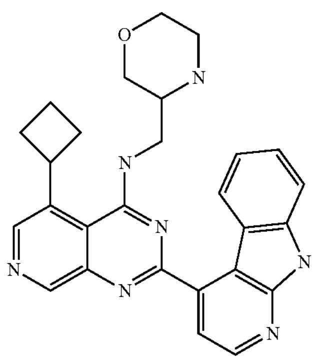 [SMILES: c1ccc2c(c1)[nH]c1nccc(-c3nc(NCC4COCCN4)c4c(C5CCC5)cncc4n3)c12] | [D3] | 466.3 (MH)+ | (400 MHz, d6-DMSO, δ): 12.05 (s, 1H), 9.16 (s, 1H), 9.07-8.96 (m, 1H), 8.86-8.75 (m, 1H), 8.63 (d, J = 8.2 Hz, 1H), 8.60-8.56 (m, 2H), 7.85 (d, J = 5.1 Hz, 1H), 7.55 (d, J = 7.9 Hz, 1H), 7.50-7.45 (m, 1H), 7.36 (t, J = 5.6 Hz, 1H), 7.19-7.14 (m, 1H), 4.51-4.41 (m, 1H), 4.00-3.94 (m, 2H), 3.87-3.57 (m, 4H), 3.34-2.27 (m, 1H), 3.10-2.98 (m, 1H), 2.64-2.53 (m, 2H), 2.40-2.28 (m, 2H), 2.19-2.07 (m, 1H), 1.93-1.83 (m, 1H). | [5-Cyclobutyl-2-(9H-pyrido[2,3-b]indol-4-yl)-pyrido[3,4-d]pyrimidin-4-yl]-morpholin-3-ylmethyl-amine |
| 252 | 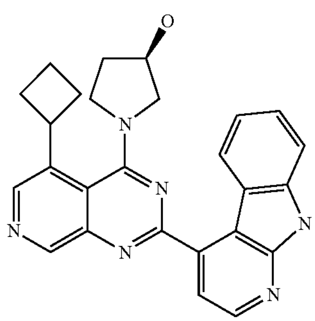 [SMILES: O[C@@H]1CCN(c2nc(-c3ccnc4[nH]c5ccccc5c34)nc3cncc(C4CCC4)c23)C1] | [D3] | 437.3 (MH)+ | (400 MHz, d6-DMSO, δ): 12.12 (s, 1H), 9.05 (s, 1H), 8.73 (s, 1H), 8.59 (d, J = 5.1 Hz, 1H), 8.48 (br s, 1H), 7.84 (d, J = 5.0 Hz, 1H), 7.55 (d, J = 8.0 Hz, 1H), 7.51-7.46 (m, 1H), 7.18-7.13 (m, 1H), 4.37-4.33 (m, 2H), 4.20-3.89 (m, 6H), 3.66-3.56 (m, 1H), 3.46-3.34 (m, 1H), 2.68-2.60 (m, 1H), 2.30-2.23 (m, 1H), 2.14-2.02 (m, 2H), 1.95-1.83 (m, 2H). | (R)-1-[5-Cyclobutyl-2-(9H-pyrido[2,3-b]indol-4-yl)-pyrido[3,4-d]pyrimidin-4-yl]-pyrrolidin-3-ol |
| 253 | 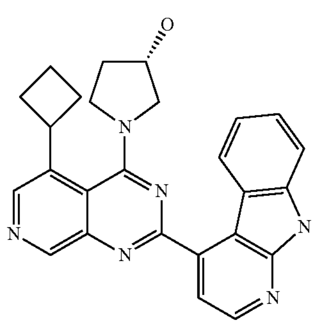 [SMILES: O[C@H]1CCN(c2nc(-c3ccnc4[nH]c5ccccc5c34)nc3cncc(C4CCC4)c23)C1] | [D3] | 437.3 (MH)+ | (400 MHz, d6-DMSO, δ): 12.12 (s, 1H), 9.05 (s, 1H), 8.73 (s, 1H), 8.59 (d, J = 5.0 Hz, 1H), 8.48 (br s, 1H), 7.84 (d, J = 5.0 Hz, 1H), 7.55 (d, J = 8.0 Hz, 1H), 7.51-7.46 (m, 1H), 7.18-7.13 (m, 1H), 4.37-4.33 (m, 1H), 4.20-3.89 (m, 6H), 3.66-3.56 (m, 1H), 3.46-3.34 (m, 1H), 2.68-2.60 (m, 1H), 2.30-2.23 (m, 1H), 2.14-2.02 (m, 2H), 1.95-1.83 (m, 2H). | (S)-1-[5-Cyclobutyl-2-(9H-pyrido[2,3-b]indol-4-yl)-pyrido[3,4-d]pyrimidin-4-yl]-pyrrolidin-3-ol |

TABLE A-continued

| Ex | Structure | Scheme | Analysis | | Name |
| --- | --- | --- | --- | --- | --- |
| | | | LCMS | 1H-NMR | |
| 254 | 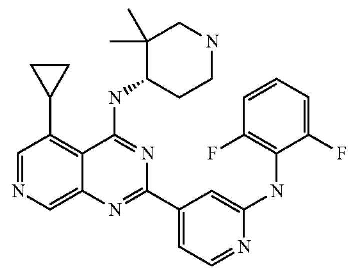 [SMILES: CC1(C)CNCC[C@@H]1Nc1nc(-c2ccnc(Nc3c(F)cccc3F)c2)nc2cncc(C3CC3)c12] | [B4], [E4] | 502.19 (M + H) | 1H NMR (400 MHz, DMSO-d6) ppm 9.06 (s, 2 H), 8.88 (br. s., 1 H), 8.50 (s, 1 H), 8.29 (d, J = 8.5 Hz, 1 H), 8.19 (d, J = 5.3 Hz, 1 H), 7.80 (s, 1 H), 7.76 (dd, J = 5.4, 1.4 Hz, 1 H), 7.61 (d, J = 8.8 Hz, 1 H), 7.26-7.37 (m, 2 H), 7.14-7.24 (m, 1 H), 4.72-4.82 (m, 1 H), 3.36 (d, J = 12.0 Hz, 1 H), 3.21 (d, J = 12.3 Hz, 1 H), 2.99-3.16 (m, 2 H), 2.54-2.64 (m, 1 H), 2.09 (d, J = 10.8 Hz, 1 H), 1.86-2.01 (m, 1 H), 1.21-1.31 (m, 1 H), 1.18 (s, 3 H), 1.11-1.17 (m, 3 H), 1.01-1.10 (m, 3 H) | {5-Cyclopropyl-2-[2-(2,6-difluoro-phenylamino)-pyridin-4-yl]-pyrido[3,4-d]pyrimidin-4-yl}-((S)-3,3-dimethyl-piperidin-4-yl)-amine |
| 255 | 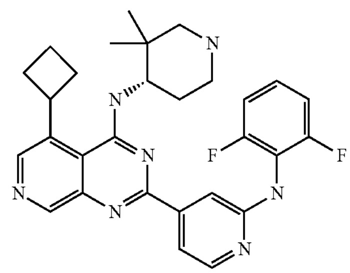 [SMILES: CC1(C)CNCC[C@@H]1Nc1nc(-c2ccnc(Nc3c(F)cccc3F)c2)nc2cncc(C3CCC3)c12] | [B4], [E4] | 516.21 (M + H) | 1H NMR (400 MHz, DMSO-d6) ppm 9.06 (s, 1 H), 9.02 (d, J = 11.8 Hz, 1 H), 8.85 (s, 1 H), 8.55 (s, 1 H), 8.28 (d, J = 10.3 Hz, 1 H), 8.19 (d, J = 5.3 Hz, 1 H), 7.77 (s, 1 H), 7.74 (dd, J = 5.3, 1.3 Hz, 1 H), 7.27-7.35 (m, 1 H), 7.19 (t, J = 7.9 Hz, 2 H), 6.54 (d, J = 8.5 Hz, 1 H), 4.70-4.79 (m, 1H), 4.41 (dt, J = 16.3, 7.9 Hz, 2 H), 3.34 (d, J = 11.8 Hz, 1 H), 3.23 (d, J = 12.8 Hz, 1 H), 2.97-3.14 (m, 2 H), 2.52-2.58 (m, 1 H), 2.46 (d, J = 3.8 Hz, 1 H), 2.19-2.41 (m, 2 H), 1.83-2.12 (m, 4 H), 1.24 (s, 3 H), 1.08 (s, 3 H) | {5-Cyclobutyl-2-[2-(2,6-difluoro-phenylamino)-pyridin-4-yl]-pyrido[3,4-d]pyrimidin-4-yl}-((S)-3,3-dimethyl-piperidin-4-yl)-amine |
| 256 | 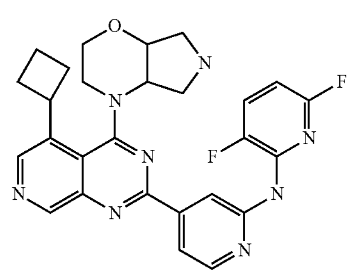 [SMILES: Fc1ccc(F)c(Nc2cc(-c3nc(N4CCOC5CNCC54)c4c(C5CCC5)cncc4n3)ccn2)n1] | [B4], [E5] | 517.17 (M + H) | 1H NMR (400 MHz, DMSO-d6) ppm 9.77 (br. s., 1 H), 9.37 (br. s., 1 H), 9.16 (s, 1 H), 9.05 (br. s., 1 H), 8.89 (s, 2 H), 8.47 (d, J = 5.8 Hz, 1 H), 7.99 (dd, J = 5.1, 1.1 Hz, 1 H), 7.88 (ddd, J = 9.7, 8.6, 6.5 Hz, 1 H), 6.64-6.82 (m, 1 H), 4.90 (br. s., 1 H), 4.59 (br. s., 1 H), 3.60-3.83 (m, 2 H), 3.25-3.54 (m, 5 H), 2.44 (d, J = 7.0 Hz, 3 H), 2.11 (dd, J = 12.7, 8.4 Hz, 2 H), 1.82-2.00 (m, 1 H) | {4-[5-Cyclobutyl-4-(hexahydro-pyrrolo[3,4-b]-1,4-oxazin-4-yl)-pyrido[3,4-d]pyrimidin-2-yl]-pyridin-2-yl}-(3,6-difluoro-pyridin-2-yl)-amine |
| 257 | 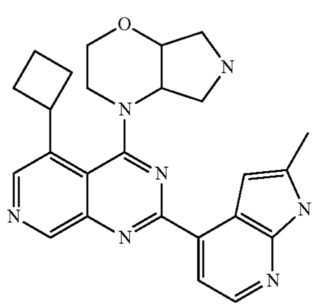 [SMILES: Cc1cc2c(-c3nc(N4CCOC5CNCC54)c4c(C5CCC5)cncc4n3)ccnc2[nH]1] | [D3], [D4], [E5] | 442.3 (M + H) | 1H NMR (400 MHz, DMSO-d6) δ ppm 11.81 (s, 1 H), 9.35 (br. s., 1 H), 9.26 (br. s., 1 H), 9.16 (br. s., 1 H), 8.86 (s, 1 H), 8.28 (d, J = 5.3 Hz, 1 H), 8.12 (d, J = 5.3 Hz, 1 H), 7.28 (s, 1 H), 4.90-5.00 (m, 1 H), 4.26-4.35 (m, 1 H), 3.99-4.15 (m, 3 H), 3.78 (br. s., 2 H), 3.50 (br. s., 1 H), 3.23-3.47 (m, 5 H), 2.45 (d, J = 7.8 Hz, 3 H), 2.02-2.19 (m, 2 H), 1.94 (br. s., 1 H) | 5-Cyclobutyl-4-(hexahydro-pyrrolo[3,4-b]-1,4-oxazin-4-yl)-2-(2-methyl-1H-pyrrolo[2,3-b]pyridin-4-yl)-pyrido[3,4-d]pyrimidine |

TABLE A-continued

| Ex | Structure | Scheme | LCMS | 1H-NMR | Name |
|---|---|---|---|---|---|
| 258 | 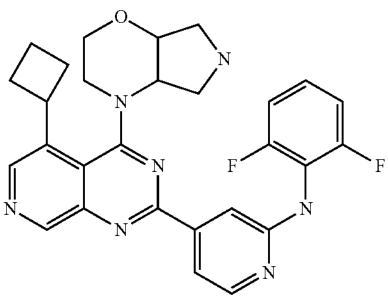 [SMILES: Fc1cccc(F)c1Nc1cc(-c2nc(N3CCOC4CNCC43)c3c(C4CCC4)cncc3n2)ccn1] | [B4], [E5] | 516.4 (M + H) | 1H NMR (400 MHz, DMSO-d6) ppm 9.34 (br. s., 1 H), 9.15 (br. s., 2 H), 8.88 (br. s., 2 H), 8.20 (d, J = 5.3 Hz, 1 H), 7.89 (s, 1 H), 7.72 (dd, J = 5.4, 1.4 Hz, 1 H), 7.24-7.34 (m, 1 H), 7.13-7.22 (m, 2 H), 4.92 (br. s., 1 H), 4.56 (br. s., 1 H), 3.82 (br. s., 2 H), 3.65 (br. s., 1 H), 3.20-3.52 (m, 6 H), 2.44 (br. s., 3 H), 2.00-2.17 (m, 2 H), 1.95 (br. s., 1 H) | {4-[5-Cyclobutyl-4-(hexahydro-pyrrolo[3,4-b]-1,4-oxazin-4-yl)-pyrido[3,4-d]pyrimidin-2-yl]-pyridin-2-yl}-(2,6-difluoro-phenyl)-amine |
| 259 | 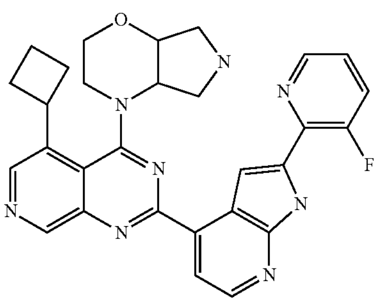 [SMILES: Fc1cccnc1-c1cc2c(-c3nc(N4CCOC5CNCC54)c4c(C5CCC5)cncc4n3)ccnc2[nH]1] | [D3], [D4], [E5] | 523.4 (M + H) | 1H NMR (400 MHz, DMSO-d6) ppm 12.46 (br. s., 1 H), 9.35 (br. s., 1 H), 9.21 (s, 1 H), 9.07 (br. s., 1 H), 8.90 (s, 1 H), 8.59-8.66 (m, 1 H), 8.51 (d, J = 4.8 Hz, 1 H), 8.21 (d, J = 5.0 Hz, 2 H), 7.94 (ddd, J = 11.7, 8.3, 1.0 Hz, 1 H), 7.54 (dt, J = 8.3, 4.2 Hz, 1 H), 4.96 (br. s., 1 H), 4.61 (br. s., 1 H), 4.25-4.44 (m, 1 H), 4.03-4.16 (m, 2 H), 3.24-3.53 (m, 6 H), 2.46 (d, J = 6.5 Hz, 3 H), 2.04-2.21 (m, 2 H), 1.95 (br. s., 1 H) | 5-Cyclobutyl-2-[2-(3-fluoro-pyridin-2-yl)-1H-pyrrolo[2,3-b]pyridin-4-yl]-4-(hexahydro-pyrrolo[3,4-b]-1,4-oxazin-4-yl)-pyrido[3,4-d]pyrimidine |
| 260 | 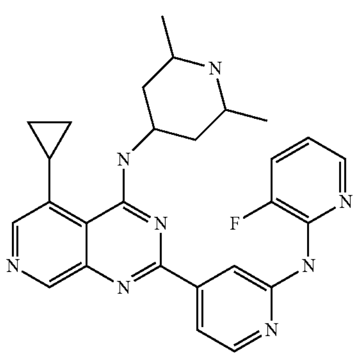 [SMILES: CC1CC(Nc2nc(-c3ccnc(Nc4ncccc4F)c3)nc3cncc(C4CC4)c23)CC(C)N1] | [B4] | 485.22 | 1H NMR (400 MHz, DMSO-d6) ppm 11.90 (br. s., 1 H), 9.07-9.16 (m, 1 H), 8.87-9.05 (m, 2 H), 8.76-8.84 (m, 1 H), 8.57 (s, 1 H), 8.17-8.25 (m, 1H), 7.98-8.11 (m, 2 H), 7.89 (br. s., 1 H), 7.74 (dd, J = 14.4, 5.9 Hz, 1 H), 7.19-7.28 (m, 1 H), 4.69-4.92 (m, 1 H), 3.61-3.74 (m, 2 H), 2.62-2.71 (m, 1 H), 2.25-2.42 (m, 1 H), 2.10-2.24 (m, 1 H), 1.83-1.99 (m, 1 H), 1.64-1.81 (m, 1 H), 1.38-1.56 (m, 3 H), 1.16-1.37 (m, 6 H), 1.04 (br. s., 2 H) | {5-Cyclopropyl-2-[2-(3-fluoro-pyridin-2-ylamino)-pyridin-4-yl]-pyrido[3,4-d]pyrimidin-4-yl}-(2,6-dimethyl-piperidin-4-yl)-amine |
| 261 | 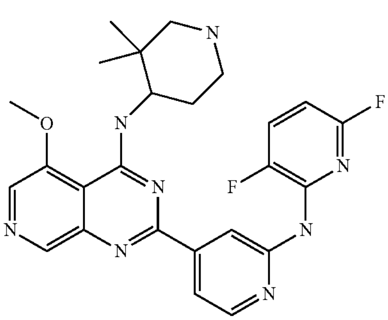 [SMILES: COc1cncc2nc(-c3ccnc(Nc4nc(F)ccc4F)c3)nc(NC3CCNCC3(C)C)c12] | [B4] | 493.17 (M + H) | 1H NMR (400 MHz, DMSO-d6) δ 9.72 (s, 1H), 8.98 (d, J = 9.5 Hz, 1H), 8.83 (s, 1H), 8.80 (s, 1H), 8.39-8.50 (m, 2H), 8.25-8.38 (m, 1H), 7.93-8.05 (m, 2H), 7.87 (ddd, J = 9.8, 8.5, 6.5 Hz, 1H), 6.64-6.77 (m, 1H), 4.56-4.66 (m, 1H), 4.19 (s, 3H), 3.32 (d, J = 10.8 Hz, 1H), 3.21 (d, J = 12.8 Hz, 1H), 2.91-3.12 (m, 3H), 2.10-2.20 (m, 1H), 1.82-1.97 (m, 1H), 1.18 (s, 3H), 1.05 (s, 3H) | rac-2-[2-[(3,6-difluoro-2-pyridyl)amino]-4-pyridyl]-N-(3,3-dimethyl-4-piperidyl)-5-methoxy-pyrido[3,4-d]pyrimidin-4-amine |

TABLE A-continued

| Ex | Structure | Scheme | Analysis | | Name |
| --- | --- | --- | --- | --- | --- |
| | | | LCMS | 1H-NMR | |
| 262 | 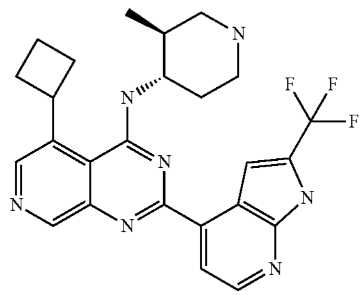 [SMILES: C[C@H]1CNCC[C@@H]1Nc1nc(-c2ccnc3[nH]c(C(F)(F)F)cc23)nc2cncc(C3CCC3)c12] | [D3], [D4] | 482.16 (M + H) | 1H NMR (400 MHz, DMSO-d6) δ 13.13 (br. s., 1H), 9.17 (s, 1H), 8.87 (d, J = 10.5 Hz, 1H), 8.62 (d, J = 4.8 Hz, 1H), 8.48 (s, 2H), 8.29 (d, J = 4.8 Hz, 1H), 7.97 (s, 1H), 6.97 (d, J = 8.3 Hz, 1H), 4.54-4.70 (m, 2H), 3.44 (br. s., 3H), 3.06-3.19 (m, 1H), 2.83-2.97 (m, 1H), 2.53-2.60 (m, 1H), 2.18-2.34 (m, 4H), 2.01-2.16 (m, 1H), 1.78-1.99 (m, 2H), 0.99 (d, J = 6.8 Hz, 3H) | rac-5-cyclobutyl-N-[(3S,4S)-3-methyl-4-piperidyl]-2-[2-(trifluoromethyl)-1H-pyrrolo[2,3-b]pyridin-4-yl]pyrido[3,4-d]pyrimidin-4-amine |
| 263 | 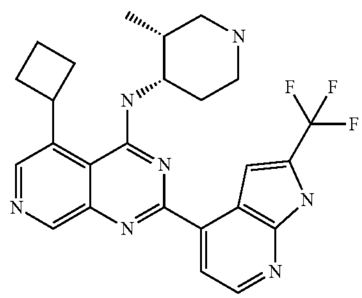 [SMILES: C[C@@H]1CNCC[C@@H]1Nc1nc(-c2ccnc3[nH]c(C(F)(F)F)cc23)nc2cncc(C3CCC3)c12] | [D3], [D4] | 482.18 (M + H) | 1H NMR (400 MHz, DMSO-d6) δ 13.15 (br. s., 1H), 9.20 (br. s., 1H), 8.84 (br. s., 1H), 8.63 (d, J = 5.0 Hz, 1H), 8.37-8.57 (m, 2H), 8.27 (d, J = 5.0 Hz, 1H), 7.98 (s, 1H), 6.83 (d, J = 7.0 Hz, 1H), 4.78-4.92 (m, 1H), 4.51 (quin, J = 8.2 Hz, 1H), 3.28 (br. s., 4H), 2.61-2.74 (m, 1H), 2.55 (br. s., 1H), 2.15-2.36 (m, 3H), 2.04-2.15 (m, 2H), 1.82-1.93 (m, 1H), 1.12 (d, J = 7.0 Hz, 3H) | rac-5-cyclobutyl-N-[(3R,4S)-3-methyl-4-piperidyl]-2-[2-(trifluoromethyl)-1H-pyrrolo[2,3-b]pyridin-4-yl]pyrido[3,4-d]pyrimidin-4-amine |
| 264 | 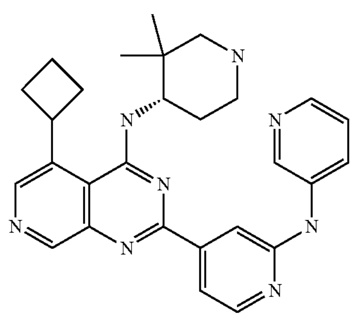 [SMILES: CC1(C)CNCC[C@@H]1Nc1nc(-c2ccnc(Nc3cccnc3)c2)nc2cncc(C3CCC3)c12] | [B4], [E4] | 481.27 (M + H) | 1H NMR (400 MHz, DMSO-d6) δ 10.39 (s, 1H), 9.47 (d, J = 2.0 Hz, 1H), 9.20 (d, J = 11.0 Hz, 1H), 9.07 (s, 1H), 8.57 (s, 1H), 8.55 (dt, J = 8.8, 1.3 Hz, 1H), 8.48 (d, J = 5.3 Hz, 1H), 8.42 (d, J = 5.0 Hz, 2H), 8.06 (s, 1H), 7.98 (dd, J = 5.3, 1.5 Hz, 1H), 7.88 (dd, J = 8.7, 5.4 Hz, 1H), 6.60 (d, J = 8.8 Hz, 1H), 4.91-4.81 (m, 2H), 4.43 (t, J = 8.2 Hz, 2H), 3.36 (d, J = 11.5 Hz, 1H), 3.29-3.07 (m, 3H), 2.47 (m, 1H), 2.41-2.21 (m, 2H), 2.12-1.95 (m, 3H), 1.89 (d, J = 10.0 Hz, 1H), 1.26 (s, 3H), 1.11 (s, 3H) | 5-cyclobutyl-N-[(4S)-3,3-dimethyl-4-piperidyl]-2-[2-(3-pyridylamino)-4-pyridyl]pyrido[3,4-d]pyrimidin-4-amine |
| 265 | 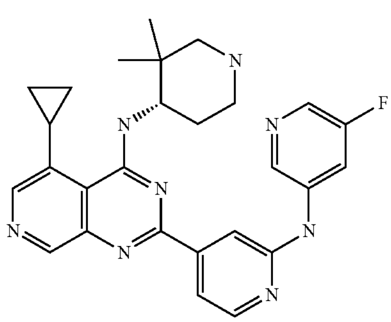 [SMILES: CC1(C)CNCC[C@@H]1Nc1nc(-c2ccnc(Nc3cncc(F)c3)c2)nc2cncc(C3CC3)c12] | [B4], [E4] | 485.24 (M + H) | 1H NMR (400 MHz, DMSO-d6) δ 9.93 (s, 1H), 9.07 (s, 2H), 8.61 (s, 1H), 8.51 (s, 1H), 8.47 (t, J = 2.4 Hz, 1H), 8.44 (d, J = 4.8 Hz, 1H), 8.32 (d, J = 9.5 Hz, 1H), 8.11 (d, J = 2.5 Hz, 1H), 8.00 (s, 1H), 7.91 (dd, J = 5.3, 1.3 Hz, 1H), 7.64 (d, J = 8.8 Hz, 1H), 4.86 (br. s., 1H), 3.35 (br. s., 1H), 3.29-3.09 (m, 3H), 2.59 (br. s., 1H), 2.10 (br. s., 1H), 2.02-1.87 (m, 1H), 1.33-1.23 (m, 1H), 1.23-1.17 (m, 4H), 1.17-1.12 (m, 2H), 1.10 (s, 3H) | 5-cyclopropyl-N-[(4S)-3,3-dimethyl-4-piperidyl]-2-[2-[(5-fluoro-3-pyridyl)amino]-4-pyridyl]pyrido[3,4-d]pyrimidin-4-amine |

TABLE A-continued

| Ex | Structure | Scheme | LCMS | 1H-NMR | Name |
|---|---|---|---|---|---|
| 266 | 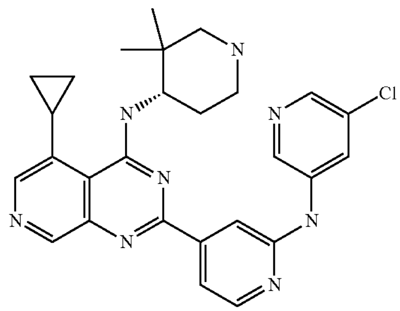 [SMILES: CC1(C)CNCC[C@@H]1Nc1nc(-c2ccnc(Nc3cncc(Cl)c3)c2)nc2cncc(C3CC3)c12] | [B4], [E4] | 501.20 (M + H) | 1H NMR (400 MHz, DMSO-d6) δ 9.87 (s, 1H), 9.06 (s, 2H), 8.71 (d, J = 2.0 Hz, 1H), 8.63 (t, J = 2.1 Hz, 1H), 8.51 (s, 1H), 8.45 (d, J = 5.3 Hz, 1H), 8.30 (d, J = 10.5 Hz, 1H), 8.14 (d, J = 2.3 Hz, 1H), 7.99 (s, 1H), 7.91 (dd, J = 5.3, 1.3 Hz, 1H), 7.63 (d, J = 8.8 Hz, 1H), 4.92-4.80 (m, 1H), 3.35 (br. s., 1H), 3.28-3.10 (m, 3H), 2.59 (t, J = 5.9 Hz, 1H), 2.10 (br. s., 1H), 2.02-1.88 (m, 1H), 1.34-1.22 (m, 1H), 1.19 (s, 3H), 1.18-1.12 (m, 3H), 1.10 (s, 3H) | 2-[2-[(5-chloro-3-pyridyl)amino]-4-pyridyl]-5-cyclopropyl-N-[(4S)-3,3-dimethyl-4-piperidyl]pyrido[3,4-d]pyrimidin-4-amine |
| 267 | 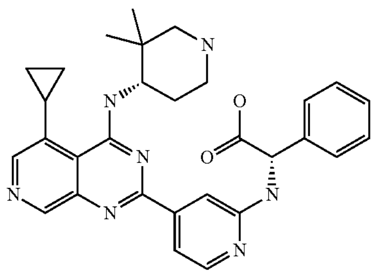 [SMILES: CC1(C)CNCC[C@@H]1Nc1nc(-c2ccnc(N[C@H](C(=O)O)c3ccccc3)c2)nc2cncc(C3CC3)c12] | [B4], [E4] | 524.26 (M + H) | 1H NMR (400 MHz, DMSO-d6) δ 9.35-9.22 (m, 1H), 9.06 (s, 1H), 8.52 (s, 1H), 8.50 (br s, 1H), 8.16 (d, J = 5.8 Hz, 1H), 8.09 (br. s., 1H), 7.75 (m, 2H), 7.61-7.55 (m, 2H), 7.49-7.35 (m, 3H), 5.76 (br. s., 1H), 4.89-4.78 (m, 1H), 3.32 (br. s., 1H), 3.16 (br. s., 3H), 2.59 (t, J = 6.3 Hz, 1H), 2.15-2.02 (m, 1H), 2.00-1.85 (m, 1H), 1.27-1.11 (m, 8H), 1.07 (d, J = 6.0 Hz, 3H) | (2S)-2-[[4-[5-cyclopropyl-4-[[(4S)-3,3-dimethyl-4-piperidyl]amino]pyrido[3,4-d]pyrimidin-2-yl]-2-pyridyl]amino]-2-phenyl-acetic acid |
| 268 | 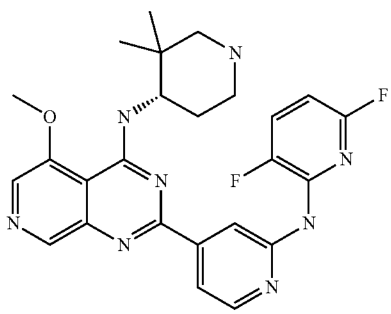 [SMILES: COc1cncc2nc(-c3ccnc(Nc4nc(F)ccc4F)c3)nc(N[C@H]3CCNCC3(C)C)c12] | [B4], [E4] | 493.19 (M + H) | 1H NMR (400 MHz, DMSO-d6) δ 13.15 (br. s., 1H), 9.20 (br. s., 1H), 8.84 (br. s., 1H), 8.63 (d, J = 5.0 Hz, 1H), 8.37-8.57 (m, 2H), 8.27 (d, J = 5.0 Hz, 1H), 7.98 (s, 1H), 6.83 (d, J = 7.0 Hz, 1H), 4.78-4.92 (m, 1H), 4.51 (quin, J = 8.2 Hz, 1H), 3.28 (br. s., 4H), 2.61-2.74 (m, 1H), 2.55 (br. s., 1H), 2.15-2.36 (m, 3H), 2.04-2.15 (m, 2H), 1.82-1.93 (m, 1H), 1.12 (d, J = 7.0 Hz, 3H) | 2-[2-[(3,6-difluoro-2-pyridyl)amino]-4-pyridyl]-N-[(4S)-3,3-dimethyl-4-piperidyl]-5-methoxy-pyrido[3,4-d]pyrimidin-4-amine |
| 269 | 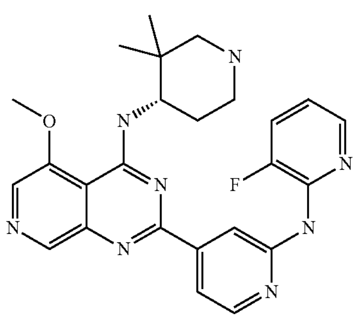 [SMILES: COc1cncc2nc(-c3ccnc(Nc4ncccc4F)c3)nc(N[C@H]3CCNCC3(C)C)c12] | [B4], [E4] | 475.20 (M + H) | 1H NMR (400 MHz, DMSO-d6) δ 10.03 (br. s., 1H), 8.97 (br. s., 1H), 8.85 (s, 1H), 8.80 (s, 1H), 8.46-8.40 (m, 2H), 8.30 (br. s., 1H), 8.20 (d, J = 5.0 Hz, 1H), 8.07-7.95 (m, 2H), 7.83-7.74 (m, 1H), 7.16 (dd, J = 7.9, 3.6 Hz, 1H), 4.66-4.54 (m, 1H), 4.20 (s, 3H), 3.25-2.95 (m, 5H), 2.14 (d, J = 11.3 Hz, 1H), 2.00-1.80 (m, 1H), 1.18 (s, 3H), 1.06 (s, 3H). | N-[(4S)-3,3-dimethyl-4-piperidyl]-2-[2-[(3-fluoro-2-pyridyl)amino]-4-pyridyl]-5-methoxy-pyrido[3,4-d]pyrimidin-4-amine |
| 270 | 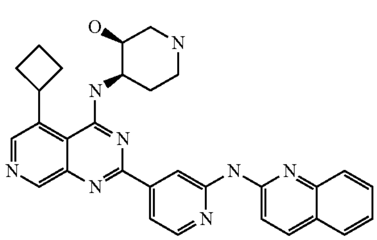 [SMILES: O[C@H]1CNCC[C@H]1Nc1nc(-c2ccnc(Nc3ccc4ccccc4n3)c2)nc2cncc(C3CCC3)c12] | [B4], [E4] | 519 [M + H] | 1H NMR (400 MHz, METHANOL-d4) δ ppm 9.08 (s, 1 H) 8.70-8.77 (m, 1 H) 8.61 (d, J = 9.29 Hz, 1 H) 8.53 (d, J = 0.75 Hz, 1 H) 8.44 (s, 1 H) 8.40 (dd, J = 5.65, 1.38 Hz, 1 H) 8.14 (d, J = 8.53 Hz, 1 H) 8.02 (d, J = 8.03 Hz, 1 H) 7.93 (s, 1 H) 7.67 (s, 1 H) 7.45 (d, J = 9.03 Hz, 1 H) 4.88-4.94 (m, 1 H) 4.38 (br. s., 1 H) 4.19 (t, J = 8.28 Hz, 1 H) 3.50 (br. s., 3 H) 3.37-3.44 (m, 1 H) 2.67 (br. s., 2 H) 2.33-2.56 (m, 3 | rac-(3S,4R)-4-{5-Cyclobutyl-2-[2-(quinolin-2-ylamino)-pyridin-4-yl]-pyrido[3,4-d]pyrimidin-4-ylamino}-piperidin-3-ol |

TABLE A-continued

| Ex | Structure | Scheme | Analysis LCMS | 1H-NMR | Name |
|---|---|---|---|---|---|
| | | | | H) 2.12-2.28 (m, 2 H) 1.96-2.04 (m, 1 H) | |
| 271 | 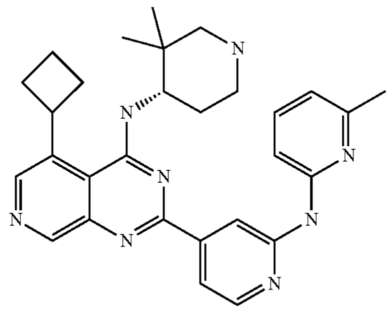 [SMILES: Cc1cccc(Nc2cc(-c3nc(N[C@H]4CCNCC4(C)C)c4c(C5CCC5)cncc4n3)ccn2)n1] | [B4], [E4] | 495 [M + H] | 1H NMR (400 MHz, METHANOL-d4) δ ppm 9.12 (s, 1 H) 8.57-8.63 (m, 2 H) 8.37 (dd, J = 1.51, 0.75 Hz, 1 H) 8.32 (dd, J = 5.77, 1.51 Hz, 1 H) 8.05 (dd, J = 8.53, 7.53 Hz, 1 H) 7.19 (dd, J = 15.31, 8.03 Hz, 2 H) 4.98-5.04 (m, 1 H) 4.25-4.37 (m, 1 H) 3.48-3.56 (m, 1 H) 3.32-3.40 (m, 2 H) 3.25 (s, 1 H) 2.57-2.70 (m, 2 H) 2.51 (s, 2 H) 1.98-2.28 (m, 4 H) 1.37 (s, 3 H) 1.22 (s, 3 H) | {5-Cyclobutyl-2-[2-(6-methyl-pyridin-2-ylamino)-pyridin-4-yl]-pyrido[3,4-d]pyrimidin-4-yl}-((S)-3,3-dimethyl-piperidin-4-yl)-amine |
| 272 | 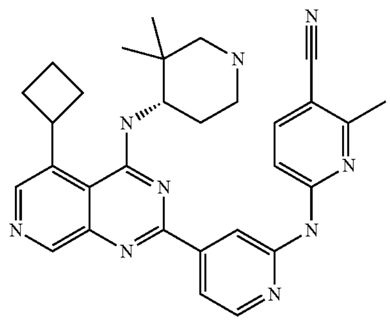 [SMILES: Cc1nc(Nc2cc(-c3nc(N[C@H]4CCNCC4(C)C)c4c(C5CCC5)cncc4n3)ccn2)ccc1C#N] | [B4], [E4] | 520 [M + H] | 1H NMR (400 MHz, METHANOL-d4) δ ppm 9.13 (s, 1 H) 8.63 (d, J = 0.75 Hz, 1 H) 8.56-8.60 (m, 2 H) 8.41 (dd, J = 6.27, 1.51 Hz, 1 H) 8.14 (d, J = 8.78 Hz, 1 H) 7.29 (d, J = 8.78 Hz, 1 H) 5.01 (dd, J = 11.80, 4.27 Hz, 1 H) 4.31 (t, J = 8.28 Hz, 1 H) 3.52 (d, J = 12.80 Hz, 1 H) 3.34-3.41 (m, 2 H) 3.20-3.27 (m, 1 H) 2.64 (td, J = 8.09, 2.89 Hz, 2 H) 2.35-2.56 (m, 2 H) 1.99-2.29 (m, 4 H) 1.37 (s, 3 H) 1.21 (s, 3 H) | 6-{4-[5-Cyclobutyl-4-((S)-3,3-dimethyl-piperidin-4-ylamino)-pyrido[3,4-d]pyrimidin-2-yl]-pyridin-2-ylamino}-2-methyl-nicotinonitrile |
| 273 | 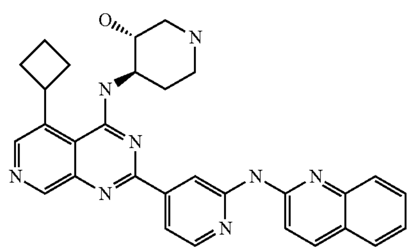 [SMILES: O[C@@H]1CNCC[C@H]1Nc1nc(-c2ccnc(Nc3ccc4ccccc4n3)c2)nc2cncc(C3CCC3)c12] | [B4] | 519 [M + H] | 1H NMR (400 MHz, METHANOL-d4) δ ppm 9.10 (s, 1 H) 8.76 (d, J = 6.27 Hz, 1 H) 8.64 (d, J = 9.03 Hz, 1 H) 8.55 (d, J = 1.00 Hz, 1 H) 8.45 (s, 1 H) 8.40 (dd, J = 5.65, 1.38 Hz, 1 H) 8.17 (d, J = 8.53 Hz, 1 H) 8.05 (d, J = 7.53 Hz, 1 H) 7.92-8.00 (m, 1 H) 7.69 (t, J = 7.28 Hz, 1 H) 7.45 (d, J = 9.04 Hz, 1 H) 4.65 (td, J = 9.22, 4.14 Hz, 1H) 4.33-4.45 (m, 1 H) 4.24 (td, J = 9.03, 4.27 Hz, 1 H) 3.60 (dd, J = 12.05, 4.27 Hz, 1 H) 3.39-3.55 (m, 2 H) 3.11-3.20 (m, 1 H) 2.74-2.85 (m, 2 H) 2.59-2.70 (m, 1 H) 2.46 (quin, J = 9.54 Hz, 2 H) 2.19-2.29 (m, 1 H) 1.90-2.05 (m, 2 H) | rac-(3R,4R)-4-{5-Cyclobutyl-2-[2-(quinolin-2-ylamino)-pyridin-4-yl]-pyrido[3,4-d]pyrimidin-4-ylamino}-piperidin-3-ol |
| 274 | 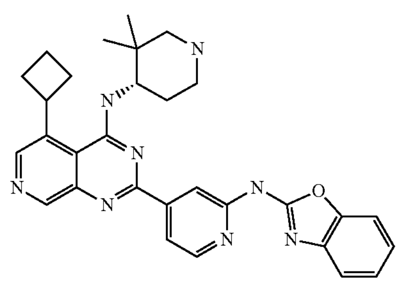 [SMILES: CC1(C)CNCC[C@@H]1Nc1nc(-c2ccnc(Nc3nc4ccccc4o3)c2)nc2cncc(C3CCC3)c12] | [B4], [E4] | 521 [M + H] | 1H NMR (400 MHz, METHANOL-d4) δ ppm 9.20 (s, 1 H) 8.86 (s, 1 H) 8.65 (d, J = 1.00 Hz, 1 H) 8.54 (d, J = 5.77 Hz, 1 H) 8.33 (dd, J = 6.02, 1.51 Hz, 1 H) 7.56-7.62 (m, 2 H) 7.32-7.45 (m, 2 H) 5.01-5.09 (m, 1 H) 4.29-4.41 (m, 1 H) 3.50-3.58 (m, 1 H) 3.39 (d, J = 1.25 Hz, 1 H) 3.28-3.33 (m, 1 H) 3.21 (d, J = 13.05 Hz, 1 H) 2.61-2.75 (m, 2 H) 2.39-2.59 (m, 2 H) 2.01-2.34 (m, 4 H) 1.41 (s, 3 H) 1.29 (s, 3 H) | {2-[2-(Benzoxazol-2-ylamino)-pyridin-4-yl]-5-cyclobutyl-pyrido[3,4-d]pyrimidin-4-yl}-((S)-3,3-dimethyl-piperidin-4-yl)-amine |

| Ex | Structure | Scheme | LCMS | 1H-NMR | Name |
|---|---|---|---|---|---|
| 275 | 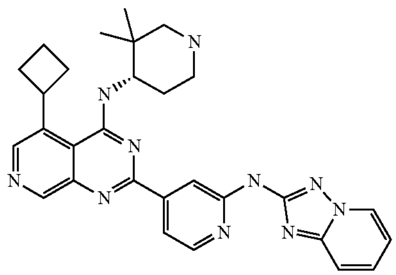 | [B4], [E4] | 521 [M + H] | 1HNMR (400 MHz, METHANOL-d4) δ ppm 9.19 (d, J = 0.75 Hz, 1 H) 8.85 (dt, J = 6.78, 1.00 Hz, 1 H) 8.66 (dd, J = 11.42, 0.88 Hz, 2 H) 8.56 (d, J = 7.03 Hz, 1 H) 8.41 (dd, J = 6.52, 1.51 Hz, 1 H) 7.82-7.90 (m, 2 H) 7.34 (td, J = 6.40, 2.26 Hz, 1 H) 5.03 (dd, J = 11.80, 4.27 Hz, 1 H) 4.35 (t, J = 8.28 Hz, 1 H) 3.57 (d, J = 12.80 Hz, 1 H) 3.37-3.43 (m, 2 H) 3.23 (d, J = 13.05 Hz, 1 H) 2.61-2.75 (m, 2 H) 2.39-2.61 (m, 2 H) 2.03-2.36 (m, 5 H) 1.42 (s, 3 H) 1.26 (s, 3 H) | {5-Cyclobutyl-2-[2-([1,2,4]triazolo[1,5-a]pyridin-2-ylamino)-pyridin-4-yl]-pyrido[3,4-d]pyrimidin-4-yl}-((S)-3,3-dimethyl-piperidin-4-yl)-amine |
| 276 | 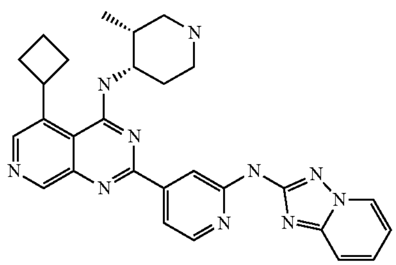 [SMILES: C[C@@H]1CNCC[C@@H]1Nc1nc(-c2ccnc(Nc3nc4ccccn4n3)c2)nc2cncc(C3CCC3)c12] | [B4] | 507 [M + H] | 1H NMR (400 MHz, METHANOL-d4) δ ppm 9.19 (s, 1 H) 8.85 (dt, J = 6.78, 1.00 Hz, 1 H) 8.64 (dd, J = 9.79, 1.25 Hz, 2 H) 8.56 (d, J = 6.52 Hz, 1 H) 8.39 (dd, J = 6.52, 1.51 Hz, 1 H) 7.79-7.91 (m, 2 H) 7.34 (td, J = 6.53, 2.01 Hz, 1 H) 4.95-5.04 (m, 1 H) 4.41 (s, 1 H) 3.38-3.60 (m, 4 H) 2.87 (br. s., 1 H) 2.61-2.75 (m, 2 H) 2.40-2.54 (m, 2 H) 2.17-2.39 (m, 3 H) 2.07 (d, J = 10.54 Hz, 1 H) 1.29 (d, J = 7.28 Hz, 3 H) | {5-Cyclobutyl-2-[2-([1,2,4]triazolo[1,5-a]pyridin-2-ylamino)-pyridin-4-yl]-pyrido[3,4-d]pyrimidin-4-yl}-(rac-(3R,4S)-3-methyl-piperidin-4-yl)-amine |
| 277 | 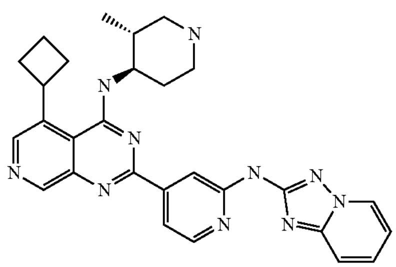 [SMILES: C[C@@H]1CNCC[C@H]1Nc1nc(-c2ccnc(Nc3nc4ccccn4n3)c2)nc2cncc(C3CCC3)c12] | [B4] | 507 [M + H] | 1H NMR (400 MHz, METHANOL-d4) δ ppm 9.17 (d, J = 0.75 Hz, 1 H) 8.85 (dt, J = 6.78, 1.00 Hz, 1 H) 8.64 (d, J = 1.51 Hz, 1 H) 8.60 (d, J = 1.25 Hz, 1 H) 8.56 (dd, J = 6.53, 0.75 Hz, 1 H) 8.39 (dd, J = 6.53, 1.51 Hz, 1 H) 7.81-7.90 (m, 2 H) 7.34 (td, J = 6.40, 2.26 Hz, 1 H) 4.79 (td, J = 11.23, 4.14 Hz, 1H) 4.46 (quin, J = 8.66 Hz, 1 H) 3.56-3.68 (m, 2 H) 3.36-3.42 (m, 1 H) 3.05 (t, J = 12.55 Hz, 1 H) 2.69 (q, J = 8.03 Hz, 2 H) 2.20-2.53 (m, 5 H) 1.99-2.12 (m, 2 H) 1.18 (d, J = 6.78 Hz, 3 H) | {5-Cyclobutyl-2-[2-([1,2,4]triazolo[1,5-a]pyridin-2-ylamino)-pyridin-4-yl]-pyrido[3,4-d]pyrimidin-4-yl}-(rac-(3R,4R)-3-methyl-piperidin-4-yl)-amine |
| 278 | 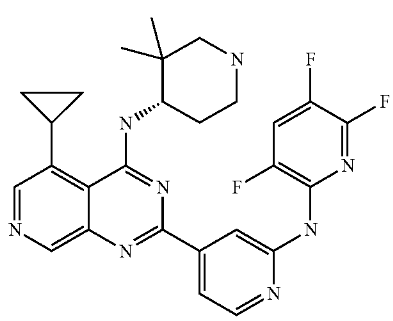 [SMILES: CC1(C)CNCC[C@@H]1Nc1nc(-c2ccnc(Nc3nc(F)c(F)cc3F)c2)nc2cncc(C3CC3)c12] | [B4], [E4] | 521 [M + H] | 1H NMR (400 MHz, METHANOL-d4) δ ppm 9.02 (s, 1 H) 8.79-8.85 (m, 1 H) 8.44 (d, J = 1.00 Hz, 1 H) 8.33-8.38 (m, 1 H) 8.22 (dd, J = 6.02, 1.51 Hz, 1 H) 7.97 (td, J = 8.85, 7.40 Hz, 1 H) 4.92-4.98 (m, 1 H) 3.42 (br. s., 1 H) 3.22-3.28 (m, 1 H) 3.07-3.18 (m, 2 H) 2.44 (t, J = 7.03 Hz, 1 H) 2.19 (dd, J = 14.31, 3.26 Hz, 1 H) 2.03 (d, J = 4.02 Hz, 1 H) 1.29-1.36 (m, 1 H) 1.19-1.24 (m, 5 H) 1.12 (s, 3 H) 1.00-1.08 (m, 1 H | {5-Cyclopropyl-2-[2-(3,5,6-trifluoro-pyridin-2-ylamino)-pyridin-4-yl]-pyrido[3,4-d]pyrimidin-4-yl}-((S)-3,3-dimethyl-piperidin-4-yl)-amine |

TABLE A-continued

| Ex | Structure | Scheme | Analysis | | Name |
| --- | --- | --- | --- | --- | --- |
| | | | LCMS | 1H-NMR | |
| 279 | 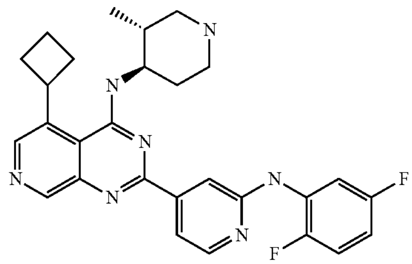 [SMILES: C[C@@H]1CNCC[C@H]1Nc1nc(-c2ccnc(Nc3cc(F)ccc3F)c2)nc2cncc(C3CCC3)c12] | [B4] | 503 [M + H] | 1H NMR (400 MHz, METHANOL-d4) δ ppm 9.00 (s, 1 H) 8.90 (s, 1 H) 8.44 (s, 1 H) 8.38 (d, J = 6.02 Hz, 1 H) 8.20 (dd, J = 6.15, 1.38 Hz, 1 H) 7.77 (d, J = 5.52 Hz, 1 H) 6.70 (d, J = 8.53 Hz, 1 H) 4.68 (td, J = 11.23, 4.14 Hz, 1 H) 4.32 (t, J = 8.28 Hz, 1 H) 3.41-3.52 (m, 2 H) 3.07-3.19 (m, 1 H) 2.83-2.94 (m, 1 H) 2.51-2.61 (m, 2 H) 2.33 (d, J = 1.76 Hz, 3 H) 2.07-2.24 (m, 2 H) 1.82-1.99 (m, 2 H) 1.04 (d, J = 6.78 Hz, 3 H) | {5-Cyclobutyl-2-[2-(3,6-difluoro-pyridin-2-ylamino)-pyridin-4-yl]-pyrido[3,4-d]pyrimidin-4-yl}-((3R,4R)-3-methyl-piperidin-4-yl)-amine or enantiomer |
| 280 | 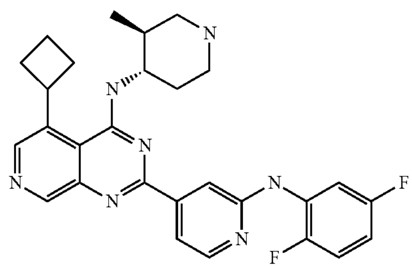 [SMILES: C[C@H]1CNCC[C@@H]1Nc1nc(-c2ccnc(Nc3cc(F)ccc3F)c2)nc2cncc(C3CCC3)c12] | [B4] | 503 [M + H] | 1H NMR (400 MHz, METHANOL-d4) δ ppm 9.01 (br. s., 1 H) 8.89 (s, 1 H) 8.45 (br. s., 1 H) 8.39 (d, J = 6.02 Hz, 1 H) 8.22 (dd, J = 6.02, 1.26 Hz, 1 H) 7.78 (td, J = 9.16, 6.02 Hz, 1 H) 6.72 (d, J = 8.53 Hz, 1 H) 4.68 (d, J = 4.02 Hz, 1 H) 4.32 (t, J = 8.28 Hz, 1 H) 3.41-3.52 (m, 2 H) 3.07-3.19 (m, 1 H) 2.89 (s, 1 H) 2.50-2.63 (m, 2 H) 2.33 (br. s., 3 H) 2.05-2.23 (m, 2 H) 1.79-1.98 (m, 2 H) 1.05 (d, J = 6.78 Hz, 3 H) | {5-Cyclobutyl-2-[2-(3,6-difluoro-pyridin-2-ylamino)-pyridin-4-yl]-pyrido[3,4-d]pyrimidin-4-yl}-((3S,4S)-3-methyl-piperidin-4-yl)-amine or enantiomer |
| 281 | 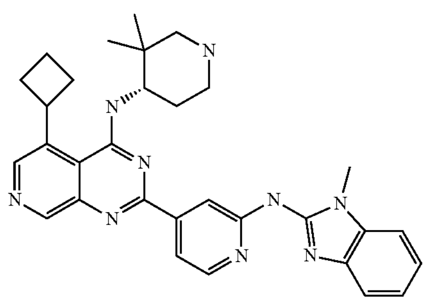 [SMILES: Cn1c(Nc2cc(-c3nc(N[C@H]4CCNCC4(C)C)c4c(C5CCC5)cncc4n3)ccn2)nc2ccccc21] | [B4], [E4] | 534 [M + H] | 1H NMR (400 MHz, METHANOL-d4) δ ppm 9.13 (s, 1 H) 8.71 (br. s., 1 H) 8.63 (d, J = 1.00 Hz, 1 H) 8.53-8.57 (m, 1 H) 8.34 (d, J = 5.02 Hz, 1 H) 7.79 (d, J = 6.78 Hz, 1 H) 7.71 (d, J = 7.28 Hz, 1 H) 7.45-7.58 (m, 2 H) 5.05 (dd, J = 11.92, 4.14 Hz, 1 H) 4.34 (quint, J = 8.34 Hz, 1 H) 4.03 (s, 3 H) 3.50-3.59 (m, 1H) 3.36-3.43 (m, 2 H) 3.22-3.30 (m, 1 H) 2.61-2.74 (m, 2 H) 2.38-2.61 (m, 2 H) 2.06-2.33 (m, 4 H) 1.41 (s, 3 H) 1.26 (s, 3 H) | {5-Cyclobutyl-2-[2-(1-methyl-1H-benzimidazol-2-ylamino)-pyridin-4-yl]-pyrido[3,4-d]pyrimidin-4-yl}-((S)-3,3-dimethyl-piperidin-4-yl)-amine |
| 282 | 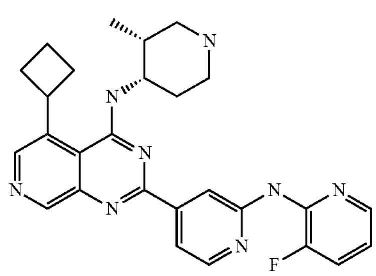 [SMILES: C[C@@H]1CNCC[C@@H]1Nc1nc(-c2ccnc(Nc3ncccc3F)c2)nc2cncc(C3CCC3)c12] | [B4] | 485 [M + H] | 1H NMR (400 MHz, METHANOL-d4) δ ppm 9.18 (s, 1 H) 8.76-8.82 (m, 1 H) 8.65 (d, J = 1.00 Hz, 1 H) 8.53 (d, J = 6.02 Hz, 1 H) 8.43 (dd, J = 6.53, 1.51 Hz, 1 H) 8.37 (dd, J = 5.02, 1.25 Hz, 1 H) 7.92 (ddd, J = 10.79, 8.28, 1.25 Hz, 1 H) 7.38 (ddd, J = 8.41, 4.89, 3.76 Hz, 1 H) 5.03 (dt, J = 8.34, 4.24 Hz, 1 H) 4.41 (t, J = 8.16 Hz, 1 H) 3.37-3.56 (m, 4 H) 2.77-2.89 (m, 1 H) 2.63-2.74 (m, 2 H) 2.47 (d, J = 9.03 Hz, 2 H) 2.33 (br. s., 3 H) 2.03-2.11 (m, 1 H) 1.27 (d, J = 7.28 Hz, 3 H) | {5-Cyclobutyl-2-[2-(3-fluoro-pyridin-2-ylamino)-pyridin-4-yl]-pyrido[3,4-d]pyrimidin-4-yl}-(rac-(3R,4S)-3-methyl-piperidin-4-yl)-amine |

TABLE A-continued

| Ex | Structure | Scheme | LCMS | 1H-NMR | Name |
|---|---|---|---|---|---|
| 283 | 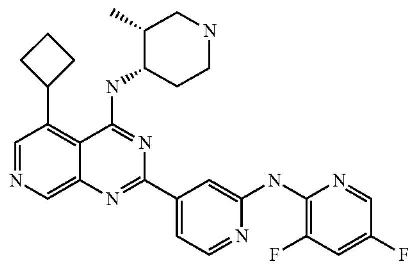 [SMILES: C[C@@H]1CNCC[C@@H]1Nc1nc(-c2ccnc(Nc3ncc(F)cc3F)c2)nc2cncc(C3CCC3)c12] | [B4] | 503 [M + H] | 1H NMR (400 MHz, METHANOL-d4) δ ppm 9.17 (d, J = 0.75 Hz, 1 H) 8.81 (dd, J = 1.51, 0.75 Hz, 1 H) 8.66 (d, J = 1.00 Hz, 1 H) 8.47 (d, J = 0.75 Hz, 1 H) 8.43 (d, J = 1.51 Hz, 1 H) 8.34 (d, J = 2.51 Hz, 1 H) 7.94-8.02 (m, 1 H) 4.97-5.05 (m, 1 H) 4.32-4.47 (m, 1 H) 3.39-3.56 (m, 4 H) 2.83 (br. s., 1 H) 2.65-2.75 (m, 2 H) 2.41-2.53 (m, 2 H) 2.19-2.39 (m, 3 H) 2.05-2.12 (m, 1 H) 1.27 (d, J = 7.03 Hz, 3 H) | {5-Cyclobutyl-2-[2-(3,5-difluoro-pyridin-2-ylamino)-pyridin-4-yl]-pyrido[3,4-d]pyrimidin-4-yl}-(rac-(3R,4S)-3-methyl-piperidin-4-yl)-amine |
| 284 | 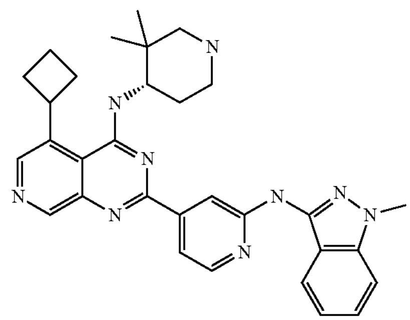 [SMILES: Cn1nc(Nc2cc(-c3nc(N[C@H]4CCNCC4(C)C)c4c(C5CCC5)cncc4n3)ccn2)c2ccccc21] | [B4], [E4] | 534 [M + H] | 1H NMR (400 MHz, METHANOL-d4) δ ppm 9.17 (d, J = 0.75 Hz, 1 H) 8.66-8.73 (m, 2 H) 8.48 (dd, J = 6.78, 0.75 Hz, 1 H) 8.33 (dd, J = 6.78, 1.76 Hz, 1 H) 8.00-8.08 (m, 1 H) 7.57-7.70 (m, 2 H) 7.33 (ddd, J = 8.09, 6.71, 1.00 Hz, 1 H) 5.04 (s, 1 H) 4.28-4.42 (m, 1 H) 3.48-3.61 (m, 1 H) 3.37-3.44 (m, 2 H) 3.23-3.31 (m, 1 H) 2.38-2.76 (m, 4 H) 2.05-2.33 (m, 4 H) 1.41 (s, 3 H) 1.26 (s, 3 H) | {5-Cyclobutyl-2-[2-(1-methyl-1H-indazol-3-ylamino)-pyridin-4-yl]-pyrido[3,4-d]pyrimidin-4-yl}-((S)-3,3-dimethyl-piperidin-4-yl)-amine |
| 285 | 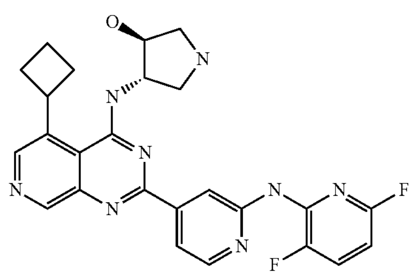 [SMILES: O[C@H]1CNC[C@@H]1Nc1nc(-c2ccnc(Nc3nc(F)ccc3F)c2)nc2cncc(C3CCC3)c12] | [B4] | 419 [M + H] | 1H NMR (400 MHz, METHANOL-d4) δ ppm 9.18 (d, J = 0.75 Hz, 1 H) 8.98-9.06 (m, 1 H) 8.60 (d, J = 1.00 Hz, 1 H) 8.50-8.56 (m, 1 H) 8.38 (dd, J = 6.02, 1.51 Hz, 1 H) 7.93 (td, J = 9.03, 6.02 Hz, 1 H) 6.87 (dt, J = 8.53, 2.51 Hz, 1 H) 4.95 (dt, J = 6.71, 3.29 Hz, 1 H) 4.79-4.84 (m, 1 H) 4.47 (t, J = 8.28 Hz, 1 H) 4.21 (dd, J = 12.80, 6.78 Hz, 1 H) 3.67 (ddd, J = 12.55, 10.16, 4.14 Hz, 2 H) 3.46-3.54 (m, 1 H) 2.62-2.77 (m, 2 H) 2.42 (t, J = 9.41 Hz, 2 H) 2.28 (d, J = 9.54 Hz, 1 H) 1.94-2.07 (m, 1 H) | rac-(3S,4S)-4-{5-Cyclobutyl-2-[2-(3,6-difluoro-pyridin-2-ylamino)-pyridin-4-yl]-pyrido[3,4-d]pyrimidin-4-ylamino}-pyrrolidin-3-ol |
| 286 | 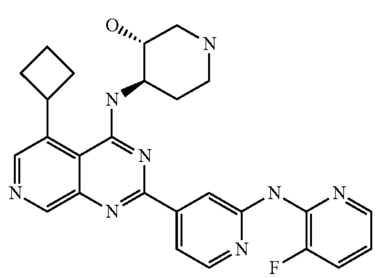 [SMILES: O[C@@H]1CNCC[C@H]1Nc1nc(-c2ccnc(Nc3ncccc3F)c2)nc2cncc(C3CCC3)c12] | [B4] | 487 [M + H] | 1H NMR (400 MHz, METHANOL-d4) δ ppm 9.02 (d, J = 0.75 Hz, 1 H) 8.67 (d, J = 1.00 Hz, 1 H) 8.48 (d, J = 1.25 Hz, 1 H) 8.36-8.43 (m, 1 H) 8.29 (dd, J = 6.52, 1.51 Hz, 1 H) 8.24 (dd, J = 5.02, 1.25 Hz, 1 H) 7.73-7.83 (m, 1 H) 7.19-7.26 (m, 1 H) 4.50-4.60 (m, 1 H) 4.24-4.36 (m, 1 H) 4.06-4.19 (m, 1 H) 3.47-3.54 (m, 1 H) 3.33-3.46 (m, 2 H) 3.04 (s, 1 H) 2.60-2.77 (m, 2 H) 2.49-2.60 (m, 1 H) 2.31-2.44 (m, 1 H) 2.08-2.29 (m, 2 H) 1.79-1.95 (m, 2 H) | rac-(3R,4R)-4-{5-Cyclobutyl-2-[2-(3-fluoro-pyridin-2-ylamino)-pyridin-4-yl]-pyrido[3,4-d]pyrimidin-4-ylamino}-piperidin-3-ol |

TABLE A-continued

| Ex | Structure | Scheme | Analysis | | Name |
|---|---|---|---|---|---|
| | | | LCMS | 1H-NMR | |
| 287 | 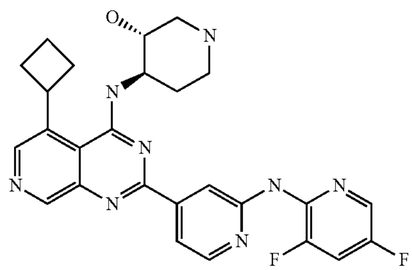 [SMILES: O[C@@H]1CNCC[C@H]1Nc1nc(-c2ccnc(Nc3ncc(F)cc3F)c2)nc2cncc(C3CCC3)c12] | [B4] | 505 [M + H] | 1H NMR (400 MHz, METHANOL-d4) δ ppm 9.02 (d, J = 0.75 Hz, 1 H) 8.69 (d, J = 0.75 Hz, 1 H) 8.48 (d, J = 1.00 Hz, 1 H) 8.31-8.36 (m, 1 H) 8.26 (dd, J = 6.53, 1.51 Hz, 1 H) 8.20 (d, J = 2.51 Hz, 1 H) 7.82 (ddd, J = 10.42, 8.03, 2.38 Hz, 1 H) 4.49-4.58 (m, 1 H) 4.25-4.37 (m, 1 H) 4.09-4.18 (m, 1 H) 3.46-3.54 (m, 1 H) 3.38 (s, 2 H) 2.99-3.06 (m, 1 H) 2.61-2.75 (m, 2 H) 2.54 (td, J = 7.28, 3.76 Hz, 1 H) 2.31-2.42 (m, 1 H) 2.20-2.30 (m, 1 H) 2.14 (dt, J = 18.20, 8.97 Hz, 1 H) 1.79-1.97 (m, 2 H) | rac-(3R,4R)-4-{5-Cyclobutyl-2-[2-(3,5-difluoro-pyridin-2-ylamino)-pyridin-4-yl]-pyrido[3,4-d]pyrimidin-4-ylamino}-piperidin-3-ol |
| 289 | 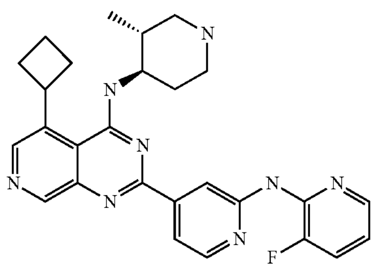 [SMILES: C[C@@H]1CNCC[C@H]1Nc1nc(-c2ccnc(Nc3ncccc3F)c2)nc2cncc(C3CCC3)c12] | [B4] | 485 [M + H] | 1H NMR(400 MHz, METHANOL-d4) δ ppm 9.02 (d, J = 0.75 Hz, 1 H) 8.69-8.73 (m, 1 H) 8.47 (d, J = 1.00 Hz, 1 H) 8.38-8.42 (m, 1 H) 8.31-8.36 (m, 1 H) 8.25 (dd, J = 5.14, 1.13 Hz, 1 H) 7.79 (ddd, J = 10.85, 8.22, 1.25 Hz, 1 H) 7.20-7.30 (m, 1 H) 4.65-4.74 (m, 2 H) 4.29-4.41 (m, 1 H) 3.42-3.55 (m, 2 H) 2.95 (t, J = 12.42 Hz, 1 H) 2.51-2.61 (m, 2H) 2.31 (qd, J = 9.08, 2.38 Hz, 3H) 2.11-2.25 (m, 2 H) 1.86-1.98 (m, 2 H) 1.04 (d, J = 6.53 Hz, 3 H) | {5-Cyclobutyl-2-[2-(3-fluoro-pyridin-2-ylamino)-pyridin-4-yl]-pyrido[3,4-d]pyrimidin-4-yl}-(rac-(3R,4R)-3-methyl-piperidin-4-yl)-amine |
| 290 | 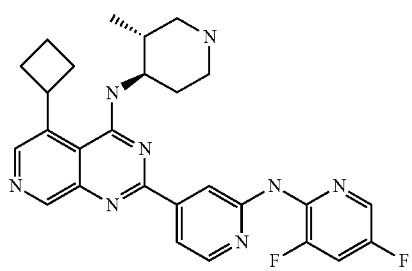 [SMILES: C[C@@H]1CNCC[C@H]1Nc1nc(-c2ccnc(Nc3ncc(F)cc3F)c2)nc2cncc(C3CCC3)c12] | [B4] | 503 [M + H] | 1H NMR (400 MHz, METHANOL-d4) δ ppm 9.02 (d, J = 0.75 Hz, 1 H) 8.72-8.75 (m, 1 H) 8.47 (d, J = 1.00 Hz, 1 H) 8.31-8.36 (m, 2 H) 8.22 (d, J = 2.51 Hz, 1 H) 7.86 (ddd, J = 10.48, 8.09, 2.51 Hz, 1 H) 4.72 (br. s., 2 H) 4.34 (t, J = 8.16 Hz, 1 H) 3.42-3.53 (m, 2 H) 2.96 (t, J = 12.42 Hz, 1 H) 2.51-2.62 (m, 2 H) 2.27-2.39 (m, 3 H) 2.10-2.25 (m, 2 H) 1.84-1.99 (m, 2 H) 1.04 (d, J = 6.53 Hz, 3 H) | {5-Cyclobutyl-2-[2-(3,5-difluoro-pyridin-2-ylamino)-pyridin-4-yl]-pyrido[3,4-d]pyrimidin-4-yl}-(rac-(3R,4R)-3-methyl-piperidin-4-yl)-amine |
| 291 | 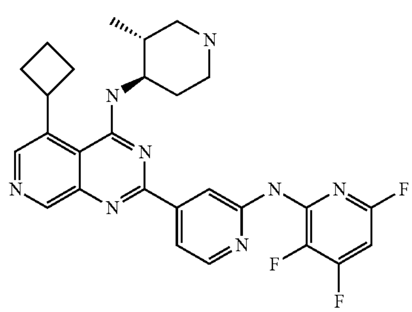 [SMILES: C[C@@H]1CNCC[C@H]1Nc1nc(-c2ccnc(Nc3nc(F)cc(F)c3F)c2)nc2cncc(C3CCC3)c12] | [B4] | 521 [M + H] | 1H NMR (400 MHz, METHANOL-d4) δ ppm 9.14 (s, 1 H) 9.04 (d, J = 0.75 Hz, 1 H) 8.57 (d, J = 1.00 Hz, 1 H) 8.49-8.54 (m, 1 H) 8.28-8.32 (m, 1 H) 6.84-6.91 (m, 1 H) 4.77-4.86 (m, 1 H) 4.41-4.51 (m, 1 H) 3.55-3.65 (m, 2 H) 3.20-3.31 (m, 1 H) 2.96-3.08 (m, 1 H) 2.64-2.75 (m, 2 H) 2.39-2.53 (m, 3 H) 2.20-2.36 (m, 2 H) 1.95-2.11 (m, 2 H) 1.18 (d, J = 6.53 Hz, 3 H) | {5-Cyclobutyl-2-[2-(3,4,6-trifluoro-pyridin-2-ylamino)-pyridin-4-yl]-pyrido[3,4-d]pyrimidin-4-yl}-(rac-(3R,4R)-3-methyl-piperidin-4-yl)-amine |

TABLE A-continued

| Ex | Structure | Scheme | Analysis | | Name |
| --- | --- | --- | --- | --- | --- |
| | | | LCMS | 1H-NMR | |
| 292 | 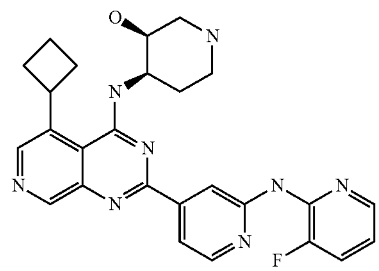 [SMILES: O[C@H]1CNCC[C@H]1Nc1nc(-c2ccnc(Nc3ncccc3F)c2)nc2cncc(C3CCC3)c12] | [B4] | 487 [M + H] | 1H NMR (400 MHz, METHANOL-d4) δ ppm 9.16 (s, 1 H) 8.80 (dd, J = 1.51, 0.75 Hz, 1 H) 8.61 (d, J = 0.75 Hz, 1 H) 8.50-8.55 (m, 1 H) 8.44 (dd, J = 6.53, 1.51 Hz, 1 H) 8.36 (dd, J = 5.14, 1.13 Hz, 1 H) 7.91 (ddd, J = 10.73, 8.22, 1.38 Hz, 1 H) 7.37 (ddd, J = 8.41, 4.89, 3.76 Hz, 1 H) 4.80 (dd, J = 4.64, 3.14 Hz, 1 H) 4.41 (br. s., 1 H) 4.25 (quin, J = 8.28 Hz, 1 H) 3.38-3.59 (m, 4 H) 2.67-2.83 (m, 2 H) 2.36-2.60 (m, 3 H) 2.14-2.31 (m, 2 H) 1.98-2.09 (m, 1 H) | rac-(3S,4R)-4-{5-Cyclobutyl-2-[2-(3-fluoro-pyridin-2-ylamino)-pyridin-4-yl]-pyrido[3,4-d]pyrimidin-4-ylamino}-piperidin-3-ol |
| 293 | 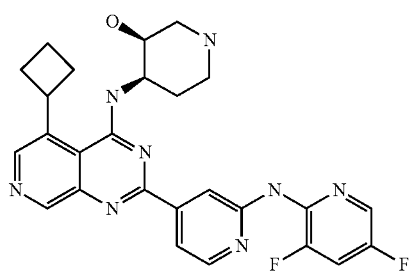 [SMILES: O[C@H]1CNCC[C@H]1Nc1nc(-c2ccnc(Nc3ncc(F)cc3F)c2)nc2cncc(C3CCC3)c12] | [B4] | 505 [M + H] | 1H NMR (400 MHz, METHANOL-d4) δ ppm 9.03 (s, 1 H) 8.66-8.70 (m, 1 H) 8.50 (d, J = 0.75 Hz, 1 H) 8.29-8.36 (m, 2 H) 8.22 (d, J = 2.51 Hz, 1 H) 7.78-7.91 (m, 1 H) 4.80 (dd, J = 4.64, 3.14 Hz, 1 H) 4.27 (br. s., 1 H) 4.13 (t, J = 8.16 Hz, 1 H) 3.25-3.46 (m, 4 H) 2.53-2.71 (m, 2 H) 2.25-2.47 (m, 3 H) 2.03-2.18 (m, 2 H) 1.84-1.98 (m, 1 H) | rac-(3S,4R)-4-{5-Cyclobutyl-2-[2-(3,5-difluoro-pyridin-2-ylamino)-pyridin-4-yl]-pyrido[3,4-d]pyrimidin-4-ylamino}-piperidin-3-ol |
| 294 | 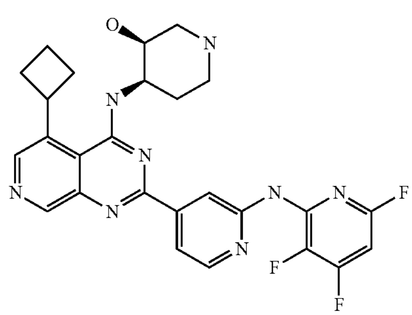 [SMILES: O[C@H]1CNCC[C@H]1Nc1nc(-c2ccnc(Nc3nc(F)cc(F)c3F)c2)nc2cncc(C3CCC3)c12] | [B4] | 523 [M + H] | 1H NMR (400 MHz, METHANOL-d4) δ ppm 9.16 (s, 1 H) 8.97 (d, J = 1.51 Hz, 1 H) 8.61 (s, 1 H) 8.50-8.57 (m, 1 H) 8.39 (dd, J = 6.15, 1.63 Hz, 1 H) 6.97 (ddd, J = 9.22, 3.95, 1.88 Hz, 1 H) 4.93 (br. s., 1 H) 4.41 (br. s., 1 H) 4.26 (quin, J = 8.28 Hz, 1 H) 3.35-3.59 (m, 4 H) 2.66-2.84 (m, 2 H) 2.36-2.60 (m, 3 H) 2.14-2.32 (m, 2 H) 1.99-2.10 (m, 1 H) | rac-(3S,4R)-4-{5-Cyclobutyl-2-[2-(3,4,6-trifluoro-pyridin-2-ylamino)-pyridin-4-yl]-pyrido[3,4-d]pyrimidin-4-ylamino}-piperidin-3-ol |
| 295 | 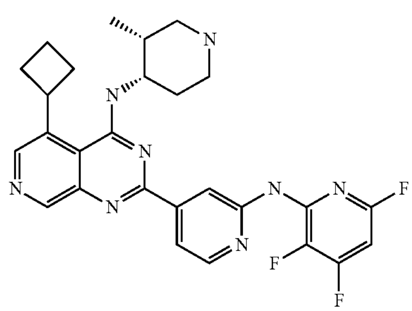 [SMILES: C[C@@H]1CNCC[C@@H]1Nc1nc(-c2ccnc(Nc3nc(F)cc(F)c3F)c2)nc2cncc(C3CCC3)c12] | [B4] | 521 [M + H] | 1H NMR (400 MHz, METHANOL-d4) δ ppm 9.17 (s, 1 H) 8.98-9.06 (m, 1 H) 8.63 (d, J = 1.00 Hz, 1 H) 8.45-8.55 (m, 1 H) 8.33 (dd, J = 6.02, 1.51 Hz, 1 H) 6.87-6.95 (m, 1 H) 4.99-5.08 (m, 1 H) 4.35-4.48 (m, 1 H) 3.47 (d, J = 3.76 Hz, 4 H) 2.84 (br. s., 1 H) 2.69 (dd, J = 7.78, 3.51 Hz, 2 H) 2.47 (d, J = 10.54 Hz, 2 H) 2.18-2.41 (m, 3 H) 2.00-2.13 (m, 1 H) 1.27 (d, J = 7.28 Hz, 3 H) | {5-Cyclobutyl-2-[2-(3,4,6-trifluoro-pyridin-2-ylamino)-pyridin-4-yl]-pyrido[3,4-d]pyrimidin-4-yl}-(rac-(3R,4S)-3-methyl-piperidin-4-yl)-amine |

TABLE A-continued

| Ex | Structure | Scheme | LCMS | 1H-NMR | Name |
|---|---|---|---|---|---|
| 296 | 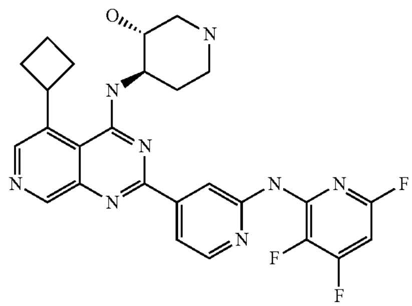 [SMILES: O[C@@H]1CNCC[C@H]1Nc1nc(-c2ccnc(Nc3nc(F)cc(F)c3F)c2)nc2cncc(C3CCC3)c12] | [B4] | 523 [M + H] | 1H NMR (400 MHz, METHANOL-d4) δ ppm 9.02 (s, 1 H) 8.83-8.90 (m, 1 H) 8.45 (s, 1 H) 8.36-8.42 (m, 1 H) 8.14-8.22 (m, 1 H) 6.71-6.79 (m, 1 H) 4.77-4.83 (m, 1 H) 4.48-4.58 (m, 1 H) 4.31 (s, 1 H) 4.12(d, J = 4.02 Hz, 1 H) 3.46-3.54 (m, 1 H) 3.38 (d, J = 1.51 Hz, 1 H) 2.97-3.04 (m, 1 H) 2.63-2.77 (m, 2 H) 2.54 (td, J = 7.28, 4.02 Hz, 1 H) 2.32-2.45 (m, 1 H) 2.18-2.31 (m, 1 H) 2.06-2.18 (m, 1 H) 1.76-1.95 (m, 2 H) | rac-(3R,4R)-4-{5-Cyclobutyl-2-[2-(3,4,6-trifluoro-pyridin-2-ylamino)-pyridin-4-yl]-pyrido[3,4-d]pyrimidin-4-ylamino}-piperidin-3-ol |
| 297 | 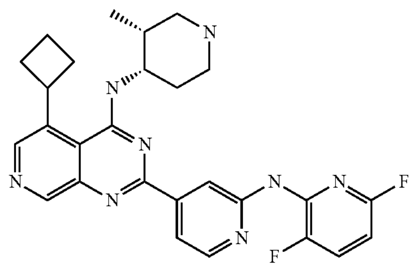 [SMILES: C[C@@H]1CNCC[C@@H]1Nc1nc(-c2ccnc(Nc3nc(F)ccc3F)c2)nc2cncc(C3CCC3)c12] | [B4] | 503 [M + H] | 1H NMR (400 MHz, METHANOL-d4) δ ppm 9.18 (s, 1 H) 8.97 (d, J = 0.75 Hz, 1 H) 8.64 (s, 1 H) 8.54 (d, J = 6.27 Hz, 1 H) 8.40 (dd, J = 6.27, 1.51 Hz, 1 H) 7.97 (td, J = 9.03, 6.02 Hz, 1 H) 6.93 (dt, J = 8.78, 2.51 Hz, 1 H) 5.04 (d, J = 4.27 Hz, 1 H) 4.42 (s, 1 H) 3.36-3.55 (m, 4 H) 2.84 (dd, J = 6.78, 3.51 Hz, 1 H) 2.69 (td, J = 7.28, 3.26 Hz, 2 H) 2.41-2.56 (m, 2 H) 2.19-2.41 (m, 3 H) 2.01-2.12 (m, 1 H) 1.27 (d, J = 7.28 Hz, 3 H) | {5-Cyclobutyl-2-[2-(3,6-difluoro-pyridin-2-ylamino)-pyridin-4-yl]-pyrido[3,4-d]pyrimidin-4-yl}-((3R,4S)-3-methyl-piperidin-4-yl)-amine or enantiomer |
| 298 | 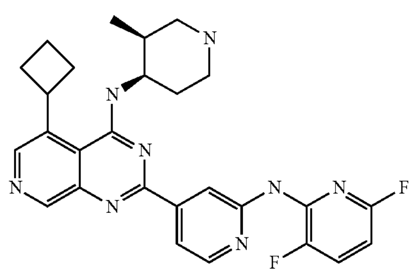 [SMILES: C[C@H]1CNCC[C@H]1Nc1nc(-c2ccnc(Nc3nc(F)ccc3F)c2)nc2cncc(C3CCC3)c12] | [B4] | 503 [M + H] | 1H NMR(400 MHz, METHANOL-d4) δ ppm 9.17 (s, 1 H) 9.01 (d, J = 1.00 Hz, 1 H) 8.64 (s, 1 H) 8.53 (d, J = 6.27 Hz, 1 H) 8.37 (dd, J = 6.27, 1.51 Hz, 1 H) 7.94 (td, J = 9.16, 6.02 Hz, 1 H) 6.89 (dt, J = 8.72, 2.42 Hz, 1 H) 5.04 (dt, J = 8.34, 4.24 Hz, 1 H) 4.41 (t, J = 8.16 Hz, 1 H) 3.37-3.55 (m, 4 H) 2.78-2.89 (m, 1 H) 2.69 (dtd, J = 11.17, 7.53, 7.53, 3.64 Hz, 2 H) 2.38-2.56 (m, 2 H) 2.20-2.36 (m, 3 H) 1.99-2.15 (m, 1 H) 1.27 (d, J = 7.28 Hz, 3 H) | {5-Cyclobutyl-2-[2-(3,6-difluoro-pyridin-2-ylamino)-pyridin-4-yl]-pyrido[3,4-d]pyrimidin-4-yl}-((3S,4R)-3-methyl-piperidin-4-yl)-amine or enantiomer |
| 299 | 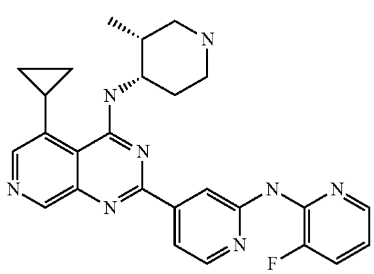 [SMILES: C[C@@H]1CNCC[C@@H]1Nc1nc(-c2ccnc(Nc3ncccc3F)c2)nc2cncc(C3CC3)c12] | [B4] | 471 [M + H] | 1H NMR (400 MHz, METHANOL-d4) δ ppm 9.15 (d, J = 0.75 Hz, 1 H) 8.79 (d, J = 0.75 Hz, 1 H) 8.58 (d, J = 1.00 Hz, 1 H) 8.50 (d, J = 6.52 Hz, 1 H) 8.41 (dd, J = 6.53, 1.51 Hz, 1 H) 8.34 (dd, J = 5.14, 1.13 Hz, 1 H) 7.89 (ddd, J = 10.79, 8.28, 1.25 Hz, 1 H) 7.34 (ddd, J = 8.41, 4.89, 3.76 Hz, 1 H) 5.04 (dt, J = 7.78, 4.14 Hz, 1 H) 3.50 (dd, J = 13.18, 3.89 Hz, 1 H) 3.38 (t, J = 5.90 Hz, 2 H) 3.23 (dd, J = 13.30, 7.78 Hz, 1 H) 2.79 (td, J = 7.40, 3.76 Hz, 1 H) 2.60 (t, J = 5.27 Hz, 1 H) 2.32-2.43 (m, 1 H) 2.21-2.31 (m, 1 H) 1.34-1.43 (m, 2 H) 1.17-1.26 (m, 5 H) | {5-Cyclopropyl-2-[2-(3-fluoro-pyridin-2-ylamino)-pyridin-4-yl]-pyrido[3,4-d]pyrimidin-4-yl}-(rac-(3R,4S)-3-methyl-piperidin-4-yl)-amine |

TABLE A-continued

| Ex | Structure | Scheme | LCMS | 1H-NMR | Name |
|---|---|---|---|---|---|
| 300 | 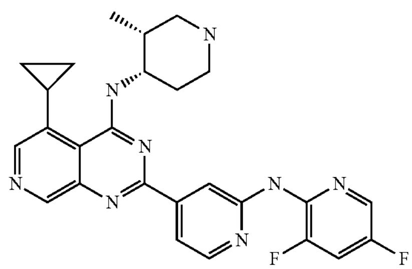 [SMILES: C[C@@H]1CNCC[C@@H]1Nc1nc(-c2ccnc(Nc3ncc(F)cc3F)c2)nc2cncc(C3CC3)c12] | [B4] | 489 [M + H] | 1H NMR(400 MHz, METHANOL-d4) δ ppm 9.15 (d, J = 0.75 Hz, 1 H) 8.80 (dd, J = 1.51, 0.75 Hz, 1 H) 8.58 (d, J = 1.00 Hz, 1 H) 8.44 (d, J = 0.75 Hz, 1 H) 8.39-8.42 (m, 1 H) 8.31 (d, J = 2.51 Hz, 1 H) 7.95 (ddd, J = 10.48, 8.09, 2.51 Hz, 1 H) 5.04 (dt, J = 7.84, 3.98 Hz, 1 H) 3.45-3.53 (m, 1 H) 3.38 (t, J = 6.15 Hz, 2 H) 3.23 (dd, J = 13.30, 7.78 Hz, 1 H) 2.77 (td, J = 7.28, 3.51 Hz, 1 H) 2.59 (t, J = 5.27 Hz, 1 H) 2.32-2.44 (m, 1 H) 2.27 (d, J = 3.76 Hz, 1 H) 1.33-1.41 (m, 2 H) 1.18-1.26 (m, 5 H) | {5-Cyclopropyl-2-[2-(3,5-difluoro-pyridin-2-ylamino)-pyridin-4-yl]-pyrido[3,4-d]pyrimidin-4-yl}-(rac-(3R,4S)-3-methyl-piperidin-4-yl)-amine |
| 301 | 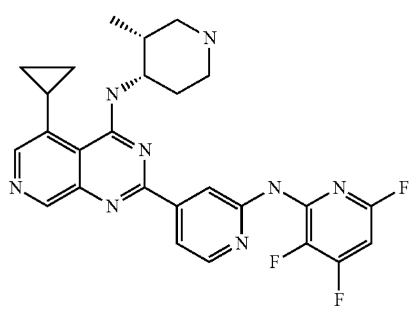 [SMILES: C[C@@H]1CNCC[C@@H]1Nc1nc(-c2ccnc(Nc3nc(F)cc(F)c3F)c2)nc2cncc(C3CC3)c12] | [B4] | 507 [M + H] | 1H NMR (400 MHz, METHANOL-d4) δ ppm 9.10-9.16 (m, 1 H) 9.01-9.06 (m, 1 H) 8.53-8.58 (m, 1 H) 8.47-8.53 (m, 1 H) 8.28-8.34 (m, 1 H) 6.83-6.92 (m, 1 H) 5.05 (dt, J = 7.78, 3.89 Hz, 1 H) 3.42-3.50 (m, 1 H) 3.33-3.39 (m, 2 H) 3.21 (dd, J = 13.30, 7.78 Hz, 1 H) 2.78 (tt, J = 7.40, 3.64 Hz, 1 H) 2.54-2.65 (m, 1 H) 2.32-2.44 (m, 1 H) 2.27 (d, J = 3.76 Hz, 1 H) 1.32-1.42 (m, 2 H) 1.16-1.26 (m, 5 H) | {5-Cyclopropyl-2-[2-(3,4,6-trifluoro-pyridin-2-ylamino)-pyridin-4-yl]-pyrido[3,4-d]pyrimidin-4-yl}-(rac-(3R,4S)-3-methyl-piperidin-4-yl)-amine |
| 302 | 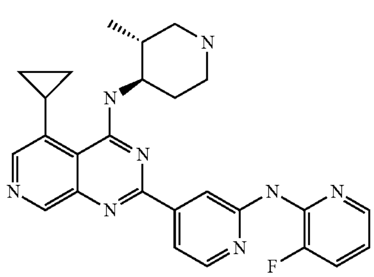 [SMILES: C[C@@H]1CNCC[C@H]1Nc1nc(-c2ccnc(Nc3ncccc3F)c2)nc2cncc(C3CC3)c12] | [B4] | 471 [M + H] | 1H NMR (400 MHz, METHANOL-d4) δ ppm 9.12 (d, J = 0.75 Hz, 1 H) 8.78 (d, J = 0.75 Hz, 1 H) 8.56 (d, J = 1.00 Hz, 1 H) 8.49 (d, J = 0.75 Hz, 1 H) 8.41-8.46 (m, 1 H) 8.32-8.37 (m, 1 H) 7.85-7.93 (m, 1 H) 7.30-7.38 (m, 1 H) 4.70 (d, J = 4.02 Hz, 1 H) 3.54-3.64 (m, 2 H) 3.33-3.41 (m, 1 H) 3.02 (t, J = 12.55 Hz, 1 H) 2.49-2.59 (m, 2 H) 2.17-2.32 (m, 1 H) 1.86-2.01 (m, 1 H) 1.33-1.41 (m, 2 H) 1.15-1.25 (m, 5 H) | {5-Cyclopropyl-2-[2-(3-fluoro-pyridin-2-ylamino)-pyridin-4-yl]-pyrido[3,4-d]pyrimidin-4-yl}-(rac-(3R,4R)-3-methyl-piperidin-4-yl)-amine |
| 303 | 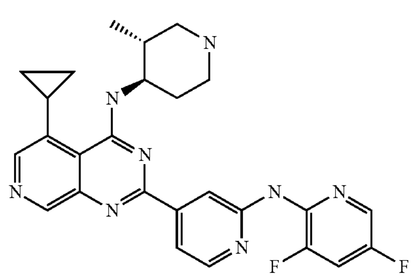 [SMILES: C[C@@H]1CNCC[C@H]1Nc1nc(-c2ccnc(Nc3ncc(F)cc3F)c2)nc2cncc(C3CC3)c12] | [B4] | 489 [M + H] | 1H NMR (400 MHz, METHANOL-d4) δ ppm 9.12 (d, J = 0.75 Hz, 1 H) 8.75-8.80 (m, 1 H) 8.57 (d, J = 1.25 Hz, 1 H) 8.41-8.48 (m, 2 H) 8.32 (d, J = 2.51 Hz, 1 H) 7.96 (ddd, J = 10.48, 8.09, 2.51 Hz, 1 H) 4.69 (td, J = 11.17, 4.27 Hz, 1 H) 3.53-3.63 (m, 2 H) 3.36 (d, J = 1.76 Hz, 1 H) 3.02 (t, J = 12.67 Hz, 1 H) 2.47-2.61 (m, 2 H) 2.23 (dd, J = 12.55, 6.02 Hz, 1 H) 1.93 (dd, J = 11.17, 4.64 Hz, 1 H) 1.32-1.40 (m, 2 H) 1.12-1.22 (m, 5 H) | {5-Cyclopropyl-2-[2-(3,5-difluoro-pyridin-2-ylamino)-pyridin-4-yl]-pyrido[3,4-d]pyrimidin-4-yl}-(rac-(3R,4R)-3-methyl-piperidin-4-yl)-amine |

TABLE A-continued

| Ex | Structure | Scheme | LCMS | 1H-NMR | Name |
|---|---|---|---|---|---|
| 304 | 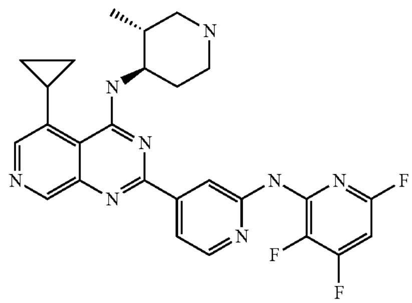 [SMILES: C[C@@H]1CNCC[C@H]1Nc1nc(-c2ccnc(Nc3nc(F)cc(F)c3F)c2)nc2cncc(C3CC3)c12] | [B4] | 507 [M + H] | 1H NMR(400 MHz, METHANOL-d4) δ ppm 9.08-9.14(m, 1 H) 8.94-9.00 (m, 1 H) 8.53-8.56 (m, 1 H) 8.48-8.52 (m, 1 H) 8.31-8.37 (m, 1 H) 6.85-6.94 (m, 1 H) 4.70 (td, J = 11.11, 4.14 Hz, 1 H) 3.51-3.61 (m, 2 H) 3.21-3.28 (m, 1 H) 2.99 (t, J = 12.55 Hz, 1 H) 2.55 (br. s., 2 H) 2.15-2.28 (m, 1 H) 1.84-1.99 (m, 1 H) 1.35 (d, J = 8.53 Hz, 2 H) 1.19 (d, J = 6.53 Hz, 5 H) | {5-Cyclopropyl-2-[2-(3,4,6-trifluoro-pyridin-2-ylamino)-pyridin-4-yl]-pyrido[3,4-d]pyrimidin-4-yl}-(rac-(3R,4R)-3-methyl-piperidin-4-yl)-amine |
| 305 | 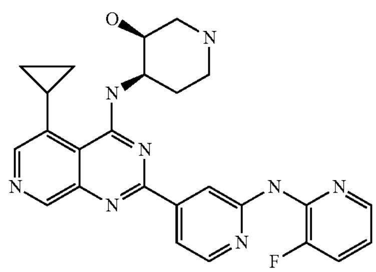 [SMILES: O[C@H]1CNCC[C@H]1Nc1nc(-c2ccnc(Nc3ncccc3F)c2)nc2cncc(C3CC3)c12] | [B4] | 473 [M + H] | 1H NMR (400 MHz, METHANOL-d4) δ ppm 9.15 (d, J = 0.75 Hz, 1 H) 8.81 (d, J = 0.75 Hz, 1 H) 8.57 (d, J = 1.00 Hz, 1 H) 8.52 (s, 1 H) 8.43-8.47 (m, 1 H) 8.35-8.40 (m, 1 H) 7.88-7.98 (m, 1 H) 7.34-7.44 (m, 1 H) 4.93-4.99 (m, 1 H) 4.41 (br. s., 1 H) 3.38-3.60 (m, 4 H) 2.38-2.55 (m, 2 H) 2.20-2.35 (m, 1 H) 1.41-1.49 (m, 2 H) 1.21-1.30 (m, 1 H) 1.07-1.17 (m, 1 H) | rac-(3S,4R)-4-{5-Cyclopropyl-2-[2-(3-fluoro-pyridin-2-ylamino)-pyridin-4-yl]-pyrido[3,4-d]pyrimidin-4-ylamino}-piperidin-3-ol |
| 306 | 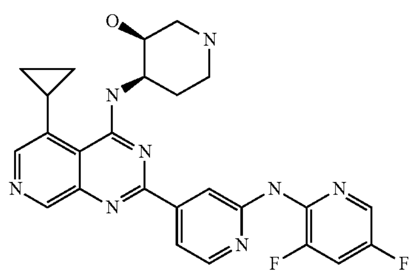 [SMILES: O[C@H]1CNCC[C@H]1Nc1nc(-c2ccnc(Nc3ncc(F)cc3F)c2)nc2cncc(C3CC3)c12] | [B4] | 491 [M + H] | 1H NMR (400 MHz, METHANOL-d4) δ ppm 9.15 (s, 1 H) 8.81 (s, 1 H) 8.57 (d, J = 1.00 Hz, 1 H) 8.46 (dd, J = 2.64, 1.13 Hz, 2 H) 8.35 (d, J = 2.51 Hz, 1 H) 7.95-8.03 (m, 1 H) 4.94 (dd, J = 4.64, 2.89 Hz, 1 H) 4.41 (br. s., 1 H) 3.40-3.58 (m, 4 H) 2.36-2.54 (m, 2 H) 2.27 (dd, J = 12.17, 4.39 Hz, 1 H) 1.45 (dd, J = 8.28, 1.51 Hz, 2 H) 1.25 (d, J = 6.27 Hz, 1 H) 1.13 (dd, J = 5.40, 2.13 Hz, 1 H) | rac-(3S,4R)-4-{5-Cyclopropyl-2-[2-(3,5-difluoro-pyridin-2-ylamino)-pyridin-4-yl]-pyrido[3,4-d]pyrimidin-4-ylamino}-piperidin-3-ol |
| 307 | 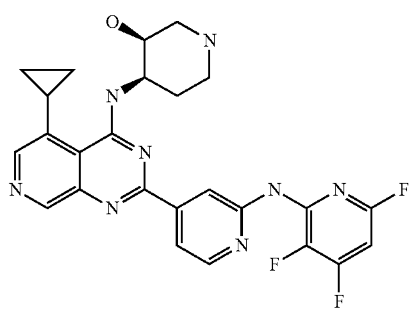 [SMILES: O[C@H]1CNCC[C@H]1Nc1nc(-c2ccnc(Nc3nc(F)cc(F)c3F)c2)nc2cncc(C3CC3)c12] | [B4] | 509 [M + H] | 1H NMR(400 MHz, METHANOL-d4) δ ppm 9.11-9.15 (m, 1 H) 8.96-9.01 (m, 1 H) 8.51-8.57 (m, 2 H) 8.33-8.39 (m, 1 H) 6.93 (ddd, J = 9.03, 4.02, 2.01 Hz, 1 H) 4.94 (dd, J = 4.89, 2.89 Hz, 1 H) 4.41 (br. s., 1 H) 3.38-3.56 (m, 4 H) 2.38-2.53 (m, 2 H) 2.22-2.35 (m, 1 H) 1.45 (dd, J = 8.28, 1.51 Hz, 2 H) 1.22-1.29 (m, 1 H) 1.08-1.15 (m, 1 H) | rac-(3S,4R)-4-{5-Cyclopropyl-2-[2-(3,4,6-trifluoro-pyridin-2-ylamino)-pyridin-4-yl]-pyrido[3,4-d]pyrimidin-4-ylamino}-piperidin-3-ol |
| 308 | 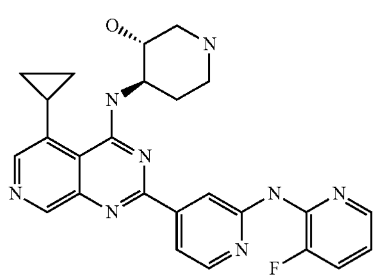 [SMILES: O[C@@H]1CNCC[C@H]1Nc1nc(-c2ccnc(Nc3ncccc3F)c2)nc2cncc(C3CC3)c12] | [B4] | 473 [M + H] | 1H NMR(400 MHz, METHANOL-d4) δ ppm 9.16 (d, J = 0.75 Hz, 1 H) 8.80 (d, J = 0.75 Hz, 1 H) 8.58 (d, J = 1.00 Hz, 1 H) 8.53 (d, J = 6.52 Hz, 1 H) 8.46 (d, J = 1.51 Hz, 1 H) 8.34-8.40 (m, 1 H) 7.87-7.95 (m, 1 H) 7.33-7.41 (m, 1 H) 4.68 (td, J = 9.03, 4.27Hz, 1 H) 4.21-4.30 (m, 1 H) 3.37-3.67 (m, 3 H) 3.17 (dd, J = 12.67, 8.91 Hz, 1 H) 2.79-2.90 (m, 1 H) 2.57-2.69 (m, 1 H) 2.01 (d, J = 10.04 Hz, 1 H) 1.36-1.49 (m, 2H) 1.21 (d, J = 2.76 Hz, 2 H) | rac-(3R,4R)-4-{5-Cyclopropyl-2-[2-(3-fluoro-pyridin-2-ylamino)-pyridin-4-yl]-pyrido[3,4-d]pyrimidin-4-ylamino}-piperidin-3-ol |

TABLE A-continued

| Ex | Structure | Scheme | LCMS | 1H-NMR | Name |
|---|---|---|---|---|---|
| 309 | 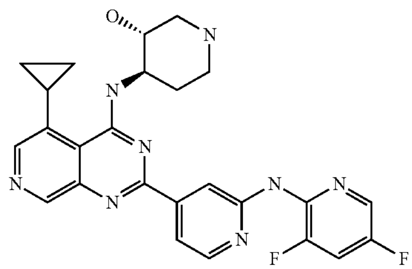 [SMILES: O[C@@H]1CNCC[C@H]1Nc1nc(-c2ccnc(Nc3ncc(F)cc3F)c2)nc2cncc(C3CC3)c12] | [B4] | 491 [M + H] | 1H NMR (400 MHz, METHANOL-d4) δ ppm 9.03 (d, J = 0.75 Hz, 1 H) 8.64-8.70 (m, 1 H) 8.42-8.48 (m, 1 H) 8.29-8.37 (m, 2 H) 8.21 (s, 1 H) 7.82-7.90 (m, 1 H) 4.55 (d, J = 4.02 Hz, 1 H) 4.11 (d, J = 4.02 Hz, 1 H) 3.46-3.53 (m, 1 H) 3.38 (s, 1 H) 3.26-3.32 (m, 1 H) 2.99-3.08 (m, 1 H) 2.65-2.75 (m, 1 H) 2.43-2.53 (m, 1 H) 1.81-1.92 (m, 1 H) 1.28 (d, J = 2.51 Hz, 2 H) 1.09 (dd, J = 4.27, 2.76 Hz, 2 H) | rac-(3R,4R)-4-{5-Cyclopropyl-2-[2-(3,5-difluoro-pyridin-2-ylamino)-pyridin-4-yl]-pyrido[3,4-d]pyrimidin-4-ylamino}-piperidin-3-ol |
| 310 | 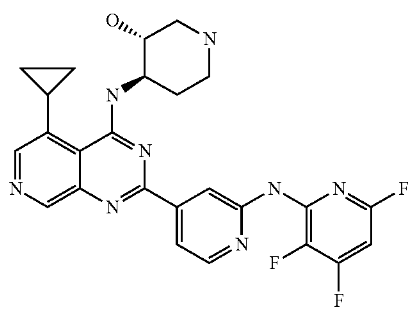 [SMILES: O[C@@H]1CNCC[C@H]1Nc1nc(-c2ccnc(Nc3nc(F)cc(F)c3F)c2)nc2cncc(C3CC3)c12] | [B4] | 509 [M + H] | 1H NMR (400 MHz, METHANOL-d4) δ ppm 9.12-9.19 (m, 1 H) 8.95-8.99 (m, 1 H) 8.56-8.61 (m, 1 H) 8.51-8.56 (m, 1 H) 8.33-8.41 (m, 1 H) 6.91-7.01 (m, 1 H) 4.67 (td, J = 9.16, 4.27 Hz, 1 H) 4.23 (td, J = 8.85, 4.14 Hz, 1 H) 3.60 (d, J = 3.76 Hz, 1 H) 3.47-3.56 (m, 1 H) 3.36-3.41 (m, 1 H) 3.12-3.20 (m, 1 H) 2.79-2.91 (m, 1 H) 2.61 (t, J = 5.52 Hz, 1 H) 1.92-2.04 (m, 1 H) 1.34-1.47 (m, 2 H) 1.16-1.29 (m, 2 H) | rac-(3R,4R)-4-{5-Cyclopropyl-2-[2-(3,4,6-trifluoro-pyridin-2-ylamino)-pyridin-4-yl]-pyrido[3,4-d]pyrimidin-4-ylamino}-piperidin-3-ol |
| 311 | 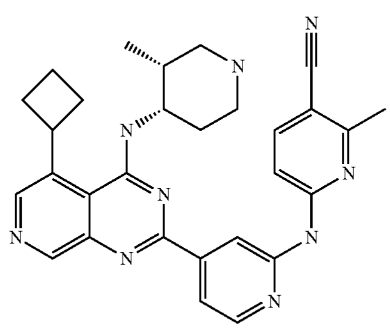 [SMILES: Cc1nc(Nc2cc(-c3nc(N[C@H]4CCNC[C@H]4C)c4c(C5CCC5)cncc4n3)ccn2)ccc1C#N] | [B4] | 506 [M + H] | 1H NMR (400 MHz, DMSO-d6) δ ppm 10.61 (s, 1 H) 9.09 (s, 1 H) 8.73-8.81 (m, 1 H) 8.69 (s, 1 H) 8.54 (s, 1 H) 8.48 (d, J = 5.27 Hz, 1 H) 8.06 (d, J = 8.78 Hz, 1 H) 7.99 (s, 1 H) 7.89-7.95 (m, 1 H) 6.78-6.88 (m, 1 H) 4.87 (br. s., 1 H) 4.41-4.59 (m, 1 H) 3.24 (br. s., 3 H) 2.59-2.71 (m, 4 H) 1.97-2.40 (m, 7 H) 1.80-1.95 (m, 1 H) 1.07-1.13 (m, 3 H) | 6-{4-[5-Cyclobutyl-4-(rac-(3R,4S)-3-methyl-piperidin-4-ylamino)-pyrido[3,4-d]pyrimidin-2-yl]-pyridin-2-ylamino}-2-methyl-nicotinonitrile |
| 312 | 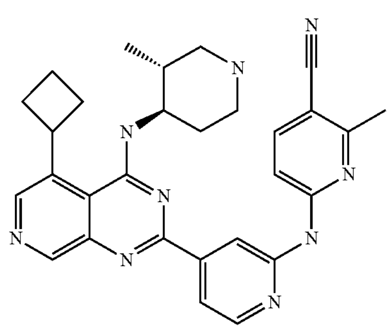 [SMILES: Cc1nc(Nc2cc(-c3nc(N[C@@H]4CCNC[C@H]4C)c4c(C5CCC5)cncc4n3)ccn2)ccc1C#N] | [B4] | 506 [M + H] | 1H NMR (400 MHz, METHANOL-d4) δ ppm 9.14 (s, 1 H) 8.55-8.64 (m, 3 H) 8.42 (dd, J = 6.40, 1.63 Hz, 1 H) 8.16 (d, J = 8.53 Hz, 1 H) 7.34 (d, J = 8.78 Hz, 1 H) 4.80 (d, J = 4.02 Hz, 1 H) 4.45 (t, J = 8.28 Hz, 1 H) 3.55-3.66 (m, 2 H) 3.01-3.12 (m, 1 H) 2.90 (s, 3 H) 2.65-2.74 (m, 2 H) 2.40-2.52 (m, 3 H) 2.27 (s, 2 H) 2.03 (d, J = 10.54 Hz, 2 H) 1.16 (d, J = 6.78 Hz, 3 H) | 6-{4-[5-Cyclobutyl-4-(rac-(3R,4R)-3-methyl-piperidin-4-ylamino)-pyrido[3,4-d]pyrimidin-2-yl]-pyridin-2-ylamino}-2-methyl-nicotinonitrile |

TABLE A-continued

| Ex | Structure | Scheme | Analysis LCMS | 1H-NMR | Name |
|---|---|---|---|---|---|
| 313 | 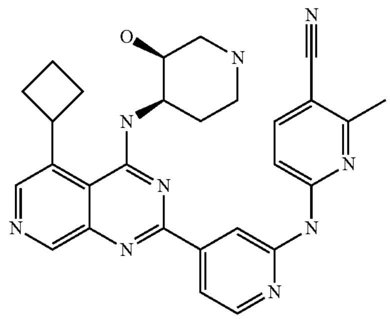 [SMILES: Cc1nc(Nc2cc(-c3nc(N[C@@H]4CCNC[C@@H]4O)c4c(C5CCC5)cncc4n3)ccn2)ccc1C#N] | [B4] | 508 [M + H] | 1H NMR (400 MHz, METHANOL-d4) δ ppm 9.01 (s, 1 H) 8.48 (s, 2 H) 8.43-8.46 (m, 1 H) 8.22-8.26 (m, 1 H) 7.97-8.03 (m, 1 H) 7.24-7.30 (m, 1 H) 4.82 (br. s., 1 H) 4.27 (br. s., 1 H) 4.12 (s, 1 H) 3.29-3.45 (m, 4 H) 2.54-2.69 (m, 2 H) 2.40-2.45 (m, 1 H) 2.23-2.34 (m, 2 H) 2.01-2.17 (m, 2 H) 1.90 (d, J = 9.54 Hz, 1 H) | 6-{4-[5-Cyclobutyl-4-(rac-(3S,4R)-3-hydroxy-piperidin-4-ylamino)-pyrido[3,4-d]pyrimidin-2-yl]-pyridin-2-ylamino}-2-methyl-nicotinonitrile |
| 314 | 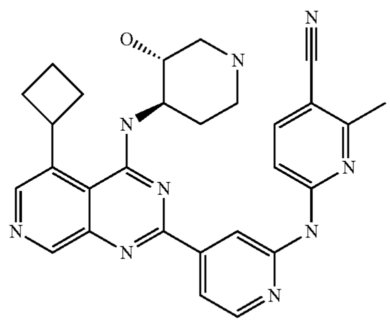 [SMILES: Cc1nc(Nc2cc(-c3nc(N[C@@H]4CCNC[C@H]4O)c4c(C5CCC5)cncc4n3)ccn2)ccc1C#N] | [B4] | 508 [M + H] | 1H NMR(400 MHz, METHANOL-d4) δ ppm 9.00-9.05 (m, 1 H) 8.43-8.51 (m, 3 H) 8.22-8.29 (m, 1 H) 7.99-8.05 (m, 1 H) 7.20-7.27 (m, 1 H) 4.55 (td, J = 9.41, 4.27 Hz, 1 H) 4.31 (t, J = 8.28 Hz, 1 H) 4.14 (td, J = 9.16, 4.27 Hz, 1 H) 3.50 (dd, J = 12.55, 4.27 Hz, 1 H) 3.36-3.44 (m, 1 H) 3.26-3.34 (m, 1 H) 2.99-3.09 (m, 1 H) 2.75 (s, 3 H) 2.60-2.73 (m, 2 H) 2.49-2.59 (m, 1 H) 2.09-2.43 (m, 3 H) 1.84 (s, 2 H) | 6-{4-[5-Cyclobutyl-4-(rac-(3R,4R)-3-hydroxy-piperidin-4-ylamino)-pyrido[3,4-d]pyrimidin-2-yl]-pyridin-2-ylamino}-2-methyl-nicotinonitrile |
| 315 | 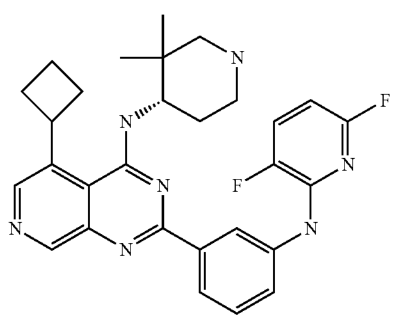 [SMILES: CC1(C)CNCC[C@@H]1Nc1nc(-c2cccc(Nc3nc(F)ccc3F)c2)nc2cncc(C3CCC3)c12] | [B4], [E4] | 516 [M + H] | 1H NMR (400 MHz, METHANOL-d4) δ ppm 8.98-9.01 (m, 1 H) 8.79-8.82 (m, 1 H) 8.47-8.51 (m, 1 H) 8.00-8.07 (m, 1 H) 7.66-7.72 (m, 1 H) 7.36-7.52 (m, 2 H) 6.23-6.30 (m, 1 H) 4.89-4.97 (m, 1 H) 4.15-4.27 (m, 1 H) 3.37-3.43 (m, 1 H) 3.01-3.19 (m, 3 H) 2.48-2.59 (m, 2 H) 2.28-2.47 (m, 2 H) 2.19 (d, J = 2.76 Hz, 1 H) 2.09 (d, J = 9.29 Hz, 1 H) 1.90-2.01 (m, 2 H) 1.41 (s, 3 H) 1.25 (s, 3 H) | {5-Cyclobutyl-2-[3-(3,6-difluoro-pyridin-2-ylamino)-phenyl]-pyrido[3,4-d]pyrimidin-4-yl}-((S)-3,3-dimethyl-piperidin-4-yl)-amine |
| 316 | 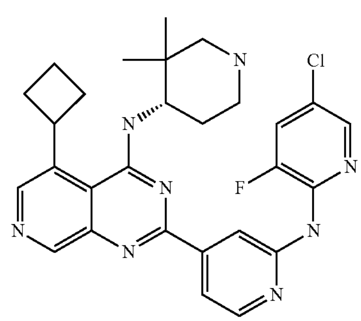 [SMILES: CC1(C)CNCC[C@@H]1Nc1nc(-c2ccnc(Nc3ncc(Cl)cc3F)c2)nc2cncc(C3CCC3)c12] | [B4], [E4] | 534 [M + H] | 1H NMR (400 MHz, METHANOL-d4) δ ppm 9.15-9.20 (m, 1 H) 8.81-8.86 (m, 1 H) 8.66-8.70 (m, 1 H) 8.45-8.53 (m, 2 H) 8.36-8.41 (m, 1 H) 8.06-8.12 (m, 1 H) 5.03 (dd, J = 11.80, 4.27 Hz, 1 H) 4.34 (t, J = 8.28 Hz, 1 H) 3.52-3.60 (m, 1 H) 3.36-3.42 (m, 2 H) 3.23 (d, J = 13.30 Hz, 1 H) 2.62-2.73 (m, 2 H) 2.39-2.61 (m, 2 H) 2.04-2.32 (m, 4 H) 1.41 (s, 3 H) 1.25 (s, 3 H) | {2-[2-(5-Chloro-3-fluoro-pyridin-2-ylamino)-pyridin-4-yl]-5-cyclobutyl-pyrido[3,4-d]pyrimidin-4-yl}-((S)-3,3-dimethyl-piperidin-4-yl)-amine |

TABLE A-continued

| Ex | Scheme | LCMS | 1H-NMR | Name |
|---|---|---|---|---|
| 317 | [B4], [E4] | 506 [M + H] | 1H NMR (400 MHz, METHANOL-d4) δ ppm 9.14-9.18 (m, 1 H) 8.63-8.69 (m, 2 H) 8.53-8.58 (m, 1 H) 8.35-8.40 (m, 1 H) 8.04-8.13 (m, 1 H) 7.61-7.74 (m, 2 H) 5.04 (dd, J = 11.80, 4.27 Hz, 1 H) 4.34 (s, 1 H) 3.49-3.58 (m, 1 H) 3.36-3.45 (m, 2 H) 3.23 - 3.30 (m, 1 H) 2.67 (td, J = 8.03, 3.01 Hz, 2 H) 2.38-2.60 (m, 2 H) 2.06-2.36 (m, 4 H) 1.41 (s, 3 H) 1.25 (s, 3 H) | 6-{4-[5-Cyclobutyl-4-((S)-3,3-dimethyl-piperidin-4-ylamino)-pyrido[3,4-d]pyrimidin-2-yl]-pyridin-2-ylamino}-pyridine-2-carbonitrile |
| 318 | [B4], [E4] | 549 [M + H] | 1H NMR (400 MHz, METHANOL-d4) δ ppm 9.12-9.17(m, 1 H) 8.70-8.74 (m, 1 H) 8.63-8.67 (m, 2 H) 8.58-8.61 (m, 1 H) 8.47-8.53 (m, 1 H) 7.84-7.89 (m, 1 H) 7.71-7.77 (m, 1 H) 7.61-7.70 (m, 1 H) 7.52-7.58 (m, 1 H) 5.07 (dd, J = 11.80, 4.27 Hz, 1 H) 4.21-4.43 (m, 1 H) 3.57 (d, J = 12.80 Hz, 1 H) 3.37-3.46 (m, 2 H) 3.32 (s, 1 H) 2.60-2.73 (m, 2 H) 2.36-2.60 (m, 2 H) 2.07-2.35 (m, 4 H) 1.42 (s, 3 H) 1.27 (s, 3 H) | {5-Cyclobutyl-2-[2-(8-fluoro-quinolin-2-ylamino)-pyridin-4-yl]-pyrido[3,4-d]pyrimidin-4-yl}-((S)-3,3-dimethyl-piperidin-4-yl)-amine |
| 319 | [B4], [E4] | 520 [M + H] | 1H NMR(400 MHz, METHANOL-d4) δ ppm 9.17 (d, J = 0.75 Hz, 1 H) 8.85 (s, 1 H) 8.61 (d, J = 1.00 Hz, 1 H) 8.48-8.54 (m, 2 H) 8.40 (d, J = 2.01 Hz, 1 H) 8.06-8.13 (m, 1 H) 5.07 (dd, J = 11.80, 4.52 Hz, 1 H) 3.56 (br. s., 1 H) 3.36-3.42 (m, 2 H) 3.21-3.28 (m, 1 H) 2.58 (t, J = 6.53 Hz, 1 H) 2.30 (dd, J = 14.18, 3.39 Hz, 1H) 2.17 (d, J = 3.51 Hz, 1 H) 1.41-1.51 (m, 1 H) 1.29-1.39 (m, 5 H) 1.25 (s, 3 H) 1.13-1.22 (m, 1 H) | {2-[2-(5-Chloro-3-fluoro-pyridin-2-ylamino)-pyridin-4-yl]-5-cyclopropyl-pyrido[3,4-d]pyrimidin-4-yl}-((S)-3,3-dimethyl-piperidin-4-yl)-amine |
| 320 | [B4], [E4] | 524 [M + H] | 1H NMR (400 MHz, METHANOL-d4) δ ppm 9.18 (s, 1 H) 8.97 (d, J = 0.75 Hz, 1 H) 8.67 (dd, J = 5.40, 1.38 Hz, 2 H) 8.58 (s, 1 H) 8.49-8.54 (m, 1 H) 8.20-8.27 (m, 1 H) 5.01-5.06 (m, 1 H) 4.81-4.83 (m, 1 H) 4.28-4.39 (m, 1 H) 3.53-3.59 (m, 1 H) 3.38-3.40 (m, 1 H) 3.19-3.27 (m, 1 H) 2.61-2.73 (m, 2 H) 2.38-2.61 (m, 2 H) 2.07 (s, 4 H) 1.41 (s, 3 H) 1.25 (s, 3 H) | 6-{4-[5-Cyclobutyl-4-((S)-3,3-dimethyl-piperidin-4-ylamino)-pyrido[3,4-d]pyrimidin-2-yl]-pyridin-2-ylamino}-5-fluoro-nicotinonitrile |

TABLE A-continued

| Ex | Structure | Scheme | LCMS | 1H-NMR | Name |
|---|---|---|---|---|---|
| 321 | 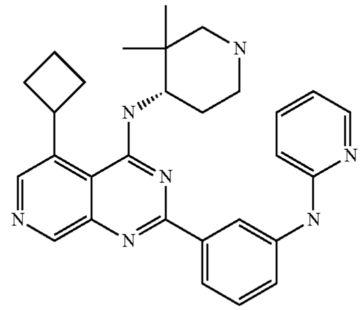 [SMILES: CC1(C)CNCC[C@@H]1Nc1nc(-c2cccc(Nc3ccccn3)c2)nc2cncc(C3CCC3)c12] | [B4], [E4] | 480 [M + H] | 1H NMR (400 MHz, METHANOL-d4) δ ppm 9.16 (s, 1 H) 8.62 (s, 1 H) 8.53 (d, J = 1.76 Hz, 2 H) 8.07-8.16 (m, 1 H) 7.97-8.02 (m, 1 H) 7.76 (s, 1 H) 7.61-7.69 (m, 1 H) 7.35 (d, J = 9.03 Hz, 1 H) 7.13 (s, 1 H) 5.05 (dd, J = 11.92, 4.39 Hz, 1 H) 4.35 (s, 1 H) 3.52 (d, J = 1.76 Hz, 1 H) 3.25-3.33 (m, 2 H) 3.18-3.25 (m, 1 H) 2.67 (ddt, J = 11.70, 7.75, 3.83, 3.83 Hz, 2 H) 2.36-2.58 (m, 2 H) 2.05-2.29 (m, 4 H) 1.40 (s, 3 H) 1.23 (s, 3 H) | {5-Cyclobutyl-2-[3-(pyridin-2-ylamino)-phenyl]-pyrido[3,4-d]pyrimidin-4-yl}-((S)-3,3-dimethyl-piperidin-4-yl)-amine |
| 323 | 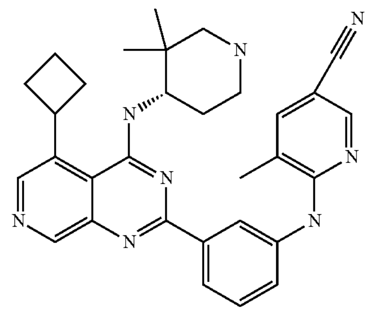 [SMILES: Cc1cc(C#N)cnc1Nc1cccc(-c2nc(N[C@H]3CCNCC3(C)C)c3c(C4CCC4)cncc3n2)c1] | [B4], [E4] | 520 [M + H] | 1H NMR (400 MHz, METHANOL-d4) δ ppm 9.04 (s, 1 H) 8.92 (d, J = 0.75 Hz, 1 H) 8.59 (d, J = 1.76 Hz, 1 H) 8.54 (s, 1 H) 8.36-8.46 (m, 2 H) 8.04 (dd, J = 2.13, 0.88 Hz, 1 H) 4.92 (dd, J = 11.80, 4.27 Hz, 1 H) 4.21 (quin, J = 8.28 Hz, 1 H) 3.41 (br. s., 1 H) 3.25-3.31 (m, 2 H) 3.11-3.17 (m, 1 H) 2.50-2.61 (m, 2 H) 2.47 (s, 3 H) 2.28-2.45 (m, 2 H) 1.94-2.19 (m, 4 H) 1.28 (s, 3 H) 1.09-1.17 (m, 3 H) | 6-{4-[5-Cyclobutyl-4-((S)-3,3-dimethyl-piperidin-4-ylamino)-pyrido[3,4-d]pyrimidin-2-yl]-pyridin-2-ylamino}-5-methyl-nicotinonitrile |
| 324 | 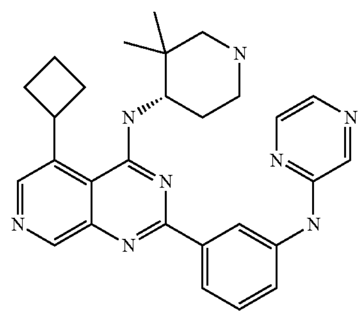 [SMILES: CC1(C)CNCC[C@@H]1Nc1nc(-c2cccc(Nc3cnccn3)c2)nc2cncc(C3CCC3)c12] | [B4], [E4] | 481 [M + H] | 1HNMR (400 MHz, METHANOL-d4) δ ppm 9.01 (s, 1 H) 8.67 (t, J = 1.88 Hz, 1 H) 8.51 (d, J = 0.75 Hz, 1 H) 8.15 (d, J = 1.51 Hz, 1 H) 8.07 (dd, J = 2.76, 1.51 Hz, 1 H) 8.00 (dt, J = 8.03, 1.13 Hz, 1 H) 7.83 (d, J = 3.01 Hz, 1 H) 7.71-7.77 (m, 1 H) 7.42 (t, J = 7.91 Hz, 1 H) 4.94 (dd, J = 11.80, 4.27 Hz, 1 H) 4.18-4.28 (m, 1 H) 3.61-3.66 (m, 1 H) 3.38-3.45 (m, 1 H) 3.03-3.17 (m, 2 H) 2.30-2.61 (m, 4 H) 1.93-2.22 (m, 4 H) 1.28 (s, 3 H) 1.15 (s, 3 H) | 5-Cyclobutyl-N-[(4S)-3,3-dimethyl-4-piperidyl]-2-[3-(pyrazin-2-ylamino)phenyl]pyrido[3,4-d]pyrimidin-4-amine |
| 325 | 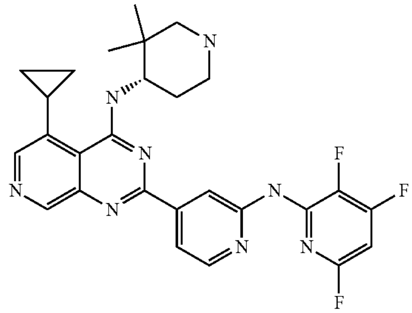 [SMILES: CC1(C)CNCC[C@@H]1Nc1nc(-c2ccnc(Nc3nc(F)cc(F)c3F)c2)nc2cncc(C3CC3)c12] | [B4], [E4] | 521 [M + H] | 1H NMR (400 MHz, METHANOL-d4) δ ppm 9.17 (s, 1 H) 8.95 (dd, J = 1.51, 0.75 Hz, 1 H) 8.59 (d, J = 1.00 Hz, 1 H) 8.56 (d, J = 6.27 Hz, 1 H) 8.46 (dd, J = 6.40, 1.63 Hz, 1 H) 7.01 (ddd, J = 9.16, 4.02, 1.88 Hz, 1 H) 5.07 (dd, J = 11.80, 4.27 Hz, 1 H) 3.57 (d, J = 13.05 Hz, 1 H) 3.36-3.41 (m, 1 H) 3.27-3.33 (m, 1 H) 3.18-3.27 (m, 1 H) 2.58 (s, 1 H) 2.27-2.36 (m, 1 H) 2.19 (s, 1 H) 1.42-1.52 (m, 1 H) 1.30-1.39 (m, 5 H) 1.25 (s, 3 H) 1.18 (d, J = 5.52 Hz, 1 H) | 5-Cyclopropyl-N-[(4S)-3,3-dimethyl-4-piperidyl]-2-[2-[(3,4,6-trifluoro-2-pyridyl)amino]-4-pyridyl]pyrido[3,4-d]pyrimidin-4-amine |

| Ex | Structure | Scheme | Analysis | | Name |
|---|---|---|---|---|---|
| | | | LCMS | 1H-NMR | |
| 326 | 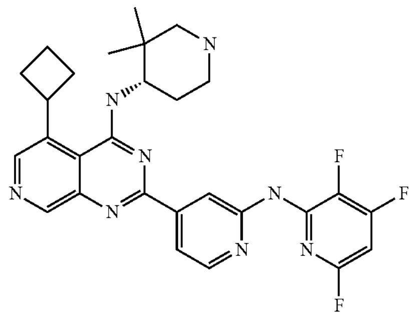 [SMILES: CC1(C)CNCC[C@@H]1Nc1nc(-c2ccnc(Nc3nc(F)cc(F)c3F)c2)nc2cncc(C3CCC3)c12] | [B4], [E4] | 535 [M + H] | 1H NMR(400 MHz, METHANOL-d4) δ ppm 9.17 (s, 1 H) 8.95-9.01 (m, 1 H) 8.65 (d, J = 1.00 Hz, 1 H) 8.53 (d, J = 6.02 Hz, 1 H) 8.37 (dd, J = 6.02, 1.51 Hz, 1 H) 6.85-6.98 (m, 1 H) 5.00-5.08 (m, 1 H) 4.27-4.40 (m, 1 H) 3.49-3.60 (m, 1 H) 3.38 (s, 1 H) 3.22-3.32 (m, 1 H) 3.21 (s, 1 H) 2.41-2.72 (m, 4 H) 2.06-2.34 (m, 4 H) 1.41 (s, 3 H) 1.25 (s, 3 H) | 5-Cyclobutyl-N-[(4S)-3,3-dimethyl-4-piperidyl]-2-[2-[(3,4,6-trifluoro-2-pyridyl)amino]-4-pyridyl]pyrido[3,4-d]pyrimidin-4-amine |
| 327 | 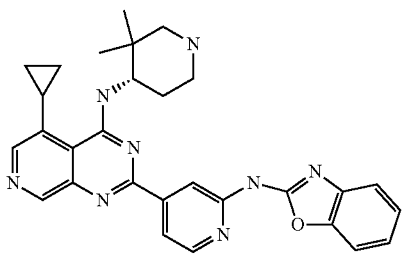 [SMILES: CC1(C)CNCC[C@@H]1Nc1nc(-c2ccnc(Nc3nc4ccccc4o3)c2)nc2cncc(C3CC3)c12] | [B4], [E4] | 507 [M + H] | 1H NMR (400 MHz, METHANOL-d4) δ ppm 9.05 (s, 1 H) 8.76 (s, 1 H) 8.43 (s, 1 H) 8.40 (d, J = 6.02 Hz, 1 H) 8.18 (dd, J = 6.02, 1.25 Hz, 1 H) 7.41-7.49 (m, 2 H) 7.17-7.32 (m, 2 H) 4.98 (dd, J = 11.80, 4.27 Hz, 1 H) 3.37-3.47 (m, 1 H) 3.08-3.15 (m, 1 H) 2.44 (br. s., 1 H) 2.16-2.25 (m, 1 H) 1.95-2.09 (m, 1 H) 1.28-1.37 (m, 1 H) 1.22 (s, 5 H) 1.17 (s, 3 H) 1.01-1.09 (m, 1 H) | N-[4-[5-Cyclopropyl-4-[[(4S)-3,3-dimethyl-4-piperidyl]amino]pyrido[3,4-d]pyrimidin-2-yl]-2-pyridyl]-1,3-benzoxazol-2-amine |
| 328 | 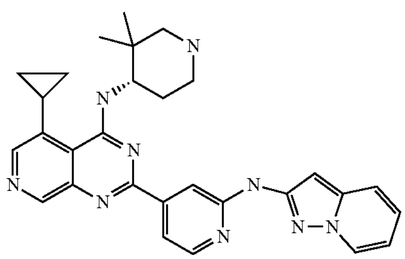 [SMILES: CC1(C)CNCC[C@@H]1Nc1nc(-c2ccnc(Nc3cc4ccccn4n3)c2)nc2cncc(C3CC3)c12] | [B4], [E4] | 506 [M + H] | 1H NMR (400 MHz, METHANOL-d4) δ ppm 9.04 (s, 1 H) 8.54 (d, J = 7.28 Hz, 1 H) 8.47 (s, 1 H) 8.41 (s, 1 H) 8.33 (d, J = 6.53 Hz, 1 H) 8.19 (dd, J = 6.78, 1.51 Hz, 1 H) 7.55 (d, J = 9.03 Hz, 1 H) 7.22-7.29 (m, 1 H) 6.87 (d, J = 1.00 Hz, 1 H) 6.34 (s, 1 H) 4.91-4.98 (m, 1 H) 3.41-3.48 (m, 1 H) 3.26-3.31 (m, 1 H) 3.10-3.16 (m, 1 H) 2.40-2.49 (m, 1 H) 2.14-2.23 (m, 1 H) 1.95-2.09 (m, 1 H) 1.28-1.38 (m, 1 H) 1.22 (s, 5 H) 1.13 (s, 3 H) 1.01-1.09 (m, 1 H) | 5-Cyclopropyl-N-[(4S)-3,3-dimethyl-4-piperidyl]-2-[2-(pyrazolo[1,5-a]pyridin-2-ylamino)-4-pyridyl]pyrido[3,4-d]pyrimidin-4-amine |
| 329 | 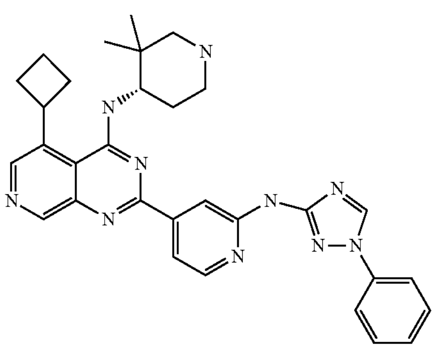 [SMILES: CC1(C)CNCC[C@@H]1Nc1nc(-c2ccnc(Nc3ncn(-c4ccccc4)n3)c2)nc2cncc(C3CCC3)c12] | [B4], [E4] | 547 [M + H] | 1H NMR (400 MHz, METHANOL-d4) δ ppm 9.13-9.19 (m, 2 H) 8.64 (d, J = 1.00 Hz, 1 H) 8.61 (d, J = 1.00 Hz, 1 H) 8.48 (d, J = 6.78 Hz, 1 H) 8.34 (dd, J = 6.65, 1.63 Hz, 1 H) 7.90-7.97 (m, 2 H) 7.56-7.66 (m, 2 H) 7.43-7.53 (m, 1 H) 4.99 (dd, J = 11.80, 4.27 Hz, 1 H) 4.32 (t, J = 8.28 Hz, 1 H) 3.50-3.59 (m, 1 H) 3.33-3.40 (m, 2 H) 3.20 (d, J = 13.30 Hz, 1 H) 2.36-2.71 (m, 4 H) 2.02-2.31 (m, 4 H) 1.39 (s, 3 H) 1.23 (s, 3 H) | 5-Cyclobutyl-N-[(4S)-3,3-dimethyl-4-piperidyl]-2-[2-[(1-phenyl-1,2,4-triazol-3-yl)amino]-4-pyridyl]pyrido[3,4-d]pyrimidin-4-amine |

TABLE A-continued

| Ex | Structure | Scheme | Analysis | | Name |
| --- | --- | --- | --- | --- | --- |
| | | | LCMS | 1H-NMR | |
| 330 | 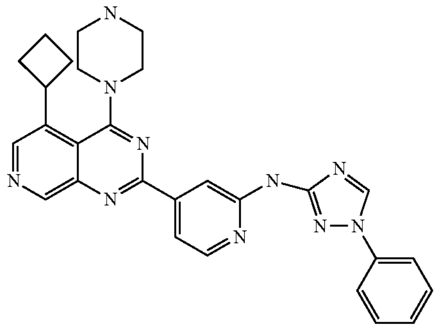 [SMILES: c1ccc(-n2cnc(Nc3cc(-c4nc(N5CCNCC5)c5c(C6CCC6)cncc5n4)ccn3)n2)cc1] | [B4] | 505 [M + H] | 1H NMR (400 MHz, METHANOL-d4) δ ppm 9.12 (s, 1 H) 9.03 (s, 1 H) 8.70 (s, 1 H) 8.62 (s, 1 H) 8.37 (d, J = 6.78Hz, 1 H) 8.16-8.20 (m, 1 H) 7.84 (dd, J = 8.66, 1.13 Hz, 2 H) 7.51 (s, 2H) 7.35-7.43 (m, 1 H) 4.21 - 4.34 (m, 1 H)3.93 (d, J = 4.27 Hz, 4 H) 3.31 -3.40 (m, 2 H) 3.22-3.29 (m, 2 H) 2.45- 2.55 (m, 2 H) 2.09-2.27 (m, 3 H) 1.86- 1.97 (m, 1 H) | 4-(5-Cyclobutyl-4-piperazin-1-yl-pyrido[3,4-d]pyrimidin-2-yl)-N-(1-phenyl-1,2,4-triazol-3-yl)pyridin-2-amine |
| 331 | 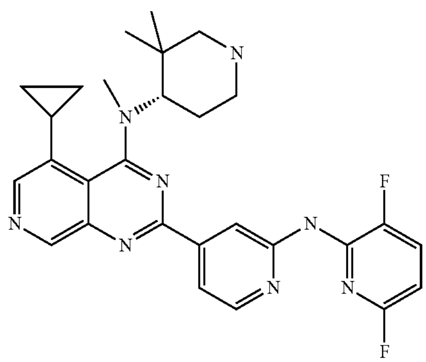 [SMILES: CN(c1nc(-c2ccnc(Nc3nc(F)ccc3F)c2)nc2cncc(C3CC3)c12)[C@H]1CCNCC1(C)C] | [B4], [E4] | 517 [M + H] | 1H NMR (400 MHz, METHANOL-d4) δ ppm 8.95 (s, 1 H) 8.65-8.91 (m, 1 H) 8.41 (d, J = 6.27 Hz, 1 H) 8.24 (dd, J = 6.27, 1.51 Hz, 1 H) 8.05 (br. s., 1 H) 7.75-7.88 (m, 1 H) 6.75 (d, J = 8.53 Hz, 1H) 3.47-3.58 (m, 1 H) 2.54- 2.97 (m, 1 H) 2.43 (br. s., 2 H) 1.77-2.06 (m, 1 H) 1.04- 1.48 (m, 8 H) 0.91 (br. s., 1 H) | 5-Cyclopropyl-2-[2-[(3,6-difluoro-2-pyridyl)amino]-4-pyridyl]-N-[(4S)-3,3-dimethyl-4-piperidyl]-N-methyl-pyrido[3,4-d]pyrimidin-4-amine |
| 332 | 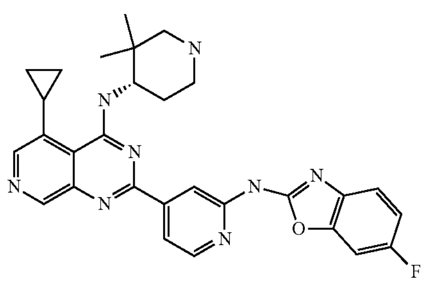 [SMILES: CC1(C)CNCC[C@@H]1Nc1nc(-c2ccnc(Nc3nc4ccc(F)cc4o3)c2)nc2cncc(C3CC3)c12] | [B4], [E4] | 525 [M + H] | 1H NMR (400 MHz, METHANOL-d4) δ ppm 9.05 (br. s., 1 H) 8.74 (br. s., 1 H) 8.33-8.47 (m, 2 H) 8.11 (br. s., 1 H) 7.41 (br.s., 1 H) 7.27 (br. s., 1 H) 7.01 (br. s., 1 H) 4.97 (dd, J = 11.80, 4.02 Hz, 1 H) 3.42 (d, J = 13.05 Hz, 1 H) 3.07-3.15 (m, 1 H) 2.45 (br. s., 1 H) 2.20 (d, J = 10.79 Hz, 1 H) 1.96-2.08 (m, 1 H) 1.28- 1.36 (m, 1 H) 1.19-1.22 (m, 5 H) 1.17 (s, 3 H) 1.02-1.09 (m, 1 H) | N-[4-[5-Cyclopropyl-4-[[(4S)-3,3-dimethyl-4-piperidyl]amino]pyrido[3,4-d]pyrimidin-2-yl]-2-pyridyl]-6-fluoro-1,3-benzoxazol-2-amine |
| 333 | 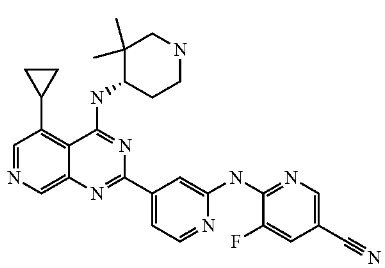 [SMILES: CC1(C)CNCC[C@@H]1Nc1nc(-c2ccnc(Nc3ncc(C#N)cc3F)c2)nc2cncc(C3CC3)c12] | [B4], [E4] | 510 [M + H] | 1H NMR (400 MHz, METHANOL-d4) δ ppm 9.04 (s, 1 H) 8.87 (d, J = 1.00 Hz, 1 H) 8.54 (d, J = 1.76 Hz, 1 H) 8.44-8.48 (m, 2 H) 8.38- 8.41 (m, 1 H) 8.11 (dd, J = 10.54, 1.76 Hz, 1 H) 4.94 (dd, J = 11.67, 4.39 Hz, 1 H) 3.44 (d, J = 12.80 Hz, 1 H) 3.24- 3.28 (m, 1 H) 3.08-3.14 (m, 1 H) 2.40-2.50 (m, 1 H) 2.13- 2.23 (m, 1 H) 1.95-2.09 (m, 1 H) 1.28-1.38 (m, 1 H) 1.21 (s, 5 H) 1.13 (s, 3 H) 1.01- 1.09 (m, 1 H) | 6-[[4-[5-Cyclopropyl-4-[[(4S)-3,3-dimethyl-4-piperidyl]amino]pyrido[3,4-d]pyrimidin-2-yl]-2-pyridyl]amino]-5-fluoro-pyridine-3-carbonitrile |

TABLE A-continued

| Ex | Structure | Scheme | Analysis | | Name |
| --- | --- | --- | --- | --- | --- |
| | | | LCMS | 1H-NMR | |
| 334 | 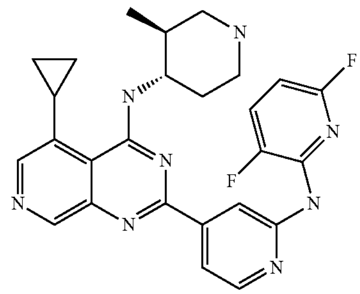 [SMILES: C[C@H]1CNCC[C@@H]1Nc1nc(-c2ccnc(Nc3nc(F)ccc3F)c2)nc2cncc(C3CC3)c12] | [B4] | 489 [M + H] | 1H NMR(400 MHz, METHANOL-d4) δ ppm 9.02 (s, 1 H) 8.86 (d, J = 0.75 Hz, 1 H) 8.45 (d, J = 0.75 Hz, 1 H) 8.40 (d, J = 6.27 Hz, 1 H) 8.27 (dd, J = 6.27, 1.51 Hz, 1 H) 7.82 (td, J = 9.16, 6.02 Hz, 1 H) 6.77 (d, J = 8.53 Hz, 1 H) 4.61 (td, J = 11.17, 4.02 Hz, 1 H) 3.43-3.54 (m, 2 H) 3.14-3.20 (m, 1 H) 2.91 (s, 1 H) 2.40-2.49 (m, 2 H) 2.07-2.20 (m, 1 H) 1.84 (br. s., 1 H) 1.22-1.30 (m, 2 H) 1.10 (d, J = 6.53 Hz, 5 H) | 5-Cyclopropyl-2-[2-[(3,6-difluoro-2-pyridyl)amino]-4-pyridyl]-N-[(3S,4S)-3-methyl-4-piperidyl]pyrido[3,4-d]pyrimidin-4-amine or enantiomer |
| 335 | 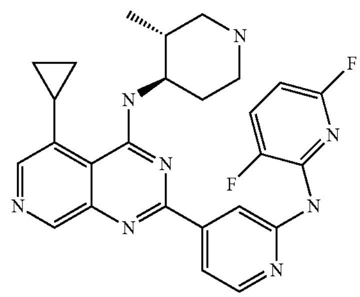 [SMILES: C[C@@H]1CNCC[C@H]1Nc1nc(-c2ccnc(Nc3nc(F)ccc3F)c2)nc2cncc(C3CC3)c12] | [B4] | 489 [M + H] | 1H NMR (400 MHz, METHANOL-d4) δ ppm 9.02 (s, 1 H) 8.82 (d, J = 1.00 Hz, 1 H) 8.45 (d, J = 0.75 Hz, 1 H) 8.41 (d, J = 6.53 Hz, 1 H) 8.31 (dd, J = 6.53, 1.51 Hz, 1 H) 7.85 (td, J = 9.10, 5.90 Hz, 1 H) 6.81 (dt, J = 8.60, 2.48 Hz, 1 H) 4.60 (d, J = 4.02 Hz, 1 H) 3.42-3.53 (m, 2 H) 3.20 (s, 1 H) 2.92 (t, J = 12.55 Hz, 1 H) 2.39-2.50 (m, 2 H) 2.08-2.21 (m, 1 H) 1.74-1.90 (m, 1 H) 1.26 (dt, J = 8.28, 2.89 Hz, 2 H) 1.08 (s, 5 H) | 5-Cyclopropyl-2-[2-[(3,6-difluoro-2-pyridyl)amino]-4-pyridyl]-N-[(3R,4R)-3-methyl-4-piperidyl]pyrido[3,4-d]pyrimidin-4-amine or enantiomer |
| 336 | 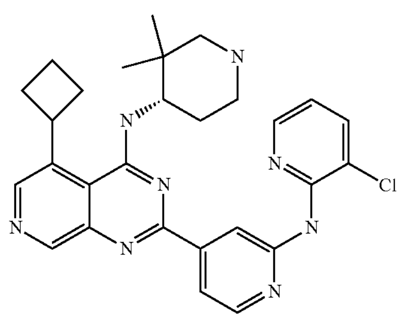 [SMILES: CC1(C)CNCC[C@@H]1Nc1nc(-c2ccnc(Nc3ncccc3Cl)c2)nc2cncc(C3CCC3)c12] | [B4], [E4] | 516 [M + H] | 1H NMR (400 MHz, METHANOL-d4) δ ppm 9.17 (s, 1 H) 9.01 (d, J = 1.00 Hz, 1 H) 8.67 (s, 1 H) 8.53-8.56 (m, 1 H) 8.47-8.52 (m, 2 H) 8.17 (dd, J = 8.03, 1.51 Hz, 1 H) 7.36 (dd, J = 8.03, 5.02 Hz, 1 H) 5.06 (dd, J = 11.80, 4.27 Hz, 1 H) 4.35 (quin, J = 8.09 Hz, 1 H) 3.56 (d, J = 12.80 Hz, 1 H) 3.36-3.42 (m, 2 H) 3.22-3.29 (m, 1 H) 2.63-2.74 (m, 2 H) 2.39-2.60 (m, 2 H) 2.06-2.31 (m, 4 H) 1.41 (s, 3 H) 1.23-1.27 (m, 3 H) | 2-[2-[(3-Chloro-2-pyridyl)amino]-4-pyridyl]-5-cyclobutyl-N-[(4S)-3,3-dimethyl-4-piperidyl]pyrido[3,4-d]pyrimidin-4-amine |
| 337 | 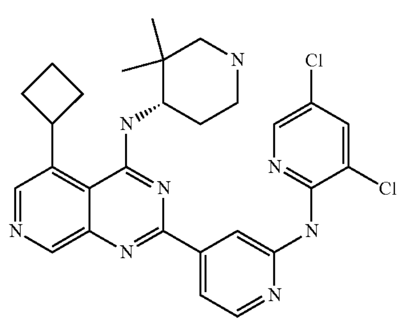 [SMILES: CC1(C)CNCC[C@@H]1Nc1nc(-c2ccnc(Nc3ncc(Cl)cc3Cl)c2)nc2cncc(C3CCC3)c12] | [B4], [E4] | 550 [M + H] | 1H NMR (400 MHz, METHANOL-d4) δ ppm 9.18 (s, 1 H) 9.03 (d, J = 1.00 Hz, 1 H) 8.67 (s, 1 H) 8.48-8.54 (m, 3 H) 8.28 (d, J = 2.26 Hz, 1 H) 5.05 (dd, J = 11.67, 4.39 Hz, 1 H) 4.35 (t, J = 8.28 Hz, 1 H) 3.53-3.60 (m, 1 H) 3.35-3.44 (m, 2 H) 3.21-3.28 (m, 1 H) 2.68 (quind, J = 8.09, 8.09, 8.09, 8.09, 3.76 Hz, 2 H) 2.36-2.59 (m, 2 H) 2.07-2.31 (m, 4 H) 1.41 (s, 3 H) 1.25 (s, 3 H) | 5-Cyclobutyl-2-[2-[(3,5-dichloro-2-pyridyl)amino]-4-pyridyl]-N-[(4S)-3,3-dimethyl-4-piperidyl]pyrido[3,4-d]pyrimidin-4-amine |

TABLE A-continued

| Ex | Structure | Scheme | Analysis | | Name |
|---|---|---|---|---|---|
| | | | LCMS | 1H-NMR | |
| 338 | 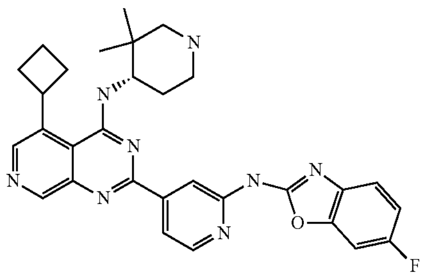 [SMILES: CC1(C)CNCC[C@@H]1Nc1nc(-c2ccnc(Nc3nc4ccc(F)cc4o3)c2)nc2cncc(C3CCC3)c12] | [B4], [E4] | 539 [M + H] | 1H NMR (400 MHz, METHANOL-d4) δ ppm 9.05 (br. s., 1 H) 8.71 (br. s., 1 H) 8.49 (br. s., 1 H) 8.37 (d, J = 5.02 Hz, 1 H) 8.09 (d, J = 4.27 Hz, 1 H) 7.40 (br. s., 1 H) 7.25 (d, J = 7.53 Hz, 1 H) 7.01 (t, J = 8.28 Hz, 1 H) 4.92 (dd, J = 11.80, 4.02 Hz, 1 H) 4.21 (quin, J = 8.22 Hz, 1 H) 3.37-3.47 (m, 1 H) 3.22-3.31 (m, 2 H) 3.09 (d, J = 13.05 Hz, 1 H) 2.54 (td, J = 7.91, 3.26 Hz, 2 H) 2.24-2.45 (m, 2 H) 1.92-2.20 (m, 4 H) 1.28 (s, 3 H) 1.17 (s, 3 H) | N-[4-[5-Cyclobutyl-4-[[(4S)-3,3-dimethyl-4-piperidyl]amino]pyrido[3,4-d]pyrimidin-2-yl]-2-pyridyl]-6-fluoro-1,3-benzoxazol-2-amine |
| 339 | 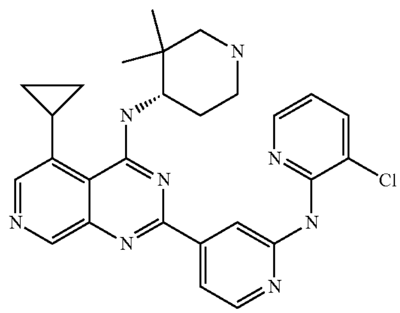 [SMILES: CC1(C)CNCC[C@@H]1Nc1nc(-c2ccnc(Nc3ncccc3Cl)c2)nc2cncc(C3CC3)c12] | [B4], [E4] | 502 [M + H] | 1H NMR (400 MHz, METHANOL-d4) δ ppm 9.17 (d, J = 0.75 Hz, 1 H) 9.00-9.04 (m, 1 H) 8.60 (d, J = 1.00 Hz, 1 H) 8.54 (d, J = 0.75 Hz, 1 H) 8.49-8.53 (m, 2 H) 8.17 (dd, J = 8.03, 1.51 Hz, 1 H) 7.36 (dd, J = 8.03, 5.02 Hz, 1 H) 5.10 (dd, J = 11.80, 4.27 Hz, 1 H) 3.58 (d, J = 13.05 Hz, 1 H) 3.35-3.43 (m, 2 H) 3.24-3.31 (m, 1 H) 2.54-2.64 (m, 1 H) 2.27-2.36 (m, 1 H) 2.08-2.24 (m, 1 H) 1.42-1.50 (m, 1 H) 1.35 (s, 5 H) 1.25 (s, 3 H) 1.12-1.22 (m, 1 H) | 2-[2-[(3-Chloro-2-pyridyl)amino]-4-pyridyl]-5-cyclopropyl-N-[(4S)-3,3-dimethyl-4-piperidyl]pyrido[3,4-d]pyrimidin-4-amine |
| 340 | 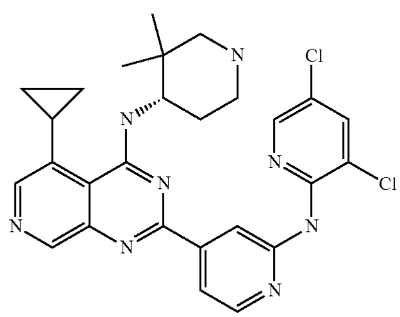 [SMILES: CC1(C)CNCC[C@@H]1Nc1nc(-c2ccnc(Nc3ncc(Cl)cc3Cl)c2)nc2cncc(C3CC3)c12] | [B4], [E4] | 536 [M + H] | 1H NMR (400 MHz, METHANOL-d4) δ ppm 9.04 (d, J = 0.75 Hz, 1 H) 8.92 (t, J = 1.00 Hz, 1 H) 8.47 (t, J = 1.26 Hz, 1 H) 8.39 (t, J = 1.38 Hz, 2 H) 8.36 (d, J = 2.26 Hz, 1 H) 8.16 (d, J = 2.26 Hz, 1 H) 4.96 (dd, J = 11.80, 4.27 Hz, 1 H) 3.44 (d, J = 12.80 Hz, 1 H) 3.24-3.30 (m, 2 H) 3.08-3.16 (m, 1 H) 2.44 (d, J = 6.78 Hz, 1 H) 2.18 (dd, J = 14.31, 3.26 Hz, 1 H) 2.01 (dd, J = 13.55, 3.26 Hz, 1 H) 1.29-1.37 (m, 1 H) 1.21 (s, 5 H) 1.12 (s, 3 H) 0.98-1.07 (m, 1 H) | 5-Cyclopropyl-2-[2-[(3,5-dichloro-2-pyridyl)amino]-4-pyridyl]-N-[(4S)-3,3-dimethyl-4-piperidyl]pyrido[3,4-d]pyrimidin-4-amine |
| 341 | 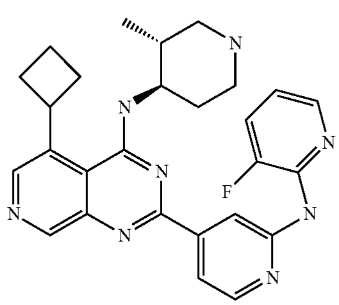 [SMILES: C[C@@H]1CNCC[C@H]1Nc1nc(-c2ccnc(Nc3ncccc3F)c2)nc2cncc(C3CCC3)c12] | [B4] | 485 [M + H] | 1H NMR (400 MHz, METHANOL-d4) δ ppm 9.15 (d, J = 0.75 Hz, 1 H) 8.76-8.83 (m, 1 H) 8.59 (d, J = 1.00 Hz, 1 H) 8.51-8.56 (m, 1 H) 8.45 (dd, J = 6.65, 1.63 Hz, 1 H) 8.37 (dd, J = 5.14, 1.13 Hz, 1 H) 7.87-7.97 (m, 1 H) 7.38 (d, J = 5.02 Hz, 1 H) 4.80 (d, J = 4.02 Hz, 1 H) 4.47 (t, J = 8.28 Hz, 1 H) 3.56-3.67 (m, 2 H) 3.37 (br. s., 1 H) 3.05 (t, J = 12.55 Hz, 1 H) 2.64-2.75 (m, 2 H) 2.22-2.51 (m, 5 H) 1.98-2.14 (m, 2 H) 1.17 (d, J = 6.53 Hz, 3 H) | 5-Cyclobutyl-2-[2-[(3-fluoro-2-pyridyl)amino]-4-pyridyl]-N-[(3R,4R)-3-methyl-4-piperidyl]pyrido[3,4-d]pyrimidin-4-amine or enantiomer |

TABLE A-continued

| Ex | Structure | Scheme | LCMS | 1H-NMR | Name |
|---|---|---|---|---|---|
| 342 | 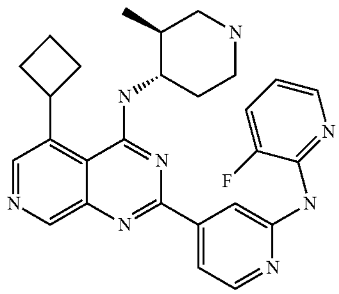 [SMILES: C[C@H]1CNCC[C@@H]1Nc1nc(-c2ccnc(Nc3ncccc3F)c2)nc2cncc(C3CCC3)c12] | [B4] | 485 [M + H] | 1H NMR (400 MHz, METHANOL-d4) δ ppm 9.15 (d, J = 0.75 Hz, 1 H) 8.76-8.83 (m, 1 H) 8.59 (d, J = 1.00 Hz, 1 H) 8.51-8.56 (m, 1 H) 8.45 (dd, J = 6.65, 1.63 Hz, 1 H) 8.37 (dd, J = 5.14, 1.13 Hz, 1 H) 7.87-7.97 (m, 1 H) 7.38 (d, J = 5.02 Hz, 1 H) 4.80 (d, J = 4.02 Hz, 1 H) 4.47 (t, J = 8.28 Hz, 1 H) 3.56-3.67 (m, 2 H) 3.37 (br. s., 1 H) 3.05 (t, J = 12.55 Hz, 1 H) 2.64-2.75 (m, 2 H) 2.22-2.51 (m, 5 H) 1.98-2.14 (m, 2 H) 1.17 (d, J = 6.53 Hz, 3 H) | 5-Cyclobutyl-2-[2-[(3-fluoro-2-pyridyl)amino]-4-pyridyl]-N-[(3S,4S)-3-methyl-4-piperidyl]pyrido[3,4-d]pyrimidin-4-amine or enantiomer |
| 343 | 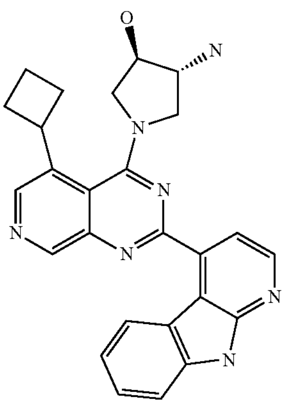 [SMILES: N[C@@H]1CN(c2nc(-c3ccnc4[nH]c5ccccc5c34)nc3cncc(C4CCC4)c23)C[C@H]1O] | [D3] | 452 [M + H] | 1H NMR (400 MHz, DMSO-d6) δ 12.06 (s, 1H), 9.11 (s, 1H), 8.79 (s, 1H), 8.51-8.71 (m, 2H), 8.11 (br. s., 2H), 7.92 (d, J = 5.0 Hz, 1H), 7.43-7.59 (m, 2H), 7.11-7.21 (m, 1H), 3.94-4.31 (m, 5H), 3.50-3.75 (m, 3H) | rac-(3R,4R)-4-Amino-1-[5-cyclobutyl-2-(9H-pyrido[2,3-b]indol-4-yl)-pyrido[3,4-d]pyrimidin-4-yl]-pyrrolidin-3-ol |
| 344 | 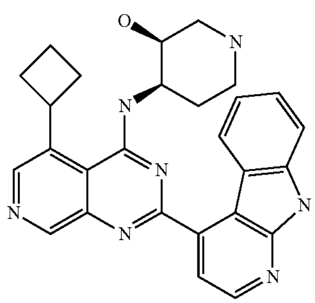 [SMILES: O[C@H]1CNCC[C@H]1Nc1nc(-c2ccnc3[nH]c4ccccc4c23)nc2cncc(C3CCC3)c12] | [D3] | 466 [M + H] | 1H NMR (400 MHz, METHANOL-d4) δ 9.13 (s, 1H), 8.64 (s, 1H), 8.52 (d, J = 5.3 Hz, 1H), 8.28 (d, J = 8.0 Hz, 1H), 7.78 (d, J = 5.3 Hz, 1H), 7.57-7.64 (m, 1H), 7.52 (td, J = 7.7, 1.0 Hz, 1H), 7.18 (td, J = 7.6, 1.1 Hz, 1H), 4.22-4.36 (m, 2H), 3.04 (td, J = 13.2, 3.4 Hz, 1H), 2.67-2.83 (m, 2H), 2.41-2.63 (m, 2H), 1.96-2.36 (m, 5H) | rac-(3S,4R)-4-[5-Cyclobutyl-2-(9H-pyrido[2,3-b]indol-4-yl)-pyrido[3,4-d]pyrimidin-4-ylamino]-piperidin-3-ol |
| 345 | 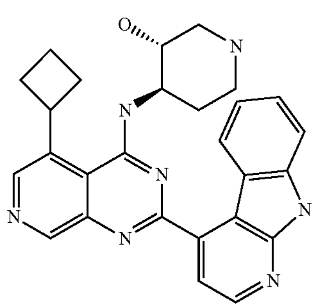 [SMILES: O[C@@H]1CNCC[C@H]1Nc1nc(-c2ccnc3[nH]c4ccccc4c23)nc2cncc(C3CCC3)c12] | [D3] | 466 [M + H] | 1H NMR (400 MHz, METHANOL-d4) δ 9.03 (d, J = 0.8 Hz, 1H), 8.52 (d, J = 1.3 Hz, 1H), 8.42 (d, J = 5.3 Hz, 1H), 8.24 (d, J = 8.0 Hz, 1H), 7.70 (d, J = 5.3 Hz, 1H), 7.47-7.53 (m, 1H), 7.37-7.46 (m, 1H), 7.09 (t, J = 7.7 Hz, 1H), 4.49 (td, J = 9.7, 4.3 Hz, 1H), 4.36 (t, J = 8.3 Hz, 1H), 4.08 (td, J = 9.4, 4.3 Hz, 1H), 3.33-3.49 (m, 2H), 2.82-3.06 (m, 2H), 2.67-2.81 (m, 1H), 2.52-2.66 (m, 2H), 2.28-2.51 (m, 2H), 2.06-2.27 (m, 1H), 1.72-2.02 (m, 2H) | rac-(3R,4R)-4-[5-Cyclobutyl-2-(9H-pyrido[2,3-b]indol-4-yl)-pyrido[3,4-d]pyrimidin-4-ylamino]-piperidin-3-ol |

TABLE A-continued

| Ex | Structure | Scheme | LCMS | 1H-NMR | Name |
|---|---|---|---|---|---|
| 346 | 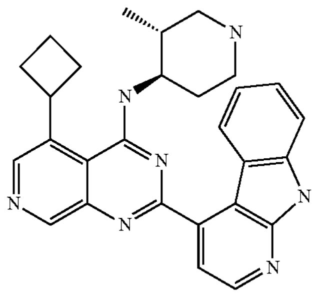 [SMILES: C[C@@H]1CNCC[C@H]1Nc1nc(-c2ccnc3[nH]c4ccccc4c23)nc2cncc(C3CCC3)c12] | [D3] | 464 [M + H] | 1H NMR (400 MHz, METHANOL-d4) δ 9.03 (d, J = 0.8 Hz, 1H), 8.52 (d, J = 1.0 Hz, 1H), 8.43 (d, J = 5.3 Hz, 1H), 8.15 (d, J = 8.0 Hz, 1H), 7.67 (d, J = 5.5 Hz, 1H), 7.47-7.55 (m, 1H), 7.42 (td, J = 7.7, 1.0 Hz, 1H), 7.07 (ddd, J = 8.1, 7.1, 1.1 Hz, 1H), 4.58 (td, J = 11.2, 4.1 Hz, 1H), 4.38 (quin, J = 8.3 Hz, 1H), 3.28-3.44 (m, 3H), 2.93 (td, J = 13.2, 3.1 Hz, 1H), 2.52-2.81 (m, 3H), 1.80-2.45 (m, 8H), 1.01 (d, J = 6.8 Hz, 3H) | [5-Cyclobutyl-2-(9H-pyrido[2,3-b]indol-4-yl)-pyrido[3,4-d]pyrimidin-4-yl]-(rac-(3R,4R)-3-methyl-piperidin-4-yl)-amine |
| 347 | 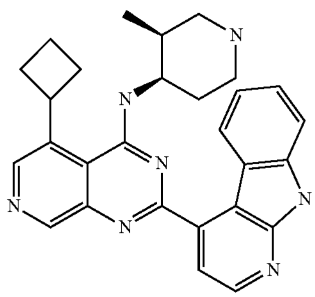 [SMILES: C[C@H]1CNCC[C@H]1Nc1nc(-c2ccnc3[nH]c4ccccc4c23)nc2cncc(C3CCC3)c12] | [D3] | 464 [M + H] | 1H NMR (400 MHz, METHANOL-d4) δ 9.04 (s, 1H), 8.55 (d, J = 1.0 Hz, 1H), 8.42 (d, J = 5.3 Hz, 1H), 8.20 (d, J = 8.0 Hz, 1H), 7.68 (d, J = 5.3 Hz, 1H), 7.47-7.54 (m, 1H), 7.41 (td, J = 7.7, 1.0 Hz, 1H), 7.07 (ddd, J = 8.2, 7.2, 1.3 Hz, 1H), 4.32 (t, J = 8.0 Hz, 1H), 2.52-2.72 (m, 3H), 2.32-2.49 (m, 2H), 1.91-2.24 (m, 4H), 1.15 (d, J = 7.3 Hz, 3H) | [5-Cyclobutyl-2-(9H-pyrido[2,3-b]indol-4-yl)-pyrido[3,4-d]pyrimidin-4-yl]-(rac-(3S,4R)-3-methyl-piperidin-4-yl)-amine |
| 348 | 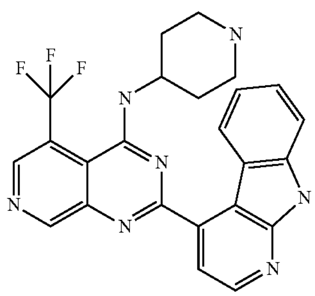 [SMILES: FC(F)(F)c1cncc2nc(-c3ccnc4[nH]c5ccccc5c34)nc(NC3CCNCC3)c12] | [D20] | 464 [M + H] | 1H NMR (400 MHz, METHANOL-d4) δ 9.46 (s, 1H), 8.99 (s, 1H), 8.43 (d, J = 5.3 Hz, 1H), 8.31(d, J = 8.0 Hz, 1H), 7.74 (d, J = 5.3 Hz, 1H), 7.37-7.55 (m, 2H), 7.09 (ddd, J = 8.2, 7.2, 1.3 Hz, 1H), 4.68 (d, J = 14.6 Hz, 1H), 3.27-3.42 (m, 3H), 2.95-3.11 (m, 3H), 2.37(dd, J = 14.1, 3.5 Hz, 2H), 1.66-1.92 (m, 2H) | Piperidin-4-yl-[2-(9H-pyrido[2,3-b]indol-4-yl)-5-trifluoromethyl-pyrido[3,4-d]pyrimidin-4-yl]-amine |
| 349 | 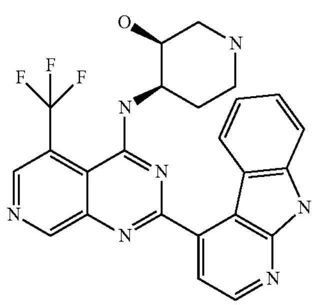 [SMILES: O[C@H]1CNCC[C@H]1Nc1nc(-c2ccnc3[nH]c4ccccc4c23)nc2cncc(C(F)(F)F)c12] | [D20] | 479 | 1H NMR (400 MHz, METHANOL-d4) δ 9.44 (s, 1H), 8.98 (s, 1H), 8.42 (d, J = 5.3 Hz, 1H), 8.26 (d, J = 8.0 Hz, 1H), 7.71 (d, J = 5.3 Hz, 1H), 7.37-7.53 (m, 2H), 7.02-7.14 (m, 1H), 4.17 (br. s., 1H), 2.85-3.15 (m, 2H), 1.98-2.29 (m, 2H) | rac-(3S,4R)-4-[2-(9H-Pyrido[2,3-b]indol-4-yl)-5-trifluoromethyl-pyrido[3,4-d]pyrimidin-4-ylamino]-piperidin-3-ol |
| 350 | 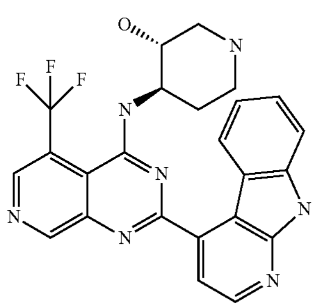 [SMILES: O[C@@H]1CNCC[C@H]1Nc1nc(-c2ccnc3[nH]c4ccccc4c23)nc2cncc(C(F)(F)F)c12] | [D20] | 479 | 1H NMR (400 MHz, METHANOL-d4) δ 9.48 (s, 1H), 9.01 (s, 1H), 8.43 (d, J = 5.0 Hz, 2H), 7.74 (d, J = 5.3 Hz, 1H), 7.33-7.55 (m, 2H), 7.00-7.15 (m, 1H), 4.43-4.56 (m, 1H), 3.86-4.10 (m, 1H), 2.55-2.73 (m, 1H), 1.65-1.94 (m, 2H) | rac-(3R,4R)-4-[2-(9H-Pyrido[2,3-b]indol-4-yl)-5-trifluoromethyl-pyrido[3,4-d]pyrimidin-4-ylamino]-piperidin-3-ol |

TABLE A-continued

| Ex | Structure | Scheme | Analysis LCMS | 1H-NMR | Name |
|---|---|---|---|---|---|
| 351 | 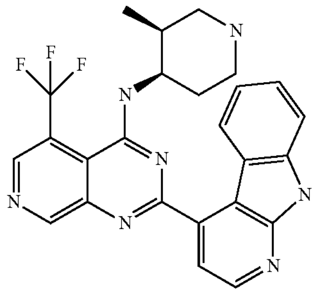 [SMILES: C[C@H]1CNCC[C@H]1Nc1nc(-c2ccnc3[nH]c4ccccc4c23)nc2cncc(C(F)(F)F)c12] | [D20] | 478 | 1H NMR (400 MHz, METHANOL-d4) δ 9.48 (s, 1H), 9.02 (s, 1H), 8.43 (d, J = 5.3 Hz, 1H), 8.31 (d, J = 8.0 Hz, 1H), 7.73 (d, J = 5.3 Hz, 1H), 7.34-7.55 (m, 2H), 7.04-7.17 (m, 1H), 4.79-4.90 (m, 2H), 2.50 (dd, J = 7.5, 3.5 Hz, 1H), 2.13-2.29 (m, 1H), 2.03 (d, J = 3.8 Hz, 1H), 1.04-1.21 (m, 3H) | rac-(3S,4R)-3-Methyl-piperidin-4-yl)-[2-(9H-pyrido[2,3-b]indol-4-yl)-5-trifluoromethyl-pyrido[3,4-d]pyrimidin-4-yl]-amine |
| 352 | 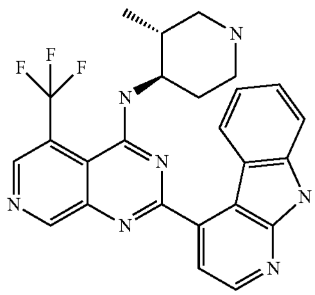 [SMILES: C[C@@H]1CNCC[C@H]1Nc1nc(-c2ccnc3[nH]c4ccccc4c23)nc2cncc(C(F)(F)F)c12] | [D20] | 478 | 1H NMR (400 MHz, METHANOL-d4) δ 9.45 (s, 1H), 8.99 (s, 1H), 8.44 (d, J = 5.3 Hz, 1H), 8.27 (d, J = 8.0 Hz, 1H), 7.73 (d, J = 5.3 Hz, 1H), 7.48-7.54 (m, 1H), 7.42 (td, J = 7.7, 1.0 Hz, 1H), 7.08 (ddd, J = 8.2, 7.1, 1.0 Hz, 1H), 4.53 (td, J = 11.1, 4.1 Hz, 1H), 3.34 (dd, J = 13.1, 4.0 Hz, 2H), 2.94 (td, J = 13.2, 2.9 Hz, 1H), 2.75 (t, J = 12.5 Hz, 1H), 2.40 (dd, J = 13.9, 3.6 Hz, 1H), 1.94-2.11 (m, 1H), 1.59-1.78 (m, 1H), 1.06 (d, J = 6.5 Hz, 3H) | (rac-(3R,4R)-3-Methyl-piperidin-4-yl)-[2-(9H-pyrido[2,3-b]indol-4-yl)-5-trifluoromethyl-pyrido[3,4-d]pyrimidin-4-yl]-amine |
| 353 | 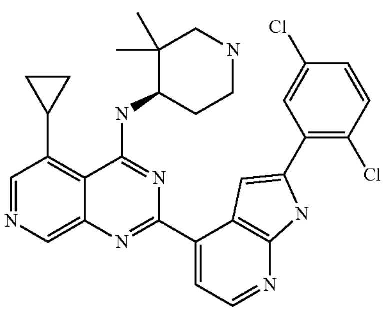 [SMILES: CC1(C)CNCC[C@H]1Nc1nc(-c2ccnc3[nH]c(-c4cc(Cl)ccc4Cl)cc23)nc2cncc(C3CC3)c12] | [D3], [D4], [E4] | 558.16 | 1H NMR (400 MHz, DMSO-d6) δ 12.32 (d, 1H, J =1.8 Hz), 9.15 (s, 1H), 9.01 (m, 1H), 8.51-8.48 (m, 2H), 8.29 (m, 1H), 8.23 (d, 1H, J = 5.0 Hz), 8.02 (d, 1H, J = 2.2 Hz), 7.94 (d, 1H, J = 2.5 Hz), 7.70 (d, 1H, J = 8.6 Hz), 7.61 (d, 1H, J = 8.8 Hz), 7.54 (m, 1H), 4.90-4.84 (m, 1H), 3.35 (m, 1H), 3.22-3.07 (m, 3H), 2.61 (m, 1H), 2.19-2.15 (m, 1H), 2.01-1.95 (m, 1H), 1.30-1.09 (m, 10H) | {5-Cyclopropyl-2-[2-(2,5-dichloro-phenyl)-1H-pyrrolo[2,3-b]pyridin-4-yl]-pyrido[3,4-d]pyrimidin-4-yl}-((S)-3,3-dimethyl-piperidin-4-yl)-amine |
| 354 | 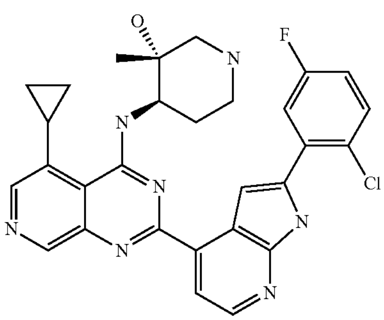 [SMILES: C[C@@]1(O)CNCC[C@H]1Nc1nc(-c2ccnc3[nH]c(-c4cc(F)ccc4Cl)cc23)nc2cncc(C3CC3)c12] | [D3], [D4], [E3] | 544.3 | 1H NMR (400 MHz, DMSO-d6) δ 12.32 (d, 1H, J = 1.8 Hz), 9.15 (s, 1H), 8.72-8.67 (m, 2H), 8.52 (s, 1H), 8.49 (d, 1H, J = 5.0 Hz), 8.21 (d, 1H, J = 5.0 Hz), 8.04 (d, 1H, J = 2.2 Hz), 7.76-7.68 (m, 3H), 7.38-7.33 (m, 1H), 4.92- 4.88 (m, 1H), 3.20-3.06 (m, 4H), 2.74-2.67 (m, 1H), 2.01-1.96 (m, 1H), 1.36 (s, 3H), 1.27-1.16 (m, 4H) | rac-(3R,4R)-4-{[2-[2-(2-Chloro-5-fluoro-phenyl)-1H-pyrrolo[2,3-b]pyridin-4-yl]-5-cyclopropyl-pyrido[3,4-d]pyrimidin-4-ylamino}-3-methyl-piperidin-3-ol |
| 355 | 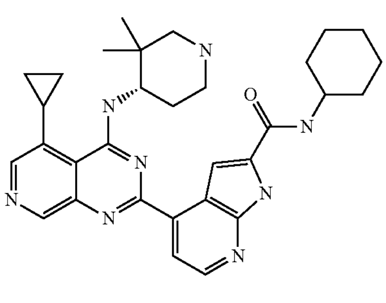 [SMILES: CC1(C)CNCC[C@@H]1Nc1nc(-c2ccnc3[nH]c(C(=O)NC4CCCCC4)cc23)nc2cncc(C3CC3)c12] | [D21], [E4] | 539.4 | 1H NMR (400 MHz, DMSO-d6) δ 12.27 (s, 1H), 9.26 (s, 1H), 9.17 (m, 1H), 8.53 (m, 2H), 8.43-8.37 (m, 2H), 8.24 (d, 1H, J = 4.9 Hz), 8.14 (d, 1H, J = 1.6 Hz), 7.62 (d, 1H, J = 8.8 Hz), 4.93-4.87 (m, 1H), 3.85 (m, 1H), 3.39 (m, 1H), 3.25-3.09 (m, 3H), 2.62 (m, 1H), 2.18 (m, 1H), 2.03-1.92 (m, 3H), 1.80-1.77 (m, 2H), 1.66-1.63 (m, 1H), 1.41-1.12 (m, 15H) | 4-[5-Cyclopropyl-4-((S)-3,3-dimethyl-piperidin-4-ylamino)-pyrido[3,4-d]pyrimidin-2-yl]-1H-pyrrolo[2,3-b]pyridine-2-carboxylic acid cyclohexylamide |

TABLE A-continued

| Ex | Structure | Scheme | Analysis | | Name |
| --- | --- | --- | --- | --- | --- |
| | | | LCMS | 1H-NMR | |
| 356 | 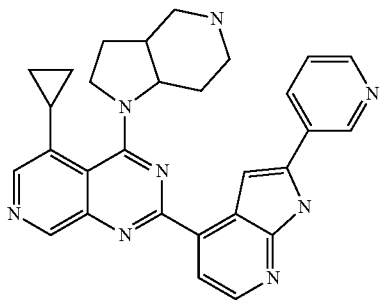 [SMILES: c1cncc(-c2cc3c(-c4nc(N5CCC6CNCCC65)c5c(C6CC6)cncc5n4)ccnc3[nH]2)c1] | [D22] | 489.3 | 1H NMR (400 MHz, DMSO-d6) δ 12.58 (s, 1H), 9.33 (d, 1H, J = 1.4 Hz), 9.24 (s, 1H), 8.65 (m, 3H), 8.54 (m, 1H), 8.46 (d, 1H, J = 5.0 Hz), 8.22 (s, 1H), 8.11 (d, 1H, J = 5.0 Hz), 8.08 (d, 1H, J = 2.1 Hz), 7.68-7.64 (m, 1H), 4.64 (m, 1H), 4.44-4.37 (m, 2H), 3.44-3.26 (m, 3H), 2.99 (m, 2H), 2.82-2.73 (m, 2H), 2.24-2.21 (m, 1H), 1.94-1.91 (m, 1H), 1.79-1.76 (m, 1H), 1.48-1.44 (m, 1H), 1.22-1.15 (m, 1H), 1.12-1.06 (m, 1H), 0.96-0.90 (m, 1H) | 5-Cyclopropyl-4-(octahydro-pyrrolo[3,2-c]pyridin-1-yl)-2-(2-pyridin-3-yl-1H-pyrrolo[2,3-b]pyridin-4-yl)-pyrido[3,4-d]pyrimidine |
| 357 | 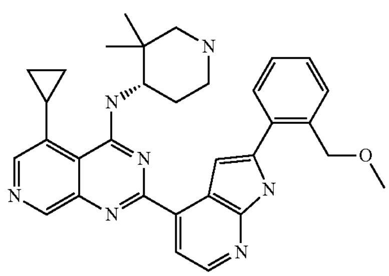 [SMILES: COCc1ccccc1-c1cc2c(-c3nc(N[C@H]4CCNCC4(C)C)c4c(C5CC5)cncc4n3)ccnc2[nH]1] | [D3], [D4], [E4] | 534.4 | 1H NMR (400 MHz, DMSO-d6) δ 12.04 (d, 1H, J = 1.8 Hz), 9.15 (s, 1H), 9.00 (m, 1H), 8.49 (d, 1H, J = 0.7 Hz), 8.42 (d, 1H, J = 5.0 Hz), 8.27-8.21 (m, 2H), 7.75-7.72 (m, 2H), 7.62-7.57 (m, 2H), 7.52-7.45 (m, 2H), 4.92-4.86 (m, HI), 4.64 (s, 2H), 3.35 (m, 4H), 3.21-3.10 (m, 3H), 2.62-2.58 (m, 1H), 2.15 (m, 1H), 2.01-1.91 (m, 1H), 1.28-1.11 (m, 10H) | {5-Cyclopropyl-2-[2-(2-methoxymethyl-phenyl)-1H-pyrrolo[2,3-b]pyridin-4-yl]-pyrido[3,4-d]pyrimidin-4-yl}-((S)-3,3-dimethyl-piperidin-4-yl)-amine |
| 358 | 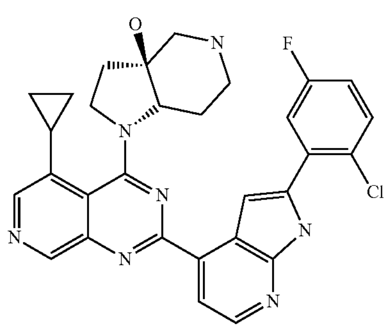 | [D3], [D4], [E2] | 556.3 | 1H NMR (400 MHz, DMSO-d6) δ 12.34 (d, 1H, J = 1.8 Hz), 9.07 (s, 1H), 8.79-8.71 (m, 2H), 8.49 (d, 1H, J = 5.0 Hz), 8.19 (s, 1H), 8.13 (d, 1H, J = 5.0 Hz), 8.01 (d, 1H, J = 2.2 Hz), 7.75-7.70 (m, 2H), 7.38-7.33 (m, 1H), 4.45-4.28 (m, 4H), 3.38-3.16 (m, 4H), 3.04-3.01 (m, 1H), 2.33 (m, 1H), 2.00 (m, 1H), 1.95-1.87 (m, 1H), 1.47-1.43 (m, 1H), 1.21-1.07 (m, 2H), 0.96-0.90 (m, 1H) | rac(1R,3aS)-1-{2-[2-(2-Chloro-5-fluoro-phenyl)-1H-pyrrolo[2,3-b]pyridin-4-yl]-5-cyclopropyl-pyrido[3,4-d]pyrimidin-4-yl}-octahydro-pyrrolo[3,2-c]pyridin-3a-ol |
| 359 | 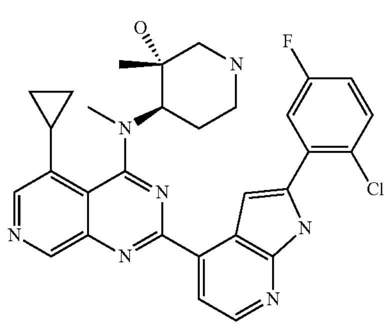 [SMILES: CN(c1nc(-c2ccnc3[nH]c(-c4cc(F)ccc4Cl)cc23)nc2cncc(C3CC3)c12)[C@@H]1CCNC[C@@]1(C)O] | [D3], [D4], [E3] | 558.4 | 1H NMR (400 MHz, DMSO-d6) δ 12.43-12.33 (m, 1H), 9.53-9.34 (m, 1H), 9.04-8.99 (m, 2H), 8.56-8.53 (m, 1H), 8.49-8.41 (m, 1H), 8.18 (m, 1H), 8.12-8.05 (m, 2H), 7.77-7.69 (m, 2H), 7.40-7.33 (m, 1H), 4.35 (m, 1H), 3.97 (m, 1H), 3.48-2.62 (m, 6H), 2.32 (m, 1H), 2.12 (m, 2H), 1.48-0.87 (m, 7H) | rac-(3R,4R)-4-({2-[2-(2-Chloro-5-fluoro-phenyl)-1H-pyrrolo[2,3-b]pyridin-4-yl]-5-cyclopropyl-pyrido[3,4-d]pyrimidin-4-yl}-methyl-amino)-3-methyl-piperidin-3-ol |

TABLE A-continued

| Ex | Structure | Scheme | Analysis | | Name |
| --- | --- | --- | --- | --- | --- |
| | | | LCMS | 1H-NMR | |
| 360 | 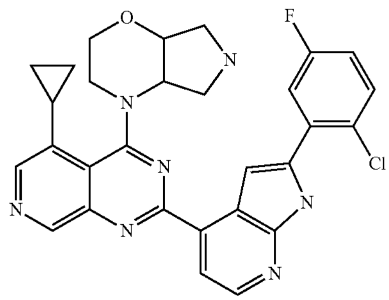 [SMILES: Fc1ccc(Cl)c(-c2cc3c(-c4nc(N5CCOC6CNCC65)c5c(C6CC6)cncc5n4)ccnc3[nH]2)c1] | [D3], [D4], [E5] | 542.3 | 1H NMR (400 MHz, DMSO-d6) δ 12.37 (d, 1H, J = 16 Hz), 9.40 (br s, 1H), 9.22-9.16 (m, 2H), 8.49 (d, 1H, J = 5.0 Hz), 8.23 (d, 1H, J = 5.0 Hz), 8.20 (s, 1H), 8.11 (br s, 1H), 7.77-7.70 (m, 2H), 7.38-7.33 (m, 1H), 5.07 (br s, 1H), 4.47 (br s, 1H), 4.04-3.34 (m, 8H), 2.71-2.68 (m, 1H), 1.29-1.09 (m, 4H) | 2-[2-(2-Chloro-5-fluoro-phenyl)-1H-pyrrolo[2,3-b]pyridin-4-yl]-5-cyclopropyl-4-(hexahydro-pyrrolo[3,4-b][1,4]oxazin-4-yl)pyrido[3,4-d]pyrimidine |
| 361 | 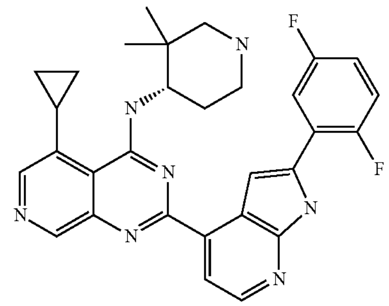 [SMILES: CC1(C)CNCC[C@@H]1Nc1nc(-c2ccnc3[nH]c(-c4cc(F)ccc4F)cc23)nc2cncc(C3CC3)c12] | [D3], [D4], [E4] | 526.24 | 1H NMR (400 MHz, DMSO-d6) δ 12.38 (s, 1H), 9.13 (s, 1H), 8.95 (m, 1H), 8.52 (s, 1H), 8.48 (d, 1H, J = 5.0 Hz), 8.21 (d, 1H, J = 5.0 Hz), 8.05 (m, 1H), 8.01-7.97 (m, 1H), 7.62 (m, 1H), 7.51-7.45 (m, 1H), 7.35-7.29 (m, 1H), 4.89-4.84 (m, 1H), 3.37 (m, 1H), 3.24-3.06 (m, 3H), 2.62 (m, 1H), 2.16 (m, 1H), 2.01-1.95 (m, 1H), 1.27-1.12 (m, 10H) | {5-Cyclopropyl-2-[2-(2,5-difluoro-phenyl)-1H-pyrrolo[2,3-b]pyridin-4-yl]-pyrido[3,4-d]pyrimidin-4-yl}-((S)-3,3-dimethyl-piperidin-4-yl)-amine |
| 362 | 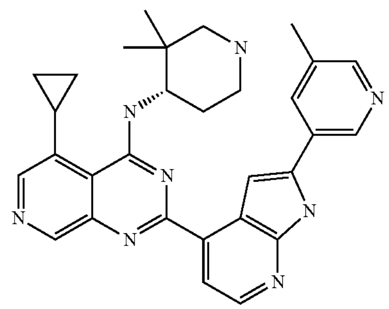 [SMILES: Cc1cncc(-c2cc3c(-c4nc(N[C@H]5CCNCC5(C)C)c5c(C6CC6)cncc5n4)ccnc3[nH]2)c1] | [D22], [E4] | 505.24 | 1H NMR (400 MHz, DMSO-d6) δ 12.56 (s, 1H), 9.41 (s, 1H), 9.23 (d, 1H, J = 1.6 Hz), 9.05 (m, 1H), 8.59 (m, 2H), 8.53 (s, 1H), 8.48 (d, 1H, J = 5.0 Hz), 8.33-8.22 (m, 3H), 7.62-7.59 (m, 1H), 4.94-4.88 (m, 3H), 3.37 (m, 1H), 3.23-3.11 (m, 3H), 2.67-2.60 (m, 1H), 2.18-2.15 (m, 1H), 2.02-1.91 (m, 1H), 1.29-1.13 (m, 11H) | {5-Cyclopropyl-2-[2-(5-methyl-pyridin-3-yl)-1H-pyrrolo[2,3-b]pyridin-4-yl]-pyrido[3,4-d]pyrimidin-4-yl}-((S)-3,3-dimethyl-piperidin-4-yl)-amine |
| 363 | 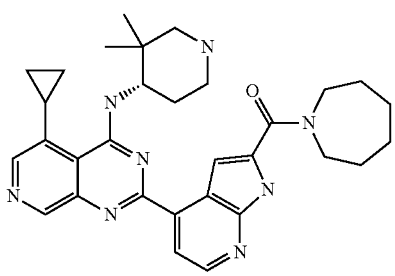 [SMILES: CC1(C)CNCC[C@@H]1Nc1nc(-c2ccnc3[nH]c(C(=O)N4CCCCCC4)cc23)nc2cncc(C3CC3)c12] | [D21], [E4] | 539.33 | 1H NMR (400 MHz, DMSO-d6) δ ppm 12.28 (d, 1H, J = 1.5 Hz), 9.14 (s, 1H), 9.07 (m, 1H), 8.51 (m, 2H), 8.30 (m, 1H), 8.23 (d, 1H, J = 4.9 Hz), 7.81 (d, 1H, J = 2.1 Hz), 7.59 (m, 1H), 4.91-4.85 (m, 1H), 3.81 (m, 2H), 3.65 (m, 2H), 3.37 (m, 1H), 3.22-3.11 (m, 3H), 2.62-2.59 (m, 1H), 2.14 (m, 1H), 2.01-1.91 (m, 1H), 1.83-1.76 (m, 4H), 1.62 (m, 4H), 1.28-1.25 (m, 1H), 1.20-1.11 (m, 9H) | Azepan-1-yl-{4-[5-cyclopropyl-4-((S)-3,3-dimethyl-piperidin-4-ylamino)-pyrido[3,4-d]pyrimidin-2-yl]-1H-pyrrolo[2,3-b]pyridin-2-yl}-methanone |
| 364 | 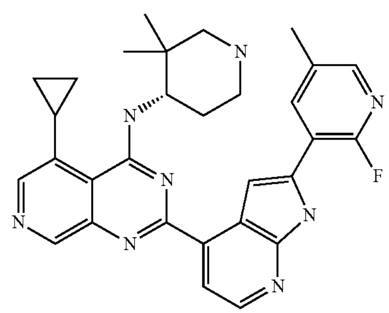 [SMILES: Cc1cnc(F)c(-c2cc3c(-c4nc(N[C@H]5CCNCC5(C)C)c5c(C6CC6)cncc5n4)ccnc3[nH]2)c1] | [D22], [E4] | 523.24 | 1H NMR (400 MHz, DMSO-d6) δ 12.43 (d, 1H, J = 1.6 Hz), 9.15 (s, 1H), 9.03 (m, 1H), 8.52-8.47 (m, 3H), 8.32 (m, 1H), 8.21 (d, 1H, J = 5.3 Hz), 8.07 (m, 1H), 8.02 (m, 1H), 7.63 (d, 1H, J = 9.0 Hz), 4.90-4.85 (m, 1H), 3.37 (m, 1H), 3.24 (m, 1H), 3.15-3.06 (m, 2H), 2.63-2.61 (m, 1H), 2.41 (s, 3H), 2.20-2.16 (m, 1H), 2.03-1.94 (m, 1H), 1.29-1.13 (m, 10H) | {5-Cyclopropyl-2-[2-(2-fluoro-5-methyl-pyridin-3-yl)-1H-pyrrolo[2,3-b]pyridin-4-yl]-pyrido[3,4-d]pyrimidin-4-yl}-((S)-3,3-dimethyl-piperidin-4-yl)-amine |

TABLE A-continued

| Ex | Structure | Scheme | LCMS | 1H-NMR | Name |
|---|---|---|---|---|---|
| 365 | 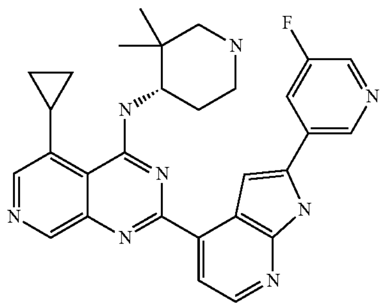 [SMILES: CC1(C)CNCC[C@@H]1Nc1nc(-c2ccnc3[nH]c(-c4cncc(F)c4)cc23)nc2cncc(C3CC3)c12] | [D22], [E4] | 509 | 1H NMR (400 MHz, DMSO-d6) δ 12.54 (d, 1H, J = 2.0 Hz), 9.44 (s, 1H), 9.22 (m, 1H), 9.01 (m, 1H), 8.59 (d, 1H, J = 2.7 Hz), 8.52 (m, 1H), 8.47 (d, 1H, J = 5.0 Hz), 8.45-8.42 (m, 1H), 8.28-8.23 (m, 3H), 7.59 (d, 1H, J = 8.8 Hz), 4.93-4.87 (m, 1H), 3.37 (m, 1H), 3.25-3.12 (m, 3H), 2.65-2.58 (m, 1H), 2.19-2.16 (m, 1H), 2.01-1.92 (m, 1H), 1.30-1.12 (m, 10H) | {5-Cyclopropyl-2-[2-(5-fluoro-pyridin-3-yl)-1H-pyrrolo[2,3-b]pyridin-4-yl]-pyrido[3,4-d]pyrimidin-4-yl}-((S)-3,3-dimethyl-piperidin-4-yl)-amine |
| 366 | 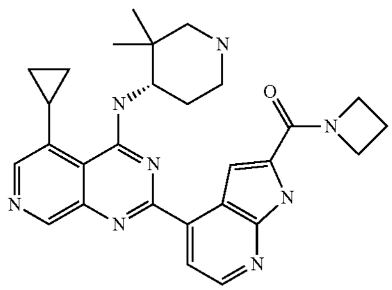 [SMILES: CC1(C)CNCC[C@@H]1Nc1nc(-c2ccnc3[nH]c(C(=O)N4CCC4)cc23)nc2cncc(C3CC3)c12] | [D21], [E4] | 497 | DMSO-d6) δ ppm 12.31 (s, 1H), 9.20 (s, 1H), 9.09 (m, 1H), 8.54 (m, 2H), 8.33 (m, 1H), 8.24 (d, 1H, J = 4.9 Hz), 7.89 (d, 1H, J = 2.0 Hz), 7.59 (m, 1H), 4.92-4.86 (m, 1H), 4.67 (m, 2H), 4.15 (m, 2H), 3.37 (m, 1H), 3.26-3.12 (m, 3H), 2.61 (m, 1H), 2.44-2.37 (m, 2H), 2.14 (m, 1H), 2.01-1.91 (m, 1H), 1.30-1.11 (m, 10H) | Azetidin-1-yl-[4-[5-cyclopropyl-4-[[(4S)-3,3-dimethyl-4-piperidyl]amino]pyrido[3,4-d]pyrimidin-2-yl]-1H-pyrrolo[2,3-b]pyridin-2-yl]methanone |
| 367 | 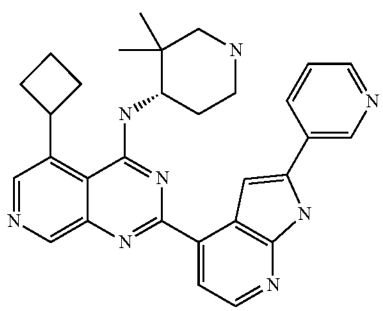 [SMILES: CC1(C)CNCC[C@@H]1Nc1nc(-c2ccnc3[nH]c(-c4cccnc4)cc23)nc2cncc(C3CCC3)c12] | [D22], [E4] | 505.27 | 1H NMR (400 MHz, DMSO-d6) δ 12.57 (s, 1H), 9.37(m, 2H), 9.03 (m, 1H), 8.67-8.57 (m, 3H), 8.47 (d, 1H, J = 5.0 Hz), 8.31 (m, 1H), 8.22 (d, 1H, J = 5.0 Hz), 8.16 (m, 1H), 7.72-7.68 (m, 1H), 6.54 (d, 1H, J = 8.6 Hz), 4.91-4.85 (m, 1H), 4.48-4.40 (m, 2H), 3.37-3.10 (m, 4H), 2.58-2.53 (m, 1H), 2.41-2.25 (m, 2H), 2.10-1.87 (m, 4H), 1.27 (s, 3H), 1.13 (s, 3H) | [5-Cyclobutyl-2-(2-pyridin-3-yl-1H-pyrrolo[2,3-b]pyridin-4-yl)-pyrido[3,4-d]pyrimidin-4-yl]-((S)-3,3-dimethyl-piperidin-4-yl)-amine |
| 368 | 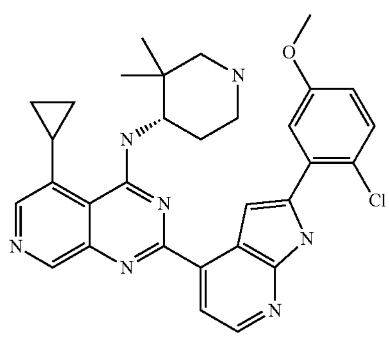 [SMILES: COc1ccc(Cl)c(-c2cc3c(-c4nc(N[C@H]5CCNCC5(C)C)c5c(C6CC6)cncc5n4)ccnc3[nH]2)c1] | [D3], [D4], [E4] | 554.23 | 1H NMR (400 MHz, DMSO-d6) δ 12.28 (d, 1H, J = 1.8 Hz), 9.13 (s, 1H), 8.99 (m, 1H), 8.51 (s, 1H), 8.46 (d, 1H, J = 5.0 Hz), 8.30-8.27 (m, 1H), 8.21 (d, 1H, J = 5.0 Hz), 8.00 (d, 1H, J = 2.2 Hz), 7.60 (m, 1H), 7.55 (d, 1H, J = 8.8 Hz), 7.40 (d, 1H, J = 3.0 Hz), 7.04 (m, 1H), 4.90-4.84 (m, 1H), 3.88 (s, 3H), 3.37-3.34 (m, 1H), 3.22-3.06 (m, 3H), 2.63-2.60 (m, 1H), 2.19-2.16 (m, 1H), 2.01-1.92 (m, 1H), 1.28-1.09 (m, 10H) | {2-[2-(2-Chloro-5-methoxy-phenyl)-1H-pyrrolo[2,3-b]pyridin-4-yl]-5-cyclopropyl-pyrido[3,4-d]pyrimidin-4-yl}-((S)-3,3-dimethyl-piperidin-4-yl)-amine |
| 369 | 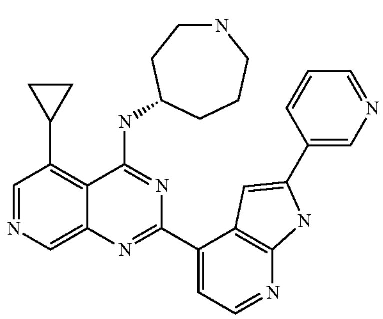 [SMILES: c1cncc(-c2cc3c(-c4nc(N[C@H]5CCCNCC5)c5c(C6CC6)cncc5n4)ccnc3[nH]2)c1] | [D22] | 477 | 1H NMR (400 MHz, DMSO-d6) δ 12.52 (br s, 1H), 9.32 (m, 2H), 8.62 (m, 2H), 8.50 (m, 2H), 8.44 (d, 1H, J = 4.9 Hz), 8.16 (d, 1H, J = 4.9 Hz), 8.11 (m, 1H), 7.84 (m, 1H), 7.62-7.59 (m, 1H), 4.71 (m, 1H), 3.36-3.17 (m, 4H), 2.19 (m, 2H), 2.02-1.94 (m, 4H), 1.25-1.08 (m, 5H) | (S)-Azepan-4-yl-[5-cyclopropyl-2-(2-pyridin-3-yl-1H-pyrrolo[2,3-b]pyridin-4-yl)-pyrido[3,4-d]pyrimidin-4-yl]-amine |

TABLE A-continued

| Ex | Structure | Scheme | LCMS | 1H-NMR | Name |
|---|---|---|---|---|---|
| 370 | 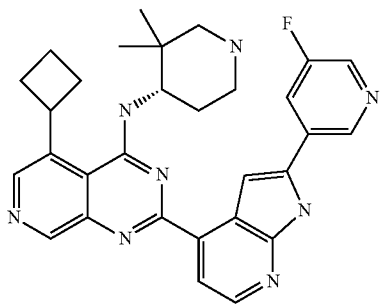 [SMILES: CC1(C)CNCC[C@@H]1Nc1nc(-c2ccnc3[nH]c(-c4cncc(F)c4)cc23)nc2cncc(C3CCC3)c12] | [D22], [E4] | 523 [M + H] | 1H NMR (400 MHz, DMSO-d6) δ 12.54 (d, 1H, J = 1.9 Hz), 9.42 (s, 1H), 9.22 (m, 1H), 9.00 (m, 1H), 8.59 (d, 1H, J = 2.6 Hz), 8.57 (s, 1H), 8.46 (d, 1H, J = 5.0 Hz), 8.45-8.41 (m, 1H), 8.28 (m, 1H), 8.22 (m, 2H), 6.52 (d, 1H, J = 8.6 Hz), 4.90-4.84 (m, 1H), 4.47-4.39 (m, 1H), 3.36-3.33 (m, 1H), 3.24-3.10 (m, 3H), 2.58-2.54 (m, 1H), 2.41-2.25 (m, 2H), 2.10-1.87 (m, 4H), 1.26 (s, 3H), 1.13 (s, 3H) | {5-Cyclobutyl-2-[2-(5-fluoro-pyridin-3-yl)-1H-pyrrolo[2,3-b]pyridin-4-yl]-pyrido[3,4-d]pyrimidin-4-yl}-((S)-3,3-dimethyl-piperidin-4-yl)-amine |
| 371 | 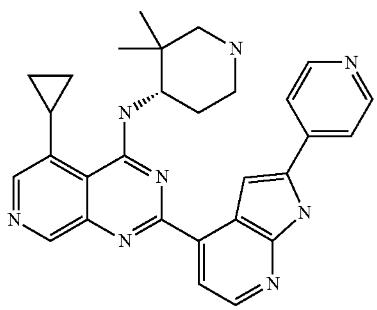 [SMILES: CC1(C)CNCC[C@@H]1Nc1nc(-c2ccnc3[nH]c(-c4ccncc4)cc23)nc2cncc(C3CC3)c12] | [D22], [E4] | 491 [M + H] | 1H NMR (400 MHz, DMSO-d6) δ 12.93 (br s, 1H), 9.43 (s, 1H), 9.18 (m, 1H), 8.90 (d, 2H, J = 6.5 Hz), 8.60 (d, 1H, J = 4.9 Hz), 8.57 (s, 1H), 8.53 (m, 3H), 8.42 (m, 1H), 8.31 (d, 1H, J = 4.9 Hz), 7.62 (d, 1H, J = 8.9 Hz), 4.95-4.89 (m, 1H), 3.39 (m, 1H), 3.26-3.13 (m, 3H), 2.65-2.59 (m, 1H), 2.18-2.15 (m, 1H), 2.03-1.93(m, 1H), 1.32-1.27 (m, 1H), 1.22-1.12 (m, 9H) | 5-Cyclopropyl-N-[(4S)-3,3-dimethyl-4-piperidyl]-2-[2-(4-pyridyl)-1H-pyrrolo[2,3-b]pyridin-4-yl]pyrido[3,4-d]pyrimidin-4-amine |
| 372 | 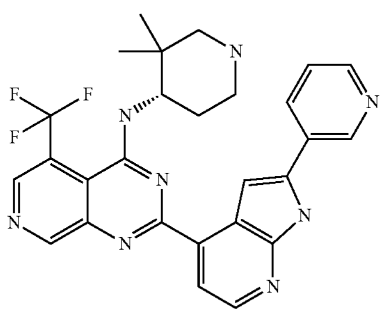 [SMILES: CC1(C)CNCC[C@@H]1Nc1nc(-c2ccnc3[nH]c(-c4cccnc4)cc23)nc2cncc(C(F)(F)F)c12] | [D20], [D22], [E4] | 519 [M + H] | 1H NMR (400 MHz, DMSO-d6) δ 12.62 (d, 1H, J = 1.4 Hz), 9.87 (s, 1H), 9.40 (d, 1H, J = 1.8 Hz), 9.14-9.08 (m, 2H), 8.67-8.62 (m, 2H), 8.49 (d, 1H, J = 5.0 Hz), 8.35 (m, 1H), 8.26 (d, 1H, J = 5.0 Hz), 8.22 (m, 1H), 7.70-7.67 (m, 1H), 6.31-6.28 (m, 1H), 4.87-4.82 (m, 1H), 3.37-3.34 (m, 1H), 3.22-3.14 (m, 3H), 2.22-2.18(m, 1H), 1.88-1.77 (m, 1H), 1.20 (s, 3H), 1.12 (s, 3H) | N-[(4S)-3,3-dimethyl-4-piperidyl]-2-[2-(3-pyridyl)-1H-pyrrolo[2,3-b]pyridin-4-yl]-5-(trifluoromethyl)pyrido[3,4-d]pyrimidin-4-amine |
| 373 | 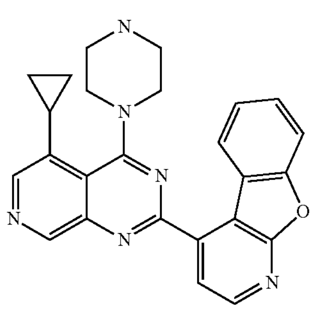 [SMILES: c1ccc2c(c1)oc1nccc(-c3nc(N4CCNCC4)c4c(C5CC5)cncc4n3)c12] | [A7] | 424 | 1H NMR (400 MHz, METHANOL-d4) δ 9.24 (s, 1H), 8.96 (d, J = 7.3 Hz, 1H), 8.56 (d, J = 5.3 Hz, 1H), 8.32 (d, J = 5.3 Hz, 1H), 8.26 (s, 1H), 7.70-7.75 (m, 1H), 7.64 (td, J = 7.8, 1.3 Hz, 1H), 7.46 (td, J = 7.7, 1.0 Hz, 1H), 4.11 (br. s., 4H), 3.45 (t, J = 5.1 Hz, 4H), 2.78-2.88 (m, 1H), 1.34-1.47 (m, 2H), 1.11-1.24 (m, 2H) | 4-(5-Cyclopropyl-4-piperazin-1-yl-pyrido[3,4-d]pyrimidin-2-yl)-benzofuro[2,3-b]pyridine |

TABLE A-continued

| Ex | Structure | Scheme | Analysis | | Name |
| --- | --- | --- | --- | --- | --- |
| | | | LCMS | 1H-NMR | |
| 374 | 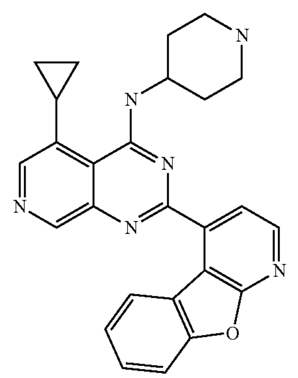 [SMILES: c1ccc2c(c1)oc1nccc(-c3nc(NC4CCNCC4)c4c(C5CC5)cncc4n3)c12] | [A7] | 437 [M + H] | 1H NMR (400 MHz, METHANOL-d4) δ 9.18 (d, J = 0.8 Hz, 1H), 8.79 (d, J = 7.3 Hz, 1H), 8.51-8.61 (m, 2H), 8.21 (d, J = 5.3 Hz, 1H), 7.70-7.76 (m, 1H), 7.63 (td, J = 7.8, 1.3 Hz, 1H), 7.43 (td, J = 7.7, 1.0 Hz, 1H), 4.69-4.82 (m, 1H), 3.44-3.58 (m, 3H), 3.11-3.28 (m, 2H), 2.46-2.66 (m, 3H), 1.86-2.03 (m, 2H), 1.14-1.44 (m, 5H) | 2-(benzofuro[2,3-b]pyridin-4-yl)-5-cyclopropyl-N-(4-piperidyl)pyrido[3,4-d]pyrimidin-4-amine |
| 375 | 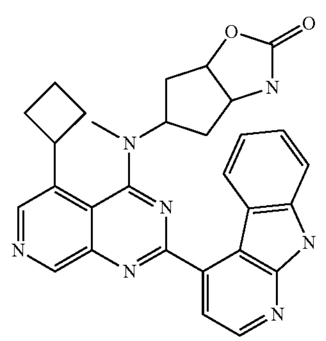 [SMILES: CN(c1nc(-c2ccnc3[nH]c4ccccc4c23)nc2cncc(C3CCC3)c12)C1CC2NC(=O)OC2C1] | [D3] | 506 [M + H] | 1H NMR (400 MHz, DMSO-d6) δ 9.15 (s, 1H), 8.68-8.76 (m, 2H), 8.57 (d, J = 5.3 Hz, 1H), 7.88 (d, J = 5.0 Hz, 2H), 7.42-7.57 (m, 2H), 7.10-7.42 (m, 1H), 6.94 (s, 1H), 4.95 (br. s., 1H), 4.65-4.77 (m, 1H), 3.99-4.31 (m, 3H), 3.04 (s, 3H), 2.59-2.74 (m, 2H), 1.84-2.36 (m, 8H) | 5-{[5-Cyclobutyl-2-(9H-pyrido[2,3-b]indol-4-yl)-pyrido[3,4-d]pyrimidin-4-yl]-methyl-amino}-hexahydro-cyclopentoxazol-2-one |
| 376 | 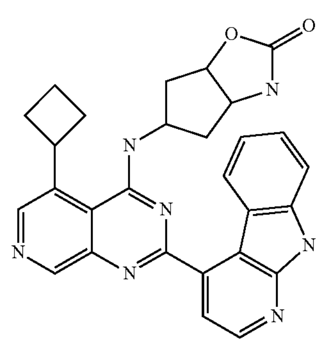 [SMILES: O=C1NC2CC(Nc3nc(-c4ccnc5[nH]c6ccccc6c45)nc4cncc(C5CCC5)c34)CC2O1] | [D3] | 492 [M + H] | 1H NMR (400 MHz, DMSO-d6) δ 12.02 (s, 1H), 9.13 (s, 1H), 8.53-8.66 (m, 3H), 8.41 (br. s., 2H), 7.96 (s, 1H), 7.82 (d, J = 5.3 Hz, 1H), 7.42-7.56 (m, 2H), 7.11-7.20 (m, 1H), 6.98 (d, J = 6.3 Hz, 1H), 5.01-5.15 (m, 1H), 4.72-4.88 (m, 1H), 4.14-4.41 (m, 2H), 3.62 (d, J = 3.5 Hz, 5H), 3.14 (dd, J = 7.0, 3.8 Hz, 5H), 2.79 (quin, J = 7.0 Hz, 2H), 2.15-2.44 (m, 8H) | 5-[5-Cyclobutyl-2-(9H-pyrido[2,3-b]indol-4-yl)-pyrido[3,4-d]pyrimidin-4-ylamino]-hexahydro-cyclopentoxazol-2-one |
| 377 | 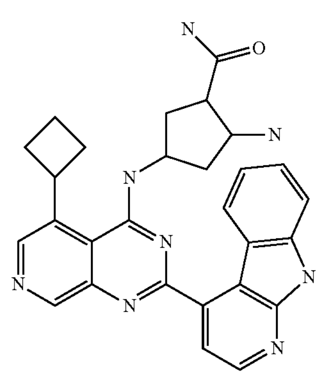 [SMILES: NC(=O)C1CC(Nc2nc(-c3ccnc4[nH]c5ccccc5c34)nc3cncc(C4CCC4)c23)CC1N] | [D3] | 493 [M + H] | 1H NMR (400 MHz, METHANOL-d4) δ ppm 9.10 (1 H, s) 8.47-8.58 (2 H, m) 8.29 (1 H, d, J = 8.0 Hz) 7.79 (1 H, d, J = 5.3 Hz) 7.45-7.65 (2 H, m) 7.13-7.22 (1 H, m) 5.13-5.29 (1 H, m) 4.47-4.65 (1 H, m) 4.02-4.18 (1 H, m) 2.99 (1H, dt, J = 8.9, 6.3 Hz) 2.59-2.76 (3 H, m) 1.90-2.55 (8 H, m) | 2-amino-4-[[5-cyclobutyl-2-(9H-pyrido[2,3-b]indol-4-yl)pyrido[3,4-d]pyrimidin-4-yl]amino]cyclopentane carboxamide |

TABLE A-continued

| Ex | Structure | Scheme | Analysis | | Name |
|---|---|---|---|---|---|
| | | | LCMS | 1H-NMR | |
| 378 | 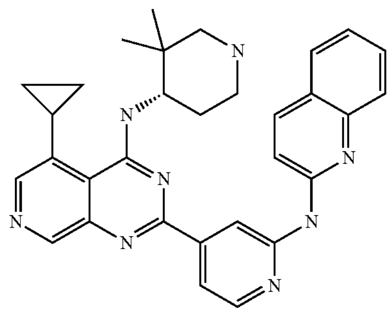 [SMILES: CC1(C)CNCC[C@@H]1Nc1nc(-c2ccnc(Nc3ccc4ccccc4n3)c2)nc2cncc(C3CC3)c12] | [B4], [E4] | 517 [M + H] | 1H NMR (400 MHz, METHANOL-d4) δ ppm 9.11 (s, 1 H) 8.77 (d, J = 5.27 Hz, 1 H) 8.64 (d, J = 9.29 Hz, 1 H) 8.54 (d, J = 1.00 Hz, 1 H) 8.50 (s, 1 H) 8.45 (dd, J = 5.65, 1.38 Hz, 1 H) 8.17 (d, J = 8.53 Hz, 1 H) 8.05 (d, J = 8.03 Hz, 1 H) 7.96 (s, 1 H) 7.70 (s, 1 H) 7.46 (d, J = 9.29 Hz, 1 H) 5.00-5.11 (m, 1 H) 3.51-3.58 (m, 1 H) 3.36-3.43 (m, 2 H) 2.50-2.59 (m, 1 H) 2.22-2.34 (m, 1 H) 2.04-2.15 (m, 1 H) 1.37-1.47 (m, 1 H) 1.27-1.35 (m, 6 H) 1.23 (s, 3 H) 1.10-1.19 (m, 1 H) | {5-Cyclopropyl-2-[2-(quinolin-2-ylamino)-pyridin-4-yl]-pyrido[3,4-d]pyrimidin-4-yl}-((S)-3,3-dimethyl-piperidin-4-yl)-amine |
| 379 | 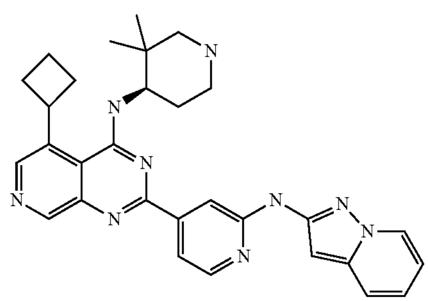 [SMILES: CC1(C)CNCC[C@H]1Nc1nc(-c2ccnc(Nc3cc4ccccn4n3)c2)nc2cncc(C3CCC3)c12] | [B4], [E4] | 520 [M + H] | 1H NMR (400 MHz, METHANOL-d4) δ ppm 9.04 (s, 1 H) 8.50-8.58 (m, 2 H) 8.40 (d, J = 1.00 Hz, 1 H) 8.33 (d, J = 6.78 Hz, 1 H) 8.18 (dd, J = 6.78, 1.51 Hz, 1 H) 7.55 (d, J = 9.03 Hz, 1 H) 7.18-7.32 (m, 1 H) 6.87 (td, J = 6.90, 1.25 Hz, 1 H) 6.33 (d, J = 0.75 Hz, 1 H) 4.91 (dd, J = 11.80, 4.27 Hz, 1 H) 4.21 (t, J = 8.28 Hz, 1 H) 3.42 (br. s., 1 H) 3.24-3.30 (m, 2 H) 3.08-3.17 (m, 1 H) 2.54 (qd, J = 7.99, 4.89 Hz, 2 H) 2.26-2.46 (m, 2 H) 1.92-2.20 (m, 4 H) 1.28 (s, 3 H) 1.13 (s, 3 H) | {5-Cyclobutyl-2-[2-(pyrazolo[1,5-a]pyridin-2-ylamino)-pyridin-4-yl]-pyrido[3,4-d]pyrimidin-4-yl}-((R)-3,3-dimethyl-piperidin-4-yl)-amine |
| 380 | 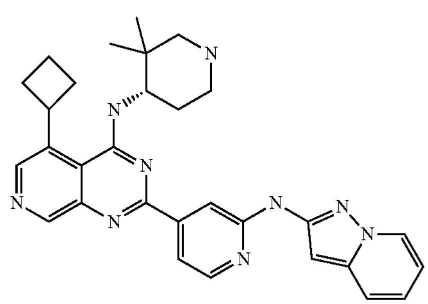 [SMILES: CC1(C)CNCC[C@@H]1Nc1nc(-c2ccnc(Nc3cc4ccccn4n3)c2)nc2cncc(C3CCC3)c12] | [B4], [E4] | 520 [M + H] | 1H NMR (400 MHz, METHANOL-d4) δ ppm 9.43 (br. s., 1 H) 8.95 (s, 1 H) 8.60-8.75 (m, 2 H) 8.44 (d, J = 6.78 Hz, 1 H) 8.25 (dd, J = 6.78, 1.25 Hz, 1 H) 7.62 (d, J = 9.03 Hz, 1 H) 7.24-7.38 (m, 1 H) 6.95 (d, J = 1.00 Hz, 1 H) 6.51 (s, 1H) 5.28 (d, J = 6.27 Hz, 1 H) 4.48 (s, 1 H) 3.65-3.75 (m, 1 H) 3.52 (br. s., 1 H) 2.70 (br. s., 3 H) 2.48 (br. s., 3 H) 2.21 (br. s., 3 H) 2.05-2.13 (m, 1 H) 1.40 (s, 3 H) 1.25 (s, 3 H) | {5-Cyclobutyl-2-[2-(pyrazolo[1,5-a]pyridin-2-ylamino)-pyridin-4-yl]-pyrido[3,4-d]pyrimidin-4-yl}-((S)-3,3-dimethyl-piperidin-4-yl)-amine |
| 381 | 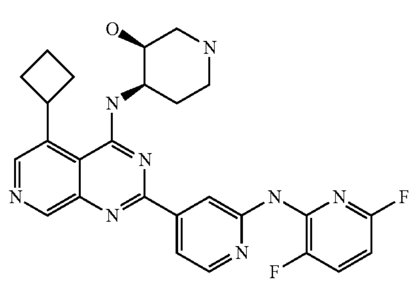 [SMILES: O[C@H]1CNCC[C@H]1Nc1nc(-c2ccnc(Nc3nc(F)ccc3F)c2)nc2cncc(C3CCC3)c12] | [B4] | 505 [M + H] | 1H NMR (400 MHz, METHANOL-d4) δ ppm 9.15 (s, 1 H) 8.97 (d, J = 1.00 Hz, 1 H) 8.62 (d, J = 0.75 Hz, 1 H) 8.53 (d, J = 5.77 Hz, 1 H) 8.39 (dd, J = 6.27, 1.51 Hz, 1 H) 7.81-8.03 (m, 1 H) 6.90 (d, J = 8.53 Hz, 1 H) 4.95 (d, J = 13.05 Hz, 2 H) 4.41 (br. s., 1 H) 4.19-4.32 (m, 1 H) 3.48-3.60 (m, 2 H) 3.38-3.46 (m, 1H) 2.69 (s, 2 H) 2.37-2.61 (m, 3 H) 2.14-2.31(m, 2 H) 1.98-2.11 (m, 1 H) | rac-(3S,4R)-4-{5-Cyclobutyl-2-[2-(3,6-difluoro-pyridin-2-ylamino)-pyridin-4-yl]-pyrido[3,4-d]pyrimidin-4-ylamino}-piperidin-3-ol |

TABLE A-continued

| Ex | Structure | Scheme | Analysis LCMS | 1H-NMR | Name |
|---|---|---|---|---|---|
| 382 | 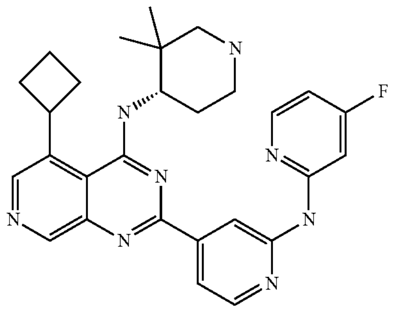 [SMILES: CC1(C)CNCC[C@@H]1Nc1nc(-c2ccnc(Nc3cc(F)ccn3)c2)nc2cncc(C3CCC3)c12] | [B4], [E4] | 499 [M + H] | 1H NMR (400 MHz, METHANOL-d4) δ ppm 9.17 (s, 1 H) 8.66 (d, J = 0.75 Hz, 1 H) 8.52-8.57 (m, 2 H) 8.50 (s, 1 H) 8.41 (dd, J = 6.27, 1.51 Hz, 1 H) 7.20 (s, 1 H) 7.12 (dd, J = 9.54, 2.26 Hz, 1 H) 4.99-5.08 (m, 1 H) 4.28-4.39 (m, 1 H) 3.51-3.60 (m, 1 H) 3.39 (s, 2 H) 3.28 (s, 1 H) 2.60-2.72 (m, 2 H) 2.38-2.60 (m, 2 H) 2.19-2.32 (m, 2 H) 2.04-2.19 (m, 2 H) 1.41 (s, 3 H) 1.25 (s, 3 H) | {5-Cyclobutyl-2-[2-(4-fluoro-pyridin-2-ylamino)-pyridin-4-yl]-pyrido[3,4-d]pyrimidin-4-yl}-((S)-3,3-dimethyl-piperidin-4-yl)-amine |
| 383 | 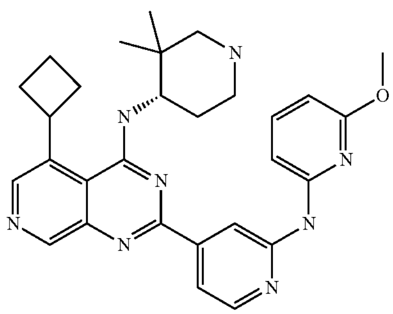 [SMILES: COc1cccc(Nc2cc(-c3nc(N[C@H]4CCNCC4(C)C)c4c(C5CCC5)cncc4n3)ccn2)n1] | [B4], [E4] | 511 [M + H] | 1H NMR (400 MHz, METHANOL-d4) δ ppm 9.12 (s, 1 H) 8.63 (d, J = 1.00 Hz, 1 H) 8.56 (d, J = 0.75 Hz, 1 H) 8.45 (d, J = 6.53 Hz, 1 H) 8.30 (dd, J = 6.53, 1.51 Hz, 1 H) 7.86 (t, J = 8.03 Hz, 1 H) 6.84 (d, J = 7.53 Hz, 1 H) 6.71 (d, J = 8.03 Hz, 1 H) 4.99 (dd, J = 11.80, 4.27 Hz, 1 H) 4.23-4.37 (m, 1 H) 4.12 (s, 3 H) 3.48-3.56 (m, 1 H) 3.34-3.40 (m, 2 H) 3.15-3.27 (m, 1 H) 2.58-2.69 (m, 2 H) 2.33-2.56 (m, 2 H) 2.15-2.30 (m, 2 H) 2.00-2.14 (m, 2 H) 1.37 (s, 3 H) 1.22 (s, 3 H) | {5-Cyclobutyl-2-[2-(6-methoxy-pyridin-2-ylamino)-pyridin-4-yl]-pyrido[3,4-d]pyrimidin-4-yl}-((S)-3,3-dimethyl-piperidin-4-yl)-amine |
| 384 | 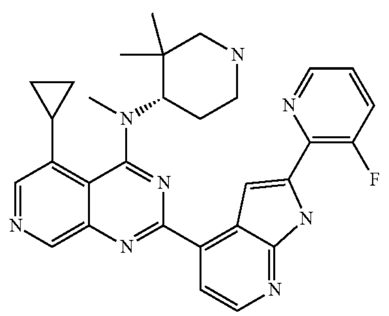 [SMILES: CN(c1nc(-c2ccnc3[nH]c(-c4ncccc4F)cc23)nc2cncc(C3CC3)c12)[C@H]1CCNCC1(C)C] | [D3], [D4], [E4] | 523.23 (M + H) | 1H NMR (400 MHz, DMSO-d6) δ ppm 12.40 (s, 1 H), 9.04 (s, 1 H), 8.97 (br. s., 1 H), 8.57-8.67 (m, 1 H), 8.50 (d, J = 5.0 Hz, 1 H), 8.03-8.36 (m, 4 H), 7.93 (ddd, J = 11.8, 8.4, 1.1 Hz, 1 H), 7.53 (dt, J = 8.3, 4.2 Hz, 1 H), 3.16 (br. s., 5H), 1.84-2.36 (m, 3 H), 1.06-1.58 (m, 8 H), 0.99 (br. s., 2 H) | {5-Cyclopropyl-2-[2-(3-fluoro-pyridin-2-yl)-1H-pyrrolo[2,3-b]pyridin-4-yl]-pyrido[3,4-d]pyrimidin-4-yl}-((S)-3,3-dimethyl-piperidin-4-yl)-methyl-amine |
| 385 | 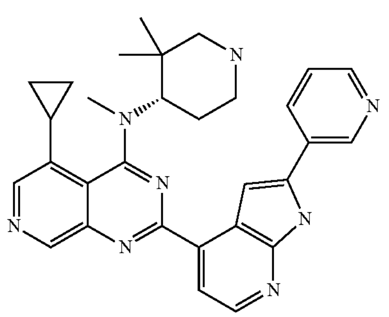 [SMILES: CN(c1nc(-c2ccnc3[nH]c(-c4cccnc4)cc23)nc2cncc(C3CC3)c12)[C@H]1CCNCC1(C)C] | [D22], [E4] | 505.21 | 1H NMR (400 MHz, DMSO-d6) δ 12.53 (s, 1H), 9.31-8.95 (m, 2H), 8.62 (m, 1H), 8.44 (m, 2H), 8.19-8.14 (m, 2H), 8.08 (m, 1H), 7.61-7.58 (m, 1H), 3.78 (m, 9H), 3.42 (m, 2H), 3.16 (m, 3H), 1.37-0.86 (m, 7H) | [5-Cyclopropyl-2-(2-pyridin-3-yl-1H-pyrrolo[2,3-b]pyridin-4-yl)-pyrido[3,4-d]pyrimidin-4-yl]-((S)-3,3-dimethyl-piperidin-4-yl)-methyl-amine |

TABLE A-continued

| Ex | Structure | Scheme | LCMS | 1H-NMR | Name |
|---|---|---|---|---|---|
| 386 | 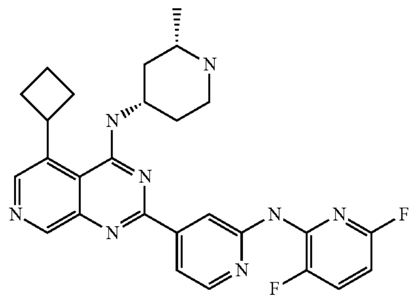 [SMILES: C[C@H]1C[C@@H](Nc2nc(-c3ccnc(Nc4nc(F)ccc4F)c3)nc3cncc(C4CCC4)c23)CCN1] | [B4] | 503 [M + H] | 1H NMR (400 MHz, METHANOL-d4) δ ppm 9.11 (s, 1 H) 8.91 (d, J = 0.75 Hz, 1 H) 8.44-8.55 (m, 2 H) 8.36 (dd, J = 6.40, 1.63 Hz, 1 H) 7.92 (td, J = 9.16, 6.02 Hz, 1 H) 6.88 (dt, J = 8.72, 2.42 Hz, 1 H) 4.84 (br. s., 1 H) 4.44 (s, 1 H) 3.58 (d, J = 2.01 Hz, 2 H) 2.65 (d, J = 1.76 Hz, 2 H) 2.46-2.59 (m, 2 H) 2.30-2.44 (m, 2 H) 2.13-2.29 (m, 1 H) 1.70-2.04 (m, 3 H) 1.44 (d, J = 6.53 Hz, 3 H) | {5-Cyclobutyl-2-[2-(3,6-difluoro-pyridin-2-ylamino)-pyridin-4-yl]-pyrido[3,4-d]pyrimidin-4-yl}-(rac-(2S,4S)-2-methyl-piperidin-4-yl)-amine |
| 387 | 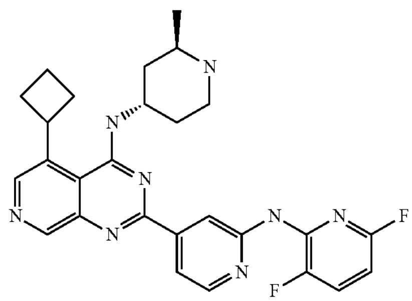 [SMILES: C[C@@H]1C[C@@H](Nc2nc(-c3ccnc(Nc4nc(F)ccc4F)c3)nc3cncc(C4CCC4)c23)CCN1] | [B4] | 503 [M + H] | 1H NMR (400 MHz, DMSO-d6) δ ppm 9.70 (s, 1 H) 9.07 (s, 1 H) 8.89 (s, 1 H) 8.72 (br. s., 1 H) 8.52 (s, 1 H) 8.45 (d, J = 5.27 Hz, 1 H) 7.98 (dd, J = 5.14, 1.13 Hz, 1 H) 7.87 (td, J = 8.97, 6.65 Hz, 1 H) 6.97 (d, J = 5.77 Hz, 1 H) 6.64-6.77 (m, 1 H) 4.75 (d, J = 4.27 Hz, 1 H) 4.58 (t, J = 8.28 Hz, 1 H) 3.32 (br. s., 4 H) 2.15-2.38 (m, 5 H) 2.09 (d, J = 9.29 Hz, 2 H) 1.76-1.99 (m, 2 H) 1.30 (d, J = 6.27 Hz, 3 H) | {5-Cyclobutyl-2-[2-(3,6-difluoro-pyridin-2-ylamino)-pyridin-4-yl]-pyrido[3,4-d]pyrimidin-4-yl}-(rac-(2R,4S)-2-methyl-piperidin-4-yl)-amine |
| 388 | 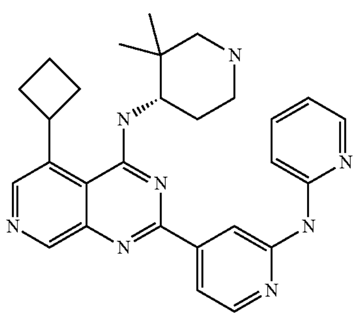 [SMILES: CC1(C)CNCC[C@@H]1Nc1nc(-c2ccnc(Nc3ccccn3)c2)nc2cncc(C3CCC3)c12] | [B4], [E4] | 481 [M + H] | 1H NMR (400 MHz, METHANOL-d4) δ ppm 9.11 (s, 1 H) 8.59-8.62 (m, 1 H) 8.55 (d, J = 5.77 Hz, 1 H) 8.36-8.43 (m, 2 H) 8.33 (dd, J = 5.90, 1.38 Hz, 1 H) 8.15 (ddd, J = 8.72, 7.22, 1.88 Hz, 1 H) 7.39 (d, J = 8.53 Hz, 1 H) 7.32 (ddd, J = 7.15, 6.02, 0.88 Hz, 1 H) 5.01 (dd, J = 11.80, 4.27 Hz, 1 H) 4.22-4.36 (m, 1 H) 3.47-3.57 (m, 1 H) 3.36 (s, 2 H) 3.25 (s, 1 H) 2.66 (s, 2 H) 2.34-2.57 (m, 2 H) 1.99-2.28 (m, 4 H) 1.37 (s, 3 H) 1.22 (s, 3 H) | {5-Cyclobutyl-2-[2-(pyridin-2-ylamino)-pyridin-4-yl]-pyrido[3,4-d]pyrimidin-4-yl}-((S)-3,3-dimethyl-piperidin-4-yl)-amine |
| 389 | 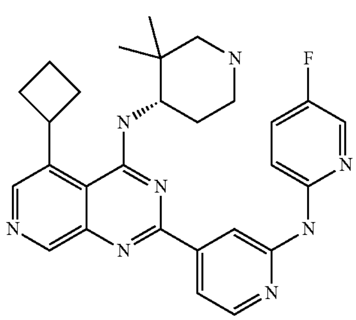 [SMILES: CC1(C)CNCC[C@@H]1Nc1nc(-c2ccnc(Nc3ccc(F)cn3)c2)nc2cncc(C3CCC3)c12] | [B4], [E4] | 499 [M + H] | 1H NMR (400 MHz, METHANOL-d4) δ ppm 9.13 (s, 1 H) 8.63 (d, J = 0.75 Hz, 1 H) 8.51 (d, J = 0.75 Hz, 1 H) 8.39-8.43 (m, 2 H) 8.31-8.37 (m, 1 H) 7.86 (ddd, J = 9.03, 8.03, 3.01 Hz, 1 H) 7.33 (dd, J = 9.03, 3.51 Hz, 1 H) 5.00 (dd, J = 11.67, 4.39 Hz, 1 H) 4.31 (t, J = 8.28 Hz, 1 H) 3.52 (d, J = 13.05 Hz, 1 H) 3.32-3.42 (m, 2 H) 3.17-3.29 (m, 1 H) 2.64 (td, J = 8.09, 2.89 Hz, 2H) 2.34-2.56 (m, 2 H) 1.99-2.28 (m, 4 H) 1.37 (s, 3 H) 1.22 (s, 3 H) | {5-Cyclobutyl-2-[2-(5-fluoropyridin-2-ylamino)-pyridin-4-yl]-pyrido[3,4-d]pyrimidin-4-yl}-((S)-3,3-dimethyl-piperidin-4-yl)-amine |

TABLE A-continued

| Ex | Structure | Scheme | LCMS | 1H-NMR | Name |
|---|---|---|---|---|---|
| 390 | 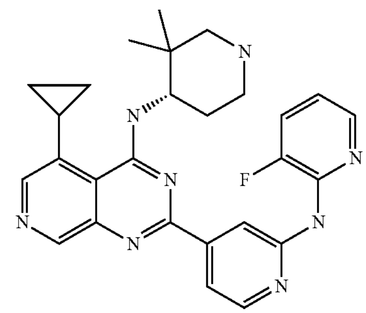 [SMILES: CC1(C)CNCC[C@@H]1Nc1nc(-c2ccnc(Nc3ncccc3F)c2)nc2cncc(C3CC3)c12] | [B4], [E4] | 485 [M + H] | 1H NMR (400 MHz, METHANOL-d4) δ ppm 9.14 (d, J = 0.75 Hz, 1 H) 8.78 (dd, J = 1.51, 0.75 Hz, 1 H) 8.57(d, J = 1.00 Hz, 1 H) 8.48-8.53 (m, 1 H) 8.41-8.48 (m, 1 H) 8.34 (dd, J = 5.14, 1.13 Hz, 1 H) 7.89 (ddd, J = 10.79, 8.28, 1.51 Hz, 1 H) 7.35 (d, J = 5.02 Hz, 1 H) 5.05 (dd, J = 11.80, 4.27 Hz, 1 H) 3.51-3.59 (m, 1 H) 3.32 (br. s., 2 H) 3.18-3.26 (m, 1 H) 2.50-2.60 (m, 1 H) 2.19-2.32 (m, 1 H) 2.03-2.18 (m, 1 H) 1.37-1.48 (m, 1 H) 1.31 (s, 5 H) 1.22 (s, 3 H) 1.06-1.19 (m, 1 H) | {5-Cyclopropyl-2-[2-(3-fluoro-pyridin-2-ylamino)-pyridin-4-yl]-pyrido[3,4-d]pyrimidin-4-yl}-((S)-3,3-dimethyl-piperidin-4-yl)-amine |
| 391 | 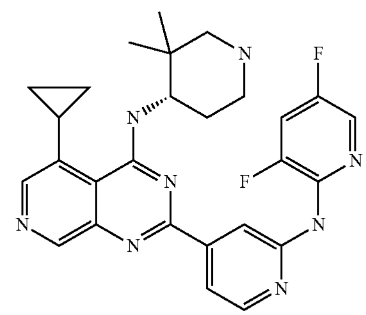 [SMILES: CC1(C)CNCC[C@@H]1Nc1nc(-c2ccnc(Nc3ncc(F)cc3F)c2)nc2cncc(C3CC3)c12] | [B4], [E4] | 503 [M + H] | 1H NMR (400 MHz, METHANOL-d4) δ ppm 9.13 (s, 1 H) 8.79 (s, 1 H) 8.57 (d, J = 1.00 Hz, 1 H) 8.44 (s, 2 H) 8.31 (d, J = 2.51 Hz, 1 H) 7.95 (s, 1 H) 5.00-5.07 (m, 1 H) 3.49-3.58 (m, 1 H) 3.32-3.38 (m, 2 H) 3.23 (s, 1 H) 2.49-2.59 (m, 1 H) 2.22-2.31 (m, 1 H) 2.05-2.18 (m, 1 H) 1.42 (d, J = 2.26 Hz, 1 H) 1.28-1.34 (m, 5 H) 1.22 (s, 3 H) 1.14 (d, J = 5.77Hz, 1 H) | {5-Cyclopropyl-2-[2-(3,5-difluoro-pyridin-2-ylamino)-pyridin-4-yl]-pyrido[3,4-d]pyrimidin-4-yl}-((S)-3,3-dimethyl-piperidin-4-yl)-amine |
| 392 | 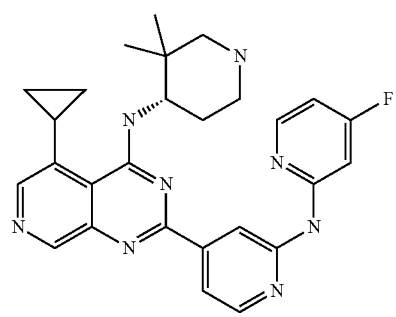 [SMILES: CC1(C)CNCC[C@@H]1Nc1nc(-c2ccnc(Nc3cc(F)ccn3)c2)nc2cncc(C3CC3)c12] | [B4], [E4] | 485 [M + H] | 1H NMR (400 MHz, METHANOL-d4) δ ppm 9.13 (s, 1 H) 8.55 (d, J = 0.75 Hz, 1 H) 8.47-8.53 (m, 3 H) 8.39 (dd, J = 6.27, 1.51 Hz, 1 H) 7.16 (s, 1 H) 7.08 (dd, J = 9.79, 2.26 Hz, 1 H) 5.05 (dd, J = 11.54, 4.27 Hz, 1 H) 3.54 (d, J = 13.05 Hz, 1H) 3.32-3.43 (m, 2 H) 3.20-3.29 (m, 1 H) 2.46-2.59 (m, 1 H) 2.22-2.33 (m, 1 H) 2.04-2.19 (m, 1 H) 1.38-1.48 (m, 1 H) 1.27-1.36 (m, 5 H) 1.22 (s, 3 H) 1.06-1.19 (m, 1 H) | {5-Cyclopropyl-2-[2-(4-fluoro-pyridin-2-ylamino)-pyridin-4-yl]-pyrido[3,4-d]pyrimidin-4-yl}-((S)-3,3-dimethyl-piperidin-4-yl)-amine |
| 393 | 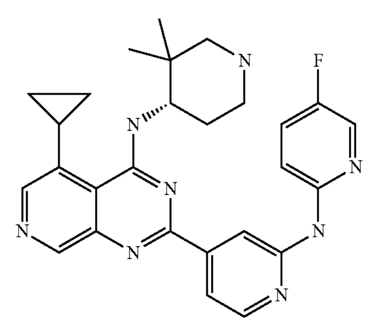 [SMILES: CC1(C)CNCC[C@@H]1Nc1nc(-c2ccnc(Nc3ccc(F)cn3)c2)nc2cncc(C3CC3)c12] | [B4], [E4] | 485 [M + H] | 1H NMR (400 MHz, METHANOL-d4) δ ppm 9.13 (d, J = 0.75 Hz, 1 H) 8.56 (d, J = 1.25 Hz, 1 H) 8.49-8.54 (m, 1 H) 8.31-8.44 (m, 3 H) 7.86 (ddd, J = 9.16, 7.91, 3.01 Hz, 1 H) 7.33 (dd, J = 9.29, 3.51 Hz, 1 H) 5.04 (s, 1 H) 3.48-3.58 (m, 1 H) 3.35 (d, J = 1.51 Hz, 2 H) 3.21-3.27 (m, 1 H) 2.54 (s, 1 H) 2.21-2.32 (m, 1 H) 2.05-2.19 (m, 1 H) 1.37-1.46 (m, 1 H) 1.27-1.35 (m, 5 H) 1.21 (s, 3 H) 1.15 (s, 1 H) | {5-Cyclopropyl-2-[2-(5-fluoro-pyridin-2-ylamino)-pyridin-4-yl]-pyrido[3,4-d]pyrimidin-4-yl}-((S)-3,3-dimethyl-piperidin-4-yl)-amine |

TABLE A-continued

| Ex | Structure | Scheme | Analysis LCMS | 1H-NMR | Name |
|---|---|---|---|---|---|
| 394 | 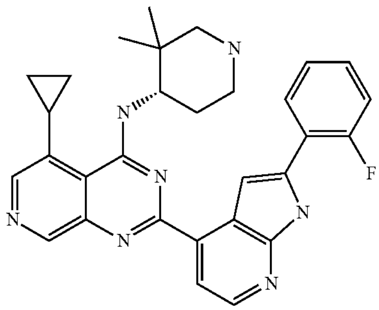 [SMILES: CC1(C)CNCC[C@@H]1Nc1nc(-c2ccnc3[nH]c(-c4ccccc4F)cc23)nc2cncc(C3CC3)c12] | [D3], [D4], [E4] | 508.24 | 1H NMR (400 MHz, DMSO-d6) δ 12.35 (s, 1H), 9.13 (s, 1H), 9.03 (m, 1H), 8.51 (s, 1H), 8.45 (d, 1H, J = 5.0 Hz), 8.29 (m, 1H), 8.20 (d, 1H, J = 5.0 Hz), 8.12-8.08 (m, 1H), 7.98 (m, 1H), 7.63 (d, 1H, J = 8.9 Hz), 7.50-7.37 (m, 3H), 4.91-4.85 (m, 1H), 3.38 (m, 2H), 3.25-3.05 (m, 3H), 2.62 (m, 1H), 2.17 (m, 1H), 2.02-1.93 (m, 1H), 1.29-1.12 (m, 9H) | {5-Cyclopropyl-2-[2-(2-fluoro-phenyl)-1H-pyrrolo[2,3-b]pyridin-4-yl]-pyrido[3,4-d]pyrimidin-4-yl}-((S)-3,3-dimethyl-piperidin-4-yl)-amine |
| 395 | 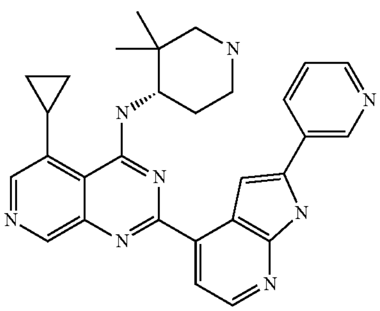 [SMILES: CC1(C)CNCC[C@@H]1Nc1nc(-c2ccnc3[nH]c(-c4cccnc4)cc23)nc2cncc(C3CC3)c12] | [D22], [E4] | 491.21 | 1H NMR (400 MHz, DMSO-d6) δ 12.60 (s, 1H), 9.39 (m, 2H), 9.10 (m, 1H), 8.68 (m, 2H), 8.52 (s, 1H), 8.47 (d, 1H, J = 5.0 Hz), 8.34 (m, 1H), 8.25 (d, 1H, J = 5.0 Hz), 8.21 (m, 1H), 7.75 (m, 1H), 7.61 (m, 1H), 4.90 (m, 1H), 3.38 (m, 1H), 3.23-3.13 (m, 3H), 2.65-3.59 (m, 1H), 2.17 (m, 1H), 2.03-1.92 (m, 1H), 1.28 (m, 1H), 1.21-1.13 (m, 9H) | [5-Cyclopropyl-2-(2-pyridin-3-yl-1H-pyrrolo[2,3-b]pyridin-4-yl)-pyrido[3,4-d]pyrimidin-4-yl]-((S)-3,3-dimethyl-piperidin-4-yl)-amine |
| 396 | 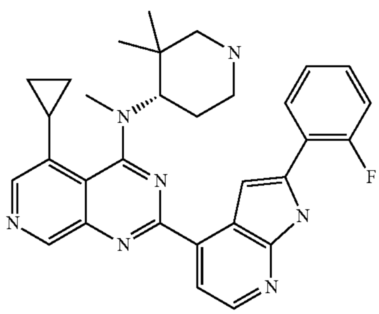 [SMILES: CN(c1nc(-c2ccnc3[nH]c(-c4ccccc4F)cc23)nc2cncc(C3CC3)c12)[C@H]1CCNCC1(C)C] | [D3], [D4], [E4] | 522.2 | 1H NMR (400 MHz, DMSO-d6) δ 12.38 (s, 1H), 9.06-9.00 (m, 2H), 8.45 (d, 1H, J = 5.0 Hz), 8.25-8.07 (m, 4H), 8.00-7.93 (m, 1H), 7.50-7.37 (m, 3H), 3.49-2.67 (m, 9H), 2.33-1.95 (m, 2H), 1.53 -0.89 (m, 9H) | {5-Cyclopropyl-2-[2-(2-fluoro-phenyl)-1H-pyrrolo[2,3-b]pyridin-4-yl]-pyrido[3,4-d]pyrimidin-4-yl}-((S)-3,3-dimethyl-piperidin-4-yl)-methyl-amine |

VI. Biology

PKCι IC$_{50}$ Assay

Assays are based on the ability of PKCι to phosphorylate a commercially available peptide substrate in vitro. The peptide substrate is FAM-PKCε pseudopeptide derived peptide, and comprises the amino acid sequence 5FAM-ERMRPRKRQGSVRRRV-NH$_2$. Recombinant, full-length human PKCι expressed in Sf21 insect cells is also commercially available. Recombinant, kinase-domain human PKCι is expressed and purified in-house.

The procedure below explains how dose response curves for inhibitors of PKCι are obtained. The screen described is for a 384 well format but the assay can be adapted to 1536 or other formats as required.

Compounds to be tested are dissolved in 100% DMSO. Compounds are diluted as required to give a final concentration of 4% DMSO (v/v) in the assay. 1 μl is plated into 384 well black low-binding flat bottomed assay plates which are used immediately. Dilutions and additions of compound to assay plates are carried out using Matrix WellMate® and Matrix PlateMate® Plus liquid handling systems.

On the day of the screen PKCι/substrate working solution, and ATP working solution, are prepared in buffer containing 20 mM tris-HCl pH7.5, 10 mM MgCl$_2$, 0.01% Triton X100, 250 μM EGTA and 1 mM DTT. The final concentration of PKCι used varies depending on the batch of protein but is typically 15 pM. The final concentration of peptide substrate in the assay is 100 nM. ATP is used at a final concentration of 150 μM or 25 μM in the assays containing full-length or kinase-domain PKCι respectively, which corresponds to five times or equal to the K$_M^{APP}$ for ATP for each enzyme, respectively. The final buffer concentration in the assay is 18 mM tris-HCl pH7.5, 9 mM MgCl$_2$, 0.009% Triton X100, 225 μM EGTA and 0.9 mM DTT. Relevant controls are included, namely no compound and no enzyme. 5 μl PKCι/substrate working solution at 30 pM and 200 nM, respectively, is added to the wells, followed by 4 μl ATP working solution at 375 μM or 62.5 μM for full-length or kinase-domain PKCι respectively, using a 16 channel Matrix pipette. The reaction is allowed to incubate for 60 minutes at room temperature, before the reaction is stopped and developed by the addition of 20 μl IMAP™ development reagent (Molecular Devices). IMAP development reagent consists of 0.25% (v/v) IMAP progressive binding reagent, 17% (v/v) IMAP progressive binding buffer A and 3% (v/v) IMAP progressive binding buffer B. The plates are then incubated for 2 hours at room temperature before being read using an appropriate plate reader, for example a Molecular Devices HT Analyst or a BMG Pherastar. Plates are read using a fluorescence polarisation protocol with excitation at 485 nm and emission at 530 nm, and dichroic mirror at 505 nm.

Percentage inhibition values are calculated from fluorescence polarisation values, using the no compound and no enzyme control values as 0% and 100% inhibition, respectively. IC50 determination is performed with ExcelFit software (IDBS) using curve fit 205. Z' factors are determined for each plate tested and are all above 0.5.

Alternatively, compounds were tested for their ability to inhibit the kinase activity of recombinant human baculovirus-expressed PKCiota using the immobilized metal-ion affinity particle (IMAP®) fluorescence polarization detection system (Molecular Devices, Sunnyvale, Calif.). PKCiota/IMAP® substrate mixture (2×) was prepared in 1×IMAP assay buffer (Molecular Devices) containing 1 mM DTT so that the final assay concentrations were 15 pM PKCiota (EMD Millipore, Billerica, Mass.) and 100 nM 5-fluorescein-amidite (FAM)-PKCε-pseudosubstrate (5-FAM-ERMRPRKRQGSVRRRV-NH2) (Molecular Devices). The 2× working solution was added at 5 μL/well into a 384-well black, non-binding, flat bottom assay plate (Corning, Corning, N.Y.). Compound serial dilutions were carried out in 100% DMSO, then 100 nL transferred to the assay plate containing 5 μL of the 2× enzyme/substrate solution using a BioMek NX pin tool (Beckman Coulter, Indianapolis, Ind.). Enzyme reaction was initiated by the addition of 5 μL 2×ATP, so that the final assay concentration was 150 μM. Assay plates were incubated for 1 hour in a 25° C. incubator, followed by addition of 20 μL IMAP® detection reagent. The detection reagent was comprised of 85% 1× buffer A and 15% 1× buffer B and the IMAP® Binding Reagent diluted 1:400. Assay plates were then incubated for 2 hours in a 25° C. incubator. Following the incubation, fluorescence polarization was measured using a PerkinElmer Envision™ 2102 plate reader (PerkinElmer, Waltham, Mass.) with an excitation wavelength of 480 nm and an emission wavelength of 535 nm.

Results

Biological data for the Example compounds is presented in the following table. Activities are set forth as follows:

IC50 in IMAP assay against full length PKCi at 150 μM ATP:

| Example | Activity |
| --- | --- |
| 1 | ++++ |
| 2 | ++++ |
| 3 | +++ |
| 4 | +++ |
| 5 | ++ |
| 6 | +++ |
| 7 | +++ |
| 8 | ++++ |
| 9 | ++++ |
| 10 | ++++ |
| 11 | ++++ |
| 12 | ++++ |
| 13 | ++++ |
| 14 | ++++ |
| 15 | ++++ |
| 16 | ++++ |
| 17 | ++++ |
| 18 | ++++ |
| 19 | ++++ |
| 20 | ++++ |
| 21 | ++++ |
| 22 | ++++ |
| 23 | ++++ |
| 24 | ++++ |
| 25 | +++ |
| 26 | +++ |
| 27 | ++++ |
| 28 | ++++ |
| 29 | ++++ |
| 30 | + |
| 31 | ++++ |
| 32 | ++++ |
| 33 | ++++ |
| 34 | ++++ |
| 35 | ++++ |
| 36 | ++++ |
| 37 | ++++ |
| 38 | ++++ |
| 39 | +++ |
| 40 | ++++ |
| 41 | ++++ |
| 42 | ++++ |
| 43 | ++++ |
| 44 | ++++ |
| 45 | ++++ |
| 46 | ++++ |
| 47 | ++++ |
| 48 | ++++ |
| 49 | ++++ |
| 50 | ++++ |
| 51 | ++++ |
| 52 | +++ |
| 53 | +++ |
| 54 | ++++ |
| 55 | ++++ |
| 56 | ++++ |
| 57 | ++++ |
| 58 | ++++ |
| 59 | ++++ |
| 60 | ++++ |
| 61 | ++++ |
| 62 | ++++ |
| 63 | ++++ |
| 64 | ++++ |
| 65 | +++ |
| 66 | ++++ |
| 67 | ++++ |
| 68 | ++++ |
| 69 | ++++ |
| 70 | ++++ |
| 71 | ++++ |
| 72 | +++ |
| 73 | ++++ |
| 74 | ++++ |
| 75 | ++++ |
| 76 | ++++ |
| 77 | ++++ |
| 78 | ++++ |
| 79 | ++++ |
| 80 | ++++ |
| 81 | ++++ |
| 82 | ++++ |
| 83 | ++++ |
| 84 | ++++ |
| 85 | ++++ |
| 86 | ++++ |
| 87 | ++++ |
| 88 | ++++ |
| 89 | ++++ |
| 90 | +++ |
| 91 | ++++ |
| 92 | ++++ |
| 93 | ++++ |
| 94 | ++++ |
| 95 | ++++ |
| 96 | ++++ |
| 97 | ++++ |
| 98 | ++++ |
| 99 | ++++ |

347
-continued

| | |
|---|---|
| 100 | ++++ |
| 101 | ++++ |
| 102 | ++++ |
| 103 | ++++ |
| 104 | ++++ |
| 105 | +++ |
| 106 | ++++ |
| 107 | ++++ |
| 108 | ++++ |
| 109 | ++++ |
| 110 | ++++ |
| 111 | ++++ |
| 112 | ++++ |
| 113 | ++++ |
| 114 | ++++ |
| 115 | ++++ |
| 116 | ++++ |
| 117 | ++++ |
| 118 | ++++ |
| 119 | ++++ |
| 120 | ++++ |
| 121 | ++++ |
| 122 | ++++ |
| 123 | ++++ |
| 124 | ++++ |
| 125 | ++++ |
| 126 | ++++ |
| 127 | ++++ |
| 128 | ++++ |
| 129 | ++++ |
| 130 | ++++ |
| 131 | ++++ |
| 132 | ++++ |
| 133 | ++++ |
| 134 | ++++ |
| 135 | +++ |
| 136 | ++++ |
| 137 | ++++ |
| 138 | ++++ |
| 139 | ++++ |
| 140 | ++++ |
| 141 | ++++ |
| 142 | ++++ |
| 143 | ++++ |
| 151 | ++++ |
| 152 | ++ |
| 153 | +++ |
| 154 | ++++ |
| 155 | ++++ |
| 156 | ++++ |
| 157 | +++ |
| 158 | ++++ |
| 159 | ++++ |
| 160 | ++++ |
| 200 | +++ |
| 201 | ++++ |
| 202 | ++++ |
| 203 | +++ |
| 204 | ++++ |
| 205 | ++++ |
| 206 | ++++ |
| 207 | +++ |
| 208 | ++++ |
| 209 | ++++ |
| 210 | ++++ |
| 211 | ++++ |
| 212 | ++++ |
| 213 | ++++ |
| 214 | ++++ |
| 215 | +++ |
| 216 | +++ |
| 217 | ++++ |
| 218 | +++ |
| 219 | ++++ |
| 220 | ++++ |
| 221 | +++ |
| 222 | ++++ |
| 223 | ++++ |
| 224 | ++++ |

348
-continued

| | |
|---|---|
| 225 | ++++ |
| 226 | +++ |
| 227 | ++++ |
| 228 | ++++ |
| 229 | ++++ |
| 230 | ++++ |
| 231 | ++++ |
| 232 | ++++ |
| 233 | ++++ |
| 234 | ++++ |
| 235 | ++++ |
| 236 | ++++ |
| 237 | ++++ |
| 238 | ++++ |
| 239 | ++++ |
| 240 | ++++ |
| 241 | ++++ |
| 242 | ++++ |
| 243 | ++++ |
| 244 | ++++ |
| 245 | ++++ |
| 246 | ++++ |
| 247 | ++++ |
| 248 | ++++ |
| 249 | ++++ |
| 250 | ++++ |
| 251 | ++ |
| 252 | ++ |
| 253 | ++ |
| 254 | ++++ |
| 255 | ++++ |
| 256 | ++++ |
| 257 | ++++ |
| 258 | ++++ |
| 259 | ++++ |
| 260 | +++ |
| 261 | ++++ |
| 262 | ++++ |
| 263 | ++++ |
| 264 | ++++ |
| 265 | +++ |
| 266 | +++ |
| 267 | ++ |
| 268 | ++++ |
| 269 | +++ |
| 270 | ++++ |
| 271 | ++++ |
| 272 | ++++ |
| 273 | ++++ |
| 274 | ++++ |
| 275 | ++++ |
| 276 | ++++ |
| 277 | ++++ |
| 278 | ++++ |
| 279 | ++++ |
| 280 | ++++ |
| 281 | ++++ |
| 282 | ++++ |
| 283 | ++++ |
| 284 | ++++ |
| 285 | ++++ |
| 286 | ++++ |
| 287 | ++++ |
| 289 | ++++ |
| 290 | ++++ |
| 291 | ++++ |
| 292 | ++++ |
| 293 | ++++ |
| 294 | ++++ |
| 295 | ++++ |
| 296 | ++++ |
| 297 | ++++ |
| 298 | ++++ |
| 299 | +++ |
| 300 | +++ |
| 301 | ++++ |
| 302 | ++++ |
| 303 | ++++ |
| 304 | ++++ |

| | |
|---|---|
| 305 | +++ |
| 306 | +++ |
| 307 | ++++ |
| 308 | +++ |
| 309 | ++++ |
| 310 | ++++ |
| 311 | ++++ |
| 312 | ++++ |
| 313 | ++++ |
| 314 | ++++ |
| 315 | +++ |
| 316 | ++++ |
| 317 | ++++ |
| 318 | ++++ |
| 319 | ++++ |
| 320 | ++++ |
| 321 | +++ |
| 323 | ++++ |
| 324 | ++ |
| 325 | ++++ |
| 326 | ++++ |
| 327 | ++++ |
| 328 | ++++ |
| 329 | ++++ |
| 330 | ++++ |
| 331 | ++++ |
| 332 | ++++ |
| 333 | ++++ |
| 334 | ++++ |
| 335 | ++++ |
| 336 | ++++ |
| 337 | ++++ |
| 338 | ++++ |
| 339 | +++ |
| 340 | ++++ |
| 341 | ++++ |
| 342 | ++++ |
| 343 | +++ |
| 344 | ++++ |
| 345 | ++++ |
| 346 | ++++ |
| 347 | ++++ |
| 348 | ++++ |
| 349 | +++ |
| 350 | ++++ |
| 351 | +++ |
| 352 | ++++ |
| 353 | ++++ |
| 354 | ++++ |
| 355 | ++++ |
| 356 | ++++ |
| 357 | ++++ |
| 358 | ++++ |
| 359 | ++++ |
| 360 | ++++ |
| 361 | ++++ |
| 362 | ++++ |
| 363 | ++++ |
| 364 | ++++ |
| 365 | ++++ |
| 366 | ++++ |
| 367 | ++++ |
| 368 | ++++ |
| 369 | ++++ |
| 370 | ++++ |
| 371 | ++++ |
| 372 | ++++ |
| 373 | ++ |
| 374 | ++ |
| 375 | +++ |
| 376 | ++ |
| 377 | +++ |
| 378 | ++++ |
| 379 | ++++ |
| 380 | ++++ |
| 381 | ++++ |
| 382 | ++++ |
| 383 | ++++ |
| 384 | ++++ |
| 385 | ++++ |
| 386 | ++++ |
| 387 | ++++ |
| 388 | ++++ |
| 389 | ++++ |
| 390 | ++++ |
| 391 | ++++ |
| 392 | ++++ |
| 393 | ++++ |
| 394 | ++++ |
| 395 | ++++ |
| 396 | ++++ |

++++ = <100 nM
+++ = 100 nM to 1,000 nM
++ = 1,000 nM to 10,000 nM
+ = 10,000 nM to 40,000 nM

Preferably, a compound of the present application (i.e., a compound of formula (I) and/or a salt thereof) has an $IC_{50}$ in an IMAP assay against full length PKCι at 150 μM ATP of <40 μM. In one embodiment, a compound of the present application has an $IC_{50}$ in an IMAP assay against full length PKCι at 150 μM ATP of 40 μM-10 μM. More preferably, a compound of the present application has an $IC_{50}$ in an IMAP assay against full length PKCι at 150 μM ATP of 10 μM-1 μM. In one embodiment, a compound of the present application has an $IC_{50}$ in an IMAP assay against full length PKCι at 150 μM ATP of 1 μM-0.1 μM. More preferably, a compound of the present application has an $IC_{50}$ in an IMAP assay against full length PKCι at 150 μM ATP of <0.1 μM.

Preferably, a compound of the present application (i.e., a compound of formula (I) or a salt thereof) has an $IC_{50}$ in an IMAP assay against kinase domain PKCι at 25 μM ATP of <40 μM. In one embodiment, a compound of the present application has an $IC_{50}$ in an IMAP assay against kinase domain PKCι at 25 μM ATP of 40 μM-10 μM. More preferably, a compound of the present application has an $IC_{50}$ in an IMAP assay against kinase domain PKCι at 25 μM ATP of 10 μM-1 μM. In one embodiment, a compound of the present application has an $IC_{50}$ in an IMAP assay against kinase domain PKCι at 25 μM ATP of 1 μM-0.1 μM. More preferably, a compound of the present application has an $IC_{50}$ in an IMAP assay against kinase domain PKCι at 25 μM ATP of <0.1 μM.

As those skilled in the art will appreciate, numerous modifications and variations of subject matter presented herein are possible in light of the above teachings. It is therefore understood that within the scope of the appended claims, the subject matter of the application may be practiced otherwise than as specifically described herein, and the scope of the application and claims are intended to encompass all such variations.

Each publication referenced herein is incorporated by reference in its entirety for all purposes.

The invention claimed is:

1. A compound of formula (I)

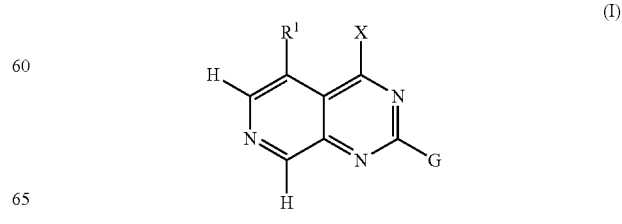

or a salt thereof, wherein:

G is a group of formula

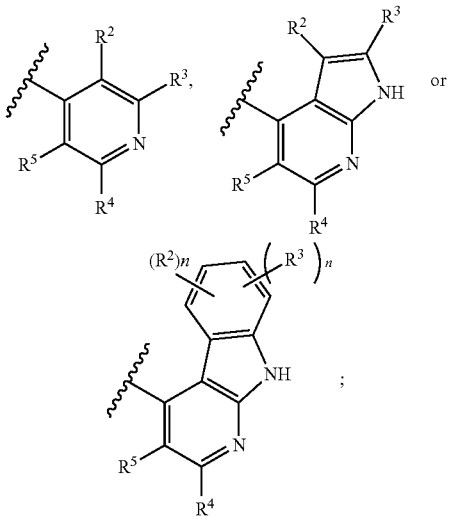

X is chosen from the group consisting of halogen, —CN, —C(=O)R$^{28}$, —C(=O)OR$^{28}$, —C(=O)NR$^{24}$R$^{28}$, —C(=O)C(=O)R$^{28}$, —NR$^{24}$R$^{28}$, —NR$^{24}$NR$^{24}$R$^{28}$, —N=NR$^{28}$, —NR$^{24}$OR$^{28}$, —NR$^{24}$C(=O)R$^{28}$, —NR$^{24}$C(=O)C(=O)R$^{28}$, —NR$^{24}$C(=O)OR$^{28}$, —NR$^{24}$C(=O)C(=O)OR$^{28}$, —NR$^{24}$C(=O)NR$^{24}$R$^{28}$, —NR$^{24}$C(=O)NR$^{24}$C(=O)R$^{28}$, —NR$^{24}$C(=O)NR$^{24}$C(=O)OR$^{28}$, —NR$^{24}$C(=O)C(=O)NR$^{24}$R$^{28}$, —NR$^{24}$S(=O)$_2$R$^{28}$, —NR$^{24}$S(=O)$_2$NR$^{24}$R$^{28}$, —OR$^{28}$, —OC(=O)R$^{28}$, —OC(=O)NR$^{24}$R$^{28}$, —OC(=O)OR$^{28}$, —OS(=O)R$^{28}$, —OS(=O)$_2$R$^{28}$, —OS(=O)$_2$OR$^{28}$, —OS(=O)$_2$NR$^{24}$R$^{28}$, —S(=O)$_n$R$^{28}$, —S(=O)$_2$NR$^{24}$R$^{28}$, and —S(=O)NR$^{24}$R$^{28}$;

or X is chosen from the group consisting of C$_{1-10}$alkyl, C$_{2-6}$ alkenyl, C$_{2-6}$ alkynyl, C$_{6-11}$aryl, C$_{7-16}$arylalkyl, C$_{3-11}$cycloalkyl, C$_{4-17}$Cycloalkylalkyl, 3-15 membered heterocycloalkyl, 4-21 membered heterocycloalkylalkyl, 5-15 membered heteroaryl, and 6-21 membered heteroarylalkyl wherein each of the foregoing are optionally substituted by 1-10 R$^{19}$, R$^1$ is chosen from the group consisting of C$_{3-11}$cycloalkyl optionally substituted with 1-10 R$^{19}$, and C$_{1-6}$ haloalkyl;

R$^2$, R$^3$, R$^4$, and R$^5$, are each independently selected from the group consisting of H, halogen, —CN, —C(=O)R$^{20}$, —C(=O)OR$^{20}$, —C(=O)NR$^{22}$R$^{23}$, —C(=O)C(=O)R$^{20}$, —C(=NR$^{25}$)R$^{20}$, —C(=NR$^{25}$)NR$^{22}$R$^{23}$, —C(=NOH)NR$^{22}$R$^{23}$, —C(=NOR$^{26}$)R$^{20}$, —C(=NNR$^{22}$R$^{23}$)R$^{20}$, —C(=NNR$^{24}$C(=O)R$^{21}$)R$^{20}$, —C(=NNR$^{24}$C(=O)OR$^{21}$)R$^{20}$, —C(=S)NR$^{22}$R$^{23}$, —NC, —NO$_2$, —NR$^{22}$R$^{23}$, —NR$^{24}$NR$^{22}$R$^{23}$, —N=NR$^{24}$, —NR$^{24}$OR$^{26}$, —NR$^{24}$C(=O)R$^{20}$, —NR$^{24}$C(=O)C(=O)R$^{20}$, —NR$^{24}$C(=O)OR$^{21}$, —NR$^{24}$C(=O)C(=O)OR$^{21}$, —NR$^{24}$C(=O)NR$^{22}$R$^{23}$, —NR$^{24}$C(=O)NR$^{24}$C(=O)R$^{20}$, —NR$^{24}$C(=O)NR$^{24}$C(=O)OR$^{20}$, —NR$^{24}$C(=NR$^{25}$)NR$^{22}$R$^{23}$, —NR$^{24}$C(=O)C(=O)NR$^{22}$R$^{23}$, —NR$^{24}$C(=S)R$^{20}$, —NR$^{24}$C(=S)NR$^{22}$R$^{23}$, —NR$^{24}$S(=O)$_2$R$^{21}$, —NR$^{24}$S(=O)$_2$NR$^{22}$R$^{23}$, —NR$^{24}$P(=O)R$^{38}$R$^{38}$, —NR$^{24}$P(=O)(NR$^{22}$R$^{23}$)(NR$^{22}$R$^{23}$), —NR$^{24}$P(=O)(OR$^{20}$)(OR$^2$), —NR$^{24}$P(=O)(SR$^{20}$)(SR$^2$), —OR$^{20}$, —OCN, —OC(=O)R$^{20}$, —OC(=O)NR$^{22}$R$^{23}$, —OC(=O)OR$^{20}$, —OC(=NR$^{25}$)NR$^{22}$R$^{23}$, —OS(=O)R$^{20}$, —OS(=O)$_2$R$^{20}$, —OS(=O)$_2$NR$^{22}$R$^{23}$, —OP(=O), —OS(=O)$_{20}$R$^{20}$, —OP(=O)R$^{38}$R$^{38}$, —OP(=O)(NR$^{22}$R$^{23}$)(NR$^{22}$R$^{23}$), —OP(=O)(OR$^{20}$)(OR$^{20}$), —OP(=O)(SR$^{20}$)(SR$^{20}$), —Si(R$^{24}$)$_3$, —SCN, —S(=O)$_n$R$^{20}$, —S(=O)$_2$OR$^{20}$, —SO$_3$R$^{27}$, —S(=O)$_2$NR$^{22}$R$^{23}$, —S(=O)NR$^{22}$R$^{23}$, —SP(=O)R$^{38}$R$^{38}$, —SP(=O)(NR$^{22}$R$^{23}$)(NR$^{22}$R$^{23}$), —SP(=O)(OR$^{20}$)(OR$^{20}$), —SP(=O)(SR$^{20}$)(SR$^{20}$), —P(=O)R$^{38}$R$^{38}$, —P(=O)(NR$^{22}$R$^{23}$)(NR$^{22}$R$^{23}$), —P(=O)(OR$^{20}$)(OR$^{20}$), and —P(=O)(SR$^{20}$)(SR$^{20}$);

or R$^2$, R$^3$, R$^4$, and, R$^5$, are each independently selected from the group consisting of C$_{1-6}$alkyl, C$_{2-6}$ alkenyl, C$_{2-6}$ alkynyl, C$_{6-11}$aryl, C$_{7-16}$ arylalkyl, C$_{3-11}$cycloalkyl, C$_{4-17}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted with 1-10 R$^{19}$, or any of R$^2$ and R$^3$ or R$^4$ and R$^5$ can, together with the atoms to which they are attached, form a C$_{6-11}$aryl, C$_{3-11}$cycloalkyl, 3-15 membered heterocycloalkyl or a 5-15 membered heteroaryl wherein each of the foregoing groups may be optionally substituted by 1-10 R$^{19}$;

R$^{19}$ at each occurrence is independently chosen from the group consisting of C$_{1-6}$alkyl optionally substituted by 1-13 R$^{39}$, C$_{2-6}$ alkenyl optionally substituted by 1-11 R$^{39}$, C$_{2-6}$alkynyl optionally substituted by 1-9 R$^{39}$, C$_{6-11}$aryl optionally substituted by 1-11 R$^{39}$, C$_{7-16}$arylalkyl optionally substituted by 1-19 R$^{39}$, C$_{3-11}$cycloalkyl optionally substituted by 1-21 R$^{39}$, C$_{4-17}$cycloalkylalkyl optionally substituted by 1-32 R$^{39}$, 3-15 membered heterocycloalkyl optionally substituted by 1-28 R$^{39}$, 4-21 membered heterocycloalkylalkyl optionally substituted by 1-40 R$^{39}$, 5-15 membered heteroaryl optionally substituted by 1-15 R$^{39}$, 6-21 membered heteroarylalkyl optionally substituted by 1-27 R$^{39}$, halogen, —CN, —C(=O)R$^{30}$, —C(=O)OR$^{30}$, —C(=O)NR$^{32}$R$^{33}$, —C(=O)C(=O)R$^{30}$, —C(=NR$^{35}$)R$^{30}$, —C(=NR$^{35}$)NR$^{32}$R$^{33}$, —C(=NOH)NR$^{32}$R$^{33}$, —C(=NOR$^{36}$)R$^{30}$, —C(=NNR$^{32}$R$^{33}$)R$^{30}$, —C(=NNR$^{34}$C(=O)R$^{31}$)R$^{30}$, —C(=NNR$^{34}$C(=O)OR$^{31}$)R$^{30}$, —C(=S)NR$^{32}$R$^{33}$, —NC, —NO$_2$, —NR$^{32}$R$^{33}$, —NR$^{34}$NR$^{32}$R$^{33}$, —N=NR$^{34}$, =NR$^{30}$, =NOR$^{30}$, —NR$^{34}$OR$^{36}$, —NR$^{34}$C(=O)R$^{30}$, —NR$^{34}$C(=O)C(=O)R$^{30}$, —NR$^{34}$C(=O)OR$^{31}$, —NR$^{34}$C(=O)C(=O)OR$^{31}$, —NR$^{34}$C(=O)NR$^{32}$R$^{33}$, —NR$^{34}$C(=O)NR$^{34}$C(=O)R$^{30}$, —NR$^{34}$C(=O)NR$^{34}$C(=O)OR$^{30}$, —NR$^{34}$C(=NR$^{35}$)NR$^{32}$R$^{33}$, —NR$^{34}$C(=O)C(=O)NR$^{32}$R$^{33}$, —NR$^{34}$C(=S)R$^{30}$, —NR$^{34}$C(=S)OR$^{30}$, —NR$^{34}$C(=S)NR$^{32}$R$^{33}$, —NR$^{34}$S(=O)$_2$R$^{31}$, —NR$^{34}$S(=O)$_2$NR$^{32}$R$^{33}$, —NR$^{34}$P(=O)R$^{38}$R$^{38}$, —NR$^{34}$P(=O)(NR$^{32}$R")(NR$^{32}$R"), —NR$^{34}$P(=O)(OR$^{30}$)(OR$^{30}$), —NR$^{34}$P(=O)(SR$^{30}$)(SR$^{30}$), —OR$^{30}$, =O, —OCN, —OC(=O)R$^{30}$, —OC(=O)NR$^{32}$R$^{33}$, —OC(=O)OR$^{30}$), —OC(=NR$^{35}$)NR$^{32}$R$^{33}$, —OS(=O)R$^{30}$, —OS(=O)$_2$R$^{30}$, —OS(=O)$_2$OR$^{30}$, —OS(=O)$_2$NR$^{32}$R$^{33}$, —OP(=O)R$^{38}$R$^{38}$, —OP(=O)(NR$^{32}$R$^{33}$)(NR$^{32}$R$^{33}$), —OP(=O)(OR$^{30}$)(OR$^{30}$), —OP(=O)(SR$^{30}$)(SR$^{30}$), —Si(R$^{34}$)$_3$, —SCN, =S, —S(=O)R$^{30}$, —S(=O)$_2$OR$^{30}$, —SO$_3$R$^{37}$, —S(=O)$_2$NR$^{32}$R$^{33}$, —S(=O)NR$^{32}$R$^{33}$, —SP(=O)R$^{38}$R$^{38}$, —SP(=O)(NR$^{32}$R$^{33}$)(NR$^{32}$R$^{33}$), —SP(=O)(OR$^{30}$)(OR$^{30}$), —SP(=O)(SR$^{30}$)(SR$^{30}$), —P(=O)R$^{38}$R$^{38}$, —P(=O)(NR$^{32}$R$^{33}$)(NR$^{32}$R$^{33}$), —P(=O)(OR$^{30}$)(OR$^{30}$), and —P(=O)(SR$^{30}$)(SR$^{30}$);

$R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from the group consisting of H, $C_{1-6}$ alkyl, $C_{2-6}$ alkenyl, $C_{2-6}$alkynyl, $C_{6-11}$ aryl, $C_{7-16}$ arylalkyl, $C_{3-11}$cycloalkyl, $C_{4-17}$Cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups (except for Hydrogen) may be optionally substituted by 1-10 $R^{19}$;

$R^{28}$ at each occurrence is independently chosen from the group consisting of $C_{1-10}$alkyl, $C_{2-10}$alkenyl, $C_{2-6}$alkynyl, $C_{6-11}$ aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted by 1-10 $R^{19}$;

$R^{22}$, $R^{23}$, $R^{32}$ and $R^{33}$ at each occurrence is independently chosen from the group consisting of H, $C_{1-6}$ alkyl, $C_{2-6}$ alkenyl, $C_{2-6}$ alkynyl, $C_{6-11}$aryl, $C_{7-16}$ arylalkyl, $C_{3-11}$cycloalkyl, $C_{4-17}$ cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups (except for Hydrogen) may be optionally substituted by 1-10 $R^{19}$;

or any $R^{22}$ and $R^{23}$ and/or $R^{32}$ and $R^{33}$ may form, together with the nitrogen atom to which they are attached, a 3-15 membered heterocycloalkyl optionally substituted by 1-10 $R^{19}$ or a 5-15 membered heteroaryl optionally substituted by 1-10 $R^{19}$;

$R^{38}$ at each occurrence is independently chosen from the group consisting of $C_{1-6}$ alkyl, $C_{2-6}$ alkenyl, $C_{2-6}$ alkynyl, $C_{6-11}$aryl, $C_{7-16}$ arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted by 1-10 $R^{19}$;

or any two $R^{38}$ attached to the same phosphorus atom can, together with the phosphorus atom linking them, form a 3-10 membered heterocycloalkyl optionally substituted by 1-6 $R^{19}$;

$R^{39}$ at each occurrence is independently chosen from the group consisting of $C_{1-6}$ alkyl optionally substituted by 1-13 halogen, $C_{2-6}$ alkenyl, $C_{2-6}$ alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{40}$, —C(=O)O$R^{40}$, —C(=O)N$R^{40}R^{40}$, —C(=O)C(=O)$R^{40}$, —C(=N$R^{40}$)$R^{40}$, —C(=N$R^{40}$)N$R^{40}R^{40}$, —C(=NOH)N$R^{40}R^{40}$, —C(=NO$R^{40}$)$R^{40}$, —C(=NN$R^{40}R^{40}$)$R^{40}$, —C(=NN$R^{40}$C(=O)$R^{40}$)$R^{40}$, —C(=NN$R^{40}$)C(=O)O$R^{40}$)$R^{40}$, —C(=S)N$R^{40}R^{40}$, —NC, —NO$_2$, —N$R^{40}$)$R^{40}$, —N$R^{40}$N$R^{40}R^{40}$, —N=N$R^{40}$, =N$R^{40}$, =NO$R^{40}$, —N$R^{40}$O$R^{40}$, —N$R^{40}$C(=O)$R^{40}$, —N$R^{40}$C(=O)C(=O)$R^{40}$, —N$R^{40}$C(=O)O$R^{40}$, —N$R^{40}$C(=O)C(=O)O$R^{40}$, —N$R^{40}$C(=O)N$R^{40}R^{40}$, —N$R^{40}$C(=O)N$R^{40}$C(=O)$R^{40}$, —N$R^{40}$C(=O)N$R^{40}$C(=O)O$R^{40}$, —N$R^{40}$C(=N$R^{40}$)N$R^{40}R^{40}$, —N$R^{40}$C(=O)C(=O)N$R^{40}R^{40}$, —N$R^{40}$C(=S)$R^{40}$, —N$R^{40}$C(=S)O$R^{40}$, —N$R^{40}$C(=S)N$R^{40}R^{40}$, —N$R^{40}$S(=O)$_2$R$^{40}$, —N$R^{40}$S(=O)$_2$N$R^{40}R^{40}$, —N$R^{40}$P(=O)$R^{41}R^{41}$, —N$R^{40}$P(=O)(N$R^{40}R^{40}$)(N$R^{40}R^{40}$), —N$R^{40}$P(=O)(O$R^{40}$)(O$R^{40}$), —N$R^{40}$P(=O)(S$R^{40}$)(S$R^{40}$), —O$R^{40}$, =O, —OCN, —OC(=O)$R^{40}$, —OC(=O)N$R^{40}R^{40}$, —OC(=O)O$R^{40}$, —OC(=N$R^{40}$)N$R^{40}R^{40}$, —OS(=O)$R^{40}$, —OS(=O)$_2$R$^{40}$, —OS(=O)$_{20}R^{40}$, —OS(=O)$_2$N$R^{40}$)$R^{40}$, —OP(=O)$R^{41}R^{41}$, —OP(=O)(N$R^{40}R^{40}$)(N$R^{40}R^{40}$), —OP(=O)(O$R^{40}$)(O$R^{40}$), —OP(=O)(S$R^{40}$)(S$R^{40}$), —Si($R^{40}$)$_3$, —SCN, =S, —S(=O)$_n$R$^{40}$, —S(=O)$_{20}$R$^{40}$, —SO$_3$R$^{40}$, —S(=O)$_2$N$R^{40}R^{40}$, —S(=O)N$R^{40}R^{40}$, —SP(=O)$R^{41}R^{41}$, —SP(=O)(N$R^{40}R^{40}$)(N$R^{40}R^{40}$), —SP(=O)(O$R^{40}$)(O$R^{40}$), —SP(=O)(S$R^{40}$)(S$R^{40}$), —P(=O)$R^{41}R^{41}$, —P(=O)(N$R^{40}R^{40}$)(N$R^{40}R^{40}$), —P(=O)(O$R^{40}$)(O$R^{40}$), and —P(=O)(S$R^{40}$)(S$R^{40}$);

$R^{40}$ at each occurrence is independently chosen from the group consisting of H, $C_{1-6}$ alkyl, and $C_{1-6}$-haloalkyl;

$R^{41}$ at each occurrence is independently chosen from the group consisting of $C_{1-6}$ alkyl and $C_{1-6}$-haloalkyl; and n at each occurrence is independently selected from the group consisting of 0, 1, and 2.

2. The compound according to claim 1, wherein $R^1$ is optionally substituted cyclopropyl.

3. The compound according to claim 1, wherein $R^1$ is optionally substituted cyclobutyl.

4. The compound according to claim 1, wherein $R^1$ is $C_{1-6}$-haloalkyl.

5. The compound according to claim 1, wherein G is

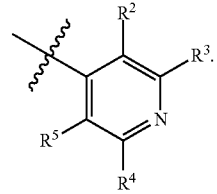

6. The compound according to claim 1, wherein G is

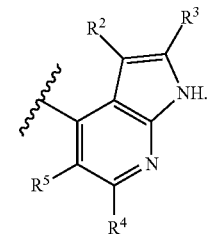

7. The compound according to claim 1, wherein G is

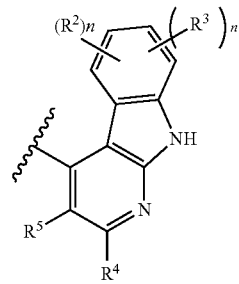

8. The compound according to claim 1, wherein X is chosen from the group consisting of 3-10 membered heterocycloalkyl optionally substituted by 1-6 $R^{19}$, 5-10 membered heteroaryl optionally substituted by 1-6 $R^{19}$, —C(=O)$R^{28}$, —C(=O)NR$^{24}R^{28}$, —NR$^{24}R^{28}$, —NR$^{24}$C(=O)$R^{28}$, —NR$^{24}$S(=O)$_2R^{28}$, —OC(=O)OR$^{28}$, —OS(=O)$R^{28}$, —OS(=O)$_2R^{28}$, and —OR$^{28}$.

9. The compound according to claim 8, wherein X is chosen from the group consisting of 3-10 membered heterocycloalkyl optionally substituted by 1-6 $R^{19}$, 5-10 membered heteroaryl optionally substituted by 1-6 $R^{19}$, and —OR$^{28}$.

10. The compound according to claim 1, wherein $R^2$ and $R^3$ are each independently chosen from the group consisting of H, halogen, —CN, —C(=O)$R^{20}$, —C(=O)OR$^{20}$, —C(=O)NR$^{22}R^{23}$, —C(=O)C(=O)$R^{20}$, —C(=NR$^{25}$)$R^{20}$, —C(=NR$^{25}$)NR$^{22}R^{23}$, —C(=NOH)NR$^{22}R^{23}$, —C(=NOR$^{26}$)$R^{20}$, —C(=NNR$^{22}R^{23}$)$R^{20}$, —C(=NNR$^{24}$C(=O)$R^{21}$)$R^{20}$, —C(=NNR$^{24}$C(=O)OR$^{21}$)$R^{20}$, —C(=S)NR$^{22}R^{23}$, —NC, —NO$_2$, —NR$^{22}R^{23}$, —NR$^{24}$NR$^{22}R^{23}$, —N=NR$^{24}$, —NR$^{24}$OR$^{26}$, —NR$^{24}$C(=O)$R^{20}$, —NR$^{24}$C(=O)C(=O)$R^{20}$, —NR$^{24}$C(=O)OR$^{21}$, —NR$^{24}$C(=O)C(=O)OR$^{21}$, —NR$^{24}$C(=O)NR$^{22}R^{23}$, —NR$^{24}$C(=O)NR$^{24}$C(=O)$R^{20}$, —NR$^{24}$C(=O)NR$^{24}$C(=O)OR$^{20}$, —NR$^{24}$C(=NR$^{25}$)NR$^{22}R^{23}$, —NR$^{24}$C(=O)C(=O)NR$^{22}R^{23}$, —NR$^{24}$C(=S)$R^{20}$, —NR$^{24}$C(=S)OR$^{20}$, —NR$^{24}$C(=S)NR$^{22}R^{23}$, —NR$^{24}$S(=O)$_2R^{21}$, —NR$^{24}$S(=O)$_2$NR$^{22}R^{23}$, —NR$^{24}$P(=O)$R^{38}R^{38}$, —NR$^{24}$P(=O)(NR$^{22}R^{23}$)(NR$^{22}R^{23}$), OR$^{20}$, —OCN, —OC(=O)$R^{20}$, —OC(=O)NR$^{22}R^{23}$, —OC(=O)OR$^{20}$, —OC(=NR$^{25}$)NR$^{22}R^{23}$, —OS(=O)$R^{20}$, —OS(=O)$_2R^{20}$, —OS(=O)$_2$OR$^{20}$, —OS(=O)$_2$NR$^{22}R^{23}$, —S(=O)$_nR^{20}$, —S(=O)$_2$OR$^{20}$, —SO$_3R^{27}$, S(=O)$_2$NR$^{22}R^{23}$, and —S(=O)NR$^{22}R^{23}$;

or $R^2$ and $R^3$ are each independently chosen from the group consisting of $C_{1-6}$ alkyl, $C_{2-6}$ alkenyl, $C_{2-6}$ alkynyl, $C_{6-11}$ aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted with 1-10 $R^{19}$.

11. The compound according to claim 10, wherein $R^2$ and $R^3$ are each independently chosen from the group consisting of H, halogen, —S(=O)$R^{20}$, —C(=O)NR$^{22}R^{23}$, NR$^{24}$S(=O)$_2R^{21}$, and —NR$^{22}R^{23}$; or $R^2$ and $R^3$ are each independently chosen from the group consisting of $C_{1-6}$ alkyl, $C_{2-6}$ alkenyl, $C_{2-6}$ alkynyl, $C_{6-11}$aryl, $C_{7-16}$ arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted with 1-10 $R^{19}$.

12. The compound according to claim 1, wherein $R^2$ and $R^3$ are taken together with the atoms to which they are attached to form a $C_{6-11}$aryl, $C_{3-11}$cycloalkyl, 3-15 membered heterocycloalkyl, or a 5-15 membered heteroaryl wherein each of the foregoing groups may be optionally substituted by 1-10 $R^{19}$.

13. The compound according to claim 1, wherein $R^1$ is optionally substituted cyclopropyl and G is

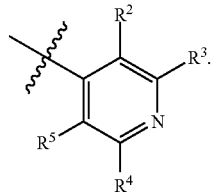

14. The compound according to claim 1, wherein $R^1$ is optionally substituted cyclobutyl and G is

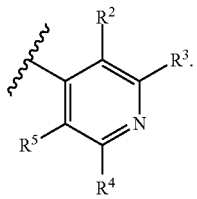

15. The compound according to claim 1, wherein $R^1$ is optionally substituted cyclopropyl and G is

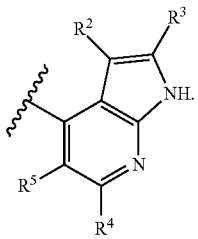

16. The compound according to claim 1, wherein $R^1$ is optionally substituted cyclobutyl and G is

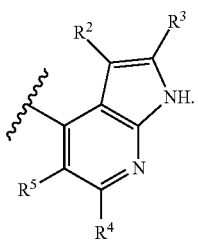

17. The compound according to claim 1, wherein $R^1$ is optionally substituted cyclopropyl and G is

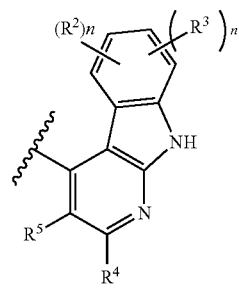

18. The compound according to claim 1, wherein $R^1$ is optionally substituted cyclobutyl and G is

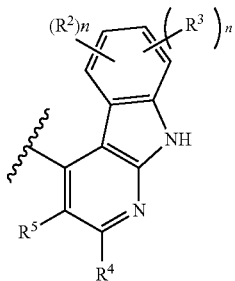

.

19. The compound according to claim 1, wherein $R^1$ is $C_{1-6}$-haloalkyl and G is

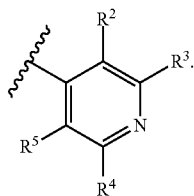

.

20. The compound according to claim 1, wherein $R^1$ is $C_{1-6}$-haloalkyl and G is

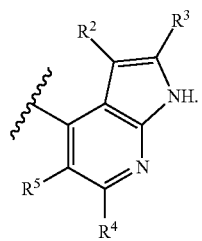

.

21. The compound according to claim 1, wherein $R^1$ is $C_{1-6}$-haloalkyl and G is

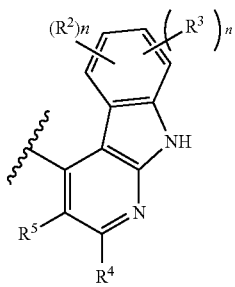

.

22. The compound according to claim 19, wherein $R^1$ is trifluoromethyl.

23. The compound according to claim 13, wherein X is chosen from the group consisting of 3-10 membered heterocycloalkyl optionally substituted by 1-6 $R^{19}$, 5-10 membered heteroaryl optionally substituted by 1-6 $R^{19}$, —C(=O)$R^{28}$, —C(=O)NR$^{24}$R$^{28}$, —NR$^{24}$R$^{28}$, —NR$^{24}$C(=O)R$^{28}$, —NR$^{24}$S(=O)$_2$R$^{28}$, —OS(=O)R$^{28}$, —OS(=O)$_2$ R$^{28}$, and —OR$^{28}$.

24. The compound according to claim 1, wherein $R^2$, $R^3$, $R^4$ and $R^5$ are all H.

25. The compound according to claim 1, wherein $R^4$ and $R^5$ are H.

26. The compound according to claim 13, wherein $R^2$ and $R^3$ are each independently chosen from the group consisting of H, halogen, —S(=O)$_n$R$^{20}$, —C(=O)NR$^{22}$R$^{23}$, —NR$^{24}$S(=O)$_2$R$^{21}$, and —NR$^{22}$R$^{23}$; or $R^2$ and $R^3$ are each independently chosen from the group consisting of $C_{1-6}$ alkyl, $C_{2-6}$ alkenyl, $C_{2-6}$ alkynyl, $C_{6-11}$ aryl, $C_{7-16}$ arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, and 6-21 membered heteroarylalkyl wherein each of the foregoing groups may be optionally substituted with 1-10 $R^{19}$.

27. The compound according to claim 26, wherein $R^4$ and $R^5$ are H.

28. The compound according to claim 1 that is:
- {5-Cyclopropyl-2-[2-(3,6-difluoro-pyridin-2-ylamino)-pyridin-4-yl]-pyrido[3,4-d]pyrimidin-4-yl}-(3,3-dimethyl-piperidin-4-yl)-methyl-amine;
- {5-Cyclobutyl-2-[2-(3,6-difluoro-pyridin-2-ylamino)-pyridin-4-yl]-pyrido[3,4-d]pyrimidin-4-yl}-(3,3-dimethyl-piperidin-4-yl)-methyl-amine;
- 4-(5-Cyclobutyl-4-piperazin-1-yl-pyrido[3,4-d]pyrimidin-2-yl)-2-methyl-8H-1,3a,7,8-tetraaza-cyclopenta[a]indene;
- {(S)-1-[5-Cyclopropyl-2-(2-trifluoromethyl-1H-pyrrolo[2,3-b]pyridin-4-yl)-pyrido[3,4-d]pyrimidin-4-yl]-piperazin-2-yl}-methanol;
- {(S)-1-[5-Cyclobutyl-2-(2-trifluoromethyl-1H-pyrrolo[2,3-b]pyridin-4-yl)-pyrido[3,4-d]pyrimidin-4-yl]-piperazin-2-yl}-methanol;
- {(R)-1-[5-Cyclopropyl-2-(2-trifluoromethyl-1H-pyrrolo[2,3-b]pyridin-4-yl)-pyrido[3,4-d]pyrimidin-4-yl]-piperazin-2-yl}-methanol;
- {(R)-1-[5-Cyclobutyl-2-(2-trifluoromethyl-1H-pyrrolo[2,3-b]pyridin-4-yl)-pyrido[3,4-d]pyrimidin-4-yl]-piperazin-2-yl}-methanol;
- (±)-5-Cyclopropyl-4-(4,7-cis)-octahydro-pyrrolo [3,4-b]pyridin-1-yl-2-(2-trifluoromethyl-1H-pyrrolo [2,3-b]pyridin-4-yl)-pyrido[3,4-d]pyrimidine;
- 4-((R)-5-Cyclobutyl-4-(R)-hexahydro-pyrrolo [3,4-b]pyrrol-1-yl-pyrido[3,4-d]pyrimidin-2-yl)-9H-pyrido[2,3-b]indole;
- 4-((S)-5-Cyclobutyl-4-(S)-hexahydro-pyrrolo [3,4-b]pyrrol-1-yl-pyrido[3,4-d]pyrimidin-2-yl)-9H-pyrido[2,3-b]indole;
- trans-N-[5-Cyclobutyl-2-(9H-pyrido[2,3-b]indol-4-yl)-pyrido[3,4-d]pyrimidin-4-yl]-cyclobutane-1,3-diamine;
- trans-N-{5-Cyclopropyl-2-[2-(2,2-difluoro-1-methyl-cyclopropyl)-1H-pyrrolo [2,3-b]pyridin-4-yl]-pyrido[3,4-d]pyrimidin-4-yl}-cyclohexane-1,4-diamine;
- 3-[4-(5-Cyclobutyl-4-piperazin-1-yl-pyrido[3,4-d]pyrimidin-2-yl)-1H-pyrrolo [2,3-b]pyridin-2-yl]-tetrahydro-thiophen-3-ol;
- 5-Cyclopropyl-2-(2-phenylsulfanyl-1H-pyrrolo [2,3-b]pyridin-4-yl)-4-piperazin-1-yl-pyrido [3,4-d]pyrimidine;
- [5-Cyclopropyl-2-(2-phenylsulfanyl-1H-pyrrolo [2,3-b]pyridin-4-yl)-pyrido[3,4-d]pyrimidin-4-yl]-methyl-piperidin-4-yl-amine;

5-Cyclopropyl-2-(2-methylsulfanyl-1H-pyrrolo [2,3-b]pyridin-4-yl)-4-piperazin-1-yl-pyrido[3,4-d]pyrimidine;

5-Cyclobutyl-2-(2-methylsulfanyl-1H-pyrrolo [2,3-b]pyridin-4-yl)-4-piperazin-1-yl-pyrido[3,4-d]pyrimidine;

5-Cyclopropyl-2-[2-(2,4-dichloro-phenyl)-1H-pyrrolo [2,3-b]pyridin-4-yl]-4-piperazin-1-yl-pyrido[3,4-d]pyrimidine;

(±)-5-Cyclopropyl-4-(3,6-cis)-hexahydro-pyrrolo [3,2-b]pyrrol-1-yl-2-(2-trifluoromethyl-1H-pyrrolo [2,3-b]pyridin-4-yl)-pyrido[3,4-d]pyrimidine;

5-Cyclopropyl-4-(3 aS,6aS)-hexahydro-pyrrolo [3,4-b]pyrrol-1-yl-2-(2-trifluoromethyl-1H-pyrrolo [2,3-b]pyridin-4-yl)-pyrido[3,4-d]pyrimidine;

5-Cyclopropyl-4-(3 aR,6aR)-hexahydro-pyrrolo [3,4-b]pyrrol-1-yl-2-(2-trifluoromethyl-1H-pyrrolo [2,3-b]pyridin-4-yl)-pyrido[3,4-d]pyrimidine;

Azepan-4-yl-[5-cyclobutyl-2-(9H-pyrido[2,3-b]indol-4-yl)-pyrido[3,4-d]pyrimidin-4-yl]-amine;

{5-Cyclopropyl-2-[2-(2-methoxy-phenyl)-1H-pyrrolo [2,3-b]pyridin-4-yl]-pyrido[3,4-d]pyrimidin-4-yl}-(3,3-dimethyl-piperidin-4-yl)-methyl-amine;

{5-Cyclopropyl-2-[2-(2,4-dichloro-phenyl)-1H-pyrrolo [2,3-b]pyridin-4-yl]-pyrido[3,4-d]pyrimidin-4-yl}-(3,3-dimethyl-piperidin-4-yl)-methyl-amine;

(1R,5S,8R)-3-Aza-bicyclo [3.2.1] oct-8-yl-{2-[2-(2-chloro-phenyl)-1H-pyrrolo [2,3-b]pyridin-4-yl]-5-cyclopropyl-pyrido[3,4-d]pyrimidin-4-yl}-amine;

(1R,5S,8S)-3-Aza-bicyclo [3.2.1] oct-8-yl-{2-[2-(2-chloro-phenyl)-1H-pyrrolo [2,3-b]pyridin-4-yl]-5-cyclopropyl-pyrido[3,4-d]pyrimidin-4-yl}-amine;

(±)-2-[2-(2-Chloro-phenyl)-1H-pyrrolo [2,3-b]pyridin-4-yl]-5-cyclopropyl-4-(3 aR,7aS)-octahydro-pyrrolo [3,2-c]pyridin-1-yl-pyrido[3,4-d]pyrimidine;

[5-Cyclobutyl-2-(2-phenylsulfanyl-1H-pyrrolo [2,3-b]pyridin-4-yl)-pyrido [3,4-d]pyrimidin-4-yl]-methyl-piperidin-4-yl-amine;

[5-Cyclopropyl-2-(2-phenylsulfanyl-1H-pyrrolo [2,3-b]pyridin-4-yl)-pyrido[3,4-d]pyrimidin-4-yl]-(3,3-dimethyl-piperidin-4-yl)-methyl-amine;

4-(5-Cyclobutyl-4-methoxy-pyrido[3,4-d]pyrimidin-2-yl)-9H-pyrido[2,3-b] indole;

[5-Cyclobutyl-2-(9H-pyrido[2,3-b]indol-4-yl)-pyrido[3,4-d]pyrimidin-4-yl]-(3,3-dimethyl-piperidin-4-yl)-methyl-amine;

{2-[2-(2-tert-Butyl-thiazol-4-yl)-1H-pyrrolo [2,3-b]pyridin-4-yl]-5-cyclopropyl-pyrido[3,4-d]pyrimidin-4-yl}-(3,3-dimethyl-piperidin-4-yl)-methyl-amine;

(2R,6S)-3-Aza-bicyclo[3.1.0]hex-6-yl-[(S)-5-cyclobutyl-2-(9H-pyrido[2,3-b] indol-4-yl)-pyrido[3,4-d]pyrimidin-4-yl]-amine;

(±)-2-[2-(2-tert-Butyl-thiazol-4-yl)-1H-pyrrolo [2,3-b]pyridin-4-yl]-5-cyclopropyl-4-(3,6-cis)-hexahydro-pyrrolo [3,2-b]pyrrol-1-yl-pyrido[3,4-d]pyrimidine;

{5-Cyclopropyl-2-[2-(pyrazolo [1,5-a]pyridin-2-ylamino)-pyridin-4-yl]-pyrido[3,4-d]pyrimidin-4-yl}-(3,3-dimethyl-piperidin-4-yl)-amine;

{5-Cyclopropyl-2-[2-(pyrazolo [1,5-a]pyridin-2-ylamino)-pyridin-4-yl]-pyrido[3,4-d]pyrimidin-4-yl}-(3,3-dimethyl-piperidin-4-yl)-methyl-amine;

[4-(5-Cyclopropyl-4-piperazin-1-yl-pyrido[3,4-d]pyrimidin-2-yl)-pyridin-2-yl]-(4-cyclopropyl-thiazol-2-yl)-amine;

[4-(5-Cyclobutyl-4-piperazin-1-yl-pyrido[3,4-d]pyrimidin-2-yl)-pyridin-2-yl]-(4-cyclopropyl-thiazol-2-yl)-amine;

{5-Cyclopropyl-2-[2-(4-cyclopropyl-thiazol-2-ylamino)-pyridin-4-yl]-pyrido[3,4-d]pyrimidin-4-yl}-(3,3-dimethyl-piperidin-4-yl)-amine;

5-Cyclopropyl-2-[2-(2,6-difluoro-pyridin-3-yl)-1H-pyrrolo [2,3-b]pyridin-4-yl]-4-piperazin-1-yl-pyrido[3,4-d]pyrimidine;

5-Cyclopropyl-2-[2-(5-methyl-thiophen-2-yl)-1H-pyrrolo [2,3-b]pyridin-4-yl]-4-piperazin-1-yl-pyrido[3,4-d]pyrimidine;

5-Cyclopropyl-2-[2-(5-methyl-furan-2-yl)-1H-pyrrolo [2,3-b]pyridin-4-yl]-4-piperazin-1-yl-pyrido[3,4-d]pyrimidine;

5-Cyclopropyl-2-[2-(2-fluoro-pyridin-3-yl)-1H-pyrrolo [2,3-b]pyridin-4-yl]-4-piperazin-1-yl-pyrido[3,4-d]pyrimidine;

Azepan-4-yl-[5-cyclobutyl-2-(9H-pyrido[2,3-b]indol-4-yl)-pyrido[3,4-d]pyrimidin-4-yl]-methyl-amine;

{5-Cyclopropyl-2-[2-(2,5-dichloro-phenyl)-1H-pyrrolo [2,3-b]pyridin-4-yl]-pyrido[3,4-d]pyrimidin-4-yl}-(3,3-dimethyl-piperidin-4-yl)-methyl-amine;

5-Cyclopropyl-2-[2-(2,5-dichloro-phenyl)-1H-pyrrolo [2,3-b]pyridin-4-yl]-4-piperazin-1-yl-pyrido[3,4-d]pyrimidine;

[5-Cyclopropyl-2-(2-phenylamino-pyridin-4-yl)-pyrido [3,4-d]pyrimidin-4-yl]-(3,3-dimethyl-piperidin-4-yl)-amine;

{5-Cyclopropyl-2-[2-(5-fluoro-pyridin-2-ylamino)-pyridin-4-yl]-pyrido[3,4-d]pyrimidin-4-yl}-(3,3-dimethyl-piperidin-4-yl)-amine;

{5-Cyclopropyl-2-[2-(3-fluoro-pyridin-2-ylamino)-pyridin-4-yl]-pyrido[3,4-d]pyrimidin-4-yl}-(3,3-dimethyl-piperidin-4-yl)-amine;

{5-Cyclopropyl-2-[2-(4-fluoro-pyridin-2-ylamino)-pyridin-4-yl]-pyrido[3,4-d]pyrimidin-4-yl}-(3,3-dimethyl-piperidin-4-yl)-amine;

{5-Cyclopropyl-2-[2-(4-trifluoromethyl-pyridin-2-ylamino)-pyridin-4-yl]-pyrido[3,4-d]pyrimidin-4-yl}-(3,3-dimethyl-piperidin-4-yl)-amine;

(4-tert-Butyl-thiazol-2-yl)-[4-(5-cyclopropyl-4-piperazin-1-yl-pyrido[3,4-d]pyrimidin-2-yl)-pyridin-2-yl]-amine;

{5-Cyclopropyl-2-[2-(4-cyclopropyl-thiazol-2-ylamino)-pyridin-4-yl]-pyrido[3,4-d]pyrimidin-4-yl}-(3,3-dimethyl-piperidin-4-yl)-methyl-amine;

(±)-5-cyclobutyl-4-(3,6-cis)-hexahydro-pyrrolo [3,2-b]pyrrol-1-yl-2-(2-trifluoromethyl-1H-pyrrolo [2,3-b]pyridin-4-yl)-pyrido[3,4-d]pyrimidine;

{3-[4-(5-Cyclobutyl-4-piperazin-1-yl-pyrido[3,4-d]pyrimidin-2-yl)-1H-pyrrolo [2,3-b]pyridin-2-yl]-prop-2-ynyl}-dimethyl-amine;

(±)-5-Cyclopropyl-2-[2-(3-fluoro-pyridin-2-yl)-1H-pyrrolo[2,3-b]pyridin-4-yl]-4-(3,6-cis)-hexahydro-pyrrolo [3,2-b]pyrrol-1-yl-pyrido[3,4-d]pyrimidine;

(±)-5-Cyclobutyl-2-[2-(3-fluoro-pyridin-2-yl)-1H-pyrrolo [2,3-b]pyridin-4-yl]-4-(3,6-cis)-hexahydro-pyrrolo [3,2-b]pyrrol-1-yl-pyrido[3,4-d]pyrimidine;

5-Cyclopropyl-4-piperazin-1-yl-2-(2-pyridin-3-yl-1H-pyrrolo [2,3-b]pyridin-4-yl)-pyrido[3,4-d]pyrimidine;

4 [5-Cyclobutyl-4-(hexahydro-pyrrolo [3,2-b]pyrrol-1-yl)-pyrido[3,4-d]pyrimidin-2-yl]-9H-pyrido[2,3-b]indole;

N-[5-Cyclobutyl-2-(9H-pyrido[2,3-b]indol-4-yl)-pyrido [3,4-d]pyrimidin-4-yl]-cyclopentane-1,3-diamine;

[5-Cyclopropyl-2-(2-pyridin-3-yl-1H-pyrrolo [2,3-b]pyridin-4-yl)-pyrido[3,4-d]pyrimidin-4-yl]-(3,3-dimethyl-piperidin-4-yl)-methyl-amine;

4-(5-Cyclopropyl-4-piperazin-1-yl-pyrido[3,4-d]pyrimidin-2-yl)-1H-pyrrolo [2,3-b]pyridine-2-carboxylic acid cyclohexylamide;

(±)-5-cyclopropyl-4-(3,7-cis)-octahydro-pyrrolo [3,2-b] pyridin-1-yl-2-(2-trifluoromethyl-1H-pyrrolo [2,3-b] pyridin-4-yl)-pyrido[3,4-d]pyrimidine;

5-Cyclopropyl-4-(octahydro-[1,5]naphthyridin-1-yl)-2-(2-trifluoromethyl-1H-pyrrolo [2,3-b]pyridin-4-yl)-pyrido[3,4-d]pyrimidine;

N-[4-(5-Cyclopropyl-4-piperazin-1-yl-pyrido[3,4-d]pyrimidin-2-yl)-pyridin-2-yl]-4-fluoro-benzenesulfonamide;

4-{5-Cyclopropyl-4-[(3,3-dimethyl-piperidin-4-yl)-methyl-amino]-pyrido[3,4-d]pyrimidin-2-yl}-1H-pyrrolo [2,3-b]pyridine-2-carboxylic acid cyclohexylamide;

{5-Cyclobutyl-2-[2-(5-fluoro-pyridin-2-ylamino)-pyridin-4-yl]-pyrido[3,4-d]pyrimidin-4-yl}-(3,3-dimethyl-piperidin-4-yl)-amine;

{5-Cyclobutyl-2-[2-(3,5-difluoro-pyridin-2-ylamino)-pyridin-4-yl]-pyrido[3,4-d]pyrimidin-4-yl}-(3,3-dimethyl-piperidin-4-yl)-amine;

{5-Cyclobutyl-2-[2-(4-fluoro-pyridin-2-ylamino)-pyridin-4-yl]-pyrido[3,4-d]pyrimidin-4-yl}-(3,3-dimethyl-piperidin-4-yl)-amine;

{5-Cyclobutyl-2-[2-(3-fluoro-pyridin-2-ylamino)-pyridin-4-yl]-pyrido[3,4-d]pyrimidin-4-yl}-(3,3-dimethyl-piperidin-4-yl)-amine;

{5-Cyclobutyl-2-[2-(3,5,6-trifluoro-pyridin-2-ylamino)-pyridin-4-yl]-pyrido[3,4-d]pyrimidin-4-yl}-(3,3-dimethyl-piperidin-4-yl)-amine;

{2-[2-(4-tert-Butyl-thiazol-2-ylamino)-pyridin-4-yl]-5-cyclobutyl-pyrido [3,4-d]pyrimidin-4-yl}-(3,3-dimethyl-piperidin-4-yl)-amine;

4-[5-Cyclobutyl-2-(9H-pyrido[2,3-b]indol-4-yl)-pyrido [3,4-d]pyrimidin-4-ylamino]-azepan-3-ol;

N-[5-Cyclobutyl-2-(9H-pyrido[2,3-b]indol-4-yl)-pyrido [3,4-d]pyrimidin-4-yl]-N-methyl-cyclobutane-1,3-diamine;

N-[5-Cyclobutyl-2-(9H-pyrido[2,3-b]indol-4-yl)-pyrido [3,4-d]pyrimidin-4-yl]-N-methyl-cyclobutane-1,3-diamine;

(±)-(3aS,7aS)-1 [5-Cyclobutyl-2-(9H-pyrido[2,3-b]indol-4-yl)-pyrido[3,4-d]pyrimidin-4-yl]-octahydro-pyrrolo [3,2-c]pyridin-3a-ol;

(±)-(3,4-trans)-4-{[5-Cyclobutyl-2-(9H-pyrido[2,3-b]indol-4-yl)-pyrido[3,4-d]pyrimidin-4-yl]-methyl-amino}-3-methyl-piperidin-3-ol; N-[5-Cyclobutyl-2-(9H-pyrido[2,3-b]indol-4-yl)-pyrido[3,4-d]pyrimidin-4-yl]-N-methyl-cyclopentane-1,3-diamine;

4-(5-Cyclopropyl-4-piperazin-1-yl-pyrido[3,4-d]pyrimidin-2-yl)-1H-pyrrolo [2,3-b]pyridine-2-carboxylic acid methylamide;

(±)-5-cyclobutyl-4-(3,7-cis)-octahydro-pyrrolo [3,2-b] pyridin-1-yl-2-(2-trifluoromethyl-1H-pyrrolo [2,3-b] pyridin-4-yl)-pyrido[3,4-d]pyrimidine;

5-Cyclobutyl-4-(octahydro-[1,5]naphthyridin-1-yl)-2-(2-trifluoromethyl-1H-pyrrolo [2,3-b]pyridin-4-yl)-pyrido [3,4-d]pyrimidine;

(±)-5-cyclopropyl-4-(3,6-cis)-hexahydro-pyrrolo [3,2-b] pyrrol-1-yl-2-(2-methyl-1H-pyrrolo [2,3-b]pyridin-4-yl)-pyrido[3,4-d]pyrimidine;

(±)-5-cyclopropyl-2-(2-methyl-1H-pyrrolo [2,3-b]pyridin-4-yl)-4-(3,7-cis)-octahydro-pyrrolo [3,2-b]pyridin-1-yl-pyrido[3,4-d]pyrimidine;

(±)-5-cyclobutyl-4-(3,6-cis)-hexahydro-pyrrolo [3,2-b] pyrrol-1-yl-2-(2-methyl-1H-pyrrolo [2,3-b]pyridin-4-yl)-pyrido[3,4-d]pyrimidine;

(±)-5-Cyclobutyl-2-(2-methyl-1H-pyrrolo [2,3-b]pyridin-4-yl)-4-(3,7-cis)-octahydro-pyrrolo [3,2-b]pyridin-1-yl-pyrido[3,4-d]pyrimidine;

{5-Cyclobutyl-2-[2-(quinolin-2-ylamino)-pyridin-4-yl]-pyrido[3,4-d]pyrimidin-4-yl}-(3,3-dimethyl-piperidin-4-yl)-amine;

{5-Cyclobutyl-2-[2-(3,4,6-trifluoro-pyridin-2-ylamino)-pyridin-4-yl]-pyrido[3,4-d]pyrimidin-4-yl}-(3,3-dimethyl-piperidin-4-yl)-amine;

{2-[2-(5-Chloro-3-fluoro-pyridin-2-ylamino)-pyridin-4-yl]-5-cyclobutyl-pyrido[3,4-d]pyrimidin-4-yl}-(3,3-dimethyl-piperidin-4-yl)-amine;

{5-Cyclobutyl-2-[2-(isoquinolin-1-ylamino)-pyridin-4-yl]-pyrido[3,4-d]pyrimidin-4-yl}-(3,3-dimethyl-piperidin-4-yl)-amine;

{5-Cyclobutyl-2-[2-(4-trifluoromethoxy-phenylamino)-pyridin-4-yl]-pyrido[3,4-d]pyrimidin-4-yl}-(3,3-dimethyl-piperidin-4-yl)-amine;

[5-Cyclobutyl-2-(2-phenylamino-pyridin-4-yl)-pyrido[3,4-d]pyrimidin-4-yl]-(3,3-dimethyl-piperidin-4-yl)-amine;

{5-Cyclobutyl-2-[2-(2-fluoro-pyridin-3-ylamino)-pyridin-4-yl]-pyrido[3,4-d]pyrimidin-4-yl}-(3,3-dimethyl-piperidin-4-yl)-amine;

{5-Cyclobutyl-2-[2-(2,6-difluoro-phenylamino)-pyridin-4-yl]-pyrido[3,4-d]pyrimidin-4-yl}-(3,3-dimethyl-piperidin-4-yl)-amine;

5-Cyclopropyl-2-(2-methyl-1H-pyrrolo [2,3-b]pyridin-4-yl)-4-(octahydro-[1,5] naphthyridin-1-yl)-pyrido[3,4-d]pyrimidine;

5-Cyclobutyl-2-(2-methyl-1H-pyrrolo [2,3-b]pyridin-4-yl)-4-(octahydro-[1,5]naphthyridin-1-yl)-pyrido[3,4-d]pyrimidine;

{5-Cyclobutyl-2-[2-(2,6-difluoro-benzylamino)-pyridin-4-yl]-pyrido[3,4-d]pyrimidin-4-yl}-(3,3-dimethyl-piperidin-4-yl)-amine;

{4-[5-Cyclobutyl-4-(hexahydro-pyrrolo [3,2-b]pyrrol-1-yl)-pyrido[3,4-d]pyrimidin-2-yl]-pyridin-2-yl}-(3,6-difluoro-pyridin-2-yl)-amine;

{4-[5-Cyclobutyl-4-(hexahydro-pyrrolo [3,2-b]pyrrol-1-yl)-pyrido[3,4-d]pyrimidin-2-yl]-pyridin-2-yl}-(3,5,6-trifluoro-pyridin-2-yl)-amine;

4 [5-Cyclopropyl-4-(octahydro-pyrrolo [3,2-c]pyridin-1-yl)-pyrido[3,4-d]pyrimidin-2-yl]-1H-pyrrolo [2,3-b] pyridine-2-carboxylic acid methylamide;

[5-Cyclopropyl-2-(2-methyl-1H-pyrrolo [2,3-b]pyridin-4-yl)-pyrido[3,4-d]pyrimidin-4-yl]-(3,3-dimethyl-piperidin-4-yl)-amine;

[5-Cyclobutyl-2-(2-methyl-1H-pyrrolo [2,3-b]pyridin-4-yl)-pyrido[3,4-d]pyrimidin-4-yl]-(3,3-dimethyl-piperidin-4-yl)-amine;

{4-[5-Cyclobutyl-4-(hexahydro-pyrrolo [3,2-b]pyrrol-1-yl)-pyrido[3,4-d]pyrimidin-2-yl]-pyridin-2-yl}-phenyl-amine;

5-Cyclopropyl-2-[2-(2,5-dichloro-phenyl)-1H-pyrrolo [2,3-b]pyridin-4-yl]-4-(hexahydro-pyrrolo [3,2-b]pyrrol-1-yl)-pyrido[3,4-d]pyrimidine;

(±)-(3 aS,7aS)-1-[5-Cyclopropyl-2-(2-trifluoromethyl-1H-pyrrolo [2,3-b]pyridin-4-yl)-pyrido[3,4-d]pyrimidin-4-yl]-octahydro-pyrrolo [3,2-c]pyridin-3a-ol;

{5-Cyclobutyl-2-[2-(4,6-difluoro-pyridin-2-ylamino)-pyridin-4-yl]-pyrido[3,4-d]pyrimidin-4-yl}-(3,3-dimethyl-piperidin-4-yl)-amine;

{5-Cyclobutyl-2-[2-(3,5,6-trifluoro-pyridin-2-ylamino)-pyridin-4-yl]-pyrido[3,4-d]pyrimidin-4-yl}-(3,3-dimethyl-piperidin-4-yl)-methyl-amine;

2-{4-[5-Cyclobutyl-4-(3,3-dimethyl-piperidin-4-ylamino)-pyrido[3,4-d]pyrimidin-2-yl]-pyridin-2-ylamino}-isonicotinonitrile;

(1S,6S)-3-Aza-bicyclo[3.1.0]hex-6-yl-{(R)-5-cyclobutyl-2-[2-(3,5,6-trifluoro-pyridin-2-ylamino)-pyridin-4-yl]-pyrido[3,4-d]pyrimidin-4-yl}-amine;

(1S,6S)-3-Aza-bicyclo [3.1.0]hex-6-yl-{(R)-5-cyclobutyl-2-[2-(3,6-difluoro-pyridin-2-ylamino)-pyridin-4-yl]-pyrido[3,4-d]pyrimidin-4-yl}-amine;

[5-Cyclobutyl-2-(2-phenylamino-pyridin-4-yl)-pyrido[3,4-d]pyrimidin-4-yl]-(3,3-dimethyl-piperidin-4-yl)-methyl-amine;

(1S,6S)-3-Aza-bicyclo [3.1.0]hex-6-yl-[(R)-5-cyclobutyl-2-(2-phenylamino-pyridin-4-yl)-pyrido[3,4-d]pyrimidin-4-yl]-amine;

5-Cyclopropyl-2-[2-(2-methoxy-thiazol-4-yl)-1H-pyrrolo [2,3-b]pyridin-4-yl]-4-piperazin-1-yl-pyrido[3,4-d]pyrimidine;

(±)-(3aS,7aS)-1-[5-Cyclopropyl-2-(9H-pyrido[2,3-b]indol-4-yl)-pyrido[3,4-d]pyrimidin-4-yl]-octahydro-pyrrolo [3,2-c]pyridin-3a-ol;

(±)-(3,4-trans)-4-{[5-Cyclopropyl-2-(9H-pyrido[2,3-b] indol-4-yl)-pyrido[3,4-d]pyrimidin-4-yl]-methyl-amino}-3-methyl-piperidin-3-ol;

[5-Cyclopropyl-2-(2-methyl-1H-pyrrolo [2,3-b]pyridin-4-yl)-pyrido[3,4-d]pyrimidin-4-yl]-(3,3-dimethyl-piperidin-4-yl)-methyl-amine;

[5-Cyclobutyl-2-(2-methyl-1H-pyrrolo [2,3-b]pyridin-4-yl)-pyrido[3,4-d]pyrimidin-4-yl]-(3,3-dimethyl-piperidin-4-yl)-methyl-amine;

(±)-(3 aS,7aS)-1-[5-Cyclobutyl-2-(2-methyl-1H-pyrrolo [2,3-b]pyridin-4-yl)-pyrido[3,4-d]pyrimidin-4-yl]-octahydro-pyrrolo [3,2-c]pyridin-3a-ol;

5-Cyclopropyl-2-[2-(2-methoxy-thiazol-4-yl)-1H-pyrrolo [2,3-b]pyridin-4-yl]-4-(octahydro-pyrrolo [3,2-c]pyridin-1-yl)-pyrido[3,4-d]pyrimidine;

[5-Cyclopropyl-2-(2-methylsulfanyl-1H-pyrrolo [2,3-b] pyridin-4-yl)-pyrido[3,4-d]pyrimidin-4-yl]-methyl-piperidin-4-yl-amine;

5-Cyclobutyl-2-(2-methanesulfonyl-1H-pyrrolo [2,3-b] pyridin-4-yl)-4-piperazin-1-yl-pyrido [3,4-d]pyrimidine;

cis-[5-Cyclobutyl-2-(9H-pyrido[2,3-b]indol-4-yl)-pyrido [3,4-d]pyrimidin-4-yl]-cyclobutane-1,3-diamine;

5-[5-Cyclobutyl-2-(9H-pyrido[2,3-b]indol-4-yl)-pyrido [3,4-d]pyrimidin-4-ylamino]-azepan-3-ol;

{4-[5-Cyclobutyl-4-(octahydro-pyrrolo [3,2-b]pyridin-1-yl)-pyrido[3,4-d]pyrimidin-2-yl]-pyridin-2-yl}-(3,5,6-trifluoro-pyridin-2-yl)-amine;

{4-[5-Cyclobutyl-4-(octahydro-pyrrolo [3,2-b]pyridin-1-yl)-pyrido[3,4-d]pyrimidin-2-yl]-pyridin-2-yl}-(3,6-difluoro-pyridin-2-yl)-amine;

{4-[5-Cyclobutyl-4-(octahydro-pyrrolo [3,2-b]pyridin-1-yl)-pyrido[3,4-d]pyrimidin-2-yl]-pyridin-2-yl}-phenyl-amine;

{5-Cyclobutyl-2-[2-(3,5,6-trifluoro-pyridin-2-ylamino)-pyridin-4-yl]-pyrido[3,4-d]pyrimidin-4-yl}-(3-methyl-piperidin-4-yl)-amine;

{5-Cyclobutyl-2-[2-(3,6-difluoro-pyridin-2-ylamino)-pyridin-4-yl]-pyrido[3,4-d]pyrimidin-4-yl}-(3-methyl-piperidin-4-yl)-amine;

2-[2-(2-Chloro-phenyl)-1H-pyrrolo [2,3-b]pyridin-4-yl]-5-cyclopropyl-4-(hexahydro-pyrrolo [3,2-b]pyrrol-1-yl)-pyrido[3,4-d]pyrimidine;

2-[2-(2-Chloro-phenyl)-1H-pyrrolo [2,3-b]pyridin-4-yl]-5-cyclopropyl-4-(octahydro-pyrrolo [3,2-b]pyridin-1-yl)-pyrido[3,4-d]pyrimidine;

2-(2-Chloro-1H-pyrrolo [2,3-b]pyridin-4-yl)-5-cyclobutyl-4-piperazin-1-yl-pyrido[3,4-d]pyrimidine;

5-Cyclobutyl-4-piperazin-1-yl-2-(2-pyrimidin-5-yl-1H-pyrrolo [2,3-b]pyridin-4-yl)-pyrido[3,4-d]pyrimidine;

5-Cyclobutyl-2[2-(1-methyl-1H-pyrazol-4-yl)-1H-pyrrolo [2,3-b]pyridin-4-yl]-4-piperazin-1-yl-pyrido[3,4-d]pyrimidine;

5-Cyclobutyl-2-(2-ethylsulfanyl-1H-pyrrolo [2,3-b]pyridin-4-yl)-4-piperazin-1-yl-pyrido[3,4-d]pyrimidine;

5-Cyclopropyl-2-(2-ethylsulfanyl-1H-pyrrolo [2,3-b]pyridin-4-yl)-4-piperazin-1-yl-pyrido[3,4-d]pyrimidine;

[5-Cyclobutyl-2-(9H-pyrido[2,3-b]indol-4-yl)-pyrido[3,4-d]pyrimidin-4-yl]-(8-oxa-3-aza-bicyclo [3.2.1] oct-6-yl)-amine;

{5-Cyclobutyl-2-[2-(pyrazolo [1,5-a]pyridin-2-ylamino)-pyridin-4-yl]-pyrido[3,4-d]pyrimidin-4-yl}-(3,3-dimethyl-piperidin-4-yl)-amine;

{5-Cyclobutyl-2-[2-(3,5,6-trifluoro-pyridin-2-ylamino)-pyridin-4-yl]-pyrido[3,4-d]pyrimidin-4-yl}-(2,2-dimethyl-piperidin-4-yl)-amine;

{5-Cyclobutyl-2-[2-(3,6-difluoro-pyridin-2-ylamino)-pyridin-4-yl]-pyrido[3,4-d]pyrimidin-4-yl}-(2,2-dimethyl-piperidin-4-yl)-amine;

2-[2-(4-Chloro-phenyl)-1-pyrrolo [2,3-b]pyridin-4-yl]-5-cyclopropyl-4-piperazin-1-yl-pyrido[3,4-d]pyrimidine;

2-[2-(4-Chloro-phenyl)-1H-pyrrolo [2,3-b]pyridin-4-yl]-5-cyclopropyl-4-(hexahydro-pyrrolo [3,2-b]pyrrol-1-yl)-pyrido[3,4-d]pyrimidine;

(R)-Azepan-4-yl-[5-cyclobutyl-2-(9H-pyrido[2,3-b]indol-4-yl)-pyrido[3,4-d]pyrimidin-4-yl]-amine;

5-Cyclopropyl-2-[2-(2,5-dichloro-phenyl)-1H-pyrrolo [2,3-b]pyridin-4-yl]-4-(octahydro-pyrrolo [3,2-b]pyridin-1-yl)-pyrido[3,4-d]pyrimidine;

(±)-(3 aS,7aS)-1-{2-[2-(2-Chloro-phenyl)-1H-pyrrolo [2,3-b]pyridin-4-yl]-5-cyclopropyl-pyrido[3,4-d]pyrimidin-4-yl}-octahydro-pyrrolo [3,2-c]pyridin-3a-ol;

{2-[2-(4-Chloro-phenyl)-1H-pyrrolo [2,3-b]pyridin-4-yl]-5-cyclopropyl-pyrido[3,4-d]pyrimidin-4-yl}-(3,3-dimethyl-piperidin-4-yl)-methyl-amine;

5-(5-cyclobutyl-4-piperazin-1-yl-pyrido[3,4-d]pyrimidin-2-yl)-3-fluoro-9H-dipyrido[2,3-b;3',2'-d]pyrrole;

4-[4-Piperazin-1-yl-5-(2,2,2-trifluoro-1-methyl-ethyl)-pyrido[3,4-d]pyrimidin-2-yl]-9H-pyrido[2,3-b] indole;

{5-Cyclobutyl-2-[2-(3,5,6-trifluoro-pyridin-2-ylamino)-pyridin-4-yl]-pyrido[3,4-d]pyrimidin-4-yl}-(2-methyl-piperidin-4-yl)-amine;

{5-Cyclobutyl-2-[2-(3,6-difluoro-pyridin-2-ylamino)-pyridin-4-yl]-pyrido[3,4-d]pyrimidin-4-yl}-(2-methyl-piperidin-4-yl)-amine;

4-[4-(5-Cyclopropyl-4-piperazin-1-yl-pyrido[3,4-d]pyrimidin-2-yl)-1H-pyrrolo [2,3-b]pyridin-2-yl]-benzamide;

2-Amino-4-[5-cyclobutyl-2-(9H-pyrido[2,3-b]indol-4-yl)-pyrido[3,4-d]pyrimidin-4-ylamino]-cyclopentanol;

(±)-(3 aS,7aS)-1-{5-Cyclopropyl-2-[2-([1,2,4]triazolo [1,5-a]pyridin-2-ylamino)-pyridin-4-yl]-pyrido[3,4-d] pyrimidin-4-yl}-octahydro-pyrrolo[3,2-c]pyridin-3a-ol;

{4-[5-Cyclopropyl-4-(octahydro-pyrrolo [3,2-c]pyridin-1-yl)-pyrido[3,4-d]pyrimidin-2-yl]-pyridin-2-yl}-1,2,4] triazolo [1,5-a]pyridin-2-yl-amine;

[5-Cyclopropyl-2-(2-methyl-1H-pyrrolo[2,3-b]pyridin-4-yl)-pyrido[3,4-d]pyrimidin-4-yl]-((S)-3,3-dimethyl-piperidin-4-yl)-amine;

[5-Cyclopropyl-2-(2-methyl-1H-pyrrolo[2,3-b]pyridin-4-yl)-pyrido[3,4-d]pyrimidin-4-yl]-((R)-3,3-dimethyl-piperidin-4-yl)-amine;

5-Cyclopropyl-4-(hexahydro-pyrrolo [3,4-b] [1,4] oxazin-4-yl)-2-(2-trifluoromethyl-1H-pyrrolo [2,3-b]pyridin-4-yl)-pyrido[3,4-d]pyrimidine;

4-{4-[5-Cyclopropyl-4-(3,3-dimethyl-piperidin-4-ylamino)-pyrido[3,4-d]pyrimidin-2-yl]-1H-pyrrolo[2,3-b]pyridin-2-yl}-benzamide;

{5-Cyclopropyl-2-[2-(3,6-difluoro-pyridin-2-ylamino)-pyridin-4-yl]-pyrido[3,4-d]pyrimidin-4-yl}-((R)-3,3-dimethyl-piperidin-4-yl)-amine;

{5-Cyclopropyl-2-[2-(3,6-difluoro-pyridin-2-ylamino)-pyridin-4-yl]-pyrido[3,4-d]pyrimidin-4-yl}-((S)-3,3-dimethyl-piperidin-4-yl)-amine;

Azepan-4-yl-{5-cyclobutyl-2-[2-(3,5,6-trifluoro-pyridin-2-ylamino)-pyridin-4-yl]-pyrido[3,4-d]pyrimidin-4-yl}-amine;

Azepan-4-yl-{5-cyclobutyl-242-(3,6-difluoro-pyridin-2-ylamino)-pyridin-4-yl]-pyrido[3,4-d]pyrimidin-4-yl}-amine;

5 Cyclopropyl-4-(hexahydro-pyrrolo [3,4-b] [1,4] oxazin-6-yl)-2-(2-trifluoromethyl-1H-pyrrolo [2,3-b]pyridin-4-yl)-pyrido[3,4-d]pyrimidine;

4-{4-[5-Cyclopropyl-4-(octahydro-pyrrolo [3,2-b]pyridin-1-yl)-pyrido[3,4-d]pyrimidin-2-yl]-1H-pyrrolo [2,3-b]pyridin-2-yl}-benzamide;

[4-(5-Cyclopropyl-4-piperazin-1-yl-pyrido[3,4-d]pyrimidin-2-yl)-pyridin-2-yl]-(1-methyl-1H-[1,2,4]triazol-3-yl)-amine;

[4-(5-Cyclopropyl-4-piperazin-1-yl-pyrido[3,4-d]pyrimidin-2-yl)-pyridin-2-yl]-(1-ethyl-1H-[1,2,4]triazol-3-yl)-amine;

5-Cyclopropyl-2-[2-(6-methyl-pyridin-3-yl)-1H-pyrrolo [2,3-b]pyridin-4-yl]-4-piperazin-1-yl-pyrido[3,4-d]pyrimidine;

{5-Cyclopropyl-2-[2-(3-fluoro-pyridin-2-yl)-1H-pyrrolo [2,3-b]pyridin-4-yl]-pyrido[3,4-d]pyrimidin-4-yl}-((S)-3,3-dimethyl-piperidin-4-yl)-amine;

{5-Cyclopropyl-2-[2-(3-fluoro-pyridin-2-yl)-1H-pyrrolo [2,3-b]pyridin-4-yl]-pyrido[3,4-d]pyrimidin-4-yl}-((R)-3,3-dimethyl-piperidin-4-yl)-amine;

5-Cyclopropyl-2-[2-(3-fluoro-pyridin-2-yl)-1H-pyrrolo [2,3-b]pyridin-4-yl]-4-(octahydro-pyrrolo [3,2-b]pyridin-1-yl)-pyrido[3,4-d]pyrimidine;

5-Cyclobutyl-2-[2-(3-fluoro-pyridin-2-yl)-1H-pyrrolo [2,3-b]pyridin-4-yl]-4-(octahydro-pyrrolo [3,2-b]pyridin-1-yl)-pyrido[3,4-d]pyrimidine;

4-{4-[5-Cyclopropyl-4-(octahydro-pyrrolo [3,2-c]pyridin-1-yl)-pyrido[3,4-d]pyrimidin-2-yl]-1H-pyrrolo [2,3-b]pyridin-2-yl}-benzamide;

(±)-{5-Cyclobutyl-2-[2-(3,5,6-trifluoro-pyridin-2-ylamino)-pyridin-4-yl]-pyrido[3,4-d]pyrimidin-4-yl}-((3,4-cis)-3-methoxy-piperidin-4-yl)-amine;

(±)-{5-Cyclobutyl-2-[2-(3,6-difluoro-pyridin-2-ylamino)-pyridin-4-yl]-pyrido[3,4-d]pyrimidin-4-yl}-((3,4-cis)-3-methoxy-piperidin-4-yl)-amine;

(±)-(3,4-trans)-4-({5-Cyclobutyl-2-[2-(3,5,6-trifluoro-pyridin-2-ylamino)-pyridin-4-yl]-pyrido[3,4-d]pyrimidin-4-yl}-methyl-amino)-3-methyl-piperidin-3-ol;

{5-Cyclobutyl-2-[2-(quinolin-2-ylamino)-pyridin-4-yl]-pyrido[3,4-d]pyrimidin-4-yl}-(3,3-dimethyl-piperidin-4-yl)-methyl-amine;

4-[5-Cyclopropyl-4-(3,3-dimethyl-piperidin-4-ylamino)-pyrido[3,4-d]pyrimidin-2-yl]-1H-pyrrolo [2,3-b]pyridine-2-carboxylic acid cyclohexylamide;

[4-(5-Cyclopropyl-4-piperazin-1-yl-pyrido[3,4-d]pyrimidin-2-yl)-pyridin-2-yl]-(1-phenyl-1H-[1,2,4]triazol-3-yl)-amine;

(1-Benzyl-1H-[1,2,4] triazol-3-yl)-[4-(5-cyclopropyl-4-piperazin-1-yl-pyrido[3,4-d]pyrimidin-2-yl)-pyridin-2-yl]-amine;

{5-Cyclobutyl-2-[2-(3,6-difluoro-pyridin-2-ylamino)-pyridin-4-yl]-pyrido[3,4-d]pyrimidin-4-yl}-((R)-3,3-dimethyl-piperidin-4-yl)-amine;

{5-Cyclobutyl-2-[2-(3,6-difluoro-pyridin-2-ylamino)-pyridin-4-yl]-pyrido[3,4-d]pyrimidin-4-yl}-((S)-3,3-dimethyl-piperidin-4-yl)-amine;

{5-Cyclobutyl-2-[2-(quinolin-2-ylamino)-pyridin-4-yl]-pyrido[3,4-d]pyrimidin-4-yl}-((R)-3,3-dimethyl-piperidin-4-yl)-amine;

{5-Cyclobutyl-2-[2-(quinolin-2-ylamino)-pyridin-4-yl]-pyrido[3,4-d]pyrimidin-4-yl}-((S)-3,3-dimethyl-piperidin-4-yl)-amine;

(±)-(3,4-trans)-4-{2-[2-(2-Chloro-phenyl)-1H-pyrrolo [2,3-b]pyridin-4-yl]-5-cyclopropyl-pyrido[3,4-d]pyrimidin-4-ylamino}-piperidin-3-ol;

2-Amino-4-[5-cyclobutyl-2-(9H-pyrido[2,3-b]indol-4-yl)-pyrido[3,4-d]pyrimidin-4-ylamino]-cyclopentanecarboxylic acid amide;

2-Amino-4-{[5-cyclobutyl-2-(9H-pyrido[2,3-b]indol-4-yl)-pyrido[3,4-d]pyrimidin-4-yl]-methyl-amino}-cyclopentanol;

[4-(5-Cyclopropyl-4-piperazin-1-yl-pyrido[3,4-d]pyrimidin-2-yl)-pyridin-2-yl]-(1,5-dimethyl-1H-[1,2,4] triazol-3-yl)-amine;

(±)-{5-Cyclobutyl-2-[2-(3,5,6-trifluoro-pyridin-2-ylamino)-pyridin-4-yl]-pyrido[3,4-d]pyrimidin-4-yl}-((3,4-cis)-3-methyl-piperidin-4-yl)-amine;

(±)-{5-Cyclobutyl-2-[2-(3,6-difluoro-pyridin-2-ylamino)-pyridin-4-yl]-pyrido[3,4-d]pyrimidin-4-yl}-((3,4-cis)-3-methyl-piperidin-4-yl)-amine;

(±)-(3,4-trans)-4-{5-Cyclobutyl-2-[2-(3,5,6-trifluoro-pyridin-2-ylamino)-pyridin-4-yl]-pyrido[3,4-d]pyrimidin-4-ylamino}-piperidin-3-ol;

(±)-(3,4-trans)-4-{5-Cyclobutyl-2-[2-(3,6-difluoro-pyridin-2-ylamino)-pyridin-4-yl]-pyrido[3,4-d]pyrimidin-4-ylamino}-piperidin-3-ol;

[5-Cyclobutyl-2-(2-methyl-1H-pyrrolo [2,3-b]pyridin-4-yl)-pyrido[3,4-d]pyrimidin-4-yl]-((S)-3,3-dimethyl-piperidin-4-yl)-amine;

{5-Cyclobutyl-2-[2-(3-fluoro-pyridin-2-yl)-1H-pyrrolo [2,3-b]pyridin-4-yl]-pyrido[3,4-d]pyrimidin-4-yl}-((S)-3,3-dimethyl-piperidin-4-yl)-amine;

(±)-[5-Cyclobutyl-2-(2-methyl-1H-pyrrolo [2,3-b]pyridin-4-yl)-pyrido[3,4-d]pyrimidin-4-yl]-((3,4-cis)-3-methyl-piperidin-4-yl)-amine;

(±)-{5-Cyclobutyl-2-[2-(3,5,6-trifluoro-pyridin-2-ylamino)-pyridin-4-yl]-pyrido[3,4-d]pyrimidin-4-yl}-((3,4-trans)-3-methyl-piperidin-4-yl)-amine;

(±)-{5-Cyclobutyl-2-[2-(3,6-difluoro-pyridin-2-ylamino)-pyridin-4-yl]-pyrido[3,4-d]pyrimidin-4-yl}-((3,4-trans)-3-methyl-piperidin-4-yl)-amine;

(±)-[5-Cyclobutyl-2-(2-methyl-1H-pyrrolo [2,3-b]pyridin-4-yl)-pyrido[3,4-d]pyrimidin-4-yl]-((3,4-trans)-3-methyl-piperidin-4-yl)-amine;

5-Cyclopropyl-2-[2-(3-fluoro-pyridin-2-yl)-1H-pyrrolo [2,3-b]pyridin-4-yl]-4-(hexahydro-pyrrolo [3,4-b][1,4] oxazin-4-yl)-pyrido[3,4-d]pyrimidine;

{2-[2-(2-Chloro-phenyl)-1H-pyrrolo [2,3-b]pyridin-4-yl]-5-cyclopropyl-pyrido[3,4-d]pyrimidin-4-yl}-((S)-3,3-dimethyl-piperidin-4-yl)-amine;

(3-Aza-bicyclo [4.1.0]hept-6-yl)45-cyclobutyl-2-(9H-pyrido[2,3-b]indol-4-yl)-pyrido[3,4-d]pyrimidin-4-yl]-amine;

[4-(5-Cyclopropyl-4-piperazin-1-yl-pyrido[3,4-d]pyrimidin-2-yl)-pyridin-2-yl]-(5-ethyl-1-methyl-1H-[1,2,4]triazol-3-yl)-amine;

[5-Cyclobutyl-2-(9H-pyrido[2,3-b]indol-4-yl)-pyrido[3,4-d]pyrimidin-4-yl]-((S)-3,3-dimethyl-piperidin-4-yl)-amine;

{4-[5-Cyclopropyl-4-(hexahydro-pyrrolo [3,4-b] [1,4]oxazin-4-yl)-pyrido[3,4-d]pyrimidin-2-yl]-pyridin-2-yl}-(6-fluoro-pyridin-2-yl)-amine;

{4-[5-Cyclopropyl-4-(hexahydro-pyrrolo [3,4-b] [1,4]oxazin-4-yl)-pyrido[3,4-d]pyrimidin-2-yl]-pyridin-2-yl}-(3,5,6-trifluoro-pyridin-2-yl)-amine;

{4-[5-Cyclopropyl-4-(hexahydro-pyrrolo [3,4-b] [1,4]oxazin-4-yl)-pyrido[3,4-d]pyrimidin-2-yl]-pyridin-2-yl}-(3,6-difluoro-pyridin-2-yl)-amine;

2,4,6-Triisopropyl-benzenesulfonic acid 5-cyclobutyl-2-(9H-pyrido[2,3-b] indol-4-yl)-pyrido[3,4-d]pyrimidin-4-yl ester;

[4-(5-Cyclopropyl-4-piperazin-1-yl-pyrido[3,4-d]pyrimidin-2-yl)-pyridin-2-yl]-(5,6,7,8-tetrahydro-[1,2,4] triazolo [1,5-a]pyridin-2-yl)-amine;

4-[5-Cyclobutyl-4-(hexahydro-pyrrolo[3,4-b][1,4]oxazin-4-yl)-pyrido[3,4-d] pyrimidin-2-yl]-9H-pyrido[2,3-b] indole;

(±)-(1S,3S,4S)—N*1*-[5-Cyclobutyl-2-(9H-pyrido[2,3-b]indol-4-yl)-pyrido[3,4-d]pyrimidin-4-yl]-4-fluoro-cyclopentane-1,3-diamine;

(3-Aza-bicyclo [4.1.0]hept-6-yl)-{5-cyclobutyl-2-[2-(3,5,6-trifluoro-pyridin-2-ylamino)-pyridin-4-yl]-pyrido[3,4-d]pyrimidin-4-yl}-amine;

(3-Aza-bicyclo [4.1.0]hept-6-yl)-{5-cyclobutyl-2-[2-(3,6-difluoro-pyridin-2-ylamino)-pyridin-4-yl]-pyrido[3,4-d]pyrimidin-4-yl}-amine;

{5-Cyclobutyl-2-[2-(3-fluoro-pyridin-2-ylamino)-pyridin-4-yl]-pyrido[3,4-d]pyrimidin-4-yl}-((S)-3,3-dimethyl-piperidin-4-yl)-amine;

{5-Cyclobutyl-2-[2-(3,5-difluoro-pyridin-2-ylamino)-pyridin-4-yl]-pyrido[3,4-d]pyrimidin-4-yl}-((S)-3,3-dimethyl-piperidin-4-yl)-amine;

[5-Cyclopropyl-2-(2-methyl-1H-pyrrolo [2,3-b]pyridin-4-yl)-pyrido[3,4-d]pyrimidin-4-yl]-((S)-3,3-dimethyl-piperidin-4-yl)-methyl-amine;

[2-(2-tert-Butyl-1H-pyrrolo [2,3-b]pyridin-4-yl)-5-cyclobutyl-pyrido[3,4-d]pyrimidin-4-yl]-methyl-piperidin-4-yl-amine;

1-[5-Cyclobutyl-2-(9H-pyrido[2,3-b]indol-4-yl)-pyrido[3,4-d]pyrimidin-4-yl]-pyrrolidin-3-ylamine;

4-(4-Piperazin-1-yl-5-trifluoromethyl-pyrido[3,4-d]pyrimidin-2-yl)-9H-pyrido[2,3-b]indole;

4-((3R,6R)-4-Hexahydro-pyrrolo [3,4-b]pyrrol-1-yl-5-trifluoromethyl-pyrido[3,4-d]pyrimidin-2-yl)-9H-pyrido[2,3-b]indole;

((S)-3,3-Dimethyl-piperidin-4-yl)-[2-(9H-pyrido[2,3-b]indol-4-yl)-5-trifluoromethyl-pyrido[3,4-d]pyrimidin-4-yl]-amine;

cis-N-[2-(9H-Pyrido [2,3-b]indol-4-yl)-5-trifluoromethyl-pyrido[3,4-d]pyrimidin-4-yl]-cyclobutane-1,3-diamine;

5-[2-(9H-Pyrido [2,3-b]indol-4-yl)-5-trifluoromethyl-pyrido[3,4-d]pyrimidin-4-ylamino]-azepan-3-ol;

2-Amino-4-{methyl-[2-(9H-pyrido[2,3-b]indol-4-yl)-5-trifluoromethyl-pyrido[3,4-d]pyrimidin-4-yl]-amino}-cyclopentanol;

1-[2-(9H-Pyrido [2,3-b]indol-4-yl)-5-trifluoromethyl-pyrido[3,4-d]pyrimidin-4-yl]-pyrrolidin-3-ylamine;

2-[2-(2-Chloro-5-fluoro-phenyl)-1H-pyrrolo [2,3-b]pyridin-4-yl]-5-cyclopropyl-4-piperazin-1-yl-pyrido[3,4-d]pyrimidine;

(±)-{5-Cyclopropyl-2-[2-(3,6-difluoro-pyridin-2-ylamino)-pyridin-4-yl]-pyrido[3,4-d]pyrimidin-4-yl}-((3,4-trans)-3-methyl-piperidin-4-yl)-amine;

(±)-{5-Cyclopropyl-2-[2-(3,6-difluoro-pyridin-2-ylamino)-pyridin-4-yl]-pyrido[3,4-d]pyrimidin-4-yl}-((3,4-cis)-3-methyl-piperidin-4-yl)-amine;

(±)-{5-Cyclopropyl-2-[2-(3,6-difluoro-pyridin-2-ylamino)-pyridin-4-yl]-pyrido[3,4-d]pyrimidin-4-yl}((2,4-cis)-2-methyl-piperidin-4-yl)-amine;

(±)-{5-Cyclopropyl-2-[2-(3,6-difluoro-pyridin-2-ylamino)-pyridin-4-yl]-pyrido[3,4-d]pyrimidin-4-yl}((2,4-trans)-2-methyl-piperidin-4-yl)-amine;

[5-Cyclopropyl-2-(2-trifluoromethyl-1H-pyrrolo [2,3-b]pyridin-4-yl)-pyrido[3,4-d]pyrimidin-4-yl]-((S)-3,3-dimethyl-piperidin-4-yl)-amine;

[5-Cyclobutyl-2-(2-trifluoromethyl-1H-pyrrolo [2,3-b]pyridin-4-yl)-pyrido [3,4-d]pyrimidin-4-yl]-((S)-3,3-dimethyl-piperidin-4-yl)-amine;

{2-[2-(2-Chloro-5-fluoro-phenyl)-1H-pyrrolo [2,3-b]pyridin-4-yl]-5-cyclopropyl-pyrido[3,4-d]pyrimidin-4-yl}-((S)-3,3-dimethyl-piperidin-4-yl)-amine;

Cis- or trans-(±)-5[5-Cyclobutyl-2-(9H-pyrido[2,3-b]indol-4-yl)-pyrido[3,4-d]pyrimidin-4-ylamino]-azepan-3-ol;

Trans- or cis-(±)-5-[5-Cyclobutyl-2-(9H-pyrido[2,3-b]indol-4-yl)-pyrido[3,4-d]pyrimidin-4-ylamino]-azepan-3-ol; or

[5-Cyclobutyl-2-(9H-pyrido[2,3-b] indol-4-yl)-pyrido[3,4-d]pyrimidin-4-yl]-(6-fluoro-azepan-4-yl)-amine;

rac-{5-Cyclopropyl-2-[2-(1-phenyl-1H-1,2,4-triazol-3-ylamino)-pyridin-4-yl]-pyrido[3,4-d]pyrimidin-4-yl}-(3,3-dimethyl-piperidin-4-yl)-amine;

rac-{5-Cyclopropyl-2-[2-(1-phenyl-1H-1,2,4-triazol-3-ylamino)-pyridin-4-yl]-pyrido[3,4-d]pyrimidin-4-yl}-(3,3-dimethyl-piperidin-4-yl)-methyl-amine;

{4-[5-Cyclopropyl-4-(octahydro-pyrrolo [3,2-c]pyridin-1-yl)-pyrido[3,4-d]pyrimidin-2-yl]-pyridin-2-yl}-(1-phenyl-1H-1,2,4-triazol-3-yl)-amine;

rac-(3aS,7aS)-1-{5-Cyclopropyl-2-[2-(1-phenyl-1H-1,2,4-triazol-3-ylamino)-pyridin-4-yl]-pyrido[3,4-d]pyrimidin-4-yl}-octahydro-pyrrolo [3,2-c]pyridin-3a-ol;

rac-{2-[2-(1-Benzyl-1H-1,2,4-triazol-3-ylamino)-pyridin-4-yl]-5-cyclopropyl-pyrido[3,4-d]pyrimidin-4-yl}-(3,3-dimethyl-piperidin-4-yl)-amine;

rac-{2-[2-(1-Benzyl-1H-1,2,4-triazol-3-ylamino)-pyridin-4-yl]-5-cyclopropyl-pyrido[3,4-d]pyrimidin-4-yl}-(3,3-dimethyl-piperidin-4-yl)-methyl-amine;

(1-Benzyl-1H-1,2,4-triazol-3-yl)-{4-[5-cyclopropyl-4-(octahydro-pyrrolo [3,2-c]pyridin-1-yl)-pyrido[3,4-d]pyrimidin-2-yl]-pyridin-2-yl}-amine;

rac-(3aS,7aS)-1-{2-[2-(1-Benzyl-1H-1,2,4-triazol-3-ylamino)-pyridin-4-yl]-5-cyclopropyl-pyrido[3,4-d]pyrimidin-4-yl}-octahydro-pyrrolo [3,2-c]pyridin-3a-ol;

{5-Cyclopropyl-2-[2-([1,2,4]triazolo [1,5-a]pyridin-2-ylamino)-pyridin-4-yl]-pyrido[3,4-d]pyrimidin-4-yl}-((S)-3,3-dimethyl-piperidin-4-yl)-amine;

{2-[2-(1-Benzyl-1H-1,2,4-triazol-3-ylamino)-pyridin-4-yl]-5-cyclopropyl-pyrido[3,4-d]pyrimidin-4-yl}-((S)-3,3-dimethyl-piperidin-4-yl)-amine;

{5-Cyclopropyl-2-[2-(1-phenyl-1H-1,2,4-triazol-3-ylamino)-pyridin-4-yl]-pyrido[3,4-d]pyrimidin-4-yl1-((S)-3,3-dimethyl-piperidin-4-yl)-amine;

{4-[5-Cyclopropyl-4-(octahydro-pyrrolo [3,2-b]pyridin-1-yl)-pyrido[3,4-d]pyrimidin-2-yl]-pyridin-2-yl}-[1,2,4]triazolo [1,5-a]pyridin-2-yl-amine;

{4-[5-Cyclopropyl-4-(octahydro-pyrrolo [3,2-b]pyridin-1-yl)-pyrido[3,4-d]pyrimidin-2-yl]-pyridin-2-yl}-(1-phenyl-1H-1,2,4-triazol-3-yl)-amine;

rac-(3R,4R)-4-[5-Cyclobutyl-2-(9H-pyrido[2,3-b] indol-4-yl)-pyrido[3,4-d]pyrimidin-4-ylamino]-3-methyl-piperidin-3-ol;

rac-(3R,4R)-4-[5-Cyclopropyl-2-(9H-pyrido[2,3-b] indol-4-yl)-pyrido[3,4-d]pyrimidin-4-ylamino]-3-methyl-piperidin-3-ol;

C—{(S)-1-[5-Cyclobutyl-2-(9H-pyrido[2,3-b]indol-4-yl)-pyrido[3,4-d]pyrimidin-4-yl]-pyrrolidin-3-yl}-methylamine;

C—{(R)-1-[5-Cyclobutyl-2-(9H-pyrido[2,3-b]indol-4-yl)-pyrido[3,4-d]pyrimidin-4-yl]-pyrrolidin-3-yl}-methylamine;

4-[5-Cyclobutyl-4-(2,7-diaza-spiro [4.5]dec-2-yl)-pyrido [3,4-d]pyrimidin-2-yl]-9H-pyrido[2,3-b] indole;

[5-Cyclobutyl-2-(9H-pyrido[2,3-b]indol-4-yl)-pyrido[3,4-d]pyrimidin-4-yl]-morpholin-3-ylmethyl-amine;

(R)-1-[5-Cyclobutyl-2-(9H-pyrido[2,3-b]indol-4-yl)-pyrido[3,4-d]pyrimidin-4-yl]-pyrrolidin-3-ol;

(S)-1-[5-Cyclobutyl-2-(9H-pyrido[2,3-b]indol-4-yl)-pyrido[3,4-d]pyrimidin-4-yl]-pyrrolidin-3-ol;

{5-Cyclopropyl-2-[2-(2,6-difluoro-phenylamino)-pyridin-4-yl]-pyrido[3,4-d]pyrimidin-4-yl}-((S)-3,3-dimethyl-piperidin-4-yl)-amine;

{5-Cyclobutyl-2-[2-(2,6-difluoro-phenylamino)-pyridin-4-yl]-pyrido[3,4-d]pyrimidin-4-yl}-((S)-3,3-dimethyl-piperidin-4-yl)-amine;

{4-[5-Cyclobutyl-4-(hexahydro-pyrrolo [3,4-b]-1,4-oxazin-4-yl)-pyrido[3,4-d]pyrimidin-2-yl]-pyridin-2-yl}-(3,6-difluoro-pyridin-2-yl)-amine;

5-Cyclobutyl-4-(hexahydro-pyrrolo [3,4-b]-1,4-oxazin-4-yl)-2-(2-methyl-1H-pyrrolo [2,3-b]pyridin-4-yl)-pyrido[3,4-d]pyrimidine;

{4-[5-Cyclobutyl-4-(hexahydro-pyrrolo [3,4-b]-1,4-oxazin-4-yl)-pyrido[3,4-d]pyrimidin-2-yl]-pyridin-2-yl}-(2,6-difluoro-phenyl)-amine;

5-Cyclobutyl-2-[2-(3-fluoro-pyridin-2-yl)-1H-pyrrolo [2,3-b]pyridin-4-yl]-4-(hexahydro-pyrrolo [3,4-b]-1,4-oxazin-4-yl)-pyrido[3,4-d]pyrimidine;

{5-Cyclopropyl-2-[2-(3-fluoro-pyridin-2-ylamino)-pyridin-4-yl]-pyrido[3,4-d]pyrimidin-4-yl}-((2S,6R)-2,6-dimethyl-piperidin-4-yl)-amine;

rac-2-[2-[(3,6-difluoro-2-pyridyl)amino]-4-pyridyl]-N-(3,3-dimethyl-4-piperidyl)-5-methoxy-pyrido[3,4-d]pyrimidin-4-amine;

rac-5-cyclobutyl-N-[(3S,4S)-3-methyl-4-piperidyl]-2[2-(trifluoromethyl)-1H-pyrrolo [2,3-b]pyridin-4-yl]pyrido[3,4-d]pyrimidin-4-amine;

rac-5-cyclobutyl-N-[(3R,4S)-3-methyl-4-piperidyl]-2[2-(trifluoromethyl)-1H-pyrrolo [2,3-b]pyridin-4-yl]pyrido[3,4-d]pyrimidin-4-amine;

5-cyclobutyl-N-[(4S)-3,3-dimethyl-4-piperidyl]-2-[2-(3-pyridylamino)-4-pyridyl]pyrido[3,4-d]pyrimidin-4-amine;

5-cyclopropyl-N-[(4S)-3,3-dimethyl-4-piperidyl]-2-[2-[(5-fluoro-3-pyridyl)amino]-4-pyridyl]pyrido[3,4-d]pyrimidin-4-amine;

2-[2-[(5-chloro-3-pyridyl)amino]-4-pyridyl]-5-cyclopropyl-N-[(4S)-3,3-dimethyl-4-piperidyl]pyrido[3,4-d]pyrimidin-4-amine;

(2S)-2-[[4-[5-cyclopropyl-4-[[(4S)-3,3-dimethyl-4-piperidyl] amino]pyrido[3,4-d]pyrimidin-2-yl]-2-pyridyl] amino]-2-phenyl-acetic acid;

2-[2-[(3,6-difluoro-2-pyridyl)amino]-4-pyridyl]-N-[(4S)-3,3-dimethyl-4-piperidyl]-5-methoxy-pyrido[3,4-d]pyrimidin-4-amine;

N-[(4S)-3,3-dimethyl-4-piperidyl]-2-[2-[(3-fluoro-2-pyridyl)amino]-4-pyridyl]-5-methoxy-pyrido[3,4-d]pyrimidin-4-amine;

rac-(3S,4R)-4-{5-Cyclobutyl-2-[2-(quinolin-2-ylamino)-pyridin-4-yl]-pyrido[3,4-d]pyrimidin-4-ylaminol-piperidin-3-ol;

{5-Cyclobutyl-2-[2-(6-methyl-pyridin-2-ylamino)-pyridin-4-yl]-pyrido[3,4-d]pyrimidin-4-yl}-((S)-3,3-dimethyl-piperidin-4-yl)-amine;

6-{4-[5-Cyclobutyl-4-((S)-3,3-dimethyl-piperidin-4-ylamino)-pyrido[3,4-d]pyrimidin-2-yl]-pyridin-2-ylamino}-2-methyl-nicotinonitrile;

rac-(3R,4R)-4-{5-Cyclobutyl-2-[2-(quinolin-2-ylamino)-pyridin-4-yl]-pyrido[3,4-d]pyrimidin-4-ylamino}-piperidin-3-ol;

{2-[2-(Benzoxazol-2-ylamino)-pyridin-4-yl]-5-cyclobutyl-pyrido[3,4-d]pyrimidin-4-yl}-((S)-3,3-dimethyl-piperidin-4-yl)-amine;

{5-Cyclobutyl-2-[2-([1,2,4]triazolo[1,5-a]pyridin-2-ylamino)-pyridin-4-yl]-pyrido[3,4-d]pyrimidin-4-yl1-((S)-3,3-dimethyl-piperidin-4-yl)-amine;

{5-Cyclobutyl-2-[2-([1,2,4] triazolo [1,5-a]pyridin-2-ylamino)-pyridin-4-yl]-pyrido[3,4-d]pyrimidin-4-yl}-(rac-(3R,4S)-3-methyl-piperidin-4-yl)-amine;

{5-Cyclobutyl-2-[2-([1,2,4]triazolo[1,5-a]pyridin-2-ylamino)-pyridin-4-yl]-pyrido[3,4-d]pyrimidin-4-yl}-(rac-(3R,4R)-3-methyl-piperidin-4-yl)-amine;

{5-Cyclopropyl-2-[2-(3,5,6-trifluoro-pyridin-2-ylamino)-pyridin-4-yl]-pyrido [3,4-d]pyrimidin-4-yl}-((S)-3,3-dimethyl-piperidin-4-yl)-amine;

{5-Cyclobutyl-2-[2-(3,6-difluoro-pyridin-2-ylamino)-pyridin-4-yl]-pyrido[3,4-d]pyrimidin-4-yl}-((3R,4R)-3-methyl-piperidin-4-yl)-amine;

{5-Cyclobutyl-2-[2-(3,6-difluoro-pyridin-2-ylamino)-pyridin-4-yl]-pyrido[3,4-d]pyrimidin-4-yl}-((3S,4S)-3-methyl-piperidin-4-yl)-amine;

{5-Cyclobutyl-2-[2-(1-methyl-1H-benzimidazol-2-ylamino)-pyridin-4-yl]-pyrido[3,4-d]pyrimidin-4-yl}-((S)-3,3-dimethyl-piperidin-4-yl)-amine;

{5-Cyclobutyl-2-[2-(3-fluoro-pyridin-2-ylamino)-pyridin-4-yl]-pyrido[3,4-d]pyrimidin-4-yl}-(rac-(3R,4S)-3-methyl-piperidin-4-yl)-amine;

{5-Cyclobutyl-2-[2-(3,5-difluoro-pyridin-2-ylamino)-pyridin-4-yl]-pyrido[3,4-d]pyrimidin-4-yl}-(rac-(3R,4S)-3-methyl-piperidin-4-yl)-amine;

{5-Cyclobutyl-2-[2-(1-methyl-1H-indazol-3-ylamino)-pyridin-4-yl]-pyrido[3,4-d]pyrimidin-4-yl1-((S)-3,3-dimethyl-piperidin-4-yl)-amine;

rac-(3S,4S)-4-{5-Cyclobutyl-2-[2-(3,6-difluoro-pyridin-2-ylamino)-pyridin-4-yl]-pyrido[3,4-d]pyrimidin-4-ylamino}-pyrrolidin-3-ol;

rac-(3R,4R)-4-{5-Cyclobutyl-2-[2-(3-fluoro-pyridin-2-ylamino)-pyridin-4-yl]-pyrido[3,4-d]pyrimidin-4-ylamino}-piperidin-3-ol;

rac-(3R,4R)-4-{5-Cyclobutyl-2-[2-(3,5-difluoro-pyridin-2-ylamino)-pyridin-4-yl]-pyrido[3,4-d]pyrimidin-4-ylamino}-piperidin-3-ol;
{5-Cyclobutyl-2-[2-(3-fluoro-pyridin-2-ylamino)-pyridin-4-yl]-pyrido[3,4-d]pyrimidin-4-yl}-(rac-(3R,4R)-3-methyl-piperidin-4-yl)-amine;
{5-Cyclobutyl-2-[2-(3,5-difluoro-pyridin-2-ylamino)-pyridin-4-yl]-pyrido[3,4-d]pyrimidin-4-yl}-(rac-(3R,4R)-3-methyl-piperidin-4-yl)-amine;
{5-Cyclobutyl-2-[2-(3,4,6-trifluoro-pyridin-2-ylamino)-pyridin-4-yl]-pyrido[3,4-d]pyrimidin-4-yl}-(rac-(3R,4R)-3-methyl-piperidin-4-yl)-amine;
rac-(3S,4R)-4-{5-Cyclobutyl-2-[2-(3-fluoro-pyridin-2-ylamino)-pyridin-4-yl]-pyrido[3,4-d]pyrimidin-4-ylamino 1-piperidin-3-ol;
rac-(3S,4R)-4-{5-Cyclobutyl-2-[2-(3,5-difluoro-pyridin-2-ylamino)-pyridin-4-yl]-pyrido[3,4-d]pyrimidin-4-ylamino}-piperidin-3-ol;
rac-(3S,4R)-4-{5-Cyclobutyl-2-[2-(3,4,6-trifluoro-pyridin-2-ylamino)-pyridin-4-yl]-pyrido[3,4-d]pyrimidin-4-ylamino}-piperidin-3-ol;
{5-Cyclobutyl-2-[2-(3,4,6-trifluoro-pyridin-2-ylamino)-pyridin-4-yl]-pyrido[3,4-d]pyrimidin-4-yl}-(rac-(3R,4S)-3-methyl-piperidin-4-yl)-amine;
rac-(3R,4R)-4-{5-Cyclobutyl-2-[2-(3,4,6-trifluoro-pyridin-2-ylamino)-pyridin-4-yl]-pyrido[3,4-d]pyrimidin-4-ylamino}-piperidin-3-ol;
{5-Cyclobutyl-2-[2-(3,6-difluoro-pyridin-2-ylamino)-pyridin-4-yl]-pyrido[3,4-d]pyrimidin-4-yl}-((3R,4S)-3-methyl-piperidin-4-yl)-amine;
{5-Cyclobutyl-2-[2-(3,6-difluoro-pyridin-2-ylamino)-pyridin-4-yl]-pyrido[3,4-d]pyrimidin-4-yl}-((3S,4R)-3-methyl-piperidin-4-yl)-amine;
{5-Cyclopropyl-2-[2-(3-fluoro-pyridin-2-ylamino)-pyridin-4-yl]-pyrido[3,4-d]pyrimidin-4-yl}-(rac-(3R,4S)-3-methyl-piperidin-4-yl)-amine;
{5-Cyclopropyl-2-[2-(3,5-difluoro-pyridin-2-ylamino)-pyridin-4-yl]-pyrido[3,4-d]pyrimidin-4-yl}-(rac-(3R,4S)-3-methyl-piperidin-4-yl)-amine;
{5-Cyclopropyl-2-[2-(3,4,6-trifluoro-pyridin-2-ylamino)-pyridin-4-yl]-pyrido [3,4-d]pyrimidin-4-yl}-(rac-(3R,4S)-3-methyl-piperidin-4-yl)-amine;
{5-Cyclopropyl-2-[2-(3-fluoro-pyridin-2-ylamino)-pyridin-4-yl]-pyrido[3,4-d]pyrimidin-4-yl}-(rac-(3R,4R)-3-methyl-piperidin-4-yl)-amine;
{5-Cyclopropyl-2-[2-(3,5-difluoro-pyridin-2-ylamino)-pyridin-4-yl]-pyrido[3,4-d]pyrimidin-4-yl}-(rac-(3R,4R)-3-methyl-piperidin-4-yl)-amine;
{5-Cyclopropyl-2-[2-(3,4,6-trifluoro-pyridin-2-ylamino)-pyridin-4-yl]-pyrido [3,4-d]pyrimidin-4-yl}-(rac-(3R,4R)-3-methyl-piperidin-4-yl)-amine;
rac-(3S,4R)-4-{5-Cyclopropyl-2-[2-(3-fluoro-pyridin-2-ylamino)-pyridin-4-yl]-pyrido[3,4-d]pyrimidin-4-ylamino}-piperidin-3-ol;
rac-(3S,4R)-4-{5-Cyclopropyl-2-[2-(3,5-difluoro-pyridin-2-ylamino)-pyridin-4-yl]-pyrido[3,4-d]pyrimidin-4-ylamino}-piperidin-3-ol;
rac-(3S,4R)-4-{5-Cyclopropyl-2-[2-(3,4,6-trifluoro-pyridin-2-ylamino)-pyridin-4-yl]-pyrido[3,4-d]pyrimidin-4-ylamino}-piperidin-3-ol;
rac-(3R,4R)-4-{5-Cyclopropyl-2-[2-(3-fluoro-pyridin-2-ylamino)-pyridin-4-yl]-pyrido[3,4-d]pyrimidin-4-ylamino}-piperidin-3-ol;
rac-(3R,4R)-4-{5-Cyclopropyl-2-[2-(3,5-difluoro-pyridin-2-ylamino)-pyridin-4-yl]-pyrido[3,4-d]pyrimidin-4-ylamino}-piperidin-3-ol;
rac-(3R,4R)-4-{5-Cyclopropyl-2-[2-(3,4,6-trifluoro-pyridin-2-ylamino)-pyridin-4-yl]-pyrido[3,4-d]pyrimidin-4-ylamino}-piperidin-3-ol;
6-{4-[5-Cyclobutyl-4-(rac-(3R,4S)-3-methyl-piperidin-4-ylamino)-pyrido[3,4-d]pyrimidin-2-yl]-pyridin-2-ylamino}-2-methyl-nicotinonitrile;
6-{4-[5-Cyclobutyl-4-(rac-(3R,4R)-3-methyl-piperidin-4-ylamino)-pyrido[3,4-d]pyrimidin-2-yl]-pyridin-2-ylamino}-2-methyl-nicotinonitrile;
6-{4-[5-Cyclobutyl-4-(rac-(3S,4R)-3-hydroxy-piperidin-4-ylamino)-pyrido[3,4-d]pyrimidin-2-yl]-pyridin-2-ylamino}-2-methyl-nicotinonitrile;
6-{4-[5-Cyclobutyl-4-(rac-(3R,4R)-3-hydroxy-piperidin-4-ylamino)-pyrido[3,4-d]pyrimidin-2-yl]-pyridin-2-ylamino}-2-methyl-nicotinonitrile;
{5-Cyclobutyl-2-[3-(3,6-difluoro-pyridin-2-ylamino)-phenyl]-pyrido[3,4-d]pyrimidin-4-yl}-((S)-3,3-dimethyl-piperidin-4-yl)-amine;
{2-[2-(5-Chloro-3-fluoro-pyridin-2-ylamino)-pyridin-4-yl]-5-cyclobutyl-pyrido[3,4-d]pyrimidin-4-yl}-((S)-3,3-dimethyl-piperidin-4-yl)-amine;
6-{4-[5-Cyclobutyl-4-((S)-3,3-dimethyl-piperidin-4-ylamino)-pyrido[3,4-d]pyrimidin-2-yl]-pyridin-2-ylamino}-pyridine-2-carbonitrile;
{5-Cyclobutyl-2-[2-(8-fluoro-quinolin-2-ylamino)-pyridin-4-yl]-pyrido[3,4-d]pyrimidin-4-yl}-((S)-3,3-dimethyl-piperidin-4-yl)-amine;
{2-[2-(5-Chloro-3-fluoro-pyridin-2-ylamino)-pyridin-4-yl]-5-cyclopropyl-pyrido[3,4-d]pyrimidin-4-yl}-((S)-3,3-dimethyl-piperidin-4-yl)-amine;
6-{4-[5-Cyclobutyl-4-((S)-3,3-dimethyl-piperidin-4-ylamino)-pyrido[3,4-d]pyrimidin-2-yl]-pyridin-2-ylaminol-5-fluoro-nicotinonitrile;
{5-Cyclobutyl-2-[3-(pyridin-2-ylamino)-phenyl]-pyrido[3,4-d]pyrimidin-4-yl}-((S)-3,3-dimethyl-piperidin-4-yl)-amine;
6-{4-[5-Cyclobutyl-4-((S)-3,3-dimethyl-piperidin-4-ylamino)-pyrido[3,4-d]pyrimidin-2-yl]-pyridin-2-ylamino}-5-methyl-nicotinonitrile;
5-cyclobutyl-N-[(4S)-3,3-dimethyl-4-piperidyl]-2-[3-(pyrazin-2-ylamino)phenyl]pyrido[3,4-d]pyrimidin-4-amine;
5-cyclopropyl-N-[(4S)-3,3-dimethyl-4-piperidyl]-2-[2-[(3,4,6-trifluoro-2-pyridyl)amino]-4-pyridyl]pyrido[3,4-d]pyrimidin-4-amine;
5-cyclobutyl-N-[(4S)-3,3-dimethyl-4-piperidyl]-2-[2-[(3,4,6-trifluoro-2-pyridyl)amino]-4-pyridyl]pyrido[3,4-d]pyrimidin-4-amine;
N-[4-[5-cyclopropyl-4-[[(4S)-3,3-dimethyl-4-piperidyl]amino]pyrido[3,4-d]pyrimidin-2-yl]-2-pyridyl]-1,3-benzoxazol-2-amine;
5-cyclopropyl-N-[(4S)-3,3-dimethyl-4-piperidyl]-2-[2-(pyrazolo [1,5-a]pyridin-2-ylamino)-4-pyridyl]pyrido[3,4-d]pyrimidin-4-amine;
5-cyclobutyl-N-[(4S)-3,3-dimethyl-4-piperidyl]-2-[2-[(1-phenyl-1,2,4-triazol-3-yl)amino]-4-pyridyl]pyrido[3,4-d]pyrimidin-4-amine 4-(5-cyclobutyl-4-piperazin-1-yl-pyrido[3,4-d]pyrimidin-2-yl)-N-(1-phenyl-1,2,4-triazol-3-yl)pyridin-2-amine;
5-cyclopropyl-2-[2-[(3,6-difluoro-2-pyridyl)amino]-4-pyridyl]-N-[(4S)-3,3-dimethyl-4-piperidyl]-N-methyl-pyrido[3,4-d]pyrimidin-4-amine;
N-[4-[5-cyclopropyl-4-[[(4S)-3,3-dimethyl-4-piperidyl]amino]pyrido[3,4-d]pyrimidin-2-yl]-2-pyridyl]-6-fluoro-1,3-benzoxazol-2-amine;

"6-[[4-[5-cyclopropyl-4-[[(4S)-3,3-dimethyl-4-piperidyl] amino]pyrido[3,4-d]pyrimidin-2-yl]-2-pyridyl]amino]-5-fluoro-pyridine-3-carbonitrile;

5-cyclopropyl-2-[2-[(3,6-difluoro-2-pyridyl)amino]-4-pyridyl]-N-[(3S,4S)-3-methyl-4-piperidyl]pyrido[3,4-d]pyrimidin-4-amine;

5-cyclopropyl-2-[2-[(3,6-difluoro-2-pyridyl)amino]-4-pyridyl]-N-[(3R,4R)-3-methyl-4-piperidyl]pyrido[3,4-d]pyrimidin-4-amine;

2-[2-[(3-chloro-2-pyridyl)amino]-4-pyridyl]-5-cyclobutyl-N-[(4S)-3,3-dimethyl-4-piperidyl]pyrido[3,4-d]pyrimidin-4-amine;

5-cyclobutyl-2-[2-[(3,5-dichloro-2-pyridyl)amino]-4-pyridyl]-N-[(4S)-3,3-dimethyl-4-piperidyl]pyrido[3,4-d]pyrimidin-4-amine N-[4-[5-cyclobutyl-4-[[(4S)-3,3-dimethyl-4-piperidyl] amino]pyrido[3,4-d]pyrimidin-2-yl]-2-pyridyl]-6-fluoro-1,3-benzoxazol-2-amine;

2-[2-[(3-chloro-2-pyridyl)amino]-4-pyridyl]-5-cyclopropyl-N-[(4S)-3,3-dimethyl-4-piperidyl]pyrido[3,4-d]pyrimidin-4-amine;

5-cyclopropyl-2-[2-[(3,5-dichloro-2-pyridyl)amino]-4-pyridyl]-N-[(4S)-3,3-dimethyl-4-piperidyl]pyrido[3,4-d]pyrimidin-4-amine;

5-cyclobutyl-2-[2-[(3-fluoro-2-pyridyl)amino]-4-pyridyl]-N-[(3R,4R)-3-methyl-4-piperidyl]pyrido[3,4-d]pyrimidin-4-amine;

5-cyclobutyl-2-[2-[(3-fluoro-2-pyridyl)amino]-4-pyridyl]-N-[(3S,4S)-3-methyl-4-piperidyl]pyrido[3,4-d]pyrimidin-4-amine;

rac-(3R,4R)-4-Amino-1-[5-cyclobutyl-2-(9H-pyrido[2,3-b]indol-4-yl)-pyrido[3,4-d]pyrimidin-4-yl]-pyrrolidin-3-ol;

rac-(3S,4R)-4-[5-Cyclobutyl-2-(9H-pyrido[2,3-b]indol-4-yl)-pyrido[3,4-d]pyrimidin-4-ylamino]-piperidin-3-ol;

rac-(3R,4R)-4-[5-Cyclobutyl-2-(9H-pyrido[2,3-b]indol-4-yl)-pyrido[3,4-d]pyrimidin-4-ylamino]-piperidin-3-ol;

[5-Cyclobutyl-2-(9H-pyrido[2,3-b]indol-4-yl)-pyrido[3,4-d]pyrimidin-4-yl]-((3R,4R)-3-methyl-piperidin-4-yl)-amine;

[5-Cyclobutyl-2-(9H-pyrido[2,3-b]indol-4-yl)-pyrido[3,4-d]pyrimidin-4-yl]-((3 S,4R)-3-methyl-piperidin-4-yl)-amine;

Piperidin-4-yl-[2-(9H-pyrido[2,3-b]indol-4-yl)-5-trifluoromethyl-pyrido[3,4-d]pyrimidin-4-yl]-amine;

rac-(3S,4R)-4-[2-(9H-Pyrido [2,3-b]indol-4-yl)-5-trifluoromethyl-pyrido[3,4-d]pyrimidin-4-ylamino]-piperidin-3-ol;

rac-(3R,4R)-4-[2-(9H-Pyrido [2,3-b]indol-4-yl)-5-trifluoromethyl-pyrido[3,4-d]pyrimidin-4-ylamino]-piperidin-3-ol;

rac-(3S,4R)-3-Methyl-piperidin-4-yl)-[2-(9H-pyrido[2,3-b]indol-4-yl)-5-trifluoromethyl-pyrido[3,4-d]pyrimidin-4-yl]-amine;

(rac-(3R,4R)-3-Methyl-piperidin-4-yl)-[2-(9H-pyrido[2,3-b]indol-4-yl)-5-trifluoromethyl-pyrido[3,4-d]pyrimidin-4-yl]-amine;

{5-Cyclopropyl-2-[2-(2,5-dichloro-phenyl)-1H-pyrrolo [2,3-b]pyridin-4-yl]-pyrido[3,4-d]pyrimidin-4-yl}-((S)-3,3-dimethyl-piperidin-4-yl)-amine;

rac-(3R,4R)-4-{2-[2-(2-Chloro-5-fluoro-phenyl)-1H-pyrrolo [2,3-b]pyridin-4-yl]-5-cyclopropyl-pyrido[3,4-d]pyrimidin-4-ylamino}-3-methyl-piperidin-3-ol;

4-[5-Cyclopropyl-4-((S)-3,3-dimethyl-piperidin-4-ylamino)-pyrido[3,4-d]pyrimidin-2-yl]-1H-pyrrolo [2,3-b]pyridine-2-carboxylic acid cyclohexylamide;

5-Cyclopropyl-4-(octahydro-pyrrolo [3,2-c]pyridin-1-yl)-2-(2-pyridin-3-yl-1H-pyrrolo [2,3-b]pyridin-4-yl)-pyrido[3,4-d]pyrimidine;

{5-Cyclopropyl-2-[2-(2-methoxymethyl-phenyl)-1H-pyrrolo [2,3-b]pyridin-4-yl]-pyrido[3,4-d]pyrimidin-4-yl}-((S)-3,3-dimethyl-piperidin-4-yl)-amine;

rac-(1R,3 aS)-1-{2-[2-(2-Chloro-5-fluoro-phenyl)-1H-pyrrolo [2,3-b]pyridin-4-yl]-5-cyclopropyl-pyrido[3,4-d]pyrimidin-4-yl}-octahydro-pyrrolo [3,2-c]pyridin-3a-ol;

rac-(3R,4R)-4-({2-[2-(2-Chloro-5-fluoro-phenyl)-1H-pyrrolo [2,3-b]pyridin-4-yl]-5-cyclopropyl-pyrido[3,4-d]pyrimidin-4-yl}-methyl-amino)-3-methyl-piperidin-3-ol;

2-[2-(2-Chloro-5-fluoro-phenyl)-1H-pyrrolo [2,3-b]pyridin-4-yl]-5-cyclopropyl-4-(hexahydro-pyrrolo [3,4-b][1,4] oxazin-4-yl)-pyrido[3,4-d]pyrimidine;

{5-Cyclopropyl-2-[2-(2,5-difluoro-phenyl)-1H-pyrrolo [2,3-b]pyridin-4-yl]-pyrido[3,4-d]pyrimidin-4-yl}-((S)-3,3-dimethyl-piperidin-4-yl)-amine;

{5-Cyclopropyl-2-[2-(5-methyl-pyridin-3-yl)-1H-pyrrolo [2,3-b]pyridin-4-yl]-pyrido[3,4-d]pyrimidin-4-yl1-((S)-3,3-dimethyl-piperidin-4-yl)-amine;

Azepan-1-yl-{4-[5-cyclopropyl-4-((S)-3,3-dimethyl-piperidin-4-ylamino)-pyrido[3,4-d]pyrimidin-2-yl]-1H-pyrrolo [2,3-b]pyridin-2-yl}-methanone;

{5-Cyclopropyl-2-[2-(2-fluoro-5-methyl-pyridin-3-yl)-1H-pyrrolo [2,3-b]pyridin-4-yl]-pyrido[3,4-d]pyrimidin-4-yl}-((S)-3,3-dimethyl-piperidin-4-yl)-amine;

{5-Cyclopropyl-2-[2-(5-fluoro-pyridin-3-yl)-1H-pyrrolo [2,3-b]pyridin-4-yl]-pyrido[3,4-d]pyrimidin-4-yl}-((S)-3,3-dimethyl-piperidin-4-yl)-amine;

Azetidin-1-yl-[4-[5-cyclopropyl-44[(4S)-3,3-dimethyl-4-piperidyl] amino]pyrido[3,4-d]pyrimidin-2-yl]-1H-pyrrolo [2,3-b]pyridin-2-yl]methanone;

[5-Cyclobutyl-2-(2-pyridin-3-yl-1H-pyrrolo [2,3-b]pyridin-4-yl)-pyrido[3,4-d]pyrimidin-4-yl]-((S)-3,3-dimethyl-piperidin-4-yl)-amine;

{2-[2-(2-Chloro-5-methoxy-phenyl)-1H-pyrrolo [2,3-b] pyridin-4-yl]-5-cyclopropyl-pyrido[3,4-d]pyrimidin-4-yl}-((S)-3,3-dimethyl-piperidin-4-yl)-amine;

(S)-Azepan-4-yl[5-cyclopropyl-2-(2-pyridin-3-yl-1H-pyrrolo [2,3-b]pyridin-4-yl)-pyrido[3,4-d]pyrimidin-4-yl]-amine;

{5-Cyclobutyl-2-[2-(5-fluoro-pyridin-3-yl)-1H-pyrrolo [2,3-b]pyridin-4-yl]-pyrido[3,4-d]pyrimidin-4-yl}-((S)-3,3-dimethyl-piperidin-4-yl)-amine;

5-cyclopropyl-N-[(4S)-3,3-dimethyl-4-piperidyl]-2-[2-(4-pyridyl)-1H-pyrrolo [2,3-b]pyridin-4-yl]pyrido[3,4-d]pyrimidin-4-amine;

N-[(4S)-3,3-dimethyl-4-piperidyl]-2-[2-(3-pyridyl)-1H-pyrrolo[2,3-b]pyridin-4-yl]-5-(trifluoromethyl)pyrido [3,4-d]pyrimidin-4-amine;

4-(5-Cyclopropyl-4-piperazin-1-yl-pyrido[3,4-d]pyrimidin-2-yl)-benzofuro [2,3-b]pyridine;

2-(benzofuro [2,3-b]pyridin-4-yl)-5-cyclopropyl-N-(4-piperidyl)pyrido[3,4-d]pyrimidin-4-amine;

5-{[5-Cyclobutyl-2-(9H-pyrido[2,3-b]indol-4-yl)-pyrido [3,4-d]pyrimidin-4-yl]-methyl-amino}-hexahydro-cyclopentoxazol-2-one;

5-[5-Cyclobutyl-2-(9H-pyrido[2,3-b]indol-4-yl)-pyrido [3,4-d]pyrimidin-4-ylamino]-hexahydro-cyclopentoxazol-2-one;

2-amino-4-[[5-cyclobutyl-2-(9H-pyrido[2,3-b]indol-4-yl)pyrido[3,4-d]pyrimidin-4-yl]amino]cyclopentanecarboxamide;

{5-Cyclopropyl-2-[2-(quinolin-2-ylamino)-pyridin-4-yl]-pyrido[3,4-d]pyrimidin-4-yl}-((S)-3,3-dimethyl-piperidin-4-yl)-amine;

{5-Cyclobutyl-2-[2-(pyrazolo [1,5-a]pyridin-2-ylamino)-pyridin-4-yl]-pyrido[3,4-d]pyrimidin-4-yl}-((R)-3,3-dimethyl-piperidin-4-yl)-amine;

{5-Cyclobutyl-2-[2-(pyrazolo [1,5-a]pyridin-2-ylamino)-pyridin-4-yl]-pyrido[3,4-d]pyrimidin-4-yl}-((S)-3,3-dimethyl-piperidin-4-yl)-amine;

rac-(3S,4R)-4-{5-Cyclobutyl-2-[2-(3,6-difluoro-pyridin-2-ylamino)-pyridin-4-yl]-pyrido[3,4-d]pyrimidin-4-ylamino}-piperidin-3-ol;

{5-Cyclobutyl-2-[2-(4-fluoro-pyridin-2-ylamino)-pyridin-4-yl]-pyrido[3,4-d]pyrimidin-4-yl}-((S)-3,3-dimethyl-piperidin-4-yl)-amine;

{5-Cyclobutyl-2-[2-(6-methoxy-pyridin-2-ylamino)-pyridin-4-yl]-pyrido[3,4-d]pyrimidin-4-yl}-((S)-3,3-dimethyl-piperidin-4-yl)-amine;

{5-Cyclopropyl-2-[2-(3-fluoro-pyridin-2-yl)-1H-pyrrolo[2,3-b]pyridin-4-yl]-pyrido[3,4-d]pyrimidin-4-yl}-((S)-3,3-dimethyl-piperidin-4-yl)-methyl-amine;

[5-Cyclopropyl-2-(2-pyridin-3-yl-1H-pyrrolo [2,3-b]pyridin-4-yl)-pyrido[3,4-d]pyrimidin-4-yl]-((S)-3,3-dimethyl-piperidin-4-yl)-methyl-amine;

{5-Cyclobutyl-2-[2-(3,6-difluoro-pyridin-2-ylamino)-pyridin-4-yl]-pyrido[3,4-d]pyrimidin-4-yl}-(rac-(2S,4S)-2-methyl-piperidin-4-yl)-amine;

{5-Cyclobutyl-2-[2-(3,6-difluoro-pyridin-2-ylamino)-pyridin-4-yl]-pyrido[3,4-d]pyrimidin-4-yl}-(rac-(2R,4S)-2-methyl-piperidin-4-yl)-amine;

{5-Cyclobutyl-2-[2-(pyridin-2-ylamino)-pyridin-4-yl]-pyrido[3,4-d]pyrimidin-4-yl}-((S)-3,3-dimethyl-piperidin-4-yl)-amine;

{5-Cyclobutyl-2-[2-(5-fluoro-pyridin-2-ylamino)-pyridin-4-yl]-pyrido[3,4-d]pyrimidin-4-yl}-((S)-3,3-dimethyl-piperidin-4-yl)-amine;

{5-Cyclopropyl-2-[2-(3-fluoro-pyridin-2-ylamino)-pyridin-4-yl]-pyrido[3,4-d]pyrimidin-4-yl}-((S)-3,3-dimethyl-piperidin-4-yl)-amine;

{5-Cyclopropyl-2-[2-(3,5-difluoro-pyridin-2-ylamino)-pyridin-4-yl]-pyrido[3,4-d]pyrimidin-4-yl}-((S)-3,3-dimethyl-piperidin-4-yl)-amine;

{5-Cyclopropyl-2-[2-(4-fluoro-pyridin-2-ylamino)-pyridin-4-yl]-pyrido[3,4-d]pyrimidin-4-yl}-((S)-3,3-dimethyl-piperidin-4-yl)-amine;

{5-Cyclopropyl-2-[2-(5-fluoro-pyridin-2-ylamino)-pyridin-4-yl]-pyrido[3,4-d]pyrimidin-4-yl}-((S)-3,3-dimethyl-piperidin-4-yl)-amine;

{5-Cyclopropyl-2-[2-(2-fluoro-phenyl)-1H-pyrrolo [2,3-b]pyridin-4-yl]-pyrido[3,4-d]pyrimidin-4-yl1-((S)-3,3-dimethyl-piperidin-4-yl)-amine;

[5-Cyclopropyl-2-(2-pyridin-3-yl-1H-pyrrolo[2,3-b]pyridin-4-yl)-pyrido[3,4-d]pyrimidin-4-yl]-((S)-3,3-dimethyl-piperidin-4-yl)-amine;

{5-Cyclopropyl-2-[2-(2-fluoro-phenyl)-1H-pyrrolo [2,3-b]pyridin-4-yl]-pyrido[3,4-d]pyrimidin-4-yl}-((S)-3,3-dimethyl-piperidin-4-yl)-methyl-amine;

or a salt thereof.

29. A composition comprising a compound according to claim 1 and/or a salt thereof and at least one pharmaceutically acceptable excipient.

* * * * *